United States Patent
Gao et al.

(10) Patent No.: US 11,253,576 B2
(45) Date of Patent: Feb. 22, 2022

(54) METHODS AND COMPOSITIONS FOR TREATING METABOLIC IMBALANCE IN NEURODEGENERATIVE DISEASE

(71) Applicant: University of Massachusetts, Boston, MA (US)

(72) Inventors: Guangping Gao, Westborough, MA (US); Dominic Gessler, Worcester, MA (US)

(73) Assignee: University of Massachusetts, Boston, MA (US)

( * ) Notice: Subject to any disclaimer, the term of this patent is extended or adjusted under 35 U.S.C. 154(b) by 663 days.

(21) Appl. No.: 15/769,981

(22) PCT Filed: Oct. 21, 2016

(86) PCT No.: PCT/US2016/058197
§ 371 (c)(1),
(2) Date: Apr. 20, 2018

(87) PCT Pub. No.: WO2017/070525
PCT Pub. Date: Apr. 27, 2017

(65) Prior Publication Data
US 2018/0311323 A1 Nov. 1, 2018

Related U.S. Application Data

(60) Provisional application No. 62/323,558, filed on Apr. 15, 2016, provisional application No. 62/322,101, filed on Apr. 13, 2016, provisional application No. 62/245,213, filed on Oct. 22, 2015.

(51) Int. Cl.
| | |
|---|---|
| A61K 38/50 | (2006.01) |
| A61K 48/00 | (2006.01) |
| C12N 15/00 | (2006.01) |
| G01N 33/50 | (2006.01) |
| A61P 25/28 | (2006.01) |
| A61K 9/00 | (2006.01) |
| A61K 45/06 | (2006.01) |
| C12N 7/00 | (2006.01) |
| G01N 33/66 | (2006.01) |
| G01N 33/68 | (2006.01) |
| G01N 33/84 | (2006.01) |
| G01N 33/06 | (2006.01) |

(52) U.S. Cl.
CPC ............ *A61K 38/50* (2013.01); *A61K 9/0019* (2013.01); *A61K 9/0085* (2013.01); *A61K 45/06* (2013.01); *A61K 48/00* (2013.01); *A61K 48/005* (2013.01); *A61P 25/28* (2018.01); *C12N 7/00* (2013.01); *C12N 15/00* (2013.01); *C12Y 305/01015* (2013.01); *G01N 33/06* (2013.01); *G01N 33/5038* (2013.01); *G01N 33/6896* (2013.01); *G01N 33/84* (2013.01); *C12N 2750/14143* (2013.01); *C12N 2750/14171* (2013.01); *G01N 2800/04* (2013.01); *G01N 2800/24* (2013.01); *G01N 2800/28* (2013.01); *G01N 2800/2814* (2013.01)

(58) Field of Classification Search
None
See application file for complete search history.

(56) References Cited

U.S. PATENT DOCUMENTS

| | | |
|---|---|---|
| 5,478,745 A | 12/1995 | Samulski et al. |
| 5,871,982 A | 2/1999 | Wilson et al. |
| 6,156,303 A | 12/2000 | Russell et al. |
| 6,177,403 B1 | 1/2001 | Stedman |
| 6,251,677 B1 | 6/2001 | Wilson et al. |
| 6,485,966 B2 | 11/2002 | Gao et al. |
| 6,498,244 B1 | 12/2002 | Patel et al. |
| 6,544,786 B1 | 4/2003 | Xiao et al. |
| 6,620,800 B1 | 9/2003 | Roberts |
| 6,953,690 B1 | 10/2005 | Gao et al. |
| 6,962,815 B2 | 11/2005 | Bartlett |
| 7,022,519 B2 | 4/2006 | Gao et al. |
| 7,198,951 B2 | 4/2007 | Gao et al. |
| 7,235,393 B2 | 6/2007 | Gao et al. |
| 7,282,199 B2 | 10/2007 | Gao et al. |
| 7,427,396 B2 | 9/2008 | Arbetman et al. |
| 7,456,015 B2 | 11/2008 | Bohn et al. |

(Continued)

FOREIGN PATENT DOCUMENTS

| | | |
|---|---|---|
| EP | 2261242 A1 | 12/2010 |
| EP | 2468891 A2 | 6/2012 |

(Continued)

OTHER PUBLICATIONS

Parikh et al. A Clinical Approach to the Diagnosis of Patients with Leukodystrophies and genetic Leukoencephelopathies. Molecullar Genetics and Metabolism, 2015. 114:501-515. Published online Dec. 29, 2014.*

(Continued)

*Primary Examiner* — Christopher M Babic
*Assistant Examiner* — Kimberly A Aron
(74) *Attorney, Agent, or Firm* — Wolf, Greenfield & Sacks, P.C.

(57) ABSTRACT

In some aspects, the disclosure relates to compositions and methods useful for the diagnosis and treatment of neurodegenerative diseases, such as leukodystrophies (e.g., Canavan Disease). In some embodiments, the methods comprise administering to a subject an N-acetylaspartate (NAA)-depleting agent or an N-acetylaspartate (NAA)-depleting agent based upon the subject's metabolic profile.

21 Claims, 330 Drawing Sheets
Specification includes a Sequence Listing.

(56) References Cited

U.S. PATENT DOCUMENTS

| | | |
|---|---|---|
| 7,906,111 B2 | 3/2011 | Wilson et al. |
| 8,222,221 B2 | 7/2012 | Corey et al. |
| 8,524,446 B2 | 9/2013 | Gao et al. |
| 8,734,809 B2 | 5/2014 | Gao et al. |
| 9,217,155 B2 | 12/2015 | Gao et al. |
| 9,249,424 B2 | 2/2016 | Wolf et al. |
| 9,701,984 B2 | 7/2017 | Gao et al. |
| 2001/0016355 A1 | 8/2001 | Samulski et al. |
| 2002/0164783 A1 | 11/2002 | Feldhaus |
| 2002/0192823 A1 | 12/2002 | Bartlett |
| 2003/0103939 A1 | 6/2003 | Engelhardt et al. |
| 2003/0110526 A1 | 6/2003 | Brown et al. |
| 2003/0138772 A1 | 7/2003 | Gao et al. |
| 2003/0228282 A1 | 12/2003 | Gao et al. |
| 2004/0101514 A1 | 5/2004 | Liu et al. |
| 2004/0219528 A1 | 11/2004 | Morris et al. |
| 2005/0014262 A1 | 1/2005 | Gao et al. |
| 2005/0032219 A1 | 2/2005 | Aubourg et al. |
| 2005/0197313 A1 | 9/2005 | Roelvink |
| 2005/0255086 A1 | 11/2005 | Davidson et al. |
| 2005/0255089 A1 | 11/2005 | Chiorini et al. |
| 2005/0287122 A1 | 12/2005 | Bartlett et al. |
| 2006/0018841 A1 | 1/2006 | Arbetman et al. |
| 2006/0063174 A1 | 3/2006 | Turner et al. |
| 2006/0093589 A1 | 5/2006 | Warrington et al. |
| 2006/0153826 A1 | 7/2006 | Arnould et al. |
| 2006/0189564 A1 | 8/2006 | Burright et al. |
| 2006/0228800 A1 | 10/2006 | Lin et al. |
| 2006/0292117 A1 | 12/2006 | Loiler et al. |
| 2007/0036760 A1 | 2/2007 | Wilson et al. |
| 2007/0243526 A1 | 10/2007 | Kay et al. |
| 2007/0253936 A1 | 11/2007 | Kay et al. |
| 2008/0075737 A1 | 3/2008 | Gao et al. |
| 2008/0292595 A1 | 11/2008 | Arbetman et al. |
| 2009/0042828 A1 | 2/2009 | Xu et al. |
| 2009/0111766 A1 | 4/2009 | Atkinson et al. |
| 2009/0149409 A1 | 6/2009 | Bohn et al. |
| 2009/0197338 A1 | 8/2009 | Vandenberghe et al. |
| 2009/0215879 A1 | 8/2009 | DiPrimio et al. |
| 2009/0239240 A1 | 9/2009 | Kwon et al. |
| 2010/0104561 A1 | 4/2010 | Zhong et al. |
| 2010/0183570 A1 | 7/2010 | Wang et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2012/0077870 A1 | 3/2012 | Blanks et al. |
| 2012/0137379 A1 | 5/2012 | Gao et al. |
| 2012/0270930 A1 | 10/2012 | Van Der Maarel et al. |
| 2012/0309050 A1 | 12/2012 | Kumon et al. |
| 2013/0023488 A1 | 1/2013 | Wu |
| 2013/0030042 A1 | 1/2013 | Couto |
| 2013/0101558 A1 | 4/2013 | Gao et al. |
| 2013/0109742 A1 | 5/2013 | Hewitt et al. |
| 2013/0142861 A1 | 6/2013 | Tsou et al. |
| 2013/0195801 A1 | 8/2013 | Gao et al. |
| 2013/0323226 A1 | 12/2013 | Wilson et al. |
| 2013/0323229 A1 | 12/2013 | Leone et al. |
| 2014/0142152 A1 | 5/2014 | Jaworski |
| 2014/0142161 A1 | 5/2014 | Flotte et al. |
| 2014/0142288 A1 | 5/2014 | Davidson et al. |
| 2014/0147418 A1 | 5/2014 | Chiorini et al. |
| 2014/0179770 A1 | 6/2014 | Zhang et al. |
| 2014/0201857 A1 | 7/2014 | Fahrenkrug et al. |
| 2014/0335054 A1 | 11/2014 | Gao et al. |
| 2015/0065560 A1 | 3/2015 | Bjorklund et al. |
| 2015/0160224 A1 | 6/2015 | Troyer |
| 2015/0258180 A1 | 9/2015 | Mahuran et al. |
| 2016/0017005 A1 | 1/2016 | Asokan et al. |
| 2016/0060624 A1 | 3/2016 | Davidson et al. |
| 2016/0076054 A1 | 3/2016 | Auricchio et al. |
| 2016/0153005 A1 | 6/2016 | Zhang et al. |
| 2016/0185832 A1 | 6/2016 | Drivas et al. |
| 2016/0194374 A1 | 7/2016 | Wijnholds et al. |
| 2016/0272976 A1 | 9/2016 | Kaspar |
| 2017/0029785 A1 | 2/2017 | Zhao et al. |
| 2017/0114340 A1 | 4/2017 | Mueller et al. |
| 2017/0165377 A1 | 6/2017 | Gao et al. |
| 2019/0125899 A1 | 5/2019 | Gao et al. |

FOREIGN PATENT DOCUMENTS

| | | | |
|---|---|---|---|
| WO | WO 2003/042397 | 5/2003 | |
| WO | WO 2004/108922 A2 | 12/2004 | |
| WO | WO 2005/033321 | 4/2005 | |
| WO | WO 2006/031267 A2 | 3/2006 | |
| WO | WO 2006/066066 A2 | 6/2006 | |
| WO | WO 2006/119432 A2 | 11/2006 | |
| WO | WO 2008/125846 A2 | 10/2008 | |
| WO | WO 2008/150897 A2 | 12/2008 | |
| WO | WO 2009/043936 | 4/2009 | |
| WO | WO 2009/146178 A1 | 12/2009 | |
| WO | WO 2010/027446 A2 | 3/2010 | |
| WO | WO 2010/071454 A1 | 6/2010 | |
| WO | WO 2010/099383 A2 | 9/2010 | |
| WO | WO 2010/129021 A1 | 11/2010 | |
| WO | WO 2010/138263 A2 | 12/2010 | |
| WO | WO 2011/094198 A1 | 8/2011 | |
| WO | WO-2011133890 A1 * | 10/2011 | ............... C12N 9/80 |
| WO | WO 2012/123430 A1 | 9/2012 | |
| WO | WO 2013/055865 A1 | 4/2013 | |
| WO | WO 2013/123503 A1 | 8/2013 | |
| WO | WO 2013/170078 A1 | 11/2013 | |
| WO | WO 2013/190059 A1 | 12/2013 | |
| WO | WO-2013181446 A2 * | 12/2013 | ............. A61K 35/30 |
| WO | WO 2014/160092 A1 | 10/2014 | |
| WO | WO 2014/186746 A1 | 11/2014 | |
| WO | WO 2014/197748 A2 | 11/2014 | |
| WO | 2015/127128 A2 | 8/2015 | |
| WO | WO 2015/121501 A1 | 8/2015 | |
| WO | 2015/164786 | 10/2015 | |
| WO | WO 2015/168666 A2 | 11/2015 | |
| WO | WO 2016/065001 A1 | 4/2016 | |
| WO | WO 2017/023724 A1 | 2/2017 | |

OTHER PUBLICATIONS

Gessler et al. Optimized AspA Expression Cassette Dramatically Improves Therapeutic Potency of Systemically Delivered rAAV in CNS Therapy of Canavan's Disease. Molecular Therapy, May 22, 2014. Supplement 1. p. S111.*

Extended European Search Report for Application No. EP 16858331.8, dated Jun. 4, 2019.

International Search Report and Written Opinion for Application No. PCT/US2017/027759, dated Sep. 8, 2017.

International Preliminary Report on Patentability for Application No. PCT/US2017/027759, dated Oct. 25, 2018.

Invitation to Pay Additional Fees for Application No. PCT/US2017/027759, mailed Jul. 10, 2017.

Bals et al., Transduction of well-differentiated airway epithelium by recombinant adeno-associated virus is limited by vector entry. J Virol. Jul. 1999;73(7):6085-8.

Borel et al., Recombinant AAV as a platform for translating the therapeutic potential of RNA interference. Mol Ther. Apr. 2014;22(4):692-701. doi:10.1038/mt.2013.285. Epub Dec. 19, 2013.

Gao et al., Adeno-associated virus-mediated gene transfer to non-human primate liver can elicit destructive transgene-specific T cell responses. Hum Gene Ther. Sep. 2009;20(9):930-42. doi:10.1089/hum.2009.060.

GENBANK Submission; Accession No. ADZ26851; Wilson et al.; Jun. 30, 2005.

GENBANK Submission; NCBI, Accession No. ABA71701; Schmidt et al.; May 10, 2006.

GENBANK Submission; NCBI, Accession No. ACB55301; Vandenberghe et al.; Jul. 31, 2008.

GENBANK Submission; NCBI, Accession No. ACB55310; Vandenberghe et al.; Jul. 31, 2008.

GENBANK Submission; NCBI, Accession No. NP_049542; Xiao et al.; Mar. 11, 2010.

(56) References Cited

OTHER PUBLICATIONS

GENBANK Submission; NCBI, Accession No. YP_680426; Ruffing et al.; Nov. 19, 2010.
Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.
Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.
Mtetzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi:10.1089/hum.2015.050. Epub Aug. 6, 2015.
Pfeifer et al., Pharmacological potential of RNAi—focus on miRNA. Pharmacol Ther. Jun. 2010;126(3):217-27. doi: 10.1016/j.pharmthera.2010.03.006. Epub Apr. 11, 2010.
Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.
Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.
Aartsma-Rus et al., New insights in gene-derived therapy: the example of Duchenne muscular dystrophy. Ann N Y Acad Sci. Dec. 2010;1214:199-212. doi: 10.1111/j.1749-6632.2010.05836.x. Epub Dec. 1, 2010.
Adachi et al., Drawing a high-resolution functional map of adeno-associated virus capsid by massively parallel sequencing. Nat Commun. 2014;5:3075. doi: 10.1038/ncomms4075.
Afione et al., In vivo model of adeno-associated virus vector persistence and rescue. J Virol. May 1996;70(5):3235-41.
Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].
Akache et al., The 37/67-kilodalton laminin receptor is a receptor for adeno-associated virus serotypes 8, 2, 3, and 9. J Virol. Oct. 2006;80(19):9831-6.
Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.
Arbuthnot et al., Hepatic delivery of RNA interference activators for therapeutic application. Curr Gene Ther. Apr. 2009;9(2):91-103.
Asokan et al., The AAV vector toolkit: poised at the clinical crossroads. Mol Ther. Apr. 2012;20(4):699-708. doi: 10.1038/mt.2011.287. Epub Jan. 24, 2012.
Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.
Berns et al., Biology of adeno-associated virus. Curr Top Microbiol Immunol. 1996;218:1-23.
Berns et al., Detection of adeno-associated virus (AAV)-specific nucleotide sequences in DNA isolated from latently infected Detroit 6 cells. Virology. Dec. 1975;68(2):556-60.
Beutler et al., AAV for pain: steps towards clinical translation. Gene Ther. Apr. 2009;16(4):461-9. Epub Mar. 5, 2009.
Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.
Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.
Brantly et al., Phase I trial of intramuscular injection of a recombinant adeno-associated virus serotype 2 alpha1-antitrypsin (AAT) vector in AAT-deficient adults. Hum Gene Ther. Dec. 2006;17(12):1177-86.
Buning et al., Receptor targeting of adeno-associated virus vectors. Gene Ther. Jul. 2003;10(14):1142-51.
Calcedo et al., Worldwide epidemiology of neutralizing antibodies to adeno-associated viruses. J Infect Dis. Feb. 1, 2009;199(3):381-90.
Carter et al., Adeno-associated virus gene expression and regulation. CRC Handbook of parvoviruses. 1990:227-54.
Carter, in "Handbook of Parvoviruses", ed., P. Tijsser, CRC Press, pp. 155-168 (1990).
Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.
Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.
Chadderton et al., Improved retinal function in a mouse model of dominant retinitis pigmentosa following AAV-delivered gene therapy. Mol Ther. Apr. 2009;17(4):593-9. Epub Jan. 27, 2009.
Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.
Chen et al., Efficient transduction of vascular endothelial cells with recombinant adeno-associated virus serotype 1 and 5 vectors. Hum Gene Ther. Feb. 2005;16(2):235-47.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Cheng et al., Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011.
Chiorini et al., Cloning and characterization of adeno-associated virus type 5. J Virol. Feb. 1999;73(2):1309-19.
Chirmule et al., Humoral immunity to adeno-associated virus type 2 vectors following administration to murine and nonhuman primate muscle. J Virol. Mar. 2000;74(5):2420-5.
Choudhury et al., Identification of Novel vectors capable of CNS transduction in adult mice after single round selection using DNA shuffled AAV capsid library. Mol Ther. May 1, 2013;21(1):S1/.
Cideciyan et al., Human RPE65 gene therapy for Leber congenital amaurosis: persistence of early visual improvements and safety at 1 year. Hum Gene Ther. Sep. 2009;20(9):999-1004.
Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.
Conlon et al., Ribozyme Approaches towards Down-Regulation of Pi*Z Mutant Human a-1 Anti-Trypsin. Mol. Therapy. 2004;9:S333. Abstract 875.
Conrad et al., Safety of single-dose administration of an adeno-associated virus (AAV)-CFTR vector in the primate lung. Gene Ther. Aug. 1996;3(8):658-68.
Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.
Cruz et al., The promise of gene therapy for the treatment of alpha-1 antitrypsin deficiency. Pharmacogenomics. Sep. 2007;8(9):1191-8.
Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.
Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.
Daya et al., Gene therapy using adeno-associated virus vectors. Clin Microbiol Rev. Oct. 2008;21(4):583-93. doi: 10.1128/CMR.00008-08.

(56) References Cited

OTHER PUBLICATIONS

Dominov et al., A novel dysferlin mutant pseudoexon bypassed with antisense oligonucleotides. Ann Clin Transl Neurol. Sep. 2014;1(9):703-20. doi: 10.1002/acn3.96. Epub Sep. 27, 2014.
Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.
Ehlert et al., Cellular toxicity following application of adeno-associated viral vector-mediated RNA interference in the nervous system. BMC Neurosci. Feb. 18, 2010;11:20.
Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Fischer et al., Successful transgene expression with serial doses of aerosolized rAAV2 vectors in rhesus macaques. Mol Ther. Dec. 2003;8(6):918-26.
Fisher et al., Transduction with recombinant adeno-associated virus for gene therapy is limited by leading-strand synthesis. J Virol. Jan. 1996;70(1):520-32.
Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Flotte, Recombinant adeno-associated virus (AAV) gene therapy vectors for, cystic fibrosis (CF), alpha-1-antitrypsin deficiency (AAT) and fatty oxidation disorders (FAO). Umass Medical School. Interdisciplinary Graduate Program. Last accessed at http://www.umassmed.edu/igp/faculty/flotte.cfm?start=0& on Aug. 27, 2009.
Foust et al., Intravascular AAV9 preferentially targets neonatal-neurons and adult-astrocytes. Nature Biotechnology, 27; 59-65 2009.
Foust et al., Over the barrier and through the blood: to CNS delivery we go. Cell Cycle. Dec. 15, 2009;8(24):4017-8.
Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.
Fu et al., Self-complementary adeno-associated virus serotype 2 vector: global distribution and broad dispersion of AAV-mediated transgene expression in mouse brain. Mol Ther. Dec. 2003;8(6):911-7.
Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.
Gao et al., Biology of AAV serotype vectors in liver-directed gene transfer to nonhuman primates. Mol Ther. Jan. 2006;13(1):77-87. Epub Oct. 10, 2005.
Gao et al., Clades of Adeno-associated viruses are widely disseminated in human tissues. J Virol. Jun. 2004;78(12):6381-8.
Gao et al., Erythropoietin gene therapy leads to autoimmune anemia in macaques. Blood. May 1, 2004;103(9):3300-2. Epub Dec. 24, 2003.
Gao et al., Inadvertent gene transfer of co-packaged rep and cap sequences during the production of AAV vector and its potential impact on vector performance. Molecular Therapy. May 2008; 16(Suppl. 1):S105-S106. Abstract 279.
Gao et al., New recombinant serotypes of AAV vectors. Curr Gene Ther. Jun. 2005;5(3):285-97.
Gao et al., Novel adeno-associated viruses from rhesus monkeys as vectors for human gene therapy. Proc Natl Acad Sci U S A. Sep. 3, 2002;99(18): 11854-9. Epub Aug. 21, 2002.
Gao et al., RAAV-mediated targeting in adult mice and its potential in generating animal models of tissue-specific somatic transgenics or knock down. Molecular Therapy. May 2008;16(1):S118-S119. Abstract 316.
GENBANK Submission; Accession No. AF028705.1; Rutledge et al.; Jan. 12, 1998.
GENBANK Submission; NCBI, Accession No. AAB95450; Rutledge et al.; Jan. 12, 1998.
GENBANK Submission; NCBI, Accession No. AAS99264; Gao et al.; Jun. 24, 2004.
GENBANK Submission; NCBI, Accession No. AY530579.10; 2004.
Grimm et al., Fatality in mice due to oversaturation of cellular microRNA/short hairpin RNA pathways. Nature. May 25, 2006;441(7092):537-41.
Grimm, Small silencing RNAs: state-of-the-art. Adv Drug Deliv Rev. Jul. 25, 2009;61(9):672-703. doi: 10.1016/j.addr.2009.05.002. Epub May 7, 2009.
Hauswirth et al., Treatment of leber congenital amaurosis due to RPE65 mutations by ocular subretinal injection of adeno-associated virus gene vector: short-term results of a phase I trial. Hum Gene Ther. Oct. 2008;19(10):979-90.
Hernandez et al., Latent adeno-associated virus infection elicits humoral but not cell-mediated immune responses in a nonhuman primate model. J Virol. Oct. 1999;73(10):8549-58.
Hildinger et al., Hybrid vectors based on adeno-associated virus serotypes 2 and 5 for muscle-directed gene transfer. J Virol. Jul. 2001;75(13):6199-203.
Iida et al., Systemic Delivery of Tyrosine-Mutant AAV Vectors Results in Robust Transduction of Neurons in Adult Mice. BioMed Res Int. 2013;2013.
Iwamoto et al., Global diffuse distribution in the brain and efficient gene delivery to the dorsal root ganglia by intrathecal injection of adeno-associated viral vector serotype 1. J Gene Med. Jun. 2009;11(6):498-505. doi: 10.1002/jgm.1325.
Jakobsson et al., Lentiviral vectors for use in the central nervous system. Mol Ther. Mar. 2006;13(3):484-93. Epub Jan. 3, 2006.
Janson et al., Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.
Kaspar et al., Retrograde viral delivery of IGF-1 prolongs survival in a mouse ALS model. Science. Aug. 8, 2003;301(5634):839-42.
Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.
Kotin et al., Organization of adeno-associated virus DNA in latently infected Detroit 6 cells. Virology. Jun. 1989;170(2):460-7.
Kotin et al., Site-specific integration by adeno-associated virus. Proc Natl Acad Sci U S A. Mar. 1990;87(6):2211-5.
Kumar et al., Lack of aspartoacylase activity disrupts survival and differentiation of neural progenitors and oligodendrocytes in a mouse model of Canavan disease. J Neurosci Res. Nov. 15, 2009;87(15):3415-27. doi: 10.1002/jnr.22233.
Lawlor et al., Efficient gene delivery and selective transduction of glial cells in the mammalian brain by AAV serotypes isolated from nonhuman primates. Mol Ther. Oct. 2009;17(10):1692-702. doi:10.1038/mt.2009.170.
Lebherz et al., Gene therapy with novel adeno-associated virus vectors substantially diminishes atherosclerosis in a murine model of familial hypercholesterolemia. J Gene Med. Jun. 2004;6(6):663-72.
Leone et al., Aspartoacylase gene transfer to the mammalian central nervous system with therapeutic implications for Canavan disease. Ann Neurol. Jul. 2000;48(1):27-38. Erratum in: Ann Neurol Sep. 2000;48(3):398. Bilianuk L [corrected to Bilaniuk L].
Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.
Li et al., Ex vivo transduction and transplantation of bone marrow cells for liver gene delivery of alpha1-antitrypsin. Mol Ther. Aug. 2010;18(8):1553-8. Epub Jun. 15, 2010.

(56) References Cited

OTHER PUBLICATIONS

Li et al., Protein trans-splicing as a means for viral vector-mediated in vivo gene therapy. Hum Gene Ther. Sep. 2008;19(9):958-64. doi: 10.1089/hum.2008.009.
Lin et al., Impact of preexisting vector immunity on the efficacy of adeno-associated virus-based HIV-1 Gag vaccines. Hum Gene Ther. Jul. 2008;19(7):663-9.
Liu et al., Biological Differences in rAAV Transduction of Airway Epithelia in Humans and in Old World Non-human Primates. Mol Ther. Dec. 2007;15(12):2114-23. Epub Jul. 31, 2007.
Liu et al., Comparative biology of rAAV transduction in ferret, pig and human airway epithelia. Gene Ther. Nov. 2007;14(21): 1543-8. Epub Aug. 30, 2007.
Liu et al., Species-specific differences in mouse and human airway epithelial biology of recombinant adeno-associated virus transduction. Am J Respir Cell Mol Biol. Jan. 2006;34(1):56-64. Epub Sep. 29, 2005.
Loiler et al., Targeting recombinant adeno-associated virus vectors to enhance gene transfer to pancreatic islets and liver. Gene Ther. Sep. 2003;10(18):1551-8.
Lowenstein, Crossing the rubicon. Nat Biotechnol. Jan. 2009;27(1):42-4.
Lux et al., Green fluorescent protein-tagged adeno-associated virus particles allow the study of cytosolic and nuclear trafficking. J Virol. Sep. 2005;79(18):11776-87.
Maguire et al., Directed evolution of adeno-associated virus for glioma cell transduction. J Neurooncol. Feb. 2010;96(3):337-47. doi:10.1007/s11060-009-9972-7. Epub Jul. 19, 2009.
Maguire et al., Gene therapy for the nervous system: challenges and new strategies. Neurotherapeutics. Oct. 2014;11(4):817-39. doi: 10.1007/s13311-014-0299-5.
Mandel et al., Recombinant adeno-associated viral vectors as therapeutic agents to treat neurological disorders. Mol Ther. Mar. 2006;13(3):463-83. Epub Jan. 18, 2006.
Manfredsson et al., AAV9: a potential blood-brain barrier buster. Mol Ther. Mar. 2009;17(3):403-5.
Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592. Rasko, John [corrected to Rasko, John JE]; Rustagi, Pradip K [added].
Matalon et al., Adeno-associated virus-mediated aspartoacylase gene transfer to the brain of knockout mouse for canavan disease. Mol Ther. May 2003;7(5 Pt 1):580-7.
Mattan et al., Aspartoacylase deficiency affects early postnatal development of oligodendrocytes and myelination. Neurobiol Dis. Nov. 2010;40(2):432-43. doi: 10.1016/j.nbd.2010.07.003. Epub Jul. 14, 2010.
McCarty et al., Adeno-associated virus terminal repeat (TR) mutant generates self-complementary vectors to overcome the rate-limiting step to transduction in vivo. Gene Ther. Dec. 2003;10(26):2112-8.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16): 1248-54.
McCarty, Self-complementary AAV vectors; advances and applications. Mol Ther. Oct. 2008;16(10):1648-56. Epub Aug. 5, 2008.
McCurdy et al., Sustained normalization of neurological disease after intracranial gene therapy in a feline model. Sci Transl Med. Apr. 9, 2014;6(231):231ra48. doi: 10.1126/scitranslmed.3007733.
Meijer et al., Controlling brain tumor growth by intraventricular administration of an AAV vector encoding IFN-beta. Cancer Gene Ther. Aug. 2009;16(8):664-71. doi: 10.1038/cgt.2009.8. Epub Feb. 6, 2009.
Mingozzi et al., CD8(+) T-cell responses to adeno-associated virus capsid in humans. Nat Med. Apr. 2007;13(4):419-22. Epub Mar. 18, 2007.

Moffett et al., N-Acetylaspartate in the CNS: from neurodiagnostics to neurobiology. Prog Neurobiol. Feb. 2007;81(2):89-131. Epub Jan. 5, 2007.
Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.
Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.
Mueller et al., In Vivo AAV Delivered Allele Specific shRNA for the Knockdown of Alpha-1 Antitrypsin. Molecular Therapy May 2010;18(1):S22. Abstract 53.
Mueller et al., In Vivo Allele Specific Knockdown of Mutant Alpha-1 Antitrypsin Using Recombinant AAV Delivered shRNA. Molecular Therapy May 2009;17(1):S313. Abstract 817.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., The pros and cons of immunomodulatory IL-10 gene therapy with recombinant AAV in a Cftr-/- -dependent allergy mouse model. Gene Ther. Feb. 2009;16(2):172-83. Epub Sep. 25, 2008.
Mueller et al., Using rAAV Delivered miRNAs To Knockdown Misfolded Human Alpha 1 Antitrypsin in a Transgenic Mouse Model. Molecular Therapy May 2010;18(1):S21. Abstract 51.
NCBI BLAST Protein Sequence. RID-09JSKF33114. Alignment of Seq ID Nos. 87, 179. 2016.
O'Reilly et al., RNA interference-mediated suppression and replacement of human rhodopsin in vivo. Am J Hum Genet. Jul. 2007;81(1):127-35. Epub May 23, 2007.
Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.
Scallan et al., Human immunoglobulin inhibits liver transduction by AAV vectors at low AAV2 neutralizing titers in SCID mice. Blood. Mar. 1, 2006;107(5):1810-7. Epub Oct. 25, 2005.
Schattgen et al., Cutting Edge: DNA in the Lung Microenvironment during Influenza Virus Infection Tempers Inflammation by Engaging the DNA Sensor AIM2. J Immunol. Jan. 1, 2016;196(1):29-33. doi:10.4049/jimmunol.1501048.
Schnepp et al., Characterization of adeno-associated virus genomes isolated from human tissues. J Virol. Dec. 2005;79(23):14793-803.
Seiler et al., Adeno-associated virus types 5 and 6 use distinct receptors for cell entry. Hum Gene Ther. Jan. 2006;17(1):10-9.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Sondhi et al., Enhanced survival of the LINCL mouse following CLN2 gene transfer using the rh.10 rhesus macaque-derived adeno-associated virus vector. Mol Ther. Mar. 2007;15(3):481-91. Epub Dec. 19, 2006.
Song et al., Intramuscular administration of recombinant adeno-associated virus 2 alpha-1 antitrypsin (rAAV-SERPINA1) vectors in a nonhuman primate model: safety and immunologic aspects. Mol Ther. Sep. 2002;6(3):329-35.
Stoica et al., Targeting Human SOD1 Using AAV mediated RNAi in a mouse model of amyotrophic lateral sclerosis. Mol ther. Jun. 2013;21(1):S149.
Storek et al., Intrathecal long-term gene expression by self-complementary adeno-associated virus type 1 suitable for chronic pain studies in rats. Mol Pain. Jan. 30, 2006;2:4.
Storkebaum et al., Treatment of motoneuron degeneration by intracerebroventricular delivery of VEGF in a rat model of ALS. Nat Neurosci. Jan. 2005;8(1):85-92. Epub Nov. 28, 2004.

(56) References Cited

OTHER PUBLICATIONS

Tenenbaum et al., Recombinant AAV-mediated gene delivery to the central nervous system. J Gene Med. Feb. 2004;6 Suppl 1:S212-22.
Tomar et al., Use of adeno-associated viral vector for delivery of small interfering RNA. Oncogene. Aug. 28, 2003;22(36):5712-5.
Towne et al., Systemic AAV6 delivery mediating RNA interference against SOD1: neuromuscular transduction does not alter disease progression in fALS mice. Mol Ther. Jun. 2008;16(6):1018-25. doi:10.1038/mt.2008.73. Epub Apr. 15, 2008.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
UNIPROT Submission; Accession No. A8IGP7; Nov. 13, 2013.
UNIPROT Submission; Accession No. H3GK32; Feb. 6, 2013.
UNIPROT Submission; Accession No. T2BRA8; Nov. 13, 2013.
Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.
Virella-Lowell et al., Enhancing rAAV vector expression in the lung. J Gene Med. Jul. 2005;7(7):842-50.
Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.
Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.
Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.
Wang et al., Somatically Repairing Compound Heterozygous Recessive Mutations by Chromosomal Cut-and-Paste for in Vivo Gene Therapy. May 2016. 24(1):S289. Abstract 733.
Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.
Wang et al., The design of vectors for RNAi delivery system. Curr Pharm Des. 2008;14(13):1327-40.
Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.
Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.
Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.

Watson et al., Intrathecal administration of AAV vectors for the treatment of lysosomal storage in the brains of MPS I mice. Gene Ther. Jun. 2006;13(11):917-25.
Wein et al., Efficient bypass of mutations in dysferlin deficient patient cells by antisense-induced exon skipping. Hum Mutat. Feb. 2010;31(2): 136-42. doi: 10.1002/humu.21160.
Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.
Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.
Wu et al., Alpha2,3 and alpha2,6 N-linked sialic acids facilitate efficient binding and transduction by adeno-associated virus types 1 and 6. J Virol. Sep. 2006;80(18):9093-103.
Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.
XIE et al., Characterization of positioning effect of pol III-shRNA transcription unit in scAAV vector genome on the packaging efficiency and functionality of shRNA silencing. Molecular Therapy. May 2010;18(1): S262. Abstract 671.
Xie et al., MicroRNA regulated tissue specific transduction by rAAV vector. Molecular Therapy. May 2009;17(1): S279. Abstract 732.
Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.
Xie et al., rAAV-mediated delivery of micro RNA scavengers leads to efficient and stable knock-down of cognate micro RNAs, upregulation of their natural target genes and phenotypic changes in mice. Molecular Therapy. May 2010;18(1): S140. Abstract 362.
Xu et al., Delivery of MDR1 small interfering RNA by self-complementary recombinant adeno-associated virus vector. Mol Ther. Apr. 2005;11(4):523-30.
Yan et al., Unique biologic properties of recombinant AAV1 transduction in polarized human airway epithelia. J Biol Chem. Oct. 6, 2006;281(40):29684-92. Epub Aug. 9, 2006.
Zabner et al., Adeno-associated virus type 5 (AAV5) but not AAV2 binds to the apical surfaces of airway epithelia and facilitates gene transfer. J Virol. Apr. 2000;74(8):3852-8.
Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.
Zhong et al., Chimpanzee-derived novel natural variants of aav9: vector development and interrogation of correlations between capsid structure and vector biology. Molecular Therapy. May 2010;18(1): S24. Abstract 58.
Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.
Zolotukhin et al., Production and purification of serotype 1, 2, and 5 recombinant adeno-associated viral vectors. Methods. Oct. 2002;28(2):158-67.

* cited by examiner

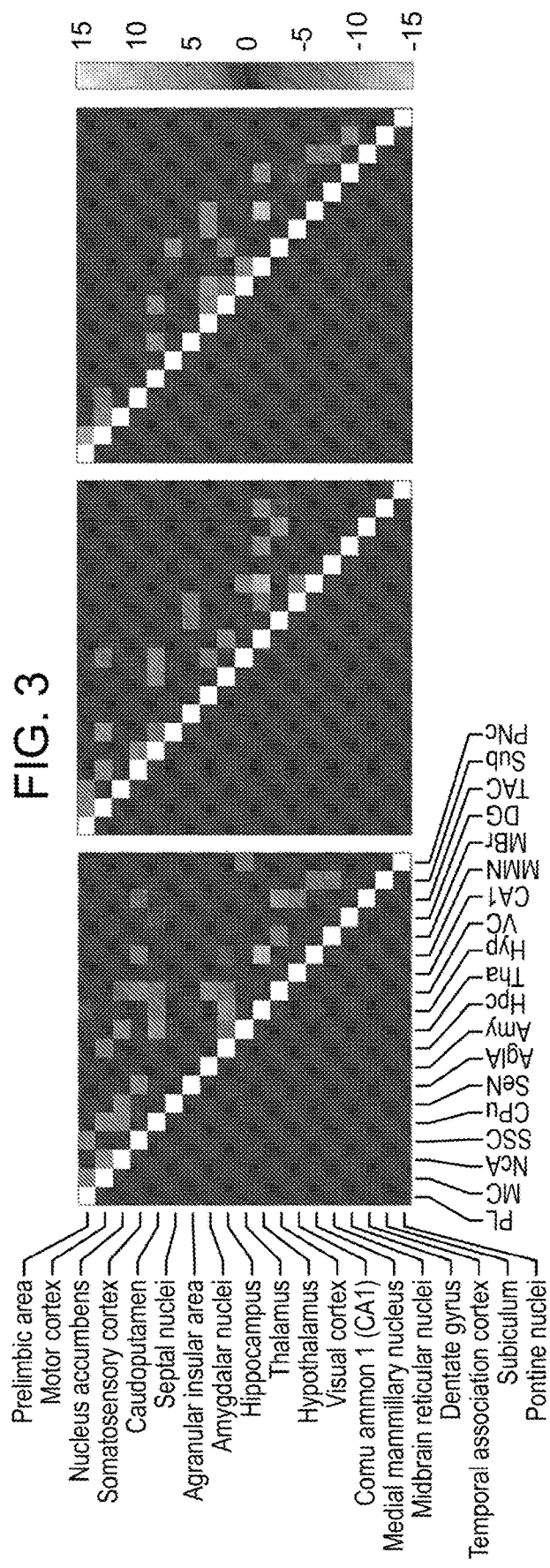
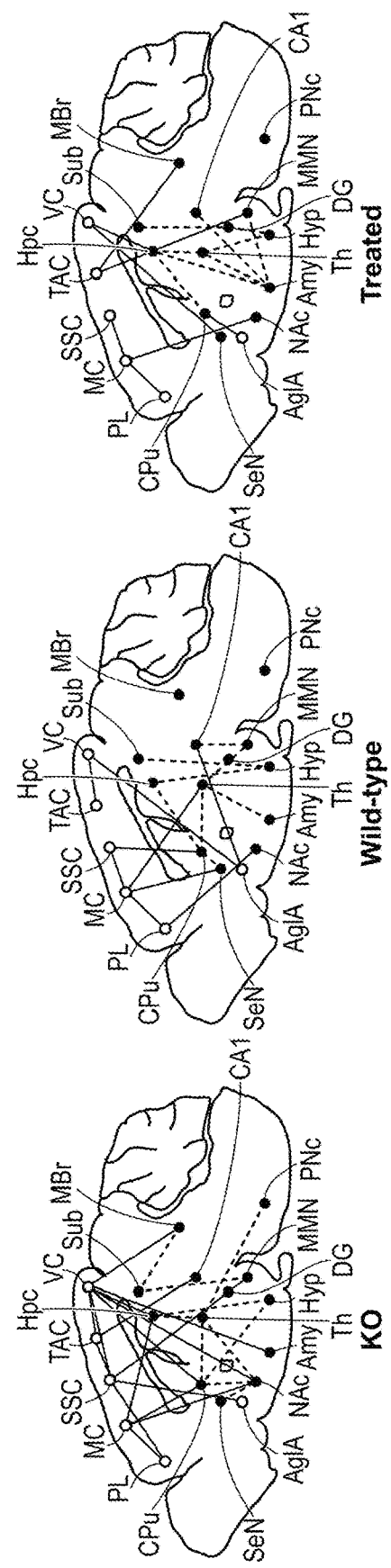
FIG. 3

* $p<0.05$;  $p<0.01$; * $p<0.001$; **** $p<0.0001$

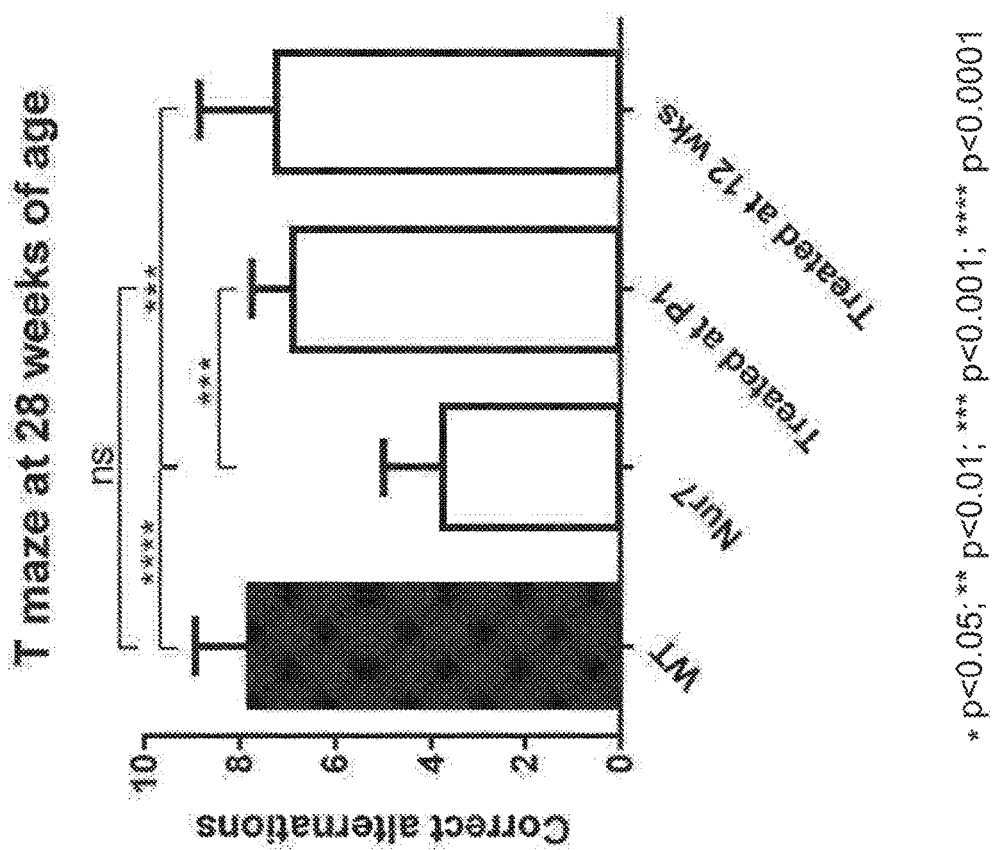
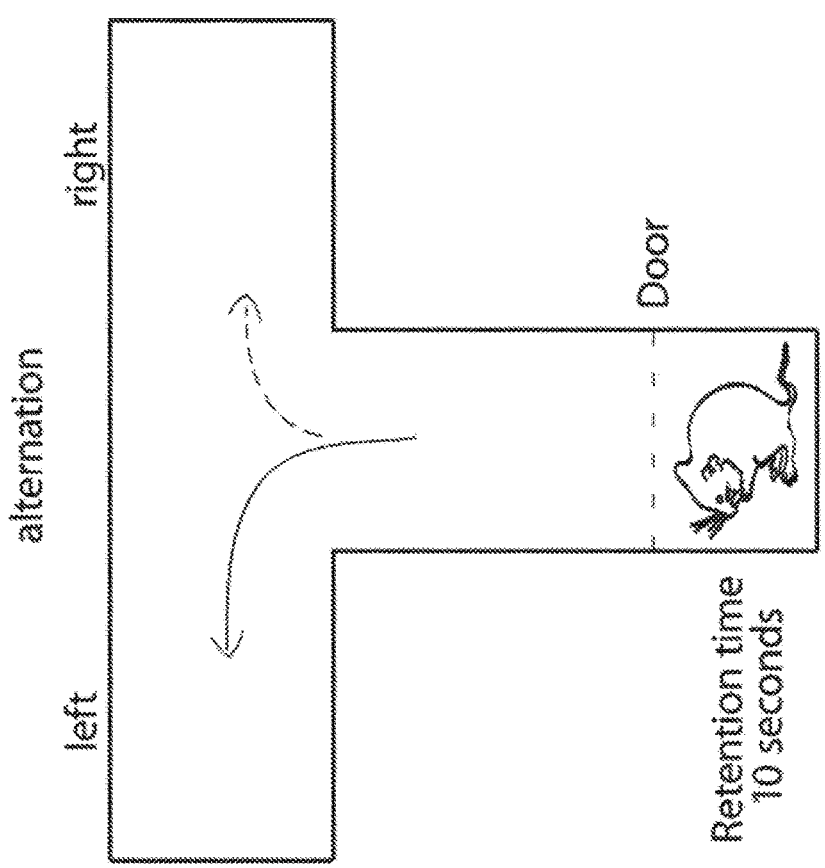
FIG. 10

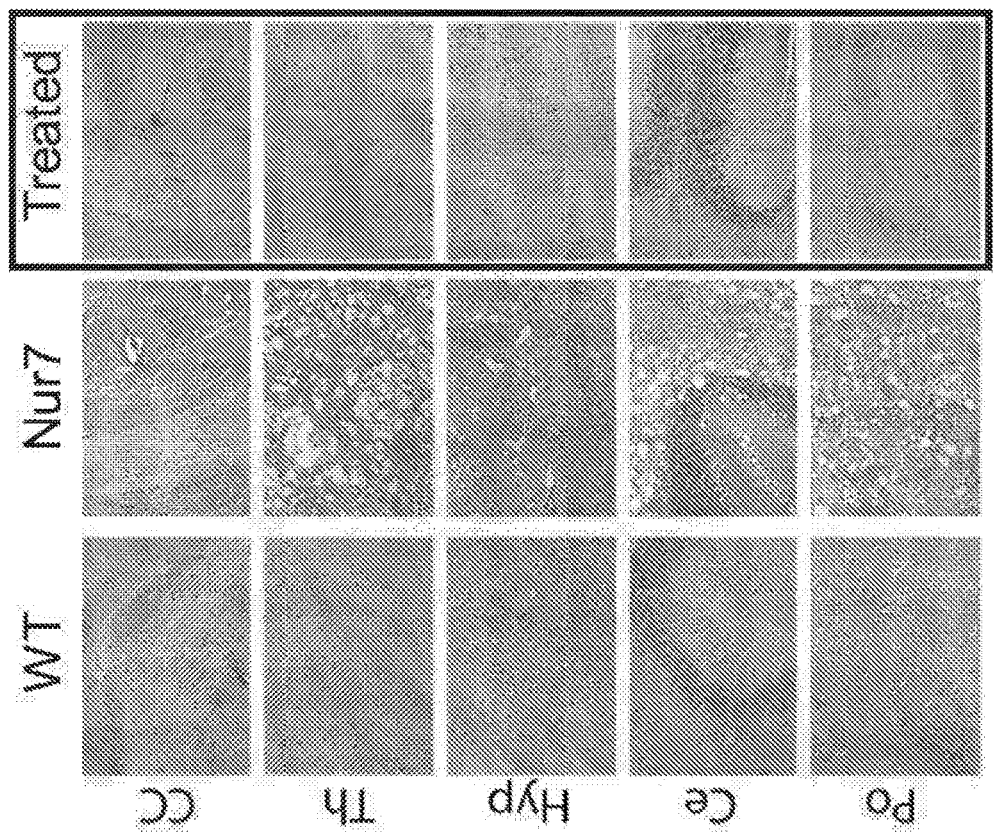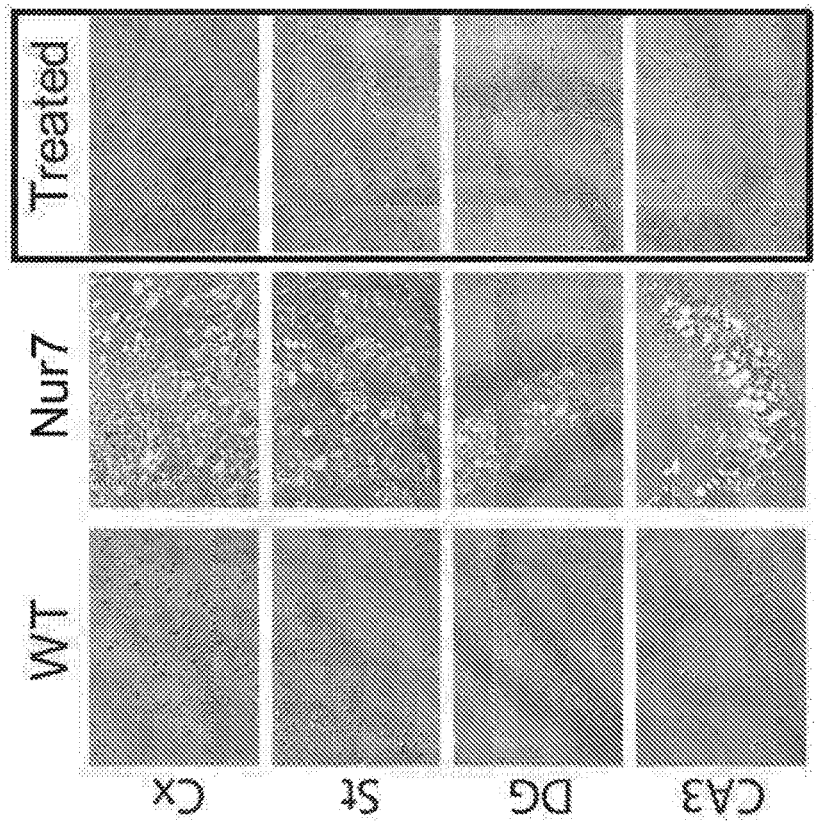
Neuropathology at postnatal day 25
FIG. 11

| sphingomyelins | KO/WT | rAAV (Tx/Ctrl) |
|---|---|---|
| palmitoyl sphingomyelin (d18:1/16:0) | 0.59 | 1.22 |
| stearoyl sphingomyelin (d18:1/18:0) | 0.84 | 1.16 |
| sphingomyelin (d18:1/18:1, d18:2/18:0) | 0.97 | 1.05 |
| sphingomyelin (d18:1/14:0, d16:1/16:0)* | 0.5 | 1.01 |
| sphingomyelin (d18:1/24:1, d18:2/24:0)* | 0.56 | 1.95 |
| sphingomyelin (d18:2/16:0, d18:1/16:1)* | 0.47 | 0.82 |
| sphingomyelin (d18:1/20:1, d18:2/20:0)* | 0.82 | 0.87 |
| behenoyl sphingomyelin (d18:1/22:0)* | 0.56 | 1.56 |
| sphingomyelin (d18:1/22:1, d18:2/22:0, d | 0.59 | 1.62 |
| sphingomyelin (d18:1/20:0, d16:1/22:0)* | 0.9 | 1.09 |
| palmitoyl dihydrosphingomyelin (d18:0/16 | 0.37 | 2.09 |
| sphingomyelin (d18:1/15:0, d16:1/17:0)* | 0.26 | 0.95 |
| sphingomyelin (d18:1/21:0, d17:1/22:0, d | 0.6 | 1.19 |
| sphingomyelin (d18:2/23:0, d18:1/23:1, d | 0.6 | 1.79 |
| sphingomyelin (d18:2/24:1, d18:1/24:2)* | 0.76 | 1.38 |
| tricosanoyl sphingomyelin (d18:1/23:0)* | 0.83 | 0.87 |
| sphingomyelin (d18:1/17:0, d17:1/18:0,d | 0.72 | 1.28 |

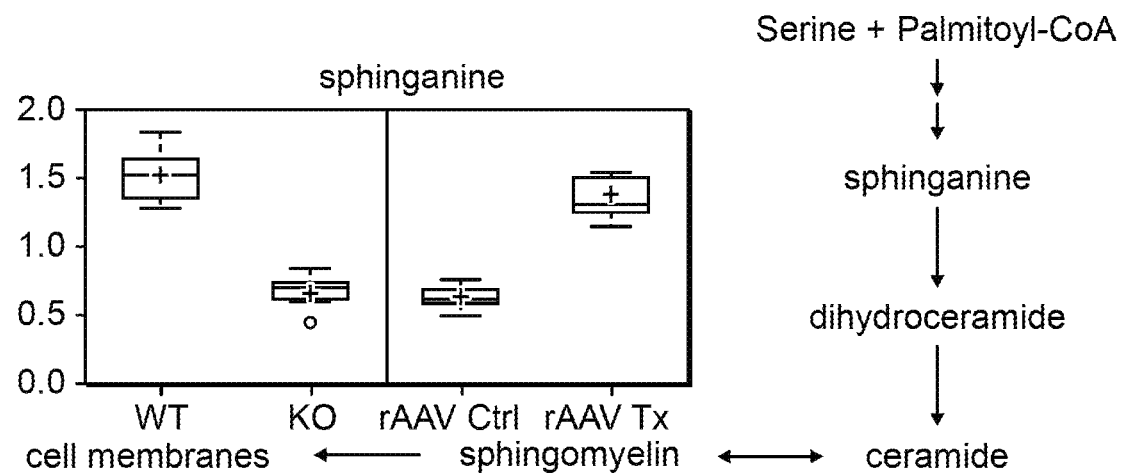

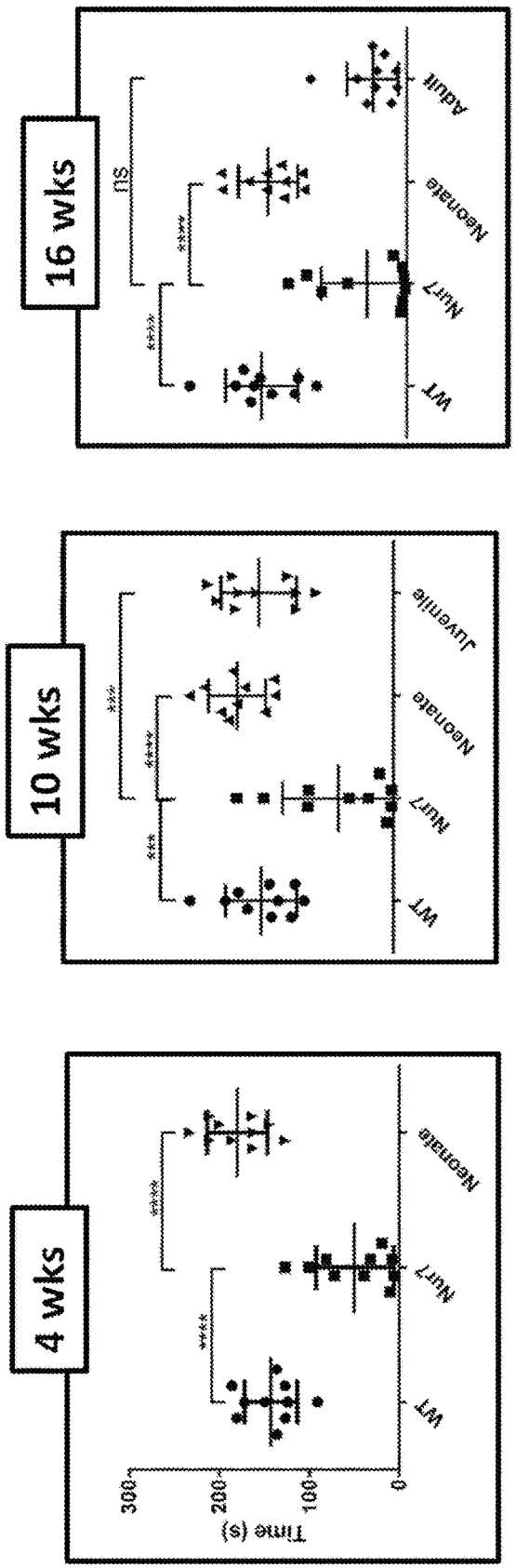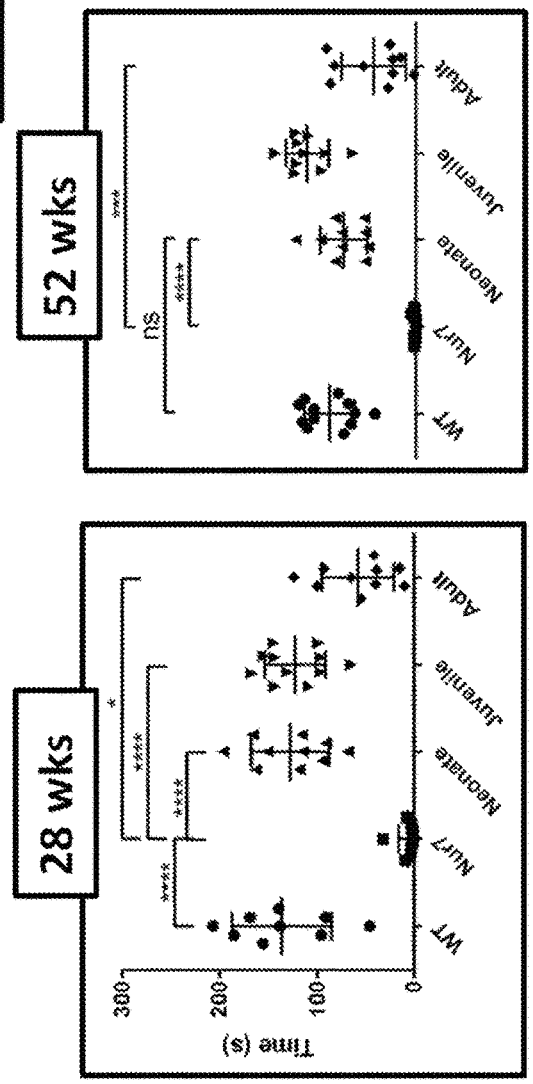
FIG. 46

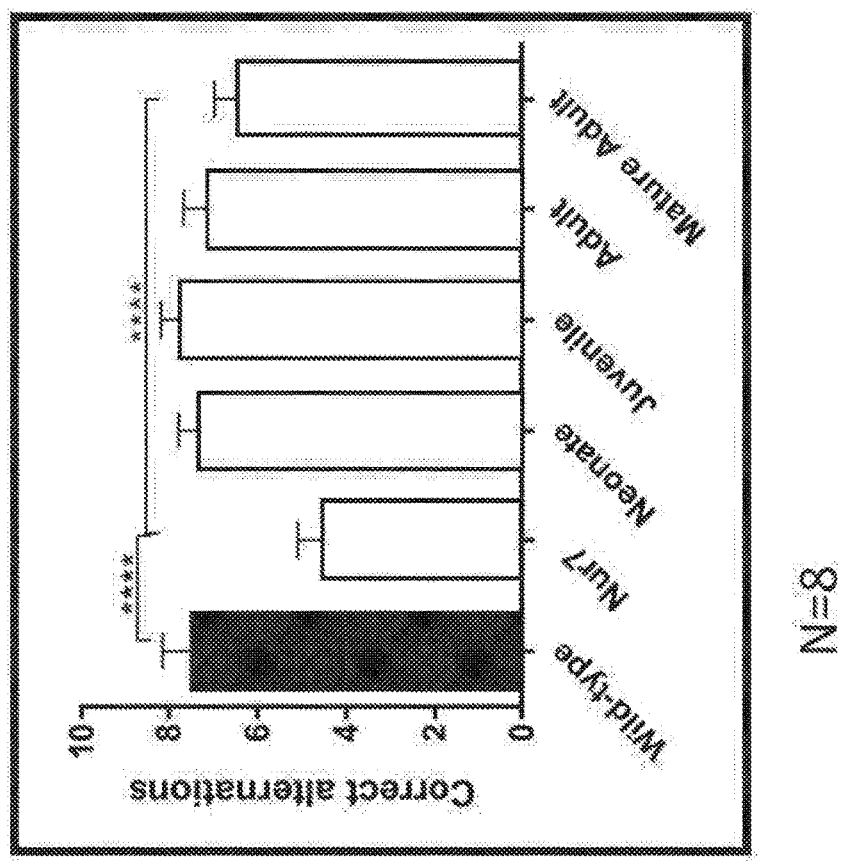
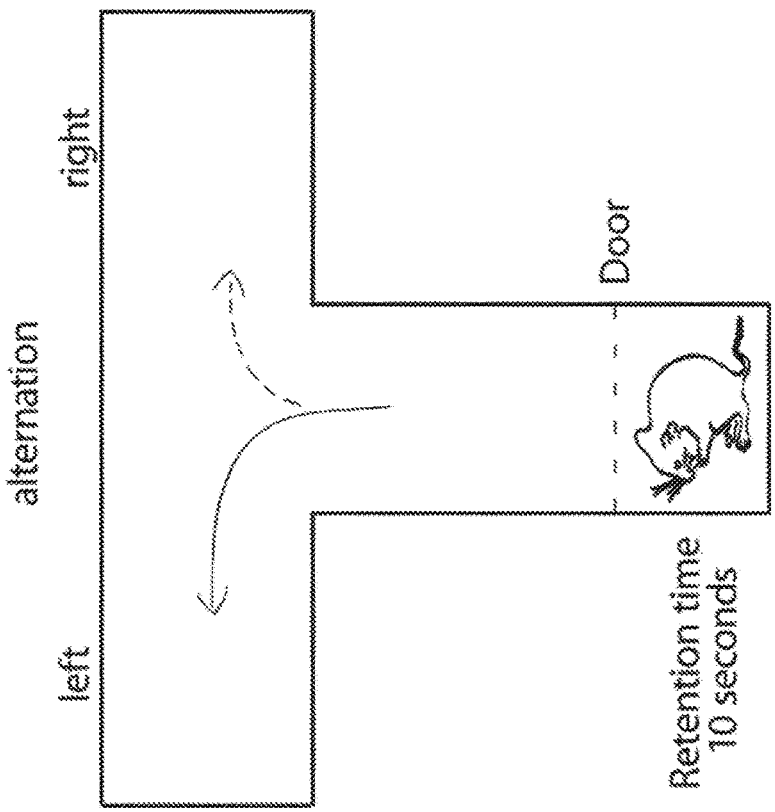
FIG. 48

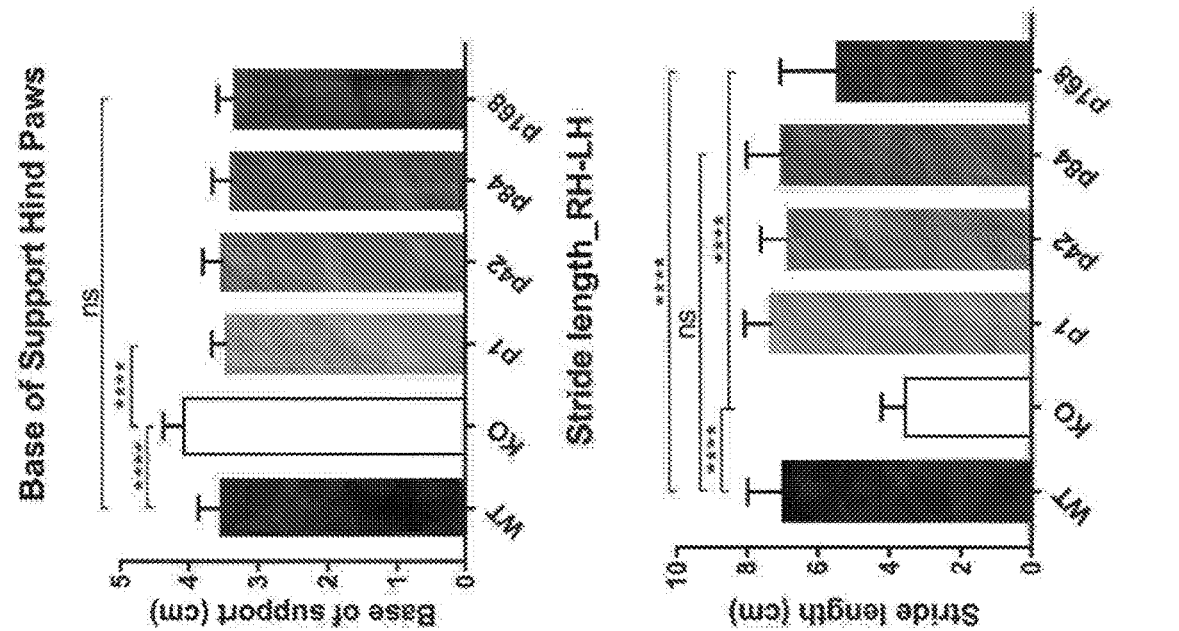
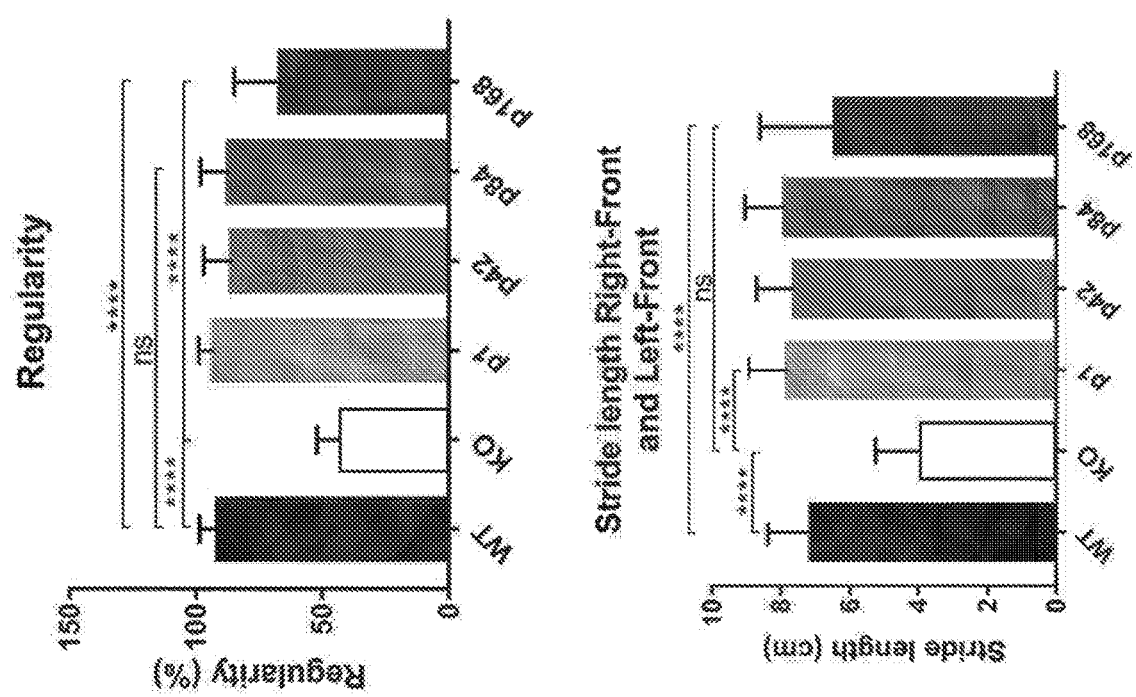
FIG. 50

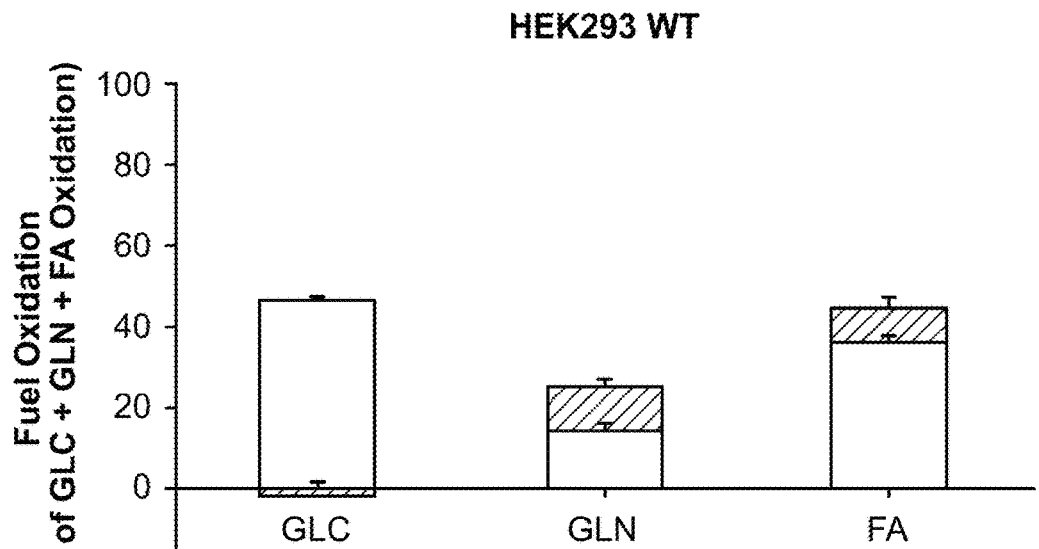
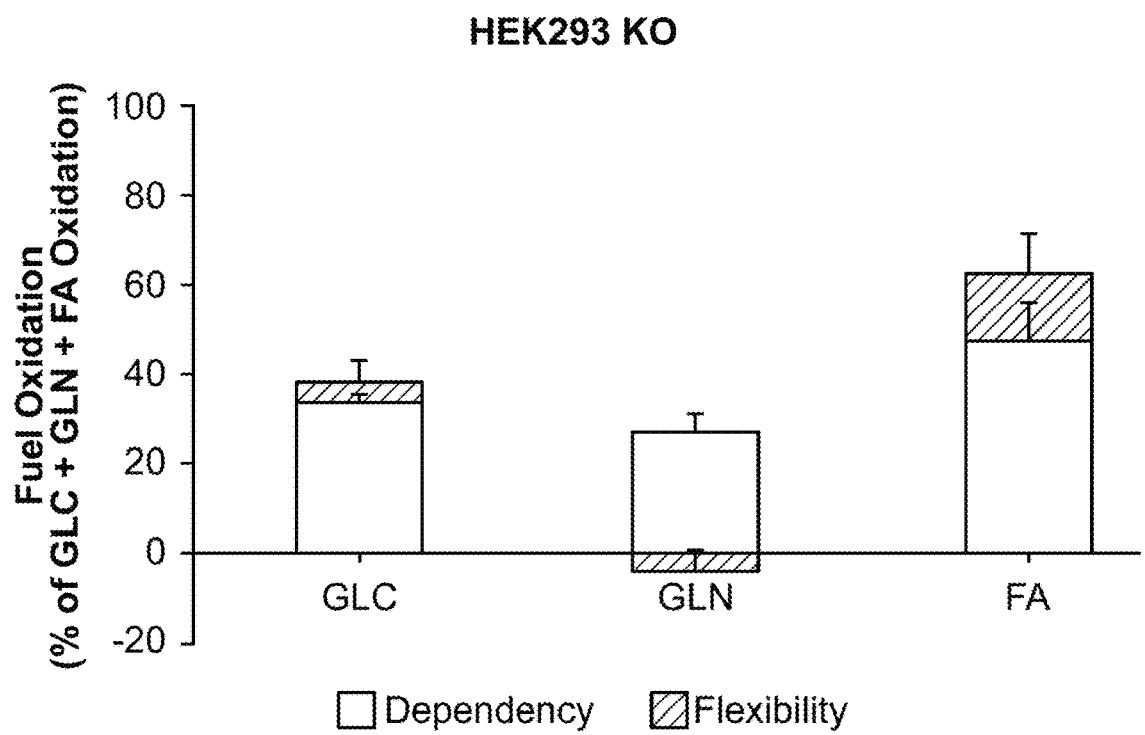
FIG. 53

| Pathway Sort Order | Super Pathway | Sub Pathway | Biochemical Name | Platform | Comp ID | KEGG | HMDB | PubChem |
|---|---|---|---|---|---|---|---|---|
| 1 | | | glycine | LC/MS pos early | 58 | C00037 | HMDB00123 | 750 |
| 2 | | | N-acetylglycine | LC/MS pos early | 27710 | | HMDB00532 | 10972 |
| 5 | | | dimethylglycine | LC/MS pos early | 5086 | C01026 | HMDB00092 | 673 |
| 6 | | | betaine | LC/MS pos early | 3141 | C00719 | HMDB00043 | 247 |
| 7 | | Glycine, Serine and Threonine Metabolism | betaine aldehyde | LC/MS pos early | 15499 | C00576 | HMDB01252 | 249 |
| 9 | | | serine | LC/MS pos early | 1648 | C00065 | HMDB00187 | 5951 |
| 10 | | | N-acetylserine | LC/MS pos early | 37076 | | HMDB02931 | 65249 |
| 14 | | | threonine | LC/MS pos early | 1284 | C00188 | HMDB00167 | 6288 |
| 15 | | | N-acetylthreonine | LC/MS neg | 33939 | | | 152204 |
| 16 | | | allo-threonine | LC/MS polar | 15142 | C05519 | HMDB04041 | 99289 |
| 18 | | | homoserine | LC/MS polar | 18351 | C00263 | HMDB00719 | 12647 |
| 25 | | | alanine | LC/MS pos early | 1126 | C00041 | HMDB00161 | 5950 |
| 26 | | | N-acetylalanine | LC/MS polar | 1585 | C02847 | HMDB00766 | 88064 |
| 28 | | Alanine and Aspartate Metabolism | aspartate | LC/MS pos early | 443 | C00049 | HMDB00191 | 5960 |

FIG. 57

| | | | | | | |
|---|---|---|---|---|---|---|
| 30 | | asparagine | LC/MS pos early | 512 | C00152 | HMDB00168 | 6267 |
| 32 | | N-acetylaspartate (NAA) | LC/MS neg | 22185 | C01042 | HMDB00812 | 65065 |
| 39 | | glutamate | LC/MS pos early | 57 | C00025 | HMDB00148 | 611 |
| 40 | | glutamine | LC/MS pos early | 53 | C00064 | HMDB00641 | 5961 |
| 41 | | N-acetylglutamate | LC/MS pos early | 15720 | C00624 | HMDB01138 | 70914 |
| 42 | Glutamate Metabolism | N-acetylglutamine | LC/MS pos early | 33943 | C02716 | HMDB06029 | 182230 |
| 43 | | N-acetyl-aspartyl-glutamate (NAAG) | LC/MS pos early | 35665 | C12270 | HMDB01067 | 5255 |
| 44 | | gamma-aminobutyrate (GABA) | LC/MS pos early | 1416 | C00334 | HMDB00112 | 119 |
| 51 | | pyroglutamine* | LC/MS pos early | 46225 | | | 134508 |
| 56 | | histidine | LC/MS neg | 59 | C00135 | HMDB00177 | 6274 |
| 57 | | N-acetylhistidine | LC/MS pos early | 33946 | C02997 | HMDB32055 | 75619 |
| 58 | | 1-methylhistidine | LC/MS pos early | 30460 | C01152 | HMDB00001 | 92105 |
| 59 | | 3-methylhistidine | LC/MS pos early | 15677 | C01152 | HMDB00479 | 64969 |
| 67 | Histidine Metabolism | imidazole propionate | LC/MS pos early | 40730 | | HMDB02271 | 70630 |
| 68 | | imidazole lactate | LC/MS pos early | 15716 | C05568 | HMDB02320 | 440129 |
| 70 | | 1-methylhistamine | LC/MS pos early | 43831 | C05127 | HMDB00898 | 3614 |
| 74 | | 1-methylimidazoleacetate | LC/MS pos early | 32350 | C05828 | HMDB02820 | 75810 |

FIG. 57 cont.

| | | | | | |
|---|---|---|---|---|---|
| 75 | | 4-imidazoleacetate | LC/MS pos early | 32349 | C02835 | HMDB02024 | 96215 |
| 78 | | lysine | LC/MS pos early | 1301 | C00047 | HMDB00182 | 5962 |
| 80 | | N6-acetyllysine | LC/MS neg | 36752 | C02727 | HMDB00206 | 92832 |
| 82 | | N6,N6,N6-trimethyllysine | LC/MS pos early | 1498 | C03793 | HMDB01325 | 440120 |
| 84 | Lysine Metabolism | saccharopine | LC/MS polar | 1495 | C00449 | HMDB00279 | 160556 |
| 85 | | 2-aminoadipate | LC/MS polar | 6146 | C00956 | HMDB00510 | 469 |
| 88 | | glutarate (pentanedioate) | LC/MS polar | 396 | C00489 | HMDB00661 | 743 |
| 89 | | glutarylcarnitine (C5) | LC/MS pos early | 44664 | | HMDB13130 | 71464488 |
| 96 | | pipecolate | LC/MS pos early | 1444 | C00408 | HMDB00070 | 849 |
| 106 | | phenylalanine | LC/MS pos early | 64 | C00079 | HMDB00159 | 6140 |
| 107 | | N-acetylphenylalanine | LC/MS neg | 33950 | C03519 | HMDB00512 | 74839 |
| 111 | | phenyllactate (PLA) | LC/MS polar | 22130 | C05607 | HMDB00779 | 3848 |
| 119 | | tyrosine | LC/MS pos early | 1299 | C00082 | HMDB00158 | 6057 |
| 120 | Phenylalanine and Tyrosine Metabolism | N-acetyltyrosine | LC/MS neg | 32390 | | HMDB00866 | 68310 |
| 130 | | 3-(4-hydroxyphenyl)lactate | LC/MS neg | 32197 | C03672 | HMDB00755 | 9378 |
| 135 | | phenol sulfate | LC/MS neg | 32553 | C02180 | HMDB60015 | 74426 |
| 138 | | p-cresol sulfate | LC/MS neg | 36103 | C01468 | HMDB11635 | 4615423 |

FIG. 57 cont.

| | | | | | | |
|---|---|---|---|---|---|---|
| 158 | | homovanillate (HVA) | LC/MS neg | 1101 | C05582 | HMDB00118 | 1738 |
| 172 | | O-methyltyrosine | LC/MS pos early | 37451 | | | 76957 |
| 209 | | tryptophan | LC/MS pos early | 54 | C00078 | HMDB00929 | 6305 |
| 213 | | indolelactate | LC/MS neg | 18349 | C02043 | HMDB00671 | 92904 |
| 218 | | 3-indoxyl sulfate | LC/MS neg | 27672 | | HMDB00682 | 10258 |
| 219 | Tryptophan Metabolism | kynurenine | LC/MS pos early | 15140 | C00328 | HMDB00684 | 161166 |
| 234 | | 5-hydroxyindoleacetate | LC/MS pos early | 437 | C05635 | HMDB00763 | 1826 |
| 235 | | serotonin | LC/MS pos early | 2342 | C00780 | HMDB00259 | 5202 |
| 250 | | C-glycosyltryptophan | LC/MS pos early | 48782 | | | 10981970 |
| 255 | | leucine | LC/MS neg | 60 | C00123 | HMDB00687 | 6106 |
| 256 | | N-acetylleucine | LC/MS neg | 1587 | C02710 | HMDB11756 | 70912 |
| 263 | | isovalerylcarnitine | LC/MS pos early | 34407 | | | 6426851 |
| 266 | | beta-hydroxyisovalerate | LC/MS polar | 12129 | | HMDB00754 | 69362 |
| 274 | | alpha-hydroxyisovalerate | LC/MS polar | 46537 | | HMDB00407 | 99823 |
| 276 | | methylsuccinate | LC/MS polar | 15745 | | HMDB01844 | 10349 |
| 284 | Amino Acid | isoleucine | LC/MS neg | 1125 | C00407 | HMDB00172 | 6306 |
| 286 | Leucine, Isoleucine and Valine | N-acetylisoleucine | LC/MS neg | 33967 | | | 2802421 |

FIG. 57 cont.

| ID | Pathway | Metabolite | Platform | | KEGG | HMDB | |
|---|---|---|---|---|---|---|---|
| 288 | Metabolism | 2-methylbutyrylcarnitine (C5) | LC/MS pos early | 45095 | | HMDB00378 | 6426901 |
| 290 | | tiglylcarnitine | LC/MS pos early | 35428 | | HMDB02366 | 22833596 |
| 293 | | 2-hydroxy-3-methylvalerate | LC/MS neg | 36746 | | HMDB00317 | 164623 |
| 295 | | ethylmalonate | LC/MS polar | 15765 | | HMDB00622 | 11756 |
| 296 | | valine | LC/MS pos early | 1649 | C00183 | HMDB00883 | 6287 |
| 297 | | N-acetylvaline | LC/MS neg | 1591 | | HMDB11757 | 66789 |
| 300 | | isobutyrylcarnitine | LC/MS pos early | 33441 | | HMDB00736 | 168379 |
| 302 | | 3-hydroxyisobutyrate | LC/MS polar | 1549 | C06001 | HMDB00336 | 87 |
| 312 | | methionine | LC/MS pos early | 1302 | C00073 | HMDB00696 | 6137 |
| 313 | | N-acetylmethionine | LC/MS neg | 1589 | C02712 | HMDB11745 | 448580 |
| 314 | | N-formylmethionine | LC/MS neg | 2829 | C03145 | HMDB01015 | 439750 |
| 317 | | methionine sulfoxide | LC/MS pos early | 18374 | C02989 | HMDB02005 | 158980 |
| 318 | | N-acetylmethionine sulfoxide | LC/MS pos early | 45428 | | | 193368 |
| 319 | | S-adenosylmethionine (SAM) | LC/MS neg | 15915 | C00019 | HMDB01185 | 34755 |
| 320 | | S-adenosylhomocysteine (SAH) | LC/MS neg | 42382 | C00021 | HMDB00939 | 439155 |
| 324 | Methionine, Cysteine, SAM and Taurine Metabolism | cystathionine | LC/MS pos early | 15705 | C02291 | HMDB00099 | 439258 |
| 329 | | cysteine | LC/MS pos early | 1868 | C00097 | HMDB00574 | 5862 |

FIG. 57 cont.

| | | | | | | |
|---|---|---|---|---|---|---|
| 337 | | cysteine sulfinic acid | LC/MS pos early | 37443 | C00606 | HMDB00996 | 109 |
| 339 | | hypotaurine | LC/MS polar | 590 | C00519 | HMDB00965 | 107812 |
| 340 | | taurine | LC/MS neg | 2125 | C00245 | HMDB00251 | 1123 |
| 341 | | N-acetyltaurine | LC/MS polar | 48187 | | | 159864 |
| 346 | | taurocyamine | LC/MS pos early | 35117 | C01959 | HMDB03584 | 68340 |
| 347 | | 2-hydroxybutyrate/2-hydroxyisobutyrate | LC/MS polar | 52281 | | | |
| 348 | Urea cycle; Arginine and Proline Metabolism | arginine | LC/MS pos early | 1638 | C00062 | HMDB00517 | 232 |
| 349 | | urea | LC/MS pos early | 1670 | C00086 | HMDB00294 | 1176 |
| 351 | | ornithine | LC/MS pos early | 1493 | C00077 | HMDB03374 | 6262 |
| 352 | | proline | LC/MS pos early | 1898 | C00148 | HMDB00162 | 145742 |
| 353 | | citrulline | LC/MS pos early | 2132 | C00327 | HMDB00904 | 9750 |
| 354 | | argininosuccinate | LC/MS pos early | 15497 | C03406 | HMDB00052 | 16950,828 |
| 355 | | homoarginine | LC/MS pos early | 22137 | C01924 | HMDB00670 | 9085 |
| 356 | | homocitrulline | LC/MS pos early | 22138 | C02427 | HMDB00679 | 65072 |
| 360 | | dimethylarginine (SDMA + ADMA) | LC/MS pos early | 36808 | C03626 | HMDB01539 | 123831 |
| 361 | | N-acetylarginine | LC/MS pos early | 33953 | C02562 | HMDB04620 | 67427 |
| 364 | | N-delta-acetylornithine | LC/MS pos early | 43249 | | | 9920500 |

FIG. 57 cont.

| | | | | | | | |
|---|---|---|---|---|---|---|---|
| 370 | | trans-4-hydroxyproline | LC/MS pos early | 32306 | C01157 | HMDB00725 | 5810 |
| 372 | | pro-hydroxy-pro | LC/MS pos early | 35127 | | HMDB06695 | 11673055 |
| 373 | | N-monomethylarginine | LC/MS pos early | 43586 | C03884 | HMDB29416 | 132862 |
| 377 | Creatine Metabolism | creatine | LC/MS pos early | 27718 | C00300 | HMDB00064 | 586 |
| 378 | | creatinine | LC/MS pos early | 513 | C00791 | HMDB00562 | 588 |
| 380 | | creatine phosphate | LC/MS polar | 33951 | C02305 | HMDB01511 | 587 |
| 383 | | guanidinoacetate | LC/MS pos early | 43802 | C00581 | HMDB00128 | 763 |
| 387 | Polyamine Metabolism | putrescine | LC/MS pos early | 1408 | C00134 | HMDB01414 | 1045 |
| 388 | | spermine | LC/MS pos late | 603 | C00750 | HMDB01256 | 1103 |
| 390 | | spermidine | LC/MS pos early | 485 | C00315 | HMDB01257 | 1102 |
| 391 | | 5-methylthioadenosine (MTA) | LC/MS pos early | 1419 | C00170 | HMDB01173 | 439176 |
| 398 | Guanidino and Acetamido Metabolism | 1-methylguanidine | LC/MS pos early | 48114 | C02294 | HMDB01522 | 10111 |
| 400 | | 4-guanidinobutanoate | LC/MS pos early | 15681 | C01035 | HMDB03464 | 500 |
| 402 | | glutathione, reduced (GSH) | LC/MS pos early | 2127 | C00051 | HMDB00125 | 124886 |
| 403 | | glutathione, oxidized (GSSG) | LC/MS pos early | 38783 | C00127 | HMDB03337 | 65359 |
| 405 | | cysteine-glutathione disulfide | LC/MS pos early | 35159 | | HMDB00656 | 4247235 |
| 406 | | S-methylglutathione | LC/MS pos early | 33944 | C11347 | | 3605667 |

FIG. 57 cont.

| | | | | | | |
|---|---|---|---|---|---|---|
| 407 | Glutathione Metabolism | S-lactoylglutathione | LC/MS pos early | 15731 | C03451 | HMDB01066 | 440018 |
| 408 | | cysteinylglycine | LC/MS pos early | 35637 | C01419 | HMDB00078 | 439498 |
| 410 | | 5-oxoproline | LC/MS neg | 1494 | C01879 | HMDB00267 | 7405 |
| 411 | | ophthalmate | LC/MS pos early | 34592 | | HMDB05765 | 7018721 |
| 414 | | 4-hydroxy-nonenal-glutathione | LC/MS neg | 48487 | | | |
| 418 | Gamma-glutamyl Amino Acid | gamma-glutamylalanine | LC/MS pos early | 37063 | C03451 | HMDB29142 | 440103 |
| 420 | | gamma-glutamylglutamate | LC/MS pos early | 36738 | C05282 | HMDB11737 | 92865 |
| 421 | | gamma-glutamylglutamine | LC/MS pos early | 2730 | C05283 | HMDB11738 | 150914 |
| 422 | | gamma-glutamylglycine | LC/MS pos early | 33949 | | HMDB11667 | 165527 |
| 423 | | gamma-glutamylhistidine | LC/MS pos early | 18245 | | | 7017195 |
| 424 | | gamma-glutamylisoleucine* | LC/MS pos early | 34456 | | HMDB11170 | 14253342 |
| 425 | | gamma-glutamylleucine | LC/MS pos early | 18369 | | HMDB11171 | 151023 |
| 426 | | gamma-glutamyl-epsilon-lysine | LC/MS pos early | 33934 | | HMDB03869 | 65254;14284565 |
| 427 | | gamma-glutamylmethionine | LC/MS neg | 44872 | | HMDB29155 | 7009567 |
| 428 | | gamma-glutamylphenylalanine | LC/MS pos early | 33422 | | HMDB00594 | 111299 |
| 431 | | gamma-glutamyltyrosine | LC/MS neg | 2734 | | HMDB11741 | 94340 |

FIG. 57 cont.

| | | | | | | |
|---|---|---|---|---|---|---|
| 432 | Peptide | gamma-glutamylvaline | LC/MS pos early | 43829 | | 7015683 |
| 434 | | carnosine | LC/MS pos early | 1768 | C00386 | HMDB00033 | 439224 |
| 436 | Dipeptide Derivative | homocarnosine | LC/MS polar | 1633 | C00884 | HMDB00745 | 10243361 |
| 437 | | anserine | LC/MS pos early | 15747 | C01262 | HMDB00194 | 112072 |
| 560 | | glycylleucine | LC/MS pos early | 34398 | C02155 | HMDB00759 | 92843 |
| 570 | | glycylvaline | LC/MS pos early | 18357 | | HMDB28854 | 97417 |
| 594 | | isoleucylglycine | LC/MS pos early | 40008 | | | 342532 |
| 612 | Dipeptide | leucylglycine | LC/MS pos early | 40045 | | | 79070 |
| 660 | | phenylalanylalanine | LC/MS pos early | 41374 | | | 6993123;548819 6 |
| 664 | | phenylalanylglycine | LC/MS pos early | 41370 | | | 98207 |
| 681 | | prolylglycine | LC/MS pos early | 40703 | | | 7408076;642670 9 |
| 760 | | valylglycine | LC/MS pos early | 40475 | | | 136487 |
| 820 | | 1,5-anhydroglucitol (1,5-AG) | LC/MS neg | 20675 | C07326 | HMDB02712 | 64960 |
| 823 | | glucose | LC/MS polar | 20488 | C00031 | HMDB00122 | 79025 |
| 824 | | glucose 6-phosphate | LC/MS polar | 31260 | C00668 | HMDB01401 | 5958 |
| 830 | | Isobar: fructose 1,6-diphosphate, glucose 1,6-diphosphate, myo-inositol 1,4 or 1,3-diphosphate | LC/MS neg | 46896 | | | |

FIG. 57 cont.

| | | | | | | |
|---|---|---|---|---|---|---|
| | Glycolysis, Gluconeogenesis, and Pyruvate Metabolism | | | | | |
| 832 | | dihydroxyacetone phosphate (DHAP) | LC/MS neg | 15522 | C00111 | HMDB01473 | 668 |
| 837 | | 3-phosphoglycerate | LC/MS neg | 1414 | C00597 | HMDB00807 | 724 |
| 838 | | phosphoenolpyruvate (PEP) | LC/MS neg | 597 | C00074 | HMDB00263 | 1005 |
| 839 | | pyruvate | LC/MS polar | 22250 | C00022 | HMDB00243 | 1060 |
| 840 | | lactate | LC/MS polar | 527 | C00186 | HMDB00190 | 612 |
| 843 | | glycerate | LC/MS polar | 1572 | C00258 | HMDB00139 | 752 |
| 846 | Pentose Phosphate Pathway | 6-phosphogluconate | LC/MS neg | 15442 | C00345 | HMDB01316 | 91493 |
| 849 | | ribose 1-phosphate | LC/MS polar | 1763 | C00620 | HMDB01489 | 439236 |
| 851 | | sedoheptulose-7-phosphate | LC/MS neg | 35649 | C05382 | HMDB01068 | 616 |
| 857 | | ribose | LC/MS polar | 1471 | C00121 | HMDB00283 | 5779 |
| 858 | | ribitol | LC/MS polar | 15772 | C00474 | HMDB00508 | 6912 |
| 859 | Pentose Metabolism | ribonate | LC/MS polar | 27731 | C01685 | HMDB00867 | 5460677 |
| 880 | | arabitol/xylitol | LC/MS polar | 48885 | | | |
| 882 | | arabonate/xylonate | LC/MS polar | 48255 | C02052 | | |
| 886 | Glycogen Metabolism | maltotetraose | LC/MS neg | 15910 | C02052 | HMDB01296 | 446495 |
| 888 | | maltotriose | LC/MS neg | 44688 | C01835 | HMDB01262 | 439586 |

FIG. 57 cont.

| | | | | | |
|---|---|---|---|---|---|
| | | maltose | LC/MS polar | 15586 | C00208 | HMDB00163 | 10991489 |
| 891 | | fructose | LC/MS polar | 577 | C00095 | HMDB00660 | 5984 |
| 927 | Fructose, Mannose and Galactose Metabolism | mannitol/sorbitol | LC/MS polar | 46142 | C01507 | HMDB00247 | 5780 |
| 932 | | mannose | LC/MS polar | 584 | C00159 | HMDB00169 | 18950 |
| 933 | | galactonate | LC/MS polar | 27719 | C00880 | HMDB00565 | 128869 |
| 951 | | UDP-glucose | LC/MS polar | 32344 | C00029 | HMDB00286 | 8629 |
| 955 | | UDP-galactose | LC/MS polar | 15860 | C00052 | HMDB00302 | 18068 |
| 959 | | UDP-glucuronate | LC/MS neg | 2763 | C00167 | HMDB00935 | 17473 |
| 960 | Nucleotide Sugar | guanosine 5'-diphospho-fucose | LC/MS neg | 15903 | | | |
| 962 | | UDP-N-acetylglucosamine | LC/MS polar | 35162 | C00043 | HMDB00290 | 445675 |
| 964 | | UDP-N-acetylgalactosamine | LC/MS polar | 18396 | C00203 | HMDB00304 | 439185 |
| 965 | | cytidine 5'-monophospho-N-acetylneuraminic acid | LC/MS polar | 36831 | C00128 | HMDB01176 | 448209 |
| 967 | | glucosamine-6-phosphate | LC/MS polar | 580 | C00352 | HMDB01254 | 439217 |
| 973 | Aminosugar Metabolism | N-acetylglucosamine 6-phosphate | LC/MS polar | 15107 | C00357 | HMDB02817 | 439219 |
| 981 | | N-acetylneuraminate | LC/MS polar | 32377 | C00270 | HMDB00230 | 439197 |
| 988 | | erythronate* | LC/MS polar | 42420 | | HMDB00613 | 2781043 |
| 1000 | | | | | | | |

FIG. 57 cont.

| | | | | | |
|---|---|---|---|---|---|
| 1003 | Advanced Glycation End-product | N6-carboxymethyllysine | LC/MS pos early | 36713 | | |
| 1007 | | citrate | LC/MS neg | 1564 | C00158 | HMDB00094 | 311 |
| 1009 | | aconitate [cis or trans] | LC/MS neg | 46173 | C00417 | HMDB00072 | |
| 1011 | | isocitrate | LC/MS pos early | 12110 | C00311 | HMDB00193 | 1198 |
| 1012 | | alpha-ketoglutarate | LC/MS polar | 528 | C00026 | HMDB00208 | 51 |
| 1014 | TCA Cycle | succinylcarnitine | LC/MS pos early | 37058 | | | |
| 1016 | | fumarate | LC/MS polar | 1643 | C00122 | | 444972 |
| 1017 | | malate | LC/MS polar | 1303 | C00149 | HMDB00134 | 525 |
| 1027 | | 2-methylcitrate/homocitrate | LC/MS neg | 52282 | | HMDB00156 | |
| 1028 | | acetylphosphate | LC/MS polar | 15488 | C00227 | HMDB01494 | 186 |
| 1030 | Oxidative Phosphorylation | phosphate | LC/MS neg | 42109 | C00009 | HMDB01429 | 1061 |
| 1032 | | caproate (6:0) | LC/MS neg | 32489 | C01585 | HMDB00535 | 8892 |
| 1033 | | heptanoate (7:0) | LC/MS neg | 1644 | C17714 | HMDB00666 | 8094 |
| 1045 | Medium Chain Fatty Acid | palmitate (16:0) | LC/MS neg | 1336 | C00249 | HMDB00220 | 985 |
| 1046 | | palmitoleate (16:1n7) | LC/MS neg | 33447 | C08362 | HMDB03229 | 445638 |
| 1048 | | margarate (17:0) | LC/MS neg | 1121 | | HMDB02259 | 10465 |
| 1049 | | 10-heptadecenoate (17:1n7) | LC/MS neg | 33971 | | HMDB60038 | 5312435 |

FIG. 57 cont.

| | | | | | | |
|---|---|---|---|---|---|---|
| Long Chain Fatty Acid | 1050 | stearate (18:0) | LC/MS neg | | | 5281 |
| | 1058 | nonadecanoate (19:0) | LC/MS neg | 1358 | HMDB00827 | 12591 |
| | 1059 | 10-nonadecenoate (19:1n9) | LC/MS neg | 1356 | HMDB00772 | 5312513 |
| | 1064 | eicosenoate (20:1) | LC/MS neg | 33972 | HMDB13622 | 5282768 |
| | 1068 | erucate (22:1n9) | LC/MS neg | 33587 | HMDB02231 | 5281116 |
| | 1075 | oleate/vaccenate (18:1) | LC/MS neg | 1552 | HMDB02068 | |
| Polyunsaturated Fatty Acid (n3 and n6) | 1079 | eicosapentaenoate (EPA; 20:5n3) | LC/MS neg | 52285 | | |
| | 1080 | docosapentaenoate (n3 DPA; 22:5n3) | LC/MS neg | 18467 | C06428 | HMDB01999 | 446284 |
| | 1081 | docosahexaenoate (DHA; 22:6n3) | LC/MS neg | 32504 | C16513 | HMDB01976 | 6441454 |
| | 1082 | docosatrienoate (22:3n3) | LC/MS neg | 44675 | C06429 | HMDB02183 | 445580 |
| | 1085 | linoleate (18:2n6) | LC/MS neg | 32417 | C16534 | HMDB02823 | 5312556 |
| | 1087 | linolenate [alpha or gamma; (18:3n3 or 6)] | LC/MS neg | 1105 | C01595 | HMDB00673 | 5280450 |
| | 1089 | dihomo-linolenate (20:3n3 or n6) | LC/MS neg | 34035 | C06426 | HMDB03073 | 5280934 |
| | 1090 | arachidonate (20:4n6) | LC/MS neg | 35718 | C03242 | HMDB02925 | 5280581 |
| | 1091 | adrenate (22:4n6) | LC/MS neg | 1110 | C00219 | HMDB01043 | 444899 |
| | | | LC/MS neg | 32980 | C16527 | HMDB02226 | 5497181 |

| | | | | | | |
|---|---|---|---|---|---|---|
| 1092 | | docosapentaenoate (n6 DPA; 22:5n6) | LC/MS neg | 37478 | C16513 | HMDB01976 | 6441454 |
| 1093 | | docosadienoate (22:2n6) | LC/MS neg | 32415 | C16533 | HMDB61714 | 5282807 |
| 1094 | | dihomo-linoleate (20:2n6) | LC/MS neg | 17805 | C16525 | HMDB05060 | 6439848 |
| 1096 | | mead acid (20:3n9) | LC/MS neg | 35174 | | HMDB10378 | 5312531 |
| 1161 | Fatty Acid, Dicarboxylate | 2-hydroxyglutarate | LC/MS polar | 37253 | C02630 | HMDB00606 | 43 |
| 1164 | | 2-hydroxyadipate | LC/MS polar | 31934 | C02360 | HMDB00321 | 193530 |
| 1214 | Fatty Acid, Amino | 2-aminoheptanoate | LC/MS pos early | 43761 | | | 227939 |
| 1227 | Fatty Acid Synthesis | malonylcarnitine | LC/MS pos early | 37059 | | HMDB02095 | 22833583 |
| 1228 | | malonate | LC/MS polar | 15872 | C00383 | HMDB00691 | 867 |
| 1230 | Fatty Acid Metabolism | acetyl CoA | LC/MS neg | 43840 | C00024 | HMDB01206 | 444493 |
| 1241 | Fatty Acid Metabolism (also BCAA Metabolism) | butylcarnitine | LC/MS pos early | 32412 | C02862 | HMDB02013 | 439829 |
| 1244 | | propionylcarnitine | LC/MS pos early | 32452 | C03017 | HMDB00824 | 107738 |
| 1247 | | methylmalonate (MMA) | LC/MS polar | 1496 | C02170 | HMDB00202 | 487 |
| 1258 | | acetylcarnitine | LC/MS pos early | 32198 | C02571 | HMDB00201 | 1 |
| 1259 | | 3-hydroxybutyrylcarnitine (1) | LC/MS pos early | 43264 | | HMDB13127 | 53481617 |
| 1260 | | 3-hydroxybutyrylcarnitine (2) | LC/MS pos early | 52984 | | | |
| 1262 | | hexanoylcarnitine | LC/MS pos early | 32328 | | HMDB00705 | 6426853 |

| | | | | | | |
|---|---|---|---|---|---|---|
| 1268 | Fatty Acid Metabolism(Acyl Carnitine) | laurylcarnitine | LC/MS pos late | 34534 | | HMDB02250 | 10427569 |
| 1269 | | myristoylcarnitine | LC/MS pos late | 33952 | | HMDB05066 | 53477791 |
| 1271 | | palmitoylcarnitine | LC/MS pos late | 44681 | C02990 | HMDB00222 | 461 |
| 1272 | | stearoylcarnitine | LC/MS pos late | 34409 | | HMDB00848 | 6426855 |
| 1273 | | linoleoylcarnitine* | LC/MS pos late | 46223 | | HMDB06469 | 6450015 |
| 1274 | | oleoylcarnitine | LC/MS pos late | 35160 | | HMDB05065 | 6441392;53477789 |
| 1282 | Carnitine Metabolism | deoxycarnitine | LC/MS pos early | 36747 | C01181 | HMDB01161 | 134 |
| 1283 | | carnitine | LC/MS pos early | 15500 | C00318 | HMDB00062 | 10917 |
| 1288 | Ketone Bodies | 3-hydroxybutyrate (BHBA) | LC/MS polar | 542 | C01089 | HMDB00357 | 441 |
| 1289 | Neurotransmitter | acetylcholine | LC/MS pos early | 18790 | | | |
| 1293 | Fatty Acid, Monohydroxy | 2-hydroxydecanoate | LC/MS neg | 42489 | | | 21488 |
| 1296 | | 2-hydroxystearate | LC/MS neg | 17945 | C03045 | | 69417 |
| 1318 | | 13-HODE + 9-HODE | LC/MS neg | 37752 | | | 43013 |
| 1369 | Eicosanoid | prostaglandin F2alpha | LC/MS neg | 19398 | C00639 | HMDB01139 | 5280363 |
| 1405 | | 5-HETE | LC/MS neg | 37372 | C04805 | HMDB11134 | 5280733 |
| 1410 | | 12-HETE | LC/MS neg | 37536 | | HMDB06111 | 5312983 |
| 1411 | | 15-HETE | LC/MS neg | 37538 | C04742 | HMDB02110 | 5280724 |

FIG. 57 cont.

| | | | | | |
|---|---|---|---|---|---|
| 1419 | | oleoyl ethanolamide | LC/MS neg | 38102 | | HMDB02088 | 5283454 |
| 1422 | Endocannabinoid | palmitoyl ethanolamide | LC/MS pos late | 38165 | C16512 | HMDB02100 | 4671 |
| 1423 | | stearoyl ethanolamide | LC/MS pos late | 38625 | | HMDB13078 | 27902 |
| 1429 | | N-oleoyltaurine | LC/MS neg | 39732 | | | 6437033 |
| 1430 | | N-stearoyltaurine | LC/MS neg | 39730 | | | 166274 |
| 1431 | | N-palmitoyltaurine | LC/MS neg | 39835 | | | |
| 1435 | Inositol Metabolism | myo-inositol | LC/MS polar | 1124 | C00137 | HMDB00211 | 892 |
| 1443 | | inositol 1-phosphate (I1P) | LC/MS polar | 43849 | C04006 | HMDB00213 | 440194 |
| 1463 | | choline | LC/MS pos early | 15506 | C00114 | HMDB00097 | 305 |
| 1464 | | choline phosphate | LC/MS polar | 34396 | C00588 | HMDB01565 | 1014 |
| 1465 | | cytidine 5'-diphosphocholine | LC/MS pos early | 34418 | C00307 | HMDB01413 | 13804 |
| 1466 | | glycerophosphorylcholine (GPC) | LC/MS pos early | 15990 | C00670 | HMDB00086 | 71920 |
| 1470 | | phosphoethanolamine | LC/MS neg | 1600 | C00346 | HMDB00224 | 1015 |
| 1471 | | cytidine-5'-diphosphoethanolamine | LC/MS polar | 34410 | C00570 | HMDB01564 | 123727 |
| 1472 | | glycerophosphoethanolamine | LC/MS polar | 37455 | C01233 | HMDB00114 | 123874 |
| 1473 | | trimethylamine N-oxide | LC/MS pos early | 40406 | C01104 | HMDB00925 | 1145 |
| 1474 | | glycerophosphoinositol* | LC/MS pos early | 52307 | | | |

FIG. 57 cont.

| | | | | | HMDB00564 | |
|---|---|---|---|---|---|---|
| 1475 | | 1,2-dipalmitoyl-GPC (16:0/16:0) | LC/MS pos late | 19130 | | 452110 |
| 1476 | | 1-palmitoyl-2-oleoyl-GPC (16:0/18:1) | LC/MS pos late | 52461 | | 6436017 |
| 1477 | | 1-stearoyl-2-arachidonoyl-GPC (18:0/20:4) | LC/MS pos late | 42450 | | 16219824 |
| 1478 | | 1-palmitoyl-2-linoleoyl-GPC (16:0/18:2) | LC/MS pos late | 42446 | | 5287971 |
| 1480 | | 1-stearoyl-2-oleoyl-GPC (18:0/18:1) | LC/MS pos late | 52438 | | |
| 1482 | | 1,2-dioleoyl-GPC (18:1/18:1)* | LC/MS pos late | 52457 | | 10350317 |
| 1483 | | 1-palmitoyl-2-arachidonoyl-GPC (16:0/20:4) | LC/MS pos late | 52462 | | 10747814 |
| 1484 | | 1-stearoyl-2-linoleoyl-GPC (18:0/18:2)* | LC/MS pos late | 52452 | | |
| 1488 | | 1-palmitoyl-2-palmitoleoyl-GPC (16:0/16:1)* | LC/MS pos late | 52470 | | |
| 1491 | | 1-stearoyl-2-arachidonoyl-GPI (18:0/20:4) | LC/MS polar | 52449 | | |
| 1492 | | 1-oleoyl-2-linoleoyl-GPC (18:1/18:2)* | LC/MS pos late | 52453 | | |
| 1496 | Phospholipid Metabolism | 1-palmitoyl-2-arachidonoyl-GPI (16:0/20:4)* | LC/MS polar | 52467 | | |
| 1498 | | 1-palmitoyl-2-oleoyl-GPG (16:0/18:1) | LC/MS polar | 52448 | | 5283509 |

FIG. 57 cont.

| | Lipid | | | | |
|---|---|---|---|---|---|
| 1500 | 1-palmitoyl-2-oleoyl-GPE (16:0/18:1) | LC/MS pos late | 19263 | HMDB05320 | 5283496 |
| 1502 | 1-stearoyl-2-arachidonoyl-GPE (18:0/20:4) | LC/MS pos late | 52447 | | 5289133 |
| 1504 | 1-stearoyl-2-oleoyl-GPE (18:0/18:1) | LC/MS pos late | 42448 | | |
| 1505 | 1-palmitoyl-2-arachidonoyl-GPE (16:0/20:4)* | LC/MS pos late | 52464 | HMDB05323 | 9546800 |
| 1507 | 1-palmitoyl-2-linoleoyl-GPE (16:0/18:2) | LC/MS pos late | 42449 | HMDB05322 | 9546747 |
| 1524 | 1-palmitoyl-2-stearoyl-GPC (16:0/18:0) | LC/MS pos late | 52616 | | |
| 1525 | 1,2-dioleoyl-GPE (18:1/18:1) | LC/MS pos late | 52609 | | 9546757 |
| 1533 | 1-palmitoyl-2-linolenoyl-GPC (16:0/18:3)* | LC/MS pos late | 52684 | | |
| 1536 | 1-palmitoleoyl-2-linoleoyl-GPC (16:1/18:2)* | LC/MS pos late | 52683 | | |
| 1541 | 1,2-dilinoleoyl-GPC (18:2/18:2) | LC/MS pos late | 52603 | | 5288075 |
| 1544 | 1-oleoyl-2-linoleoyl-GPE (18:1/18:2)* | LC/MS pos late | 52687 | HMDB05349 | 9546753 |
| 1549 | 1-linoleoyl-2-arachidonoyl-GPC (18:2/20:4n6)* | LC/MS pos late | 52710 | | |
| 1557 | 1-palmitoyl-2-oleoyl-GPS (16:0/18:1) | LC/MS pos late | 19261 | C13880 | 5283499 |

FIG. 57 cont.

| | | | | | |
|---|---|---|---|---|---|
| 1593 | Phosphatidylserine (PS) | 1-stearoyl-2-arachidonoyl-GPS (18:0/20:4) | LC/MS pos late | 52235 | | |
| 1594 | | 1-stearoyl-2-oleoyl-GPS (18:0/18:1) | LC/MS polar | 48494 | | 9547087 |
| 1600 | | 1-palmitoyl-GPC (16:0) | LC/MS pos late | 33955 | | HMDB10382 | 86554 |
| 1601 | | 2-palmitoyl-GPC (16:0)* | LC/MS pos late | 35253 | | HMDB61702 | 15061532 |
| 1602 | | 1-palmitoleoyl-GPC (16:1)* | LC/MS pos late | 33230 | | | 24779461 |
| 1606 | | 1-stearoyl-GPC (18:0) | LC/MS pos late | 33961 | | HMDB10383 | 497299 |
| 1608 | | 1-oleoyl-GPC (18:1) | LC/MS pos late | 48258 | | HMDB02815 | 16081932 |
| 1611 | | 1-linoleoyl-GPC (18:2) | LC/MS pos late | 34419 | C04100 | HMDB10386 | 11988421 |
| 1623 | | 1-arachidonoyl-GPC (20:4n6)* | LC/MS neg | 34061 | C05208 | HMDB10395 | |
| 1633 | | 1-lignoceroyl-GPC (24:0) | LC/MS neg | 49617 | | | |
| 1636 | Lysolipid | 1-palmitoyl-GPE (16:0) | LC/MS neg | 35631 | | HMDB11503 | 9547069 |
| 1639 | | 1-stearoyl-GPE (18:0) | LC/MS neg | 42398 | | HMDB11130 | 9547068 |
| 1640 | | 2-stearoyl-GPE (18:0)* | LC/MS neg | 41220 | | | |
| 1641 | | 1-oleoyl-GPE (18:1) | LC/MS neg | 35628 | | HMDB11506 | 9547071 |
| 1645 | | 1-linoleoyl-GPE (18:2) | LC/MS neg | 32635 | | HMDB11507 | 52925130 |
| 1649 | | 1-arachidonoyl-GPE (20:4n6)* | LC/MS neg | 35186 | | HMDB11517 | 42607465 |
| 1659 | | 1-palmitoyl-GPI (16:0)* | LC/MS neg | 35305 | | HMDB61695 | |

| | | | | |
|---|---|---|---|---|
| 1662 | 1-stearoyl-GPI (18:0) | LC/MS neg | 19324 | | |
| 1664 | 1-oleoyl-GPI (18:1)* | LC/MS neg | 36602 | | |
| 1670 | 1-arachidonoyl-GPI (20:4)* | LC/MS neg | 34214 | | |
| 1672 | 1-stearoyl-GPS (18:0)* | LC/MS pos late | 45966 | | 9547101 |
| 1673 | 1-oleoyl-GPS (18:1) | LC/MS neg | 19260 | HMDB61696 | 9547099 |
| 1683 | 1-palmitoyl-GPG (16:0)* | LC/MS neg | 45970 | | 3300276 |
| 1685 | 1-palmitoyl-GPS (16:0)* | LC/MS neg | 46130 | HMDB61690 | 9547100 |
| 1688 | 1-oleoyl-GPG (18:1)* | LC/MS neg | 45968 | | |
| 1701 | 1-(1-enyl-palmitoyl)-2-oleoyl-GPE (P-16:0/18:1)* | LC/MS pos late | 52477 | | |
| 1703 | 1-(1-enyl-palmitoyl)-2-palmitoyl-GPC (P-16:0/16:0)* | LC/MS pos late | 52716 | | 11146967 |
| 1705 | 1-(1-enyl-palmitoyl)-2-arachidonoyl-GPE (P-16:0/20:4)* | LC/MS pos late | 52673 | | |
| 1707 | 1-(1-enyl-palmitoyl)-2-oleoyl-GPC (P-16:0/18:1)* | LC/MS pos late | 52478 | | |
| 1709 | 1-(1-enyl-stearoyl)-2-oleoyl-GPE (P-18:0/18:1) | LC/MS pos late | 52614 | | |
| 1711 | 1-(1-enyl-palmitoyl)-2-arachidonoyl-GPC (P-16:0/20:4)* | LC/MS pos late | 52689 | | |

Plasmalogen (rows 1701–1711)

FIG. 57 cont.

| | | | | | | |
|---|---|---|---|---|---|---|
| 1715 | | 1-(1-enyl-stearoyl)-2-arachidonoyl-GPE (P-18:0/20:4)* | LC/MS polar | 52475 | | HMDB05779 | 9547058 |
| 1721 | Lysoplasmalogen | 1-(1-enyl-palmitoyl)-GPE (P-16:0)* | LC/MS neg | 39270 | | | |
| 1723 | | 1-(1-enyl-oleoyl)-GPE (P-18:1)* | LC/MS neg | 44621 | | | |
| 1725 | | 1-(1-enyl-stearoyl)-GPE (P-18:0)* | LC/MS neg | 39271 | | | |
| 1726 | Glycerolipid Metabolism | glycerol | LC/MS pos early | 15122 | C00116 | HMDB00131 | 753 |
| 1727 | | glycerol 3-phosphate | LC/MS polar | 43847 | C00093 | HMDB00126 | 754 |
| 1732 | | glycerophosphoglycerol | LC/MS polar | 48857 | C03274 | | 439964 |
| 1738 | | 2-palmitoylglycerol (16:0) | LC/MS neg | 33419 | | HMDB11533 | 123409 |
| 1743 | | 2-oleoylglycerol (18:1) | LC/MS neg | 21232 | | | 5319879 |
| 1745 | Monoacylglycerol | 2-linoleoylglycerol (18:2) | LC/MS neg | 32506 | | HMDB11538 | 5365676 |
| 1747 | | 1-arachidonylglycerol (20:4) | LC/MS neg | 34397 | C13857 | HMDB11572 | 5282281 |
| 1748 | | 2-arachidonoylglycerol (20:4) | LC/MS neg | 19266 | C13856 | HMDB04666 | 5282280 |
| 1752 | | 1-docosahexaenoylglycerol (22:6) | LC/MS neg | 35153 | | HMDB11587 | |
| 1755 | | 2-docosahexaenoylglycerol (22:6)* | LC/MS neg | 48675 | | HMDB11557 | |
| 1767 | Diacylglycerol | 1-oleoyl-3-linoleoyl-glycerol (18:1/18:2) | LC/MS pos late | 46799 | | | |
| 1770 | | 1-palmitoyl-3-linoleoyl-glycerol (16:0/18:2)* | LC/MS pos late | 52634 | | | |

| | | | | | | |
|---|---|---|---|---|---|---|
| 1773 | Sphingolipid Metabolism | N-palmitoyl-sphinganine (d18:0/16:0) | LC/MS pos late | 52604 | | HMDB11760 | 5283572 |
| 1774 | | sphinganine | LC/MS pos late | 17769 | C00836 | HMDB00269 | 3126 |
| 1777 | | palmitoyl sphingomyelin (d18:1/16:0) | LC/MS pos late | 37506 | | | 9939941 |
| 1778 | | stearoyl sphingomyelin (d18:1/18:0) | LC/MS pos late | 19503 | C00550 | HMDB01348 | 6453725 |
| 1779 | | sphingomyelin (d18:1/18:1, d18:2/18:0) | LC/MS pos late | 37529 | | | 6443882 |
| 1783 | | sphingosine | LC/MS pos late | 17747 | C00319 | HMDB00252 | 5353955 |
| 1791 | | N-palmitoyl-sphingosine (d18:1/16:0) | LC/MS pos late | 44877 | | HMDB04949 | 5283564 |
| 1793 | | sphingomyelin (d18:1/14:0, d16:1/16:0)* | LC/MS pos late | 42463 | | | 11433862 |
| 1795 | | sphingomyelin (d18:1/24:1, d18:2/24:0)* | LC/MS pos late | 47153 | | | |
| 1796 | | sphingomyelin (d18:2/16:0, d18:1/16:1)* | LC/MS pos late | 42459 | | | |
| 1797 | | sphingomyelin (d18:1/20:1, d18:2/20:0)* | LC/MS pos late | 48491 | | | |
| 1798 | | behenoyl sphingomyelin (d18:1/22:0)* | LC/MS pos late | 48492 | | | |
| 1799 | | sphingomyelin (d18:1/22:1, d18:2/22:0, d16:1/24:1)* | LC/MS pos late | 48493 | | | |

FIG. 57 cont.

| | | | | |
|---|---|---|---|---|
| 1800 | | sphingomyelin (d18:1/20:0, d16:1/22:0)* | LC/MS pos late | 48490 | | |
| 1801 | | palmitoyl dihydrosphingomyelin (d18:0/16:0)* | LC/MS pos late | 52434 | | 9939965 |
| 1802 | | sphingomyelin (d18:1/15:0, d16:1/17:0)* | LC/MS pos late | 52433 | | |
| 1803 | | sphingomyelin (d18:1/21:0, d17:1/22:0, d16:1/23:0)* | LC/MS pos late | 52495 | | |
| 1804 | | sphingomyelin (d18:2/23:0, d18:1/23:1, d17:1/24:1)* | LC/MS pos late | 52435 | | |
| 1805 | | sphingomyelin (d18:2/24:1, d18:1/24:2)* | LC/MS pos late | 52437 | | |
| 1806 | | tricosanoyl sphingomyelin (d18:1/23:0)* | LC/MS pos late | 52436 | | |
| 1807 | | sphingomyelin (d18:1/17:0, d17:1/18:0, d19:1/16:0) | LC/MS pos late | 52615 | | |
| 1809 | | 3-sulfo-nervonoyl-galactosylceramide (d18:1/24:1) | LC/MS polar | 52621 | | |
| 1810 | | glycosyl-N-stearoyl-sphingosine | LC/MS pos late | 52234 | | |
| 1811 | | glycosyl-N-palmitoyl-sphingosine | LC/MS pos late | 53013 | | |
| 1815 | Mevalonate Metabolism | 3-hydroxy-3-methylglutarate | LC/MS polar | 531 | C03761 | HMDB00355 | 1662 |
| 1826 | | desmosterol | LC/MS pos late | 6065 | C01802 | HMDB02719 | 439577 |

FIG. 57 cont.

| | | | | | | |
|---|---|---|---|---|---|---|
| 1827 | Sterol | cholesterol | LC/MS pos late | 63 | C00187 | HMDB00067 | 11025495 |
| 1847 | | 4-cholesten-3-one | LC/MS pos late | 38125 | C00599 | HMDB00921 | 91477 |
| 1868 | | 7-hydroxycholesterol (alpha or beta) | LC/MS pos late | 47890 | | | |
| 1910 | Steroid | corticosterone | LC/MS neg | 5983 | C02140 | HMDB01547 | 5753 |
| 1995 | Primary Bile Acid Metabolism | taurocholate | LC/MS neg | 18497 | C05122 | HMDB00036 | 6675 |
| 2002 | | tauro-beta-muricholate | LC/MS neg | 33983 | | HMDB00932 | 168408 |
| 2087 | Fatty Acid Metabolism (Acyl Choline) | palmitoylcholine | LC/MS pos late | 52944 | | | 151731 |
| 2598 | | inosine 5'-monophosphate (IMP) | LC/MS pos early | 2133 | C00130 | HMDB00175 | 8582 |
| 2599 | | inosine | LC/MS neg | 1123 | C00294 | HMDB00195 | 6021 |
| 2600 | | hypoxanthine | LC/MS neg | 3127 | C00262 | HMDB00157 | 790 |
| 2601 | | xanthine | LC/MS pos early | 3147 | C00385 | HMDB00292 | 1188 |
| 2603 | Purine Metabolism, (Hypo)Xanthine/Inosine containing | xanthosine | LC/MS neg | 15136 | C01762 | HMDB00299 | 64959 |
| 2606 | | 2'-deoxyinosine | LC/MS neg | 15076 | C05512 | HMDB00071 | 65058 |
| 2608 | | urate | LC/MS neg | 1604 | C00366 | HMDB00289 | 1175 |
| 2609 | | allantoin | LC/MS polar | 1107 | C02350 | HMDB00462 | 204 |
| 2613 | | adenosine 5'-diphosphate (ADP) | LC/MS neg | 3108 | C00008 | HMDB01341 | 6022 |

FIG. 57 cont.

| | | | | | | |
|---|---|---|---|---|---|---|
| 2614 | | adenosine 5'-monophosphate (AMP) | LC/MS pos early | 32342 | C00020 | HMDB00045 | 6083 |
| 2615 | | adenosine 3'-monophosphate (3'-AMP) | LC/MS neg | 35142 | C01367 | HMDB03540 | 41211 |
| 2616 | | adenosine 2'-monophosphate (2'-AMP) | LC/MS neg | 36815 | C00946 | HMDB11617 | 94136 |
| 2617 | | adenosine 3',5'-cyclic monophosphate (cAMP) | LC/MS neg | 2831 | C00575 | HMDB00058 | 6076 |
| 2621 | Purine Metabolism, Adenine containing | adenosine | LC/MS pos early | 555 | C00212 | HMDB00050 | 60961 |
| 2622 | | adenine | LC/MS pos early | 554 | C00147 | HMDB00034 | 190 |
| 2627 | | N1-methyladenosine | LC/MS pos early | 15650 | C02494 | HMDB03331 | 27476 |
| 2637 | | N6-carbamoylthreonyladenosine | LC/MS neg | 35157 | | HMDB41623 | 161466 |
| 2646 | | N6-succinyladenosine | LC/MS pos early | 48130 | | HMDB00912 | |
| 2648 | | guanosine 5'- diphosphate (GDP) | LC/MS neg | 2848 | C00035 | HMDB01201 | 8977 |
| 2649 | | guanosine 5'- monophosphate (5'-GMP) | LC/MS pos early | 2849 | C00144 | HMDB01397 | 6804 |
| 2654 | Purine Metabolism, Guanine containing | guanosine | LC/MS neg | 1573 | C00387 | HMDB00133 | 6802 |
| 2655 | | guanine | LC/MS pos early | 32352 | C00242 | HMDB00132 | 764 |
| 2657 | | 7-methylguanine | LC/MS neg | 35114 | C02242 | HMDB00897 | 11361 |
| 2663 | | N2,N2-dimethylguanosine | LC/MS pos early | 35137 | | HMDB04824 | 92919 |

FIG. 57 cont.

| | | | | | |
|---|---|---|---|---|---|
| 2671 | Pyrimidine Metabolism, Orotate containing | 2'-deoxyguanosine | LC/MS neg | 1411 | C00330 | HMDB00085 | 187790 |
| 2675 | | orotate | LC/MS polar | 1505 | C00295 | HMDB00226 | 967 |
| 2677 | | orotidine | LC/MS polar | 35172 | C01103 | HMDB00788 | 92751 |
| 2682 | | uridine 5'-monophosphate (UMP) | LC/MS polar | 2856 | C00105 | HMDB00288 | 6030 |
| 2687 | | uridine | LC/MS neg | 606 | C00299 | HMDB00296 | 6029 |
| 2688 | Pyrimidine Metabolism, Uracil containing | uracil | LC/MS polar | 605 | C00106 | HMDB00300 | 1174 |
| 2689 | | pseudouridine | LC/MS pos early | 33442 | C02067 | HMDB00767 | 15047 |
| 2701 | | 2'-deoxyuridine | LC/MS neg | 1412 | C00526 | HMDB00012 | 13712 |
| 2704 | | beta-alanine | LC/MS pos early | 55 | C00099 | HMDB00056 | 239 |
| 2710 | | cytidine 5'-monophosphate (5'-CMP) | LC/MS pos early | 2372 | C00055 | HMDB00095 | 6131 |
| 2713 | Pyrimidine Metabolism, Cytidine containing | cytidine | LC/MS pos early | 514 | C00475 | HMDB00089 | 6175 |
| 2715 | | 3-methylcytidine | LC/MS pos early | 35132 | | | 159649 |
| 2721 | | 2'-deoxycytidine 5'-monophosphate | LC/MS pos early | 533 | C00239 | HMDB01202 | 13945 |
| 2723 | | 2'-deoxycytidine | LC/MS pos early | 15949 | C00881 | HMDB00014 | 13711 |
| 2729 | Pyrimidine Metabolism, Thymine containing | thymidine | LC/MS neg | 2183 | C00214 | HMDB00273 | 5789 |
| 2734 | Purine and Pyrimidine Metabolism | methylphosphate | LC/MS pos early | 37070 | | HMDB61711 | 13130 |

FIG. 57 cont.

| | | | | | |
|---|---|---|---|---|---|
| 2740 | | nicotinamide | LC/MS pos early | 594 | C00153 | HMDB01406 | 936 |
| 2743 | | nicotinamide riboside | LC/MS pos early | 33013 | C03150 | HMDB00855 | 439924 |
| 2744 | | nicotinamide adenine dinucleotide (NAD+) | LC/MS pos early | 5278 | C00003 | HMDB00902 | 5893 |
| 2752 | Nicotinate and Nicotinamide Metabolism | 1-methylnicotinamide | LC/MS pos early | 27665 | C02918 | HMDB00699 | 10129985 |
| 2757 | | trigonelline (N'-methylnicotinate) | LC/MS pos early | 32401 | C01004 | HMDB00875 | 5570 |
| 2759 | | N1-Methyl-2-pyridone-5-carboxamide | LC/MS pos early | 40469 | C05842 | HMDB04193 | 69698 |
| 2760 | | adenosine 5'-diphosphoribose (ADP-ribose) | LC/MS neg | 558 | C00301 | HMDB01178 | 192 |
| 2762 | Riboflavin Metabolism | riboflavin (Vitamin B2) | LC/MS pos early | 1827 | C00255 | HMDB00244 | 493570 |
| 2763 | | flavin adenine dinucleotide (FAD) | LC/MS neg | 2134 | C00016 | HMDB01248 | 643975 |
| 2764 | | flavin mononucleotide (FMN) | LC/MS neg | 15797 | C00061 | HMDB01520 | 710 |
| 2765 | Pantothenate and CoA Metabolism | pantothenate | LC/MS pos early | 1508 | C00864 | HMDB00210 | 6613 |
| 2767 | | phosphopantetheine | LC/MS neg | 15504 | C01134 | HMDB01416 | 987 |
| 2768 | | 3'-dephosphocoenzyme A | LC/MS neg | 18289 | C03882 | HMDB01373 | 444485 |
| 2769 | | coenzyme A | LC/MS neg | 46322 | C00010 | HMDB01423 | 317 |
| 2773 | Cofactors and Vitamins | ascorbate (Vitamin C) | LC/MS neg | 32354 | C00072 | HMDB00044 | |

FIG. 57 cont.

| | | | | | |
|---|---|---|---|---|---|
| 2774 | Ascorbate and Aldarate Metabolism | dehydroascorbate | LC/MS neg | 34302 | C05422 | HMDB01264 | 835 |
| 2775 | | threonate | LC/MS polar | 27738 | C01620 | HMDB00943 | 151152 |
| 2777 | | oxalate (ethanedioate) | LC/MS polar | 20694 | C00209 | HMDB02329 | 971 |
| 2778 | | gulonic acid* | LC/MS polar | 46957 | | | 9794176 |
| 2779 | Tocopherol Metabolism | alpha-tocopherol | LC/MS neg | 1561 | C02477 | HMDB01893 | 14985 |
| 2801 | Tetrahydrobiopterin Metabolism | dihydrobiopterin | LC/MS pos early | 35129 | C00268 | HMDB00038 | 1879 |
| 2814 | Hemoglobin and Porphyrin Metabolism | heme | LC/MS pos late | 41754 | C00032 | HMDB03178 | 26945 |
| 2818 | | biliverdin | LC/MS pos late | 2137 | C00500 | HMDB01008 | 5353439 |
| 2826 | Thiamine Metabolism | thiamin (Vitamin B1) | LC/MS pos early | 5341 | C00378 | HMDB00235 | 1130 |
| 2827 | | thiamin monophosphate | LC/MS pos early | 15798 | C01081 | HMDB02666 | 3382778 |
| 2828 | | thiamin diphosphate | LC/MS neg | 35670 | C00068 | HMDB01372 | 1132 |
| 2833 | Vitamin A Metabolism | retinol (Vitamin A) | LC/MS pos late | 1806 | C00473 | HMDB00305 | 445354 |
| 2839 | Vitamin B6 Metabolism | pyridoxamine | LC/MS pos early | 2150 | C00534 | HMDB01431 | 1052 |
| 2840 | | pyridoxamine phosphate | LC/MS pos early | 3138 | C00647 | HMDB01555 | 1053 |
| 2842 | | pyridoxal | LC/MS pos early | 1651 | C00250 | HMDB01545 | 1050 |
| 2843 | | pyridoxate | LC/MS neg | 31555 | C00847 | HMDB00017 | 6723 |
| 2845 | Benzoate Metabolism | hippurate | LC/MS neg | 15753 | C01586 | HMDB00714 | 464 |

FIG. 57 cont.

|  |  |  |  |  |  |  |
|---|---|---|---|---|---|---|
| 2874 | Benzoate Metabolism | catechol sulfate | LC/MS neg | 35320 | C00090 | HMDB59724 | 3083879 |
| 3049 |  | gluconate | LC/MS polar | 587 | C00257 | HMDB00625 | 10690 |
| 3116 |  | ergothioneine | LC/MS pos early | 37459 | C05570 | HMDB03045 | 3032311 |
| 3118 | Food Component/Plant | erythritol | LC/MS polar | 20699 | C00503 | HMDB02994 | 222285 |
| 3172 |  | N-glycolylneuraminate | LC/MS pos early | 37123 | C03410 | HMDB00833 | 123802 |
| 3224 |  | stachydrine | LC/MS pos early | 34384 | C10172 | HMDB04827 | 115244 |
| 3246 | Xenobiotics | methyl glucopyranoside (alpha + beta) | LC/MS neg | 46144 |  |  |  |
| 3310 | Bacterial/Fungal | tartronate (hydroxymalonate) | LC/MS neg | 20693 | C02287 | HMDB35227 | 45 |
| 3522 | Drug | salicylate | LC/MS polar | 1515 | C00805 | HMDB01895 | 338 |
| 3634 | Chemical | O-sulfo-L-tyrosine | LC/MS neg | 45413 |  |  | 514186 |
| 3680 |  | S-(3-hydroxypropyl)mercapturic acid (HPMA) | LC/MS neg | 44552 |  |  | 3371179 |

FIG. 57 cont.

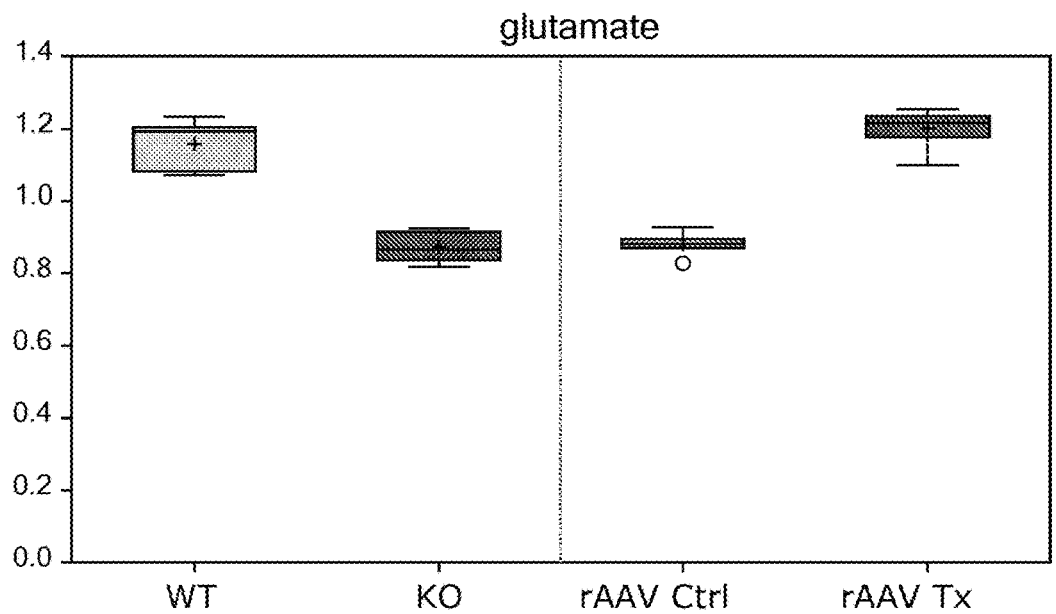
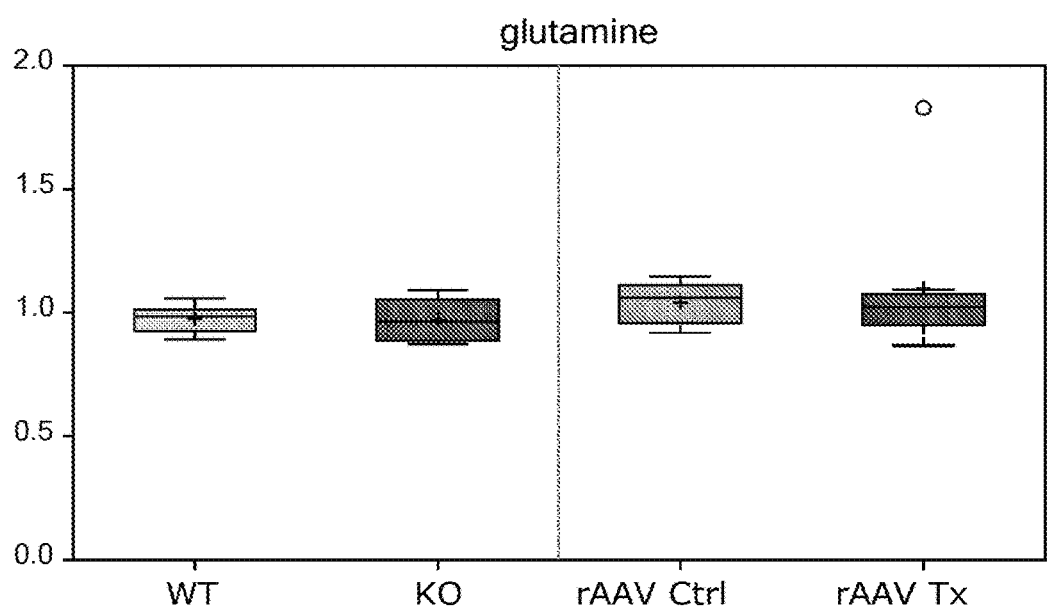
FIG. 57 cont.

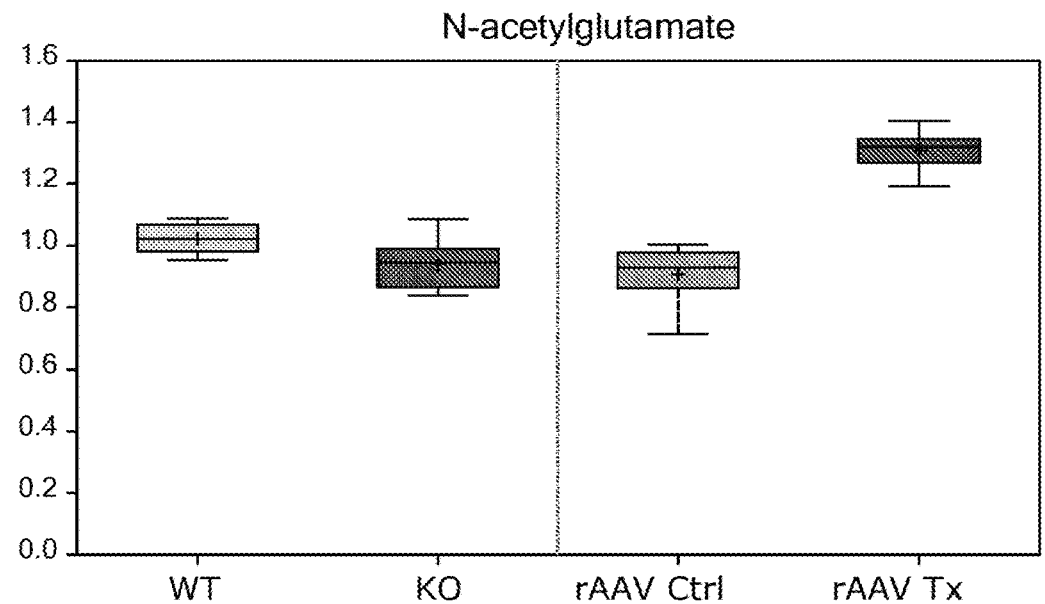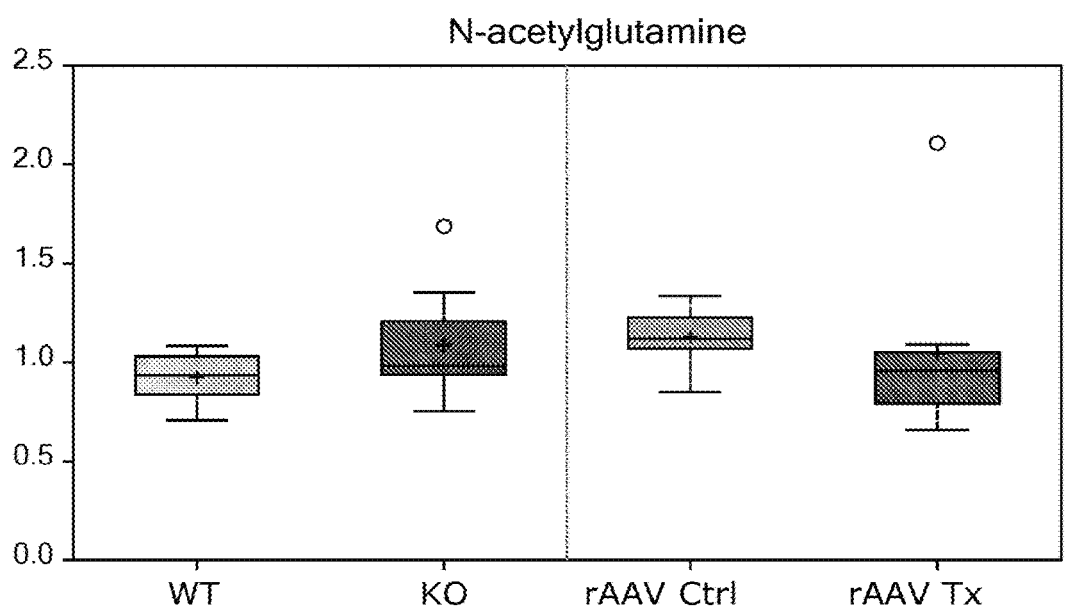
FIG. 57 cont.

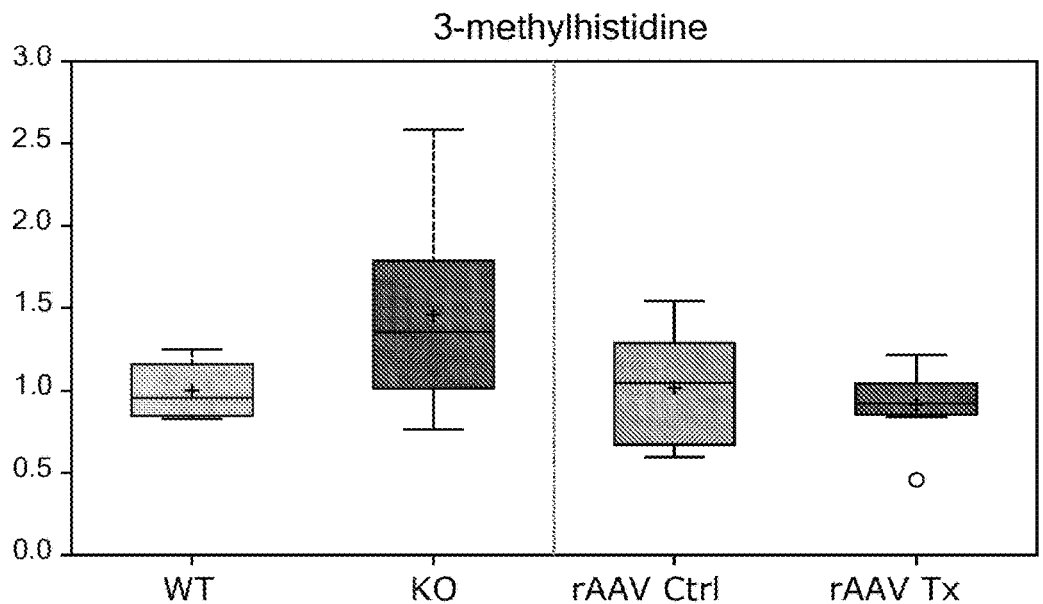
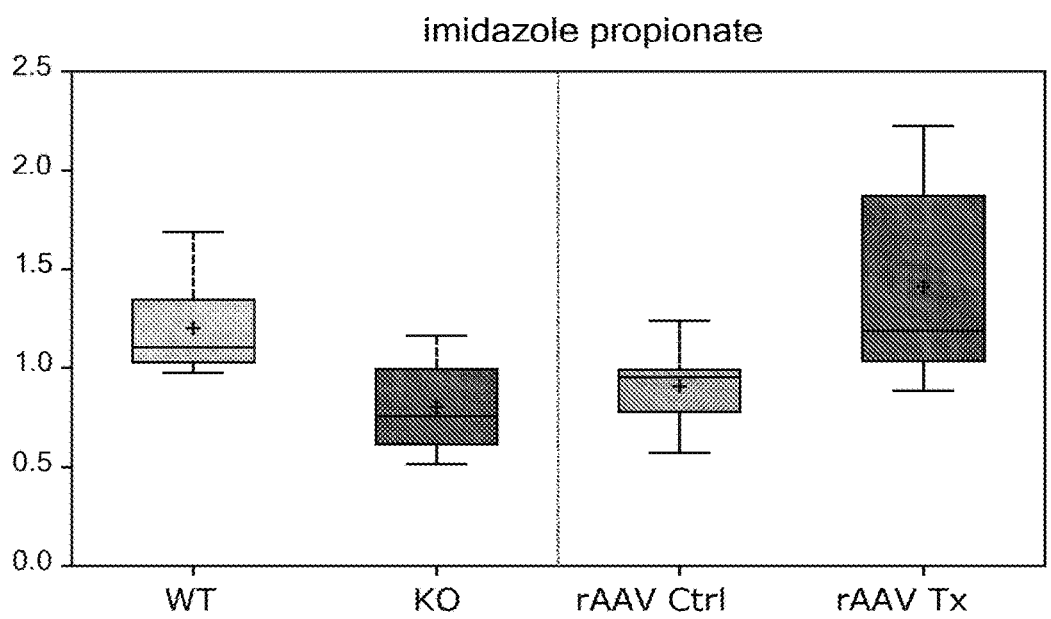
FIG. 57 cont.

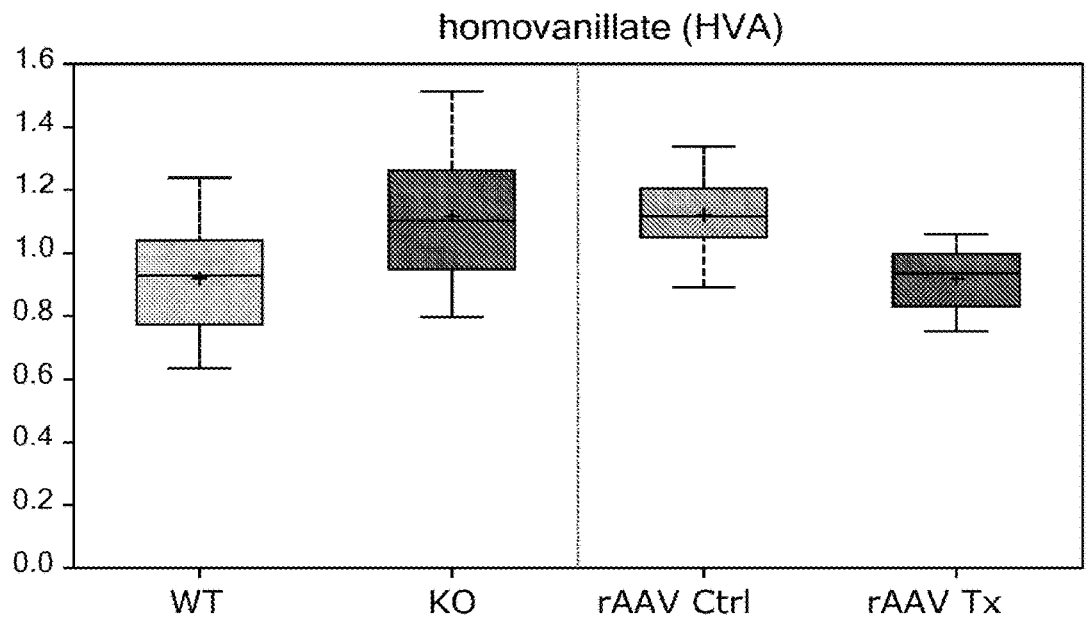
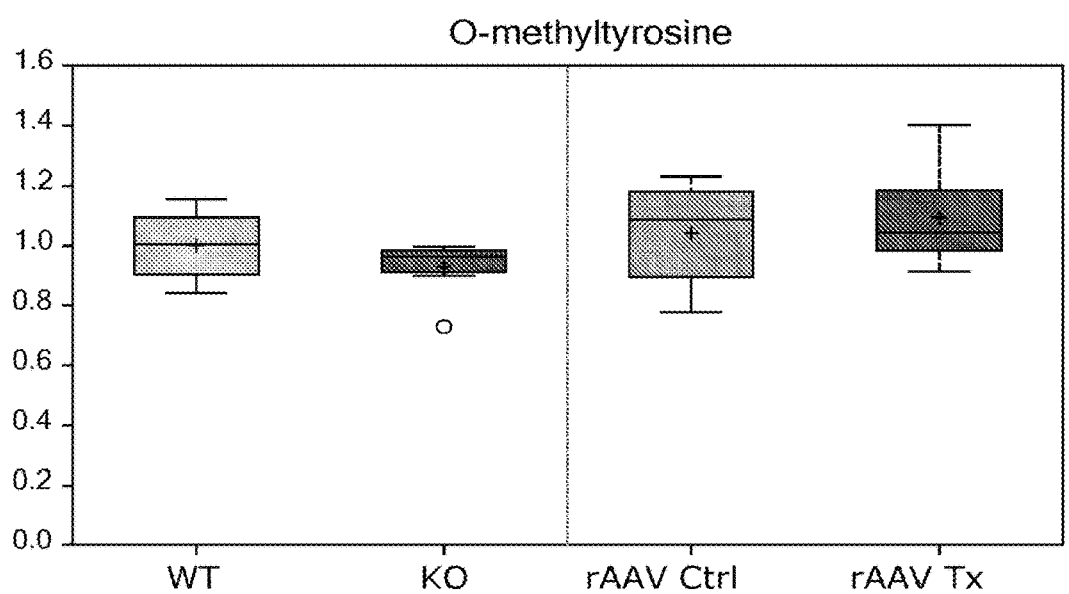
FIG. 57 cont.

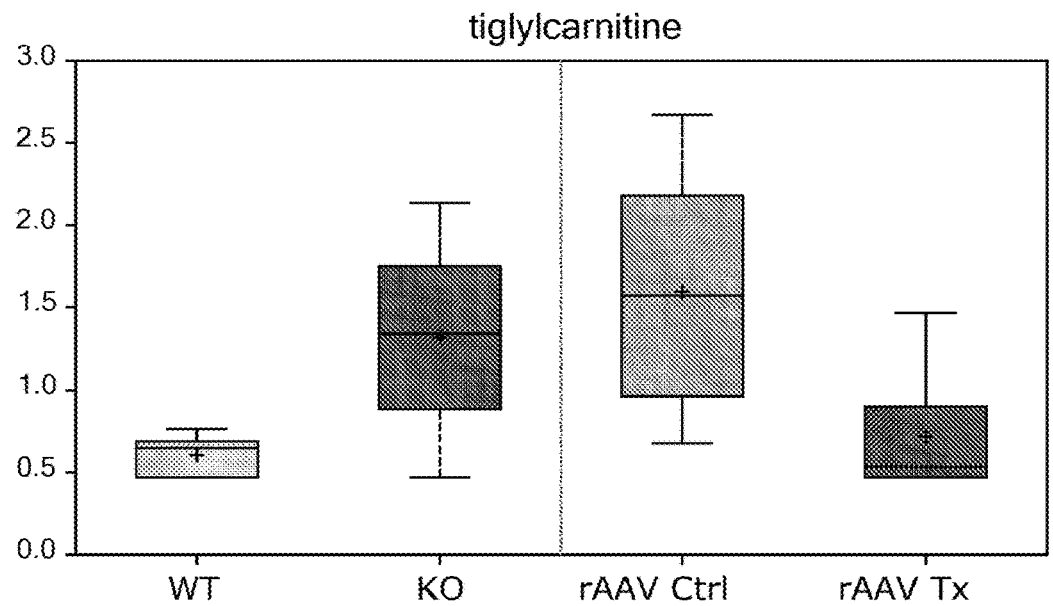
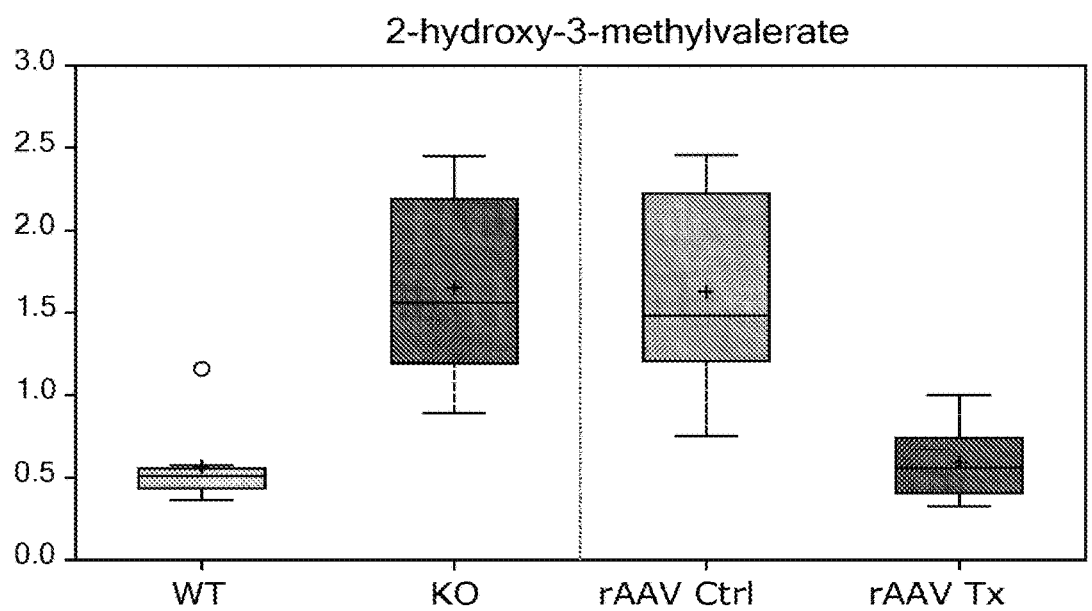
FIG. 57 cont.

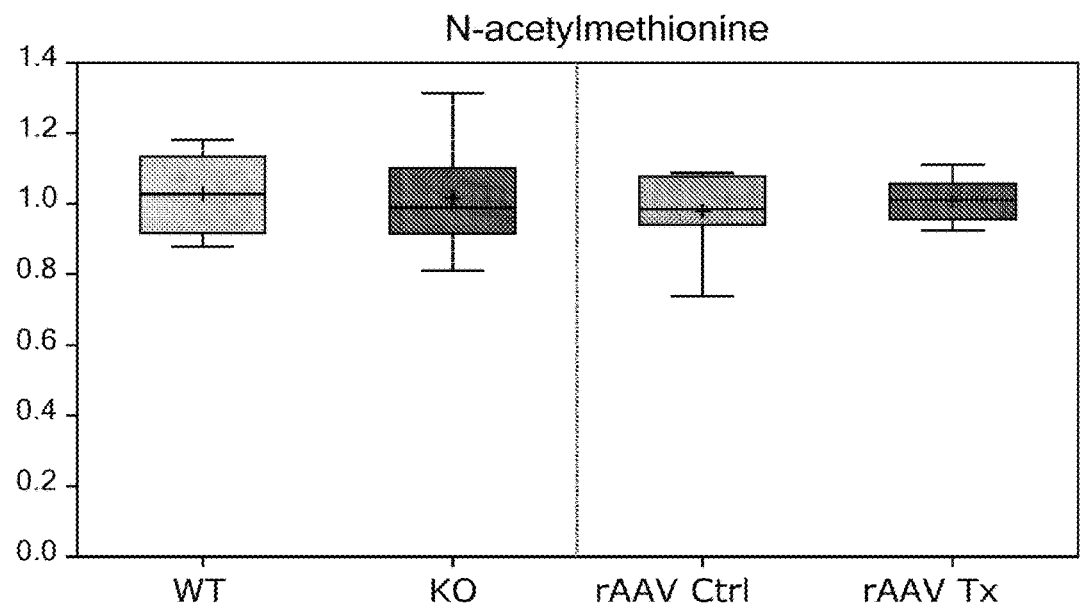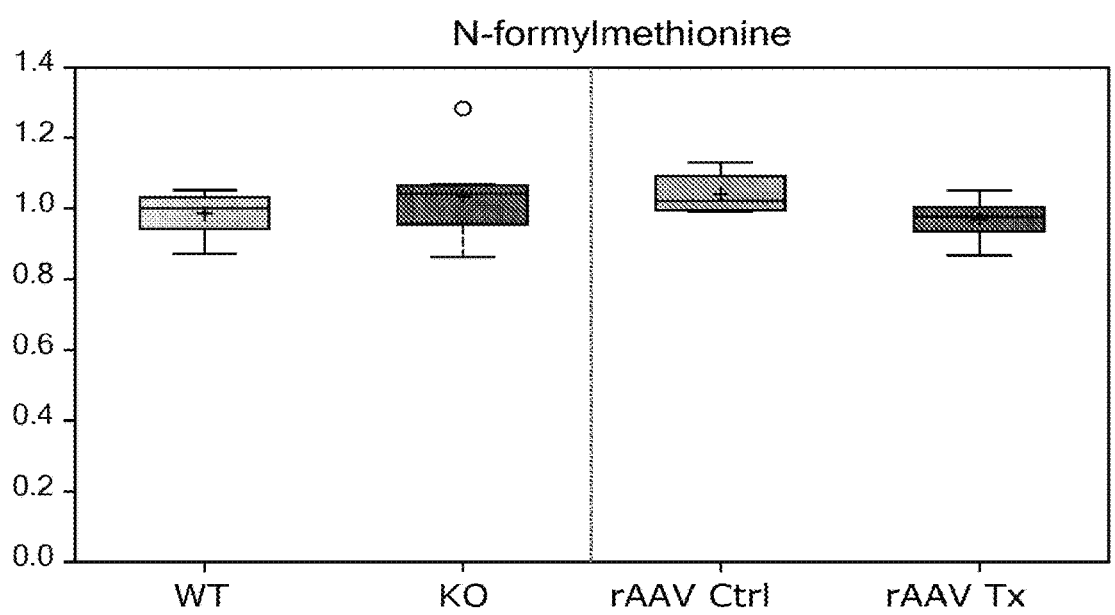
FIG. 57 cont.

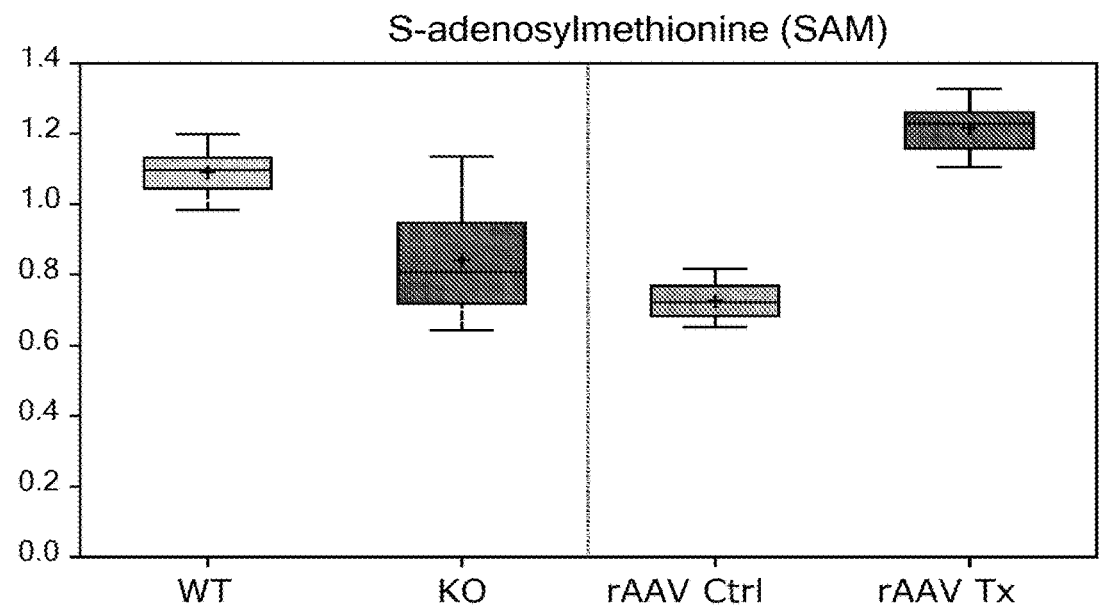
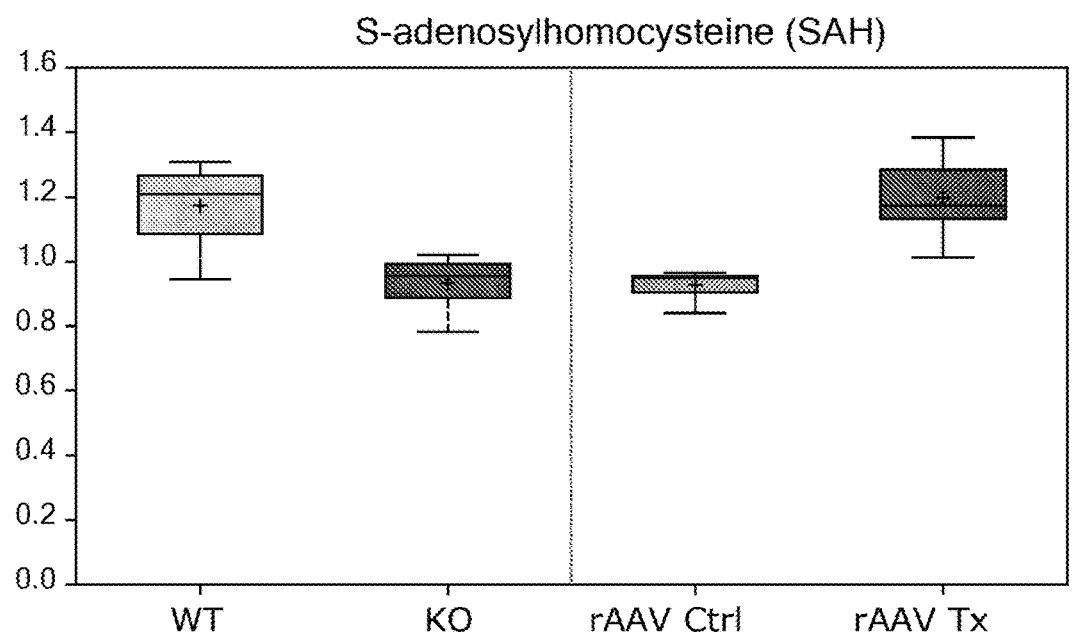
FIG. 57 cont.

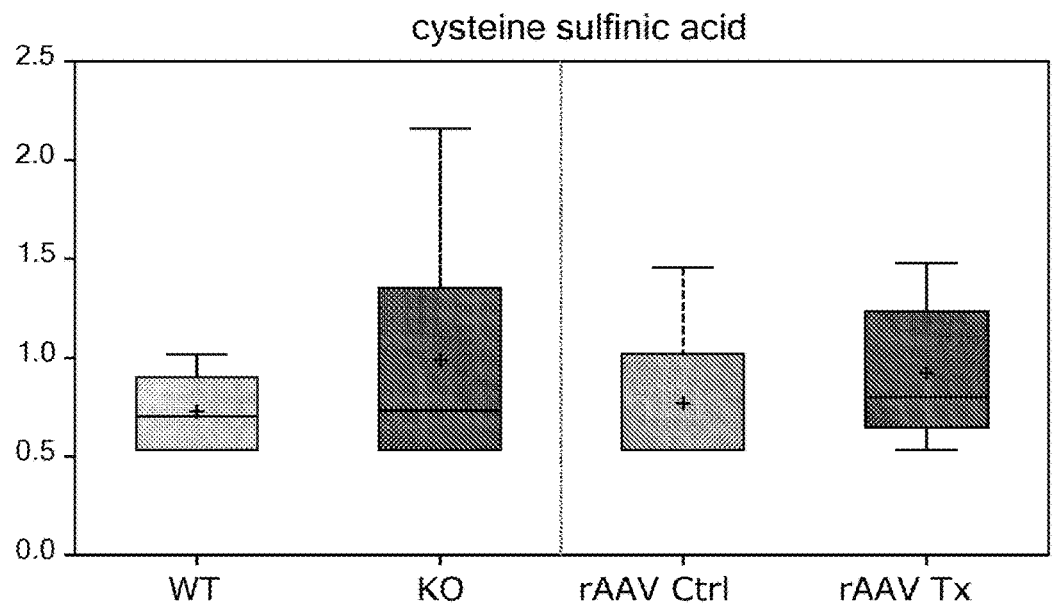
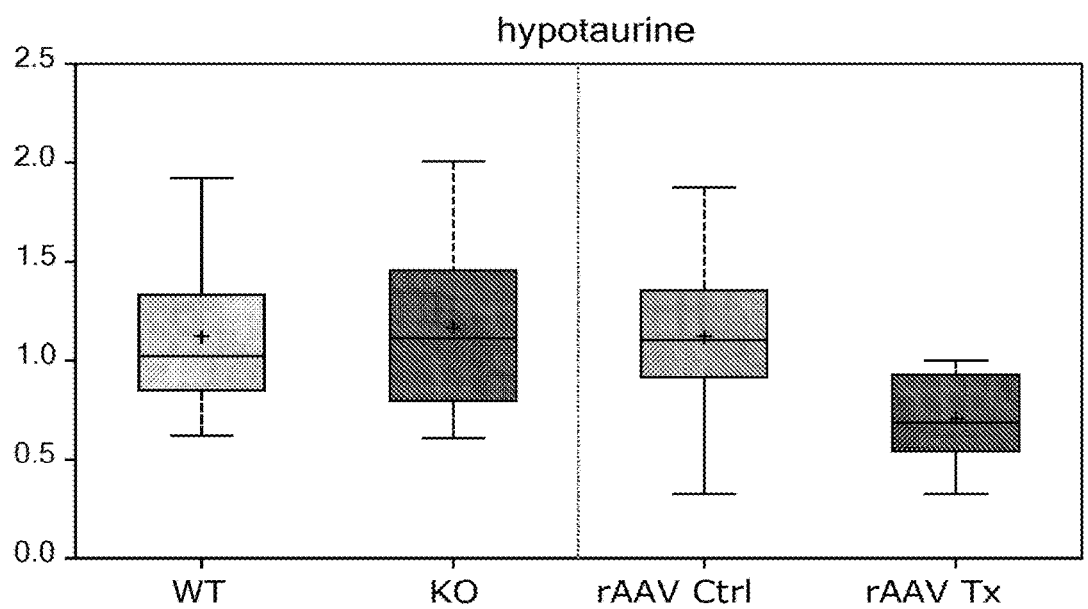
FIG. 57 cont.

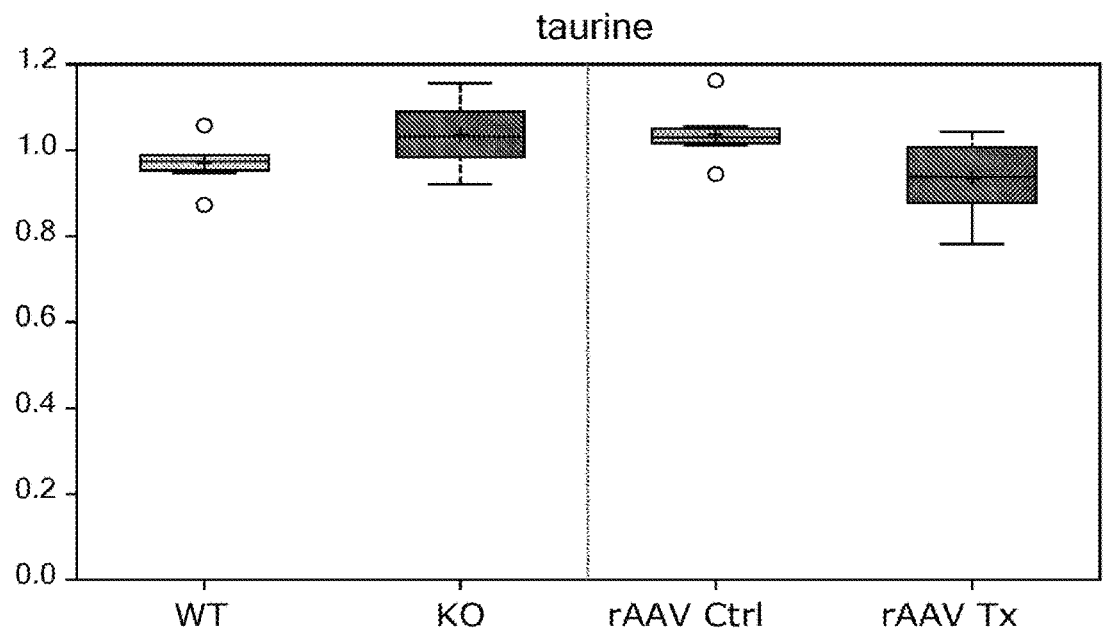
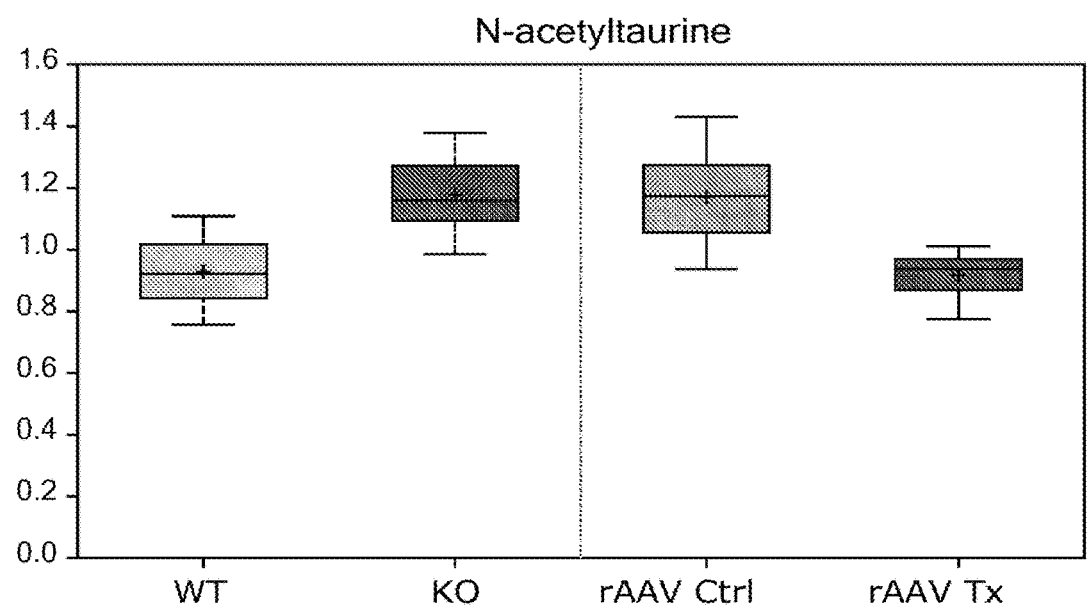
FIG. 57 cont.

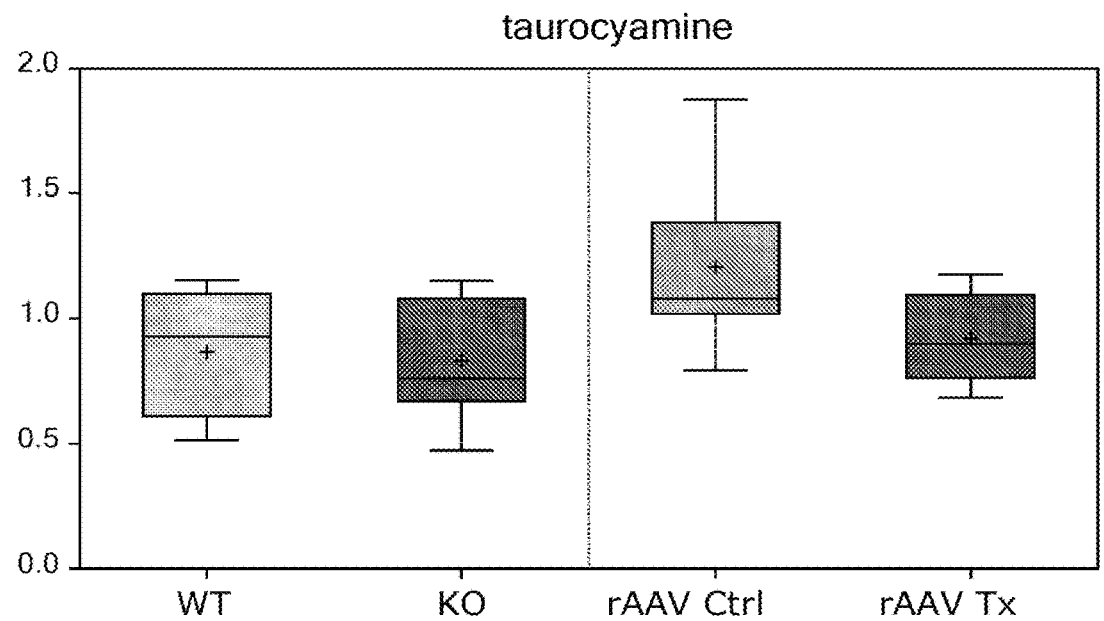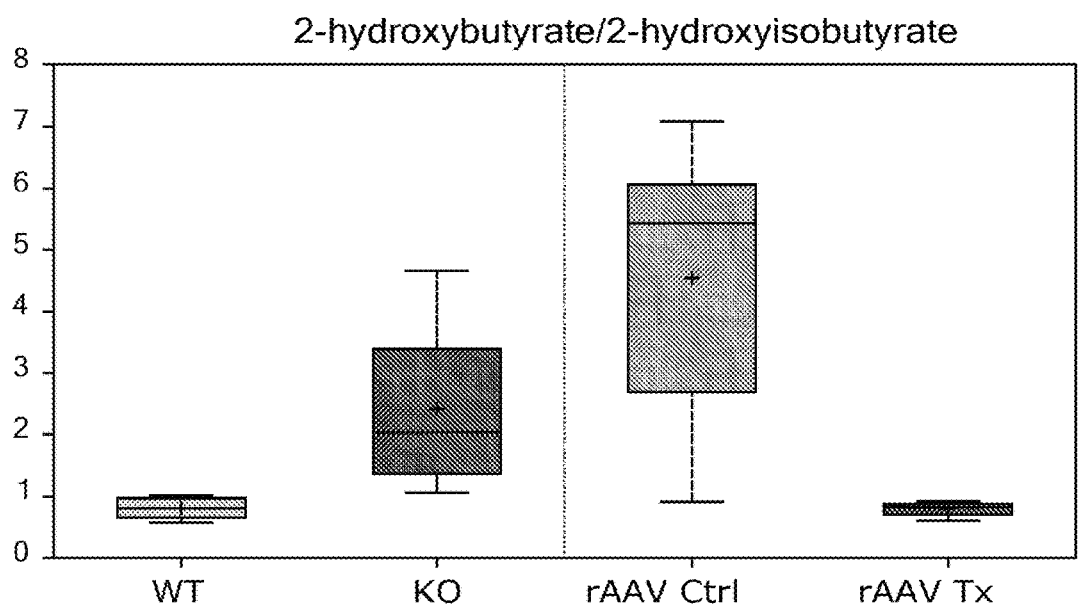
FIG. 57 cont.

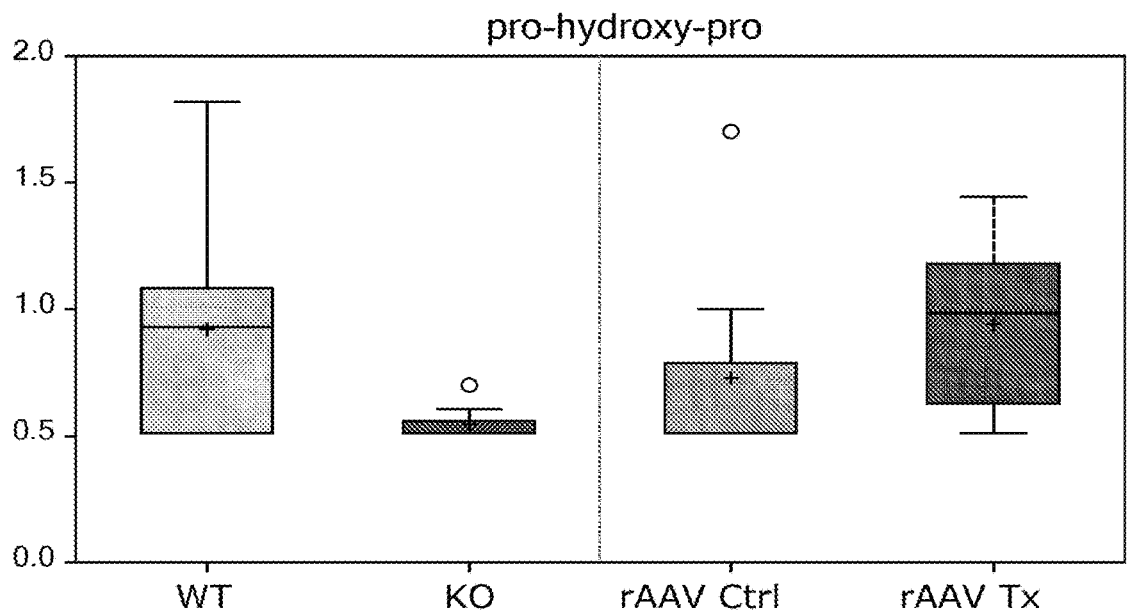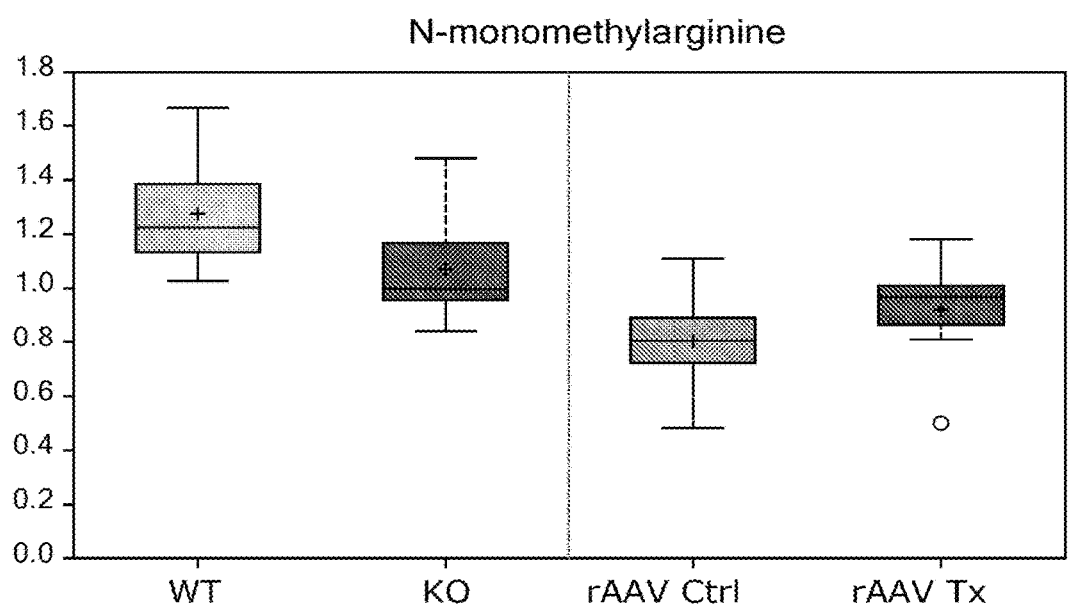
FIG. 57 cont.

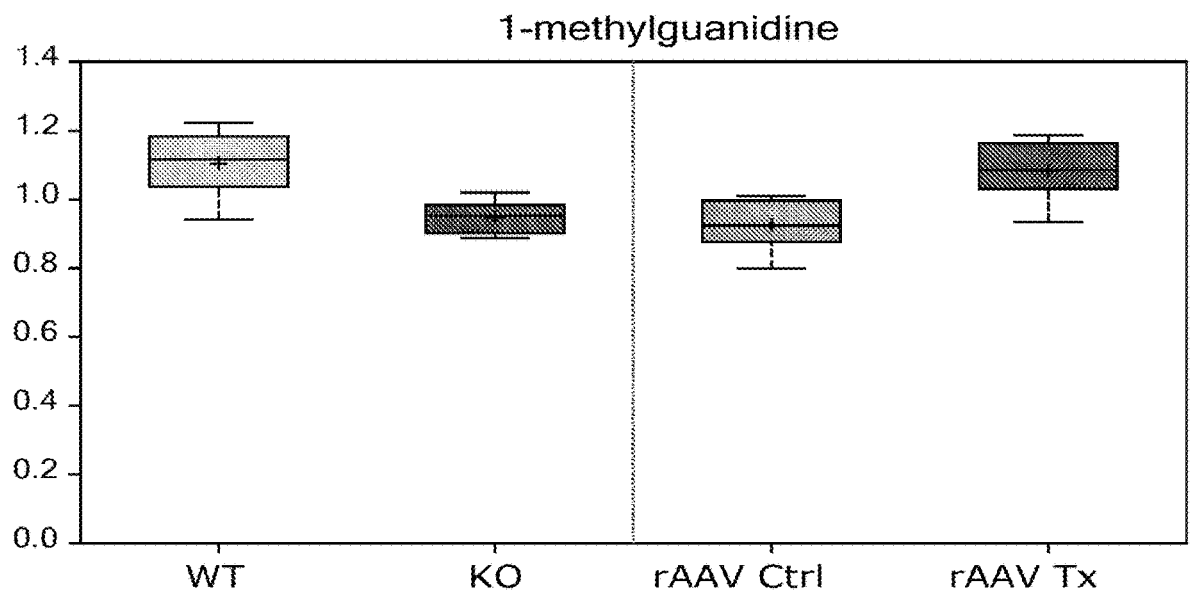
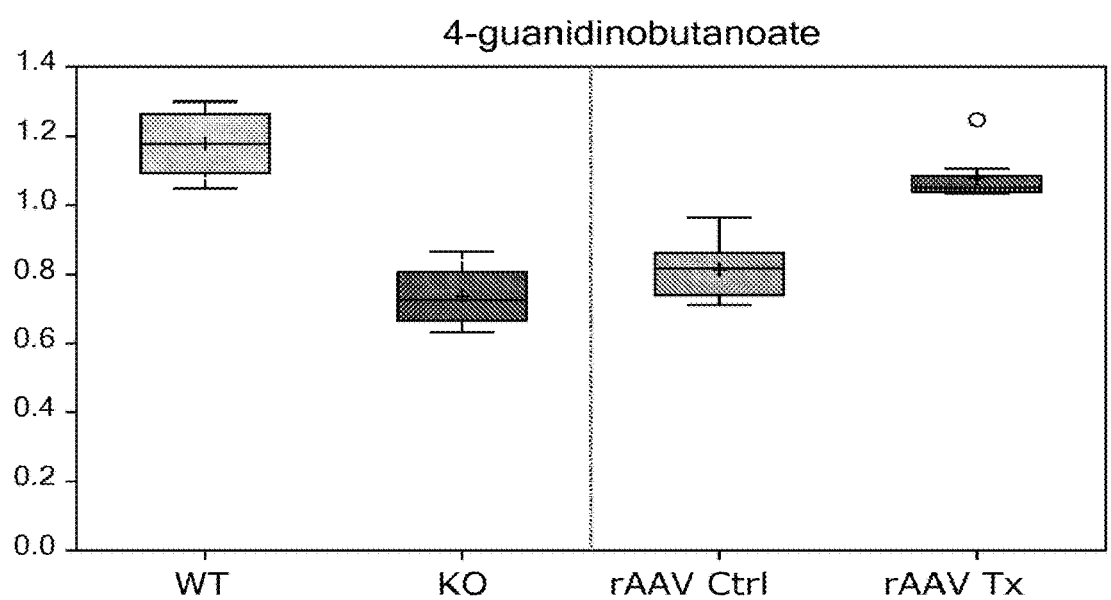
FIG. 57 cont.

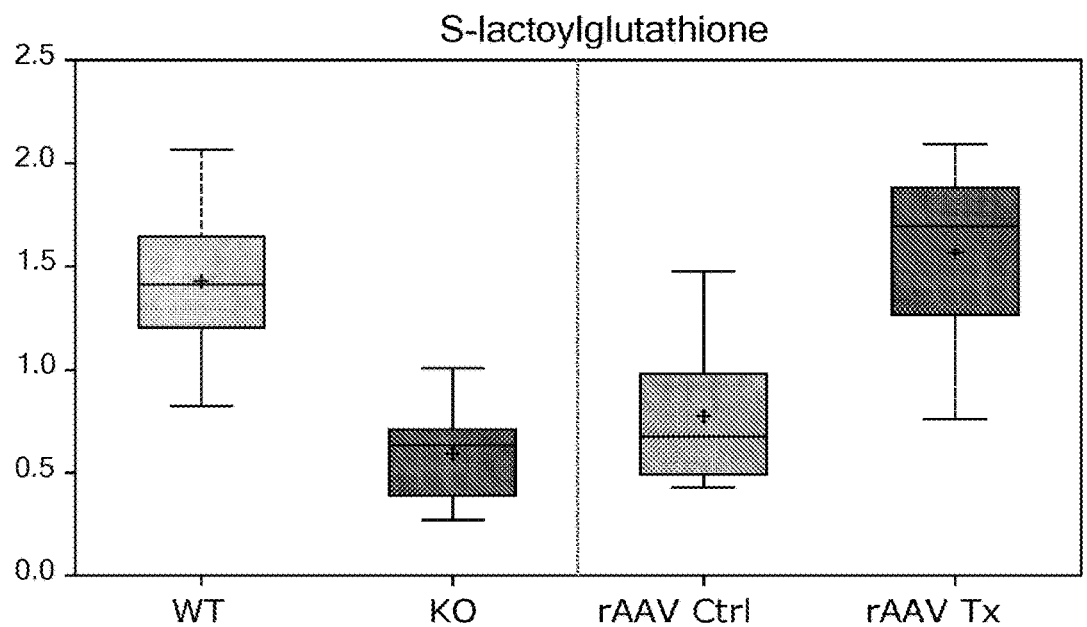
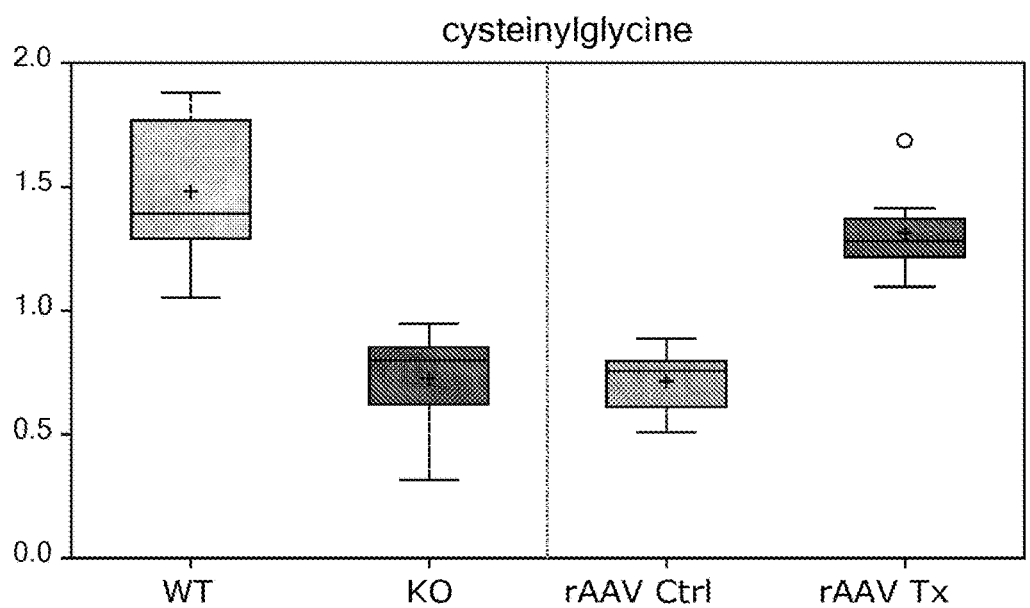
FIG. 57 cont.

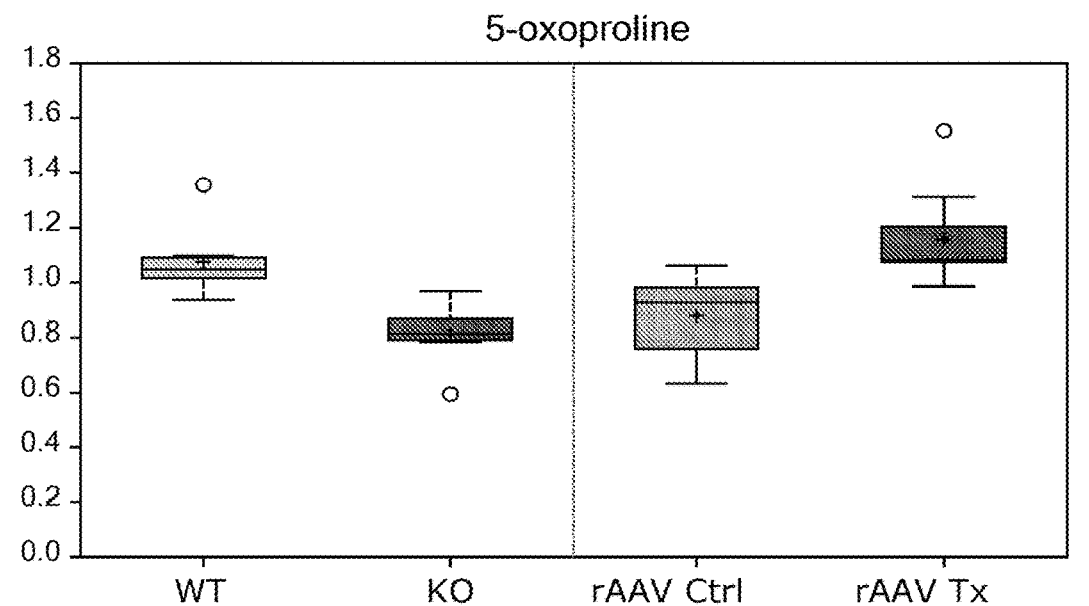
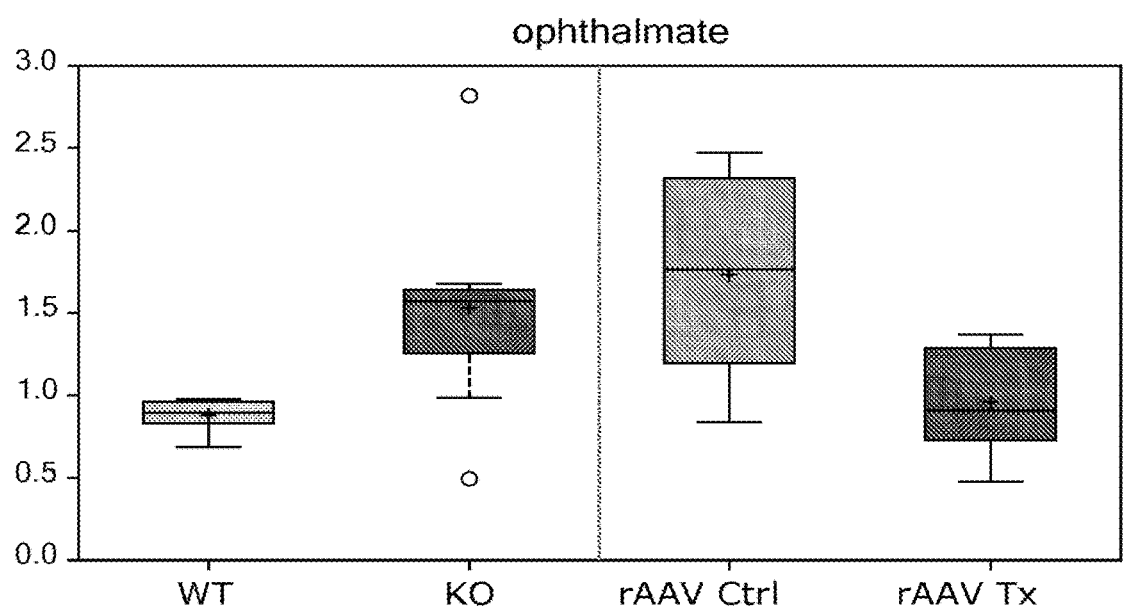
FIG. 57 cont.

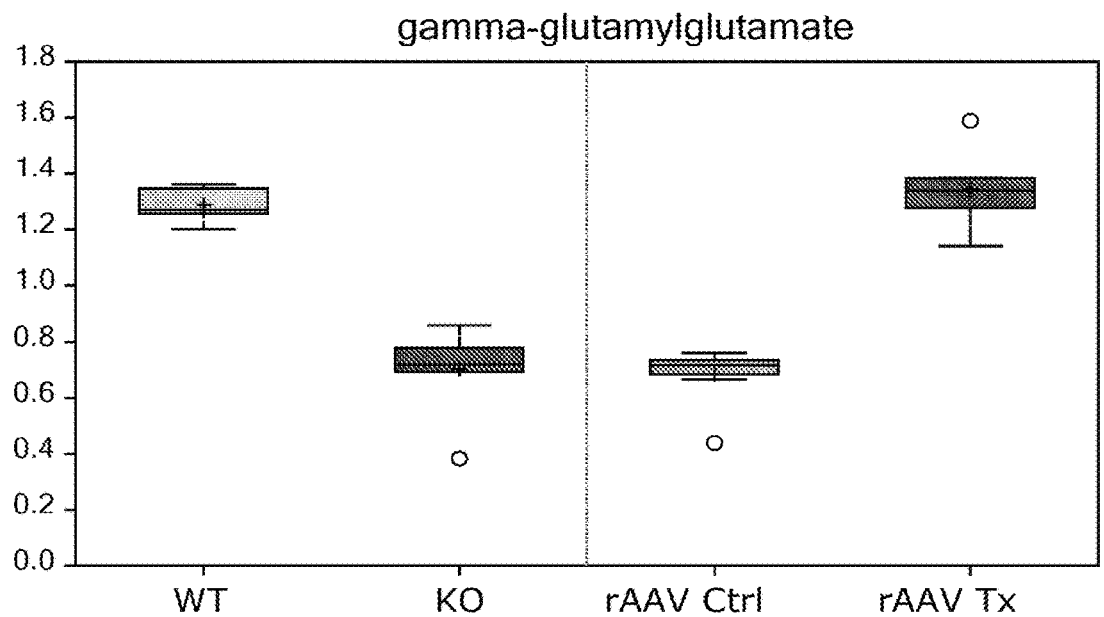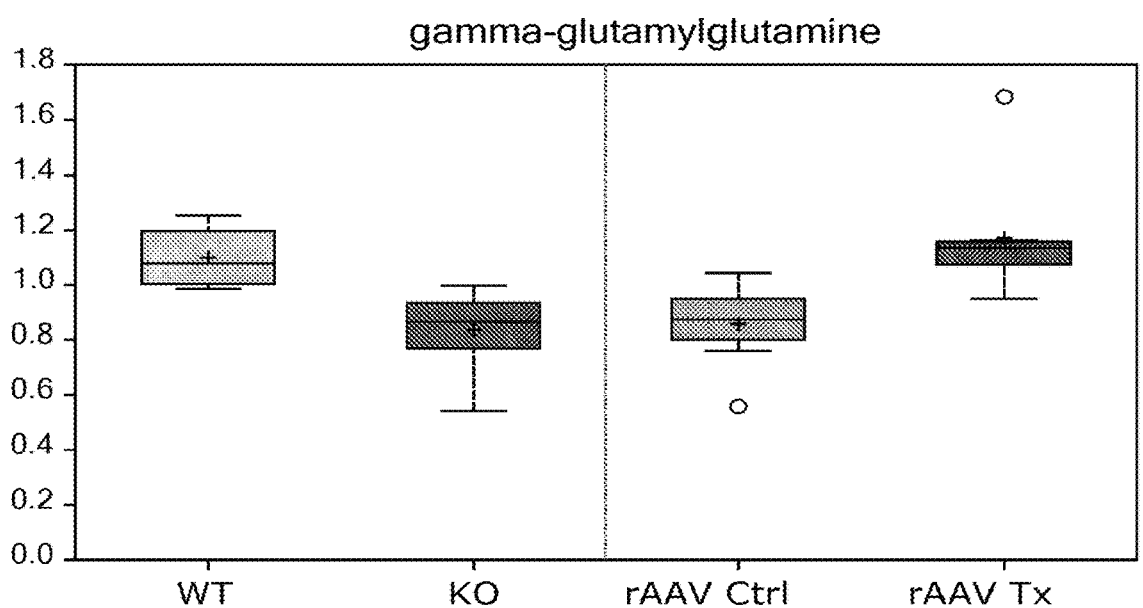
FIG. 57 cont.

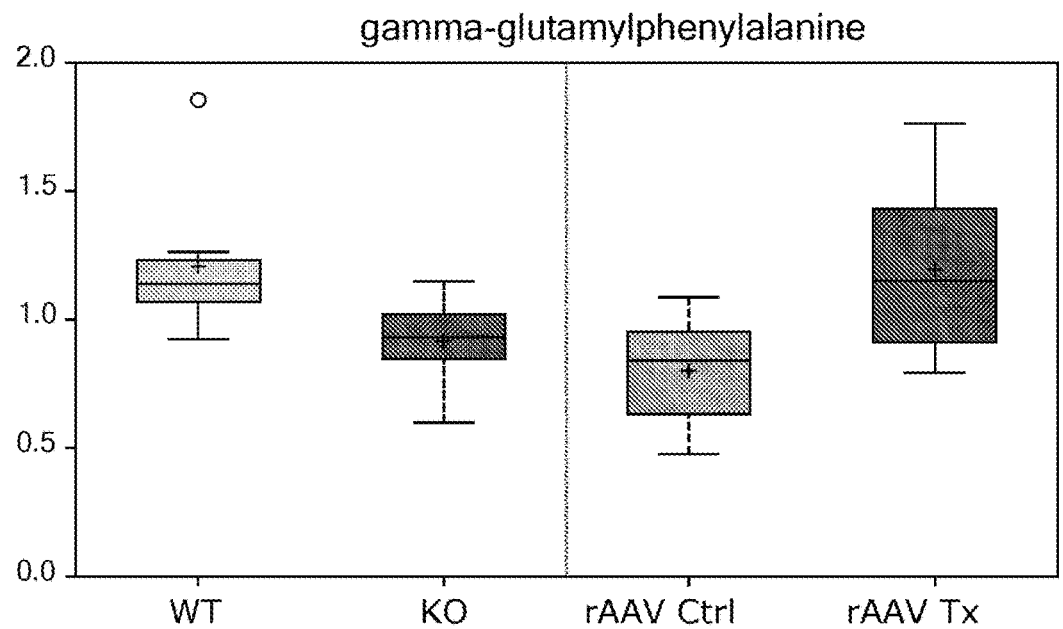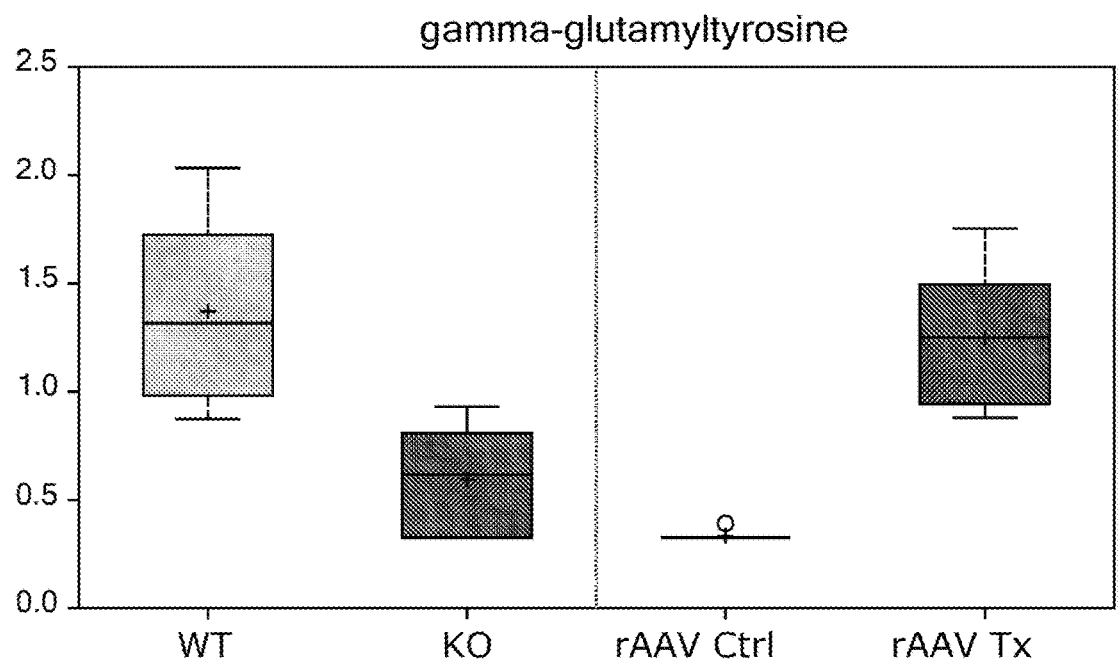
FIG. 57 cont.

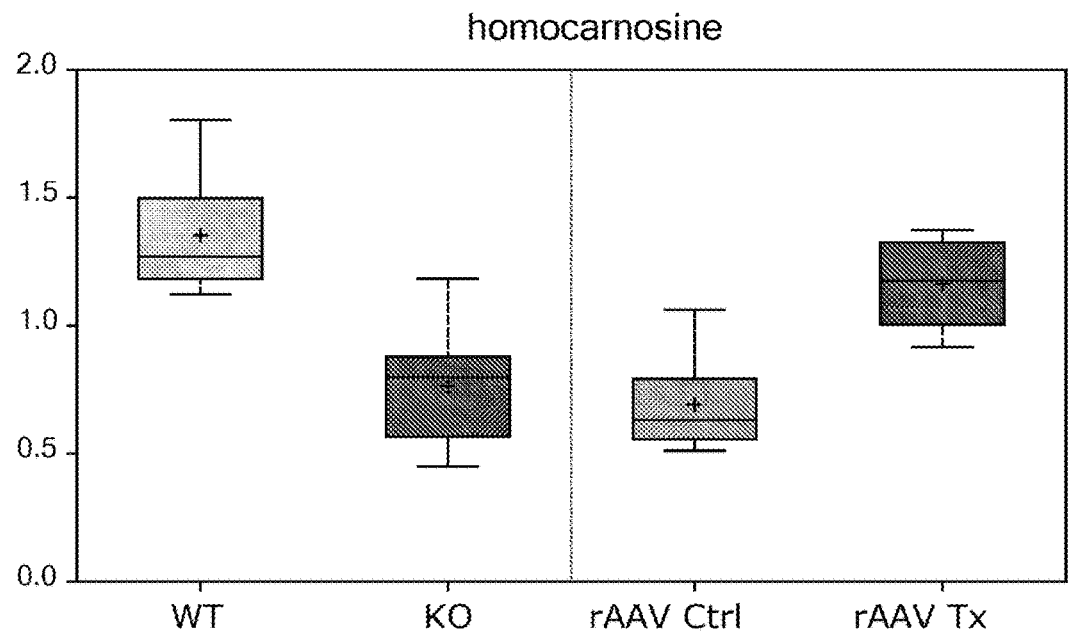
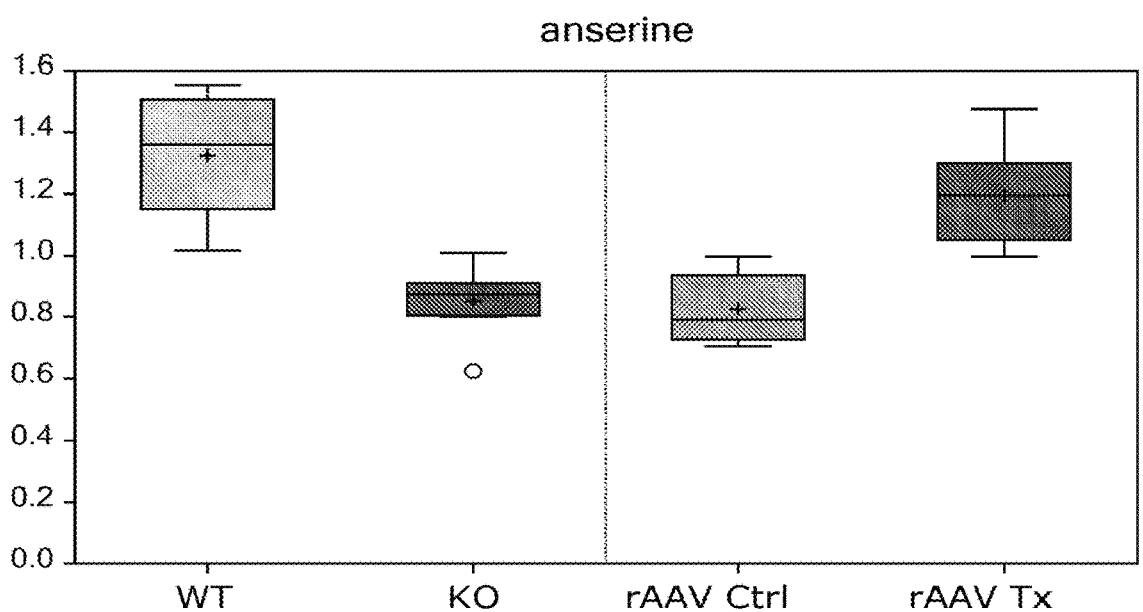
FIG. 57 cont.

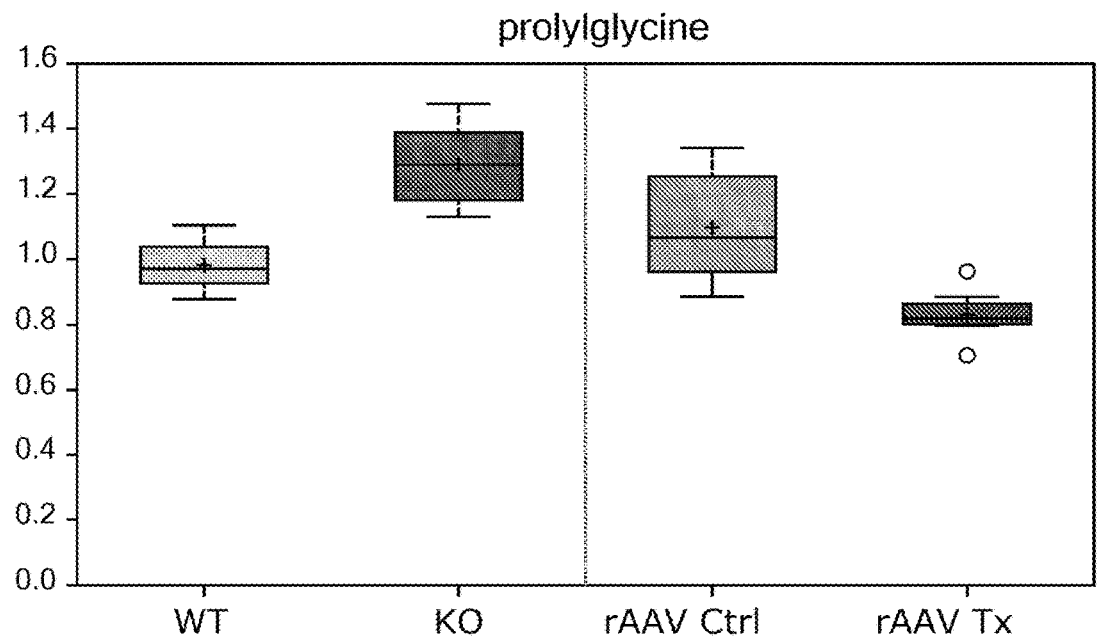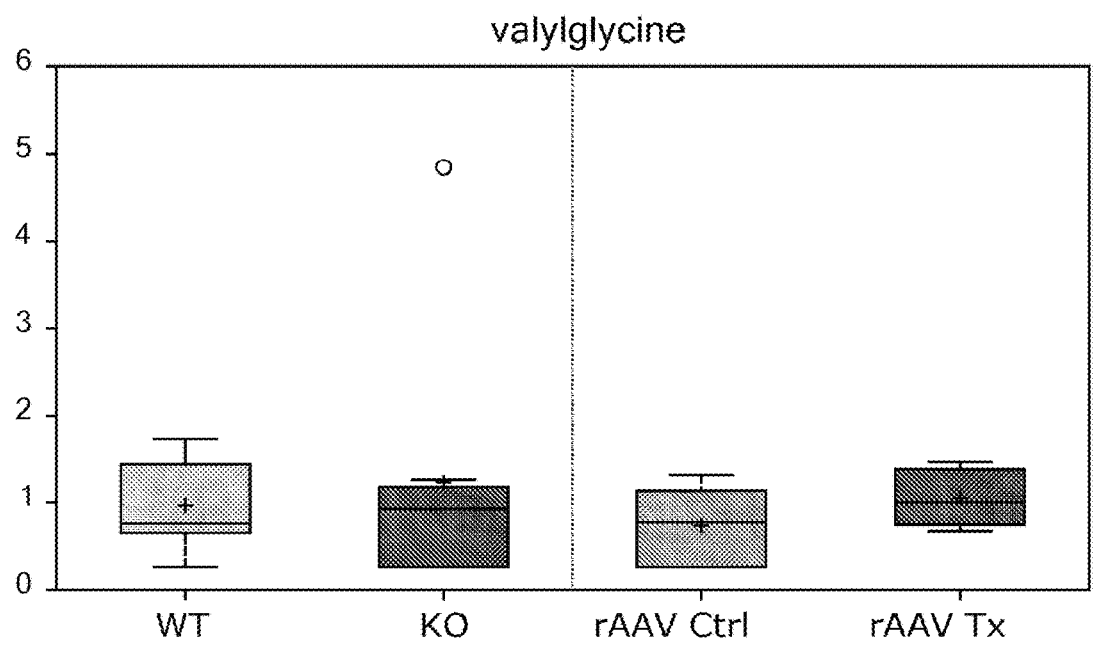
FIG. 57 cont.

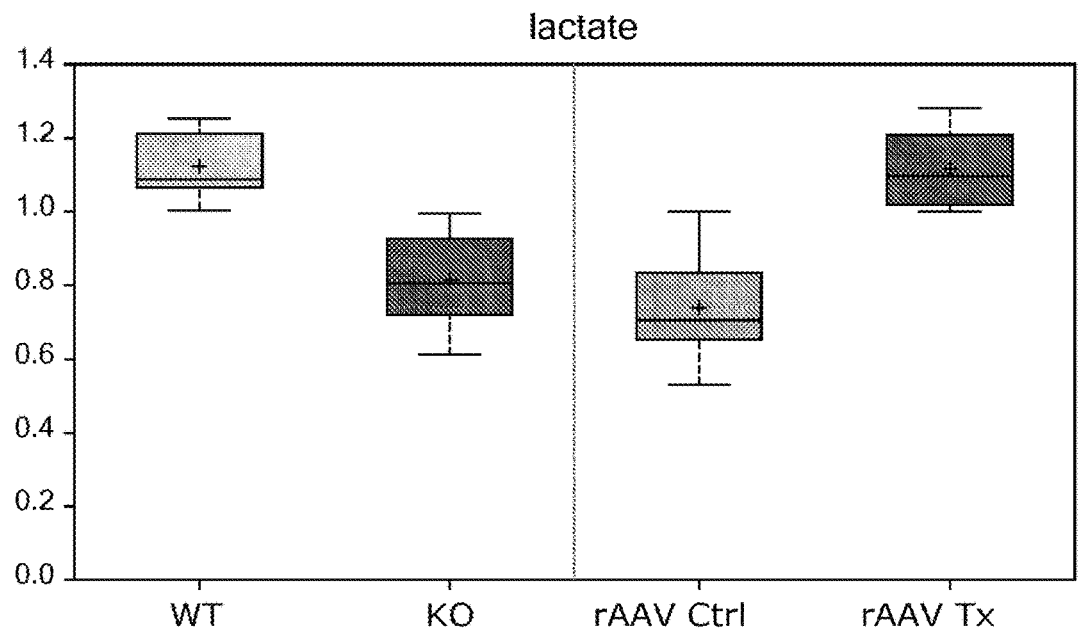
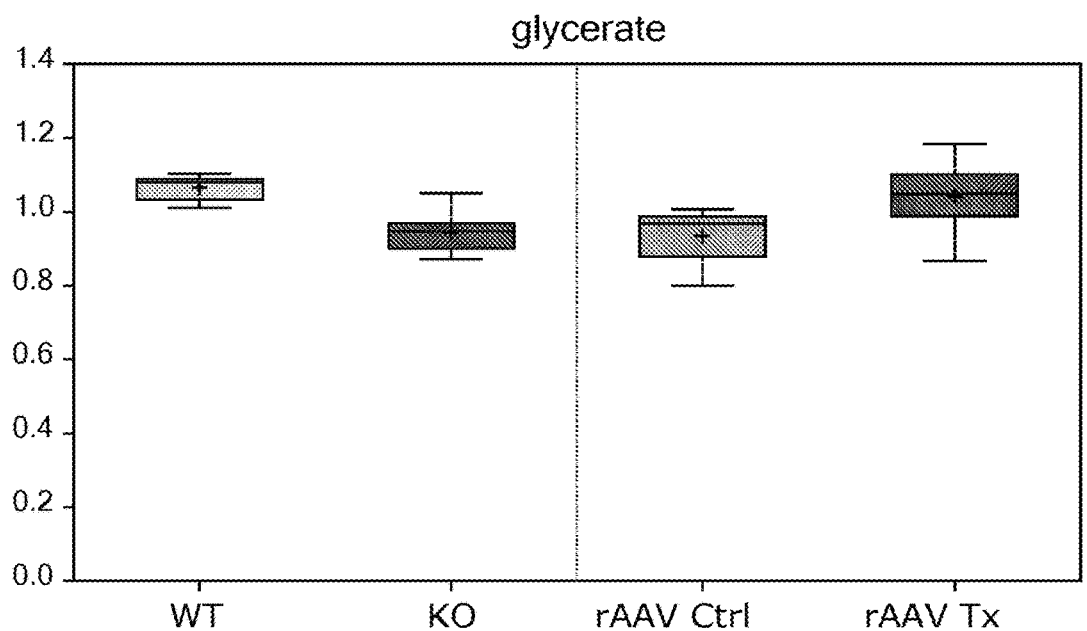
FIG. 57 cont.

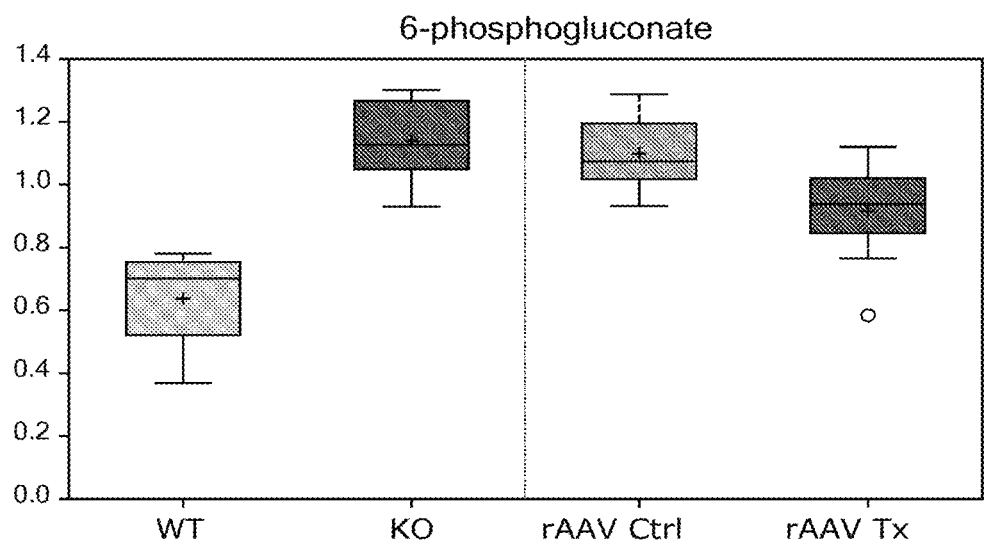
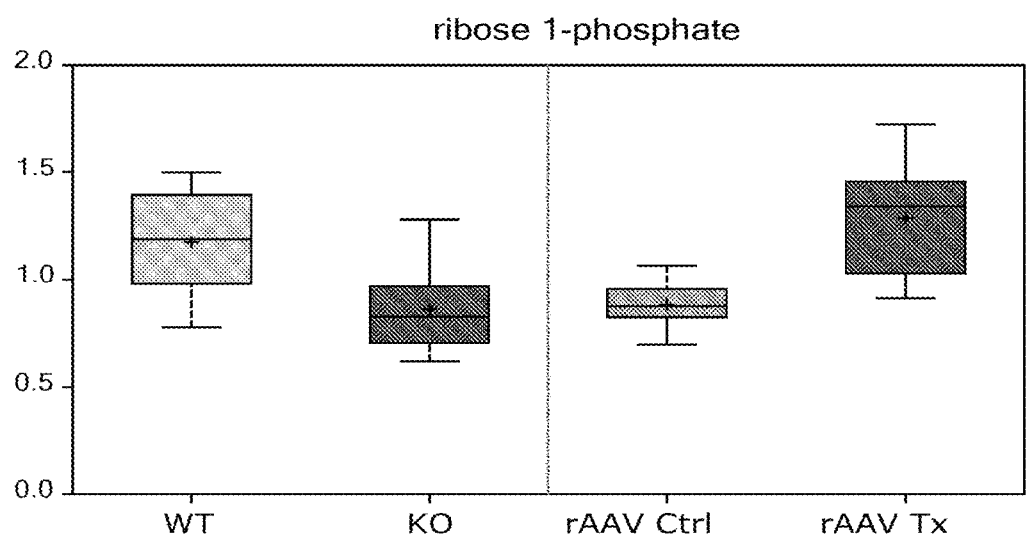
FIG. 57 cont.

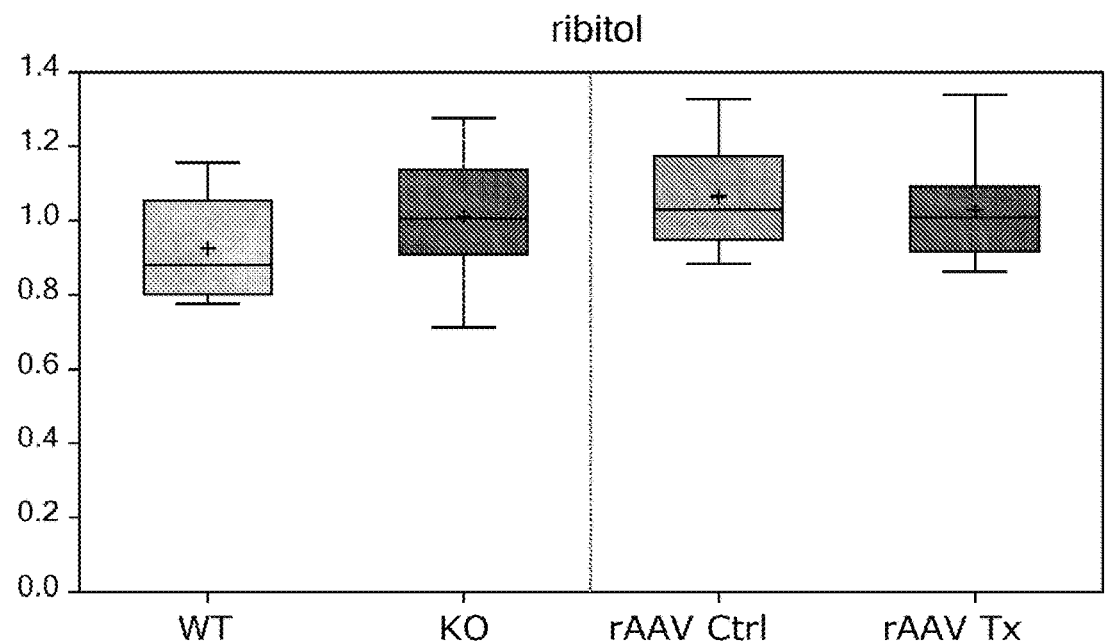
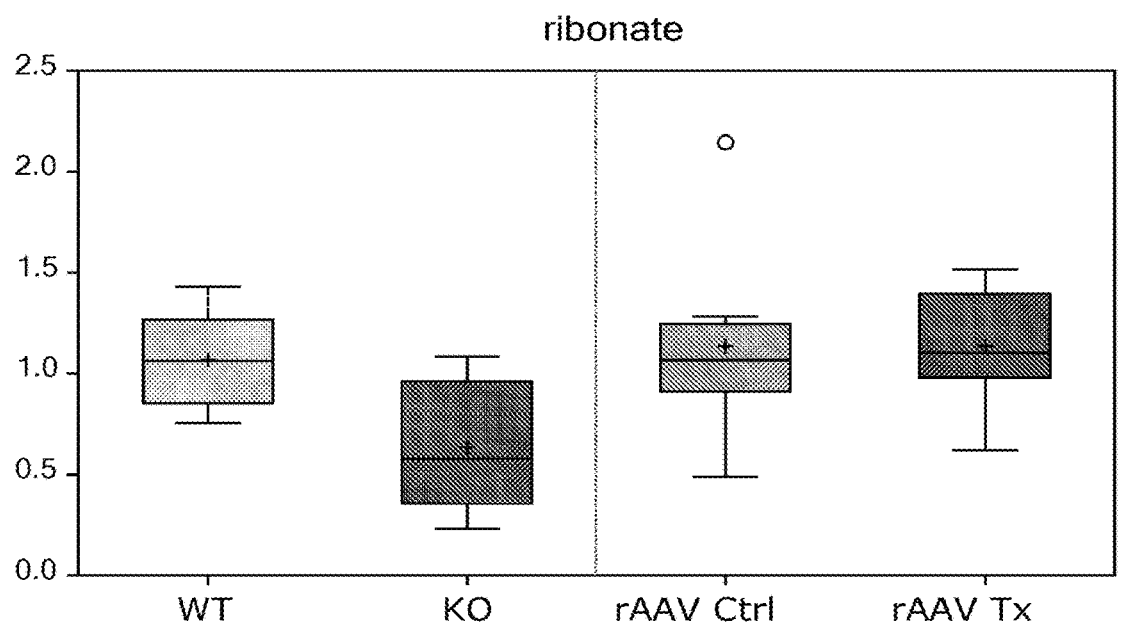
FIG. 57 cont.

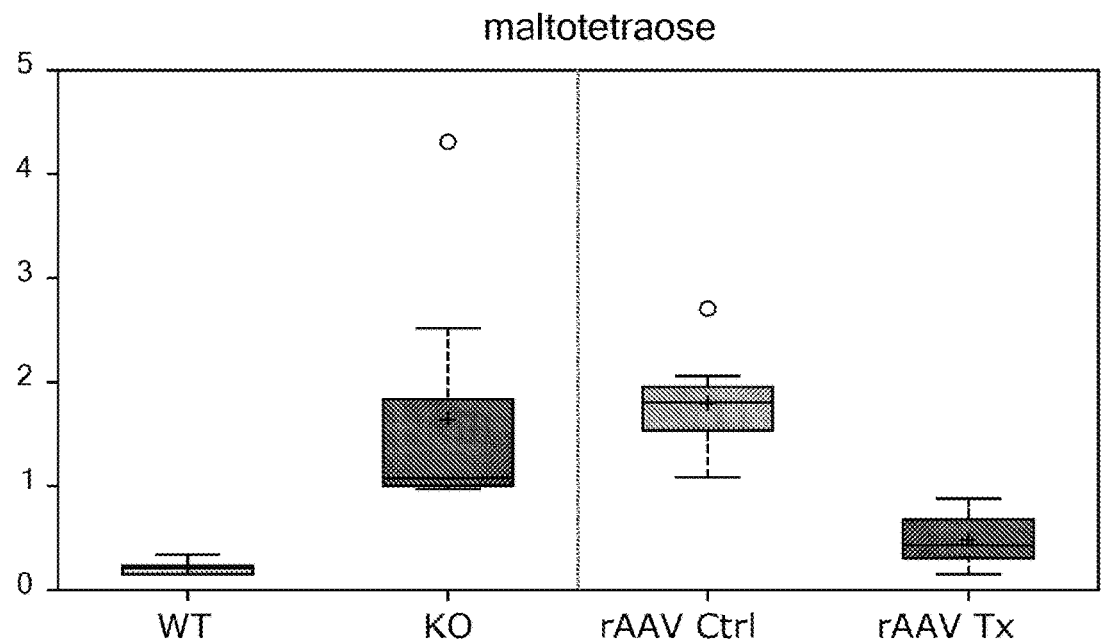
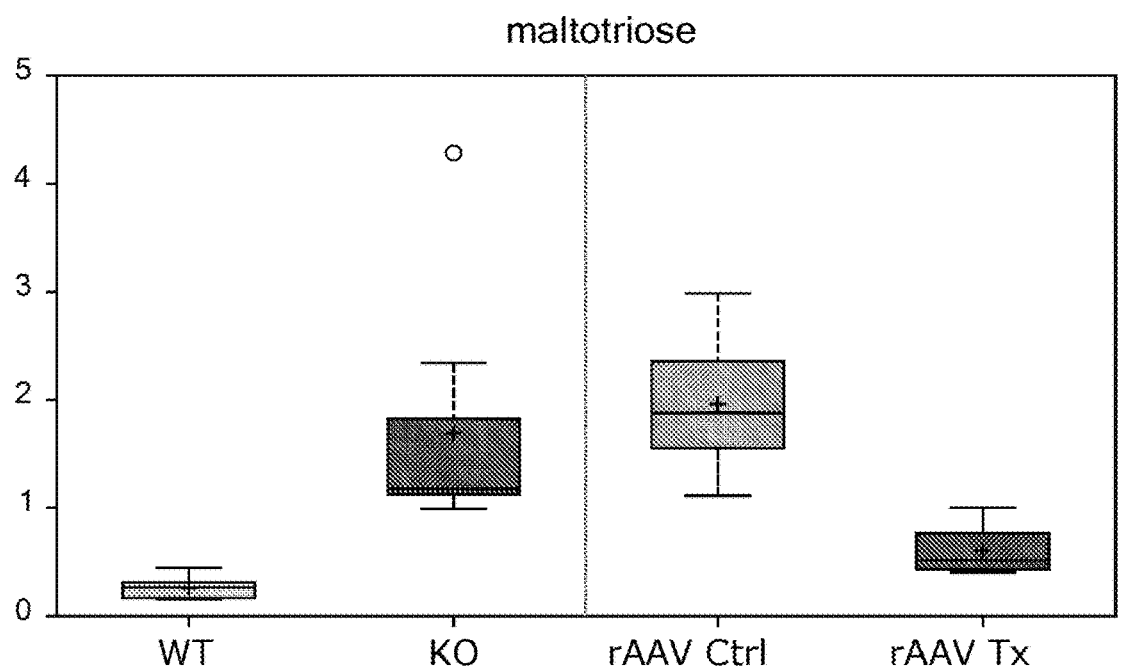
FIG. 57 cont.

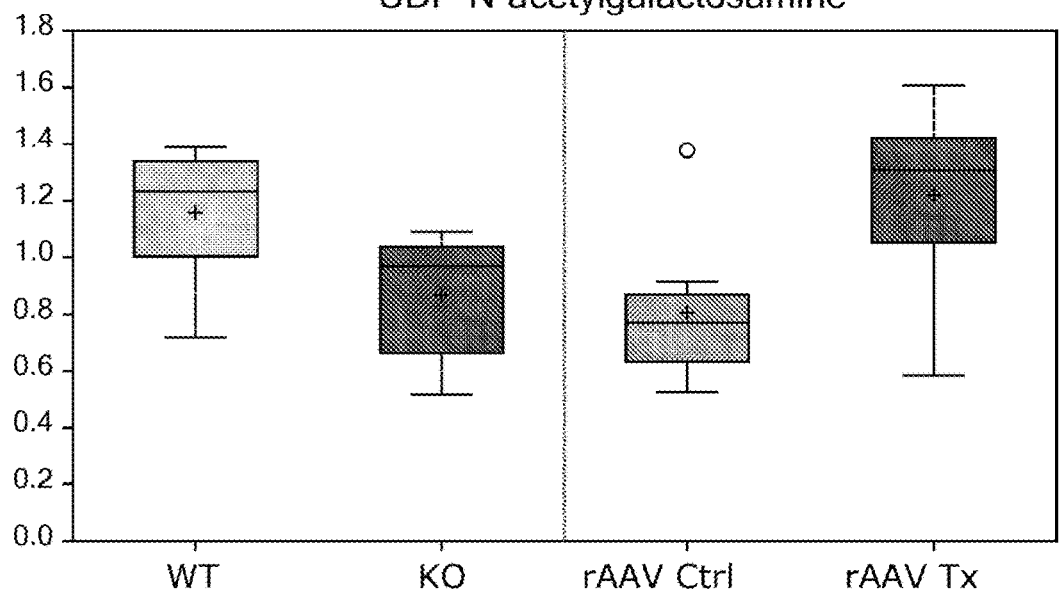
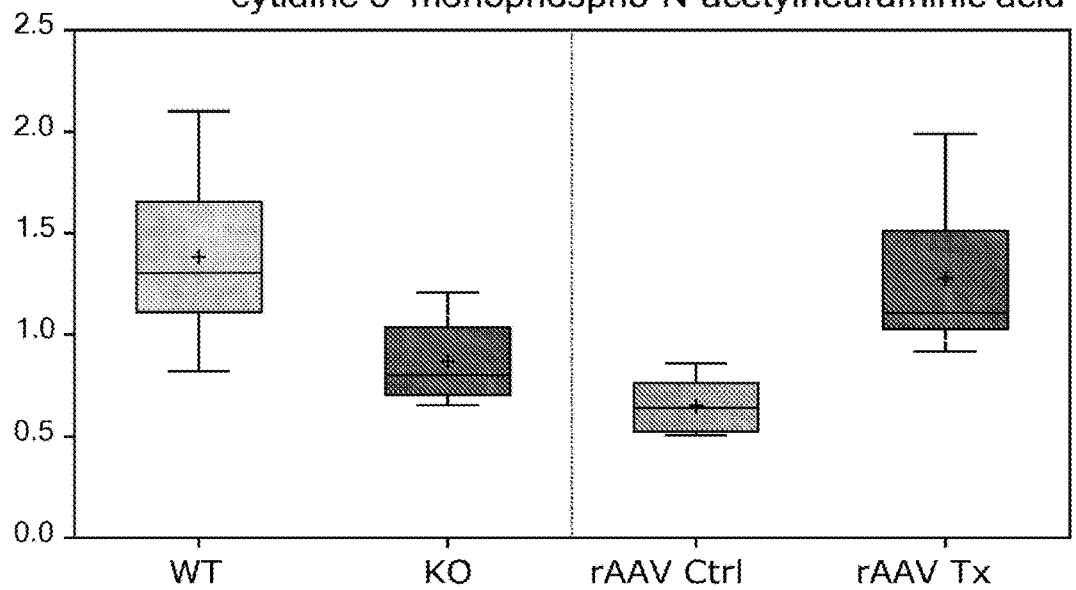
FIG. 57 cont.

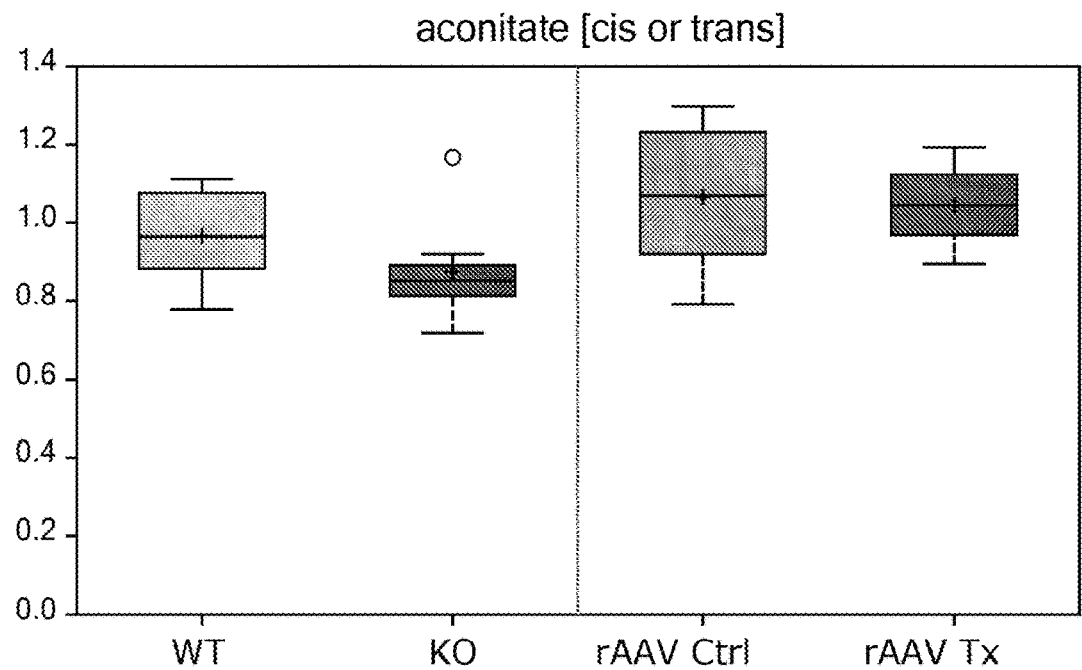
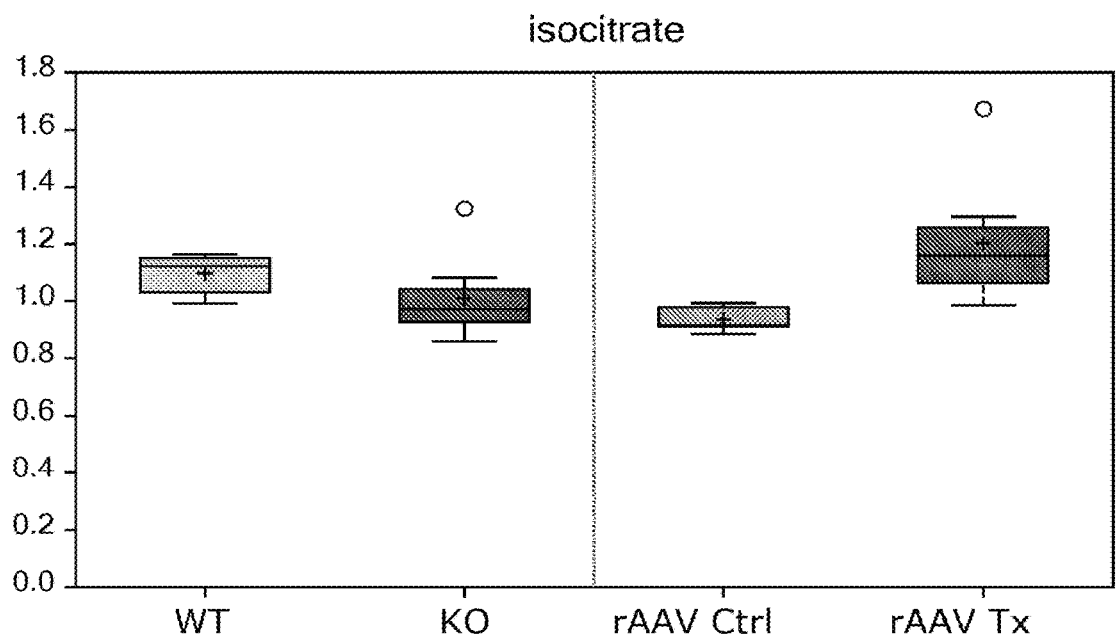
FIG. 57 cont.

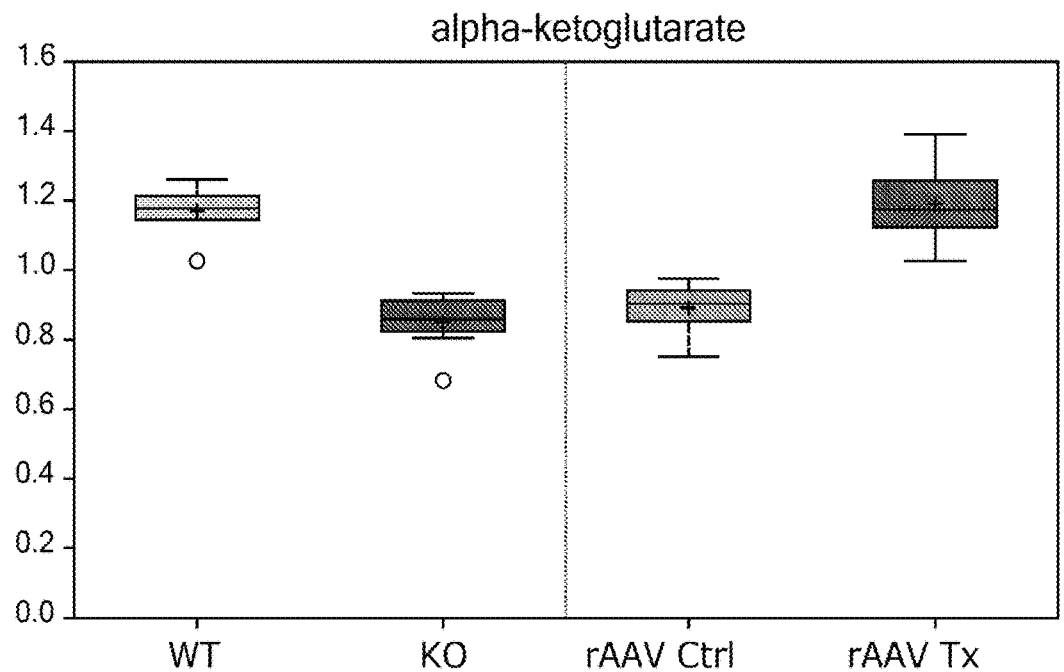
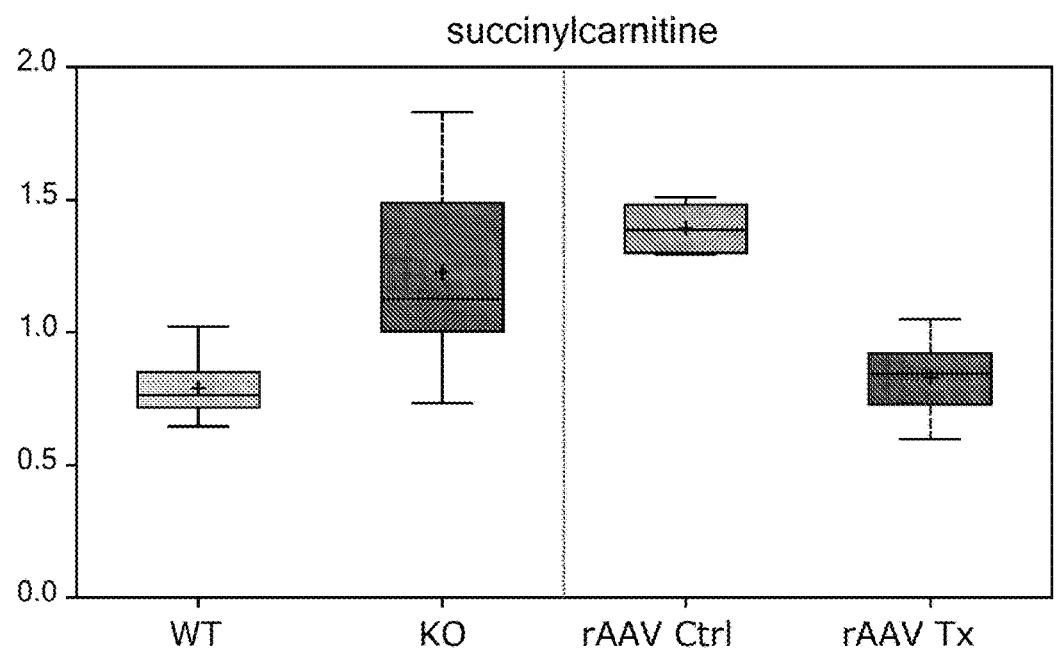
FIG. 57 cont.

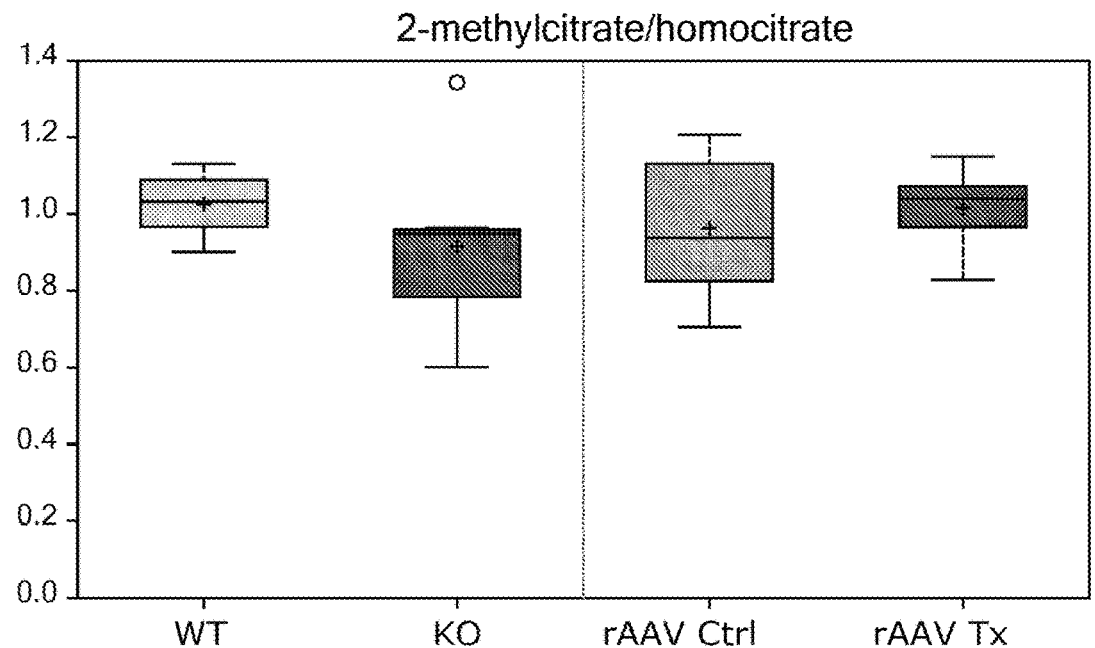
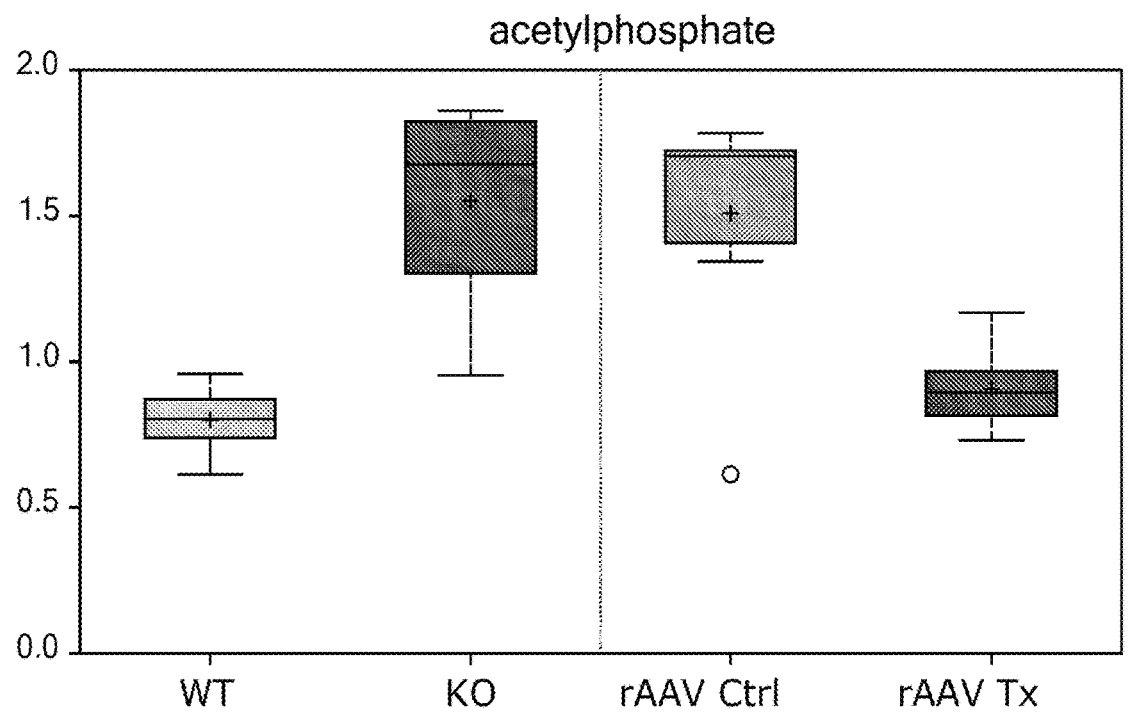
FIG. 57 cont.

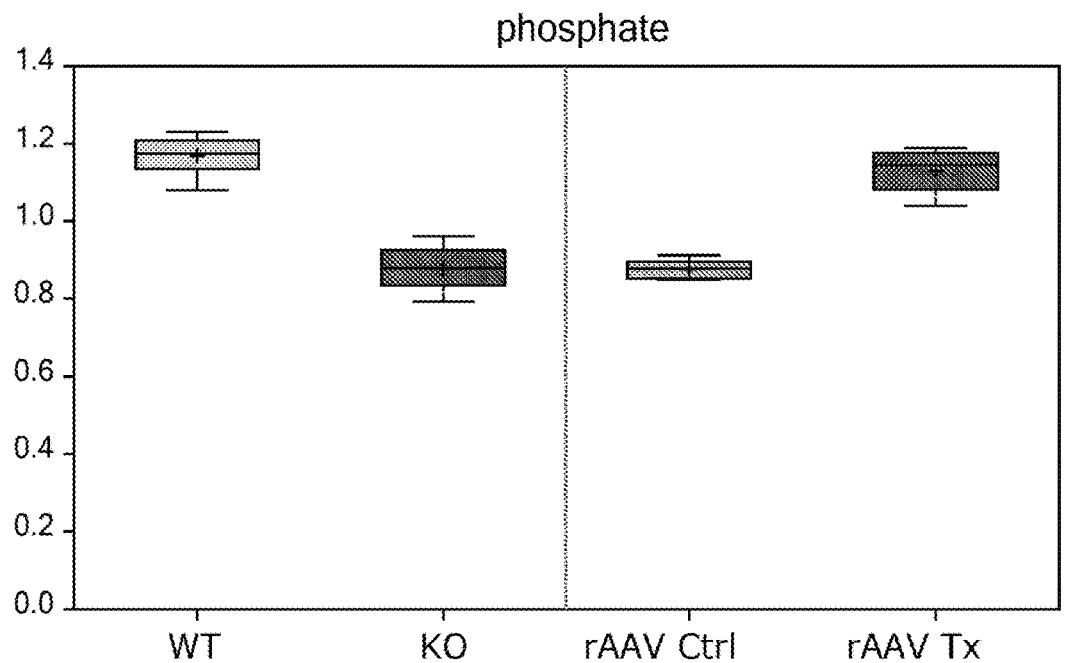
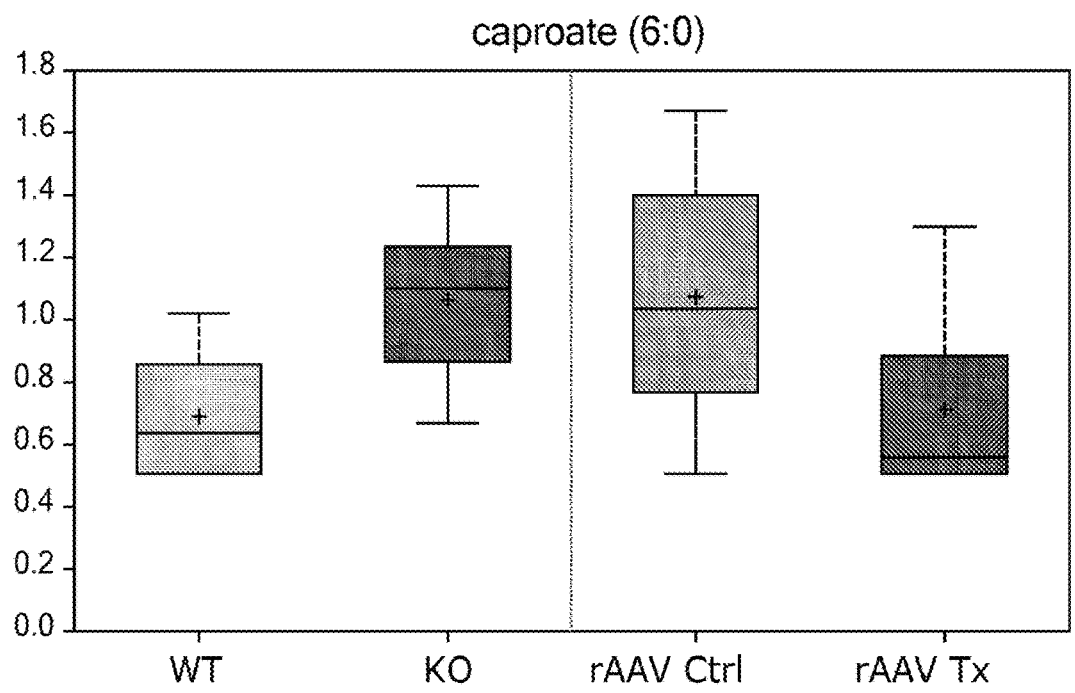
FIG. 57 cont.

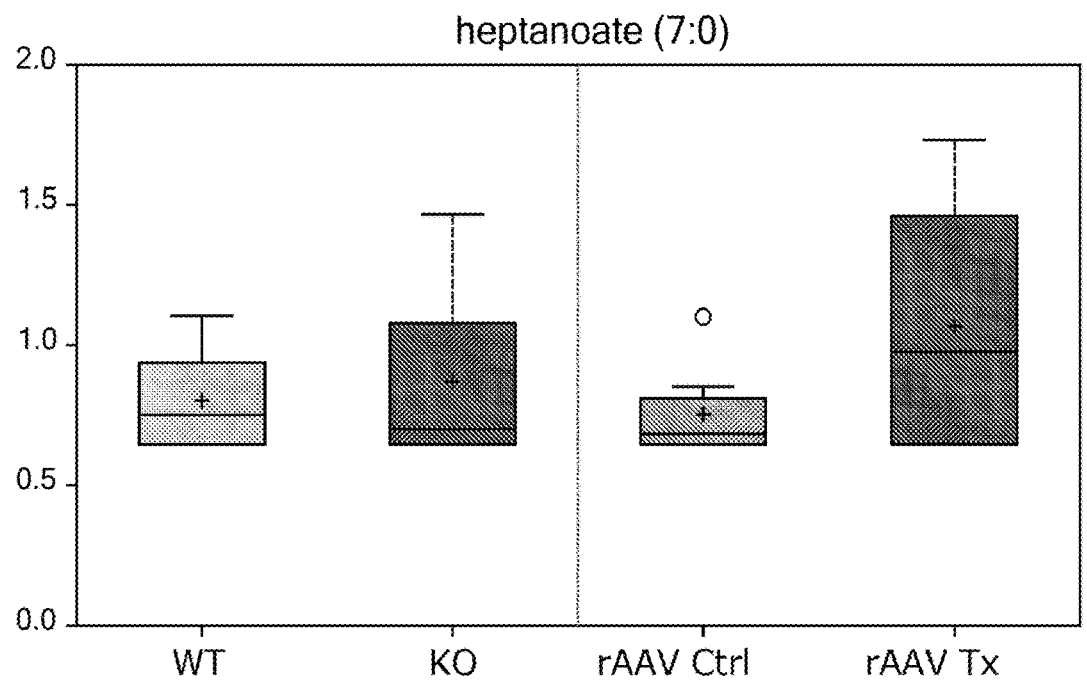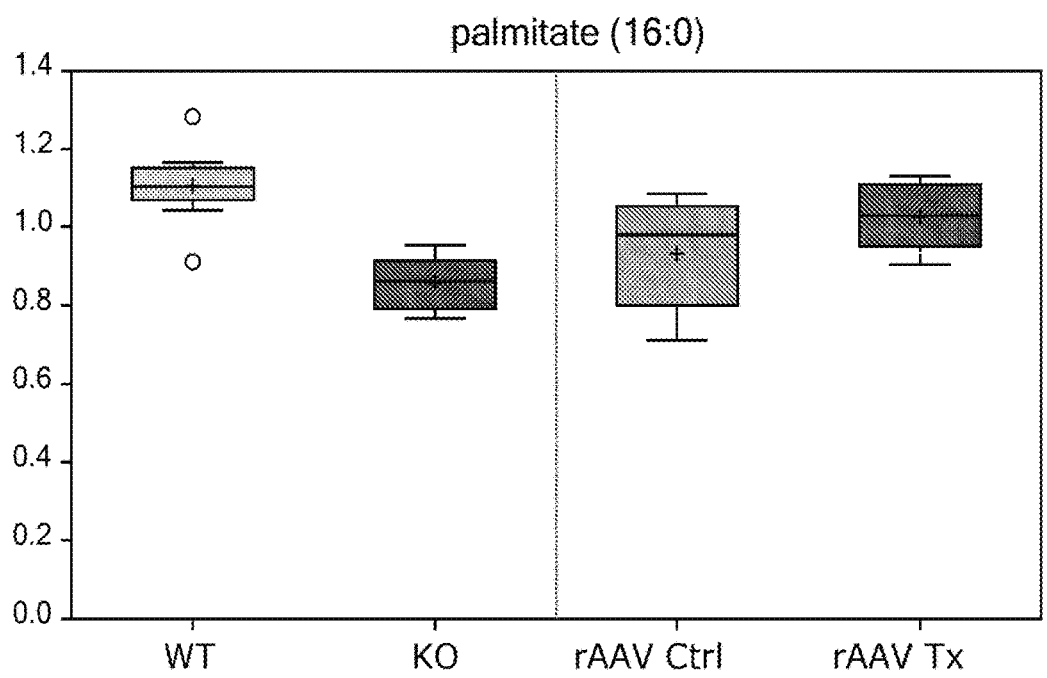
FIG. 57 cont.

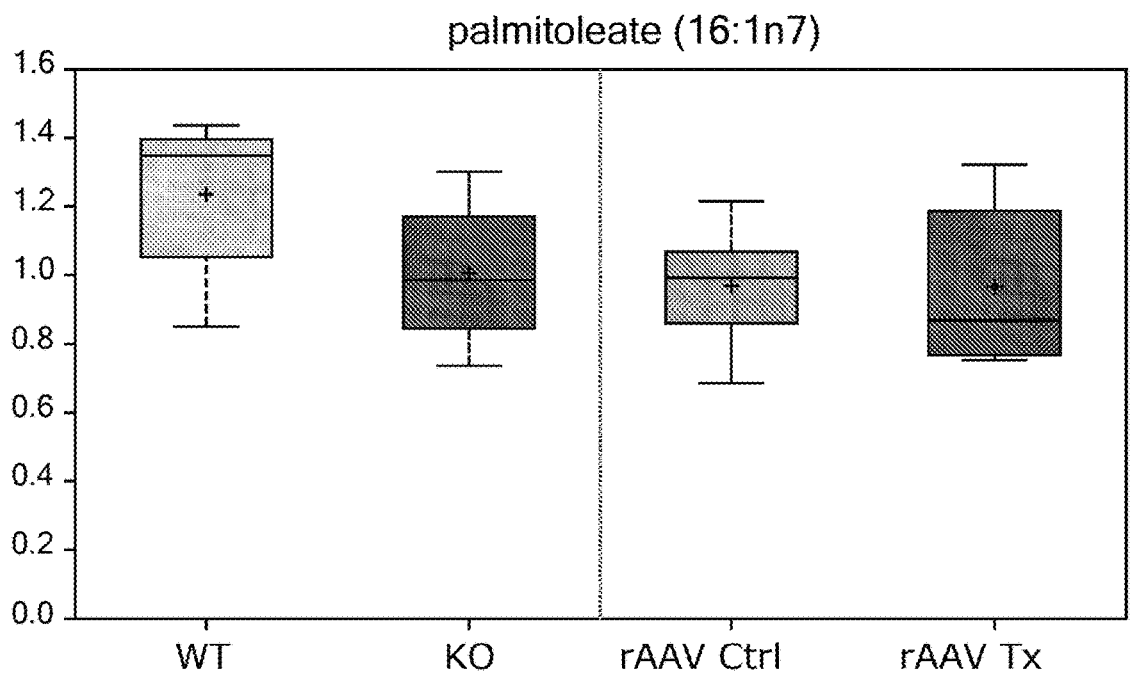
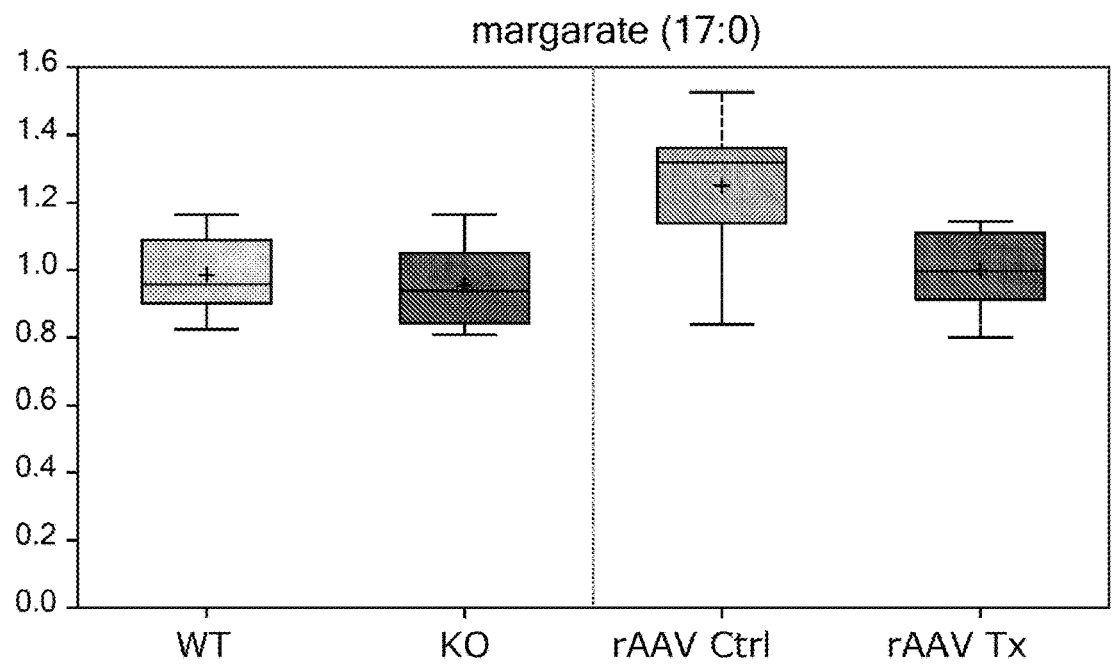
FIG. 57 cont.

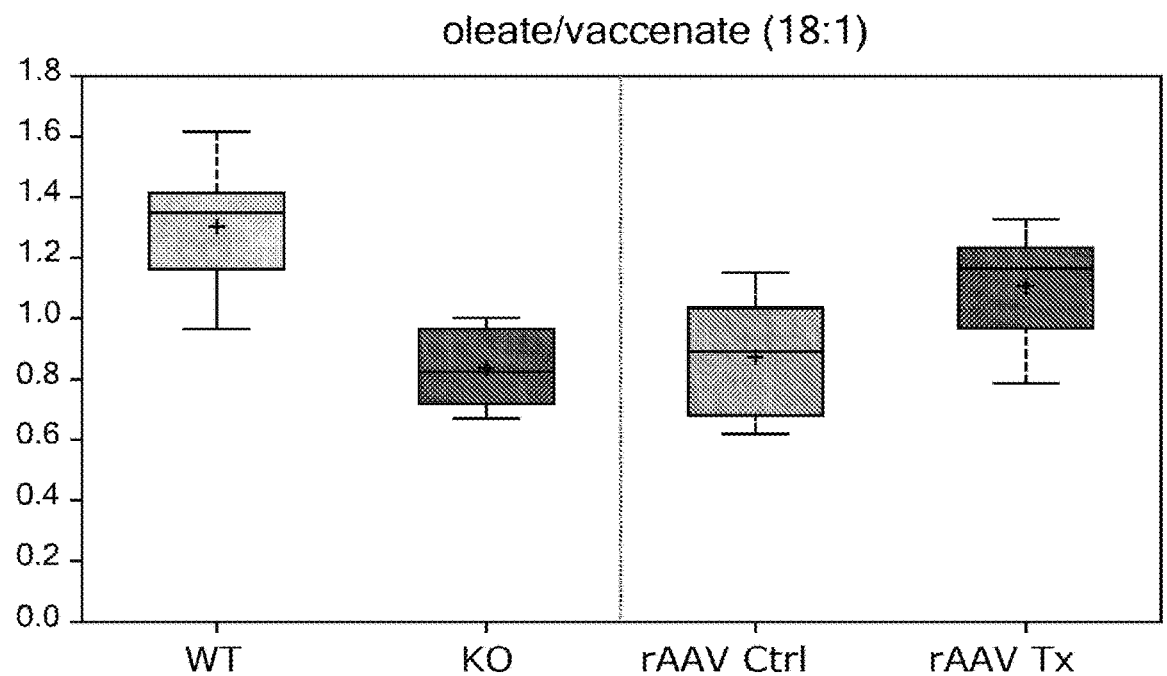
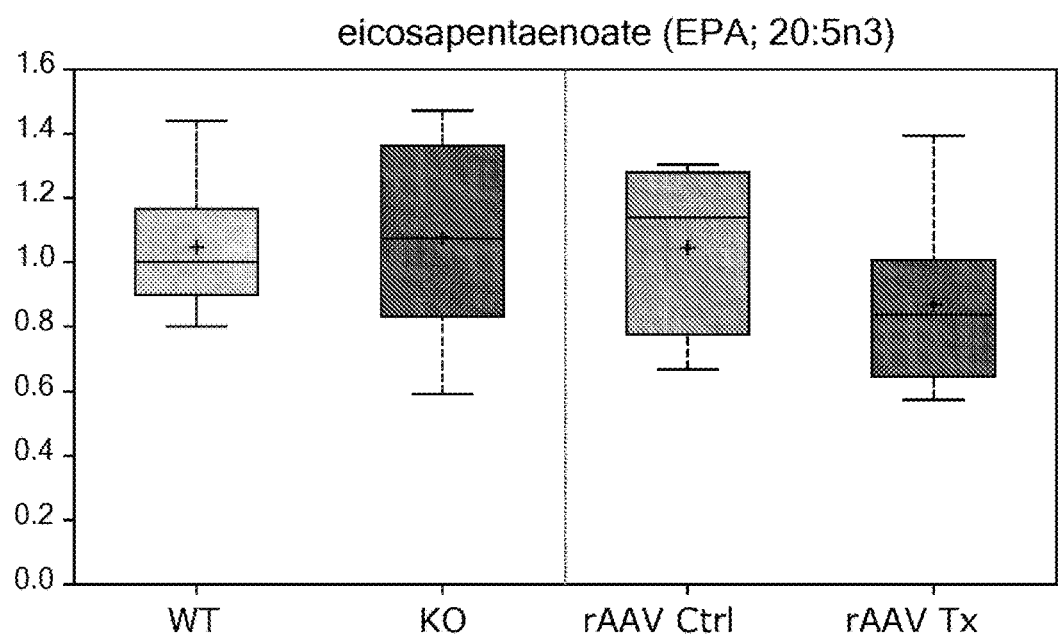
FIG. 57 cont.

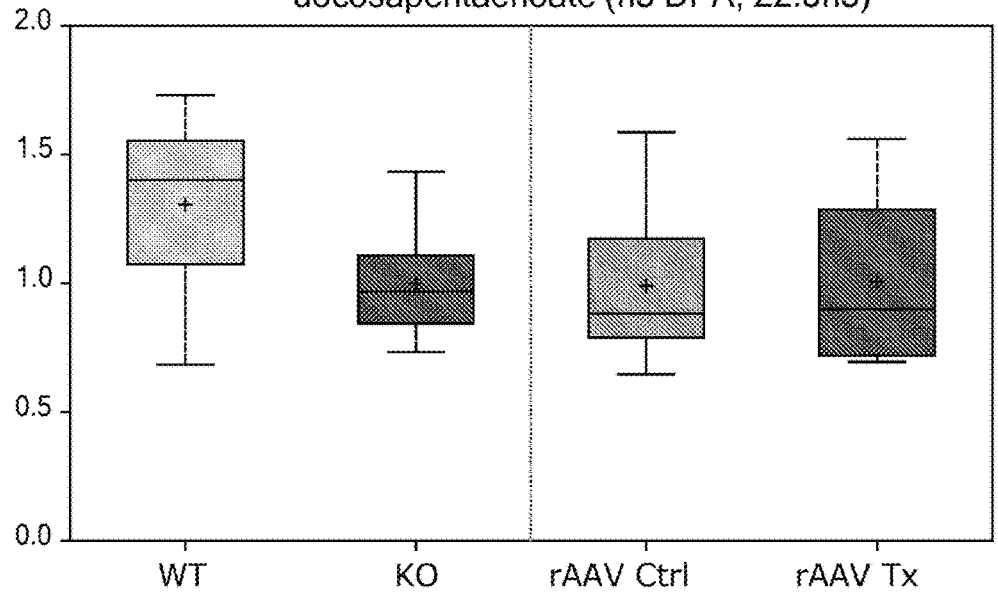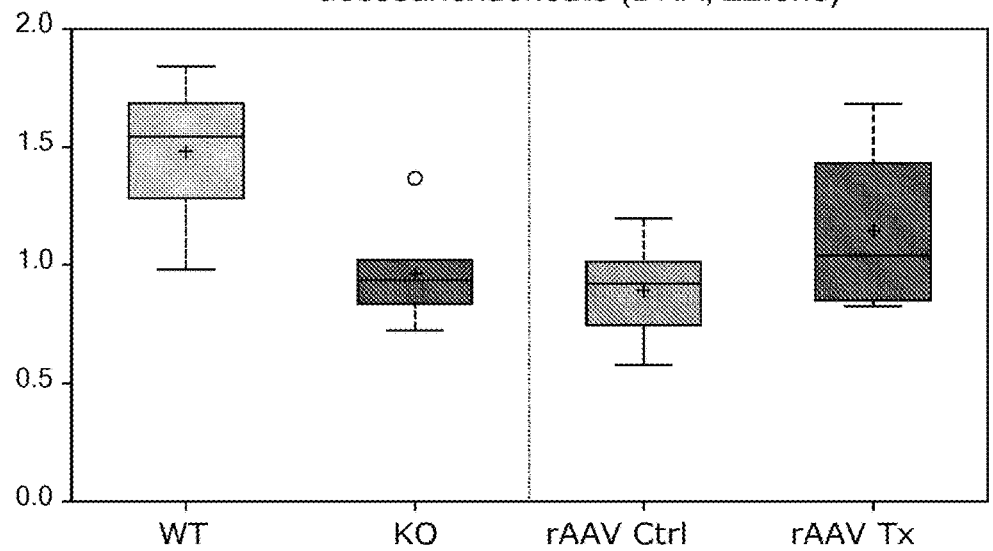
FIG. 57 cont.

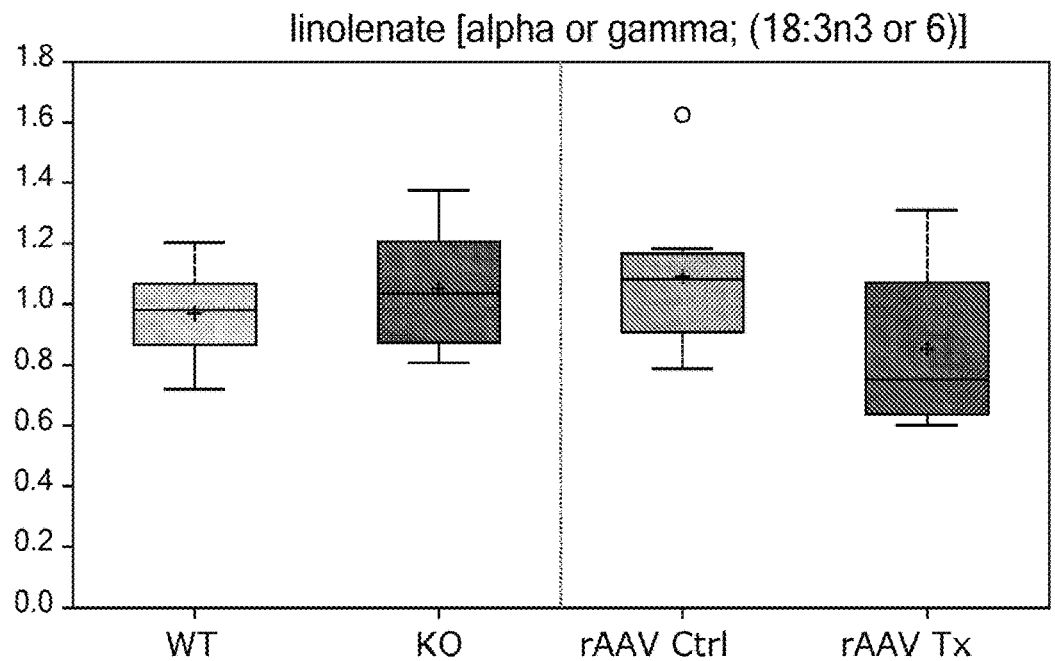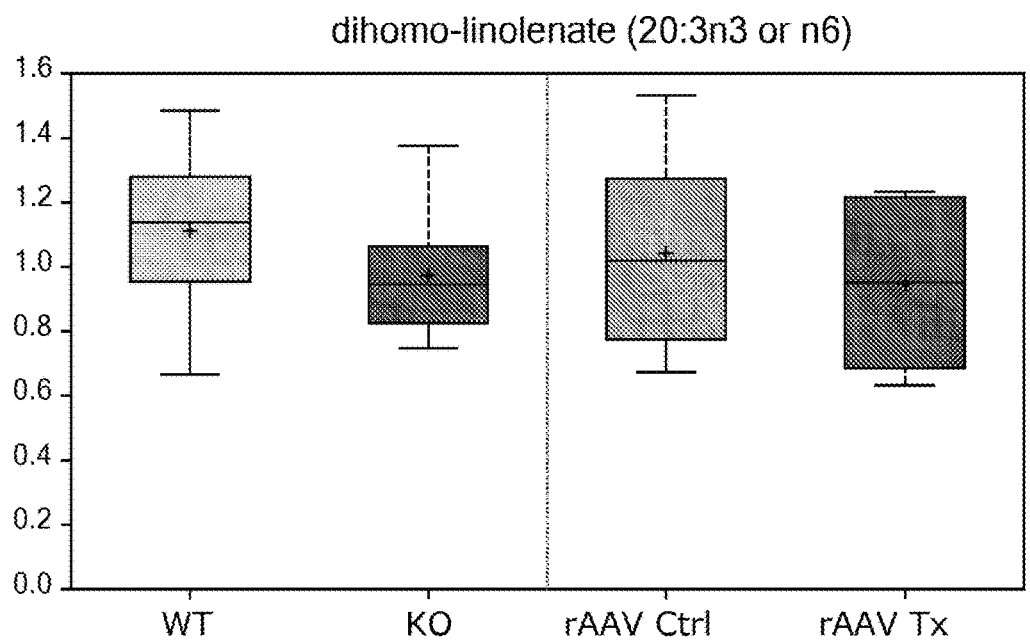
FIG. 57 cont.

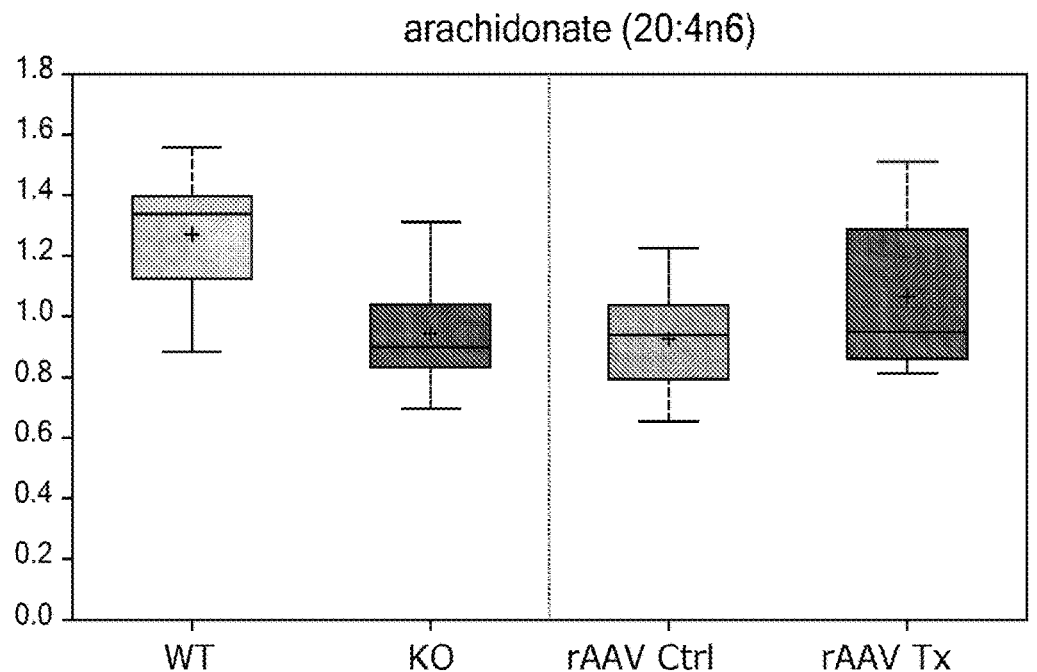
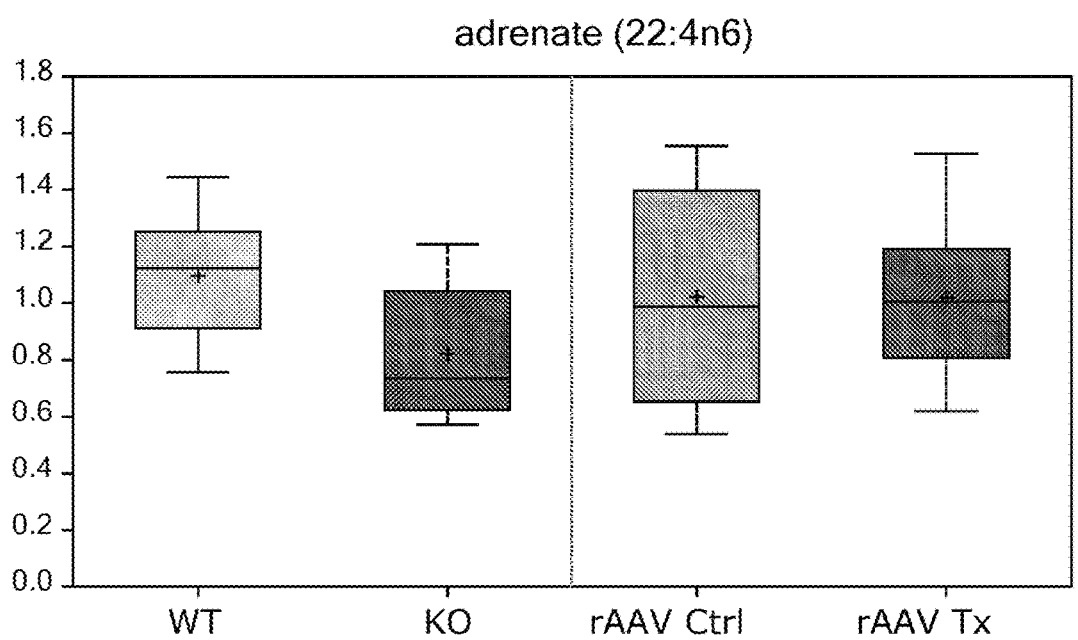
FIG. 57 cont.

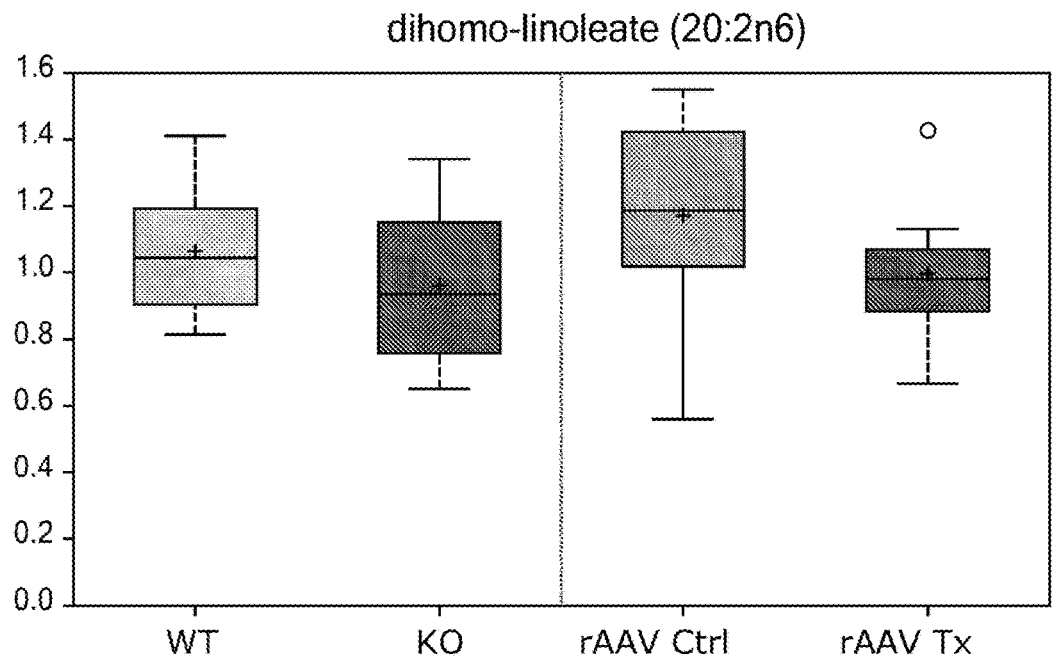
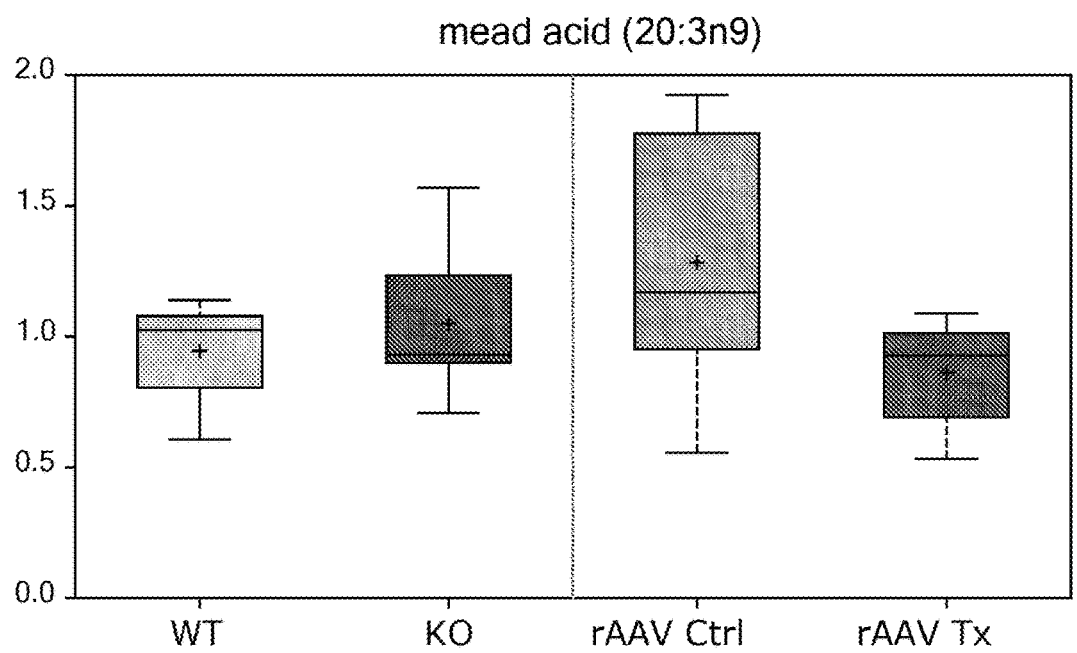
FIG. 57 cont.

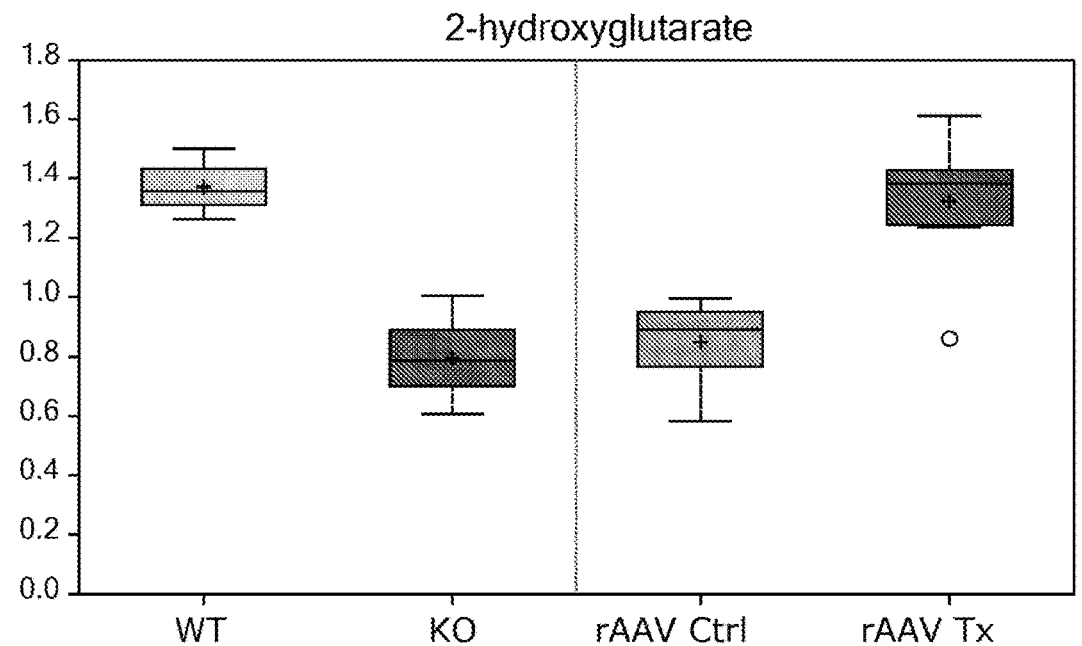
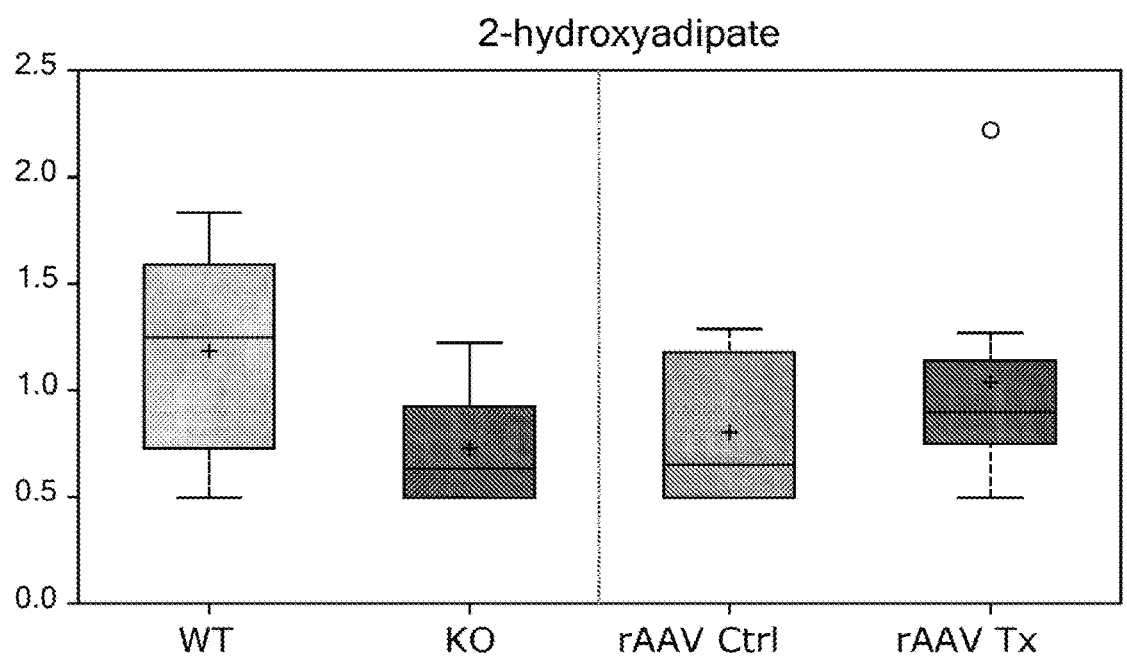
FIG. 57 cont.

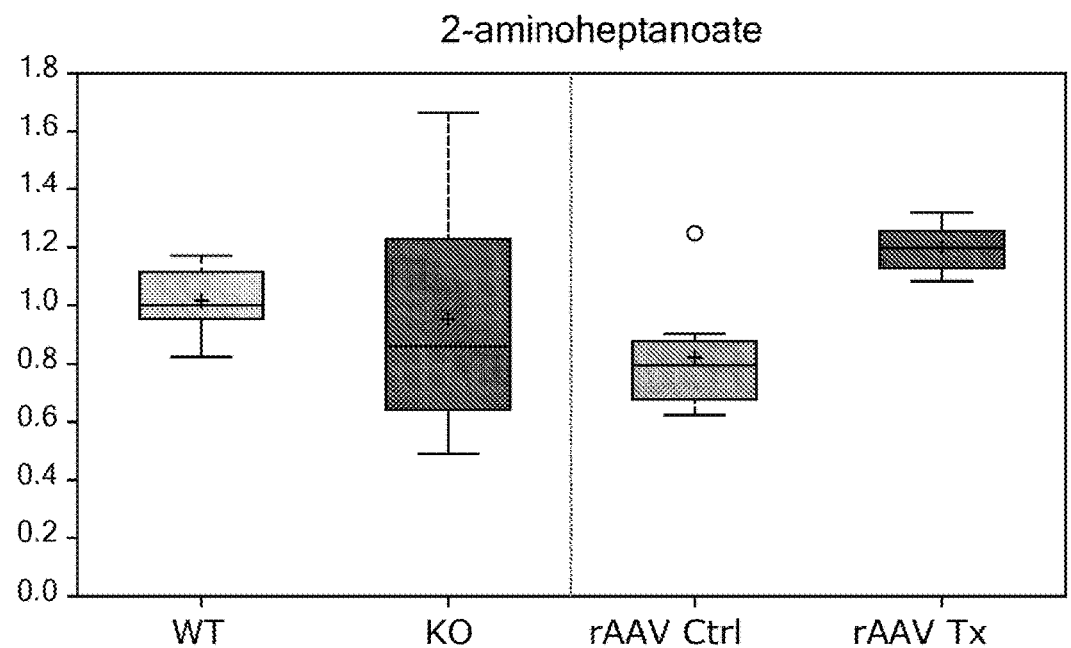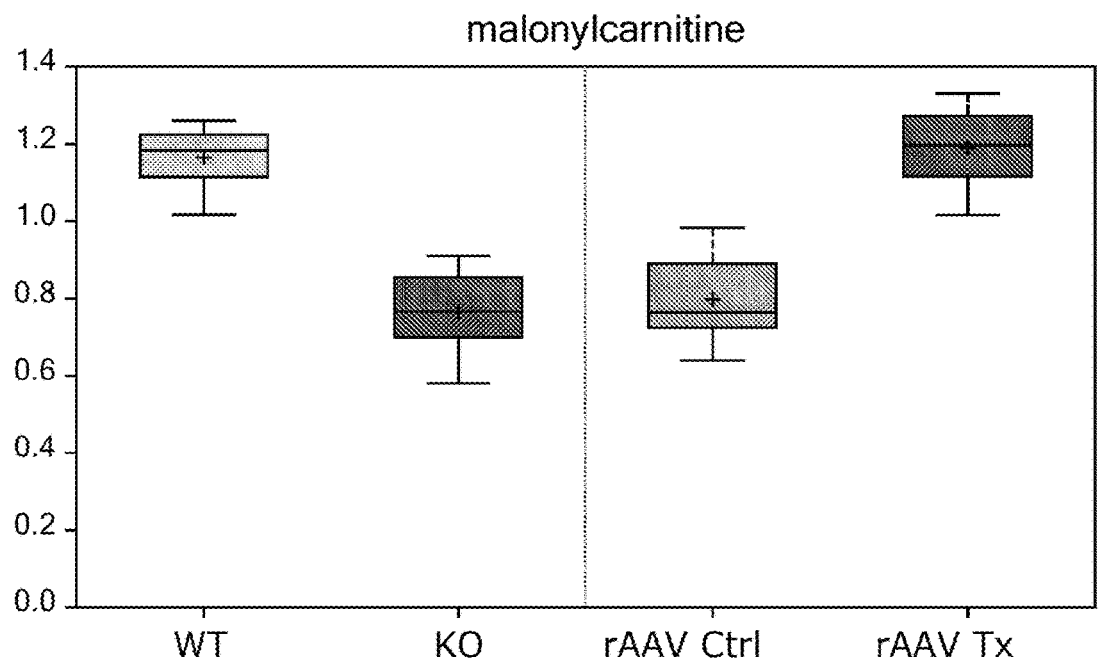
FIG. 57 cont.

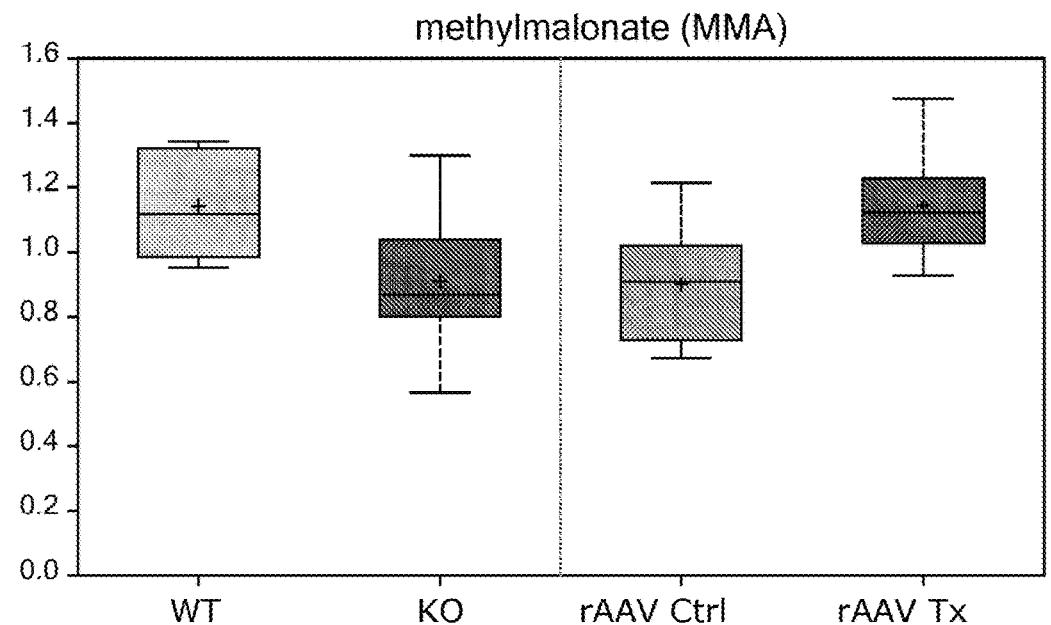
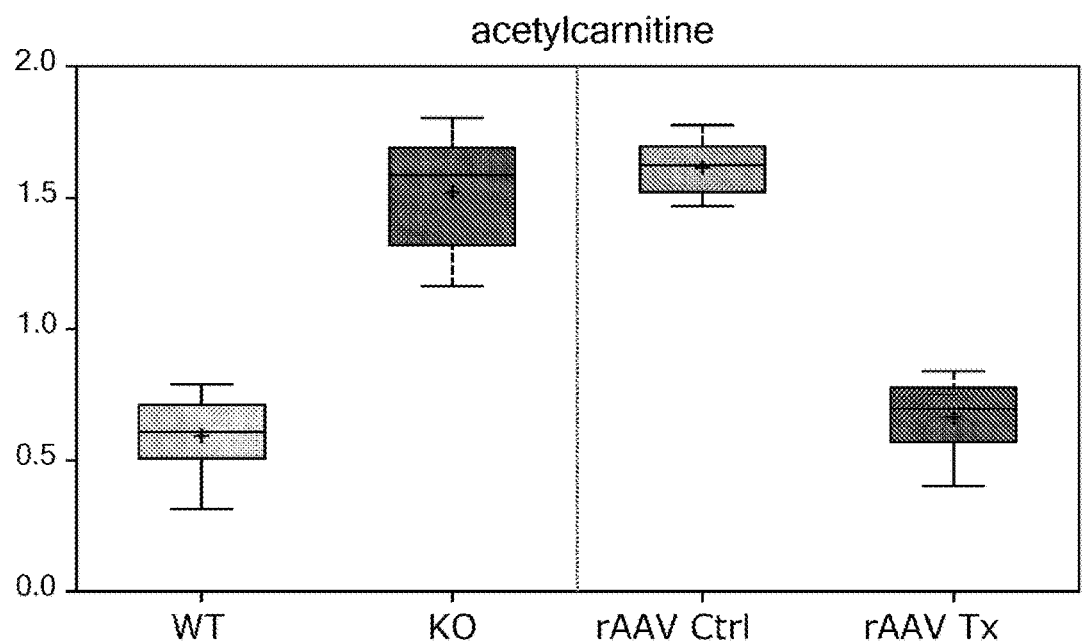
FIG. 57 cont.

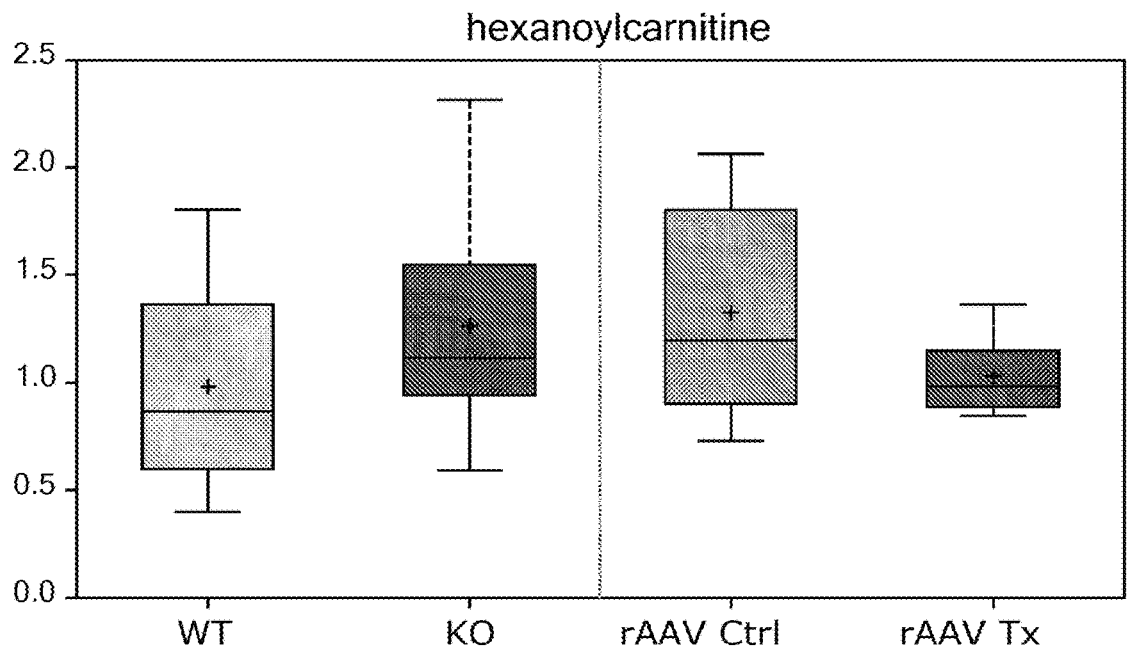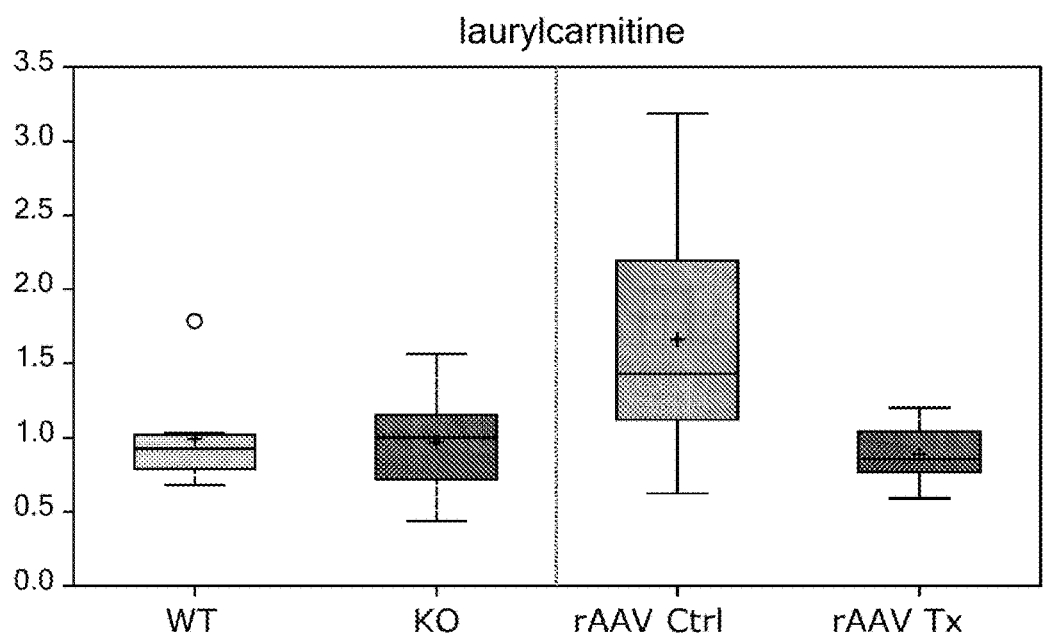
FIG. 57 cont.

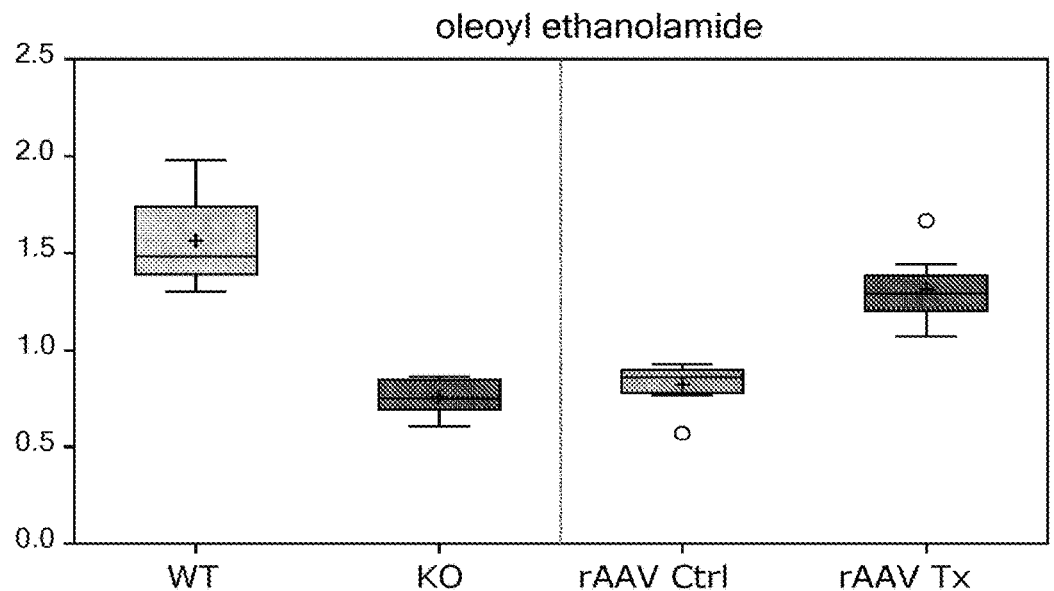
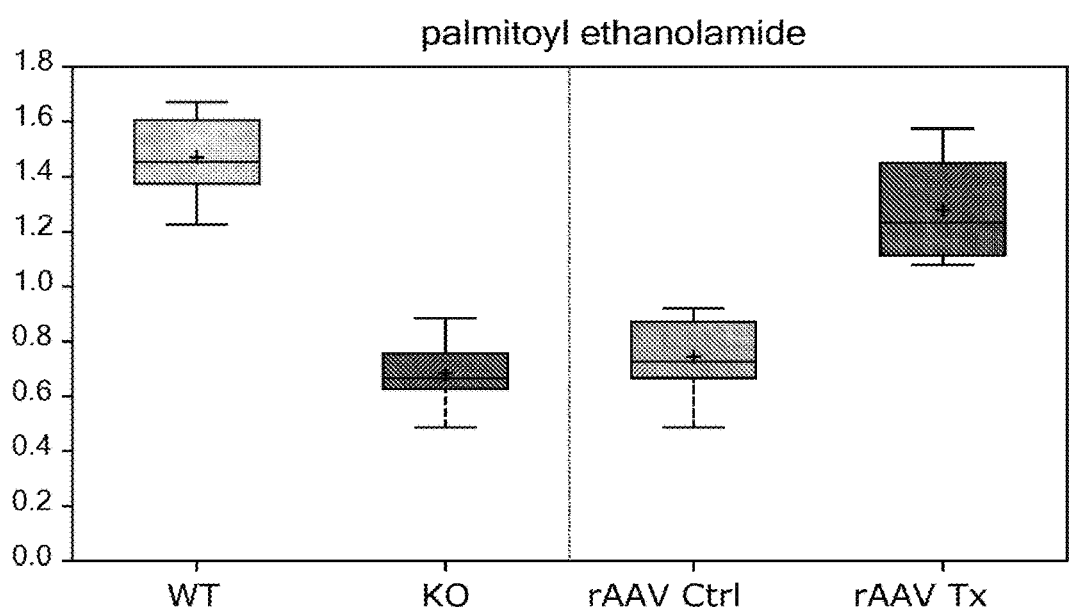
FIG. 57 cont.

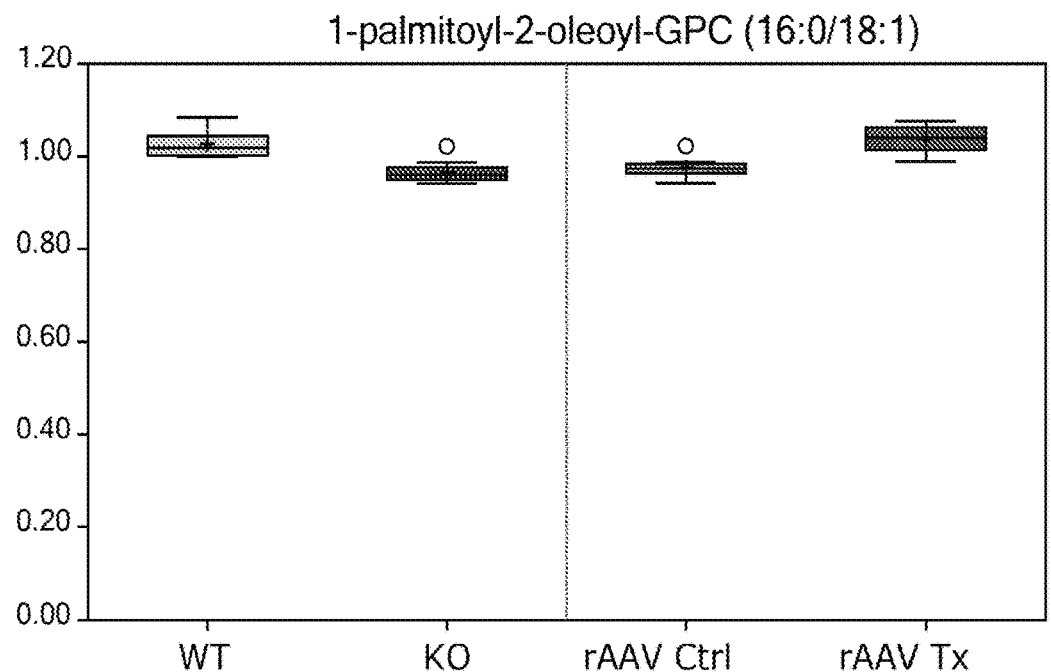
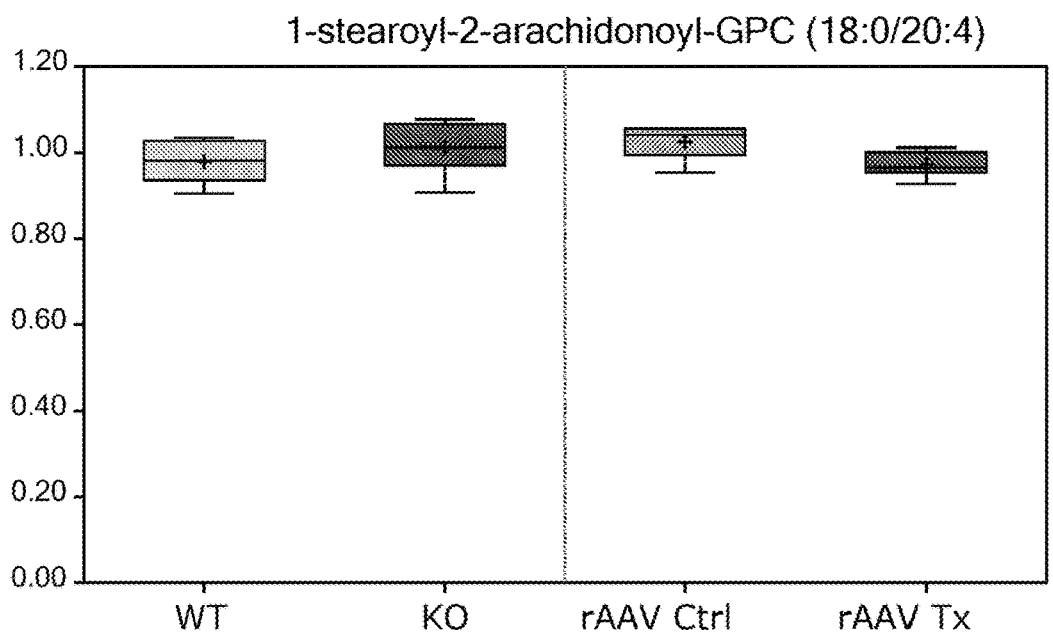
FIG. 57 cont.

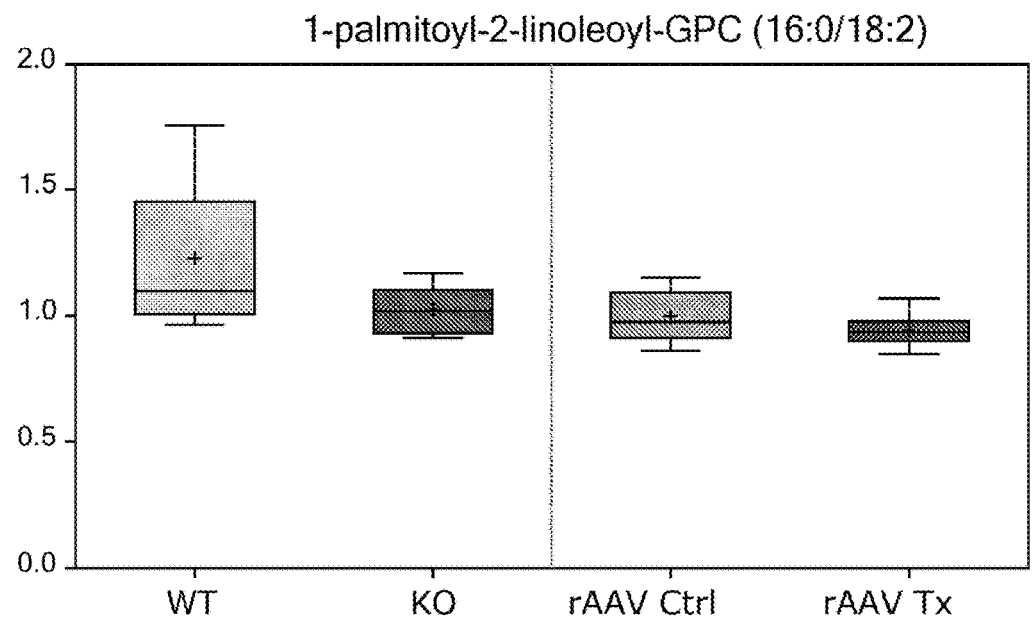
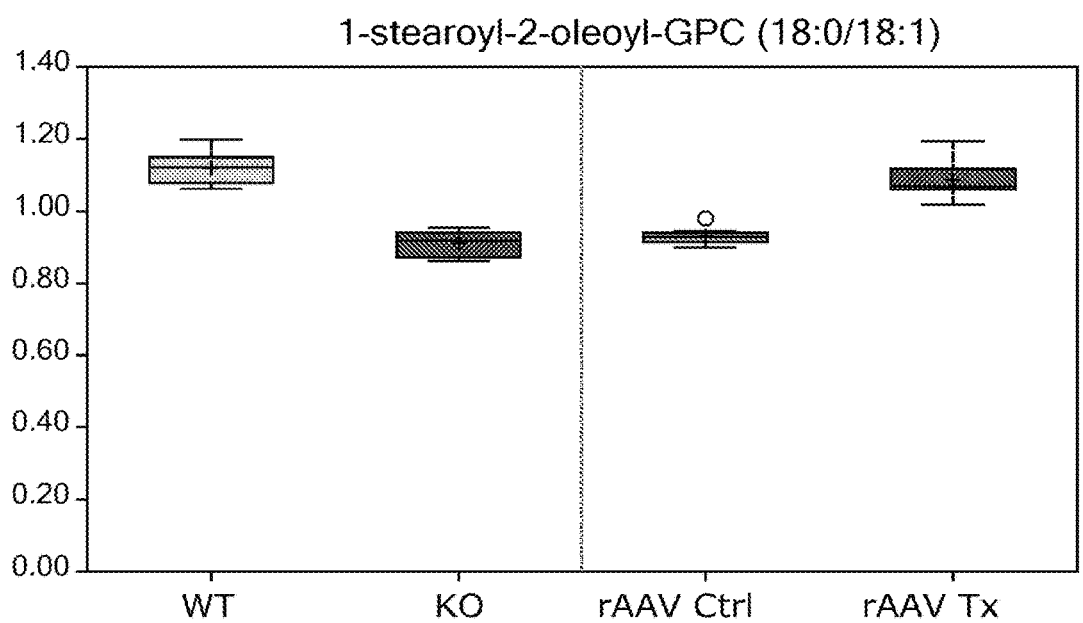
FIG. 57 cont.

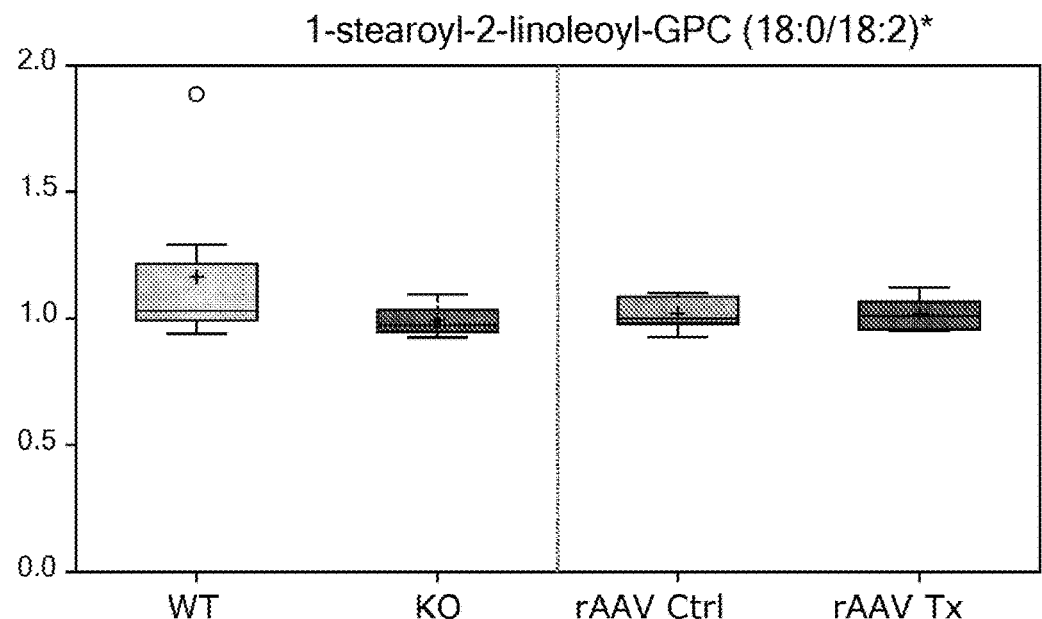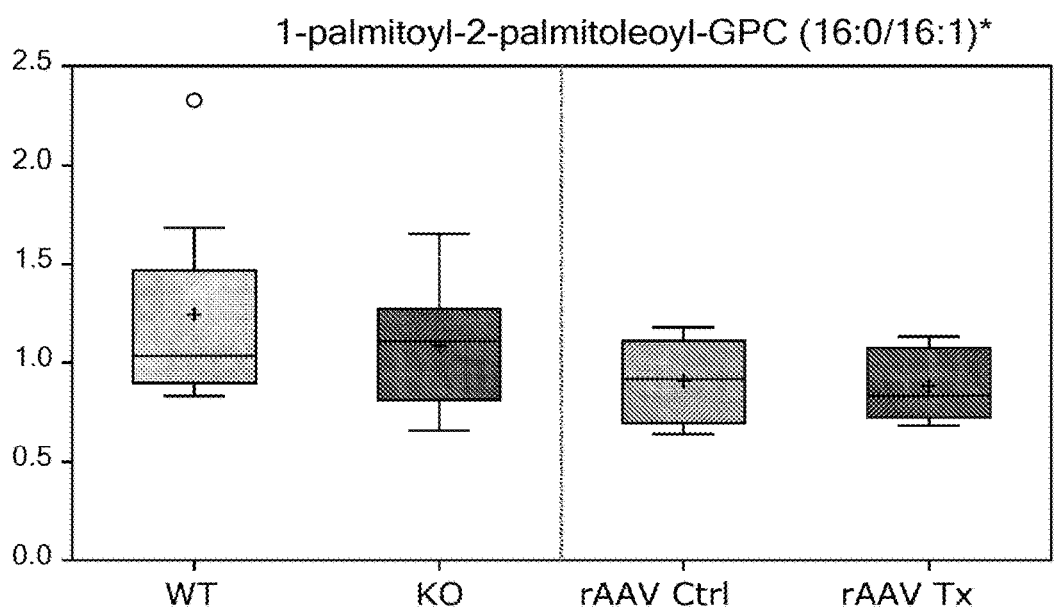
FIG. 57 cont.

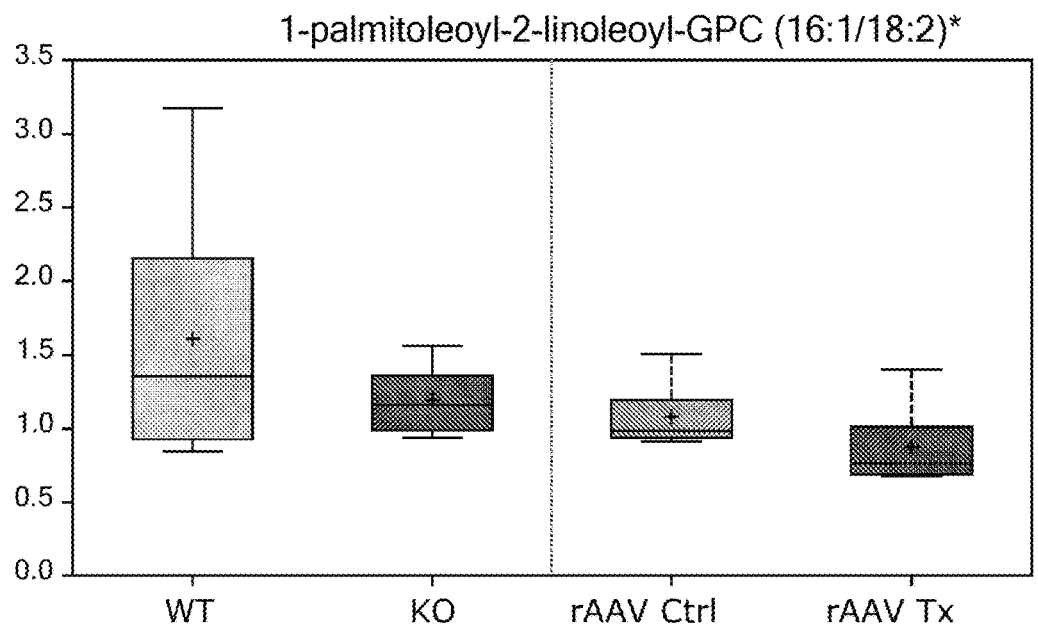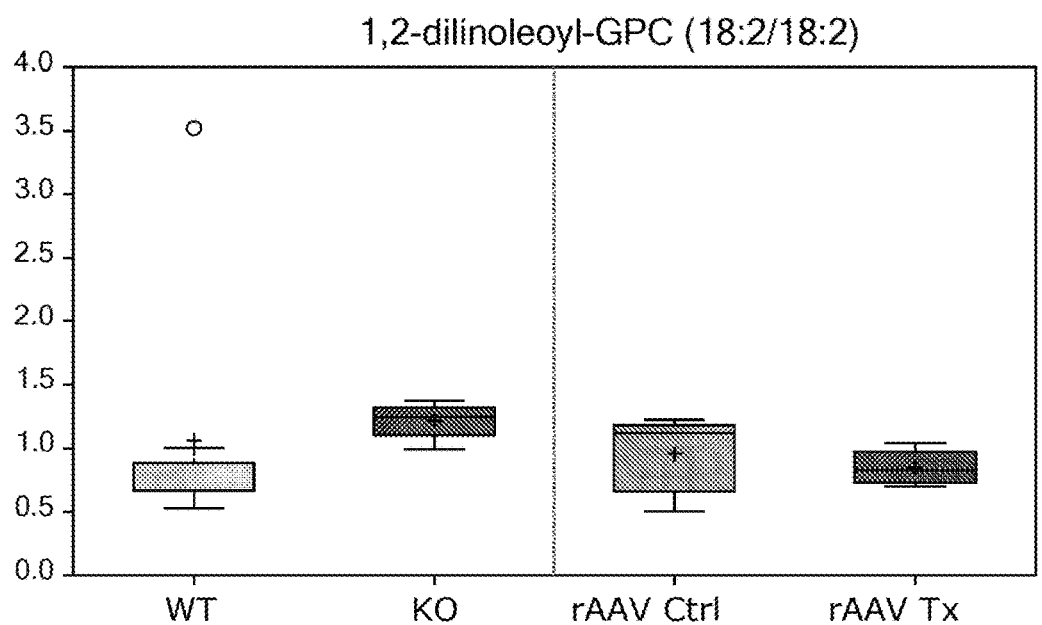
FIG. 57 cont.

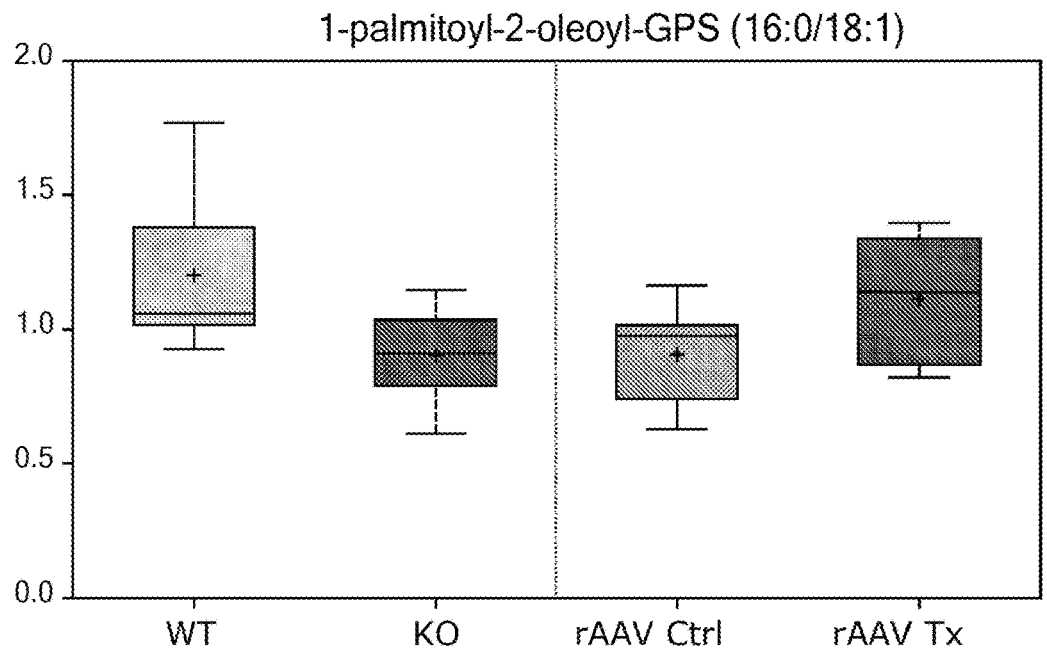
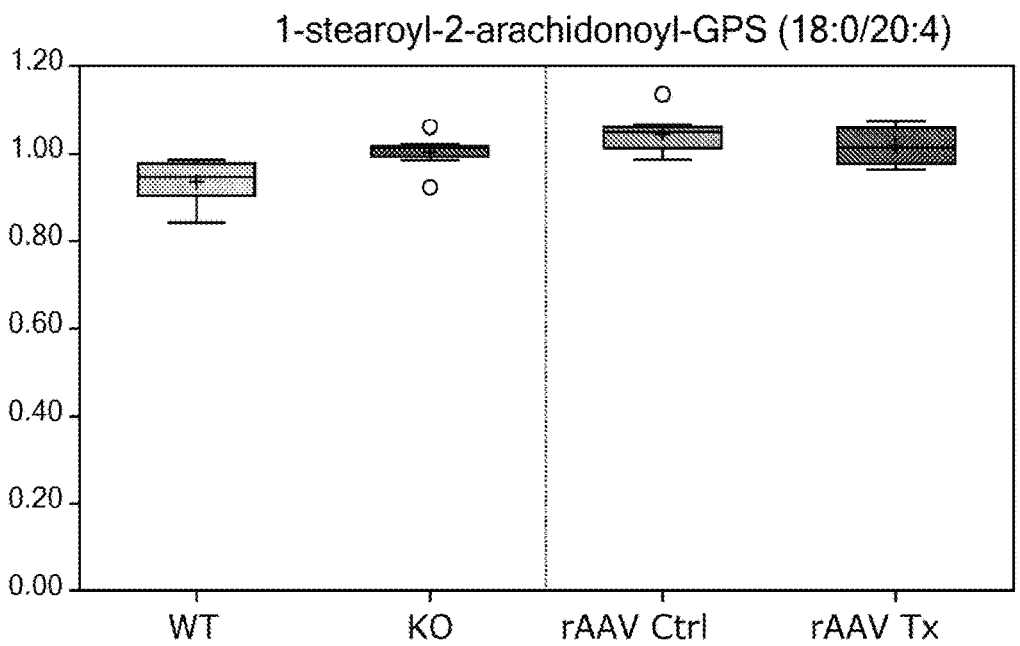
FIG. 57 cont.

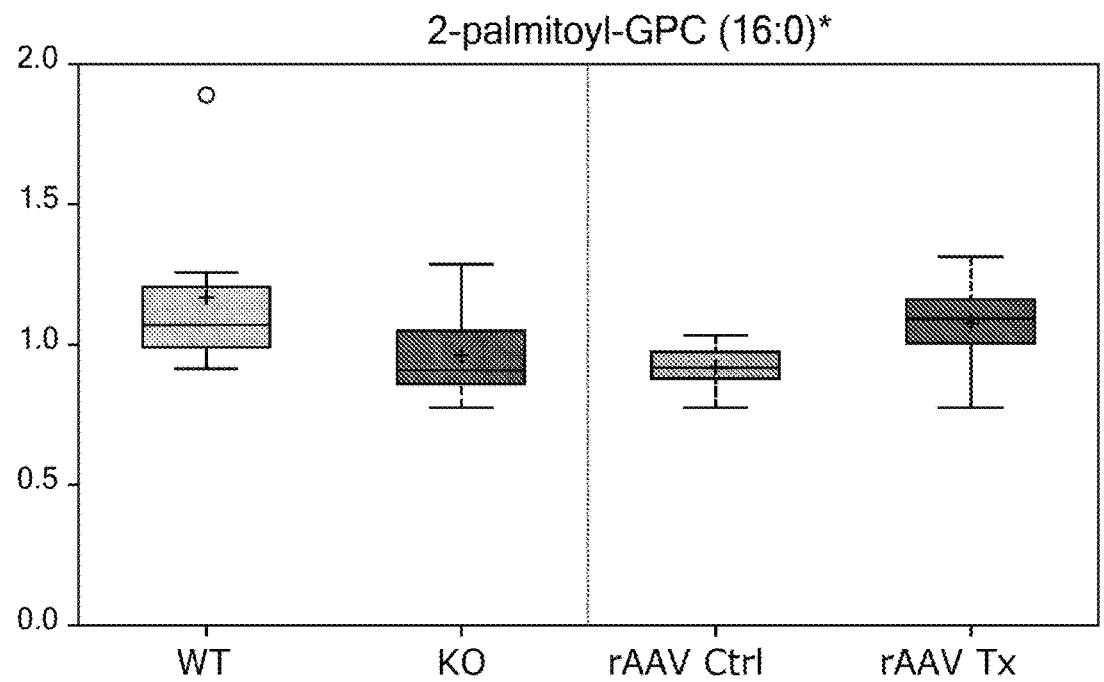
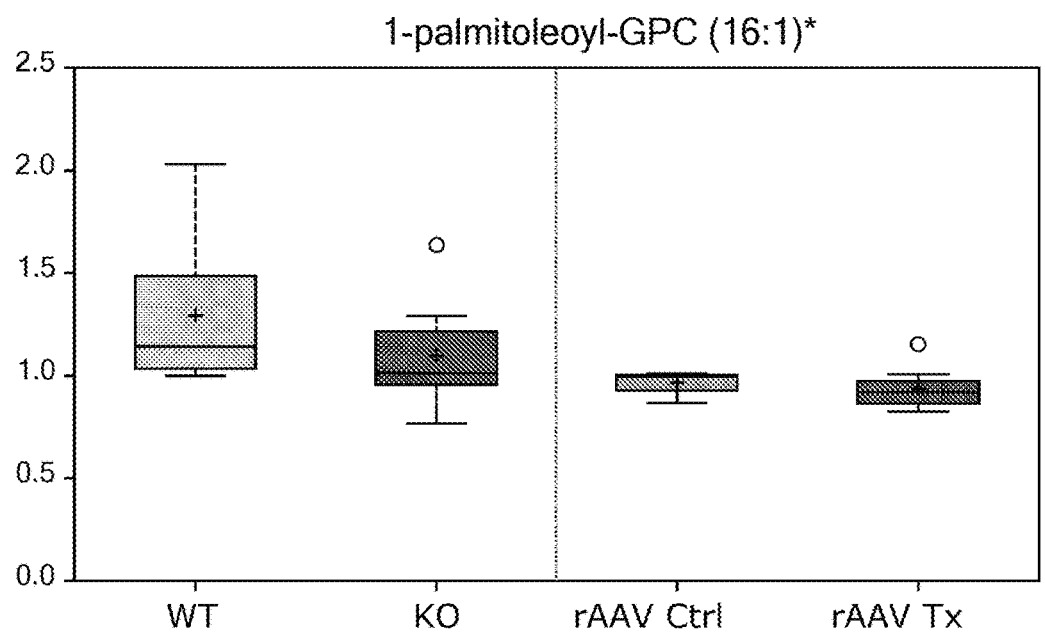
FIG. 57 cont.

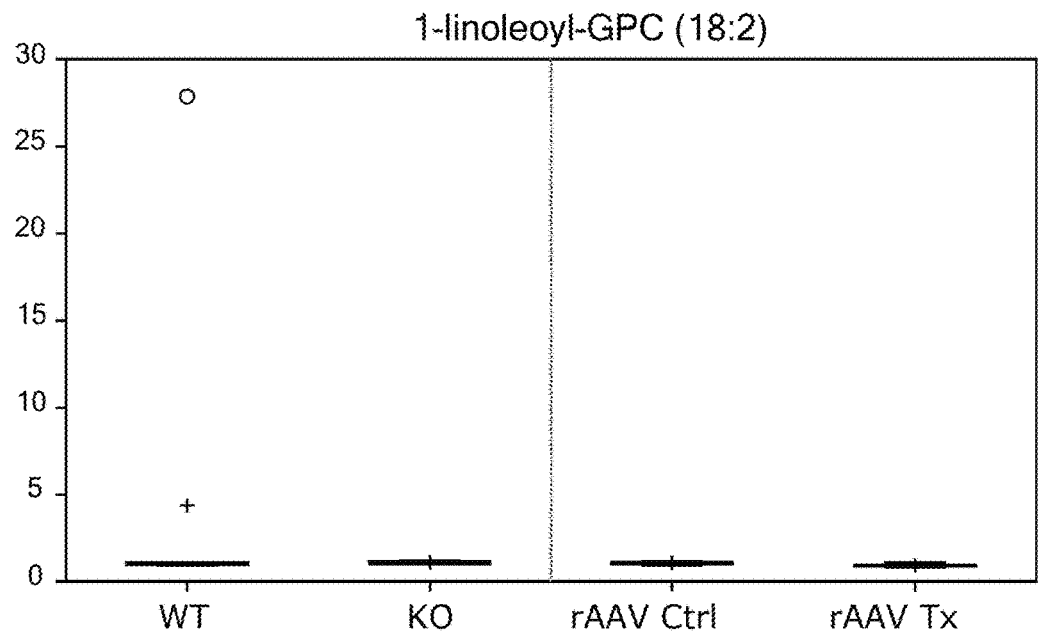
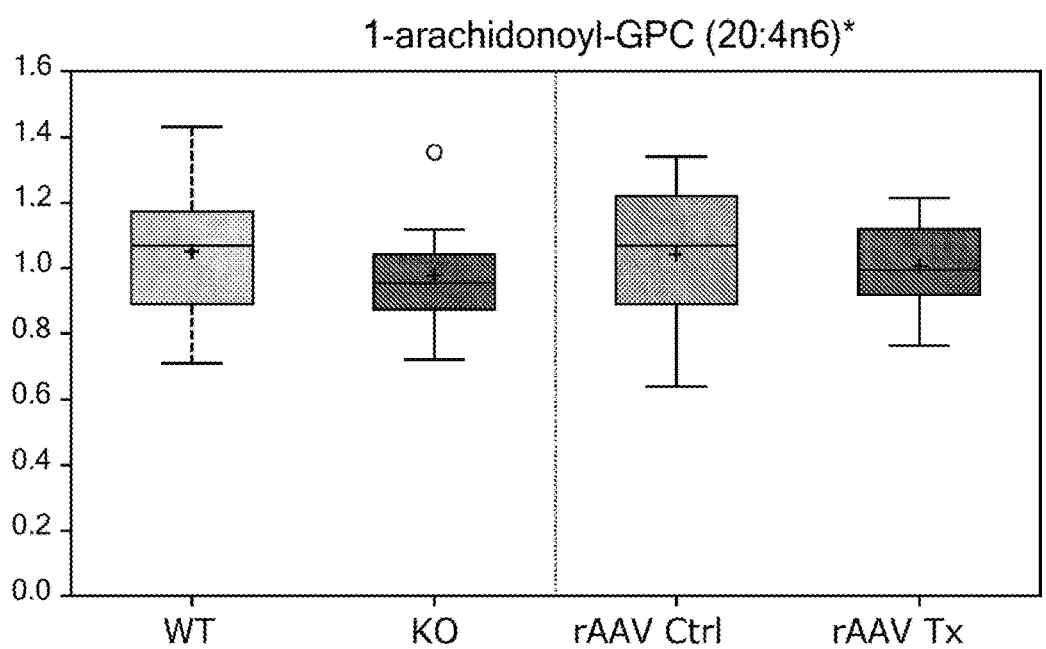
FIG. 57 cont.

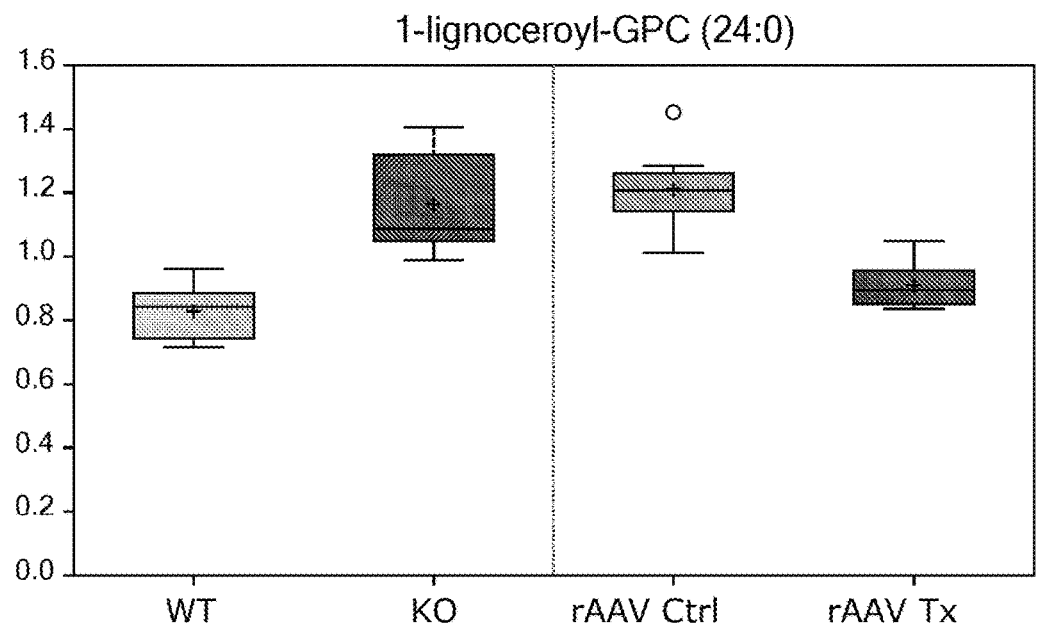
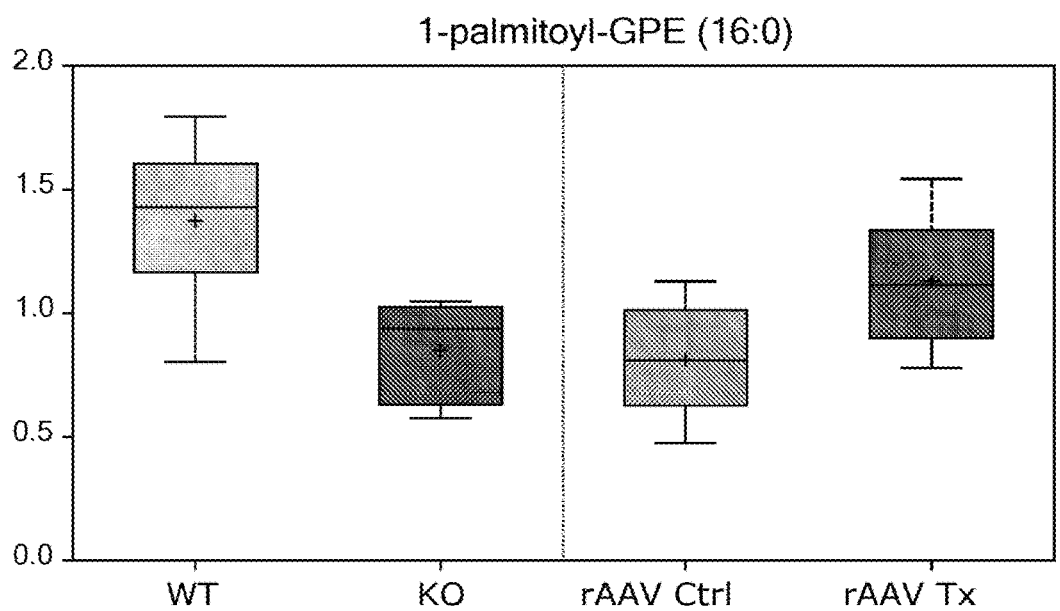
FIG. 57 cont.

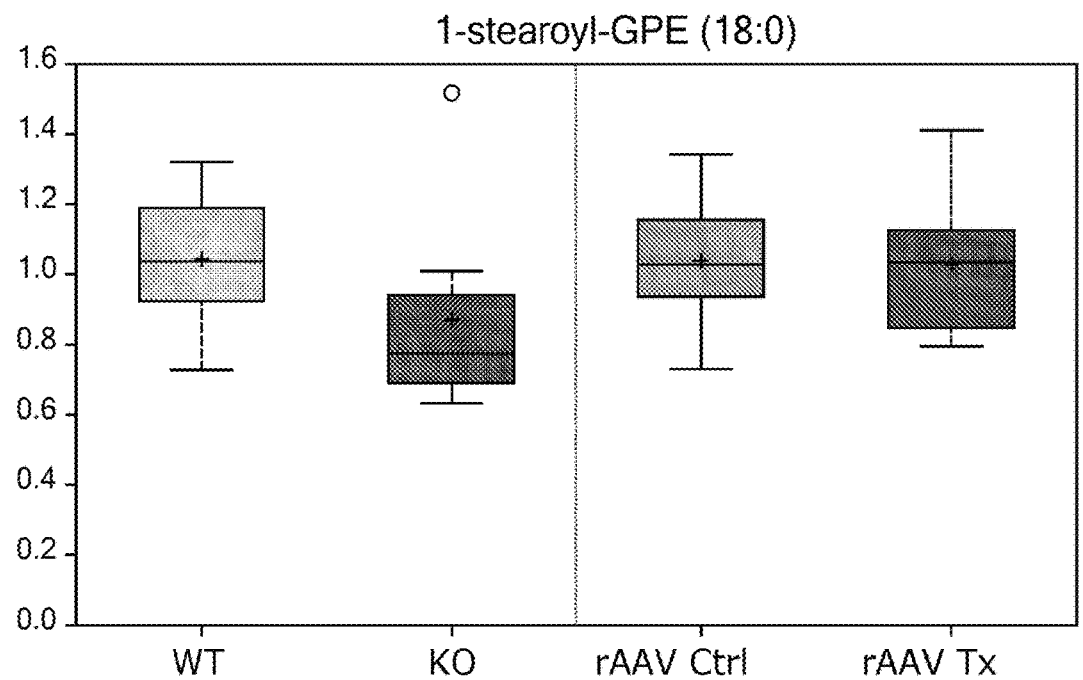
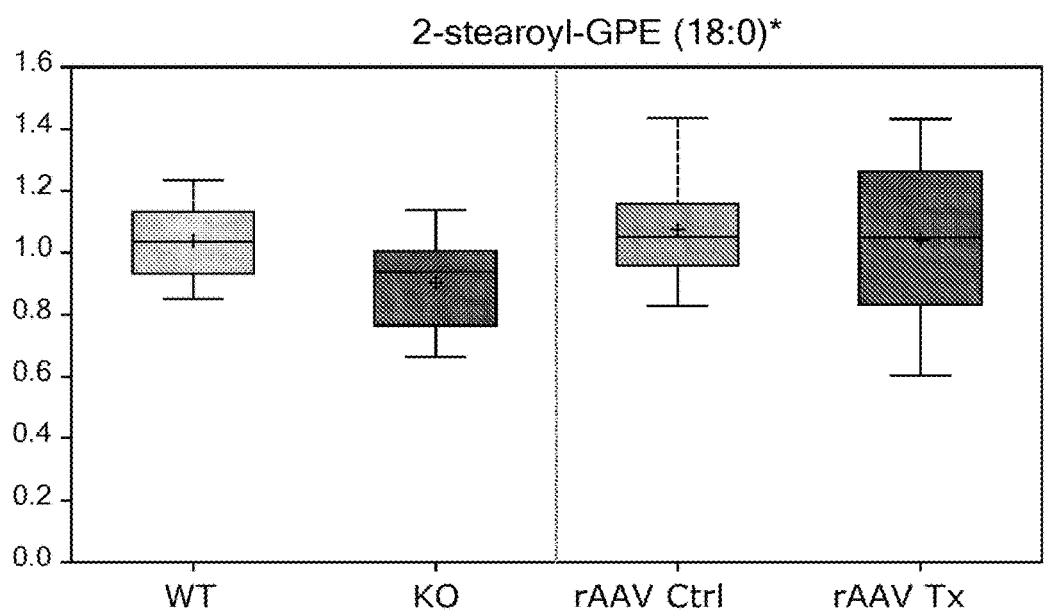
FIG. 57 cont.

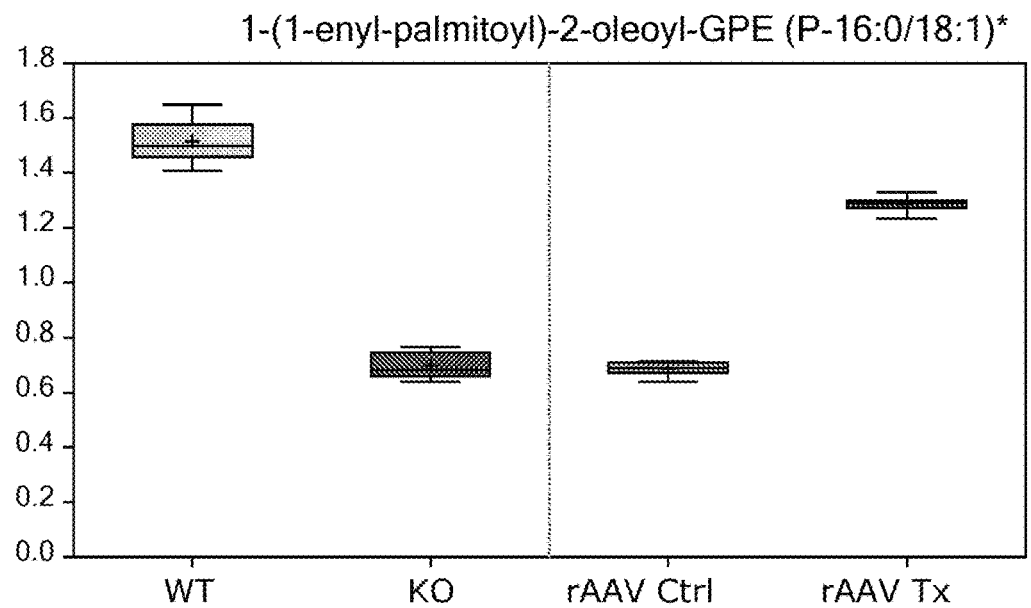
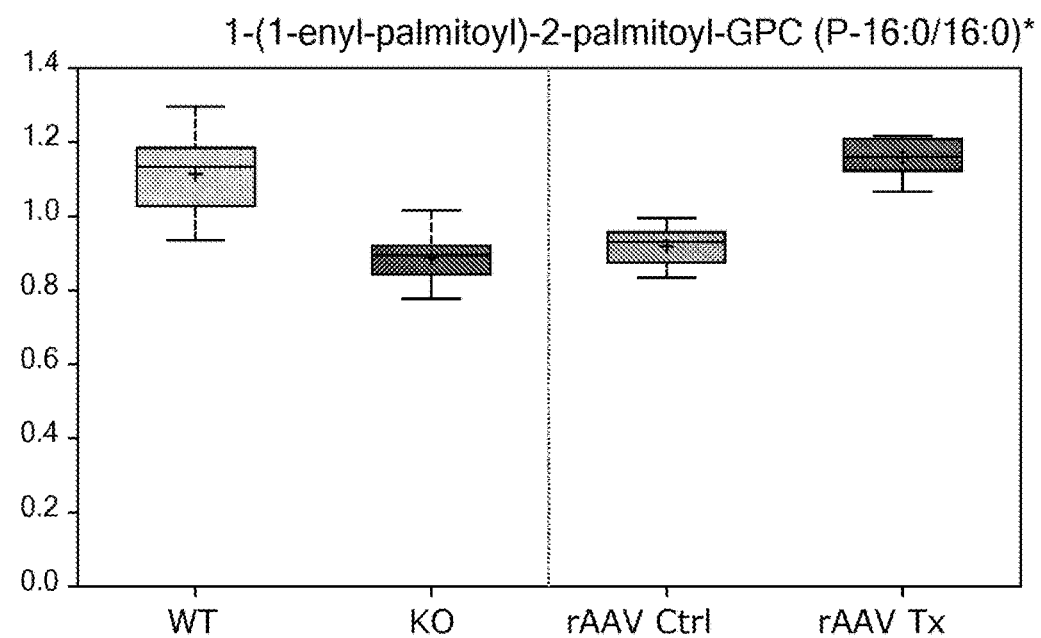
FIG. 57 cont.

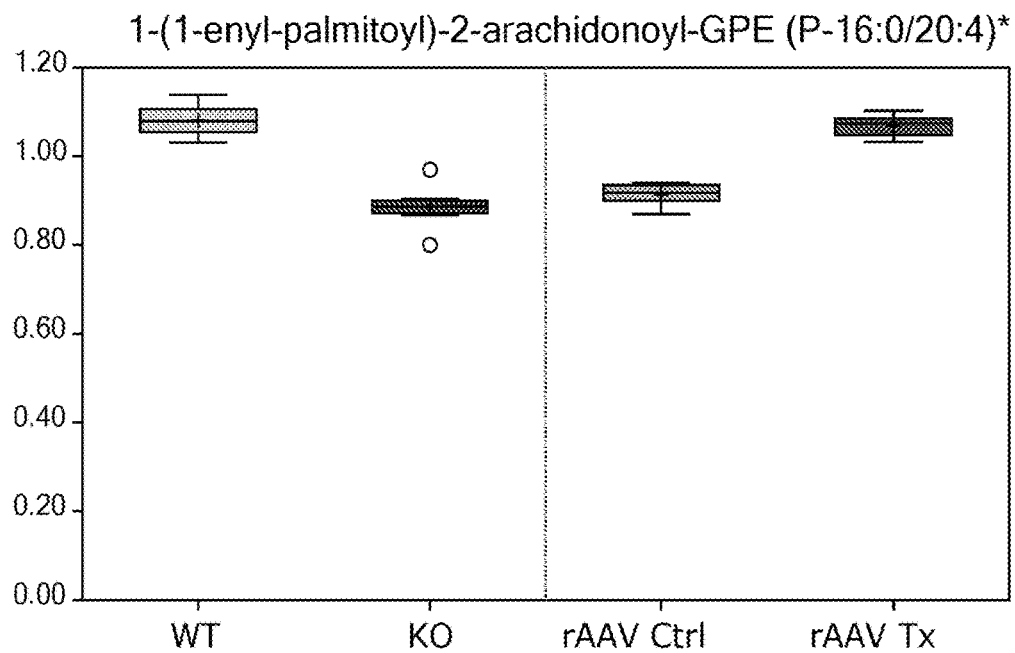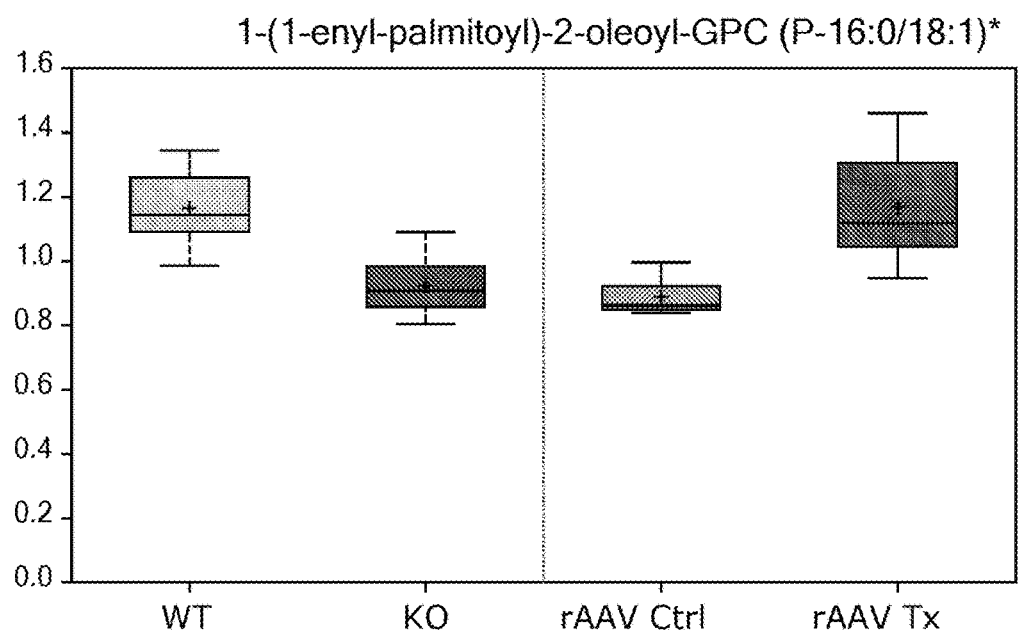
FIG. 57 cont.

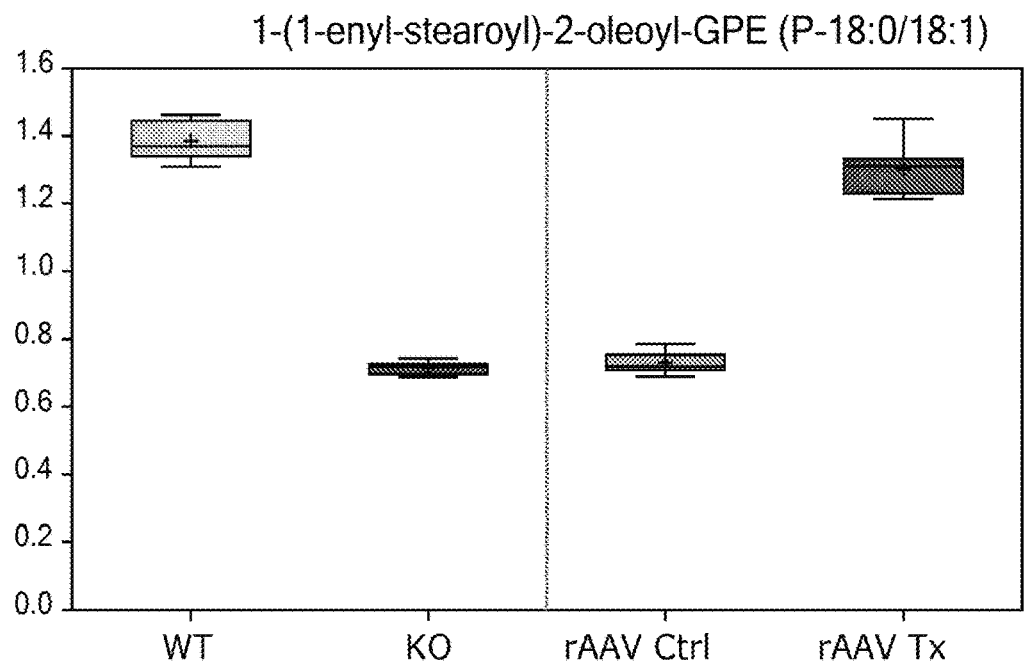
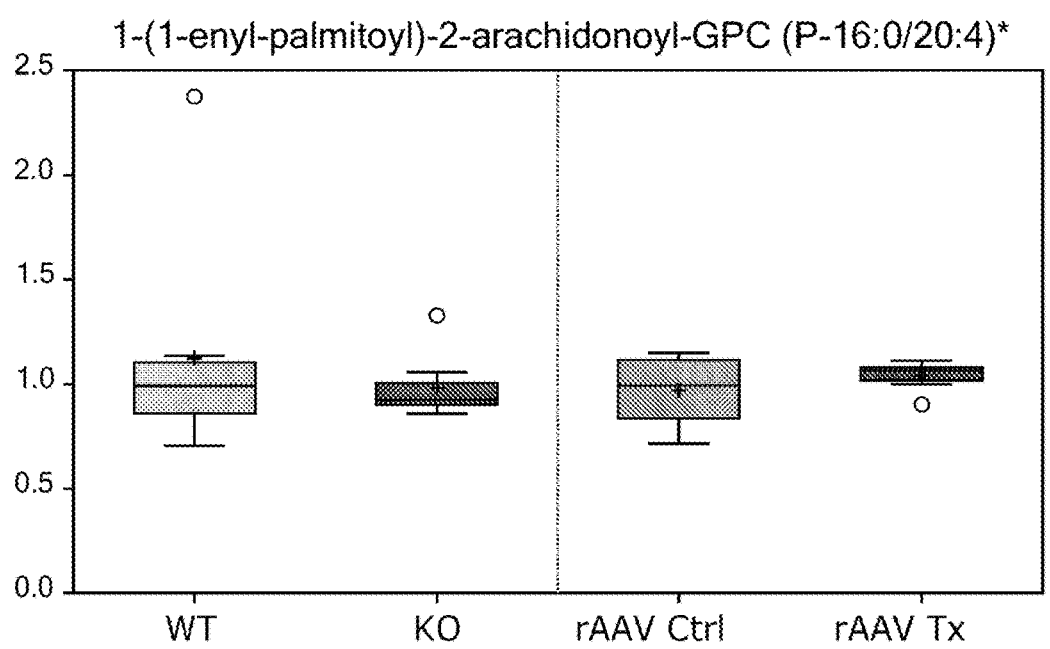
FIG. 57 cont.

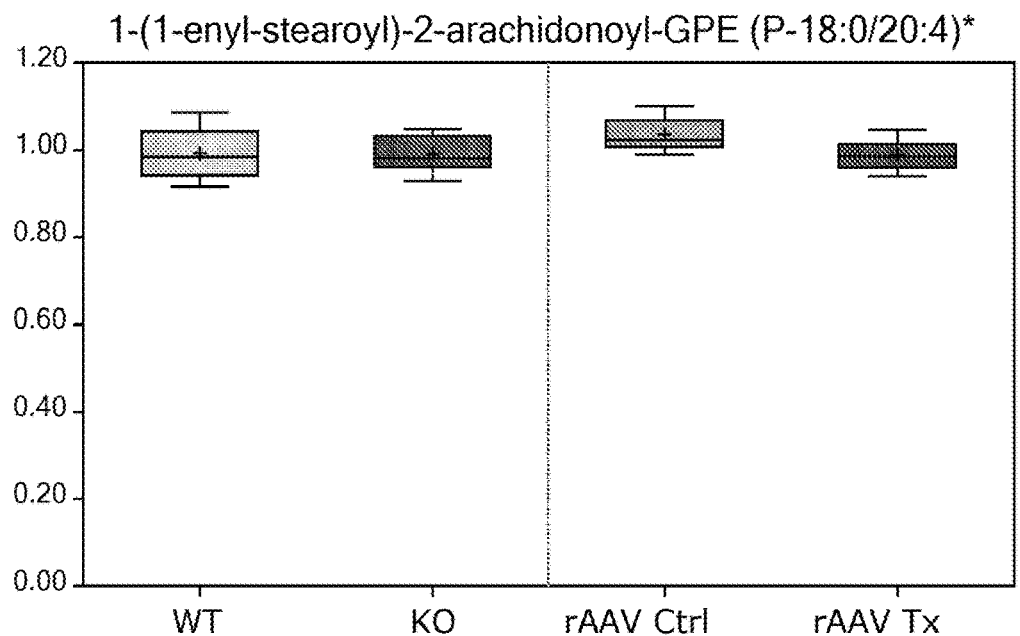
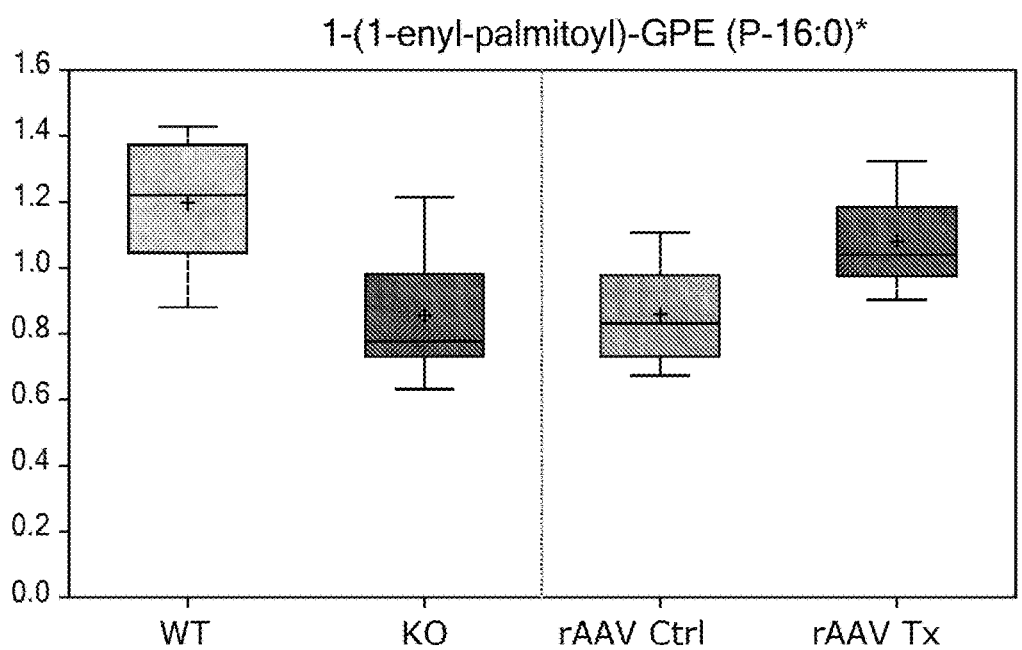
FIG. 57 cont.

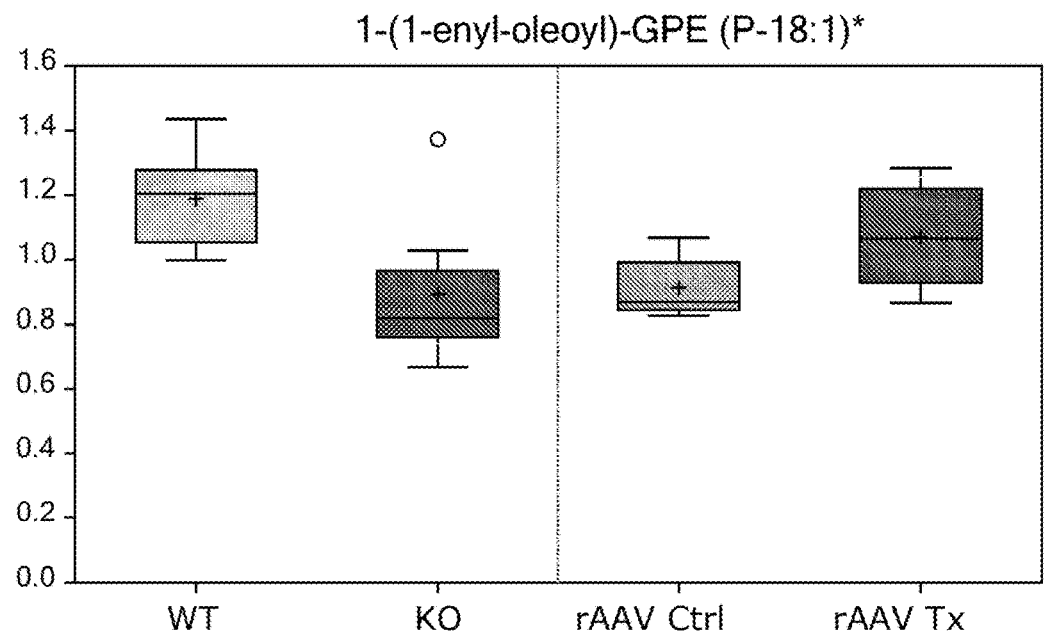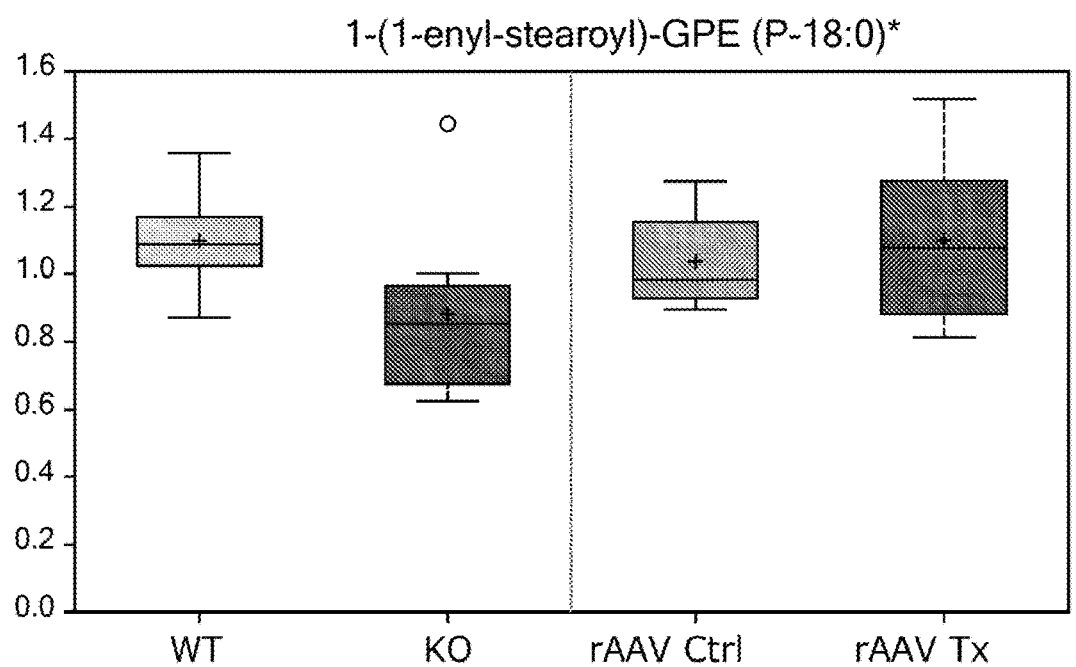
FIG. 57 cont.

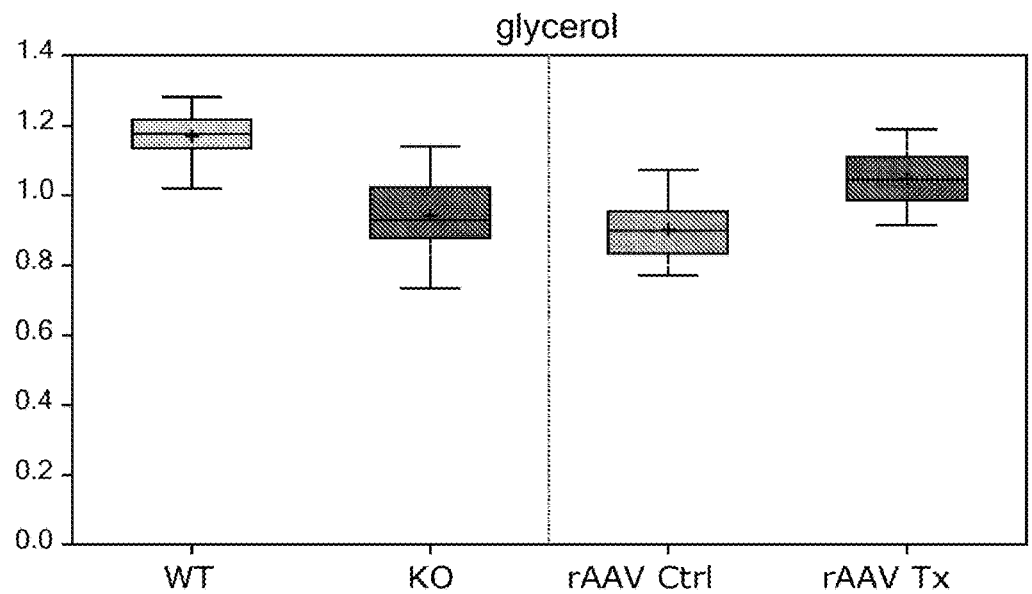
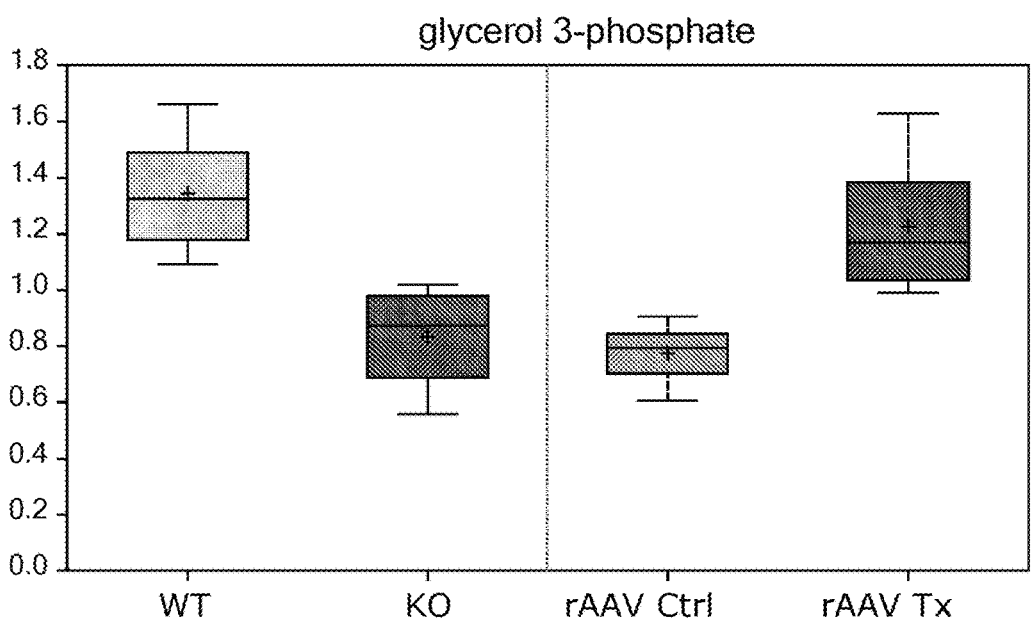
FIG. 57 cont.

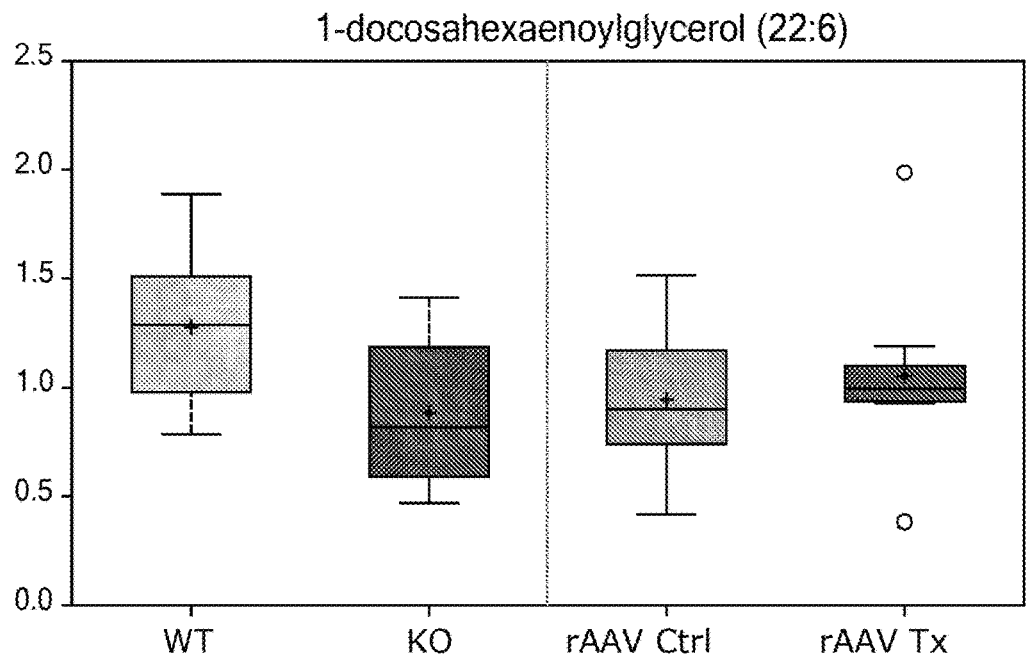
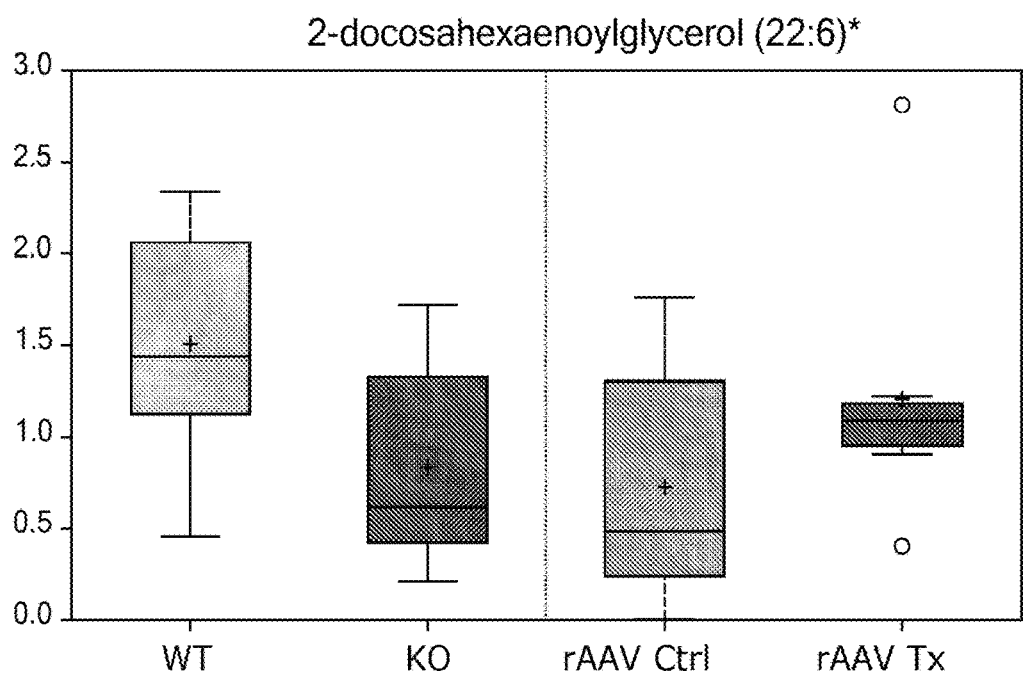
FIG. 57 cont.

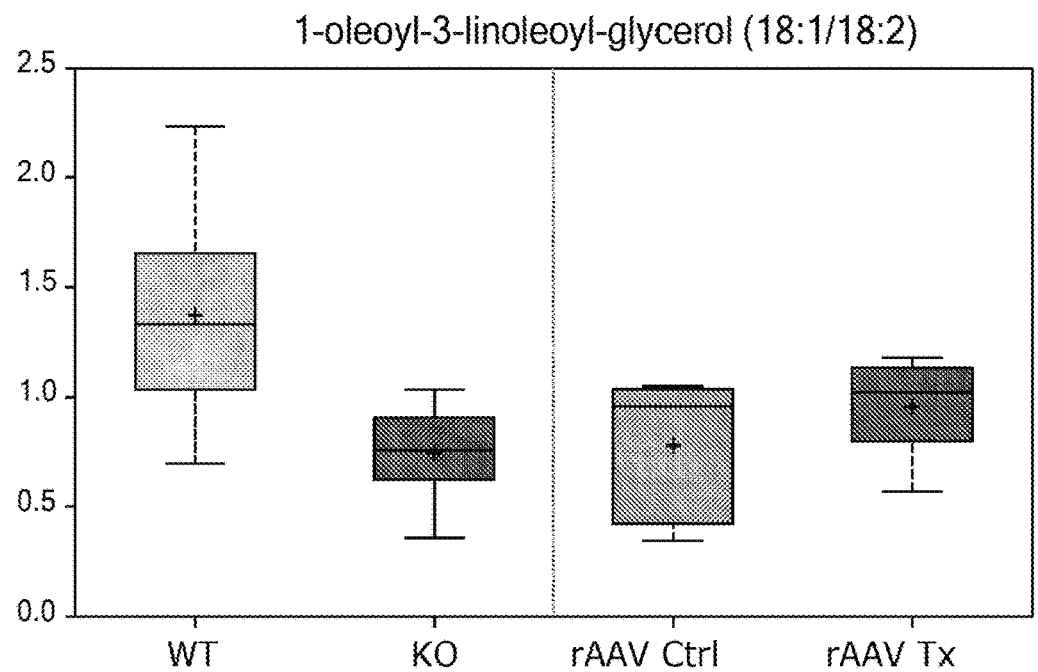
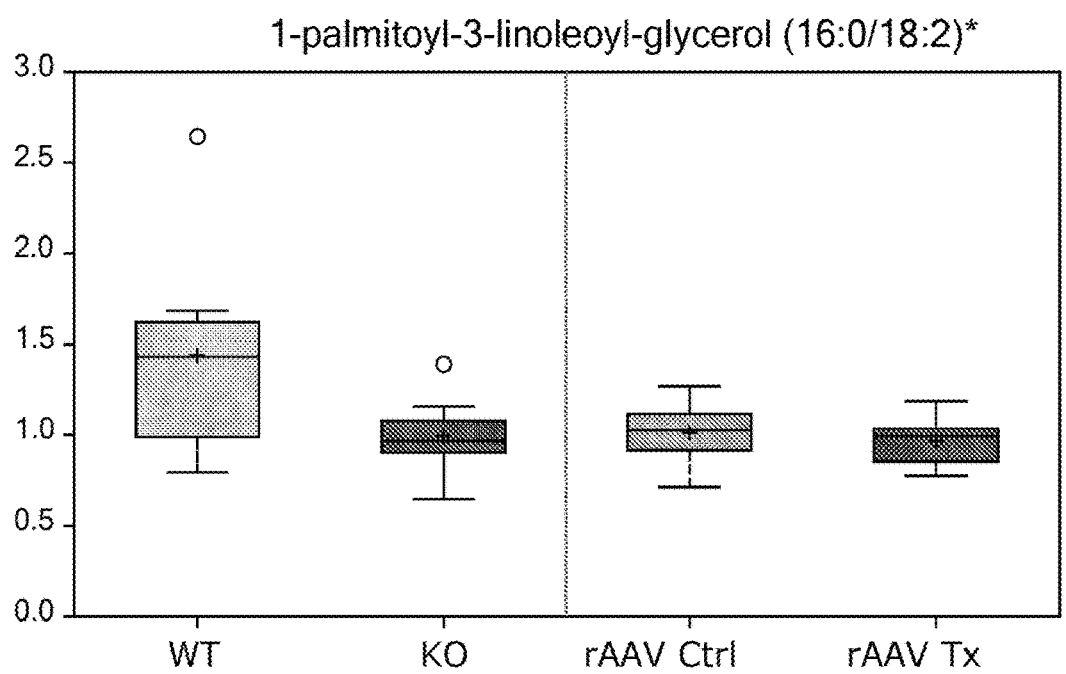
FIG. 57 cont.

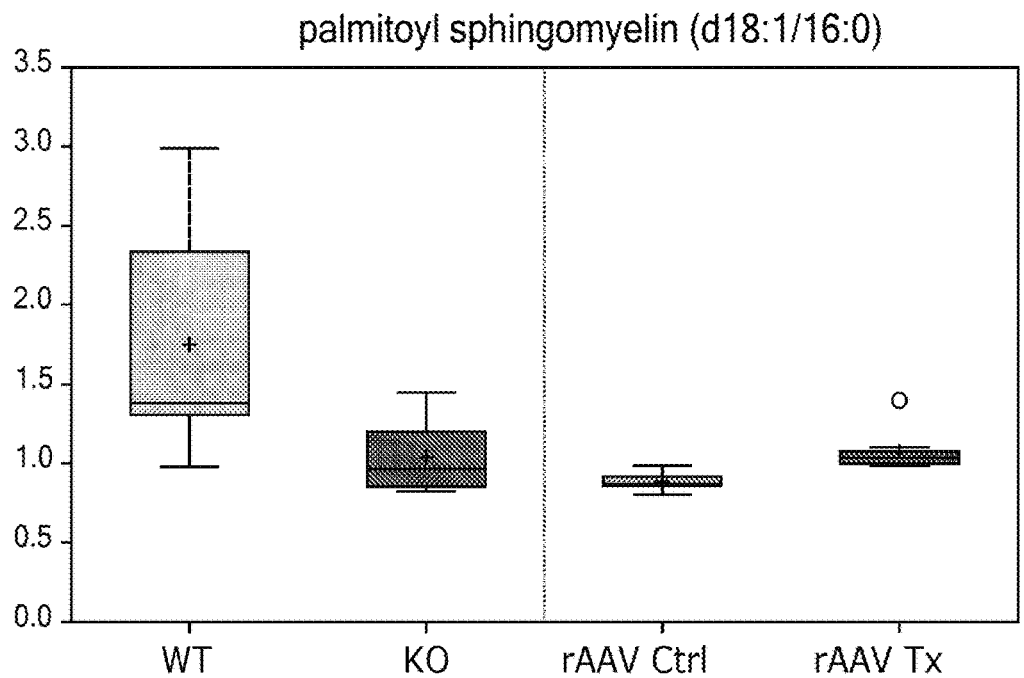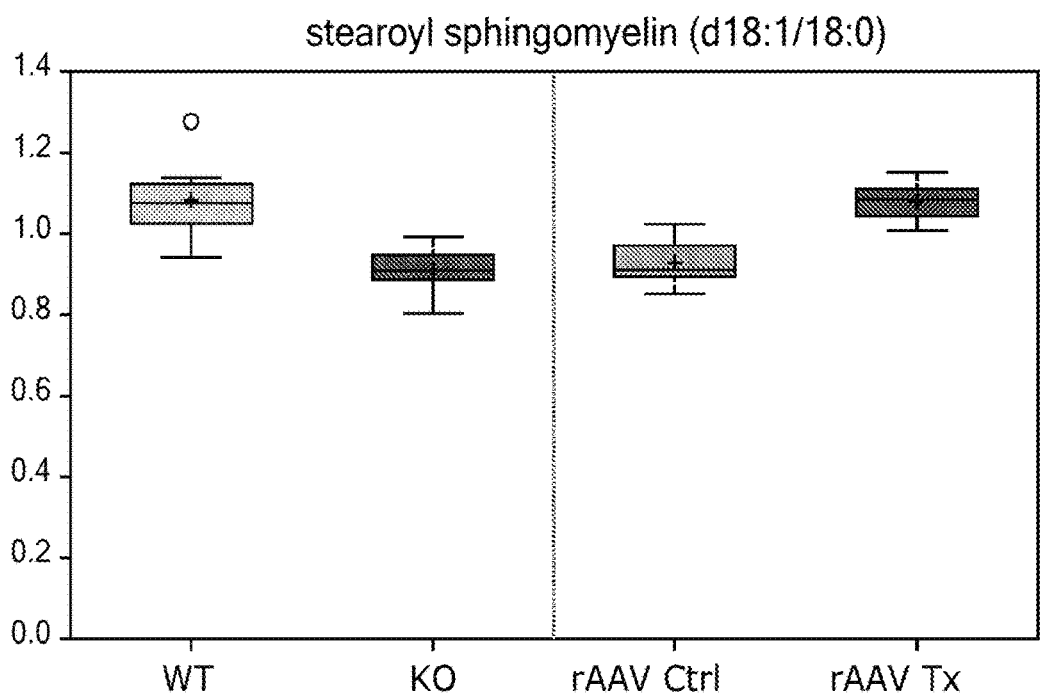
FIG. 57 cont.

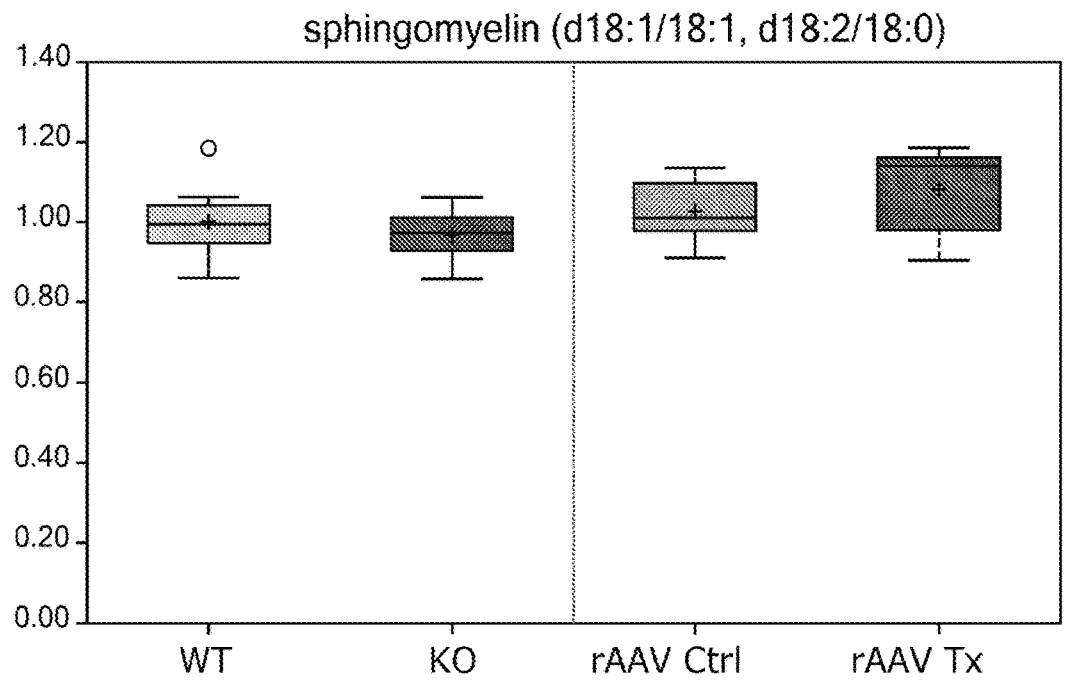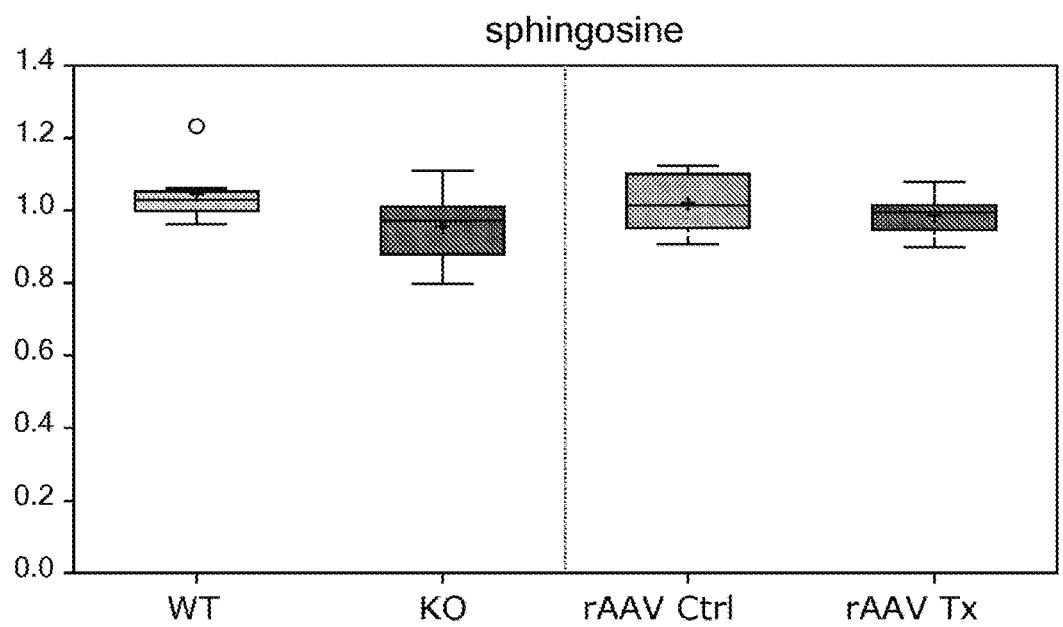
FIG. 57 cont.

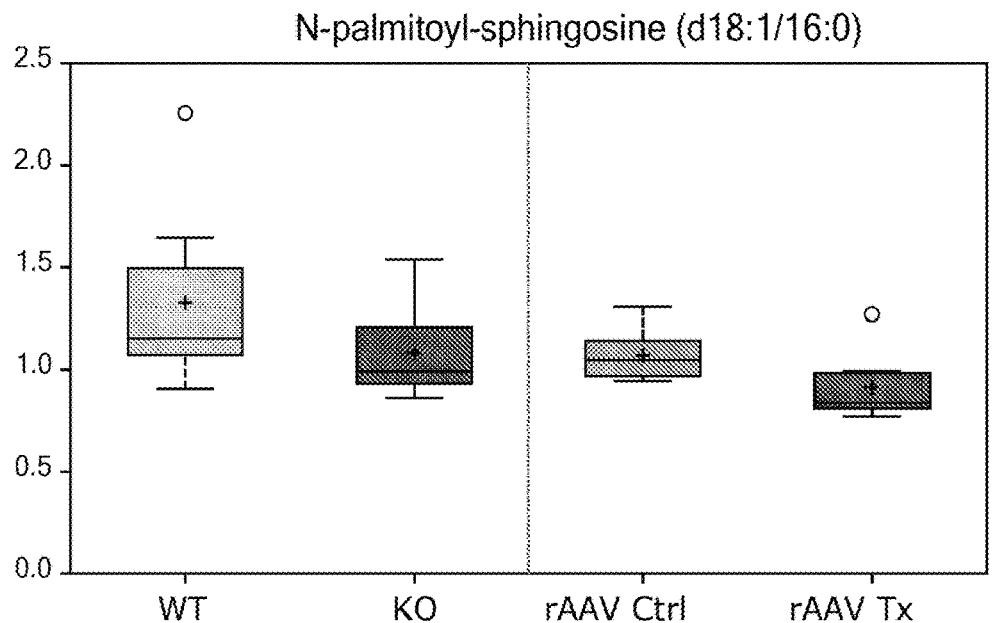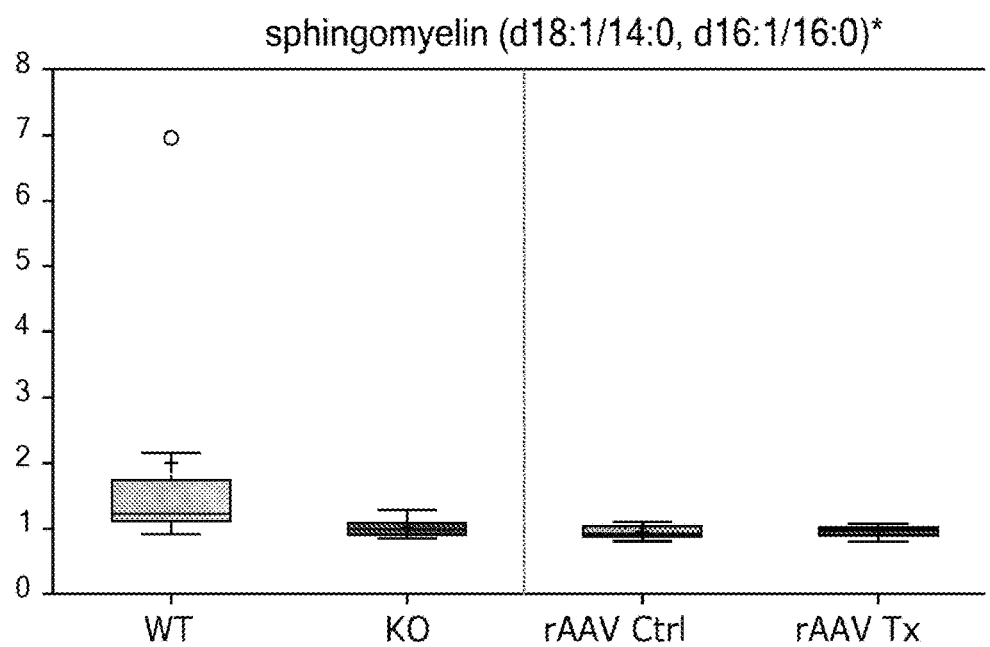
FIG. 57 cont.

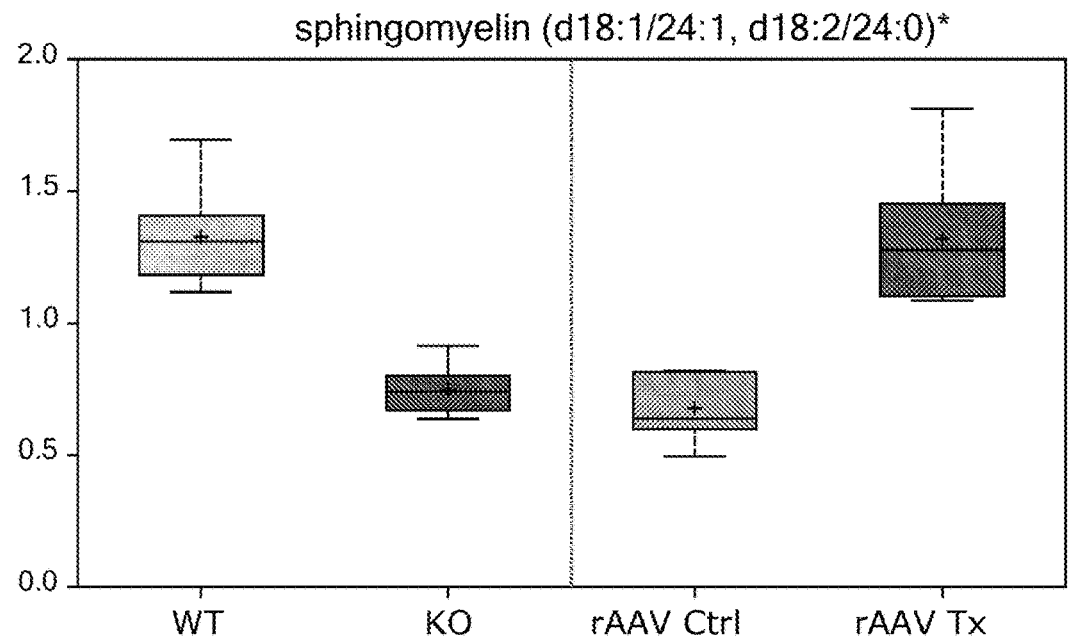
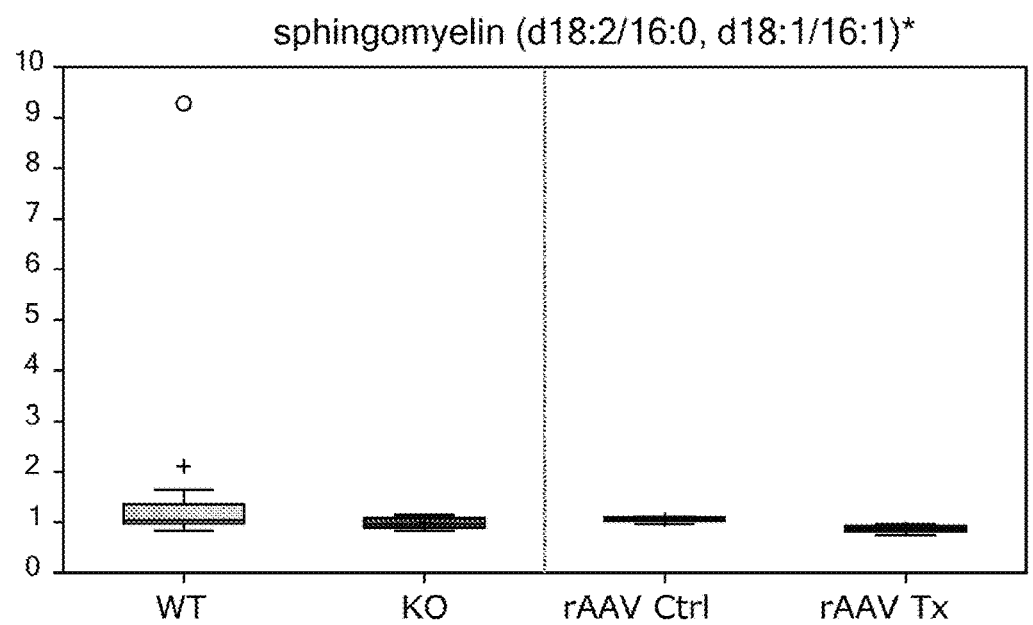
FIG. 57 cont.

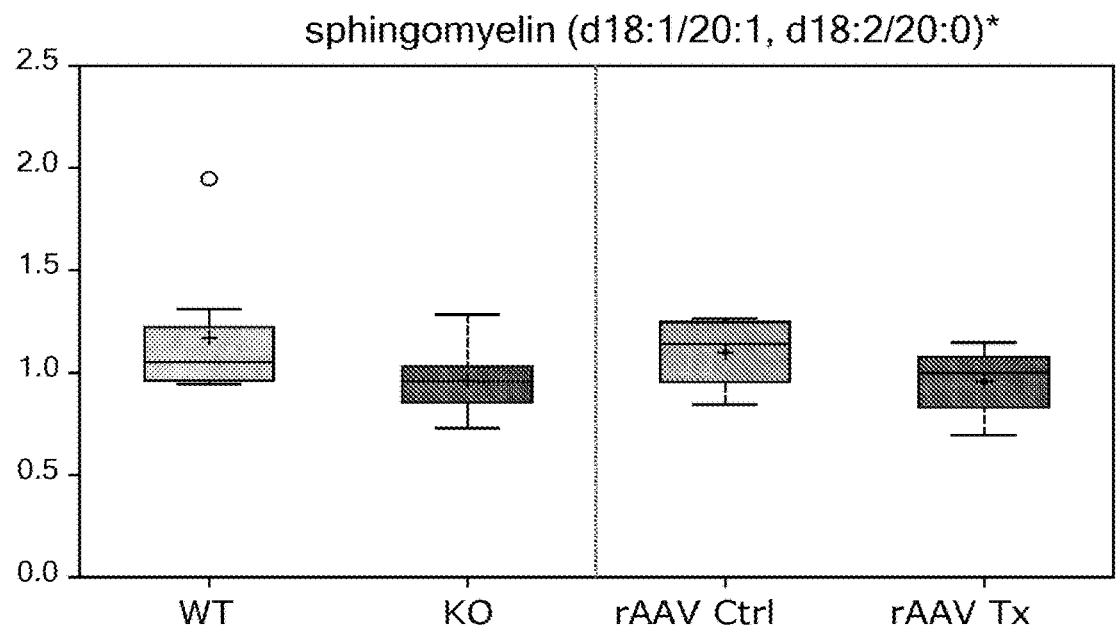
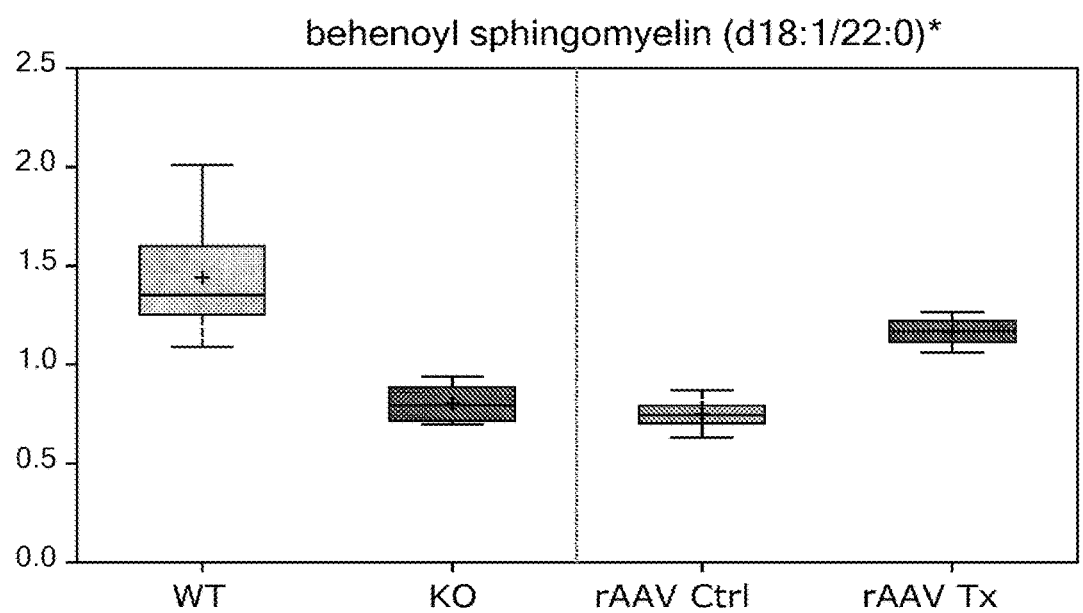
FIG. 57 cont.

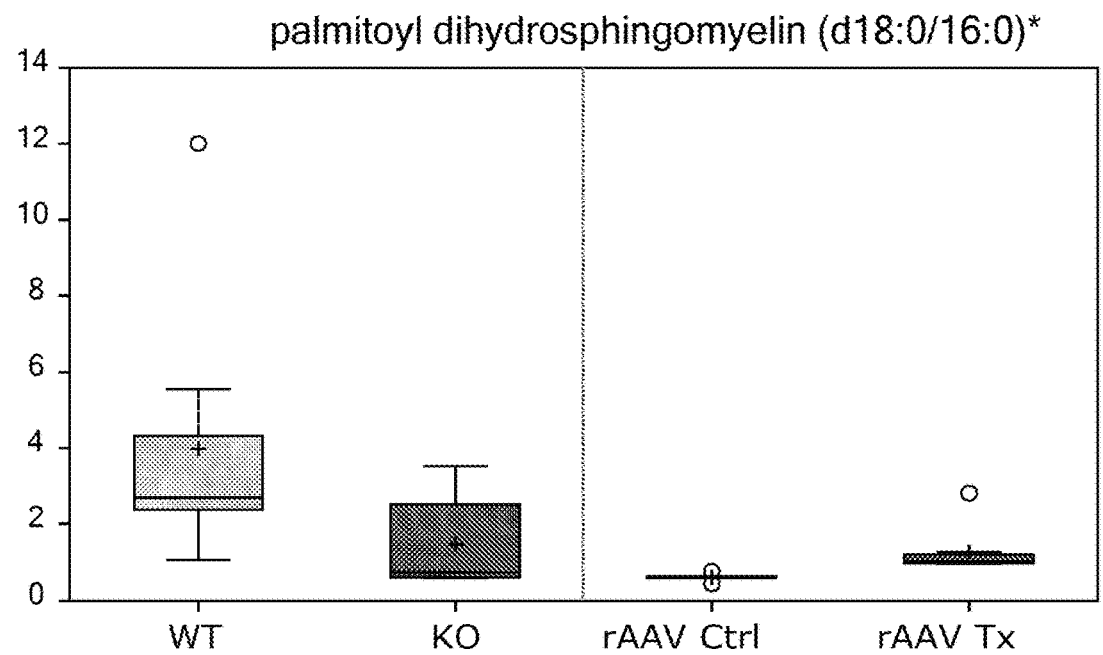
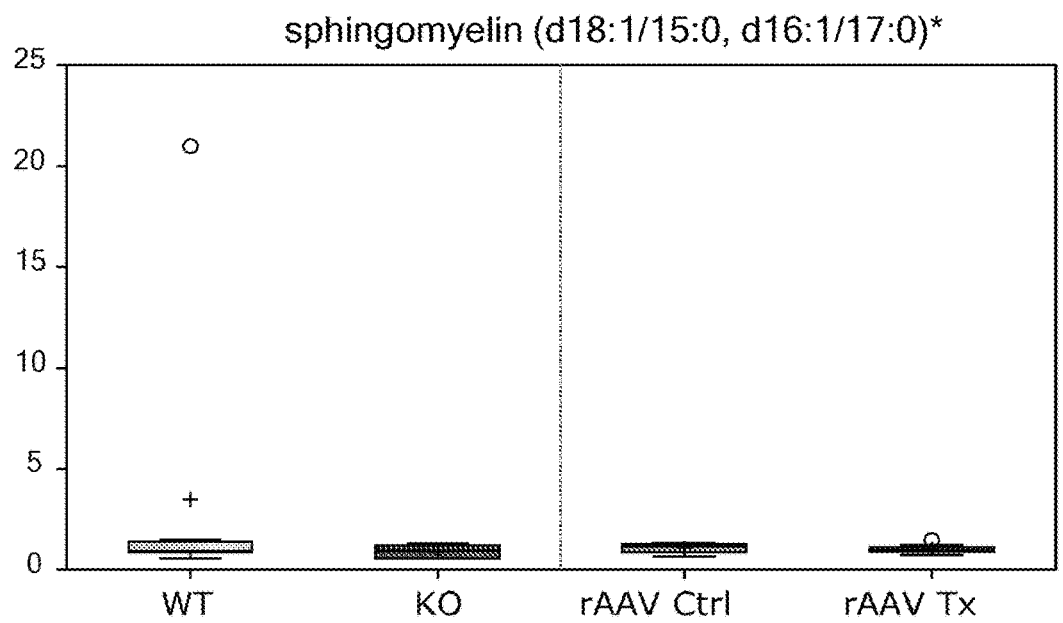
FIG. 57 cont.

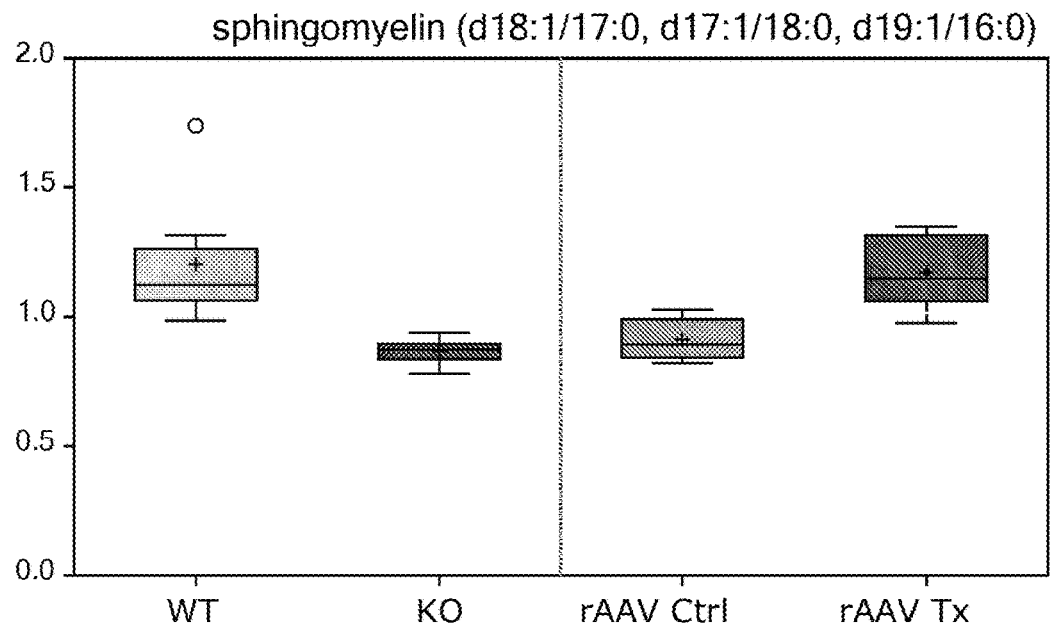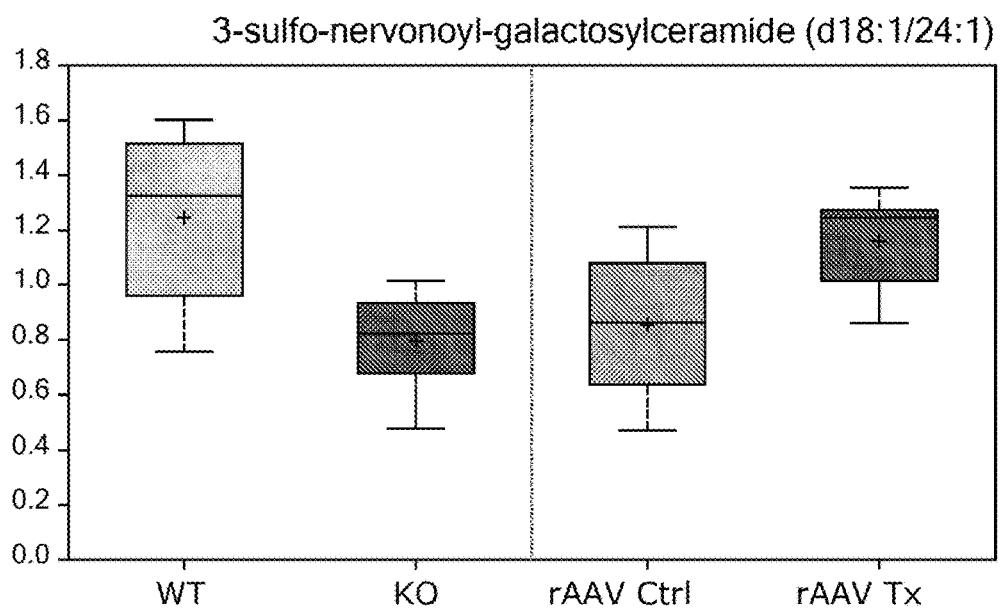
FIG. 57 cont.

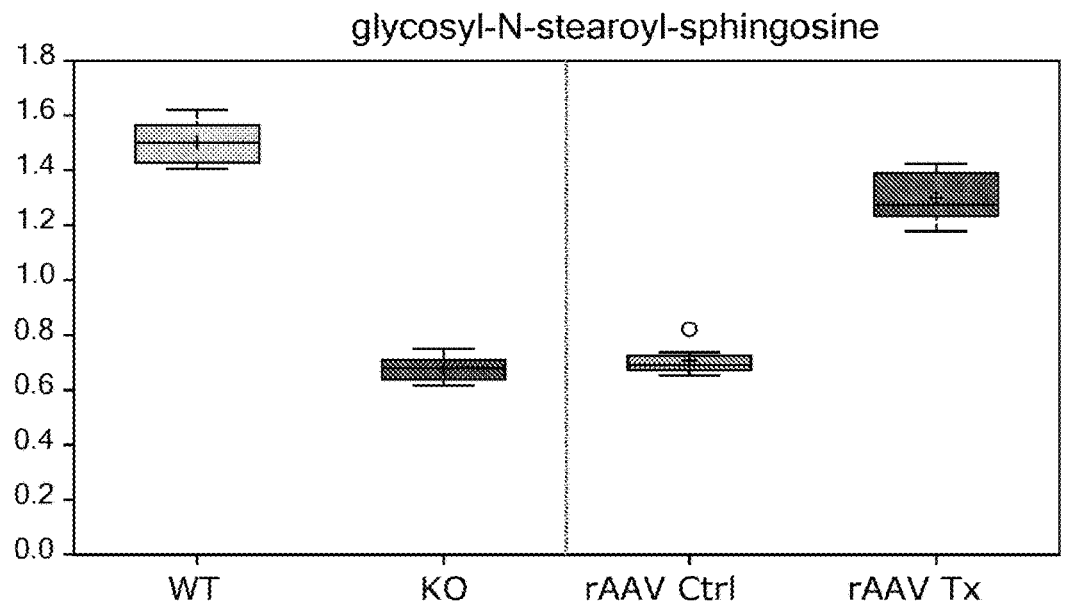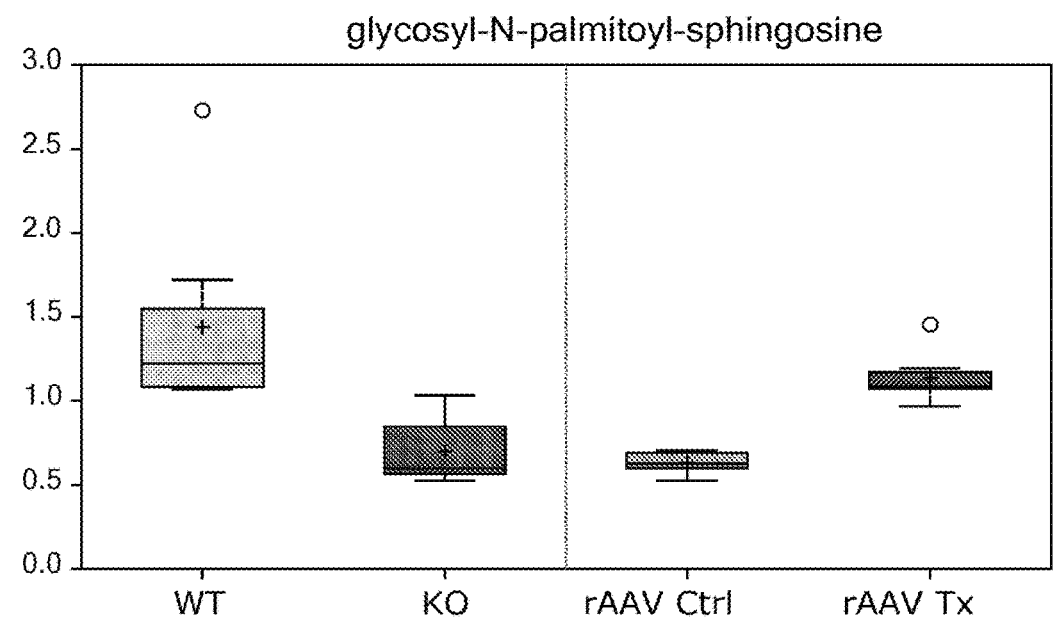
FIG. 57 cont.

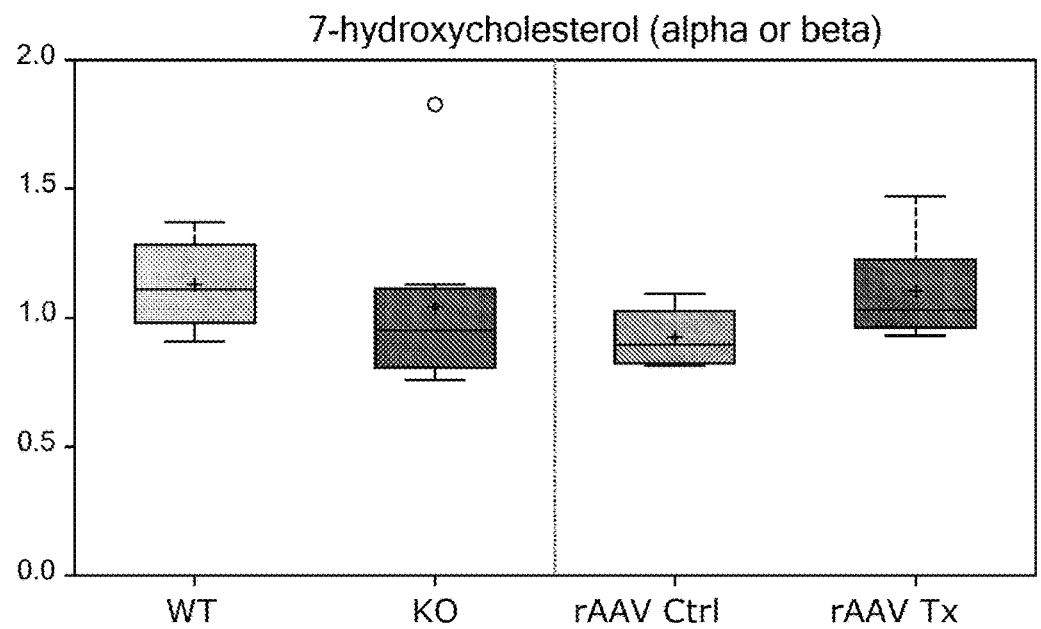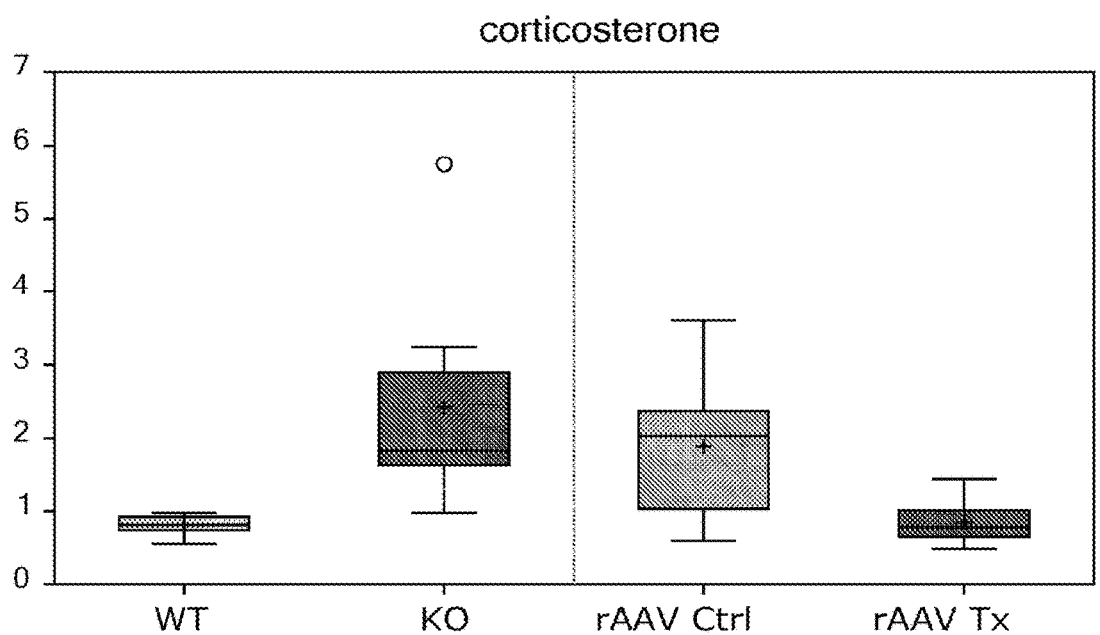
FIG. 57 cont.

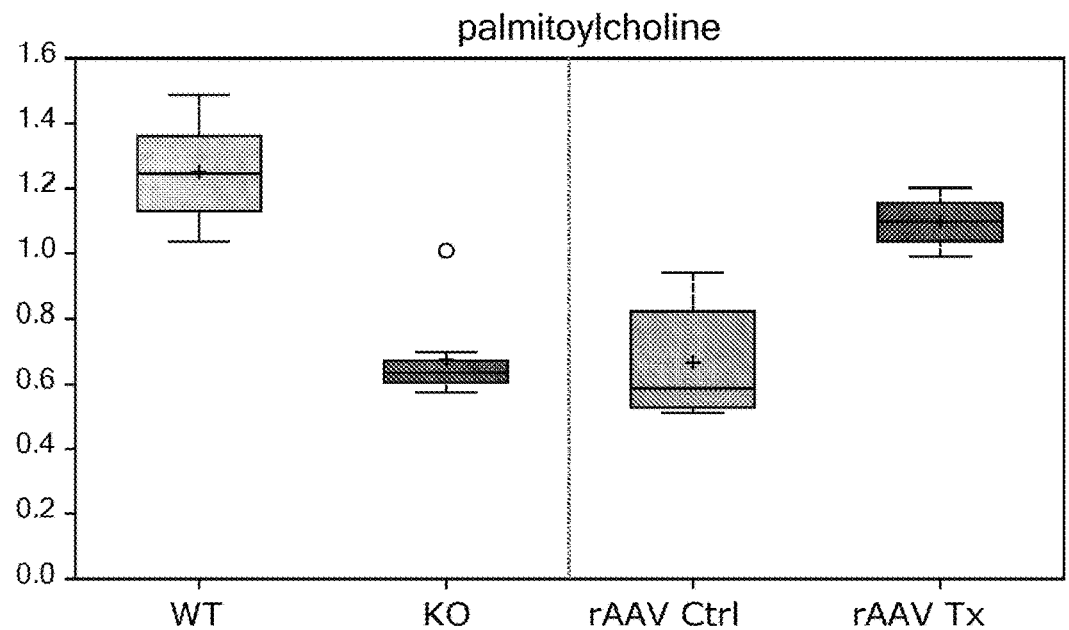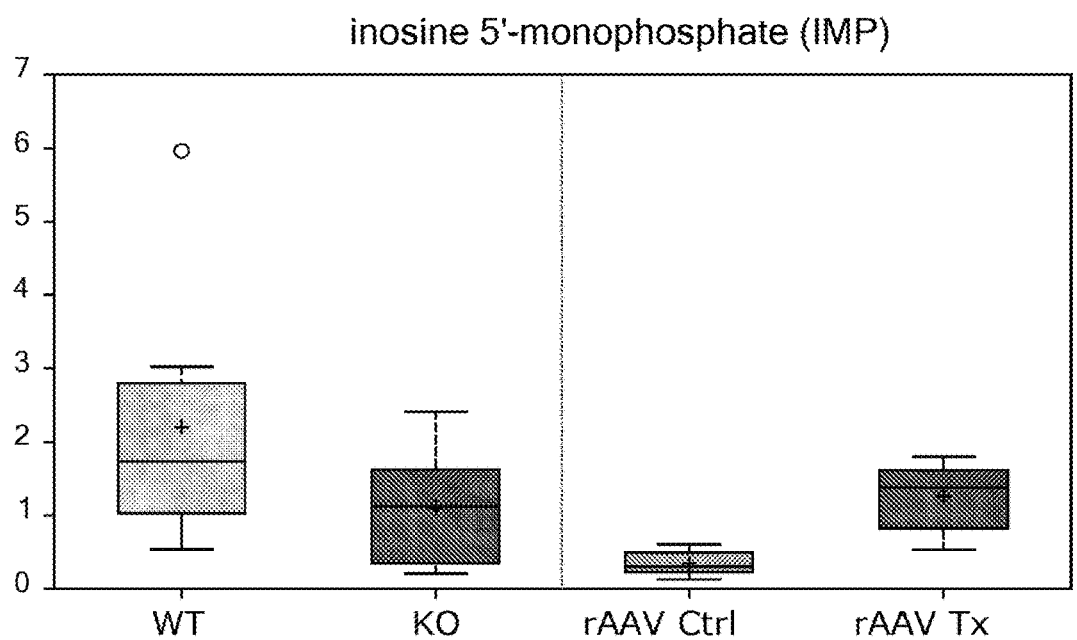
FIG. 57 cont.

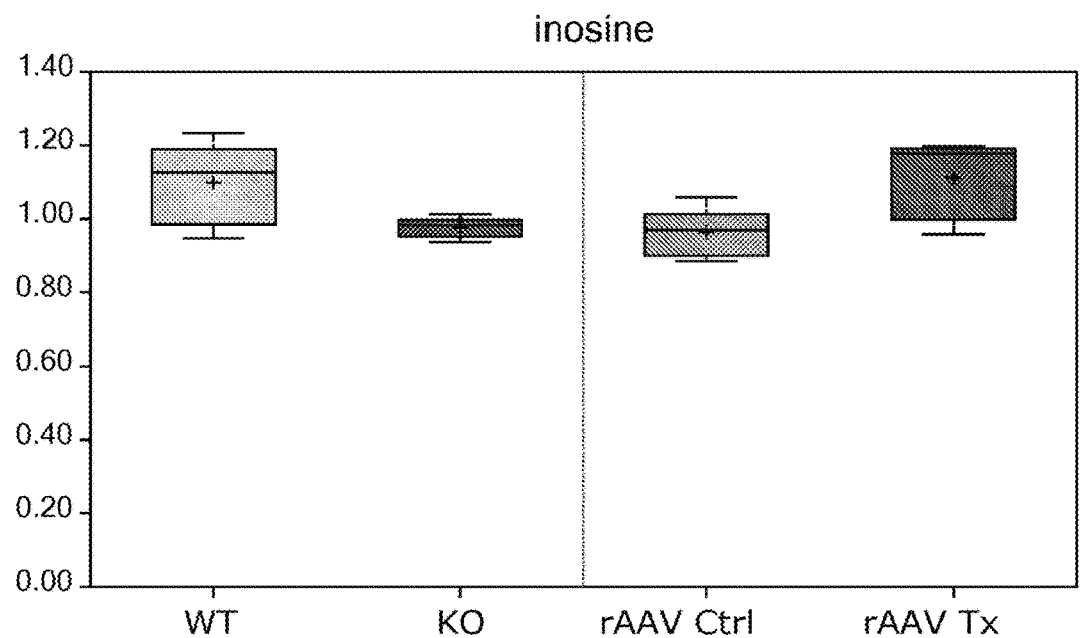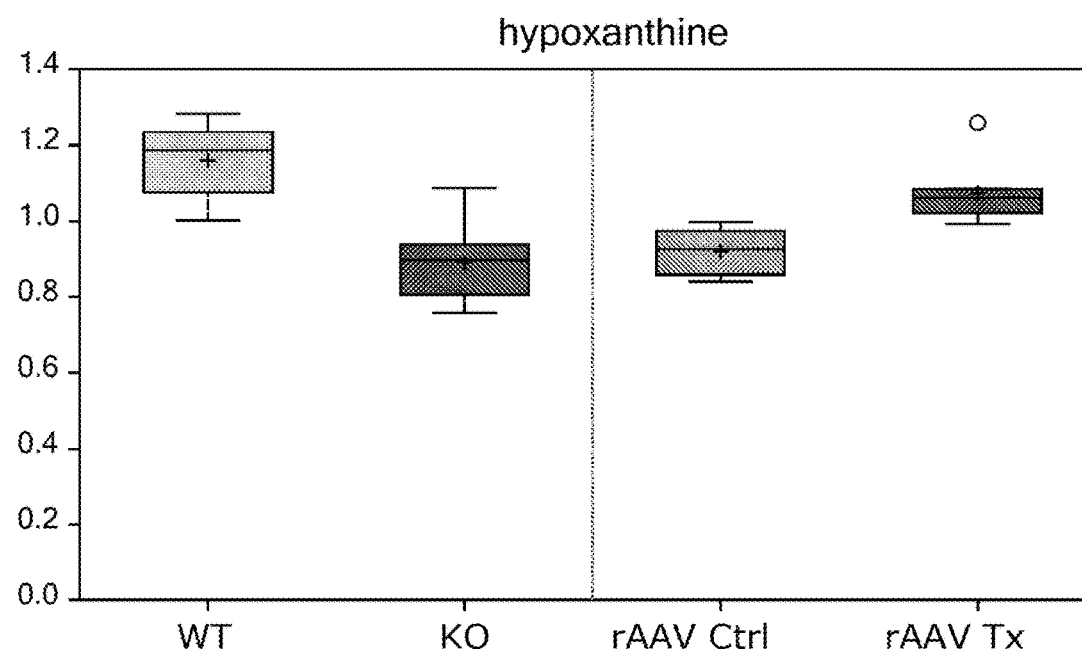
FIG. 57 cont.

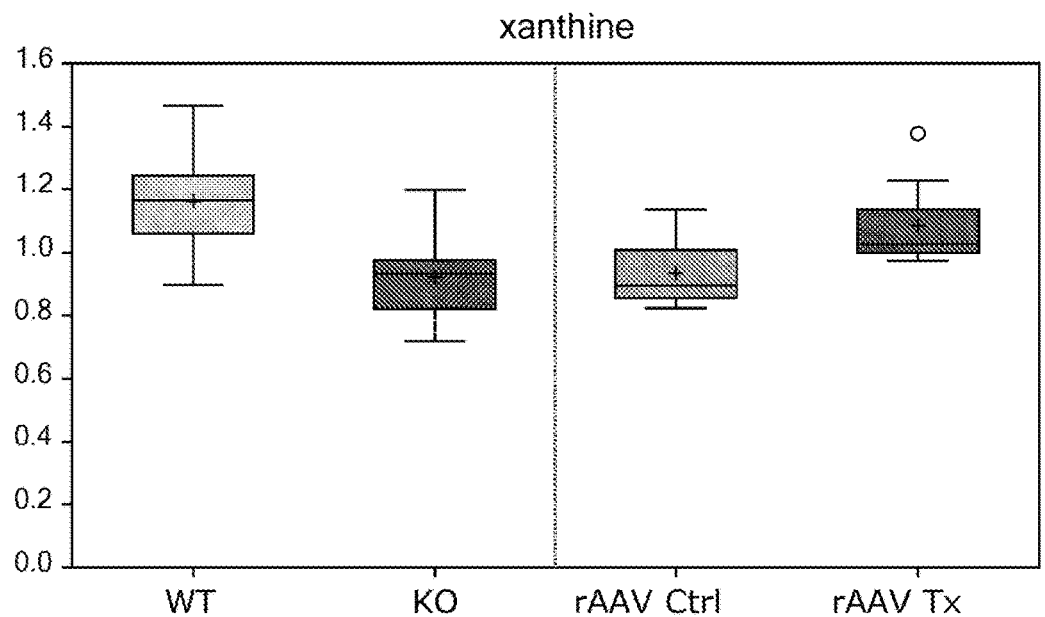
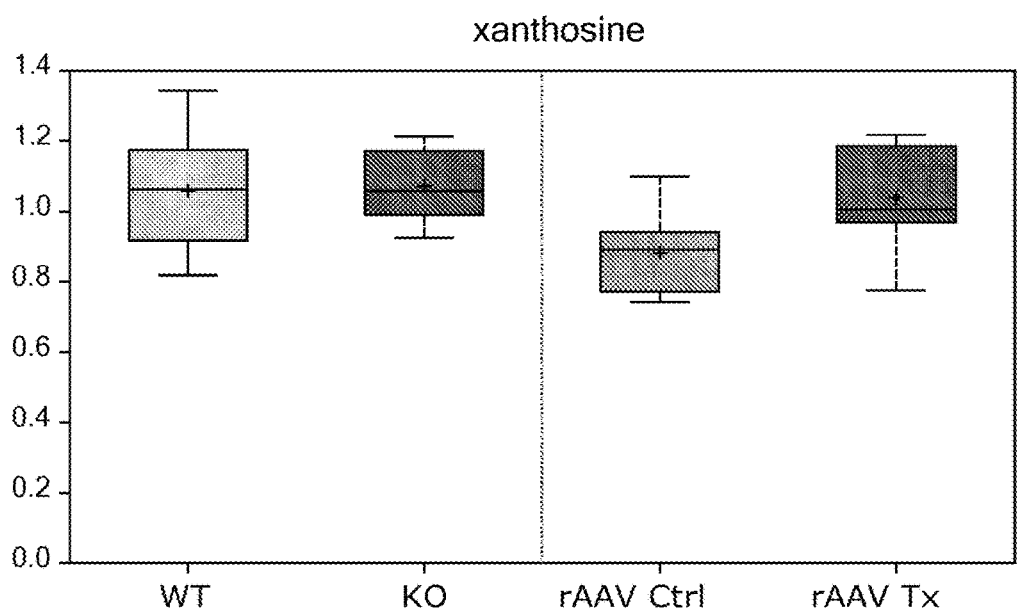
FIG. 57 cont.

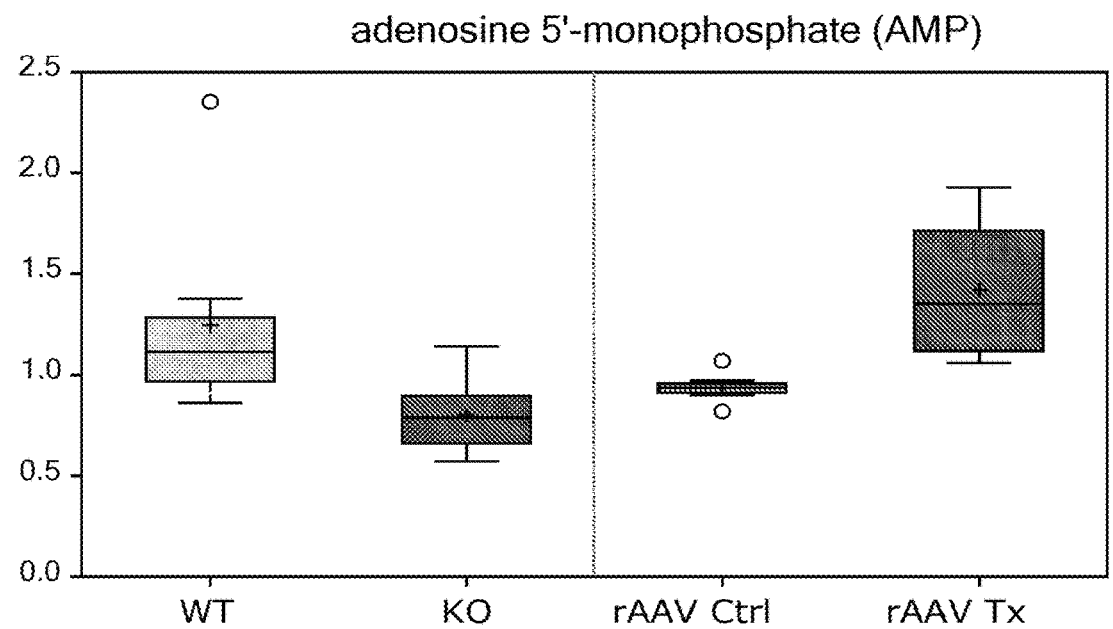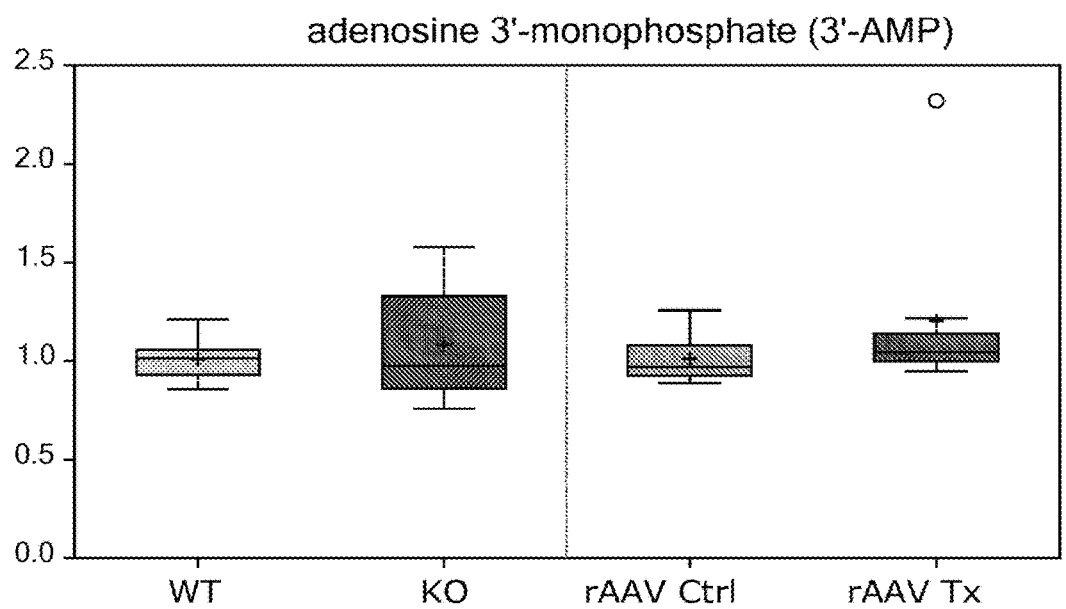
FIG. 57 cont.

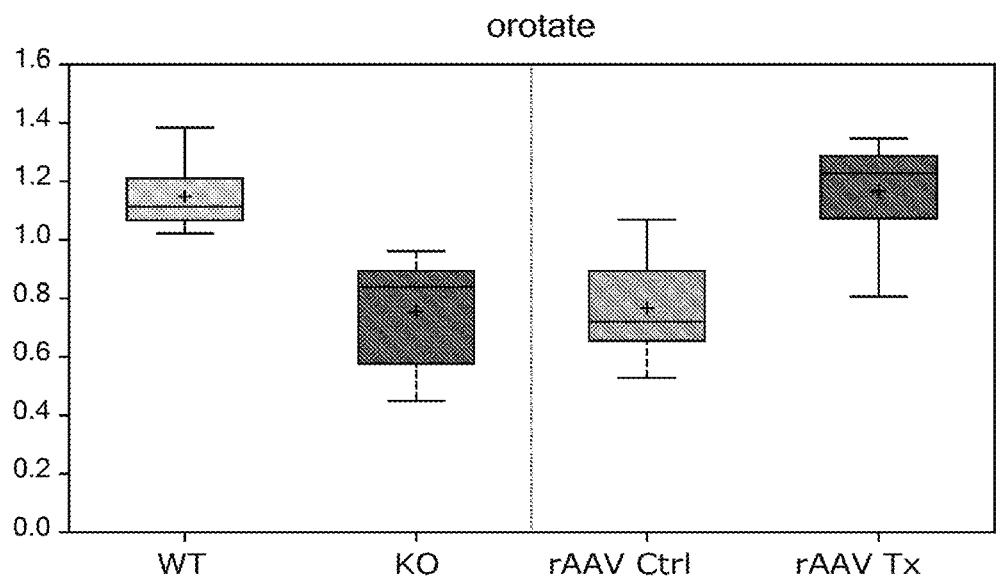
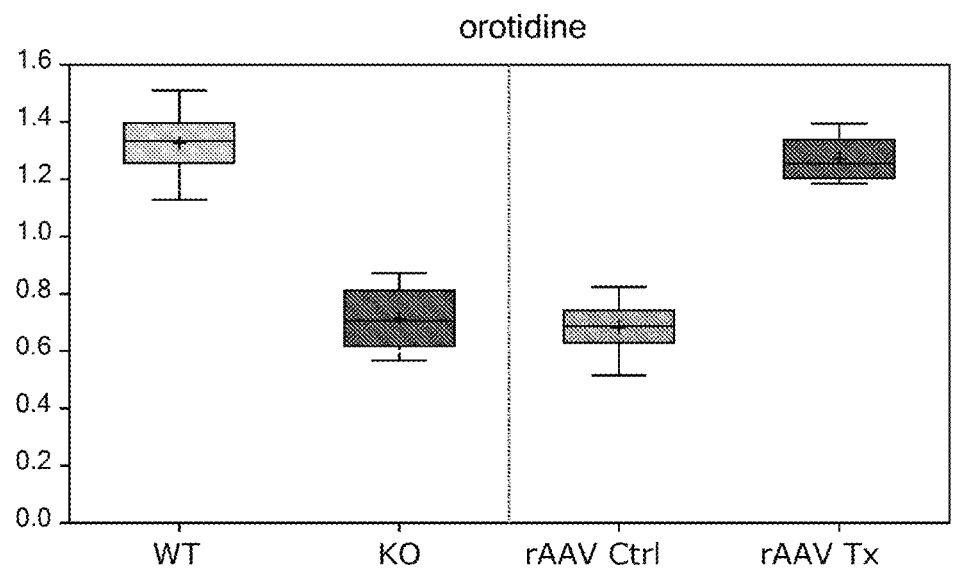
FIG. 57 cont.

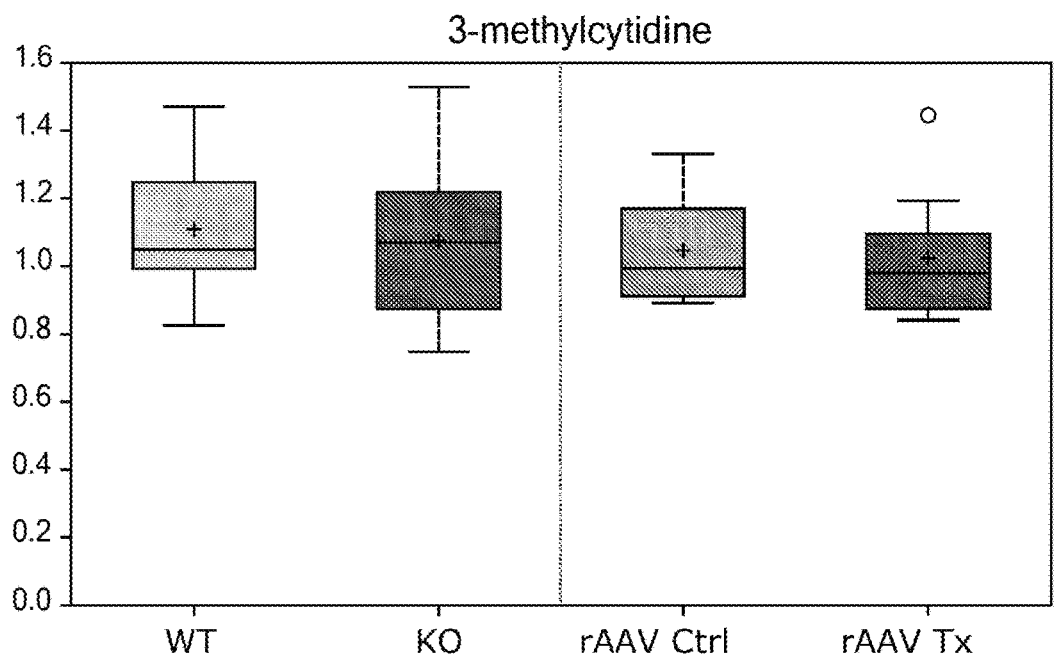
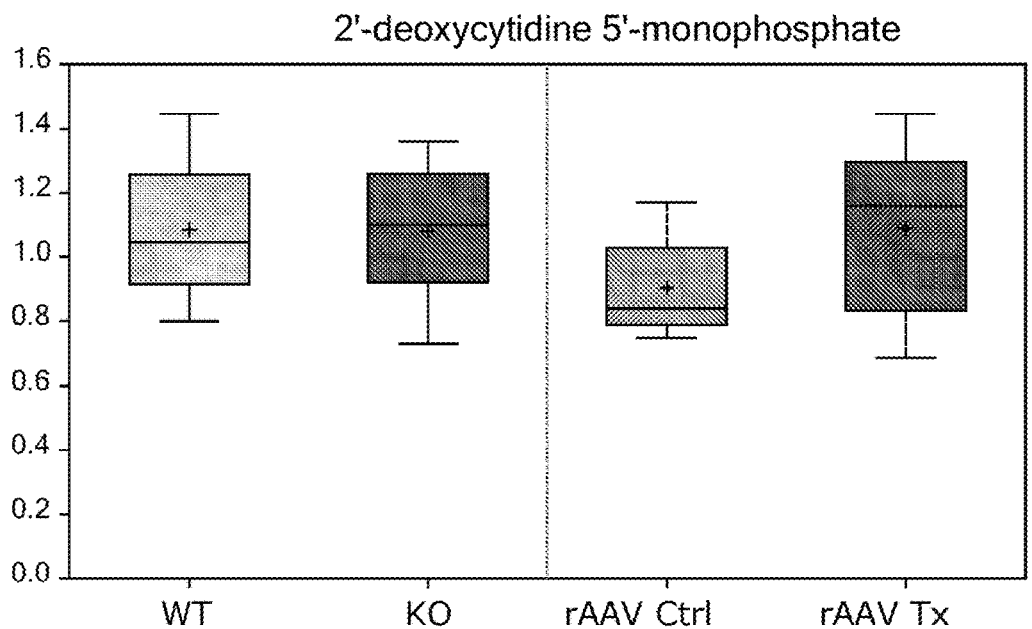
FIG. 57 cont.

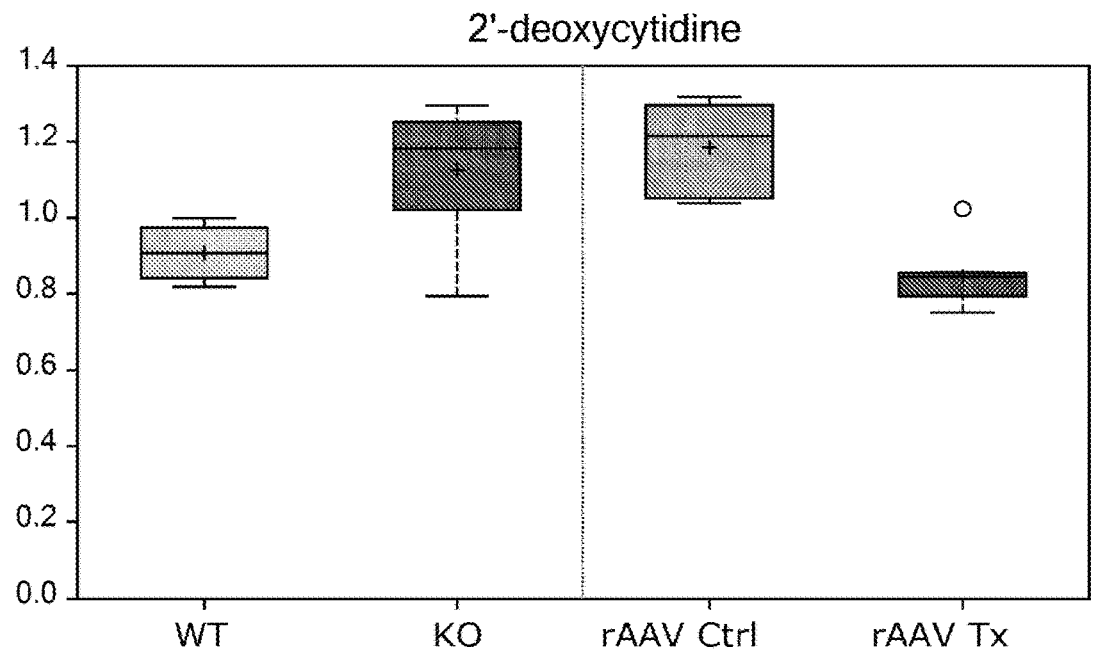
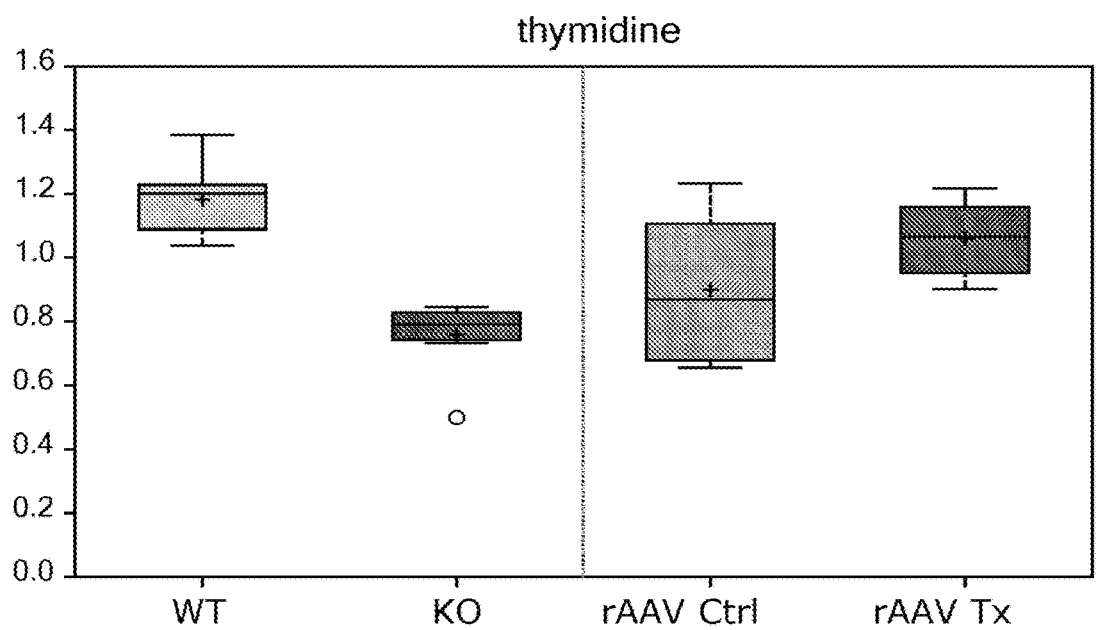
FIG. 57 cont.

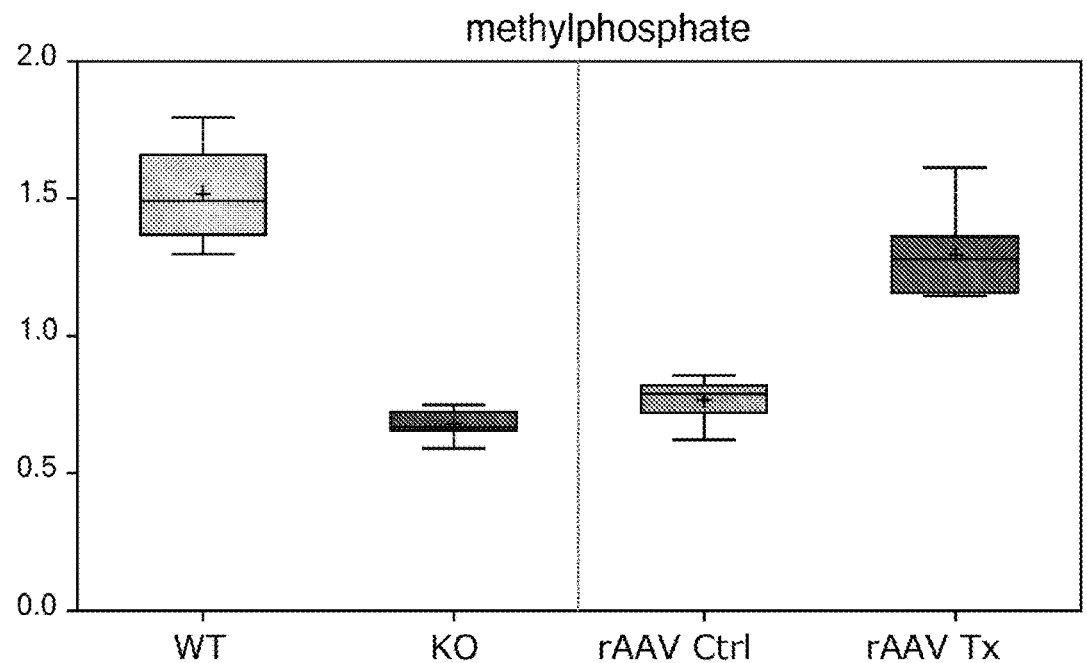
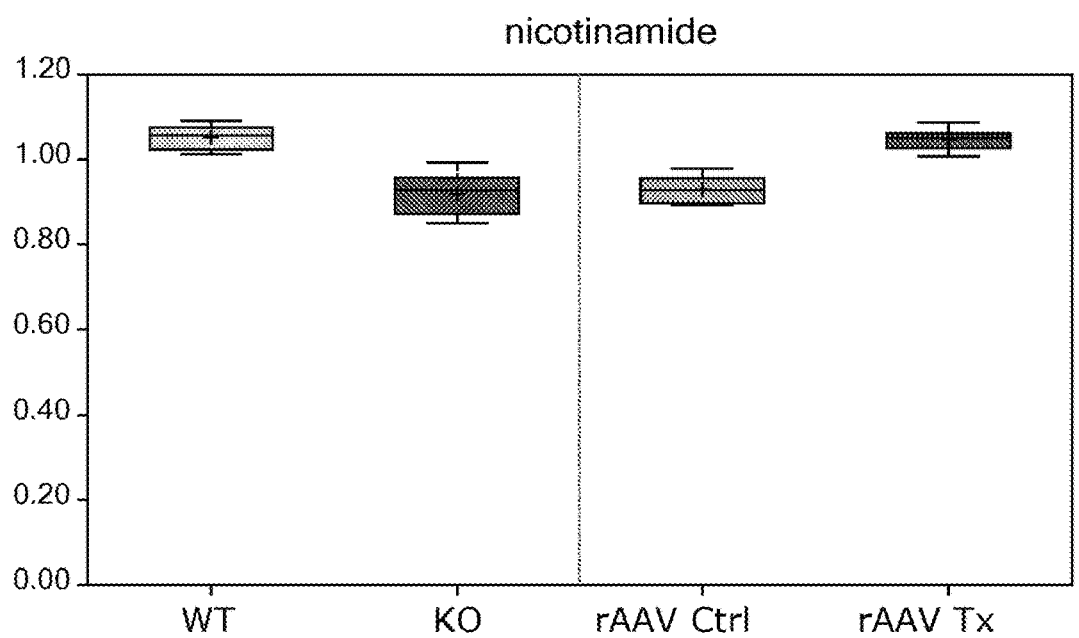
FIG. 57 cont.

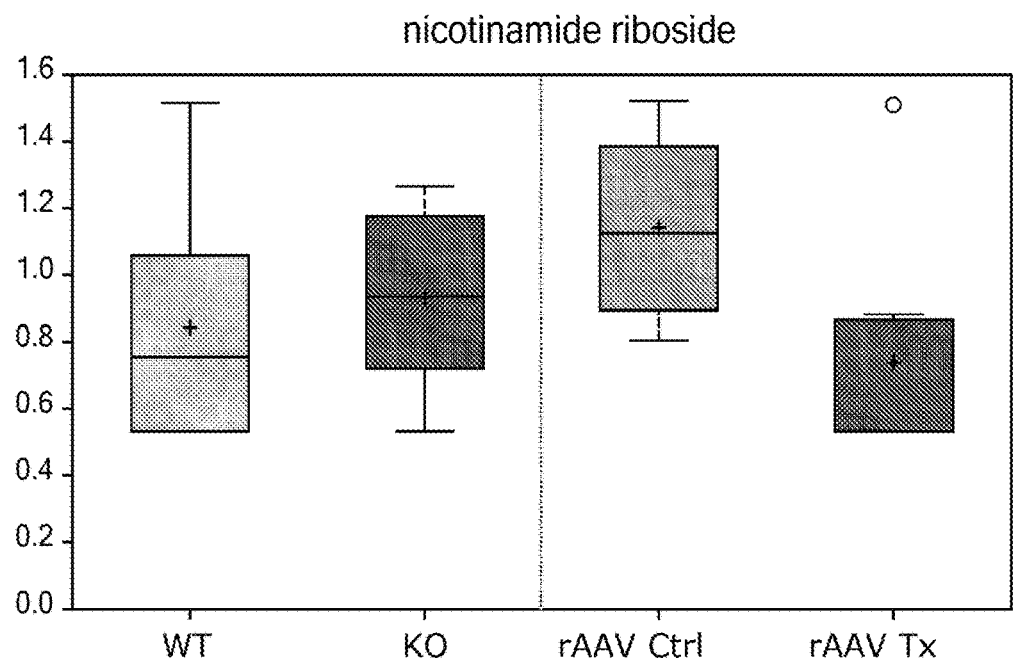
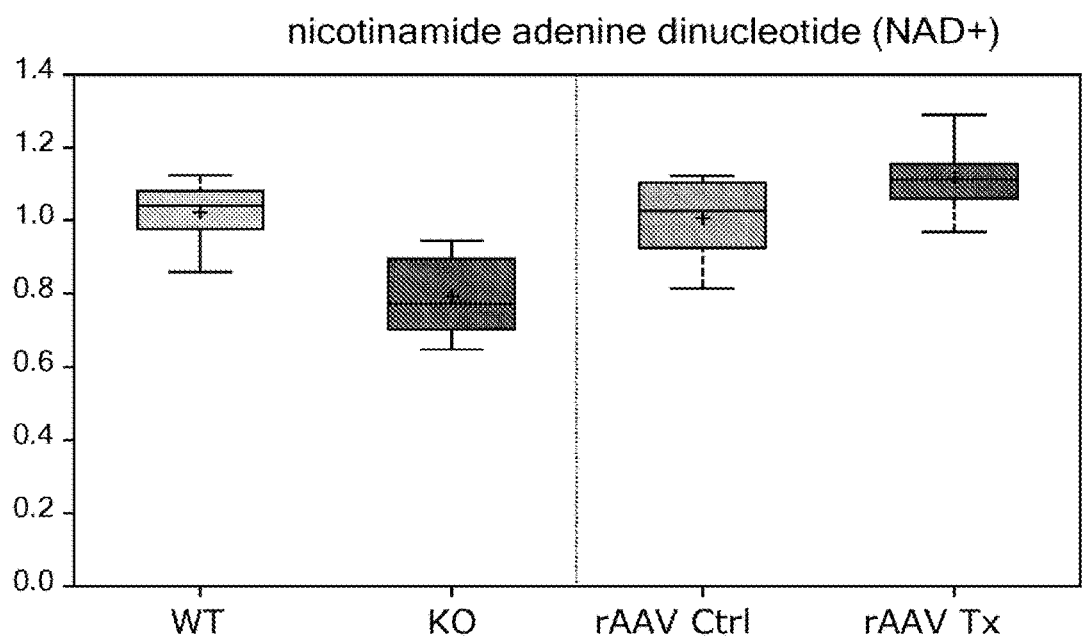
FIG. 57 cont.

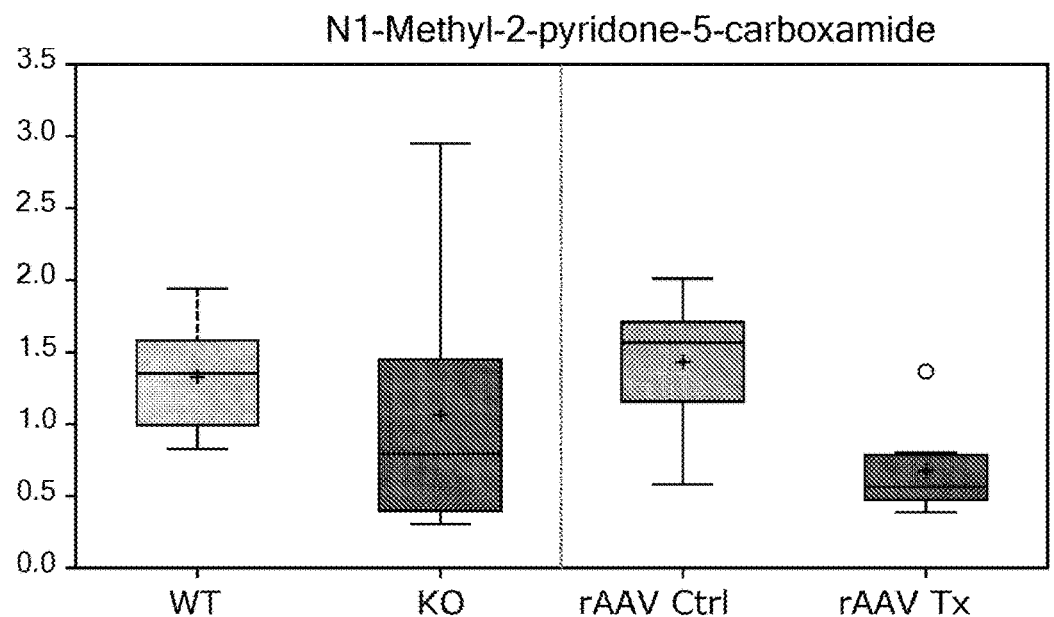
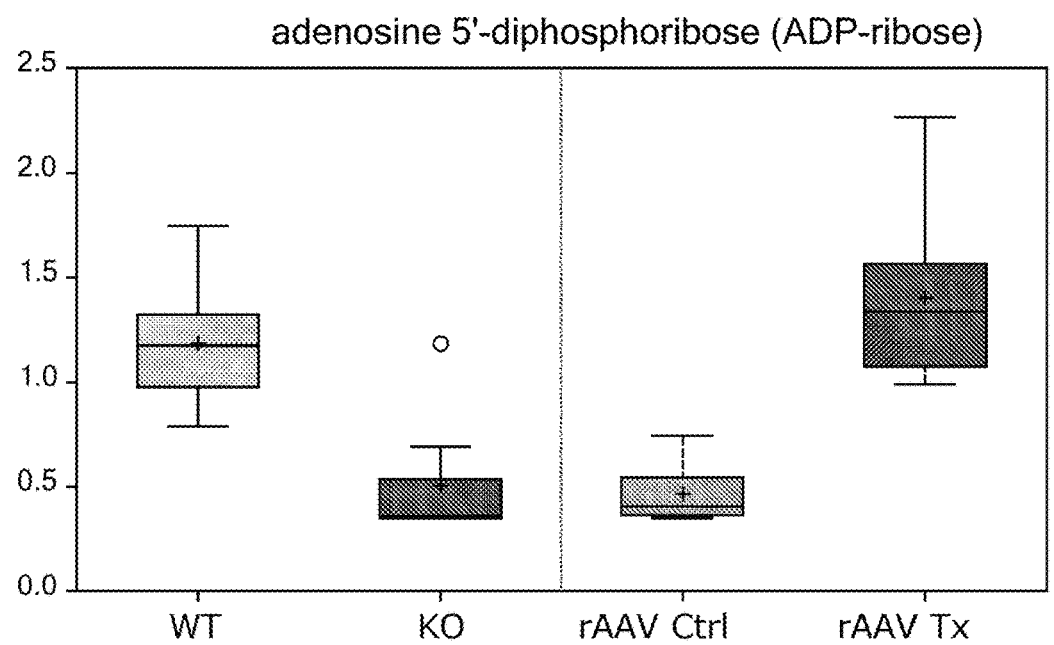
FIG. 57 cont.

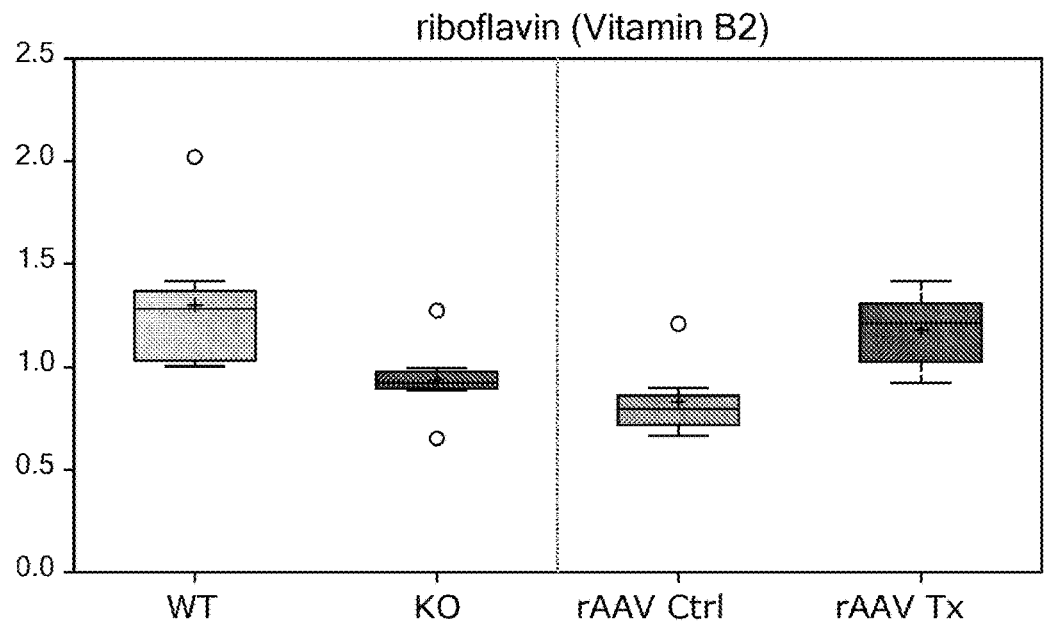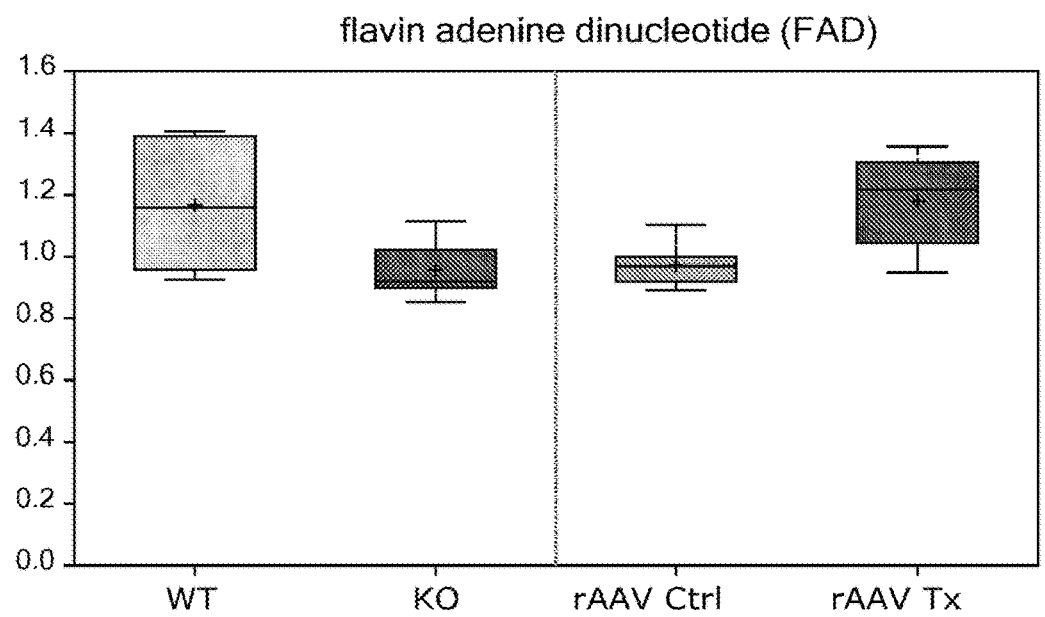
FIG. 57 cont.

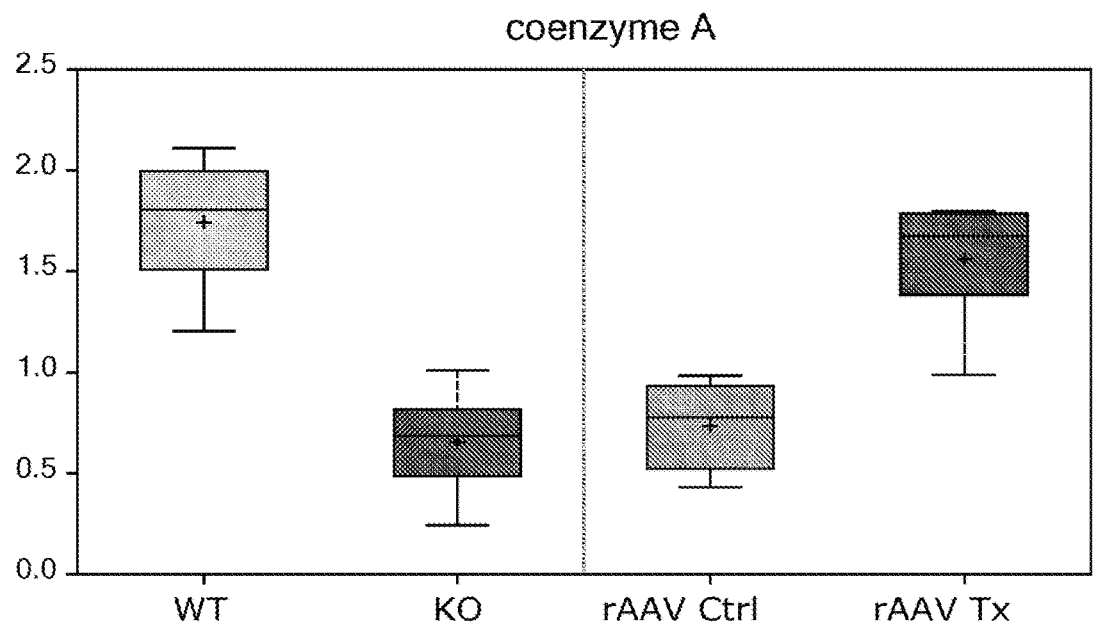
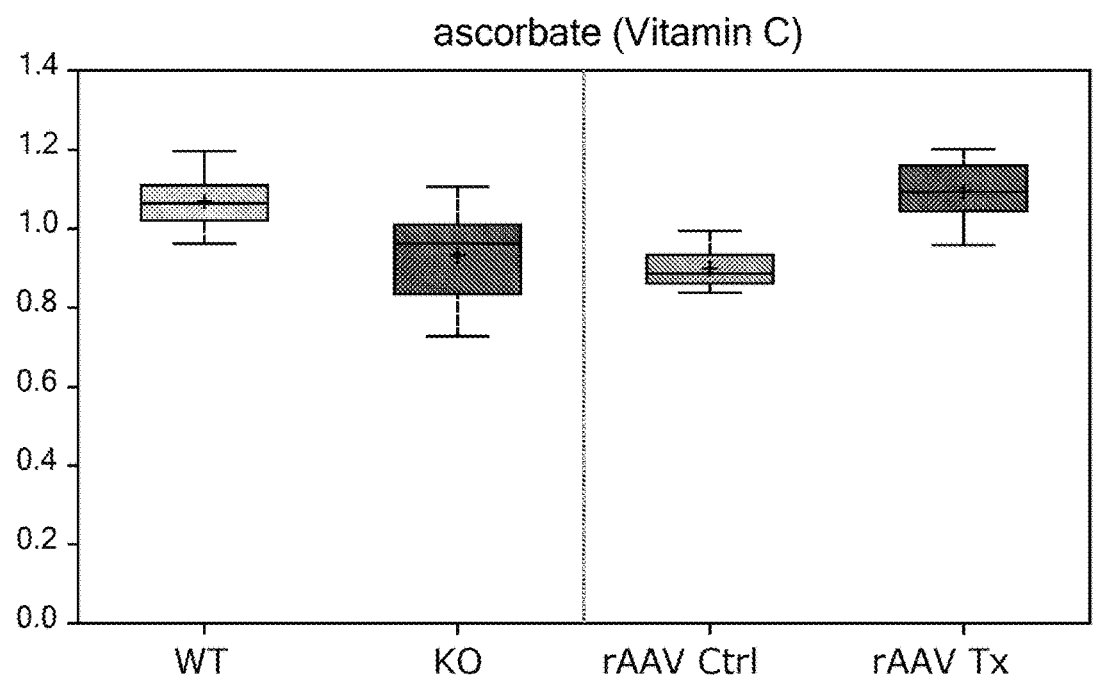
FIG. 57 cont.

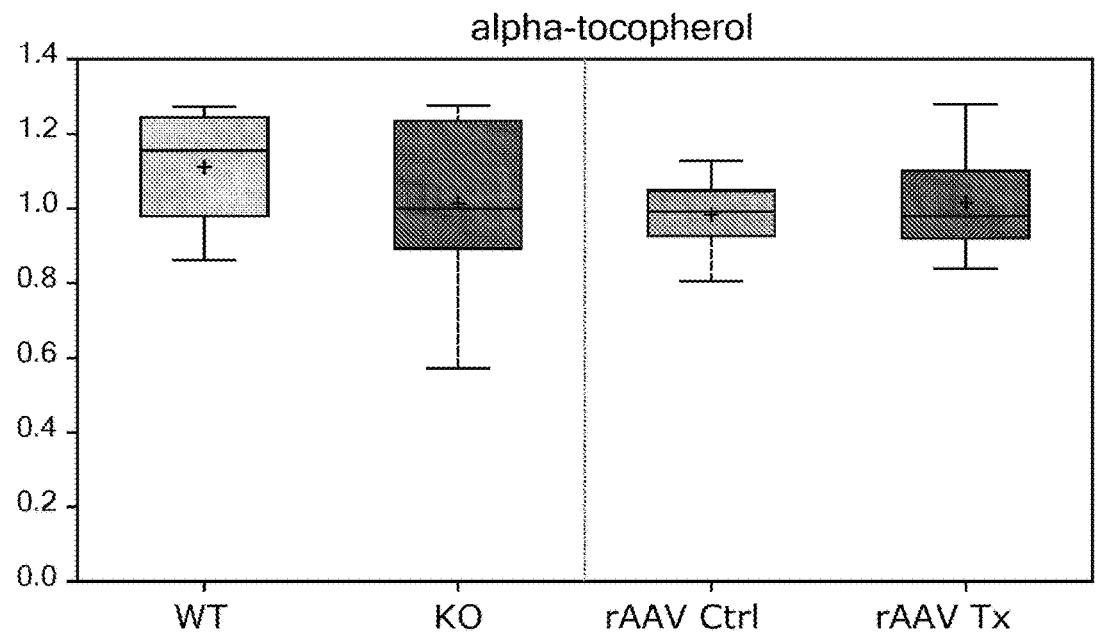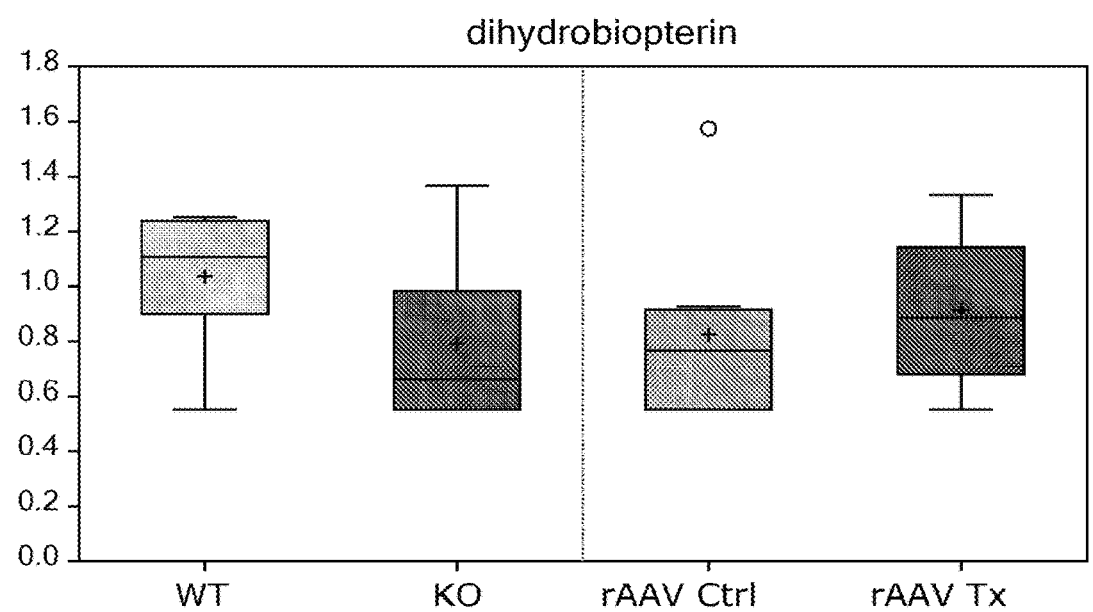
FIG. 57 cont.

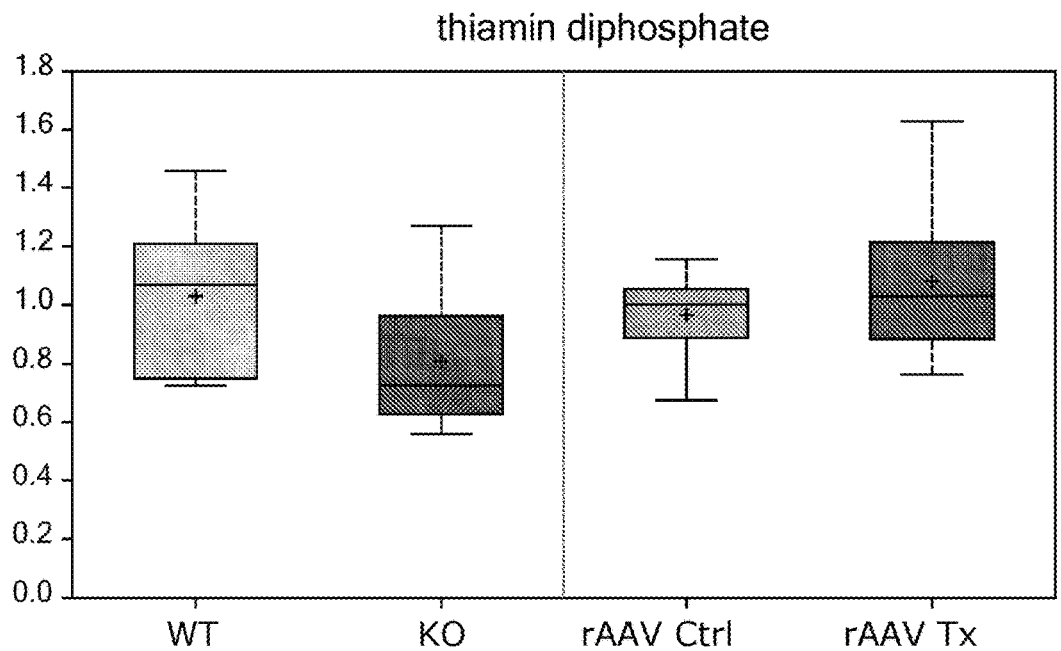
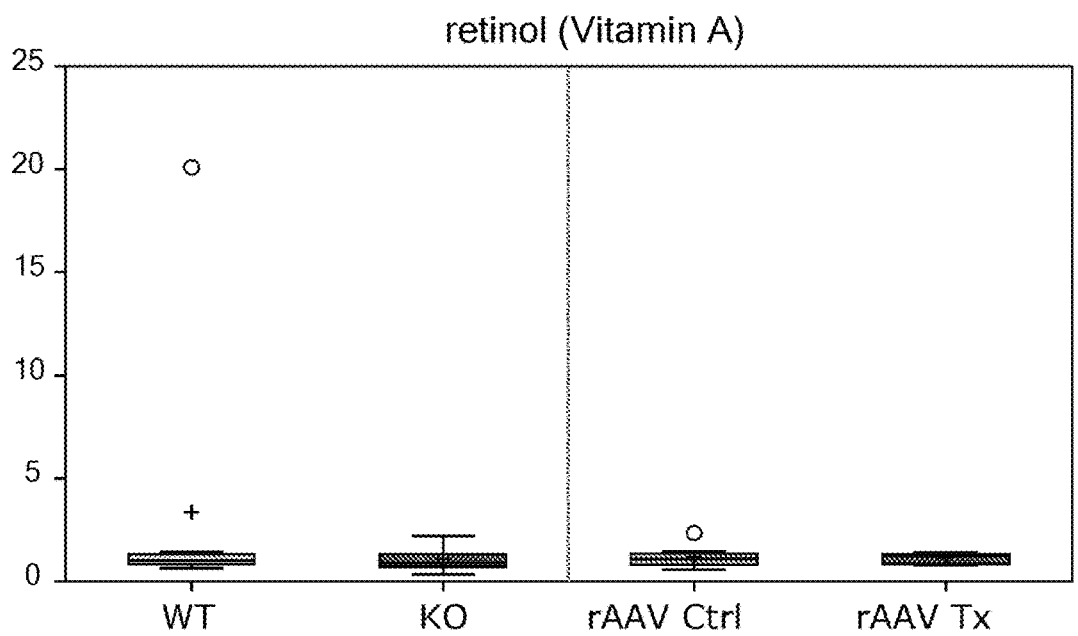
FIG. 57 cont.

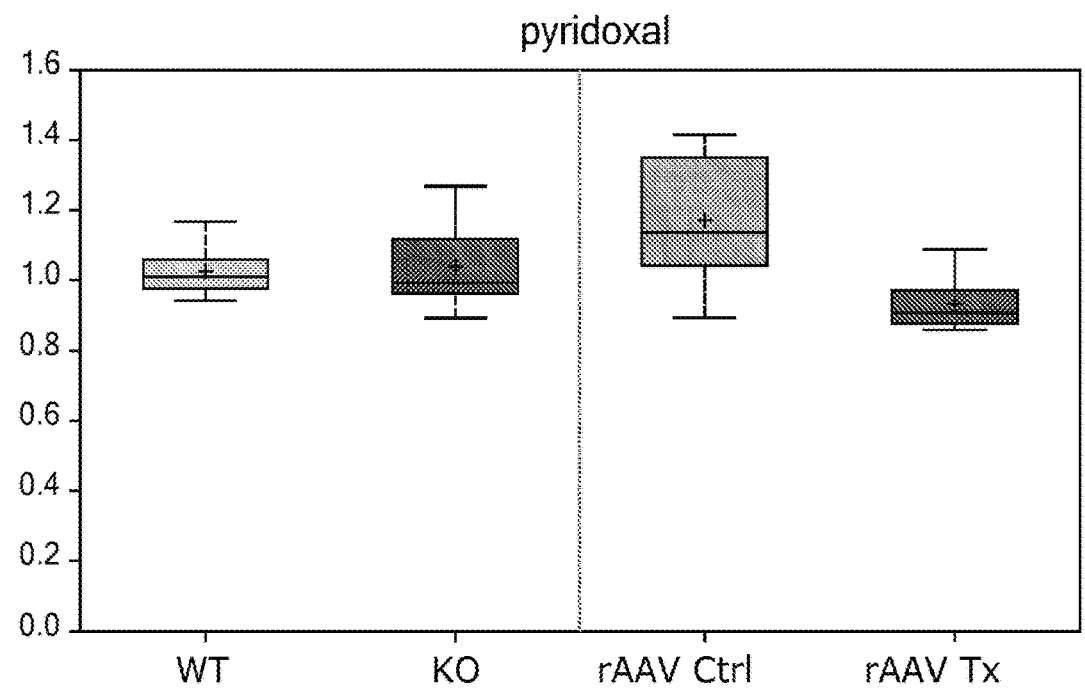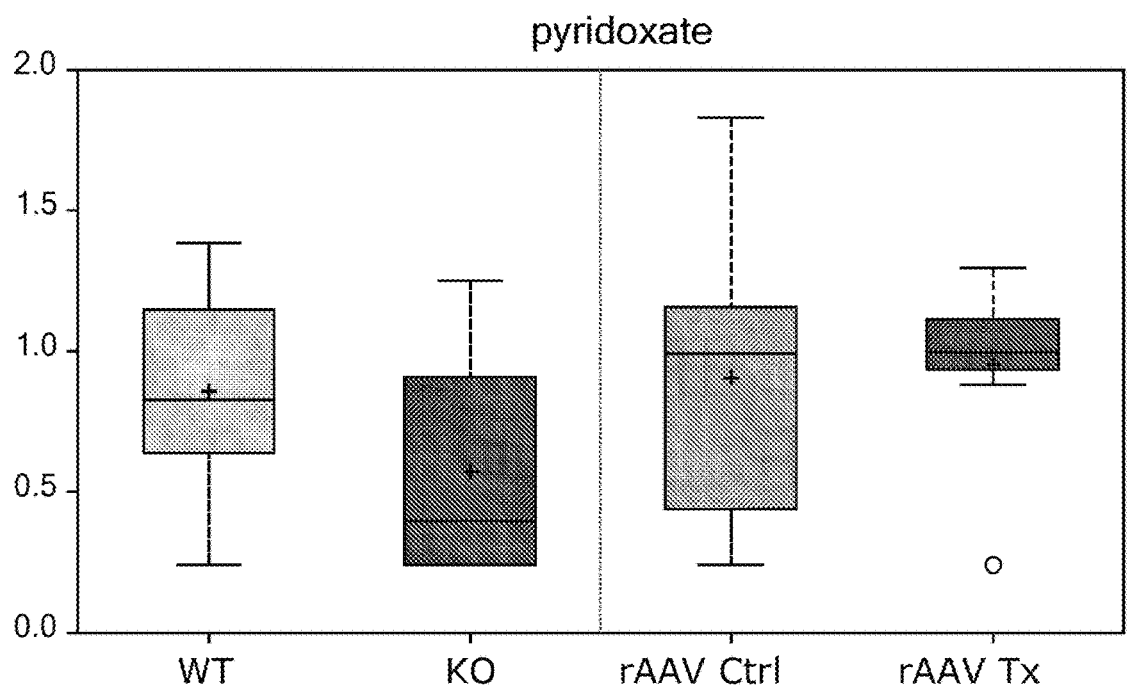
FIG. 57 cont.

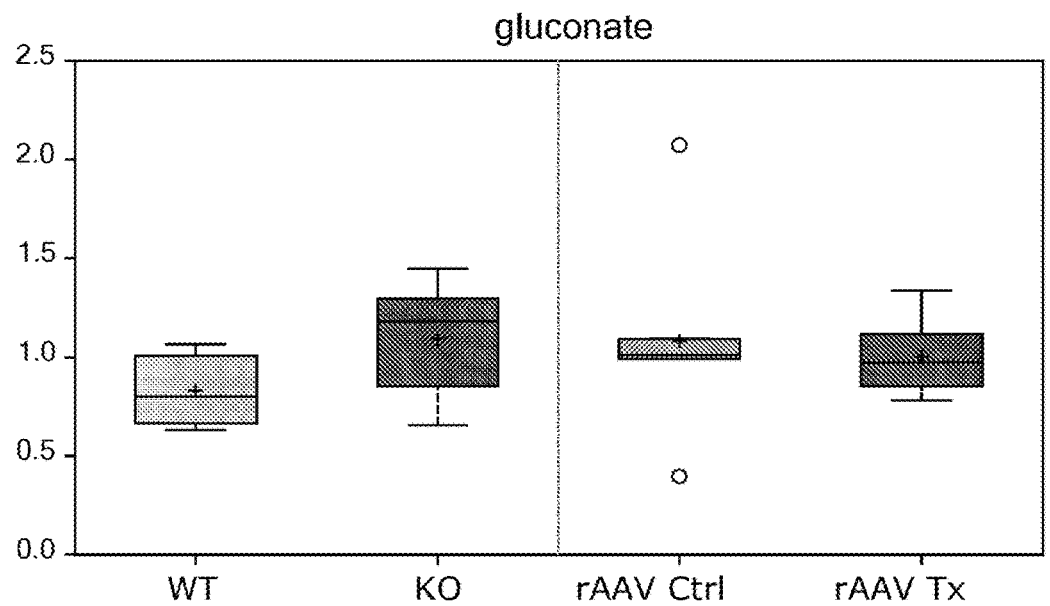
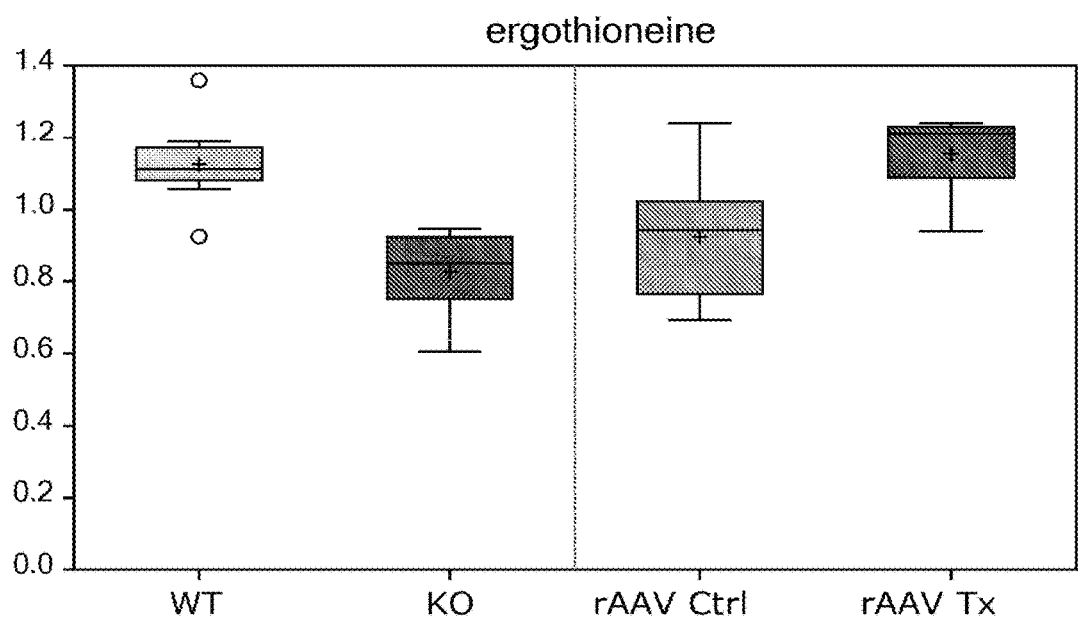
FIG. 57 cont.

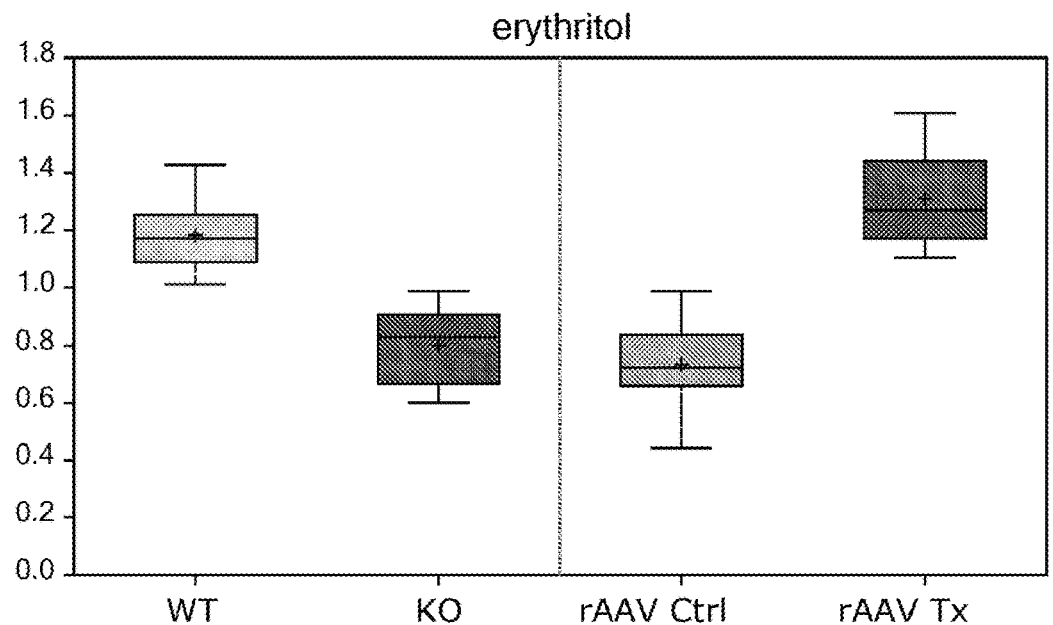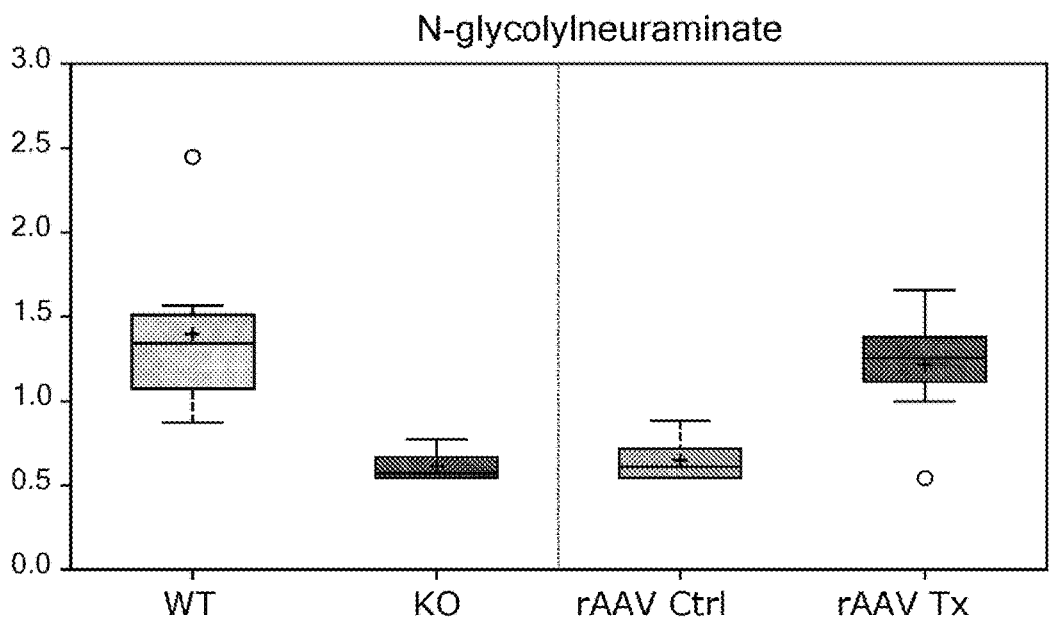
FIG. 57 cont.

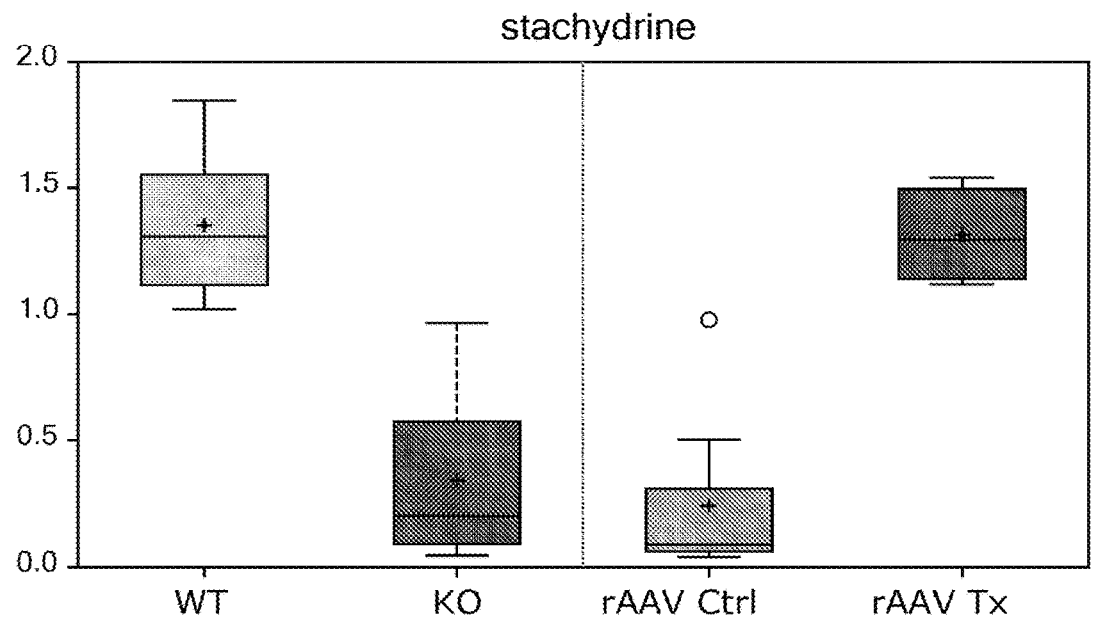
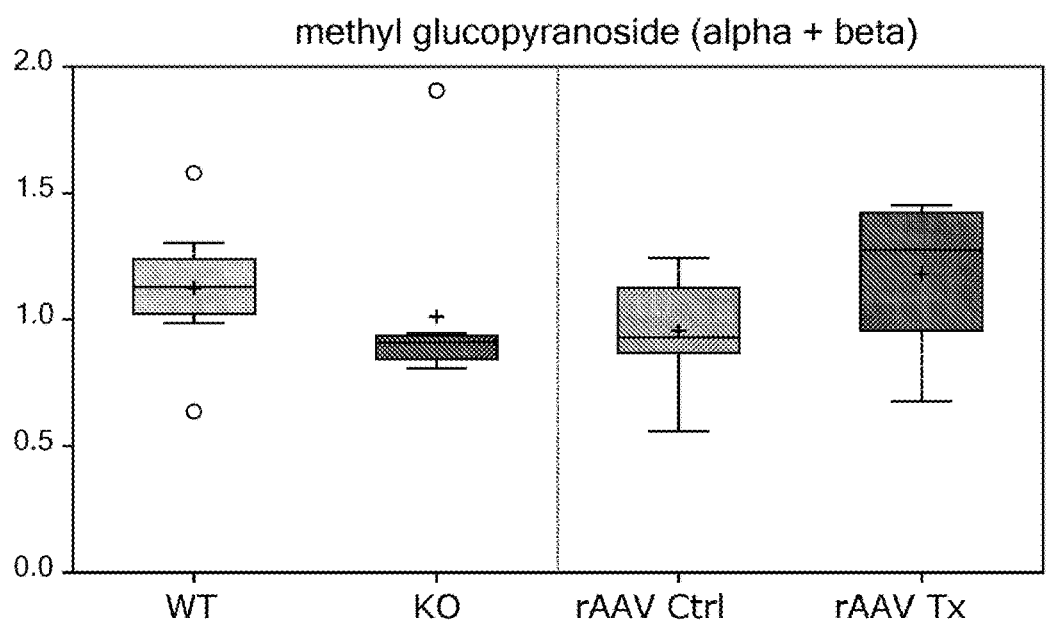
FIG. 57 cont.

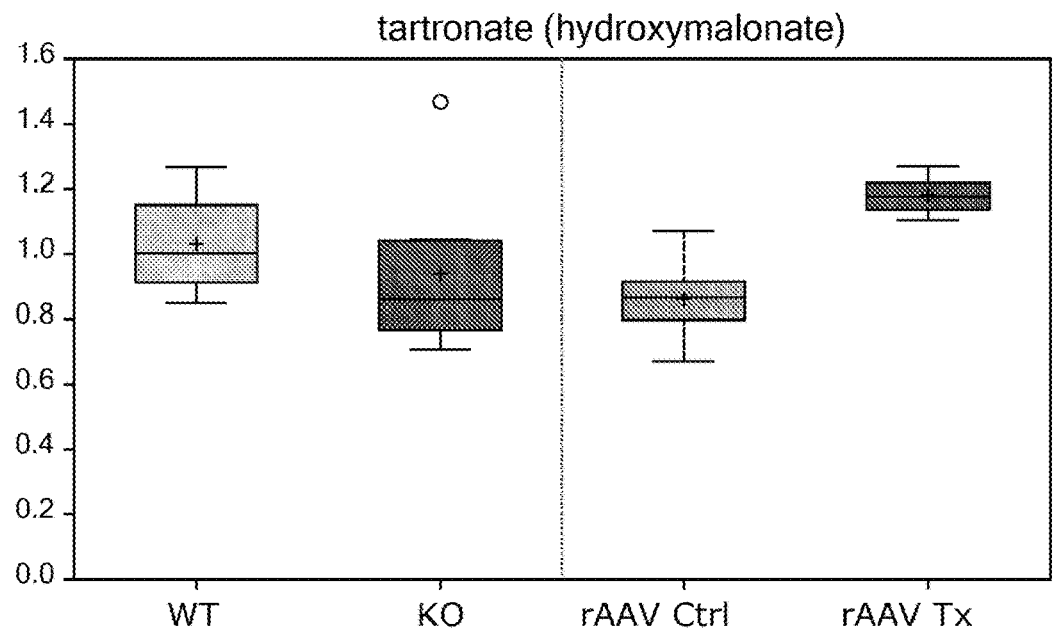
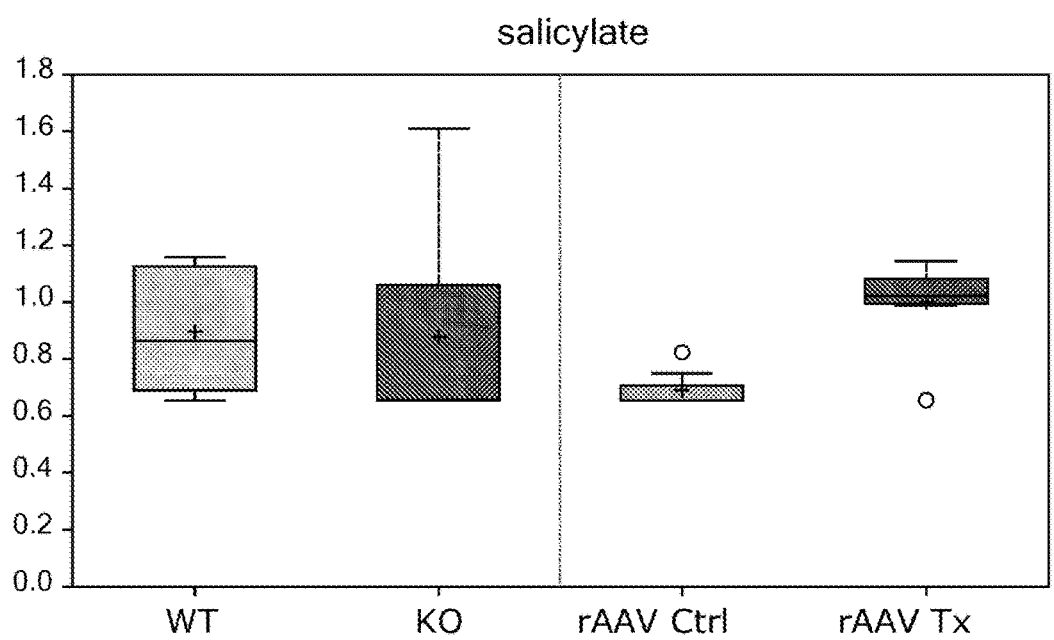
FIG. 57 cont.

METHODS AND COMPOSITIONS FOR TREATING METABOLIC IMBALANCE IN NEURODEGENERATIVE DISEASE

RELATED APPLICATIONS

This application is a National Stage Application of PCT/US2016/058197, filed Oct. 21, 2016, entitled "METHODS AND COMPOSITIONS FOR TREATING METABOLIC IMBALANCE IN NEURODEGENERATIVE DISEASE", which claims the benefit under 35 U.S.C. § 119(e) of U.S. Provisional Application Ser. No. 62/245,213, filed Oct. 22, 2015, U.S. Provisional Application Ser. No. 62/322,101, filed Apr. 13, 2016, and U.S. Provisional Application Ser. No. 62/323,558, filed Apr. 15, 2016, the entire contents of each application which are incorporated herein by reference.

BACKGROUND

Disorders of the central nervous system (CNS) are a huge financial burden for society with increasing incidence and prevalence in populations across the world. Neurodegenerative disorders are a subgroup of CNS disorders that are caused by a variety of genetic and non-genetic factors with variable disease onset, e.g., Canavan Disease, Alzheimer Disease, multiple sclerosis (MS). A subgroup of neurodegenerative disorders are leukodystrophies, which are diseases which target the white matter of the CNS. The white matter of the CNS is comprised of oligodendrocytes that form myelin, wrapping around neuronal axons. One function of oligodendrocytes is to facilitate axon potential propagation.

SUMMARY

The disclosure relates, in some aspects, to compositions and methods useful for the diagnosis and treatment of neurodegenerative diseases. In some aspects, the disclosure relates to the discovery that disturbance of N-acetylaspartate (NAA) metabolism or aspartoacylase (ASPA) deficiency shifts energy metabolism in the CNS away from glycolysis and toward beta oxidation (e.g., fatty acid metabolism) in subjects having white matter diseases (e.g., Canavan's disease), or other neurodegenerative disorders such as Alzheimer's disease and traumatic brain injury. Without wishing to be bound by any particular theory, methods and compositions described herein identify and/or correct metabolic imbalances in the CNS of a subject having a neurodegenerative disease.

Aspects of the disclosure relate to methods for treating leukodystrophy in a subject in need thereof. In some embodiments, the methods comprise administering to the subject an N-acetylaspartate (NAA)-depleting agent. In some embodiments, it has been determined that the leukodystrophy is associated with a metabolic imbalance comprising a shift from glycolysis to beta-oxidation in the subject. In some embodiments, the methods further comprise detecting the metabolic imbalance by evaluating levels of one or more glycolysis and/or beta-oxidation factors (e.g., by evaluating levels of an informative molecule or set of molecules of a metabolic pathway, for example, any one or more of those listed in FIG. 57). In some embodiments, levels of one or more glycolysis and/or beta-oxidation factors are determined using CNS fluid obtained from the subject.

In some embodiments, methods provided herein for treating a leukodystrophy comprise obtaining CNS fluid from a subject; detecting increased beta-oxidation in the CNS fluid; and based on the detected increase in beta-oxidation, administering to the subject an N-acetylaspartate (NAA)-depleting agent. In some embodiments, the NAA-depleting agent is ASPA.

In some embodiments, methods provided herein for treating a leukodystrophy comprise measuring a metabolic profile of a biological sample obtained from a subject; identifying a metabolic imbalance associated with the leukodystrophy based upon the metabolic profile; and, administering to the subject an N-acetylaspartate (NAA)-depleting agent. In some embodiments, the metabolic imbalance comprises a shift from glycolysis to beta-oxidation.

In some embodiments, a leukodystrophy is associated with a condition selected from the group consisting of Canavan disease, adrenomyeloneuropathy, Alexander disease, cerebrotendineous xanthomatosis, Krabbe disease, metachromic leukodystrophy, adrenoleukodystrophy, Pelizaeur disease, and Refum disease. In some embodiments, a leukodystrophy is associated with Canavan disease.

In some embodiments, measuring the metabolic profile comprises assaying the biological sample using liquid chromatography (LC), mass spectrometry (MS), or liquid chromatography/mass spectrometry (LC/MS). In some embodiments, measuring the metabolic profile comprises assaying the biological sample using Ultrahigh Performance Liquid Chromatography-Tandem Mass Spectroscopy (UPLC-MS/MS).

In some embodiments, the biological sample comprises CNS tissue or cerebrospinal fluid (CSF). In some embodiments, the CNS tissue is brain tissue.

In some embodiments, a metabolic profile comprises a level of a first biomarker selected from the group consisting of glucose, glucose-6-phosphate, 3-phosphoglycerate, pyruvate, lactate, and phosphoenolpyruvate. In some embodiments, a metabolic profile comprises a level of a second biomarker selected from the group consisting of carnitine, malonylcarnitine, myristoylcarnitine, palmitoylcarnitine, malonylcarnitine, and beta-hydroxybutyrate. In some embodiments, a metabolic profile further comprises a level of one or more additional biomarkers indicating a reduction in glycolysis of the subject. In some embodiments, the metabolic profile further comprises a level of one or more additional biomarkers indicating an increase in beta-oxidation of the subject.

In some embodiments, a NAA-depleting agent is selected from the group consisting of a small molecule, a protein, and a nucleic acid. In some embodiments, a NAA-depleting agent is administered using an recombinant adeno-associated virus (rAAV). In some embodiments, the rAAV comprises: a capsid protein; and, a nucleic acid comprising a promoter operably linked to a transgene, e.g., a transgene that encodes aspartoacylase (ASPA). In some embodiments, the promoter is an astrocyte-specific promoter. In some embodiments, the astrocyte-specific promoter is glial fibrillary acidic protein (GFAP) promoter.

In some embodiments, a capsid protein has a serotype selected from the group consisting of AAV1, AAV2, AAV3, AAV4, AAV5, AAV6, AAV6.2, AAV7, AAV8, AAV9 and AAV.rh10.

In some embodiments, the rAAV is administered via injection. In some embodiments, the injection is selected from the group consisting of intravenous injection, intravascular injection and intraventricular injection. In some embodiments, the administration results in expression of the gene in peripheral tissue. In some embodiments, the administration results in expression of the gene in CNS tissue. In some embodiments, administration results in astrocyte-restricted expression of the gene.

In some embodiments, methods provided herein further comprise administering a small molecule metabolic modulator to the subject. In some embodiments, methods provided herein further comprise prescribing to the subject a dietary intervention, wherein the dietary intervention promotes glycolysis and/or reduces beta-oxidation in the subject. In some embodiments, methods provided herein further comprise administering an immune-suppressing agent to the subject. In some embodiments, the immune-suppressing agent comprises prednisone or a corticosteroid. In some embodiments, the immune-suppressing agent is administered to the subject prior to the administration of the rAAV.

Aspects of the disclosure relate to methods for treating a neurodegenerative disease. In some embodiments, the methods comprise: measuring a metabolic profile of a biological sample obtained from a subject; identifying a metabolic imbalance associated with the neurodegenerative disease based upon the metabolic profile; and, administering to the subject an N-acetylaspartate (NAA)-increasing agent. In some embodiments, the metabolic imbalance comprises a decrease in N-acetylaspartate (NAA) level. In some embodiments, the methods involve evaluating levels of an informative molecule or set of molecules of a metabolic pathway to establish a metabolic profile. In some embodiments, the neurodegenerative disease is selected from the group consisting of Alzheimer's disease, traumatic brain injury (TBI), bipolar disorder, catalepsy, epilepsy (e.g., seizures), migraine, Huntington's disease, attention deficit disorder (ADD), attention deficit/hyperactivity disorder (e.g., ADHD), autism spectrum disorder (e.g., Asperger's disease, autism, etc.), Parkinson's disease, Tourette's syndrome, clinical depression, multiple sclerosis, and autoimmune disease (e.g., CNS demyelinating disease, Myastenia gravis, etc.). In some embodiments, the neurodegenerative disease is Alzheimer's disease. In some embodiments, measuring the metabolic profile comprises assaying the biological sample using liquid chromatography (LC), mass spectrometry (MS), or liquid chromatography/mass spectrometry (LC/MS). In some embodiments, measuring the metabolic profile comprises assaying the biological sample using Ultrahigh Performance Liquid Chromatography-Tandem Mass Spectroscopy (UPLC-MS/MS). In some embodiments, the biological sample comprises CNS tissue or cerebrospinal fluid (CSF). In some embodiments, the CNS tissue is brain tissue.

In some embodiments, the metabolic imbalance is not caused by an ASPA-deficiency. In some embodiments, the metabolic profile comprises a level of one or more biomarkers indicating a change in glycolysis of the subject. In some embodiments, the metabolic profile comprises a level of one or more biomarkers indicating a change in beta-oxidation of the subject.

In some embodiments, the N-acetylaspartate (NAA)-increasing agent is selected from the group consisting of a small molecule, a protein, and a nucleic acid. In some embodiments, the N-acetylaspartate(NAA)-increasing agent is administered using an recombinant adeno-associated virus (rAAV). In some embodiments, the rAAV comprises: (a) a capsid protein; and, (b) a nucleic acid comprising a promoter operably linked to a transgene, e.g., a transgene that encodes N-acetylaspartate synthetase (NAT8L). In some embodiments, the capsid protein has a serotype selected from the group consisting of AAV1, AAV2, AAV3, AAV4, AAV5, AAV6, AAV6.2, AAV7, AAV8, AAV9 and AAV.rh10. In some embodiments, the rAAV is administered via injection.

In some embodiments, the injection is selected from the group consisting of intravenous injection, intravascular injection and intraventricular injection. In some embodiments, the administration results in the ubiquitous expression of the transgene. In some embodiments, the administration results in expression of the gene in peripheral tissue. In some embodiments, the administration results in administration results in expression of the gene in CNS tissue. In some embodiments, the method further comprises administering a small molecule metabolic modulator to the subject.

Further aspects of the disclosure relate to methods of increasing ATP production in a subject. In some embodiments, the methods involve administering to a subject a recombinant adeno-associated virus (rAAV) comprising a transgene encoding ASPA enzyme, or NAT8L enzyme. In some embodiments, the subject does not have an ASPA deficiency or a neurodegenerative disease.

BRIEF DESCRIPTION OF DRAWINGS

FIG. 3 shows data illustrating that Canavan disease (CD) causes increased oxygen consumption for cortical-subcortical connectivity.

FIG. 4A shows a Principle Component Analysis (PCA) of WT (untreated/treated) and KO (untreated/treated) mice. FIG. 4B shows Hierarchical Clustering Analysis of WT (untreated/treated) and KO (untreated/treated) mice. Both FIGS. 4A and 4B show clustering of WT and KO(treated) mice, indicating that rAAV-ASPA treatment rescues metabolic phenotype in CD mice.

FIG. 10 shows data illustrating that cognitive function (e.g., working/spatial memory) is restored in Nur7 mice intravenously administered rAAV-ASPA at P1 and at 3 months.

FIG. 11 shows data illustrating the rapid and efficient elimination of spongy degeneration of the CNS in Nur7 mice receiving intravenous administration of rAAV-ASPA at P1. Neuropathology was assessed at P25.

FIG. 13 shows data illustrating that rAAV-ASPA treatment restores the myelin-lipid profile in CD mice. Compared to WT mice, KO mice have significantly reduced levels of sphingolipids and other myelin components. CD mice treated with rAAV-ASPA show a significant increase in myelin components, such as sphinganine.

FIG. 26A shows three expression cassettes were cloned carrying either half (HKz) or full Kozak (FKz) sequence and the wild-type (WT) human aspartoacylase (hASPA) cDNA or a codon-optimized (Opt) hASPA; $3^{rd}$ generation construct comprises full FKz and Opt hASPA. FIG. 26B shows mice were treated at p1 via facial vein with $4 \times 10^{11}$ genome copies (GC) of rAAV9 carrying either $1^{st}$, $2^{nd}$ or $3^{rd}$ generation expression cassette. WB of the brains 42 days post-treatment shows relative ASPA expression normalized to actin and WT; due to early lethality, untreated CD KO mice were used at p25 as control (n=3 each). FIG. 26C shows cerebral NAA levels of treated CD KO mice were quantified using magnet resonance spectroscopy (MRS) in living mice at p42; untreated CD KO mice were used at p25 as control. Displayed are total NAA (tNAA) over total creatine (tCr). Error bars indicate mean±SD; n=3; * $p<0.05$,  $p<0.01$, * $p<0.001$, **** $p<0.0001$.

FIG. 30A shows accelerated rotarod data. FIG. 30B shows balance beam tests for deficits in equilibrium sense and for ataxia. Cut-off time point was 300 seconds. FIG. 30C shows muscle/grip strength was tested on inverted screen for up to 300 seconds. Error bars indicate mean±SD; for all motor assays, n=6-8 at P27 and n=8 at p375. * $p<0.001$; ** $p<0.0001$.

FIG. 33A shows MRI imaging comparing WT and all three vector generations. FIG. 33B shows H&E staining shows degree of neuropathologic changes.

FIG. 33C shows Magnetic resonance spectroscopy (MRS) analysis of brain total NAA levels normalized against total creatine at 1 year of age. FIG. 33D shows NAA levels of urine normalized against creatinine at 1 year of age as quantified by mass spectrometry. Error bars indicate mean±SD; n=3; **** $p<0.0001$; ns=non-significant.

FIGS. 36A-36B show brain sections with astrocyte-restricted EGFP expression that co-localizes with GFAP (red in H) positive cells but not with Myelin basic protein (MBP) positive cells (n=3). FIG. 36C shows weights of wild-type mice vs. mice treated with ubiquitous or astrocyte-restricted hASPA expression (n=8-10). FIG. 36D shows motor function (accelerated rotarod, balance beam, and inverted screen) and cognitive (T maze; FIG. 36E) tests of mice with astrocyte-restricted hASPA expression (n=6-8). FIG. 36F shows MRI shows T2 signal pattern of ubiquitous vs. astrocyte-restricted hASPA expression in comparison to wild-type and untreated mice (n=3). FIGS. 36G-36H show MRS and WB of brain NAA levels and ASPA expression (n=3). FIG. 36I shows luxol fast blue staining of myelin shows a reduction of myelin fibers (light arrows) and the presence of vacuoles (black arrows) in the cerebellar white matter of CD KO mice vs. mice treated with ubiquitous or astrocyte-restricted hASPA expression (n=3). ML=molecular layer, PK=Purkinje cell layer, GR=granular layer, WM=white matter. Error bars indicate mean±SD; * $p<0.05$,  $p<0.01$, * $p<0.001$, **** $p<0.0001$.

FIG. 38A shows MRI T2 sequences of different brain regions are shown with wild-type (WT) and untreated (KO) control mice. All mice were imaged at p25 (n=3). FIG. 38B shows total NAA levels of the same mice as in FIG. 38A were quantified by MRS at p25 and normalized against total creatine (n=3). FIG. 38C shows dose-dependent H&E neuropathology of mice at p25 treated with $3^{rd}$ generation or full dose $1^{st}$ generation vectors. WT and KO were used as controls (n=3). FIG. 38D shows dose-dependent motor function was assessed on rotarod, balance beam, and inverted screen at p27 and p90 (n=6-8). Error bars indicate mean±SD; * $p<0.05$;  $p<0.01$; * $p<0.001$; **** $p<0.0001$.

FIG. 42A shows representative images for tractography of the corpus callosum. FIG. 42B shows representative images for the fractional anisotropy (FA) values for left and right external capsule (EC) and corpus callosum (CC). FIG. 42C shows 19 brain regions were selected to analyze resting state-functional magnetic resonance imaging (rs-fMRI) results and mapped on a sagittal brain map. Light and black dots indicate cortical and sub-cortical brain regions, respectively. Light lines display all connections that involve cortical regions and darker lines show sub-cortical connections only. FIG. 42D shows T score statistics of rs-fMRI are shown that indicate differences between corresponding brain regions and overall brain activity (displayed in FIG. 42C). FIG. 42E shows total N-acetylaspartate (NAA) normalized against total creatine (tCr) was measured in all mice that underwent DTI and rs-fMRI imaging. FIG. 42F shows overall functional connectivity (untreated 31, wild-type 21, treated 19) was correlated to the average accelerated rotarod performance in seconds (FIG. 33A, p27) and analyzed via linear regression analysis ($R^2=0.89$). Error bars indicate mean±SD; n=8-10; $p<0.05$;  $p<0.01$; * $p<0.001$; **** $p<0.0001$; ns=non-significant.

FIG. 46 shows rotarod assay data for male mice. Data indicates an expanded therapeutic window for ASPA gene therapy. Mice were assayed at 4 weeks, 10 weeks, 16 weeks, 28 weeks and 52 weeks.

FIG. 48 shows T maze data indicating that working/spatial memory is restored in Nur7 mice after treatment with the $3^{rd}$ generation hASPA gene therapy construct. Cognitive function of Nur7 mice treated at Neonatal, Juvenile or Adult age was tested at 1 Year of Age.

FIG. 50 shows gait analysis data indicating that mice treated at mature adult age (p168) still benefit from the $3^{rd}$ generation ASPA gene therapy treatment.

FIG. 53 shows data indicating that ASPA deficient cells use more Fatty acids and Glutamine for energy production. Data relating to the dependency, flexibility and capacity of wild-type or ASPA deficient cells to use glucose (GLC), glutamine (GLN) or fatty acids (FA) for energy production is shown.

DETAILED DESCRIPTION

Figure 1:
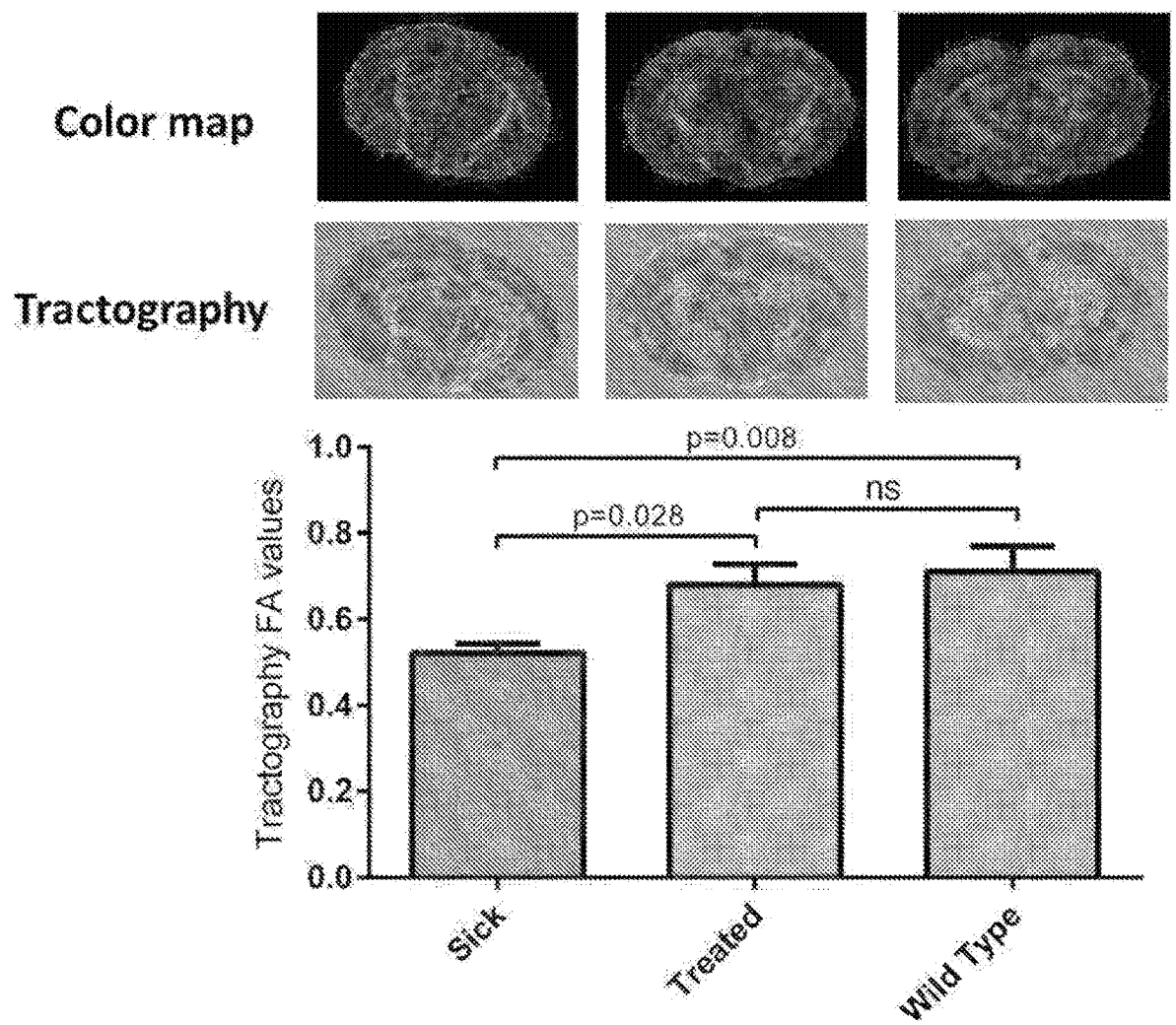
FIG. 1 shows data illustrating that rAAV-ASPA gene therapy restores the thalamo-cortical tract, as measured by diffusion tensor imaging (DTI) for brain water flow.

Aspects of the disclosure relate to methods for treating neurodegenerative disease (e.g., leukodystrophies) in a subject in need thereof. Methods provided herein, in some embodiments, involve modulating N-acetylaspartate (NAA) levels in a subject. NAA has been identified as the second most abundant molecule in the central nervous system (CNS). In some embodiments, NAA synthesis takes place in neurons. In some embodiments, NAA is not synthesized in cells or organs outside the CNS. NAA is metabolized by the enzyme aspartoacylase (ASPA) into acetate and L-aspartate. In some embodiments, ASPA is expressed in the CNS (e.g., in oligodendrocytes). In some embodiments, ASPA is expressed in peripheral organs, such as kidney, small intestines and others. In some embodiments, neurodegenerative diseases demonstrate disturbance of NAA metabolism. Accordingly, in some embodiments, NAA may be used as a disease marker for a wide range of CNS disorders, e.g., Canavan Disease, Alzheimer disease, traumatic brain injury, and psychiatric disorders. Further examples of neurodegenerative diseases include but are not limited to Alzheimer's disease, traumatic brain injury (TBI), bipolar disorder, catalepsy, epilepsy (e.g., seizures), migraine, Huntington's disease, attention deficit disorder (ADD), attention deficit/hyperactivity disorder (e.g., ADHD), autism spectrum disorder (e.g., Asperger's disease, autism, etc.), Parkinson's disease, Tourette's syndrome, clinical depression, multiple sclerosis, and autoimmune disease (e.g., CNS demyelinating disease, Myasthenia gravis, etc.).

In some embodiments, methods for treating leukodystrophy in a subject in need thereof are provided that involve administering to the subject an N-acetylaspartate (NAA)-depleting agent. As used herein, term "NAA-depleting agent" refers to an agent (e.g., nucleic acid, protein, small molecule) that depletes NAA levels directly or indirectly. In some embodiments, it has been determined that the leukodystrophy is associated with a metabolic imbalance comprising a shift from glycolysis to beta-oxidation in the subject.

Other aspects of the disclosure relate to methods for treating neurodegenerative disease in a subject in need thereof in which the methods involve administering to the subject an N-acetylaspartate (NAA)-increasing agent. As used herein, term "NAA-increasing agent" refers to an agent (e.g., nucleic acid, protein, small molecule) that increases NAA levels directly or indirectly. In some embodiments, it has been determined that the neurodegenerative disease is associated with a metabolic imbalance comprising an NAA deficiency. e.g., delivering siRNA/shRNA or miRNA, e.g., that inhibits expression of ASPA. As used herein, "metabolic imbalance" refers to a dysregulated or abnormal metabolic state in a subject. For example, in some embodiments, CNS cells of a healthy subject display a preference for glycolysis as a major mode of energy (e.g., ATP production); in subjects having certain neurodegenerative diseases (e.g., diseases associated with leukodystrophy, e.g., Canavan disease), CNS cells display a preference for fatty acid metabolism. In some embodiments, such a shift away from glycolysis and towards beta-oxidation can be referred to as a "metabolic imbalance".

In some embodiments, methods disclosed herein involve comparing biomarkers (e.g., beta-oxidation, glycolysis) with an appropriate control. An "appropriate control" refers a level of a particular biomarker (e.g., beta-oxidation, glycolysis) that is indicative of a known metabolic status. Such levels can be determined experimentally or can be pre-existing reference levels. In some embodiments, an appropriate control may be a biomarker level indicative of the presence of a metabolic imbalance. For example, an appropriate control may be level of a factor (e.g., beta-oxidation, glycolysis) in a control subject. In some embodiments, a control subject does not have a metabolic imbalance. However, in some embodiments, a control subject does have a metabolic imbalance.

Recombinant Adeno-Associated Viruses (rAAVs)

In some aspects, the disclosure provides isolated AAVs that are useful for delivering transgenes that encode NAA-modulating agents (e.g., an NAA-depleting agent, an NAA-increasing agent). As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

In some aspects, the disclosure provides an rAAV having a capsid appropriate for targeting central nervous system (CNS) tissue or other tissue (e.g., a peripheral tissue). In some embodiments, the capsid has a serotype selected from the group consisting of AAV1, AAV2, AAV5, AAV6, AV6.2, AAV7, AAV8, AAV9 and AAVrh.10. In some embodiments, an rAAV described herein may comprise variants of AAV1, AAV2, AAV5, AAV6, AV6.2, AAV7, AAV8, AAV9, and AAVrh.10 serotype capsid proteins. In some embodiments, the capsid protein comprises an amino acid sequence that is at least 70%, at least 80%, at least 90%, at least 95%, or at least 99% identical to any one of the recited capsids.

Appropriate methods may be used for obtaining recombinant AAVs having a desired capsid protein. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a gene associated with a neurodegenerative disease (e.g., a leukodystrophy). In some embodiments, the instant disclosure relates to a composition comprising the host cell described above. In some embodiments, the composition comprising the host cell above further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or functional RNA (e.g., shRNA, miRNA) from a transcribed gene.

The foregoing methods for packaging recombinant vectors in desired AAV capsids to produce the rAAVs of the disclosure are not meant to be limiting and other suitable methods will be apparent to the skilled artisan.

Isolated Nucleic Acids

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

In some embodiments, conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York.

Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

Recombinant AAV Vectors (rAAV Vectors)

"Recombinant AAV (rAAV) vectors" of the disclosure are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., shRNA, miRNA) or other gene product, of interest. The nucleic acid coding sequence is operatively linked to regulatory components in a manner which permits transgene transcription, translation, and/or expression in a cell of a target tissue.

In some embodiments, the instant disclosure relates to a recombinant AAV (rAAV) vector comprising a nucleic acid sequence including a promoter operably linked to a transgene, wherein the transgene is a gene associated with a neurodegenerative disease (e.g., leukodystrophy). In some embodiments, a rAAV vector further comprises nucleic acid sequences encoding one or more AAV inverted terminal repeat sequences (ITRs), for example AAV2 ITRs. In some embodiments, a rAAV vector further comprises nucleic acid sequences encoding one or more AAV ITRs selected from the group consisting of AAV2, AAV3, AAV4, AAV5, and AAV6.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types (e.g., AAV2, AAV3, AAV4, AAV5, or AAV6 ITR sequences).

In some embodiments, the rAAVs of the present disclosure are pseudotyped rAAVs. Pseudotyping is the process of producing viruses or viral vectors in combination with foreign viral envelope proteins. The result is a pseudotyped virus particle. With this method, the foreign viral envelope proteins can be used to alter host tropism or an increased/decreased stability of the virus particles. In some aspects, a pseudotyped rAAV comprises nucleic acids from two or more different AAVs, wherein the nucleic acid from one AAV encodes a capsid protein and the nucleic acid of at least one other AAV encodes other viral proteins and/or the viral genome. In some embodiments, a pseudotyped rAAV refers to an AAV comprising an inverted terminal repeats (ITRs) of one AAV serotype and an capsid protein of a different AAV serotype. For example, a pseudotyped AAV vector containing the ITRs of serotype X encapsidated with the proteins of Y will be designated as AAVX/Y (e.g., AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

In addition to the major elements identified above for the recombinant AAV vector, the vector also includes control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible, ubiquitous, and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA).

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and/or other vector elements may be performed, as appropriate, and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, Petal., Human Gene Therapy, 2000; 11: 1921-1931.; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an enhanced chicken β-actin promoter. In some embodiments, a promoter is an astrocyte specific promoter. In some embodiments, a promoter is an oligodendrocyte specific promoter. In some embodiments, a promoter is an CNS-specific promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan. In some embodiments, the promoter is an oligodendrocyte-specific promoter, for example the myelin basic protein (MBP) promoter (Chen et al., J. Neurosci, Res., 55(4); 504-13 (1999)).

Aspects of the disclosure relate to the discovery that astrocyte-specific (e.g., astrocyte-restricted) expression of hASPA results has a positive therapeutic effect (e.g., survival, normalized growth, restoration of normal motor function and cognitive function) in mouse models of Canavan Disease. Therefore, in some embodiments, the transgene of an rAAV described by the disclosure is operably-linked to an astrocyte-specific promoter. Examples of astrocyte-specific promoters include but are not limited to glial fibrillary acidic protein (GFAP) (Brenner et al., J. Neurosci, 14(3, Pt 1);

1030-7 (1994)), aldehyde dehydrogenase 1 family, member L1 (ALDH1L1) promoter (Cahoy et al., J. Neurosci. 28, 264-278 (2008)), and glutamate transporter promoter EAAT1 (Colin et al., Glia 57, 667-679 (2009)). In some embodiments, the astrocyte-specific promoter is the glial fibrillary acidic protein (GFAP) promoter.

In some embodiments, one or more bindings sites for one or more of miRNAs are incorporated in a transgene of a rAAV vector, to inhibit the expression of the transgene in one or more tissues of an subject harboring the transgene. The skilled artisan will appreciate that binding sites may be selected to control the expression of a transgene in a tissue specific manner. For example, binding sites for the liver-specific miR-122 may be incorporated into a transgene to inhibit expression of that transgene in the liver. The target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

Recombinant AAV Administration Methods

The rAAVs may be delivered to a subject in compositions according to any appropriate methods. In some embodiments, the rAAV, e.g., suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments, a host animal does not include a human.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

In some cases, administration of an rAAV to a subject elicits an immune response against the rAAV capsid protein in the subject. Without wishing to be bound by any particular theory, suppressing the immune system of a subject prior to administration of an rAAV results, in some embodiments, in increased therapeutic effect of the rAAV. Therefore, in some embodiments, a subject is administered one or more (e.g., 2, 3, 4, 5, or more) immune-suppressing agents prior to administration of an rAAV as described by the disclosure. An "immune-suppressing agent" is any composition (e.g., a protein, nucleic acid, small molecule, etc.) that reduces the immune response of a subject to an rAAV. An immune-suppressing agent can reduce the innate immune response, adaptive immune response, cellular immune response, humoral immune response, or any combination of the foregoing, in a subject.

Examples of biological immune-suppressing agents include but are not limited to monoclonal antibodies, such as monoclonal antibodies that block the co-stimulatory pathway (e.g., appropriate antibodies against CTLA4, ICOS, CD80, OX40, or other targets), interfering RNA (e.g., siRNA, dsRNA, shRNA, miRNA, etc.) targeting immunostimulatory molecules (e.g., cytokines), and proteins (e.g., proteasome inhibitors).

Examples of small molecule immune-suppressing molecules include but are not limited to glucocorticoids (e.g., cortisol, cortisone, prednisone, prednisolone, methylprednisolone, dexamethasone, betamethasone, triamcinolone, beclomethasone, fludrocortisone, deoxy corticosterone (DOCA), and aldosterone), cytostatics (e.g., cyclophosphamide, nitrosoureas, platinum compounds, methotrexate, azathioprine, mercaptopurine, fluorouracil, dactinomycin, etc.), immunophilin-targeting drugs (e.g., cyclosporine, tacrolimus, sirolimus, rapamycin, etc.), interferons (e.g., IFN-β), mycophenolate, fingolimod, and myriocin.

An immune-suppressing agent can be administered to a subject at between about one week and one minute prior to administration of an rAAV as described by the disclosure. In some embodiments, an immune-suppressing agent is administered to a subject between about 5 days, about 1 day, about 12 hours, about 2 hours, about 1 hour, about 30 minutes, about 10 minutes, about 5 minutes, or about 1 minute prior to administration of an rAAV. In some embodiments, a subject is administered an immune-suppressing agent on multiple (e.g. 2, 3, 4, 5, 6, 7, 8, 9, 10, or more) occasions prior to administration of an rAAV to the subject.

In some embodiments, a composition further comprises a pharmaceutically acceptable carrier. Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue (e.g., CNS tissue) and to provide sufficient levels of gene transfer and expression without undue adverse effects. Examples of pharmaceutically acceptable routes of administration include, but are not limited to, direct delivery to the selected organ (e.g., intrathecal, intracerebral), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies (gc). In some embodiments, a dosage between about $10^{10}$ and $10^{15}$ genome copies is appropriate. In some cases, a dosage between about $10^{11}$ to $10^{13}$ rAAV genome copies is appropriate. In certain embodiments, $10^{11}$ or $10^{12}$ rAAV genome copies is effective to target CNS tissue. In some embodiments, a dosage of an rAAV is calculated based upon the weight of the subject to which the rAAV is being administered. For example, in some embodiments, a dosage between $1.0 \times 10^{10}$ gc/kg and $1.0 \times 10^{15}$ gc/kg is appropriate. In some embodiments, a dosage of $2.0 \times 10^{10}$ gc/kg, $2.0 \times 10^{11}$ gc/kg, $2.0 \times 10^{12}$ gc/kg, $2.0 \times 10^{13}$ gc/kg, $2.0 \times 10^{14}$ gc/kg, or $2.0 \times 10^{15}$ gc/kg is appropriate. In some cases, stable transgenic animals are produced by multiple doses of an rAAV.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year).

In some embodiments, rAAV compositions are formulated to reduce aggregation of AAV particles in the composition, particularly where high rAAV concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, rAAVs in suitably formulated pharmaceutical compositions disclosed herein are delivered directly to target tissue, e.g., direct to CNS tissue. However, in certain circumstances it may be desirable to separately or in addition deliver the rAAV-based therapeutic constructs via another route, e.g., subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered trangenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 .ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

EXAMPLES

Example 1: Pathomechanism of Canavan's Disease

Experimental Design

Global biochemical profiles were determined in mouse brain tissue collected from postnatal day 25 (P25) mice representing treatment groups shown below in Table 1.

TABLE 1

Treatment groups

| Group | n | Description |
|---|---|---|
| WT | 8 | Wild type mouse |
| KO | 8 | Aspartoacylase gene knockout mouse |
| rAAV Ctrl | 8 | Aspartoacylase gene knockout mouse, treated with virus with a promoter-less expression construct |
| rAAV Tx | 8 | Aspartoacylase gene knockout mouse, treated with virus encoding the human ASPA gene |

Metabolomics of Healthy and Canavan Disease Mouse Brains

Figure 2:
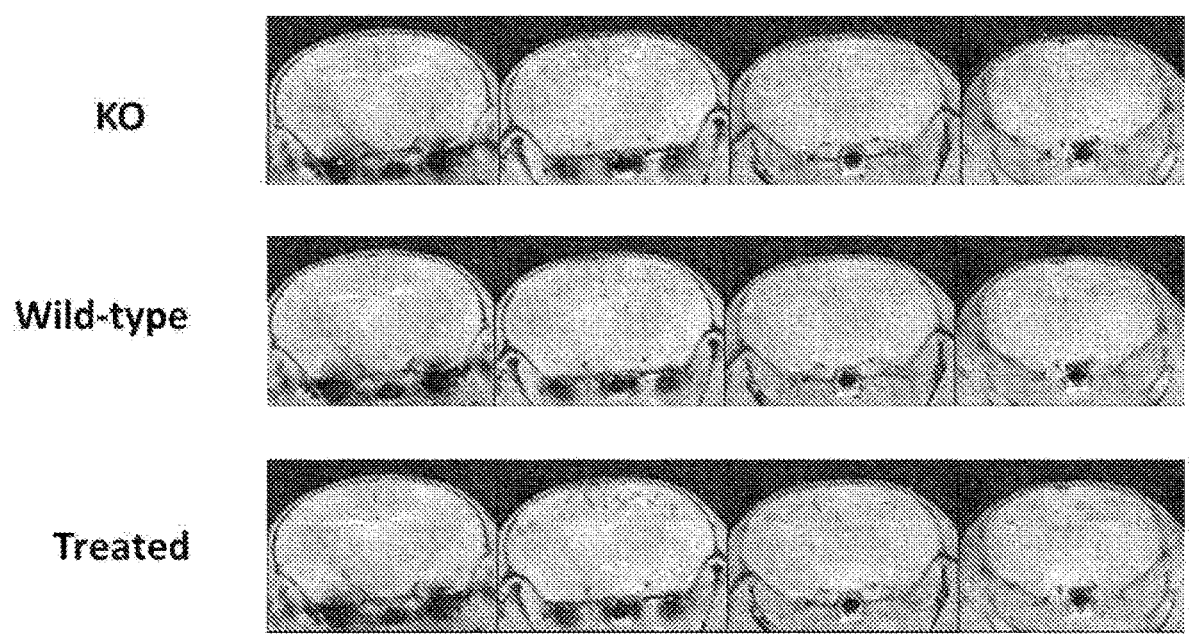
FIG. 2 shows data illustrating that Canavan disease (CD) causes increased oxygen consumption for functional neuro-connectivity, as measured by resting state functional MRI (RS-fMRI).

Results of resting state functional MRI (RS-fMRI) indicate that Canavan disease causes increased oxygen consumption for functional neuro-connectivity (FIG. 2). Further, Canavan disease causes increased oxygen consumption for cortical/sub-cortical connectivity (FIG. 3). These data indicate that Canavan disease may be characterized by an altered metabolic state in the CNS.

The molecular phenotype of brains of mice having Canavan disease was investigated by using a whole brain metabolomics approach. Canavan disease were treated with intravenous (IV) injection of rAAV-ASPA at p1. Healthy and CD mouse brains (both untreated and treated groups) were homogenized and subjected to metabolic analysis. Over 452 metabolites were quantified in each wild-type, untreated, treated and treatment control groups (Table 2). This large data set revealed several crucial and entirely new aspects about Canavan disease pathomechanism, its gene therapy, CNS metabolism and novel function of AspA in general.

TABLE 3

| | ASPA -/- | ASPA -/- % | WT | WT % | Oligo WT | Oligo WT % |
|---|---|---|---|---|---|---|
| Basal respiration | 356.1 | 25.9 | 240.1 | 26.9 | 409.2 | 20 |
| ATP Production | 181.9 | 13.2 | 139.1 | 15.6 | 335.7 | 16.4 |
| Maximal Respiration | 391.6 | 28.5 | 254.9 | 28.6 | 676 | 33.1 |
| Proton Leak | 174.2 | 12.7 | 35.5 | 4 | 73.5 | 3.6 |
| Non-Mitochondrial Respiration | 237.1 | 17.2 | 103.6 | 11.6 | 283.9 | 13.9 |
| Spare Capacity | 35.4 | 2.6 | 118.4 | 13.3 | 266.8 | 13 |

Statistical Analysis

Figure 4B:
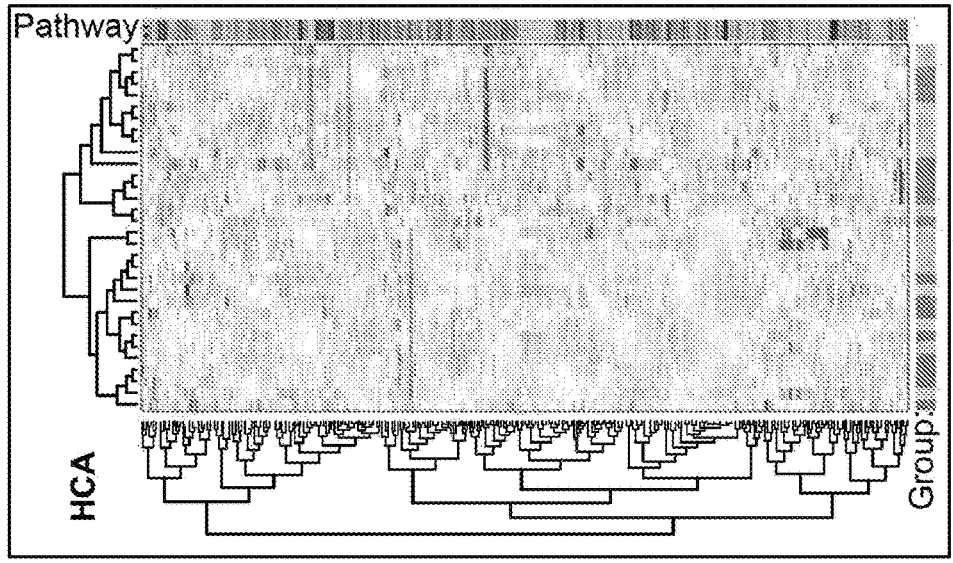
FIGS. 4A-4B show statistical analysis of whole brain metabolome in wild-type (WT) and ASPA knockout (KO) mice. Treated mice were administered rAAV-ASPA via intravenous injection at P1. Neuormetabolome data was analyzed at P25; N=8.
Figure 4A:
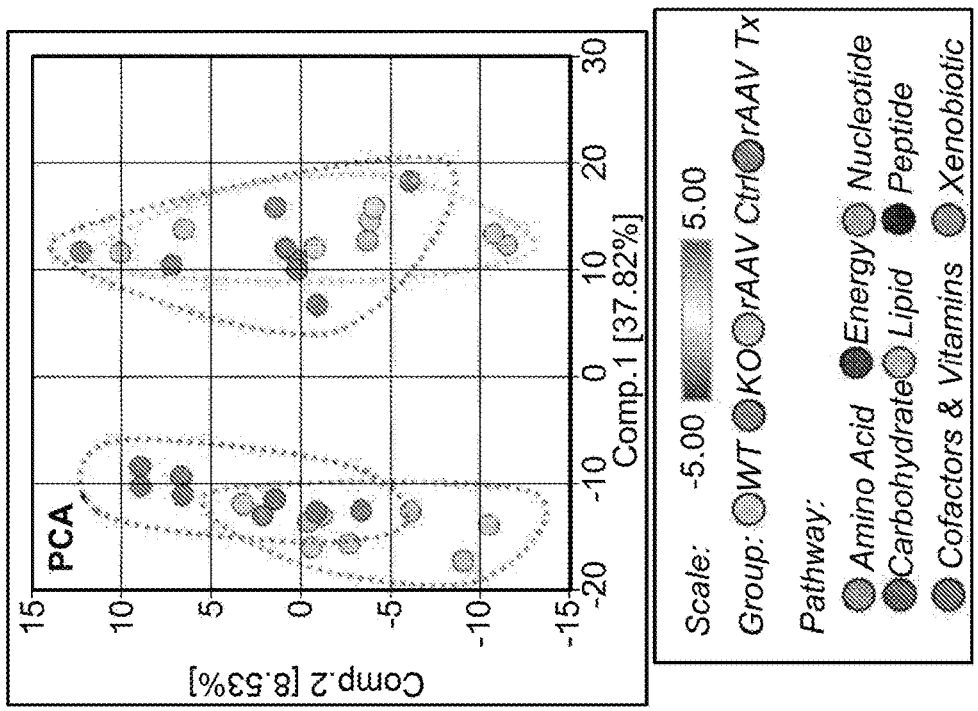

Principal component analysis (PCA) transforms a large number of metabolic variables into a smaller number of orthogonal variables (Component 1, Component 2, etc.) in order to analyze variation between groups and to provide a high-level overview of the dataset. In the PCA (FIG. 4A), samples formed into two populations; interestingly, rather than reflecting the genetic background, these two populations appeared to reflect disease state: WT and rAAV Tx formed the left-most population, with KO and rAAV Ctrl forming the right population, consistent with a "rescue" of disease by treatment.

The hierarchical clustering analysis (HCA) analyzes similarities between groups (FIG. 4B); consistent with observations in the PCA, the top-level separation of the dendrogram distinguished between WT and rAAV Tx samples (on the left) and KO and rAAV samples (on the right), with sub-clusters forming by individual samples by group. It is striking that both the PCA and HCA grouped the WT and rAAV Tx samples together. A high-level assessment of patterns of metabolic changes in the HCA indicates that WT and rAAV Tx tended to show similar trends in a number of metabolites, indicating that rAAV Tx was effective at modulating disease. Many of the observed changes in KO (compared to WT) trended in the opposite direction in rAAV (Tx vs Ctrl), consistent with "rescue" of disease-associated phenotypes. Consistent with the metabolic analysis, FIG. 1 shows that rAAV-ASPA gene therapy restores the thalmocortical tract of CD mice, as measured by diffusion tensor imaging for brain water flow.

Neurotransmitter Biosynthesis

Aspartoacylase (ASPA) is responsible for the breakdown of N-acetylaspartate (producing acetate and aspartate). Consistently, N-acetylaspartate (NAA) was increased in KO (compared to WT); treatment with rAAV-expressing ASPA resulted in a decrease in NAA (and increases in aspartate). Curiously, while NAA levels were increased (KO vs WT), the neuropeptide N-acetyl-aspartyl-glutamate (NAAG) was not significantly changed (which could reflect changes in demand or regulation of steady-state pools/pool size). Gamma-aminobutyrate (GABA) was decreased (KO vs WT), which could reflect changes in GABA-mediated signaling (GABA increased in rAAV Tx, compared to rAAV Ctrl).

Several other neurotransmitters were also detected in the dataset; while acetylcholine and serotonin were not significantly changed in KO (compared to WT), serotonin did show increases in rAAV Tx (compared to Ctrl), which could reflect changes in serotonergic signaling.

Glucose Metabolism

In the absence of disease, energetics in the brain is thought to focus on glycolytic use, with acetyl CoA input into the TCA cycle to support oxidative metabolism and macromolecule biosynthesis. Increases in glucose, glucose 6-phosphate, and an isobar of sugar diphosphates (fructose 1,6-diphosphate, glucose 1,6-diphosphate, myo-inositol 1,4 or 1,3-diphosphate) could indicate changes in glucose use or increased availability.

Glucose and related molecules (fructose, mannose and myo-inositol) were elevated, though nucleotide sugars (e.g., UDP-glucose, UDP-galactose) were decreased, which could indicate changing biosynthetic demand (KO vs WT). Three-carbon glycolytic intermediates 3-phosphoglycerate (3-PG) and phosphoenolpyruvate (PEP) were also increased; pools for these biochemicals tend to increase as glycolytic use declines.

Consistent with decreasing glycolytic use, lactate was decreased (with non-significant decrease in pyruvate). Glycogen metabolites (maltotetraose, maltotriose, and maltose) were also increased, reflecting decreased glycolytic use. Changes in energetics reflect declining energy demand (potentially associated with increased neuronal cell death or senescence) or may reflect metabolic effects of NAA accumulation in the brain.

Figure 5:
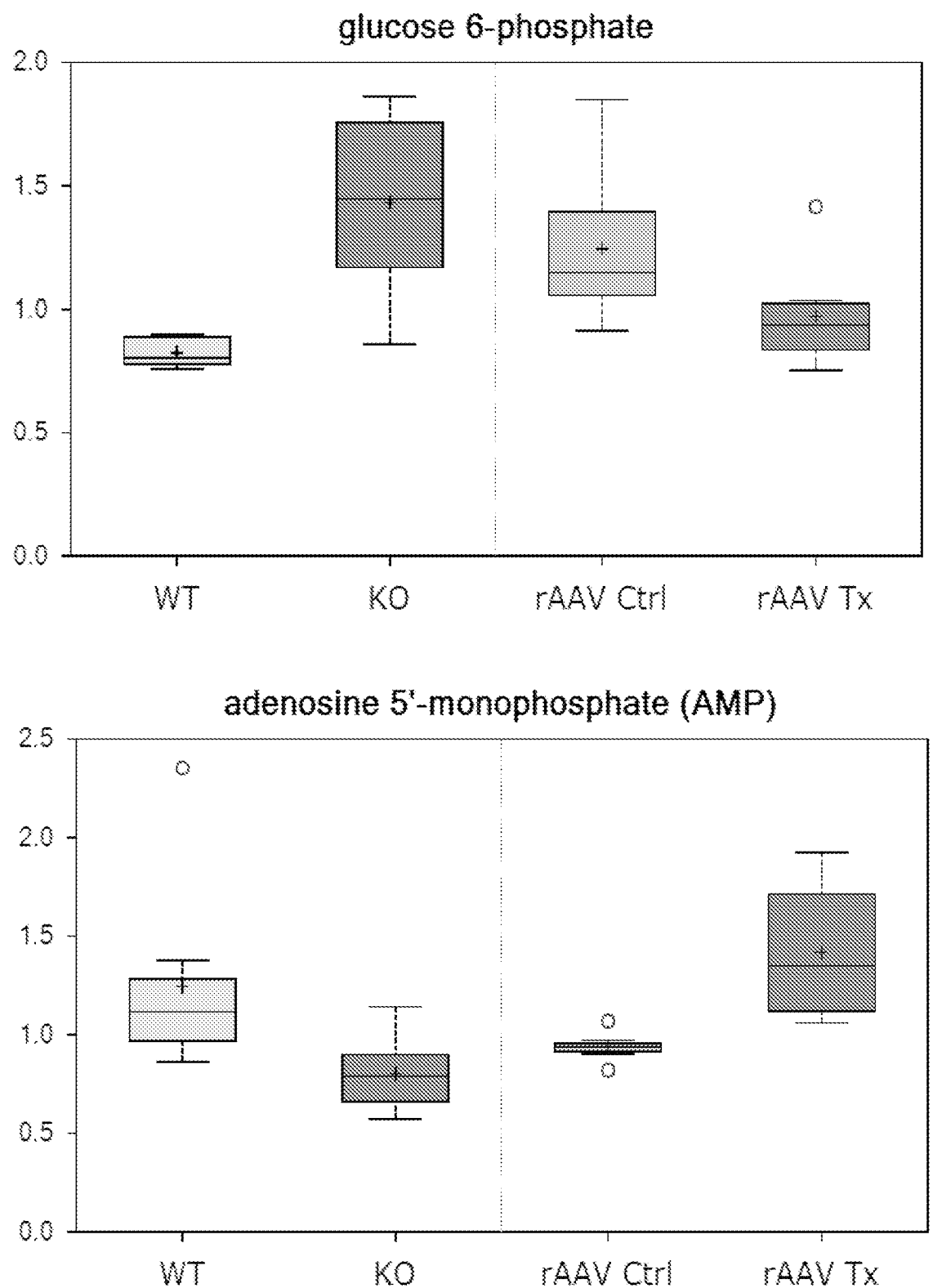
FIG. 5 shows representative data relating to levels of glucose metabolism biomarkers in WT (untreated and treated) and KO (untreated and treated) mice. Treated mice were administered rAAV-ASPA.
Figure 5:
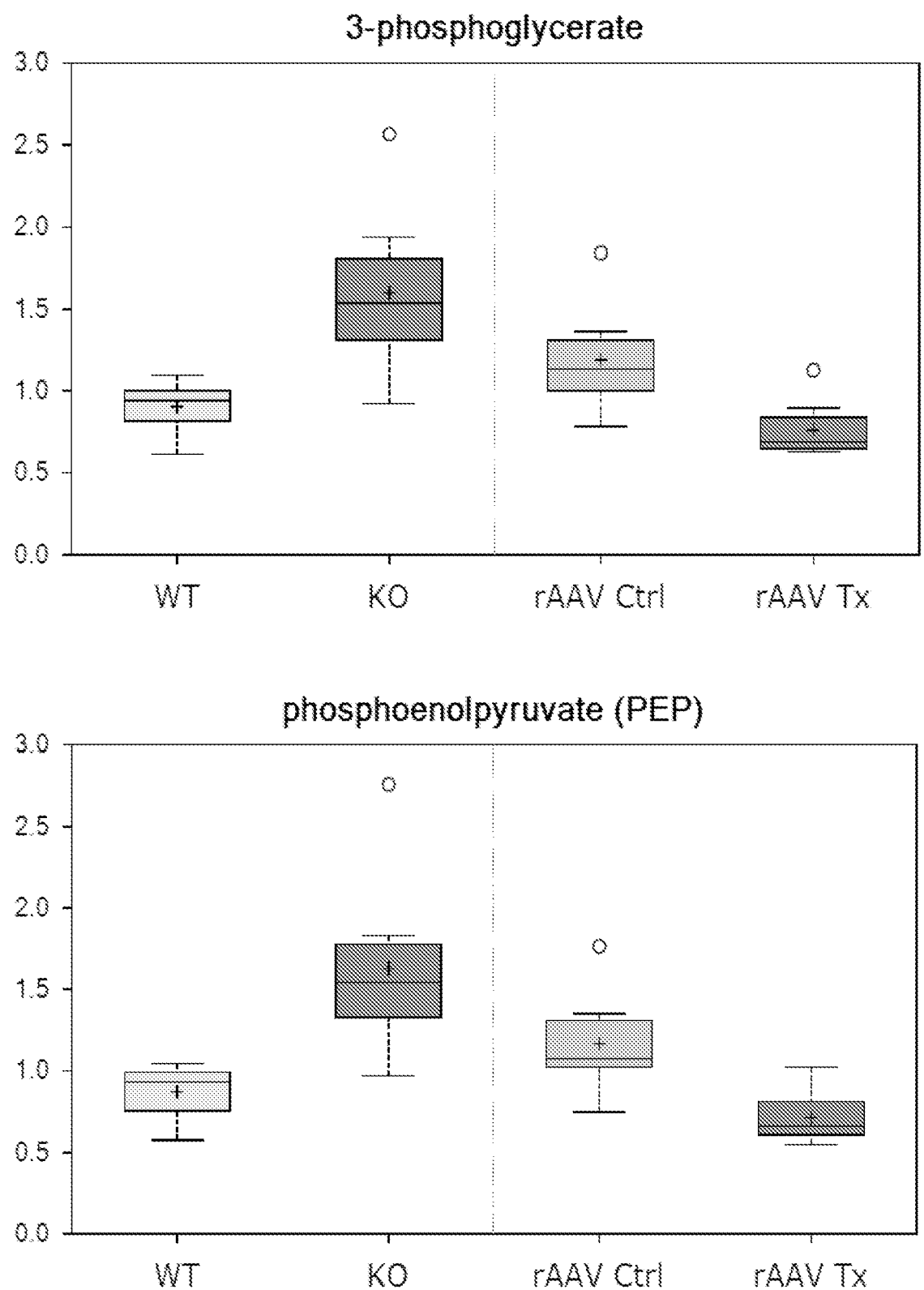
Figure 5:
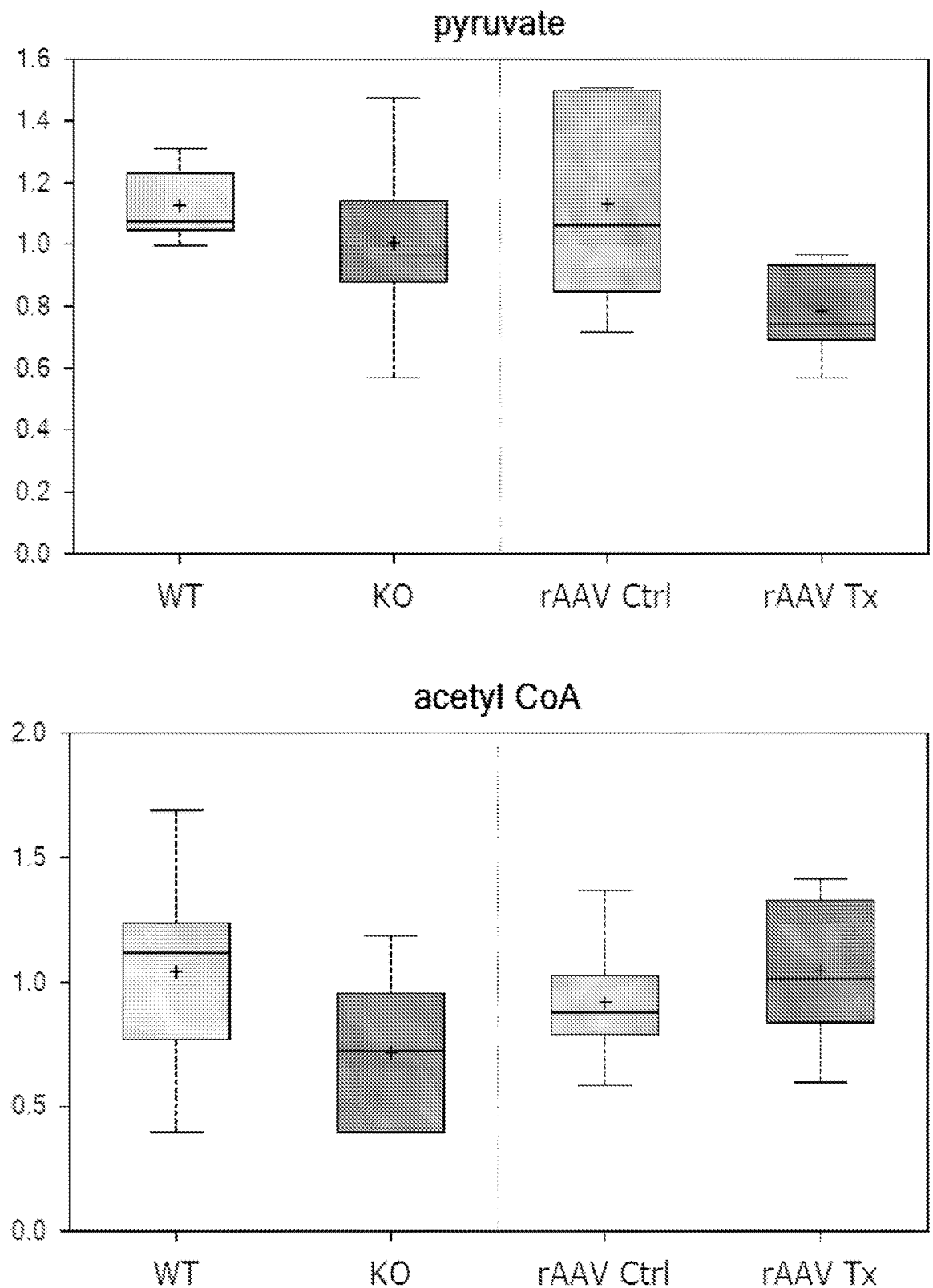
Figure 5:
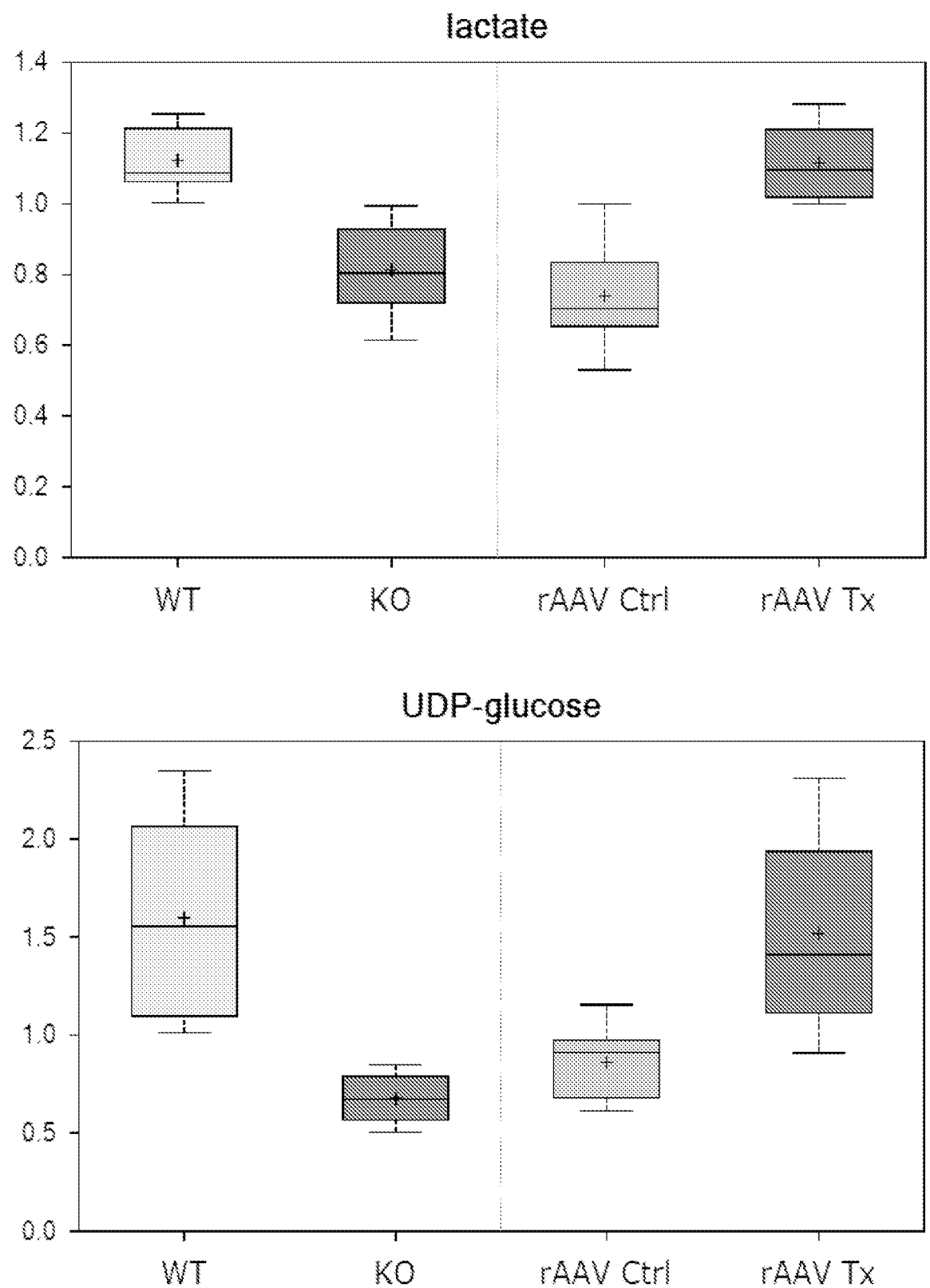
Figure 5:
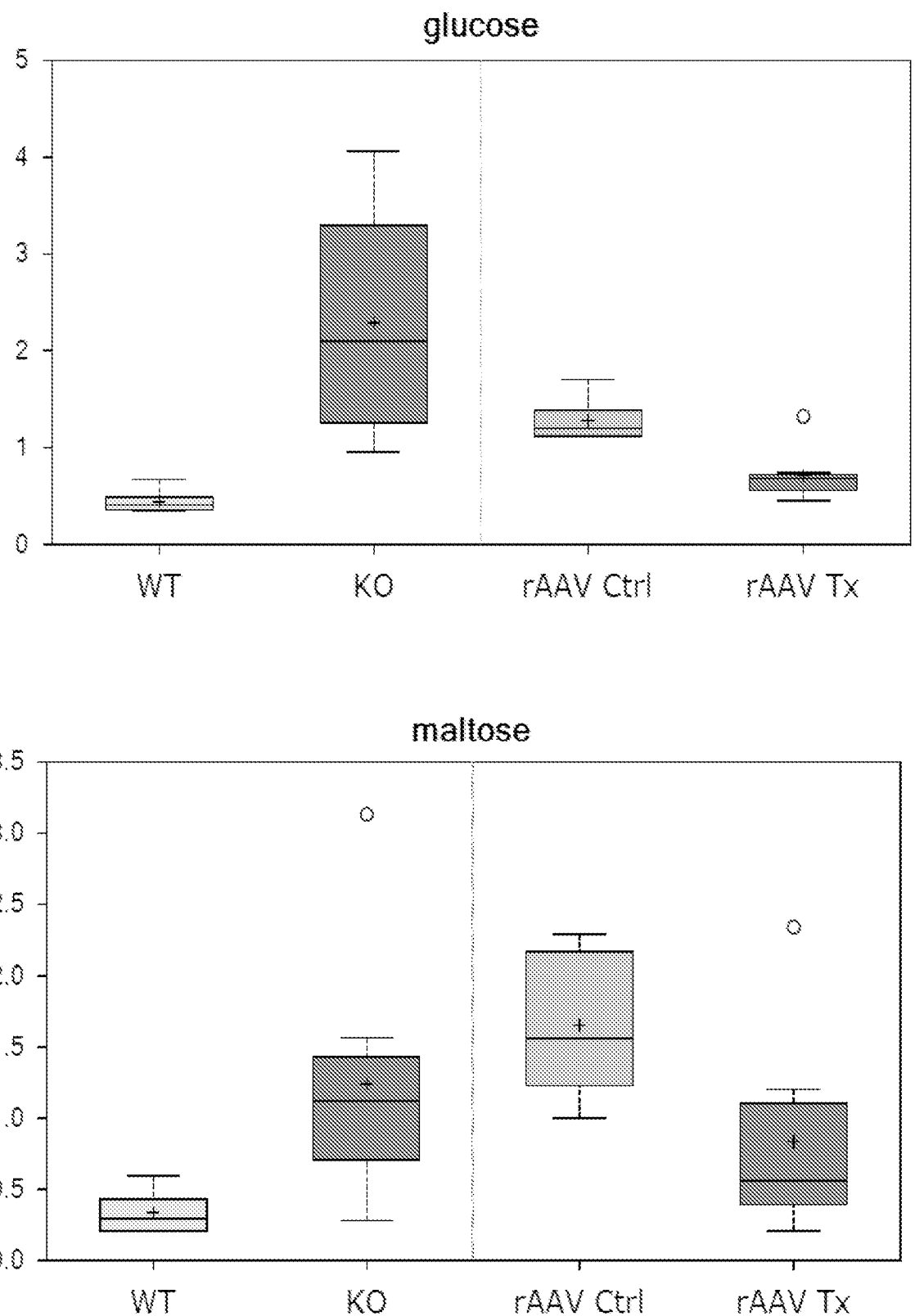
Figure 5:
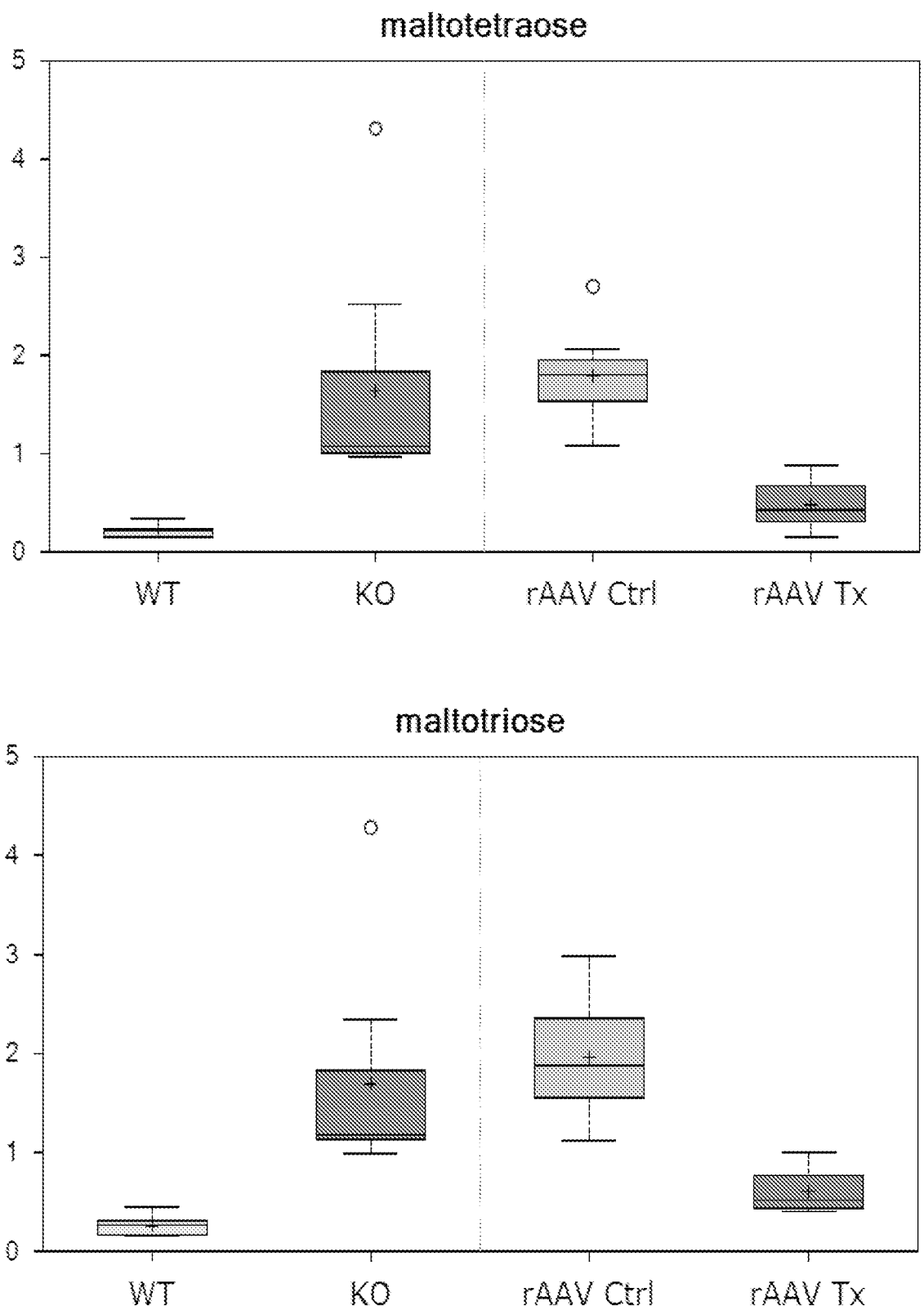

In rAAV (Tx vs Ctrl), decreases in glucose and related molecules, with increases in lactate, were indicative of increasing glycolytic use. Interestingly, DHAP was elevated in rAAV (Tx vs Ctrl), which could reflect changing use for triglyceride biosynthesis (potentially related to a restoration of lipid biosynthesis, TAGs can be used as a precursor for phospholipids). Representative data relating to glucose metabolism is provided in FIG. 5.

Lipid Metabolism

Complex lipids, sphingolipids, diacylglycerols, monoacylglycerols, and plasmalogens were all decreased, with decreases in lysolipids, long-chain (e.g., palmitate, palmitoleate, and stearate) and polyunsaturated fatty acids, and longer acylcarnitines (e.g., myristoylcarnitine, palmitoylcarnitine) indicative of changing availability or use to support beta-oxidation (KO vs WT). The ketone body 3-hydroxybutyrate (BHBA) was also elevated in KO (compared to WT), with decreases in malonylcarnitine (a surrogate reporter for malonyl CoA) indicative of a shift toward increased fatty acid beta-oxidation. Increases in BHBA may also reflect changes in liver ketogenesis (or increased brain ketone uptake to supplement energetics).

Increases in carnitine, deoxycarnitine, and changes in coenzyme A precursors (increases in pantothenate with decreases in 3'-dephosphocoenzyme A and coenzyme A) could reflect changing demand or use (KO vs WT). N-acetylaspartate has been indicated as a key carrier of 2-carbon units to oligodendrocytes for lipid biosynthesis; decreases in lipids could reflect increased demand related to decreased biosynthesis.

Figure 6:
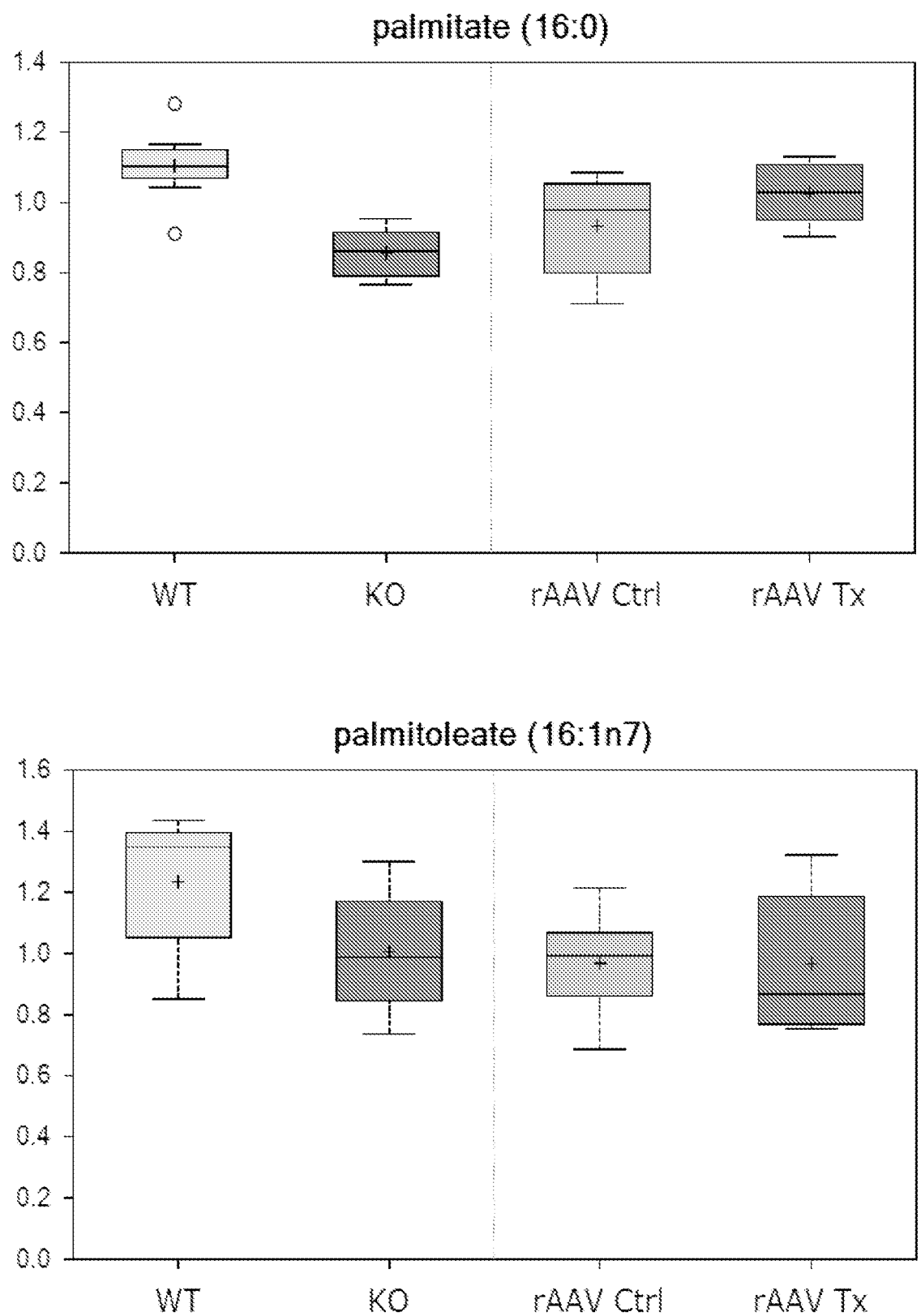
FIG. 6 shows representative data relating to levels of beta-oxidation biomarkers in WT (untreated and treated) and KO (untreated and treated) mice. Treated mice were administered rAAV-ASPA.
Figure 6:
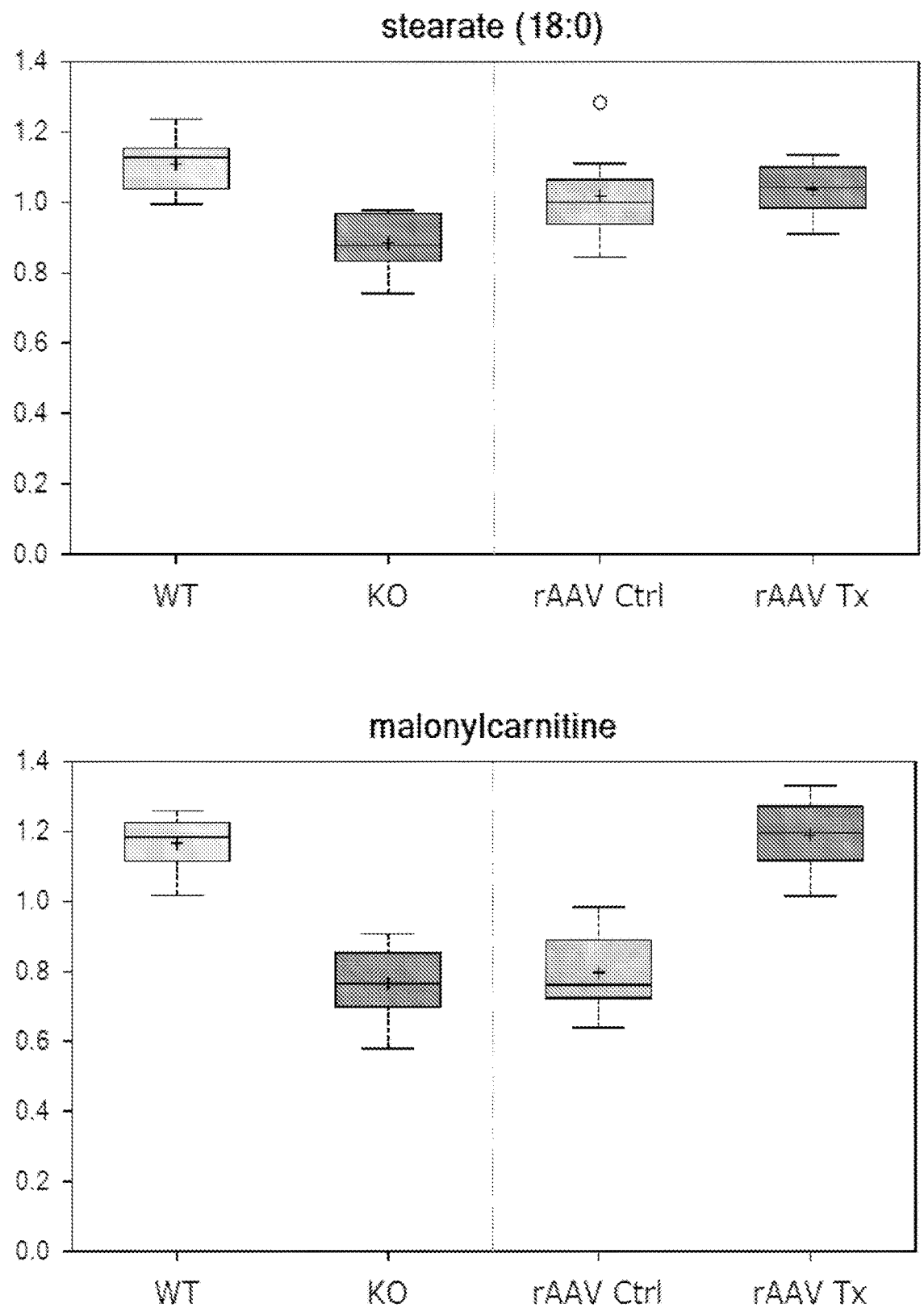
Figure 6:
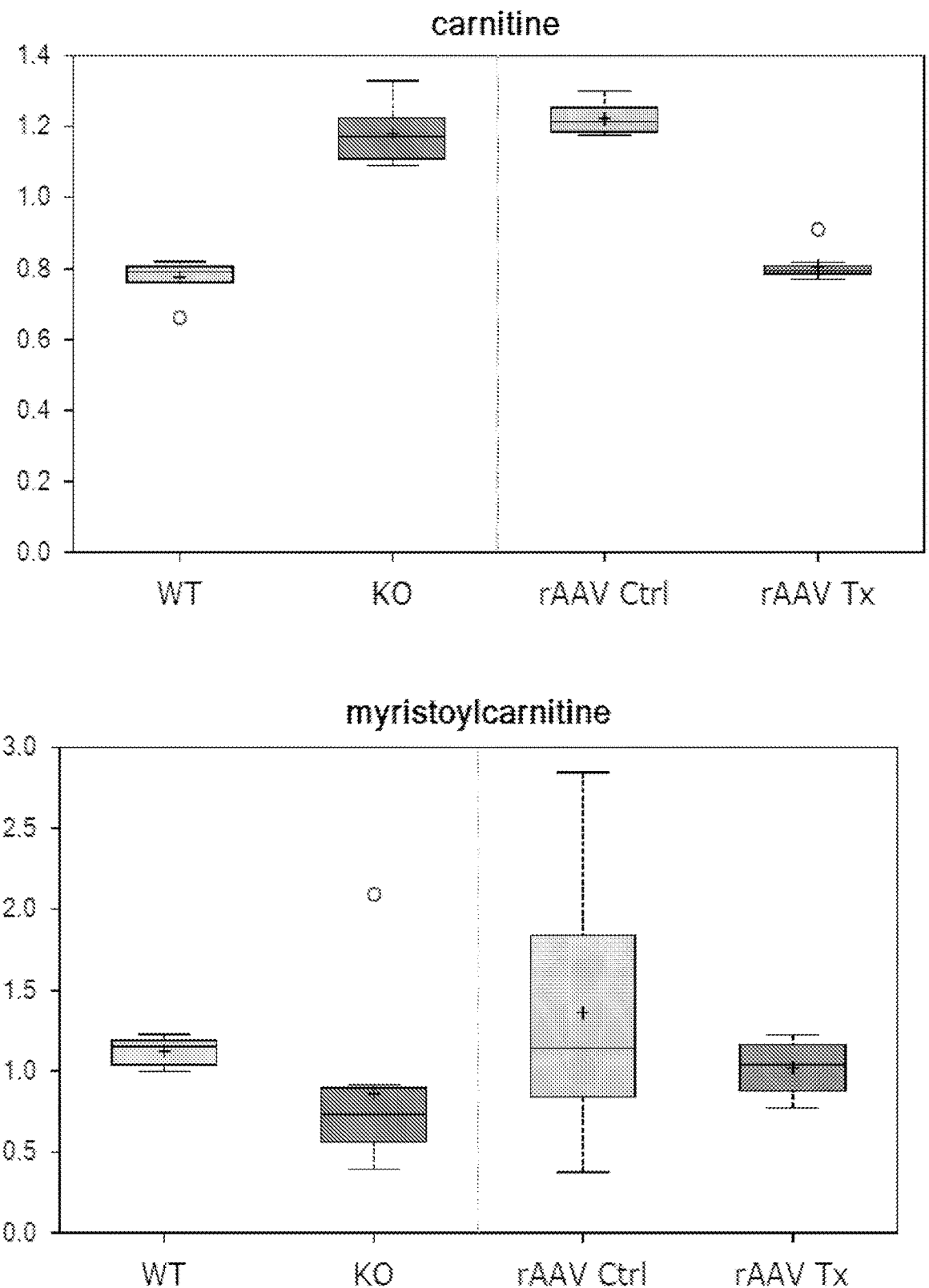
Figure 6:
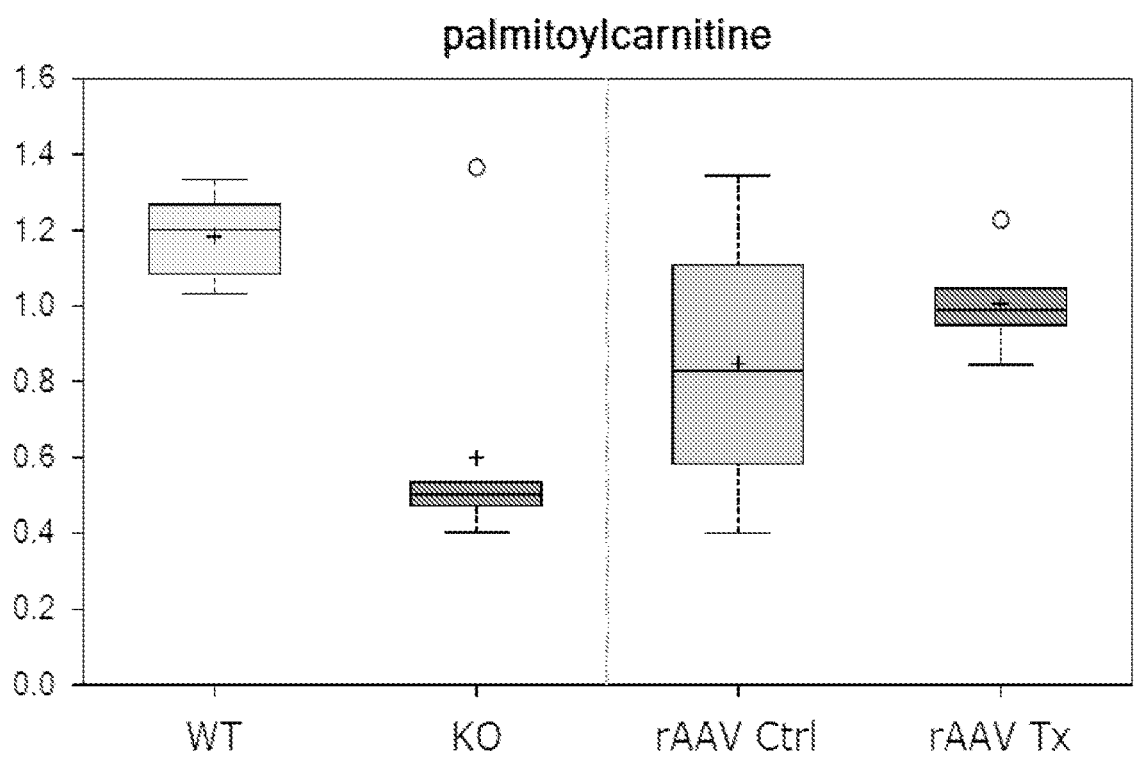

Interestingly, in rAAV (Tx vs Ctrl), increases in malonylcarnitine could imply shifts toward increased fatty acid biosynthesis; metabolites related to phospholipid biosynthesis and remodeling (e.g., choline, CDP-choline, phosphoethanolamine) were also elevated. Finally, decreases in sphingolipids (e.g., sphinganine, sphingosine, and sphingomyelins) in KO (compared to WT), with increases in serine and threonine, could reflect changing availability for myelin biosynthesis, which has been indicated as one cause of neuronal cell death in Canavan disease; rAAV (Tx vs Ctrl) showed increases in these biochemicals. Representative data relating to lipid metabolism is provided in FIG. 6.

Redox Homeostasis

Figure 7:
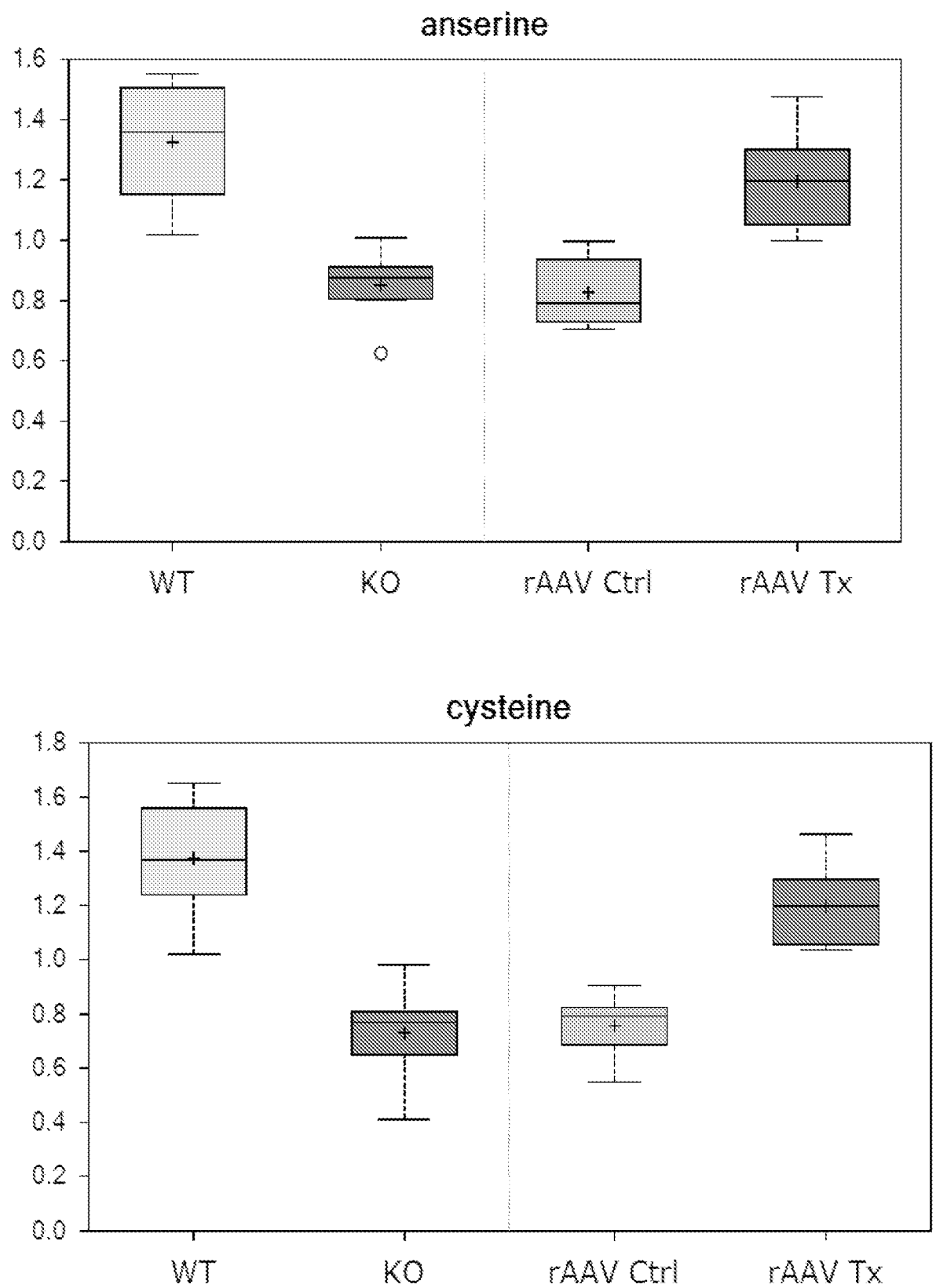
FIG. 7 shows representative data illustrating down-regulation of 02 radical scavengers (e.g., anserine) and their precursor molecules (e.g., cysteine) in CD mice (KO). Treatment with rAAV-ASPA restores anserine and cysteine levels in KO mice.

Changes in metabolites related to glutathione biosynthesis (e.g., methionine, cystathionine, and cysteine) could indicate alterations in redox homeostasis in KO (compared to WT) (FIG. 7). Glutathione (either oxidized or reduced) was decreased, as were related oxidized products (S-methylglutathione and S-lactoylglutathione), likely reflecting decreased glutathione availability. Finally, gamma-glutamyl amino acids tended to decrease as a class (potentially reflecting decreased glutathione and/or amino acid availability); decreases in 5-oxoproline could indicate declining exchange of gamma-glutamyl amino acids to regenerate glutathione. Changes in KO (compared to WT) were indicative of a less robust redox environment; however, significant differences in oxidized lipids (e.g. 4-hydroxy-nonenal-glutathione, 9/13-HODE) and products of methionine or cysteine oxidation (methionine sulfoxide, cysteine sulfinic acid) were not observed. Given the overall decrease in parent metabolites, "similar" levels in KO compared to WT may reflect a relative increase in these products (as a result of increasing oxidative stress). Changes in endogenous antioxidants, such as decreases in vitamin C metabolites (ascorbate, dehydroascorbate and threonate) and dipeptide products of histidine with anti-oxidant function (anserine (FIG. 7), homocarnosine), and increases in taurine and N-acetyl-taurine, could reflect use to balance changes in redox homeostasis. Finally, changes in rAAV (Tx vs Ctrl) were consistent with decreasing oxidative stress (essentially showing inverse changes as those observed in KO vs WT).

Gene Therapy in Canavan Disease

While gene therapy in CD patients using intraparenchymal injections of ASPA expression systems was considered safe, it failed to show clinically significant improvements. Similar results were found using acetate replacement.

Figure 8:
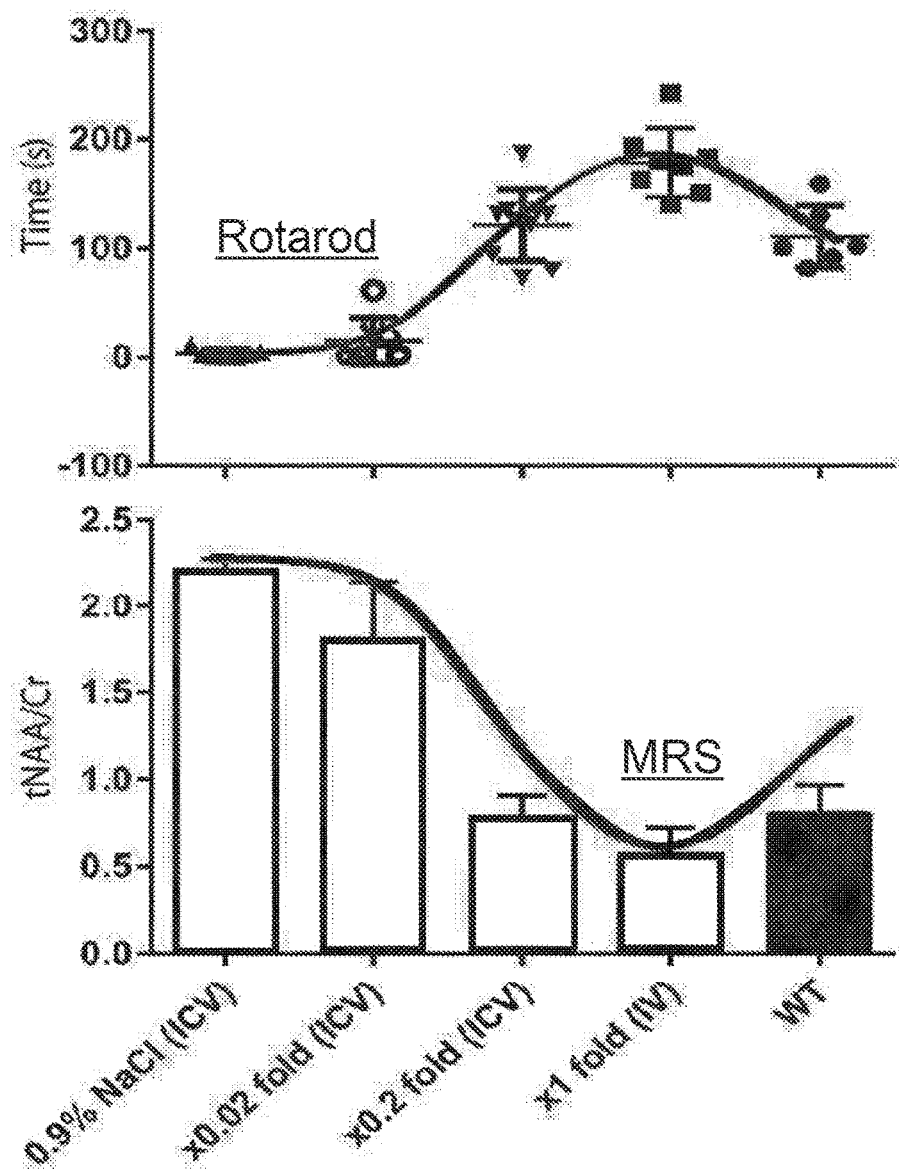
FIG. 8 shows data illustrating that CNS-restricted (intraventricular, ICV) and systemic (intravenous, IV) administration of rAAV-ASPA result in comparable therapeutic outcomes in P1 treated CD mice. Mice were assessed at P26.
Figure 9:
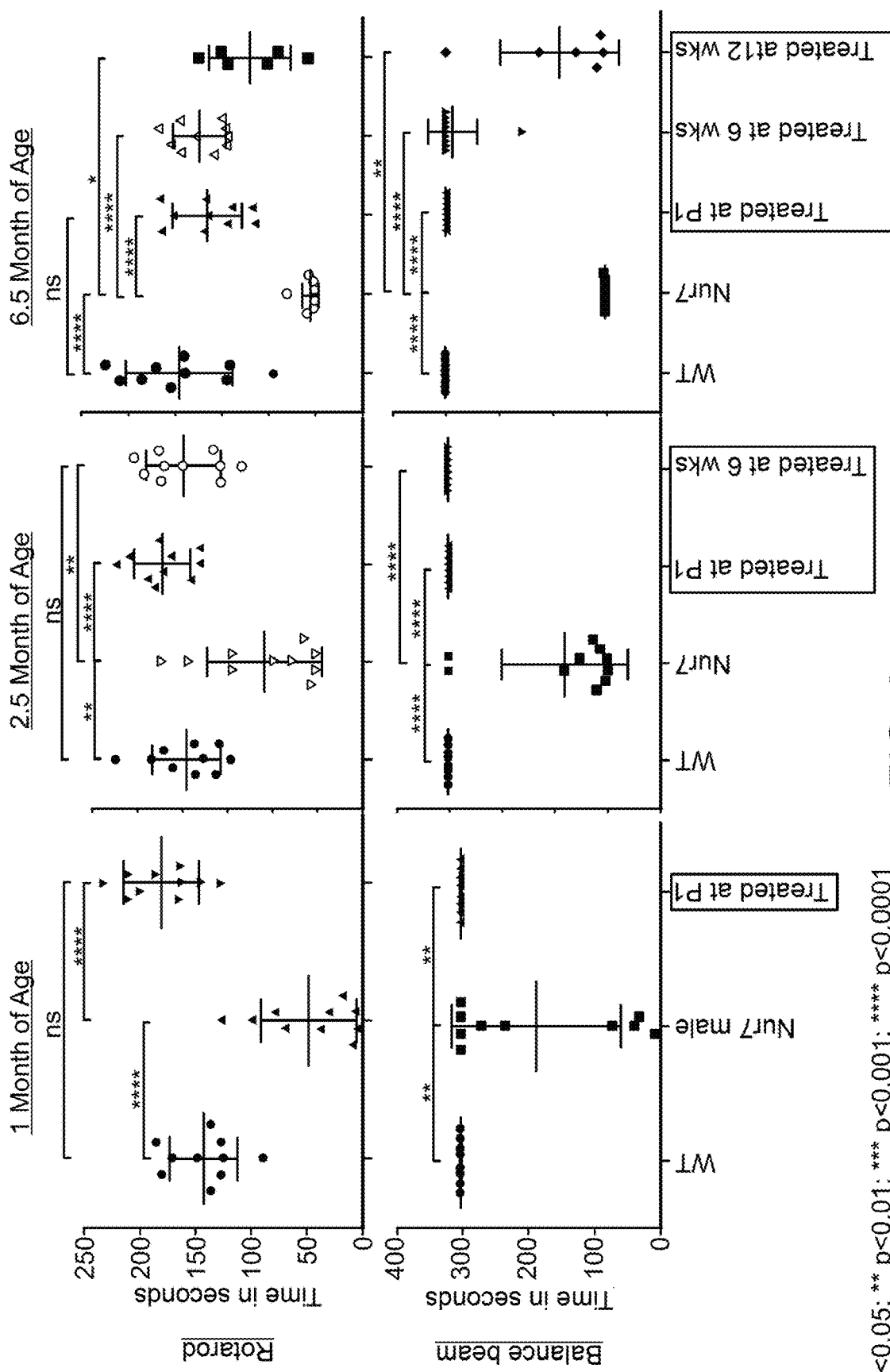
FIG. 9 shows data illustrating that administration of rAAV-ASPA restores mobility of Nur7 (a model of mild CD) mice. Mice were administered rAAV-ASPA at various time points (e.g., 1 month of age, 2.5 months of age, 6.5 months of age). Psychomotor function was assessed by rotarod and balance beam tests.
Figure 12:
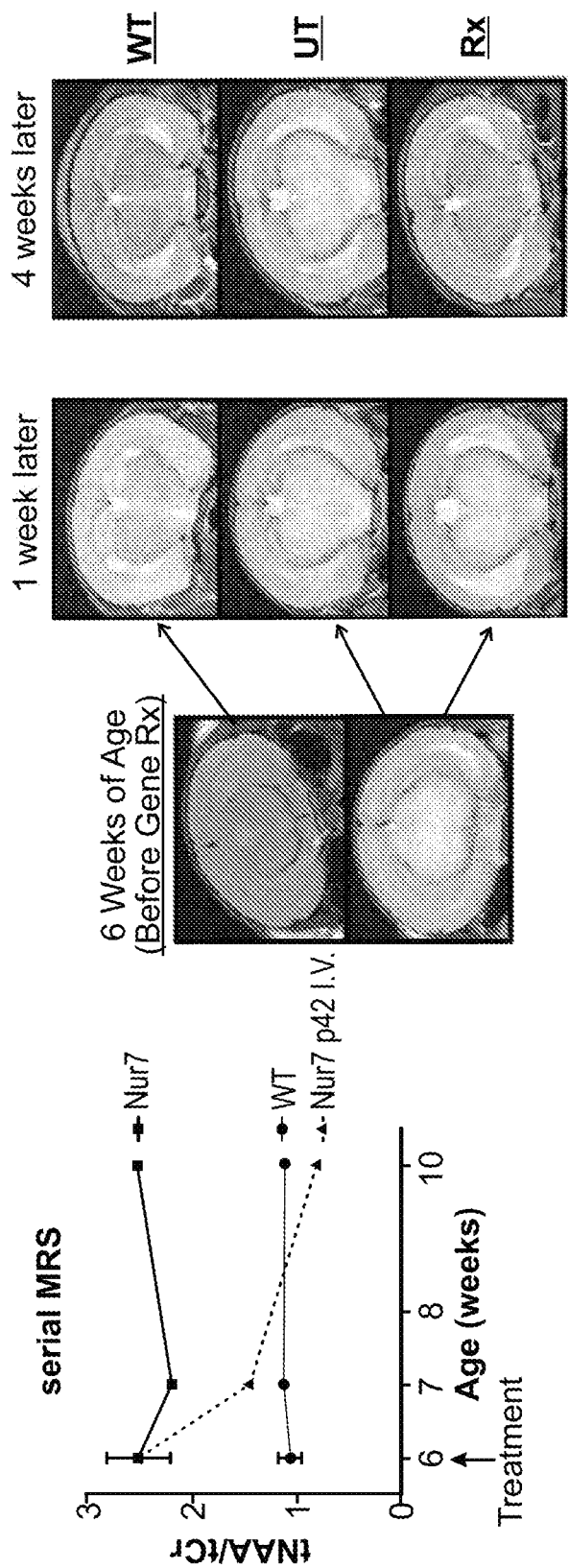
FIG. 12 shows data illustrating that administration of rAAV-ASPA rapidly reduces NAA in the brain of Nur7 mouse. Nur7 mice were treated with rAAV-ASPA at 6 weeks of age and monitored at 7 weeks and 10 weeks of age by neuroimaging.

Data described herein demonstrate that either intraventricular (e.g., direct injection) or intravenous injection (e.g., systemic) of recombinant adeno-associated virus (rAAV) expressing ASPA can cure Canavan Disease. CD mice administered rAAV expressing ASPA by either intraventricular injection show similar improvement of motor function (FIG. 8). Systemic (e.g., IV) injection of rAAV-ASPA also expands the treatment window. Experimental data indicate that rAAV-ASPA administered intravenously to Nur7 mice (a model of mild CD) as late as 3 months of age results in restoration of mobility (FIG. 9) and improvement of cognitive function (FIG. 10). Further, intravenous delivery of rAAV-ASPA results in rapid and efficient elimination of spongy degeneration of the CNS (FIG. 11) in Nur7 mice receiving treatment at P1. Importantly, intravenous administration of rAAV-ASPA results in rapid reduction of NAA in the brain of Nur7 mice (FIG. 12). Mice were treated at 6 weeks and monitored at 7 and 10 weeks by neuroimaging. Treatment of CD mice with rAAV-ASPA also restores the myelin lipid profile, as evidenced by measurement of sphingolipids in treated and control mice (FIG. 13).

A crucial finding is that high ubiquitous ASPA expression enhances motor performance in treated CD mice over wild-type mice. This may be the result of enhanced energy metabolism due to direct intervention in the ASPA-mediated metabolism of NAA.

The results from this global metabolomic study compare WT or aspartoacylase (ASPA) KO brain samples, or KO mice treated with recombinant AAV (to express ASPA or not, as control), including changes in metabolites related to energetics (carbohydrate and lipid metabolism), neurotransmitter production, inflammation, and redox homeostasis. In the principal component analysis (PCA), samples split into two groups, with WT and rAAV Tx in one, and KO and rAAV Ctrl in the other, indicating that rAAV Tx-mediated "rescued" metabolomic effects of ASPA deficiency. Consistent with loss of ASPA function, N-acetylaspartate (NAA) accumulated in brain (KO vs WT), while levels decreased following ASPA re-expression (rAAV Tx vs Ctrl). Lipids tended to show decreases across all classes, which could reflect changes in beta-oxidation and/or biosynthesis (KO vs WT); rAAV Tx (compared to rAAV Ctrl) showed increases in a marker of lipid biosynthesis, with increases in a number of lipid classes. Evidence of declining glycolytic use in KO (compared to WT) was reversed in rAAV Tx (compared to rAAV Control). Finally, changes in the dataset pointed to increasing inflammation and oxidative stress in KO (compared to WT), with decreases in rAAV Tx (compared to Ctrl).

Summary of Results

Regarding Gene Therapy:

Gene Therapy reverses the metabolic changes in Canavan disease brains.

Regarding Canavan Disease Pathomechanism and CNS Energy Metabolism:
1. Glucose metabolism in Canavan brains
   a. Substrates for glycolysis are abundant in Canavan mouse brains
      i. Substrates of glycolysis accumulate (e.g. glucose, glucose-6-phosphate, 3-phosphoglycerate, phosphoenolpyruvate) indicating a decreased rate of glycolysis.
      ii. Increased phosphoenolpyruvate inhibits the enzyme "triosephosphate isomerase" which decreases the efficacy of glycolysis by utilizing only 50% of each glucose molecule for energy production.
      iii. Glycogen, the glucose storage system of cells, is being broken down despite the abundancy of glucose in Canavan mouse brains. In a physiologic state, increased glucose leads to glycogen synthesis not break down.
   b. Products of glycolysis are unchanged or decreased in Canavan mouse brains
      i. Pyruvate is unchanged despite the abundancy of glycolysis substrates, which is paralleled by an decrease in lactate. Both indicates that the glycolytic rate is decreased.
2. Fatty acid metabolism in Canavan brains
   a. Products of fatty acid break down are changed to favor beta-oxidation (use of fatty acids for energy production).
      i. Carnitine is increased in Canavan brains. The transport into mitochondria is the rate limiting step in beta-oxidation. This transport is conducted by Carnitine palmitoyltransferase 1 and 2 (CPT1 and CPT2). Fatty acids need to be bound to carnitine in order to be transported into mitochondria. An increase in carnitine usually facilitates the esterification of fatty acids and carnitine supported fatty acid transport into mitochondria.
      ii. Several carnitine esters are increased, decreased or unchanged indicating consumption of fatty acids in Canavan brains.
      iii. Several fatty acids are decreased as well in Canavan brains, which might be because of fatty acid consumption for energy production, e.g. ATP or other energy equivalents.
      iv. Malonylcarnitine, a surrogate marker for malonyl-CoA is decreased which facilitates fatty acid transport into mitochondria for beta-oxidation (Malonyl-CoA inhibits CPT1 and thus reduces fatty acid transport into mitochondria; a reduction in malonyl-CoA removed this inhibitory stimulus). Malonyl-CoA is also a precursor for fatty acid synthesis and thus mediates between fatty acid break down and fatty acid synthesis. The fact that malonylcarnitine is decreased points towards fatty acid break down.
3. Ketone bodies in Canavan brains
   a. The ketone body beta-hydroxybutyrate is increased, which is directly broken down to acetate and feed into the TCA cycle.
   b. Beta-hydroxybutyrate also mediates between metabolism and transcription.
4. Acetate in Canavan brains
   a. Acetyl-CoA is not changed in the CD neurometabolome, which argues against the "acetate deficiency hypothesis". In addition, it might also explain why acetate supplementation failed to cure Canavan disease in patients.
   b. Acetylcarnitine, which has been reported to be crucial in energy production is highly increased and thus facilitates energy production.

5. Antioxidants
   a. Some antioxidants were decreased, some increased, which could support the oxidative stress hypothesis. However, there was a significant reduction in metabolites for the synthesis of antioxidants, indicating that the decreased in some antioxidants is an issue of supply rather than demand. This argues against the oxidative stress hypothesis as a primary disease causing factor.

NAA accumulation and/or ASPA deficiency disrupt the CNS energy metabolism by favoring fatty acids over glucose/lactate for energy production, causing "self-consumption" of fatty acids, critical components of myelin and thus white matter vacuolations and disease pathology.

NAA metabolic deficiency and/or its causative ASPA deficiency might promote fatty acid over glucose/lactate consumption for energy production.

NAA metabolism with its associated proteins such as AspA, might be a key player in regulating and communication between metabolic pathways and monitoring metabolic homeostasis of cells and organs, which is demonstrated by the fact that despite the abundancy of glucose, fatty acid metabolism is favored, glycogen is broken down and ketone bodies are formed, which are highly detrimental processes in a physiologic system but not in a state of altered NAA/ASPA metabolism. Also, in addition to be involved in NAA metabolism, AspA may play critical roles in energy metabolism.

These conclusions are further supported by the fact that rAAV mediated delivery of ASPA corrects these observed changes.

Example 2: Nur7 Mouse Model of Canavan Disease

A single intravenous (i.v.) injection of recombinant adeno-associated virus (rAAV) expressing human ASPA (hASPA) rescues early lethality and partially restores motor function ($1^{st}$ generation gene therapy) in a CD knock-out (CD KO) mouse, which resembles the congenital sub-form of CD and displays the severest phenotype of all available CD mouse models, with early death at around post-natal day (p) 28.

This example describes a $3^{rd}$ generation rAAV expressing hASPA (also referred to as FKzhAspA-Opt), which comprises the sequence represented by SEQ ID NO: 1 and cures disease in a CD KO mouse model. Interestingly, the $3^{rd}$ generation gene therapy turns CD KO mice into "super-mice", that outperform wild-type (WT) mice on rotarod motor function test. This rescue is persistent-treated mice assessed at 1.5 years of age still show no signs of disease reoccurrence. CNS pathology and magnet resonance imaging (MRI) at p25 and p365 show complete normalization.

To further support the efficacy of the $3^{rd}$ generation gene therapy, neurometabolome profiling was performed. Data indicate that over 400 characterized metabolites that showed reversal of the Canavan disease related metabolic changes including myelin associated lipids. Transcriptomic profiling was also performed.

To further evaluate the potency of the $3^{rd}$ generation gene therapy, different doses and routes of administration were tested. Of note, 200-fold lower doses intraventricularly (ICV) administered rAAV still rescues lethality, while mice treated ICV with 20-fold reduced dose draw even with WT mice on motor function testing.

Figure 14:
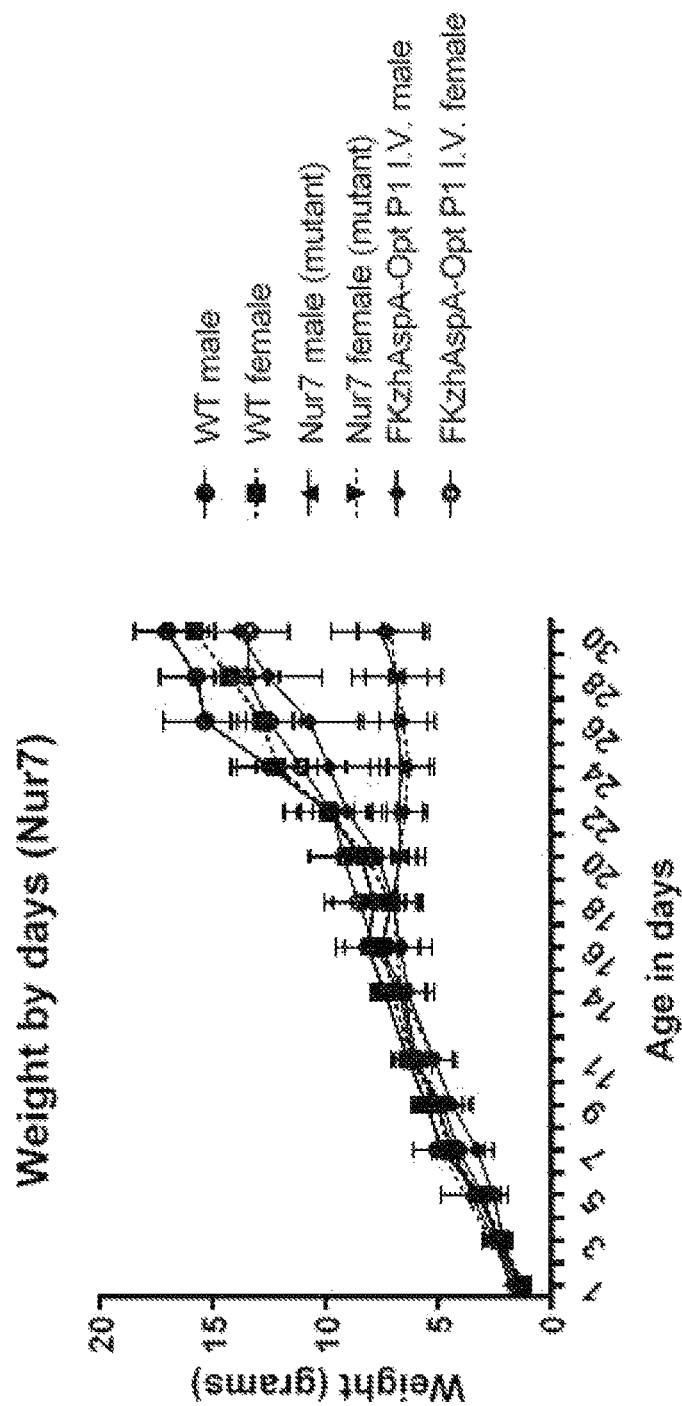
FIG. 14 shows weight loss/gain patterns in wild-type (WT) and CD model (Nur7) mice. Nur7 mice treated with i.v. administered $3^{rd}$ generation rAAV-hASPA (FKzhAspA-Opt) at P1 show growth similar to WT mice. Male and female mice show the same pattern of weight loss/gain.
Figure 15:
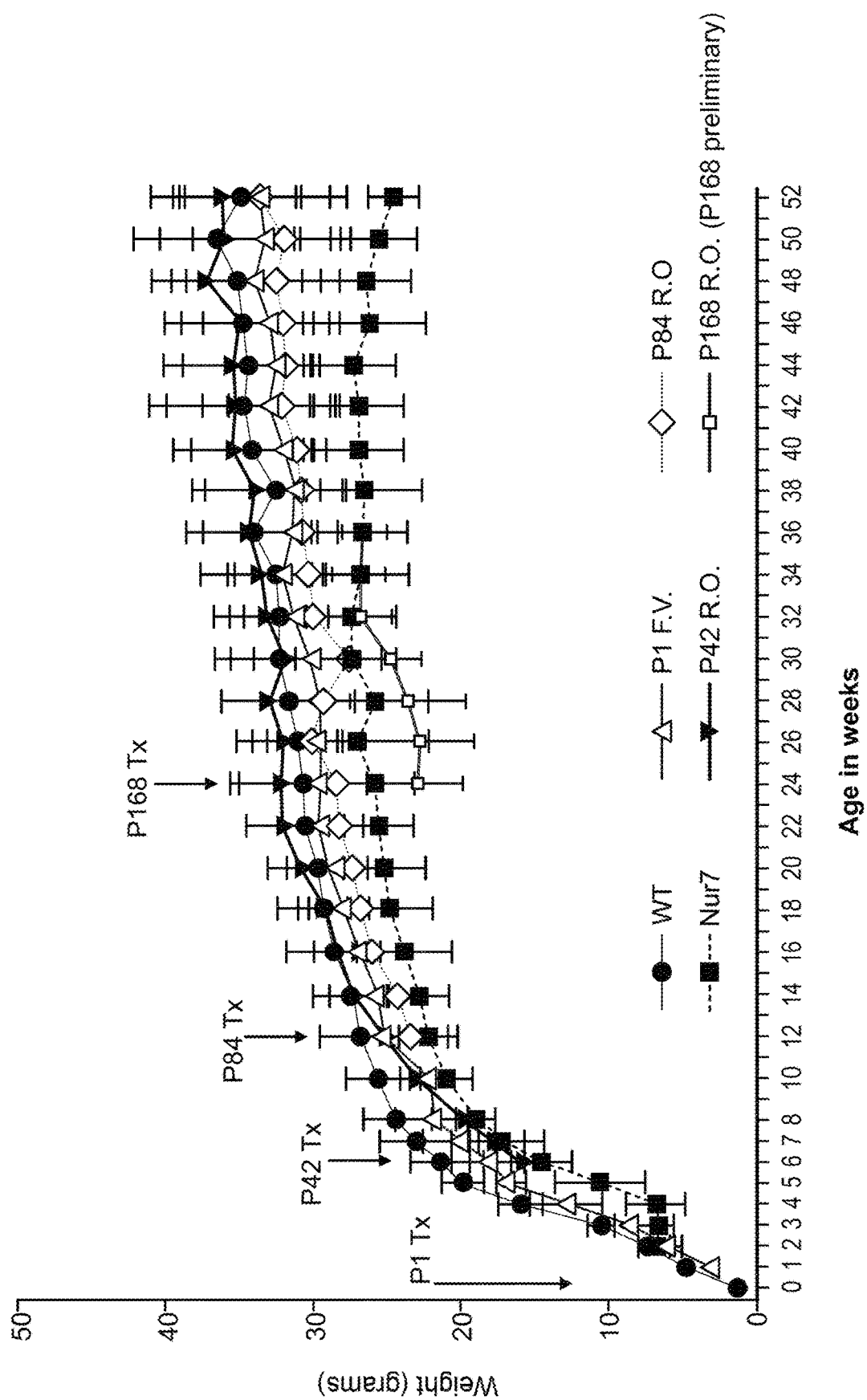
FIG. 15 shows improvement in overall health of Nur7 mice treated with rAAV-hASPA. Nur7 mice were treated with rAAV-hASPA at p1, p42, p84, or p168 and weighed. Treated mice were compared to a wild-type (WT) mouse control. All treatment groups show normalization/improvement in weight.

Next, the Nur7 mouse model, which resembles infantile and juvenile sub-form of CD, was tested. This model displays a similar disease pattern as the CD KO mouse with respect to growth curve and neurologic symptoms but eventually re-gains weight and shows survival similar to wild-type mice (FIG. 14). Again, mice received a single i.v. dose of rAAVhASPA at p1 (gold standard positive control) and subsequent groups were dosed at 6, 12, and 24 weeks of age with a dose 10-fold higher than that for neonates to determine the therapeutic window. Of note, mice treated at 6 weeks of age recovered within 4 weeks post-treatment. Mice treated later than 6 weeks require more time to recover but still showed significant improvement over Nur7 mutants (FIG. 15). This recovery was also correlated by CNS pathology and MRI.

Figure 16:
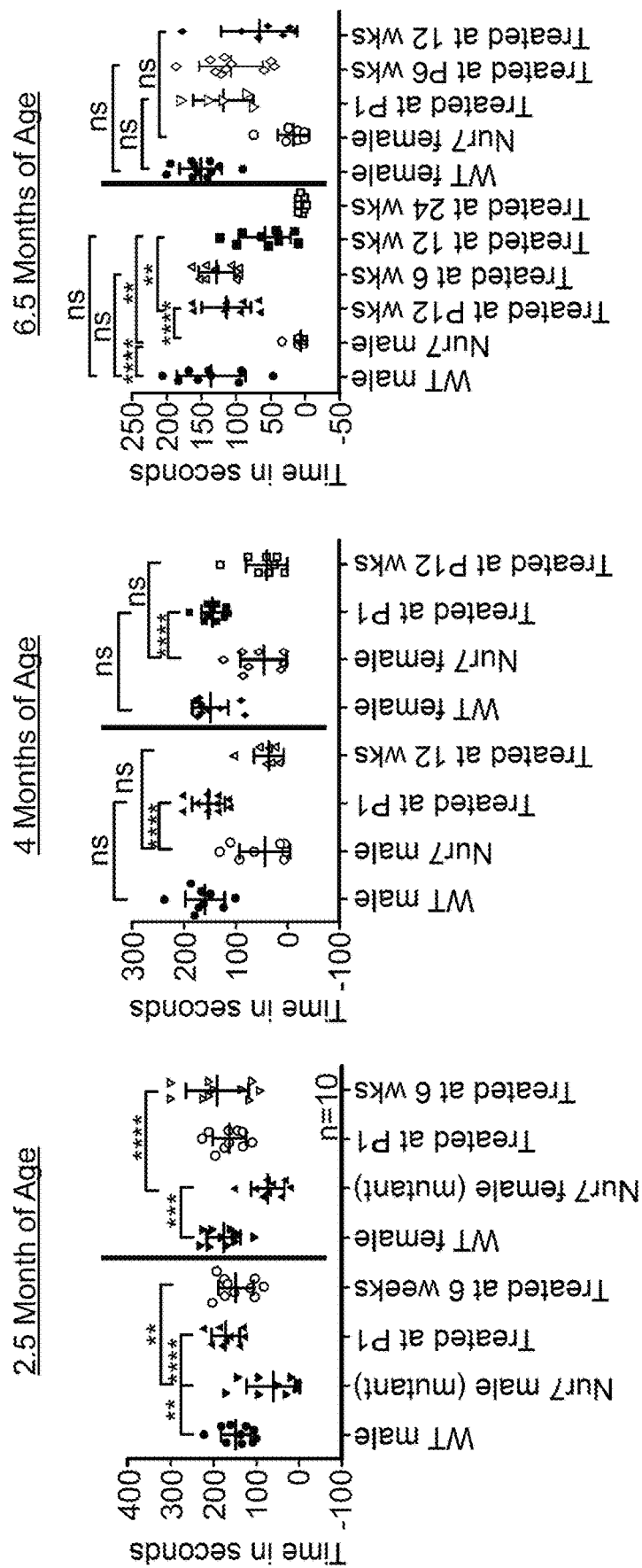
FIG. 16 shows data related to the expanded therapeutic window for treatment of CD using rAAV-hASPA. Nur7 mice treated with rAAV-hASPA at p1, p42, p84 and p168, and motor function was assessed by rotarod. Mice treated at 6 weeks of age recovered completely within 4 weeks post-injection.
Figure 17:
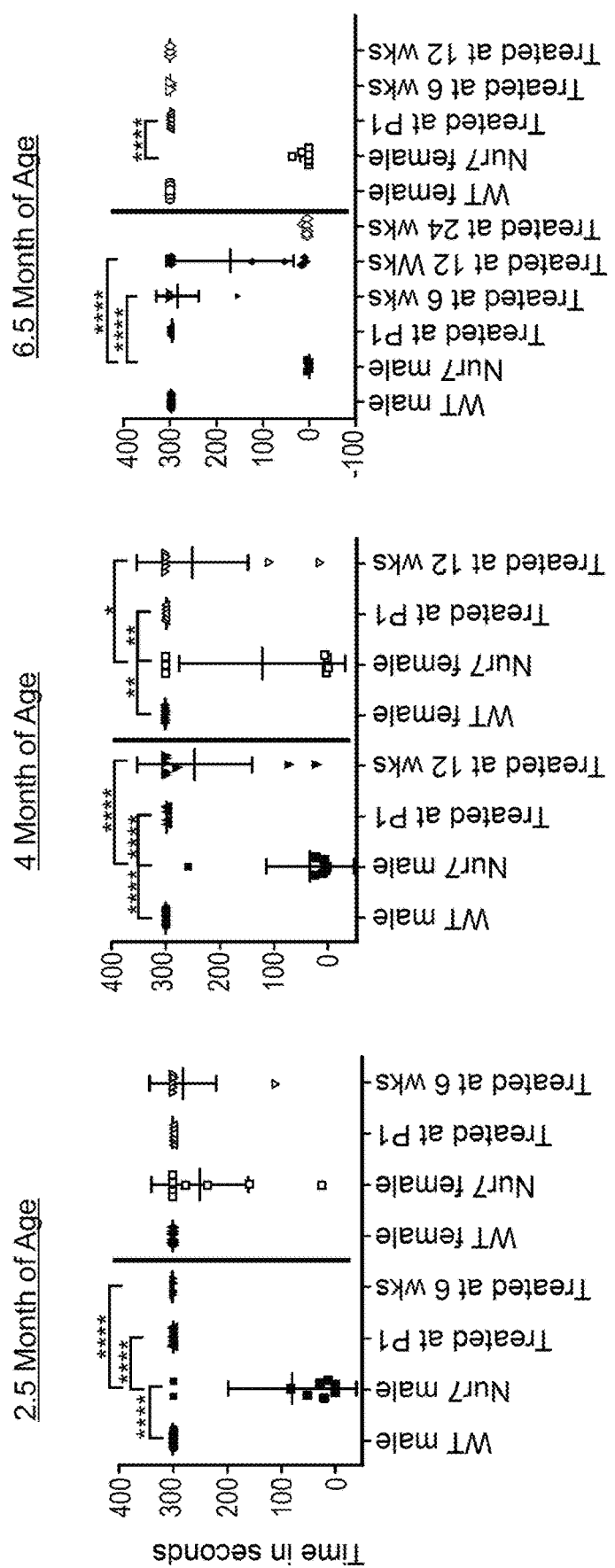
FIG. 17 shows data related to the expanded therapeutic window for treatment of CD using rAAV-hASPA. Nur7 mice treated with rAAV-hASPA at p1, p42, and p84, and motor function was assessed by balance beam.
Figure 18:
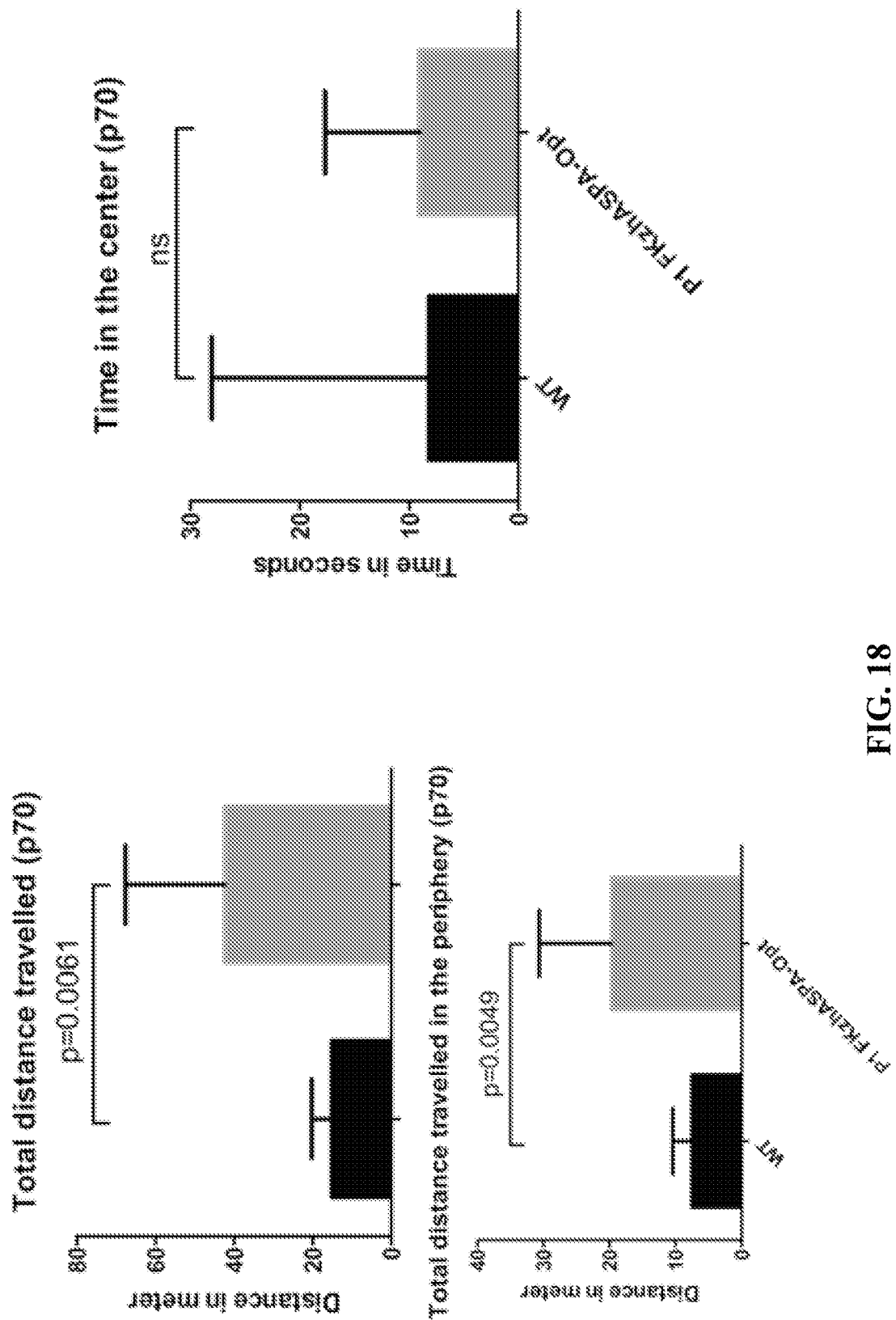
FIG. 18 shows data related to assessment of cognitive function of Nur7 mice treated with rAAV-hASPA. At p70, Nur7 mice treated with rAAV-hASPA outperformed wild-type (WT) mice with respect to total distance travelled and total distance travelled in the periphery.
Figure 19:
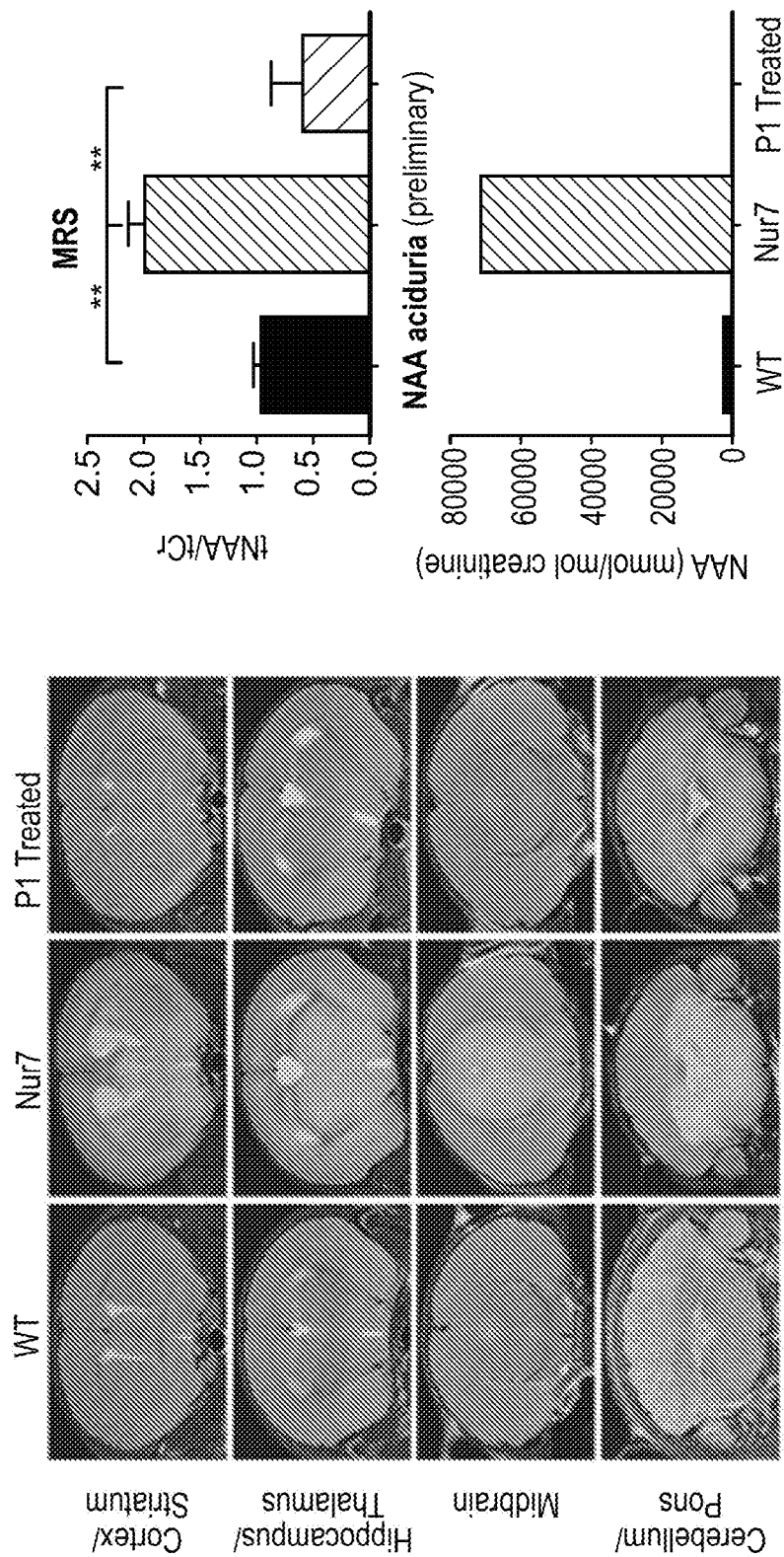
FIG. 19 shows normalization of T2 signal and NAA levels in the brains of Nur7 mice treated with rAAV-hASPA, as shown by magnetic resonance imaging (MRI), magnetic resonance spectroscopy (MRS) and measurement of NAA aciduria.
Figure 20:
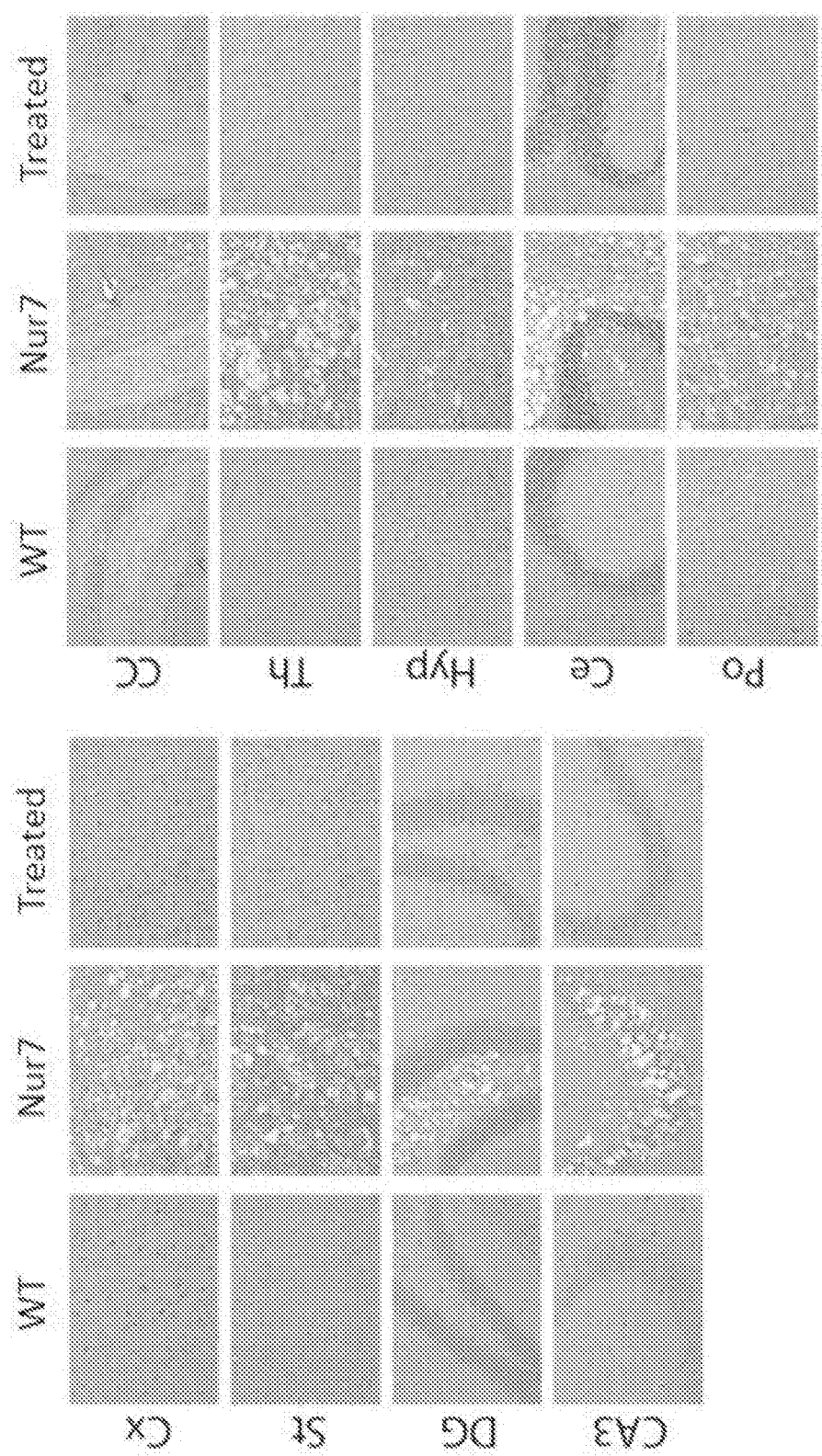
FIG. 20 shows normalization of brain morphology at p25 in Nur7 mice treated with rAAV-hASPA at p1.
Figure 21:
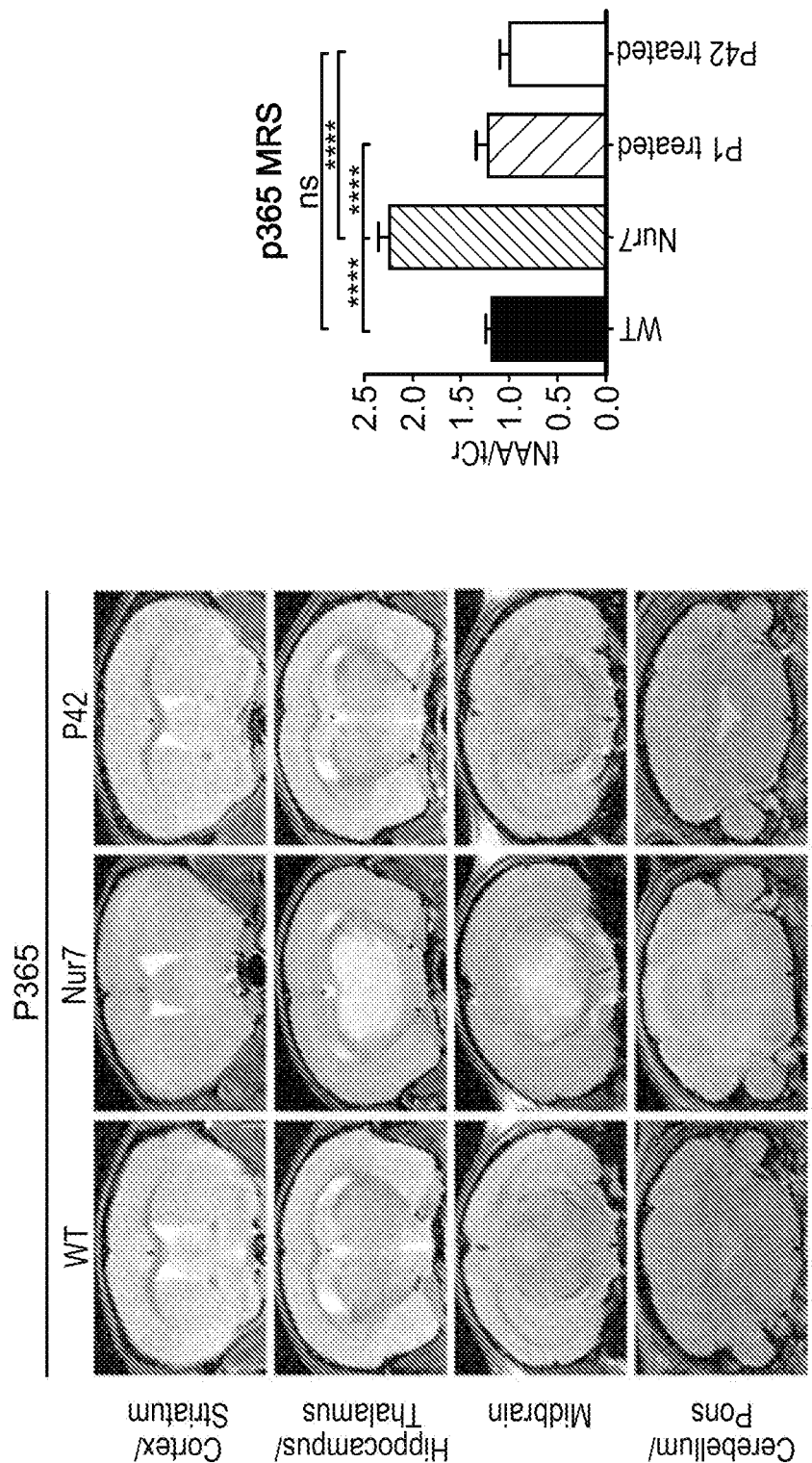
FIG. 21 shows complete normalization of T2 signal intensities and MRS in one-year old Nur7 mice that were treated with rAAV-hASPA at p42.

Motor function was tested for all mice 4 weeks after treatment and subsequent intervals up to one year of age for direct comparison (FIG. 16 and FIG. 17). Generally, the earlier mice were treated, the better the therapeutic outcome. Surprisingly, juvenile mice at 6 weeks of age recovered completely within 4 weeks post-injection (FIG. 16 and FIG. 17). Although mice treated at 3 months of age and older did not respond immediately within the first 4 weeks post-treatment, they eventually showed significant improvements over Nur7 mutant control mice. Cognitive function was also tested; representative data are shown in FIG. 18. Of note, cognitive function testing revealed that treated mice recover cognitively before motor function improves; this was even true for late treatment time points. Furthermore, response to rAAVhASPA gene therapy was confirmed via MRS for N-acetyaspartate, MRI, and neuropathology (FIGS. 19-21).

Overall, data demonstrate that rAAV mediated hASPA expression of the $3^{rd}$ generation gene therapy vector not only prevents but also rescues the clinical manifestation and pathology of the juvenile and adult model of Canavan disease at an unprecedented level, which might have implications for other CNS disorders that require treatment in later stages of life. In addition, this is confirmed on different levels of cellular complexity by MRI, fMRI, CNS pathology, and neurometabolic profiling.

Example 3: Astrocyte-Restricted hASPA Expression in CD KO Mice (Severe Phenotype)

Several tissue/cell-specific expression cassettes configured for restricting hASPA expression to either astrocytes, neurons, oligodendrocytes, liver, heart, or muscle were produced. For example, a rAAV-hASPA construct comprising an astrocyte-specific glial fibrillary acidic protein (GFAP) promoter was produced. Tissue-restricted rAAV were administered to Canavan disease knock-out (CD KO) mice. Surprisingly, mice expressing hASPA restricted to peripheral organs showed extended survival and normalization of the growth curve at later time points, indicating a contribution of peripheral organs to the disease pathomechanism.

Figure 22:
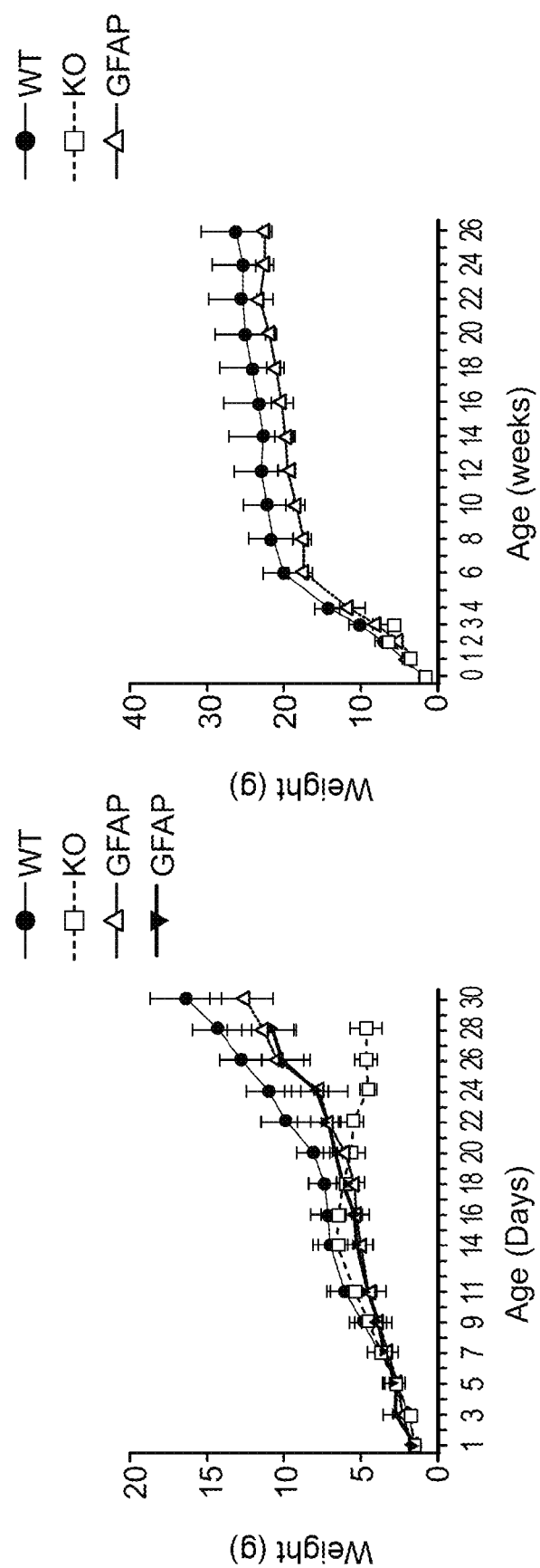
FIG. 22 shows improvement in overall health, as measured by weight gain, in CD KO mice treated with astrocyte-restricted rAAV-hASPA. The astrocyte-specific expression of ASPA was produced by using a glial fibrillary acidic protein (GFAP) promoter to drive hASPA expression. The lifespan of CD KO mice treated with astrocyte-restricted rAAV-hASPA extended beyond the 28 day lifespan of untreated KO mice and was not significantly different from the lifespan of wild-type (WT) mice.
Figure 23:
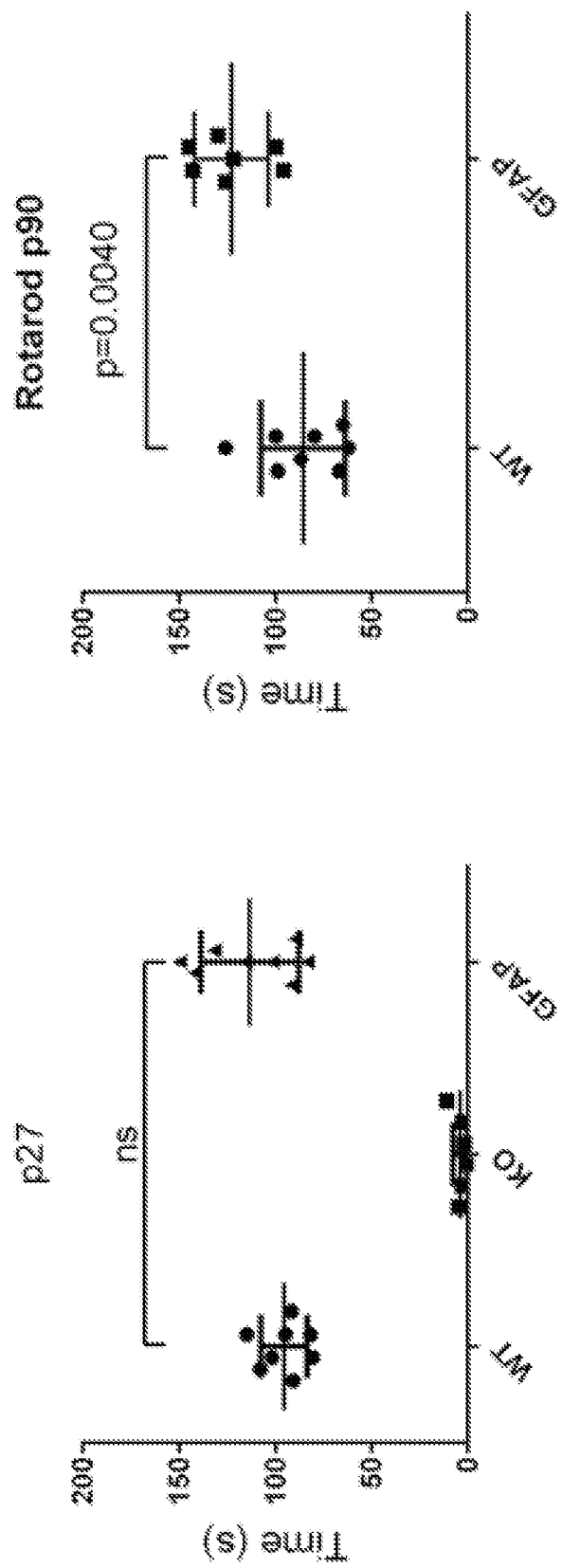
FIG. 23 shows astrocyte-restricted expression of hASPA results in normalization of motor function in CD KO mice. CD KO mice were administered astrocyte-restricted rAAV-hASPA and motor function was measured at p27 and p90. Data show that astrocyte-restricted expression of hASPA resulted in restoration of motor function in treated CD KO mice compared to wild-type (WT) mice. At p90, treated CD KO mice outperformed WT mice in a rotarod test.
Figure 24:
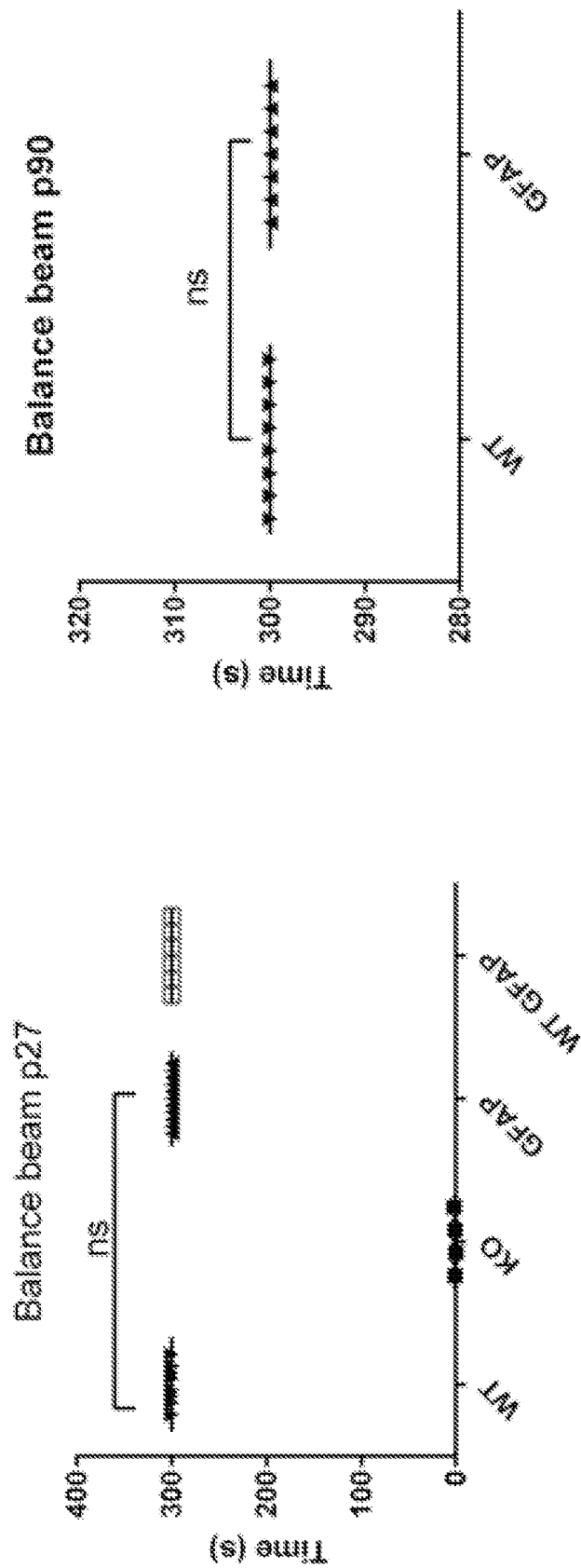
FIG. 24 shows astrocyte-restricted expression of hASPA results in normalization of motor function in CD KO mice. CD KO mice were administered astrocyte-restricted rAAV-hASPA and motor function was measured by a balance beam test at p27 and p90. Data show that astrocyte-restricted expression of hASPA resulted in restoration of motor function in treated CD KO mice compared to wild-type (WT) mice.

Astrocyte-restricted hASPA expression produced the strongest disease recovery matching the performance of wild-type (WT) mice (FIGS. 22-24). FIG. 22 shows astrocyte-restricted expression of hASPA results in survival and growth of treated CD KO mice compared to untreated control mice. FIG. 23 shows astrocyte-restricted expression of hASPA results in restoration of motor function in treated CD KO mice, as measured by rotarod test at p27 and p90. FIG. 24 shows astrocyte-restricted expression of hASPA results in restoration of motor function in treated CD KO mice, as measured by balance beam test at p27 and p90.

Figure 25:
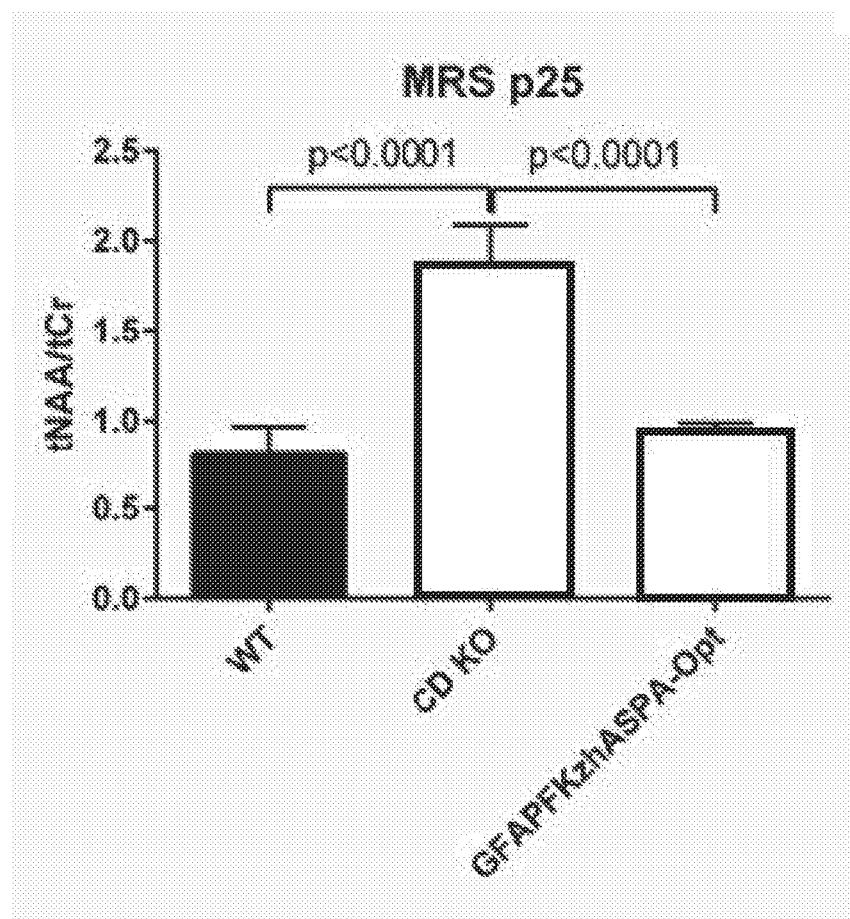
FIG. 25 shows astrocyte-restricted expression of hASPA normalizes NAA levels, as measured by MRS.

A lower dose of rAAV-hASPA was administered to mice via localized brain injections. Data indicates localized T2 hyper-intensity signal clearance on MRI was well correlated with reduction of NAA levels by MRS (FIG. 25). In other words, the further away from the injection site, the higher the NAA levels, which supports the idea of drainage and hydrolytic activity of NAA towards the injection side. Currently, we are investigating this metabolic sink theory in more detail by creating a functional map of therapeutic gene transfer in the brain by mass spectrometry quantification of NAA, and vector genome and ASPA transcripts analyses in different anatomic regions.

Overall, data indicate that hASPA expression does not have to be restored in oligodendrocytes in order to rescue lethality and Canavan disease phenotype.

Example 4: High Field In Vivo Neuroimaging

Gene therapy targeting the central nervous system (CNS) is one of the most challenging gene therapies due to the blood-brain barrier (BBB). One obstacle in the monitoring and evaluation of CNS gene therapy is the non-invasive evaluation of therapeutic outcome. While biopsies and sections of the CNS are the gold-standard to assess brain pathology and response to CNS gene therapy, the invasiveness and potentially associated complications limit its frequent use in pre-clinical as well as clinical studies.

This example describes high-field in vivo neuroimaging to monitor intravenously (i.v.) and intracerebroventricularly (i.c.v.) administered rAAV-based CNS directed gene therapy in a mouse model of Canavan disease (CD). Characteristically, Canavan disease presents with a very high NAA peak detected by magnet resonance spectrometry (MRS) and hyper intensity on T2-weighted anatomic images using magnet resonance imaging (MRI). Consequently, the efficacy of i.v. and i.c.v. gene therapy by those two means was evaluated. In congruence with motor function and pathology data described elsewhere in the disclosure, both MRI and MRS alterations have been entirely normalized by gene therapy.

Another characteristic neuropathological change on Canavan brain sections is the loss of white matter tracts, which is thought to explain neurological symptoms seen in Canavan disease patients. The ability of diffusion tensor imaging (DTI) to enable the assessment of white matter tract degeneration and recovery upon gene therapy without brain biopsies was investigated. Selecting thalamus and corpus callosum as regions of interest (ROI), DTI shows a recovery of brain white matter integrity when utilizing $3^{rd}$ generation Canavan gene therapy (e.g., FKzhAspA-Opt, SEQ ID NO: 1). Furthermore, the $3^{rd}$ generation gene therapy converts this CD mouse model with the severest phenotype into "supermouse", outperforming wild-type mouse on motor function testing.

Functional connectivity identifies brain regions that not only show response to treatment but also indicates possible explanations for this enhanced phenotype. Using resting-state functional MRI (rs-fMRI), it was shown that treated CD mice have a functional connectivity pattern that is more similar to, or even enhanced beyond, what is seen in WT brain. This indicates facilitated inter-brain-region functional connectivity, might provide a neural mechanism that subserves the observed enhanced motor function.

In summary, imaging data show that high-field in vivo neuroimaging is a valuable tool to monitor pre-clinical CNS gene therapy and pathology in detail, that it can provide insights into pathophysiology and that it has potential implications for the use in clinical trial outcome prediction and assessment.

Example 5: Redirecting N-Acetylaspartate Metabolism in the Central Nervous System Normalizes Myelination and Rescues Canavan Disease Materials and Methods
Animal Procedures Heterozygous Aspa+/− mice in a Sv129 background were bred and newborns were genotyped on the day of birth. Briefly, 1 mm tail tips were cut and genomic DNA was extracted according to manufacturer's protocol using either manual QIAamp DNA mini kit or QIAcube robot (Qiagen, Hilden, Germany). DNA extraction was followed by quantitative PCR (qPCR). Injections were performed on P1 via the right facial vein at either $4 \times 10^{\wedge}11$ (~$2.6 \times 10^{\wedge}14$ vg/kg; based on average 1.5 g weight), $1.33 \times 10^{\wedge}11$ (~$8.8 \times 10^{\wedge}13$ vg/kg; based on average 1.5 g weight) or $4 \times 10^{\wedge}10$ (~$2.6 \times 10^{\wedge}13$ vg/kg; based on average 1.5 g weight) genome copy (GC) number. After every procedure, pups were cleaned with 70% ethanol and rubbed with bedding material. The parent animal was returned after brief nose numbing with 70% ethanol. Vg=viral genomes Viral Production and Vector Design Recombinant adeno-associated virus (rAAV) was produced by transient HEK 293 cell transfection and Cesium-chloride (CsCl) sedimentation. Vector preparations were titered by quantitative PCR, and purity was assessed by 4-12% SDS-acrylamide gel electrophoresis and silver staining (Invitrogen, Carlsbad, Calif.). Morphological integrity of virions was assessed by transmission electron microscopy of negative stained rAAV. Due to packaging size restrictions, single stranded rAAV genome was used for the phGFAP-hASPA and phGFAP-EGFP constructs. All other vectors were self-complementary (sc) AAV vectors (scAAV).

Western Blot

Protein was extracted using RIPA buffer. Protein quantification was performed by BCA assay (Pierce Biotechnologies, Rockford, Ill., USA) and 10-20 µg of total protein mixed with 4× Laemmli buffer (BioRad, Hercules, Calif., USA) were loaded onto a 10-12% Tris-HCl acrylamide gel (BioRad, Hercules, Calif., USA). After electrophoresis, protein was blotted on a nitrocellulose membrane (BioRad, Hercules, Calif., USA) with the Trans-Blot Turbo Transfer System (BioRad, Hercules, Calif., USA). Subsequently, membranes were subjected to blocking at room temperature for at least one hour with Odyssey Blocking Buffer (Licor, Lincoln, Nebr., USA). Next, membranes were incubated with primary (anti-ASPA, 1:2000, ab 97454; anti-Actin, 1:5000, ab8224) antibody at 4° C. overnight and incubated with secondary antibody (Licor, Lincoln, Nebr., USA) the next day. The membranes were analyzed with Odyssey analyzer (Licor, Lincoln, Nebr., USA). Quantification was performed using ImageJ.

Isolation of Brain Regions and DNA and RNA Extraction

Mice were anesthetized with isofluorane and transcardially perfused with ice-cold phosphate buffered saline (PBS). Next, brains were removed and divided in half along the interhemispheric cleft. One brain half at a time was placed on an RNase free and ice-cooled plate under a dissection microscope. First, the olfactory bulb was removed using a cold razor blade. Next, the brain stem/midbrain was removed along the line between the cortex/thalamus and the lamina tecti. The brainstem was further subdivided into midbrain, lamina tecti, cerebellum, and brain stem. Furthermore, the thalamus/hypothalamus was removed using Wecker Micro Dissecting Spatula (Roboz Surgical Instruments Inc., Gaithersburg, Md., USA). The hippocampus was removed. Finally, part of the cortex was removed with a fresh razor blade. All samples were snap frozen immediately after removal.

DNA and RNA were extracted using the Qiagen Allprep DNA/RNA Mini kit (Qiagen, Hilden, Germany) and RNA samples were subjected to on column DNase treatment before RT-PCR. DNA was subjected to viral genome copy number determination and total RNA for RT-PCR (High Capacity cDNA Reverse Transcription kit, Applied Biosystems).

Droplet Digital PCR (ddPCR)

Multiplex ddPCR was performed on a QX200 ddPCR system (Bio-Rad, Hercules, Calif.). All assays were based on TaqMan probes, where the gene of interest probes were labelled with FAM and the reference gene as VIC. Bio-Rad ddPCR mastermix with no dUTP was used (Bio-Rad 1863024) for all ddPCR reactions.

Vector Genome Copy Number

DNA was digested with BamHI at >10 U/μg of DNA at 37 C for 1 hour. The BamHI digest ensured single copies of rAAV genomes. All vectors contained a RBG sequence, which was targeted for viral genome quantification. Viral genome numbers were normalized to the number of diploid cells by using transferrin receptor (Tfrc) as the reference gene (Invitrogen, 4458367).

Motor Function and Spatial Memory Testing

Mouse motor performance was assessed using accelerated rotarod for motor function and endurance, balance beam for vestibular function and ataxia, and inverted screen for grip strength. For each motor function test, n=8 mice were injected and tested independently.

Accelerated Rotarod

Mice were trained two days before the testing day for three runs each. On the testing day, mice were placed on the rotarod to acclimate for 1 minute. Each mouse was tested three times and the best value was used for analysis. The acceleration and timing was set to 4-40 rpm over 5 minutes.

Balance Beam

To increase the stringency of this test, the cut-off time was increased from 3 minutes to 5 minutes. Mice were placed in the middle of the balance beam and the latency until drop off was measured. Again, the best value was counted.

Inverted Screen

Mice were placed in the center of a grid (30 cm2 with 25 mm2 holes) in horizontal position and allowed to acclimate for 1 minute. Grid was turned slowly within 15 seconds to 125 degrees so that the mouse was hanging upside-down. Time was measured until drop off. The cut-off for p28 testing was 3 minutes. At all other time points, the cut-off was 5 minutes to increase the stringency of the test.

T Maze

T-maze testing was done in a spontaneous, unrewarded manner, with all arms of the T-maze open during testing. Mice were placed within the initial chamber with the door down, and the side-arm doors open for 10 s, upon which the initial chamber's door was opened, and the mice were allowed to enter and explore the T-maze. Upon the complete entry of the mouse into one of the side arms, defined as all four of the paws having passed through the edge of the arm, all doors of the T-maze were closed, and the mouse was returned to the initial chamber for a 10 s resting time. During this 10 s, the side arm doors were re-opened. This process was repeated 10 times, which provides the mouse with a total of 10 opportunities to alternate their side-arm choice. The final result is expressed as a ratio of the number of alternations over 10.

H&E and Luxol Fast Blue Staining

Mice were euthanized and perfused transcardially with ice-cold PBS and 4% paraformaldehyde (PFA). Tissues were removed and sliced using an Alto brain or spinal cord matrix (Roboz Surgical Instruments Inc., Gaithersburg, Md., USA). Subsequently, mouse tissues were stored in PFA at 4° C. overnight. Paraffin embedding, Hematoxilin & Eosin (H&E), and Luxol fast blue staining was performed. Stained sections were analyzed and pictures taken with an Axioscope 50 (Zeiss, Jena, Germany) using a DMC2900 camera (Leica Microsystems, Wetzlar, Germany).

Magnetic Resonance Imaging (MRS) and Spectroscopy (MRS)

Mice were anesthetized with 2% isofluorane and constantly monitored for vital signs during the entire time of imaging. P42 mice were imaged with a 4.7 T/40 cm horizontal magnet (Oxford, UK) equipped with a Biospec Avance Bruker console (Bruker, Germany). Experiments for all other imaging was performed using a 4.7 T/40 cm horizontal magnet (Oxford, UK) equipped with a Biospec Avance III HD Bruker console (Bruker, Germany). A $^1$H radiofrequency mouse head coil (Bruker, Germany) with inner diameter of 23 mm was used for the experiments.

T1-weighted anatomical images were acquired using FLASH sequence with the following parameters: repetition time (TR)=280.86 ms, echo time (TE)=4.5 ms, matrix size=384×384, field of view (FOV)=18×18 mm$^2$, slice number=15, slice thickness=0.5 mm, flip angle=40°, number of averages=8. T2-weighted images were acquired using TurboRARE sequence with TR=2200 ms, TE=36 ms, echo spacing=12 ms, 8 averages, and rare factor=8. $^1$H magnetic resonance spectroscopy data were acquired using single voxel PRESS (Pont Resolved Spectroscopy Sequence) (repetition time=2,500 ms, echo time=16 ms, number of averages=512, voxel size=3×3×3 mm). Functional MRI images were acquired for 10 minutes using echo planar imaging (EPI) sequence, with TR=1000 ms, TE=18 ms, matrix size=96×96, FOV=18×18 mm$^2$, slice number=15, slice thickness=0.5 mm, number of repetitions=600. Diffusion tensor imaging (DTI) data were acquired from 30 directions with B value of 650/0, TR=2300 ms, TE=21 ms, number of averages=4, with the same geometry parameters as EPI.

$^1$H Magnetic Resonance Imaging and Spectroscopy Study.

Proton spectra were fit using LCModel (Version 6.2-2B) which analyzed in vivo proton spectrum as a linear combination of model in vitro spectra from individual metabolite solutions (Provencher, 2001) and generated data as absolute fits (in institutional units) and SD %. SD was used as a measure of the reliability of the fit. The spectral inclusion criteria were SD<20% for NAA, creatine, and inositol.

Resting State Functional Connectivity (rsFC) Analysis

EPI images were preprocessed using Medical Image Visualization and Analysis (MIVA, ccni.wpi.edu/) and Matlab 2010b (the Mathworks Inc.). All EPI images were first registered to a standard anatomy, where seed regions were defined. After registration, all EPIs went through motion correction, spatial smoothing (full-width-half maximum=1 mm), and 0.002-0.1 Hz band-pass filtering. Seed-based rsFC was calculated using previously demonstrated algorithm.

Diffusion Tensor Imaging (DTI)

DTI data were analyzed using DTIstudio (mristudio.org/, Susumi Mori and Hangyi Jiang, Johns Hopkins University), including eddy current correction, motion correction, and generation of all tensor metrics (FA and eigen decomposition of the voxel-wise diffusion tensor). FA values in particular regions of interest (ROIs) were extracted from manually drawn ROIs.

For all imaging results, group comparisons were carried out by one way ANOVA, with a significance threshold of p<0.05.

Immunohistology

Mice were perfused transcardially with 4% paraformaldehyde (PFA) and kept in PFA overnight at 4° C. The next day, brains were extracted and subjected to gradient sucrose steps (10, 20 and 30%) overnight at 4° C. Brains were mounted in O.T.C. compound (Fisher HealthCare, Houston, Tex., USA) and stored at −80° C. until cryosectioning (Cryostar NX70, Thermo Fisher Scientific, Walldorf, Germany). Floating brain slices were washed in 1×PBS 3× for 5 min each. Cells were permeabilized with 1×PBS and 0.5% Triton-X 100 at room temperature for 1 hr, with subsequent blocking for 1 hr at room temperature with 5% serum (10% normal goat serum, Life technologies, 50062Z). Brain slices were incubated with primary antibodies (anti-GFAP, EMD Millipore, 1:1000, MAB360; anti-MBP, Abcam, 1:1000, ab40390) in 1.5% serum overnight at 4° C., washed the next day (1×PBS, ×3, 5 min each), and stained with secondary antibody in 1.5% serum at room temperature for 1 hr (anti-mouse or rabbit; Invitrogen, A-11031 or A-11011). Slices were mounted using Vectashield with 4′, 6-diamidino-2-phenylindole (Vector Laboratories, Burlingame, Calif.).

Brain sections were imaged and recorded using DM 5500B Upright microscope (Leica Microsystems, Wetzlar, Germany) and Leica DFC365 FX digital camera.

Software and Statistics

Image analysis and displaying was done using Imaris 8.2 Software (Bitplane Inc., South Windsor, Conn., USA). Western blots were quantified using ImageJ (National Institute of Health, USA). Graphs were analyzed and statistical calculations were performed in GraphPad Prism 7 (GraphPad Software, Inc., La Jolla, Calif., USA). Correlation between overall functional connectivity on fMRI to mean of accelerated rotarod performance was calculated and linear regression analysis was performed using GraphPad Prism 7. Statistics were performed using GraphPad Prism 7, two-way ANOVA with multi-comparison correction (Turkey) for weights, and one-way ANOVA with multi-comparison correction for all other statistics, if not stated otherwise. If not otherwise states at least n=3 mice were analyzed.

Figure 26A:
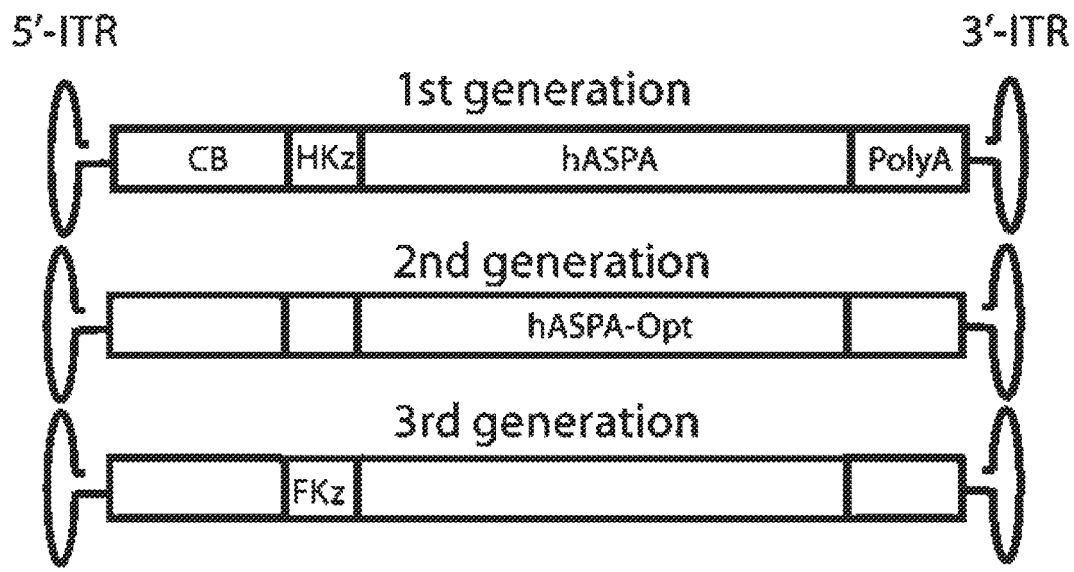
FIGS. 26A-26C show optimized gene expression cassette rescues normal ASPA and NAA protein levels in CD KO mice.
Figure 26B:
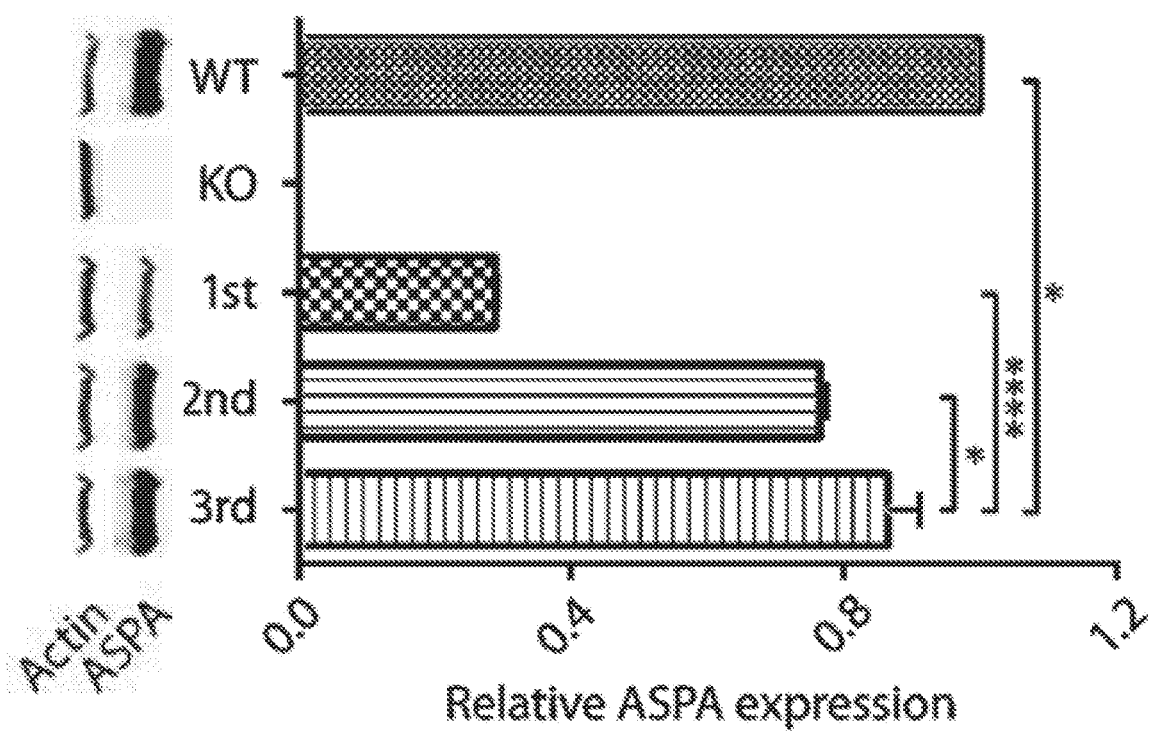
Figure 26C:
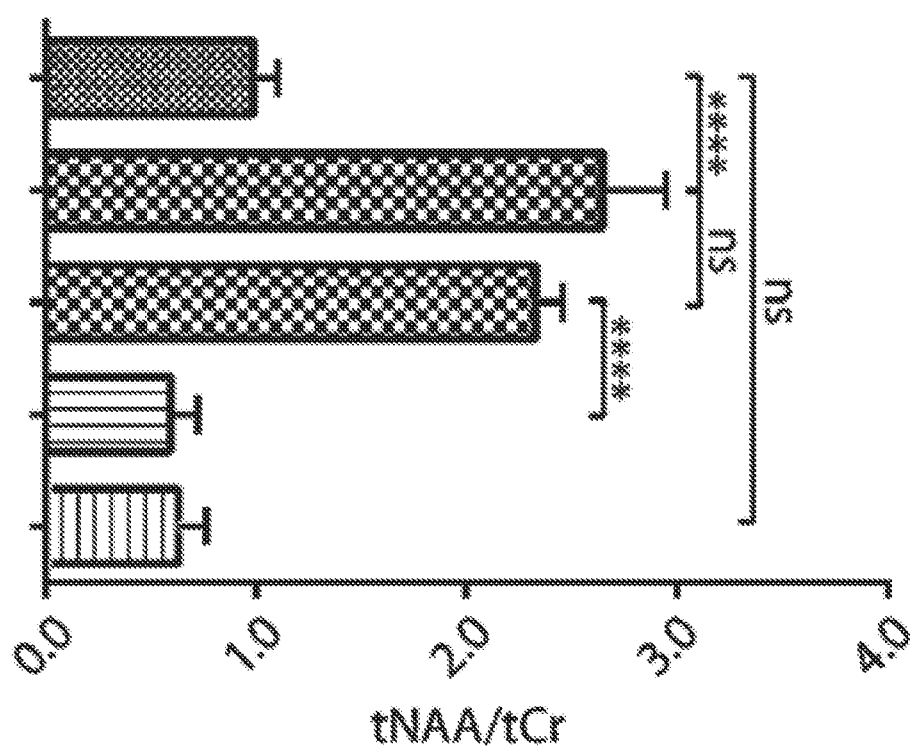
Figure 27:
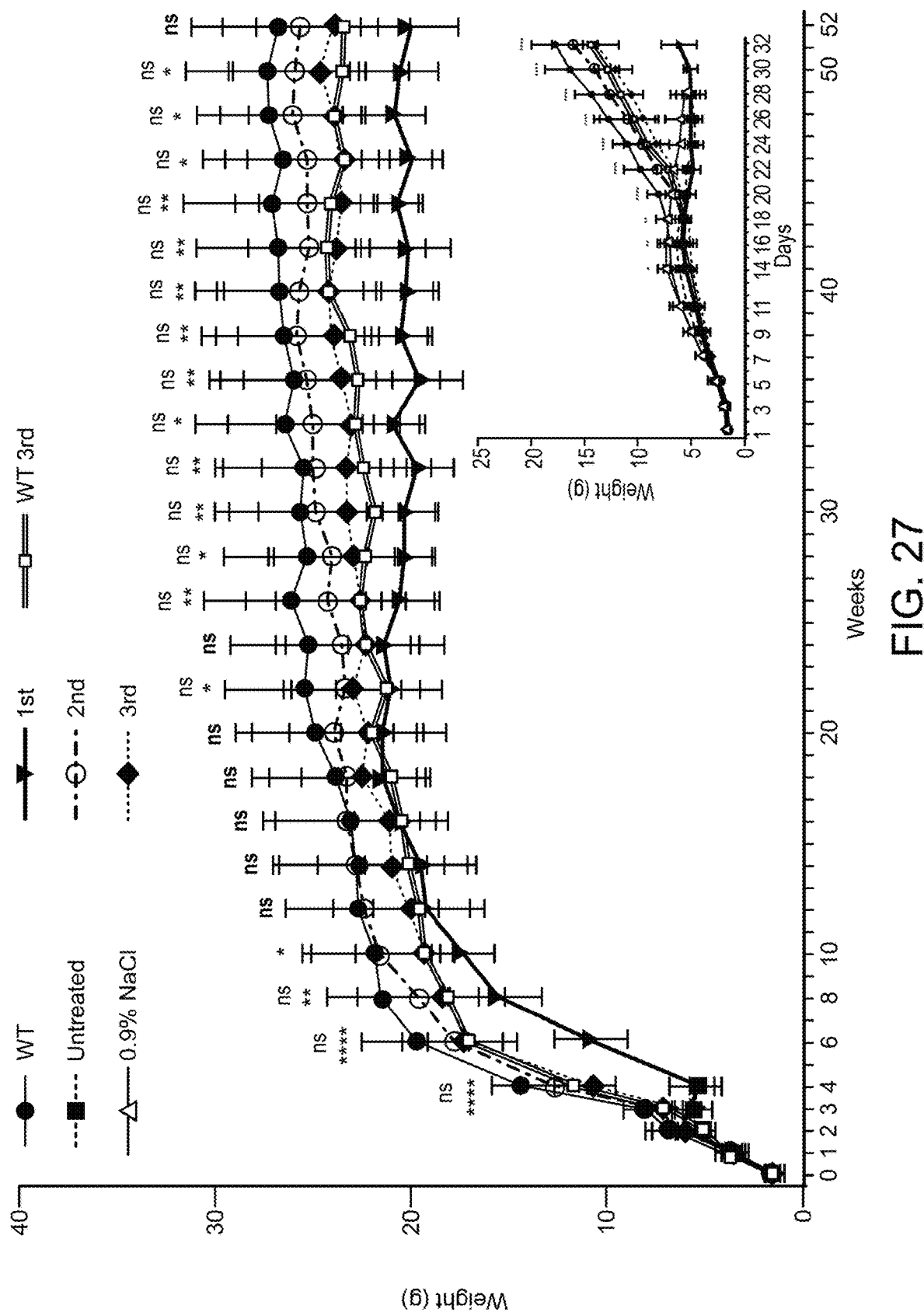
FIG. 27 shows weights of full-dose treatment groups comparing $1^{st}$, $2^{nd}$, and $3^{rd}$ generation gene replacement therapy. Mice were treated at p1 with $4 \times 10^{11}$ GC of the three different generation vectors. Weights were taken every other day for the first 32 days and biweekly afterwards (n=10 each). Error bars indicate mean±SD; * $p<0.05$; ** $p<0.01$; ns=non-significant.
Figure 28:
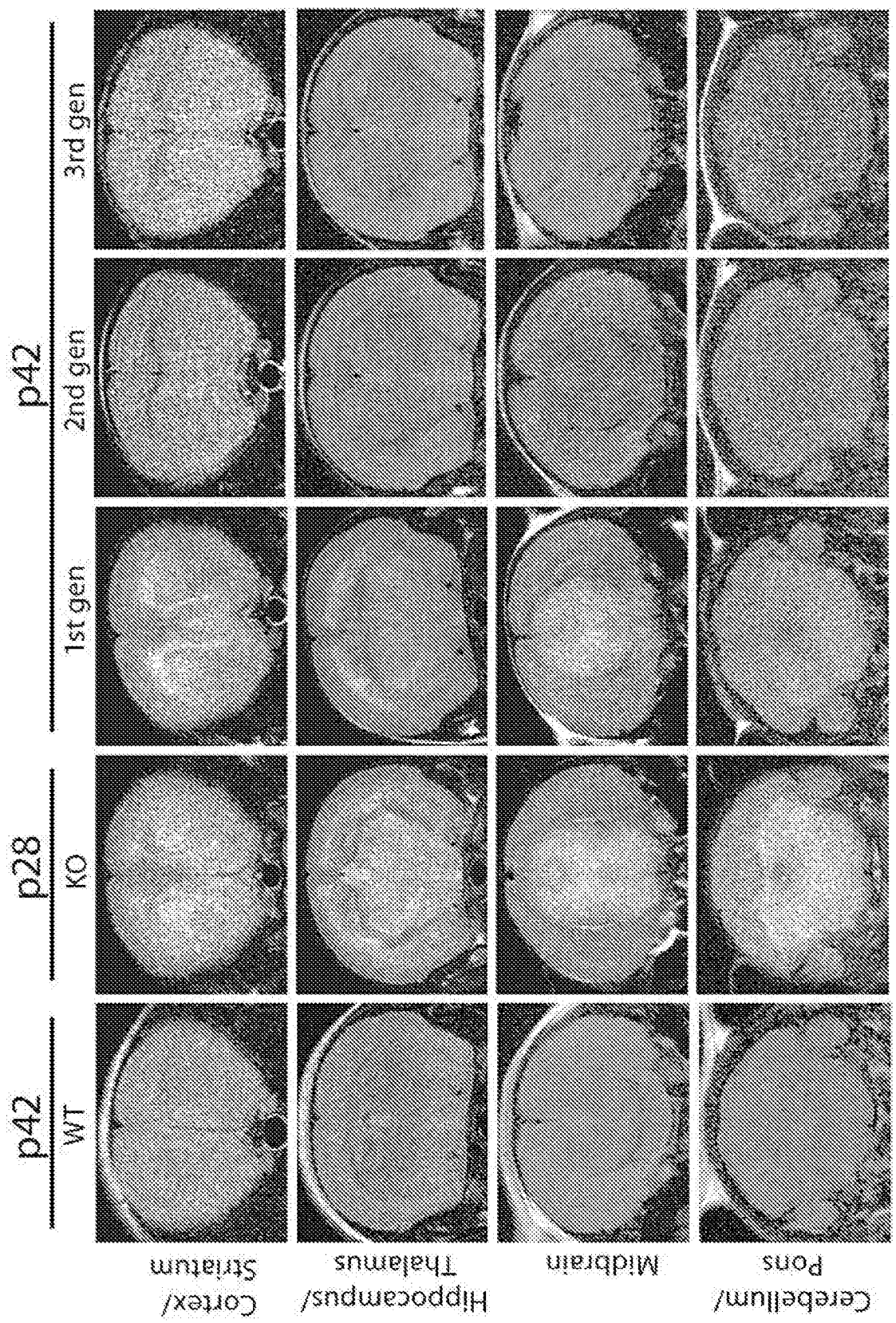
FIG. 28 shows magnetic resonance imaging (MRI) T2 sequence at p28/42. Mice treated at p1 with either $1^{st}$, $2^{nd}$, or $3^{rd}$ generation gene therapy were imaged by MRI (n=3 per group). Shown is the T2 sequence, which emphasizes signals derived from water. Treated and wild-type (WT) mice were imaged at p42. Due to early lethality, untreated (knock-out; KO) mice were imaged at p28. KO mice display strong hyperintensity (white signals) in striatum, cortex, thalamus, midbrain, and cerebellum/pons. A gradual reduction of hyperintense signals can be seen in the different treatment groups. $3^{rd}$ generation treated mice show the same signal pattern as WT mice, indicating reversal of MRI T2 pathologic signals.
Figure 29:
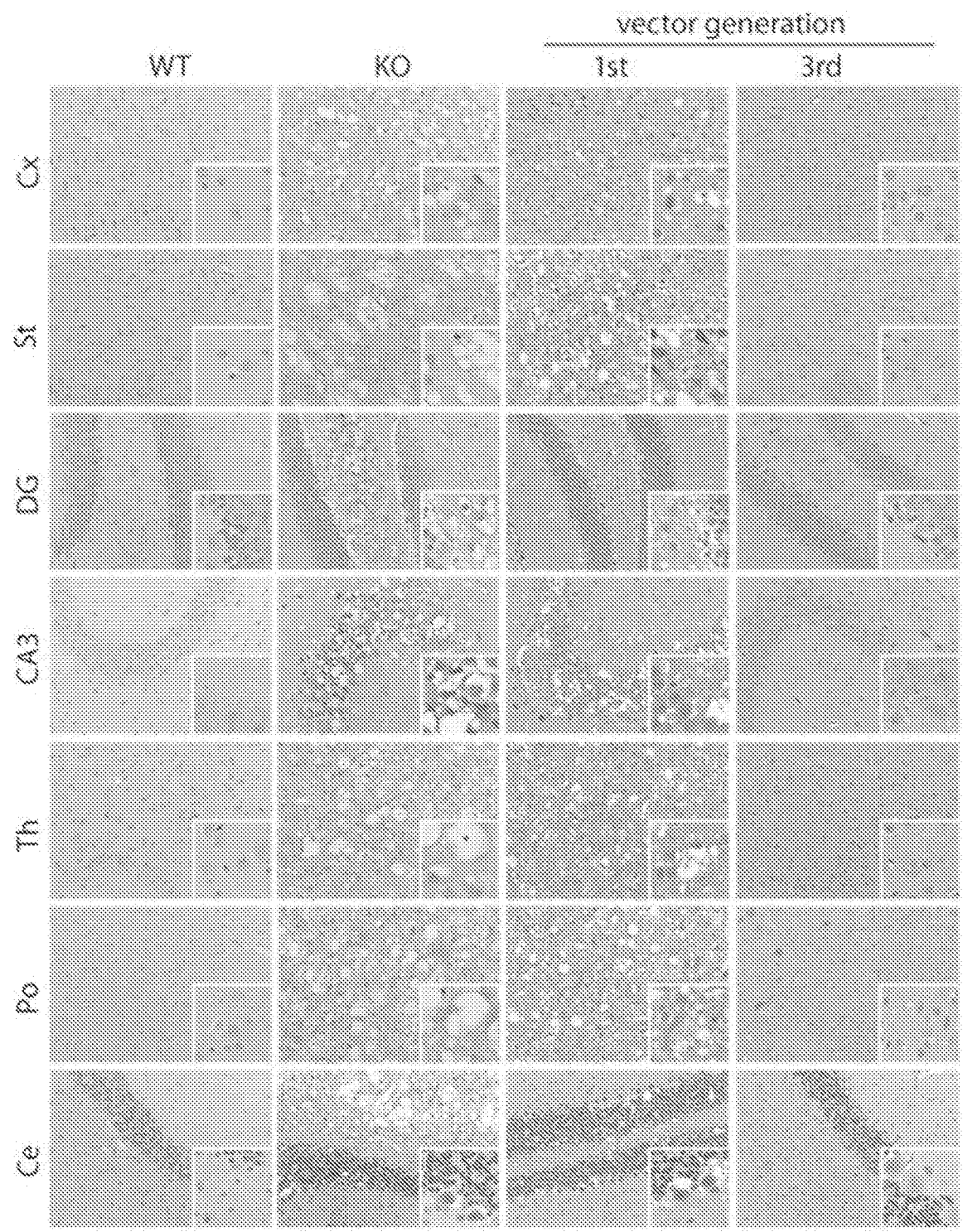
FIG. 29 shows treatment of CD KO mice with $3^{rd}$ generation gene therapy leads to rescue of neuropathology at p25. Mice (n=3 per group) were treated at P1 with $4 \times 10^{11}$ GC via facial vein and sacrificed at p25 for neuropathology. Untreated (KO) mice show extensive vacuolization across the brain. $1^{st}$ generation treated mice show less vacuole formation, but still display substantial defects. $3^{rd}$ generation treated mice are indistinguishable from wild-type (WT). Cx=cortex; St=striatum; DG=dentate gyrus; CA3=cornu ammonis 3; Th=thalamus; Po=pons; Ce=cerebellum. Images are ×10, insets are ×40.

Transgene Cassette Optimization Achieves a Rapid Therapeutic Response in Canavan Mice To overcome the challenge of efficacy and sustainability of a $1^{st}$ generation gene therapy, hASPA expression from the vector genome was increased without changing the parameters of administration route, vector dose, or serotype. Comparing the effect of Kozak sequence and cDNA optimization, two new expression cassettes with either a half or full Kozak sequence and a codon-optimized cDNA were designed and named $2^{nd}$ and $3^{rd}$ generation vectors (FIG. 26A; hereafter referred to as $2^{nd}$ or $3^{rd}$ generation), respectively. In order to test the translatability in vivo, each of the expression cassettes was packaged into the highly CNS-tropic rAAV9 vector for intravenous gene delivery to the CNS. Untreated and $1^{st}$ generation treated mice displayed the characteristic low weight at around p14-16 (FIG. 27). However, $2^{nd}$ and $3^{rd}$ generation treated mice (n=10 each) paralleled wild-type (WT) weight gain, indicating a more rapid onset of therapeutic transgene expression levels (FIG. 27). To evaluate neuropathology in the living mice, MRI was performed at p42 for treated and p28 for untreated animals. While untreated and $1^{st}$ generation treated mice showed strong hyperintense signals (white signals) on T2 sequence, particularly in deeper brain regions, the signals appeared isotense (unremarkable) in the $2^{nd}$ and $3^{rd}$ generation vector treated groups (FIG. 28), indicating normalization of brain edema. This therapeutic effect was corroborated by normalized NAA levels in the $2^{nd}$ and $3^{rd}$ generation treatment groups on MRS, which also coincided with ASPA protein expression levels (FIGS. 26B-26C). Finally, mice were assessed for neurohistopathology at p25. Again, the $1^{st}$ generation treated mice still showed vacuolization of the CNS, although to a lesser extent than untreated mice. In contrast, $2^{nd}$ and $3^{rd}$ generation treated mouse brains were indistinguishable from WT, demonstrating that the improved gene therapy effectively mitigates neuropathology (FIG. 29).

$3^{rd}$ Generation Treated Canavan Mice Sustainably Outperform Control Animals

Figure 30A:
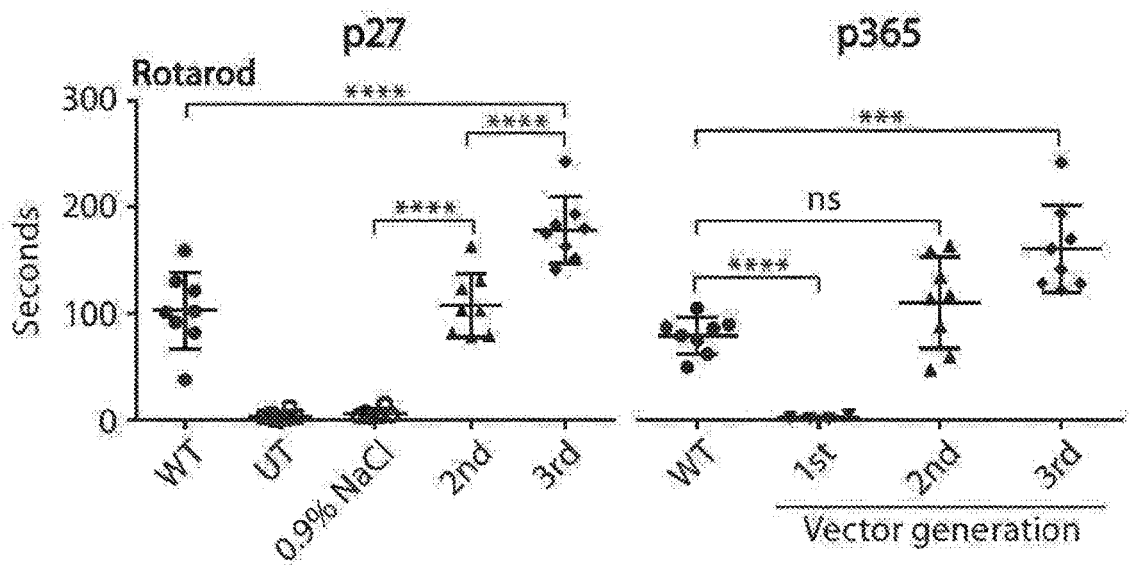
FIGS. 30A-30C show optimized gene replacement therapy normalizes motor function in CD KO mice. Each assay was performed with an independent group of CD KO mice. Mice were treated at p1 with $4\times10^{11}$ GC into the facial vein using the $2^{nd}$ or $3^{rd}$ generation gene therapy (total n=24 per vector group). Shown are testing time points at p27 and p365.
Figure 30B:
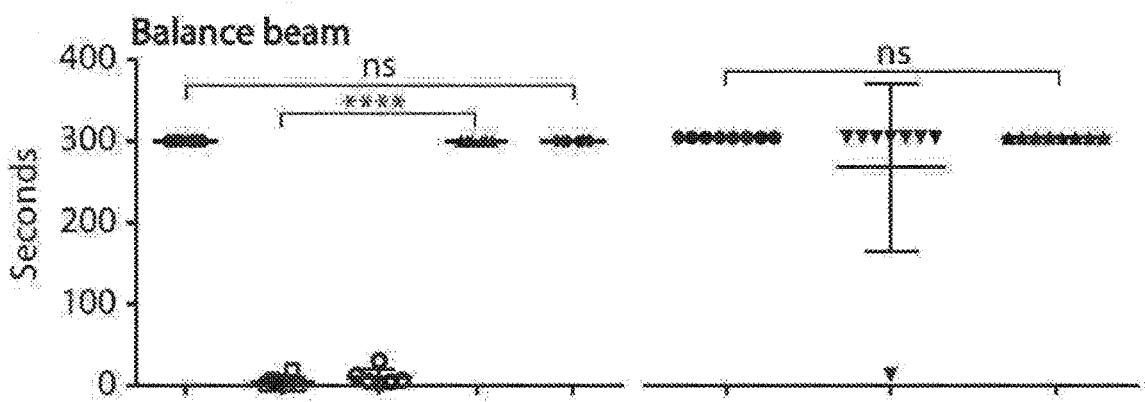
Figure 30C:
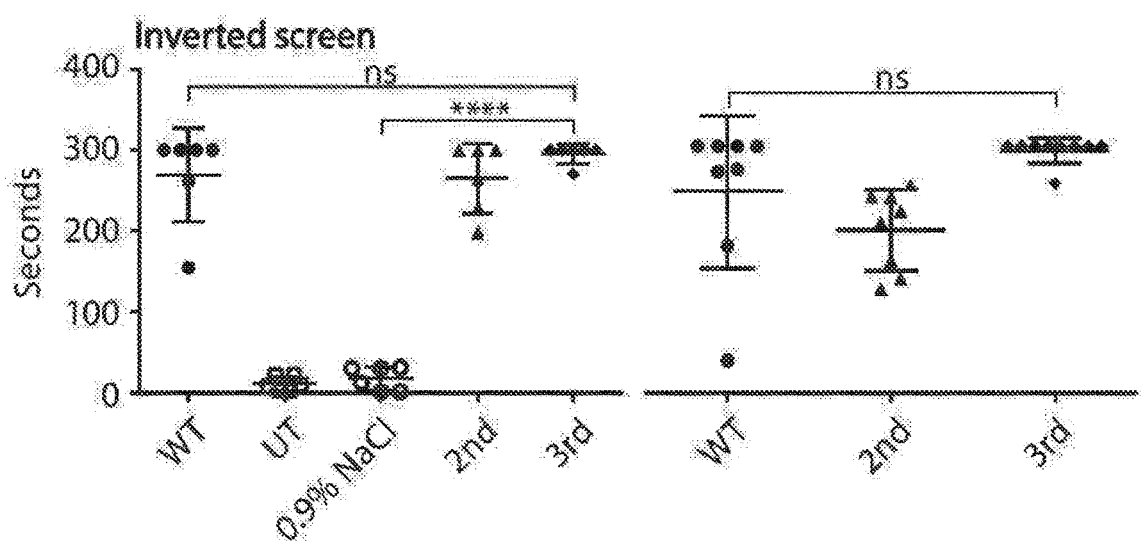
Figure 31:
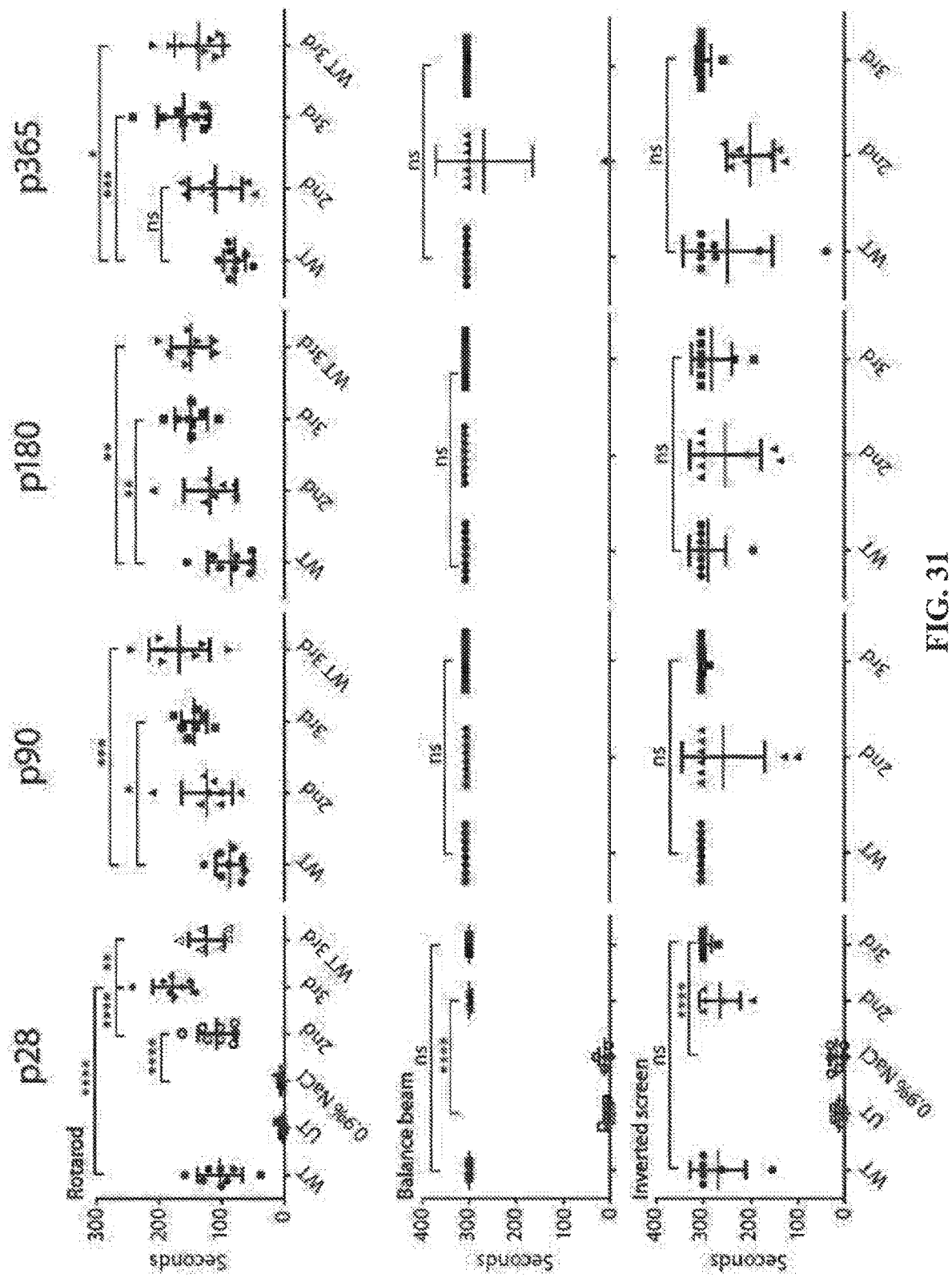
FIG. 31 shows treatment of CD KO mice with $2^{nd}$ or $3^{rd}$ generation gene therapy rescues motor function at p27, p90, p180, and p365. Mice treated at p1 with $4\times10^{11}$ GC by facial vein delivery of $2^{nd}$ or $3^{rd}$ generation gene therapy were tested on rotarod, balance beam, and inverted screen over the course of 1 year. All four testing time points are shown, demonstrating rescue of the motor function phenotype. Error bars indicate mean±SD; n=6-8; * $p<0.05$;  $p<0.01$; * $p<0.001$; **** $p<0.0001$; ns=non-significant.
Figure 32:
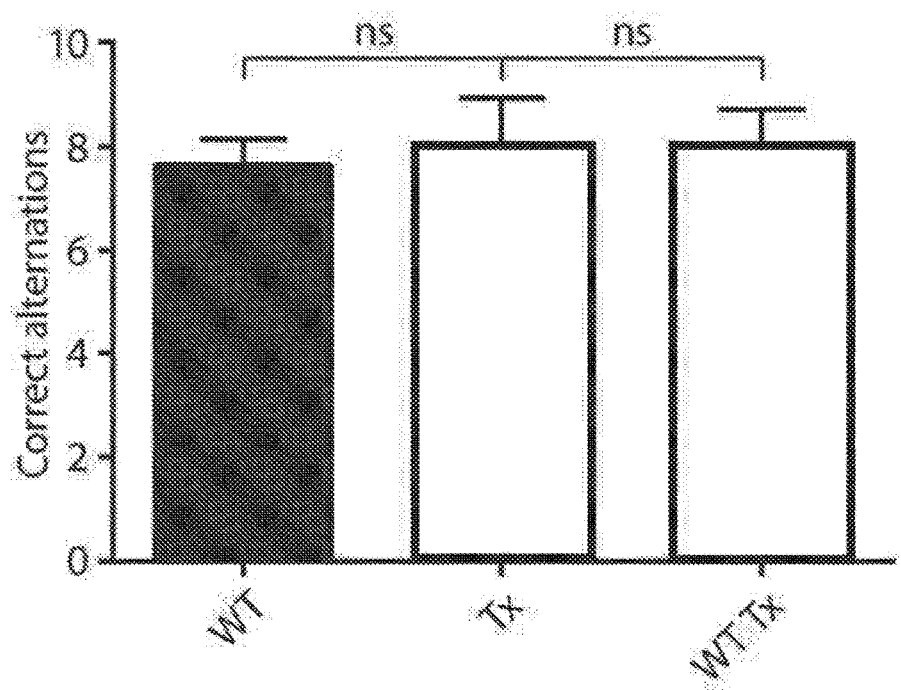
FIG. 32 shows data for the T maze at 1 year. P1 treated CD KO mice and WT mice were tested on T maze for spatial/working memory and compared to untreated WT mice. Each mouse was tested 11 times with 20 seconds retention time between each run. Error bars indicate mean±SD; n=6-8; ns=not significant.

CD KO mice recapitulate the clinical phenotype of Canavan patients, presenting with ataxia, dysbalance, muscle weakness, and cognitive impairment within the first month of life. It was observed that at 1 month of age, $2^{nd}$ generation treated CD mice performed as well as WT controls on accelerated rotarod (FIG. 30A). The $3^{rd}$ generation treatment group displayed a "supermouse" phenotype, significantly outperforming WT mice for the entire 1 year duration of the study (FIG. 30A and FIG. 31). In order to assess ataxia and the ability to balance, $2^{nd}$ and $3^{rd}$ generation treated mice were evaluated on balance beam, showing full recovery as well (FIG. 30B and FIG. 31). This was paralleled by the performance on inverted screen and was persistent throughout the study (FIG. 30C and FIG. 31). Finally, to determine the long-term ability to rescue spatial/working memory, mice were tested on T maze at 1 year, performing as well as WT control mice (FIG. 32).

Figure 33A:
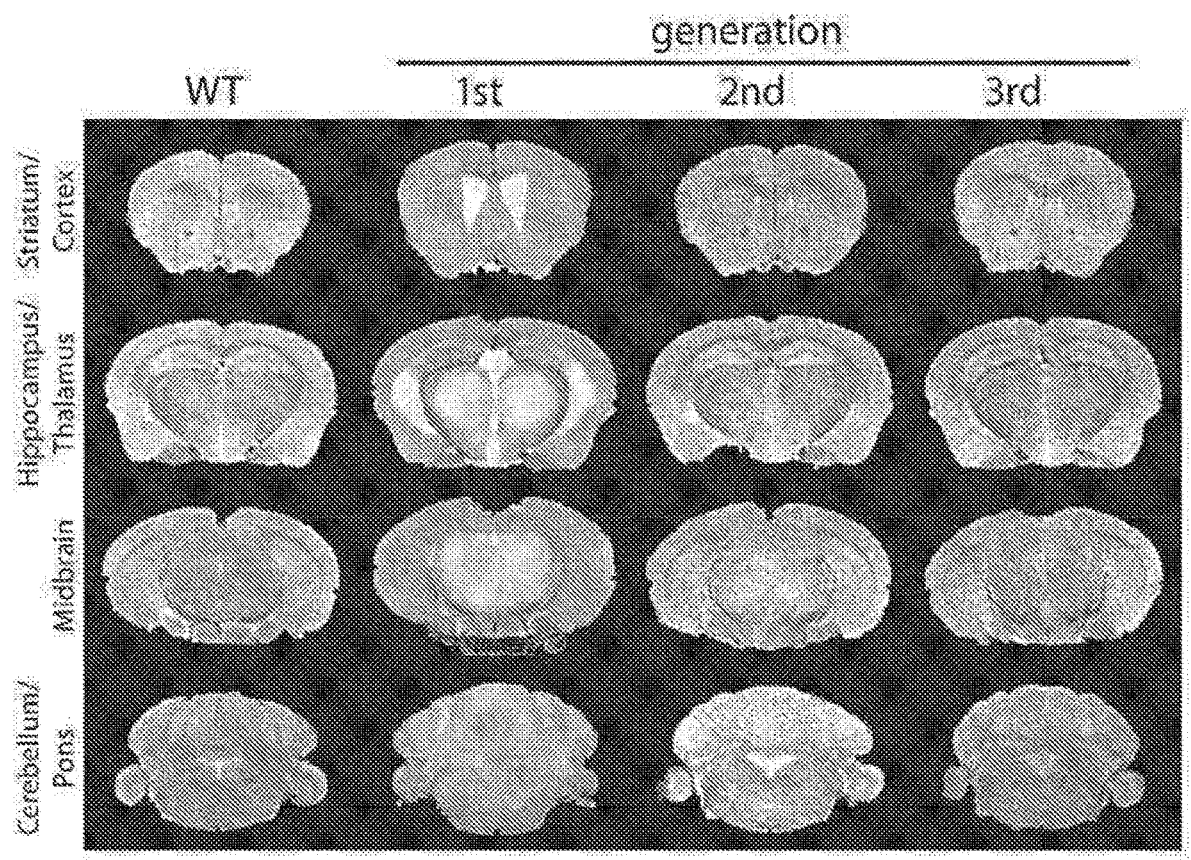
FIGS. 33A-33D show optimized gene replacement therapy leads to sustained rescue of neuropathology and biomarker expression. Mice were treated at p1 intravenously with $4\times10^{11}$ GC of $1^{st}$, $2^{nd}$, or $3^{rd}$ generation vector. Data from 1 year after treatment are shown in comparison to wild-type (WT).
Figure 33B:
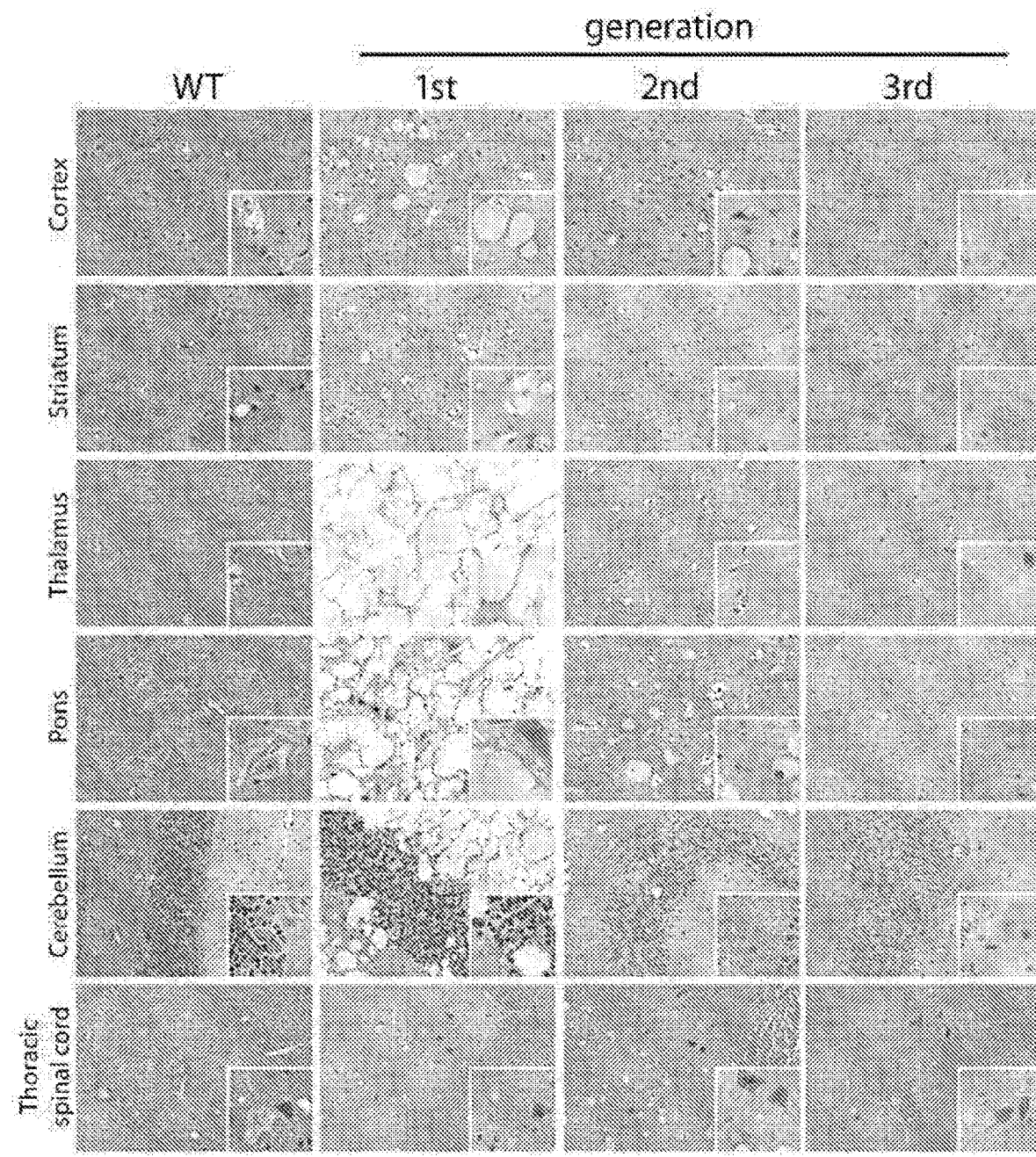
Figure 33C:
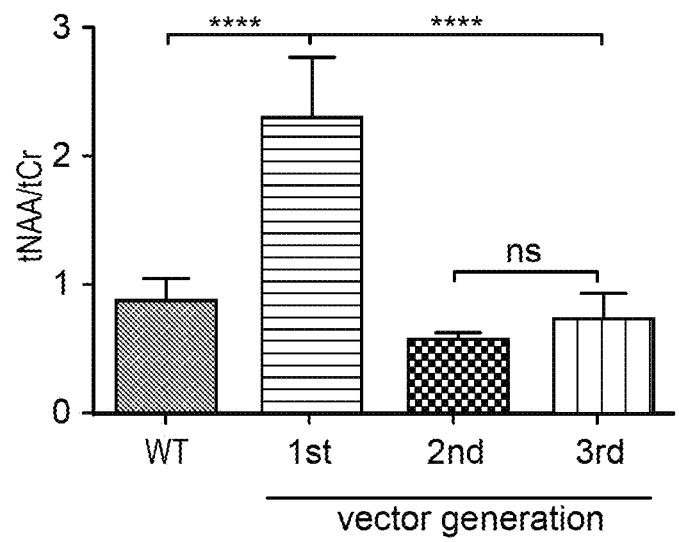
Figure 33D:
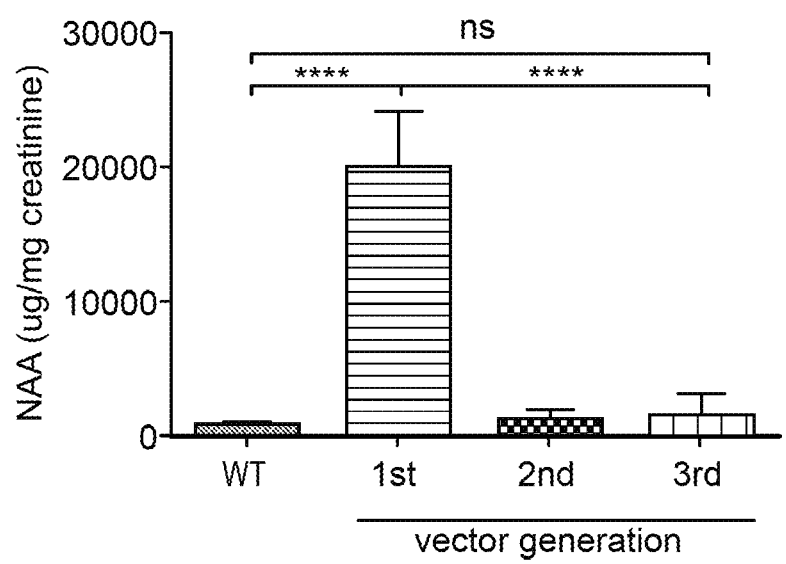
Figure 34:
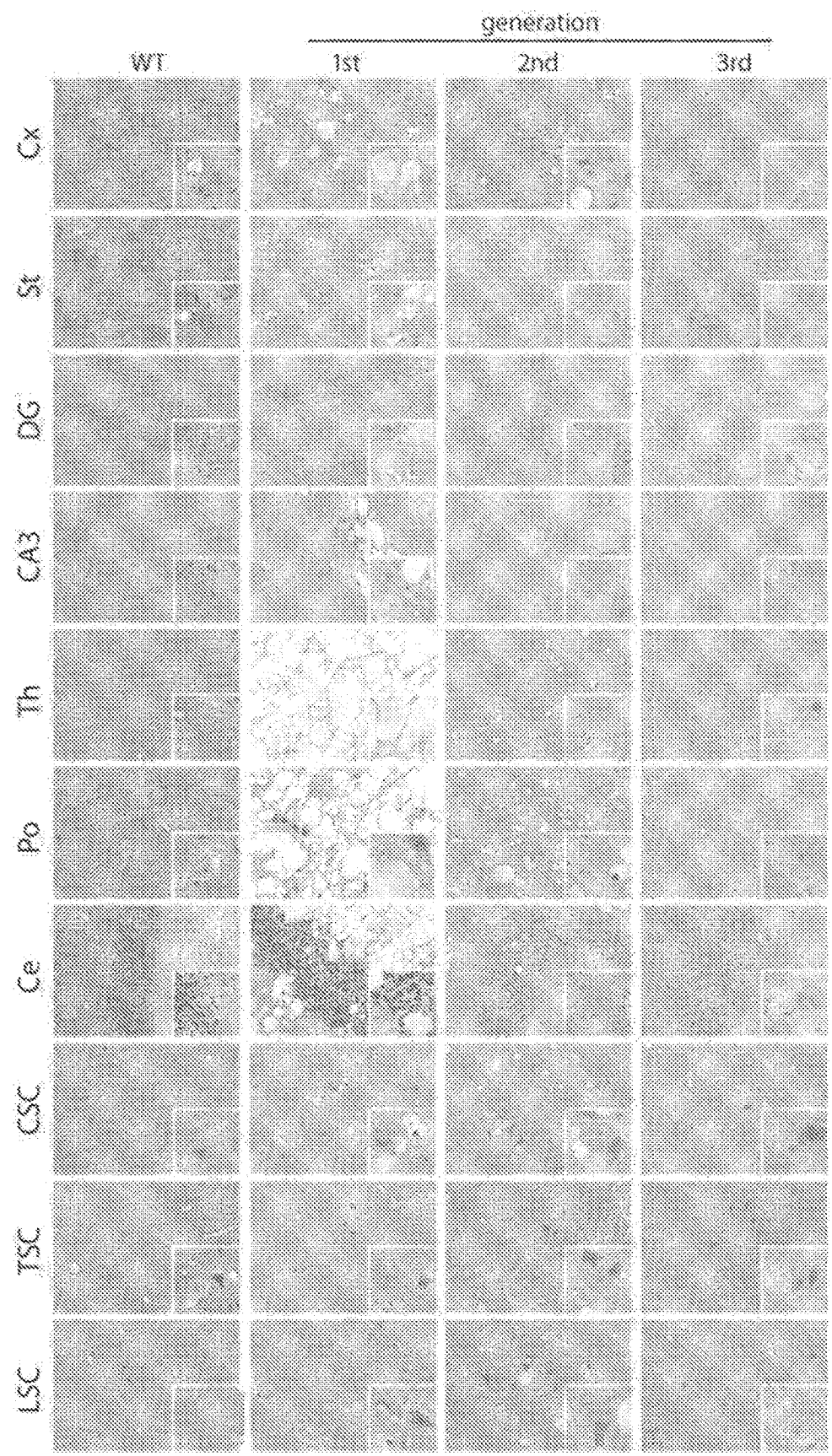
FIG. 34 shows treatment of CD KO mice with $3^{rd}$ generation gene therapy leads to sustained rescue of neuropathology at 1 year of age. Mice were treated with $4\times10^{11}$ GC of $1^{st}$, $2^{nd}$, or $3^{rd}$ generation gene therapy. Mice were sacrificed at 1 year of age and subjected to H&E staining. Shown are 10× images with 40× insets. Cx=cortex, St=striatum, DG=dentate gyrus, CA3=cornu ammonis 3, Th=thalamus, Po=pons, Ce=cerebellum, CSC=cervical spinal cord, TSC=thoracic spinal cord, LSC=lumbar spinal cord.

Efficient hASPA Gene Delivery to the CNS Persistently Eliminates Neuropathology and Normalizes NAA Levels To determine if the phenotypic rescue of psychomotor function was supported by brain pathology and NAA biomarker levels, living mice from all three treatment groups were assessed at 1 year of age. First, T2 MRI showed strong hyperintensities of $1^{st}$ generation treated mice, particularly in the thalamus, midbrain, and cerebellum (FIG. 33A). In contrast, $2^{nd}$ generation treated mice showed mild increased T2 signals in the midbrain, appearing otherwise similar to WT mice. Importantly, comparison between WT and $3^{rd}$ generation treated mice revealed no difference on T2 MRI, which was also supported by neuropathology analysis (FIG. 33B). While some regions of the CNS (e.g., thoracic spinal cord) showed similar patterns between WT and all three treatment groups, the brain regions with the strongest T2 signal also corresponded with the most severe vacuolization in the brain sections of $1^{st}$ generation treated mice (FIGS. 33A-33B and FIG. 34). When 1-year-old mice of all treatment groups were subjected to MRS for NAA quantification, $1^{st}$ generation treated mice showed a significantly higher NAA signal than WT mice, while NAA levels of $2^{nd}$ and $3^{rd}$ generation treated mice were normalized (FIG. 33C). This strongly indicates that the new generation gene therapies are significantly more efficacious and are able to normalize NAA biomarker levels, a finding which is further supported by normalized NAA levels in urine, as measured by mass spectrometry (FIG. 33D).

Astrocyte-Specific ASPA Expression is Sufficient for Generating the "Super-Mouse Phenotype"

Figure 35:
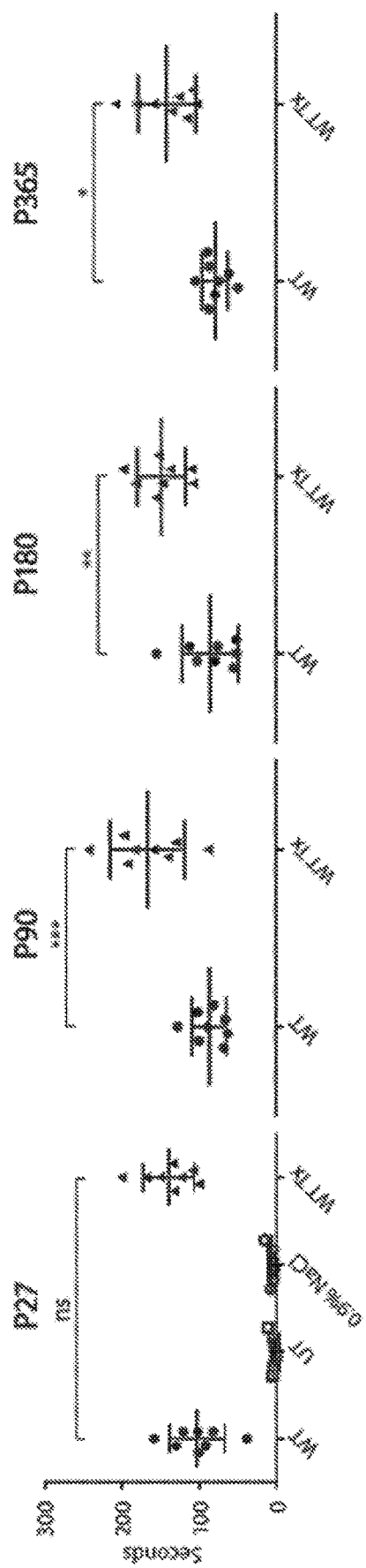
FIG. 35 shows rotarod comparing wild-type versus treated wild-type mice. Mice were treated at p1 intravenously with $4\times10^{11}$ GC of $3^{rd}$ generation gene therapy. Shown are testing time-points p27, p90, p180, and p365. Error bars indicate mean±SD; n=8; * $p<0.05$;  $p<0.01$; * $p<0.001$; **** $p<0.0001$; ns=non-significant

The way in which the $3^{rd}$ generation gene therapy accomplished performance enhancement beyond WT control animals was investigated. No reported phenotypic differences were observed between patients who are heterozygous or homozygous for the WT ASPA allele, implying that oligodendroglial ASPA and its associated NAA catabolism might not cause dose-dependent behavioral variations within the physiological range. In addition, most rAAVs including rAAV9 poorly transduce oligodendrocytes. Thus, in some embodiments, hASPA transgene expression from non-oligodendrocyte glial cells contributes to the "super-mouse" phenomenon seen on accelerated rotarod. To test whether WT mice respond to ASPA supplementation with increased motor performance, WT animals were treated with $3^{rd}$ generation gene therapy. Initially, treated WT mice showed no difference on accelerated rotarod at p28, but began significantly outperforming untreated WT controls at p90 to 1 year of age, indicating that supplementing the non-ASPA-expressing cells with ASPA by gene transfer contributes to the observed "enhanced" phenotype (FIG. 35).

Figure 36A:
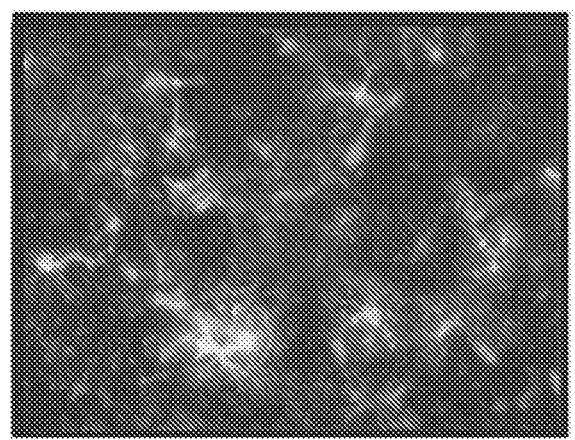
FIGS. 36A-36I show astrocyte-restricted hASPA expression rescues motor function, neuropathology, and biomarker expression in CD KO mice. Mice were treated intravenously at p1 with $4\times10^{11}$ GC of $3^{rd}$ generation gene therapy containing either a ubiquitous or a partial human glial fibrillary acid protein (phGFAP) promoter.
Figure 36B:
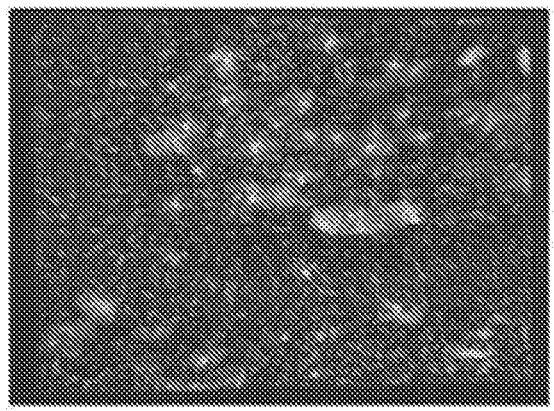
Figure 36C:
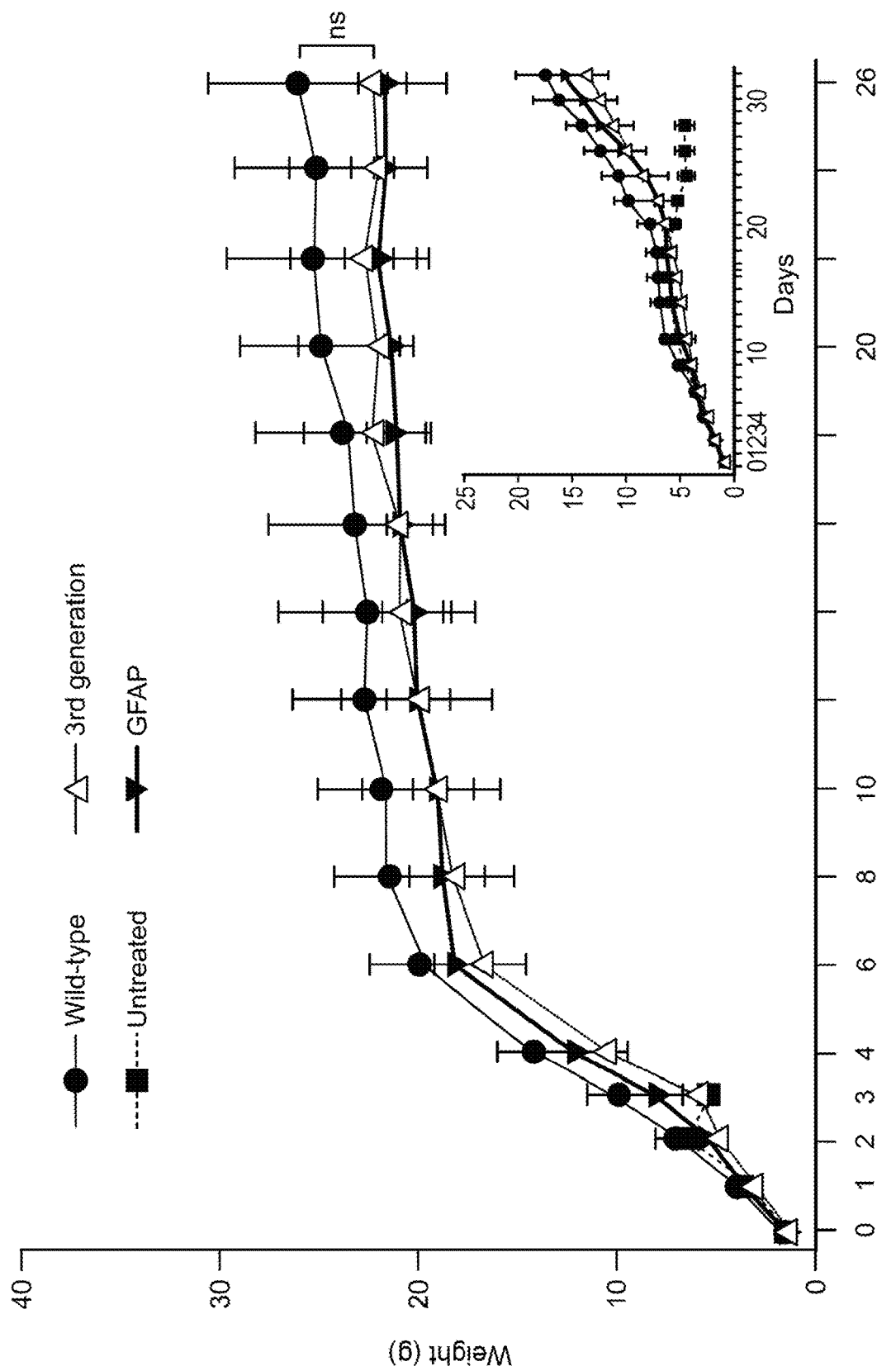
Figure 36D:
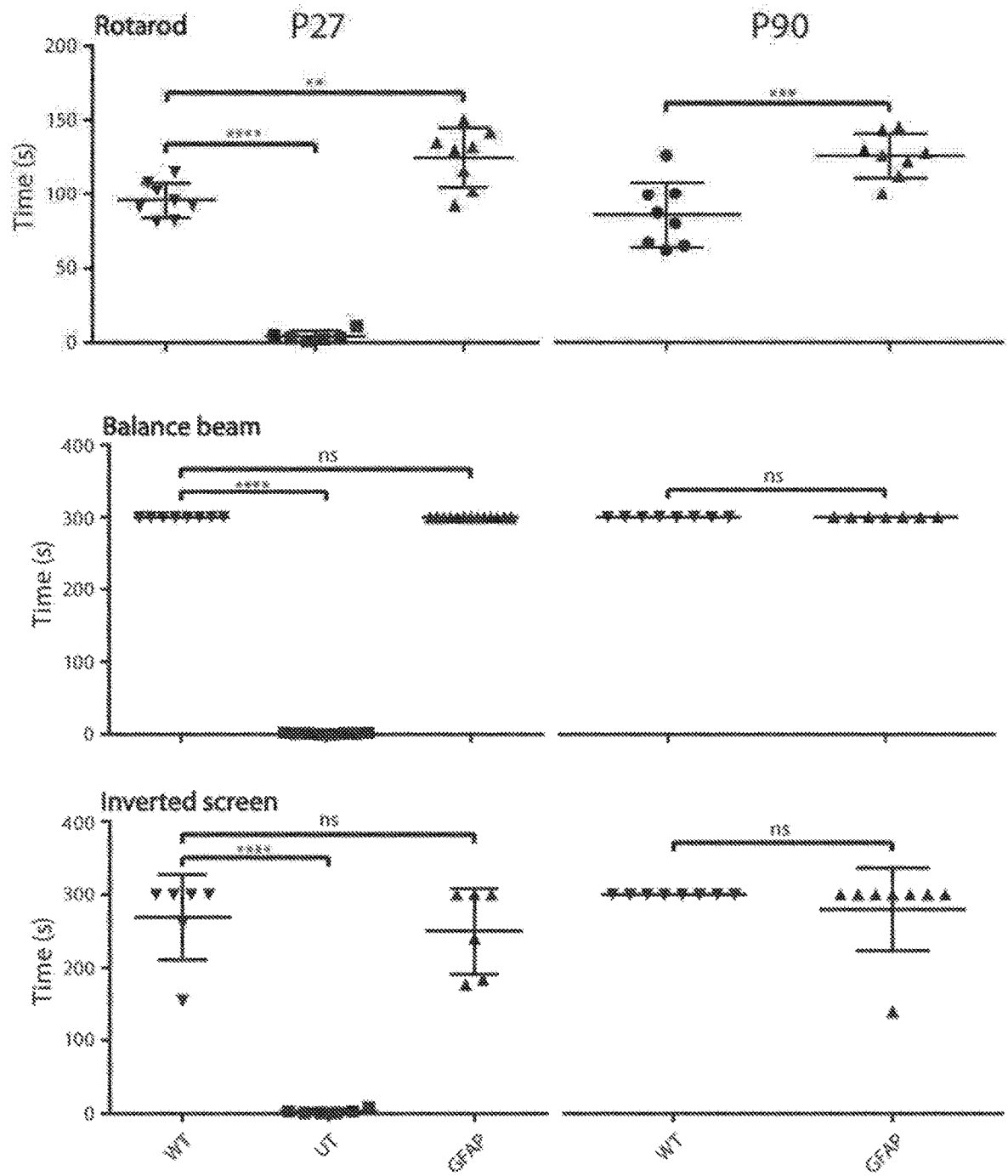
Figure 36E:
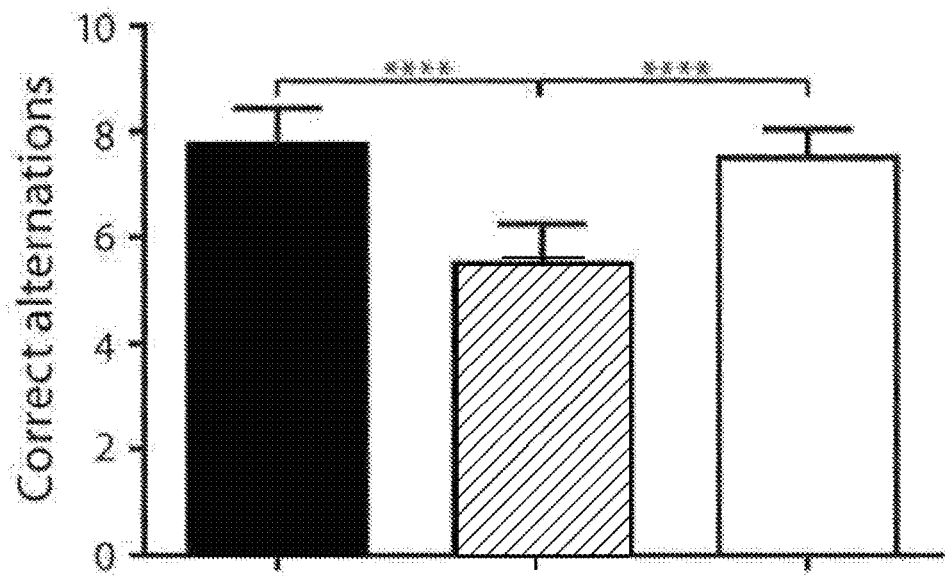
Figure 36F:
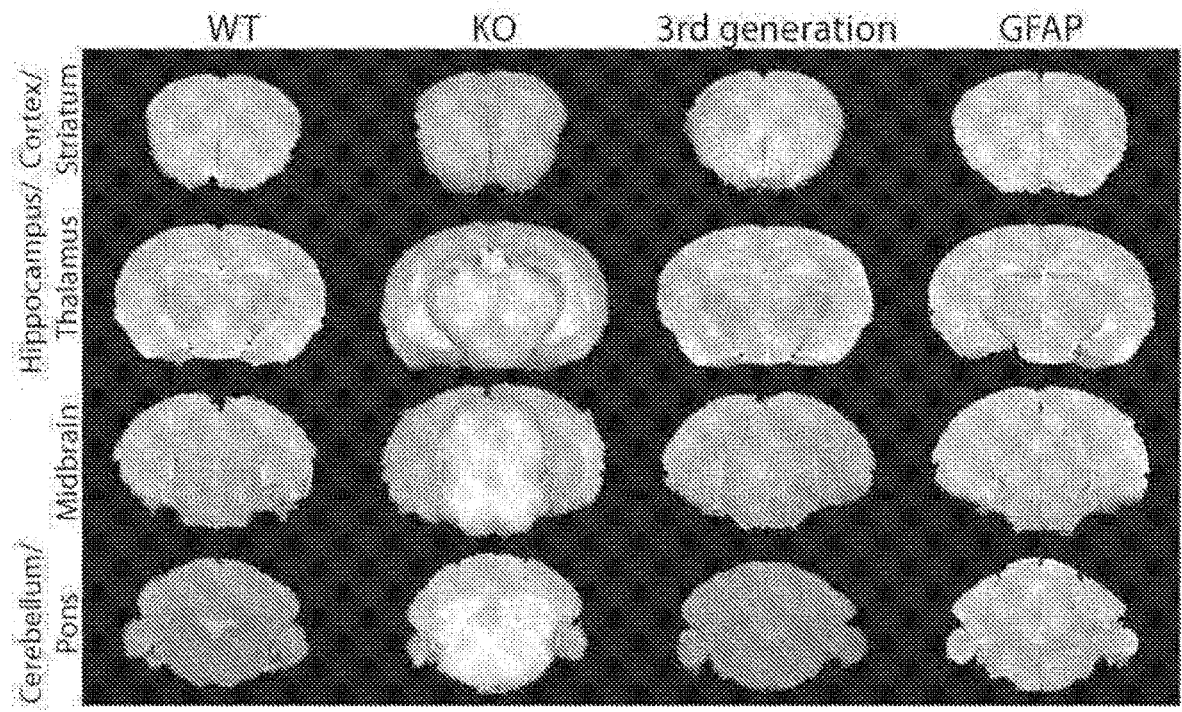
Figure 36G:
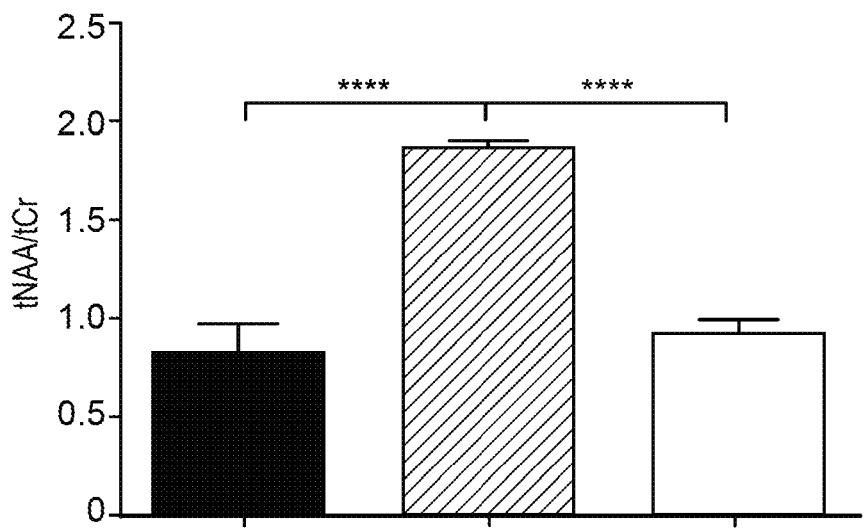
Figure 36H:
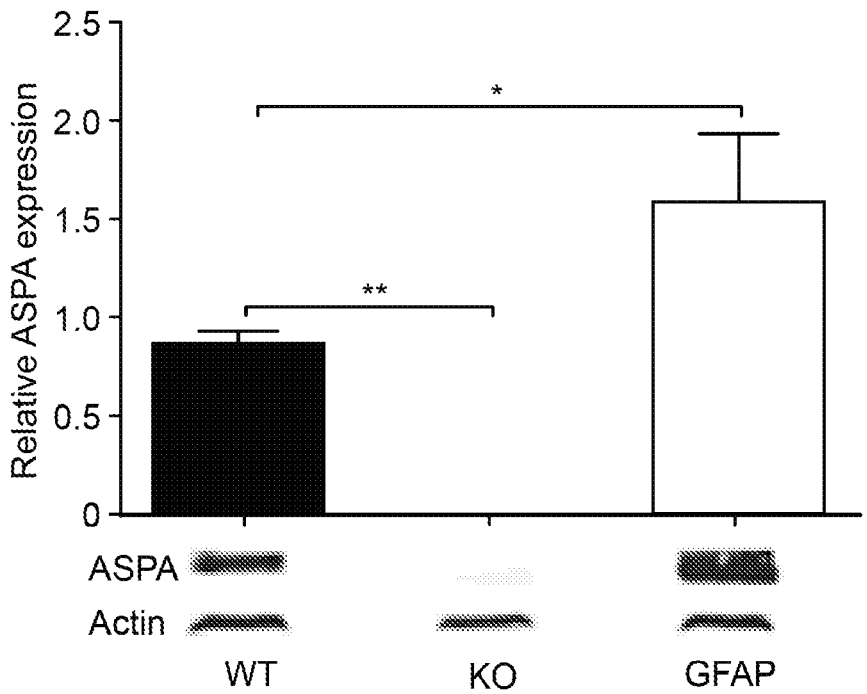
Figure 36I:
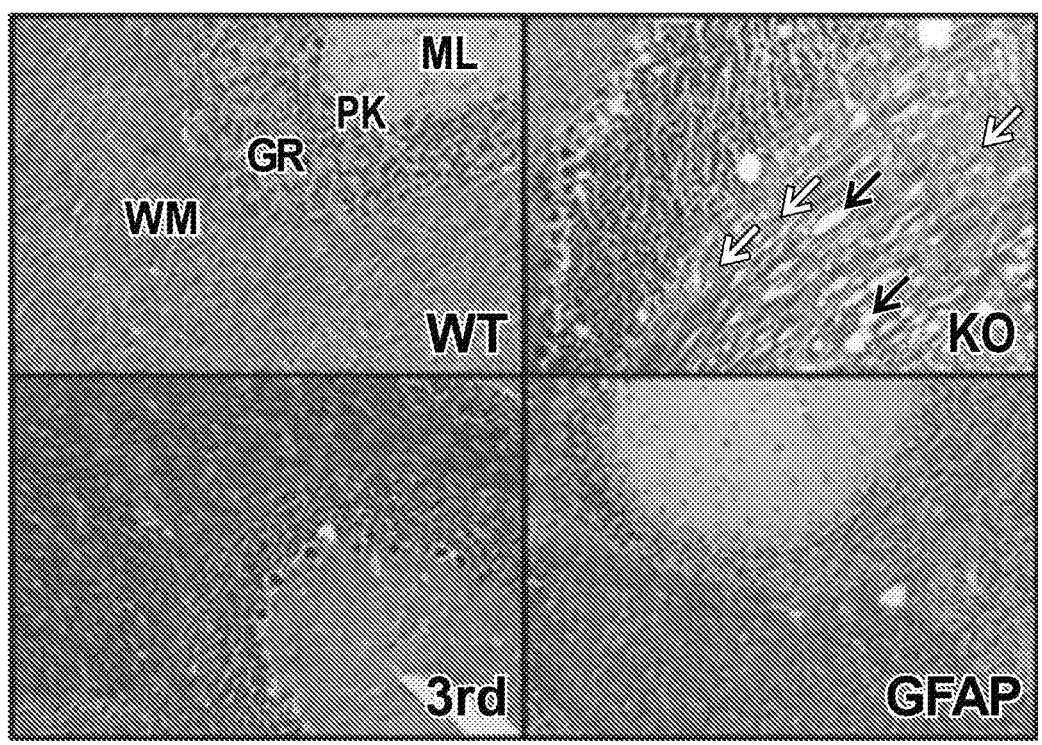

To further define the CNS cell type contributing to the "super-mouse" phenotype, the $3^{rd}$ generation hASPA construct was paired with a partial human glial fibrillary acidic protein (phGFAP) promoter. First, the astrocyte specificity of the phGFAP promoter was confirmed by expressing enhanced green fluorescent protein (EGFP), which showed co-localization with glial fibrillary acidic protein (GFAP) positive cells, but not with myelin basic protein (MBP) positive cells (FIGS. 36A-36B). Next, neonatal CD KO mice were treated with rAAVphGFAP-hASPA-Opt. Treated mice displayed the same growth curve as the group treated with ubiquitously expressed $3^{rd}$ generation gene therapy (FIG. 36C). The performance of these mice on accelerated rotarod was significantly increased over WT mice at all testing time points (e.g., p27 and p90), similar to what was seen with the $3^{rd}$ generation vector for ubiquitous hASPA expression (FIG. 36D). This data indicates that astrocyte-restricted hASPA expression contributes substantially to the enhanced performance on accelerated rotarod. It was observed that other less stringent motor function tests did not show a difference compared to WT mice (FIG. 36D). Importantly, rAAVphGFAP-hASPA-Opt treated mice performed better than untreated control mice on T maze, but showed no difference in spatial/working memory function vs. WT animals (FIG. 36E and FIG. 32). This indicates that mice with increased motor performance have normal spatial/working memory function on T maze testing. In addition, MRI and MRS showed normalization of T2 signals and NAA levels in the brains of mice receiving astrocyte-specific gene therapy (FIGS. 36E-36F), indicating that astrocyte-restricted hASPA expression alone is capable of creating an alternative metabolic sink for NAA and is rescuing neuropathology and biomarker expression in the CD mice. To corroborate that astrocyte-restricted hASPA expression can indeed rescue neuropathology, e.g., improve myelination, brain sections were stained with Luxol fast blue for myelin sheaths. The staining pattern was indistinguishable between WT, astrocyte-restricted, and ubiquitously expressed 3rd generation gene therapy treated animals, and in all cases myelination was recovered compared to untreated CD KO mice (FIG. 36I).

Figure 37:
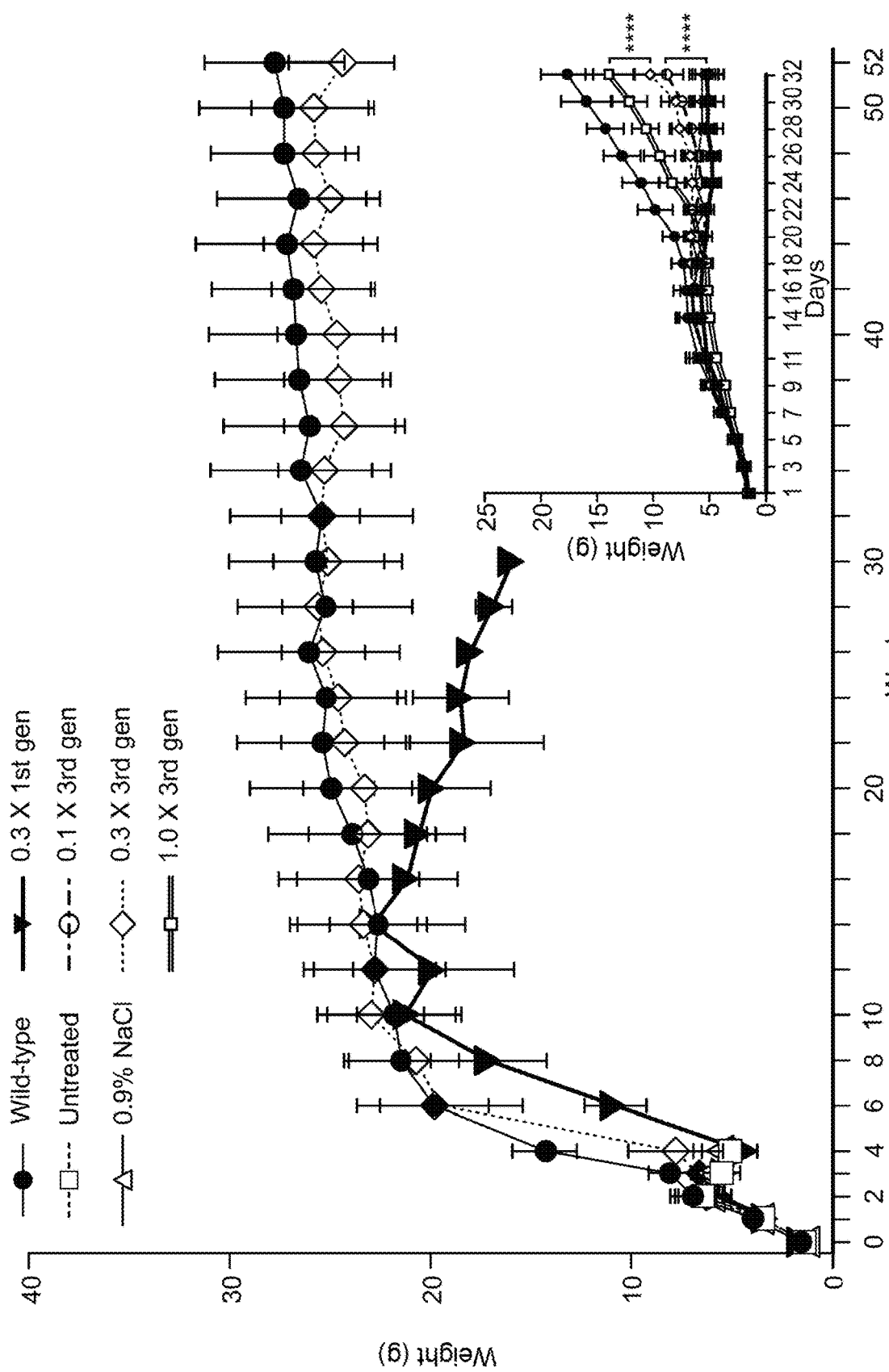
FIG. 37 shows rAAV dose-dependent weights. Shown are weights by day (inset) and week of CD KO mice treated at p1 with either full, 3- or 10-fold lower dose of the $3^{rd}$ generation gene therapy construct. For comparison, CD KO mice were treated with the $1^{st}$ generation gene therapy at 3-fold lower dose. Mice treated with 10-fold lower dose are only shown for the first four weeks. For weights by week of CD KO mice treated with full dose $3^{rd}$ generation, see FIG. 51. Error bars indicate mean±SD; n=8-10, except for $0.3\times1^{st}$ gen after 24 weeks because animals started to die; **** $p<0.0001$.
Figure 38A:
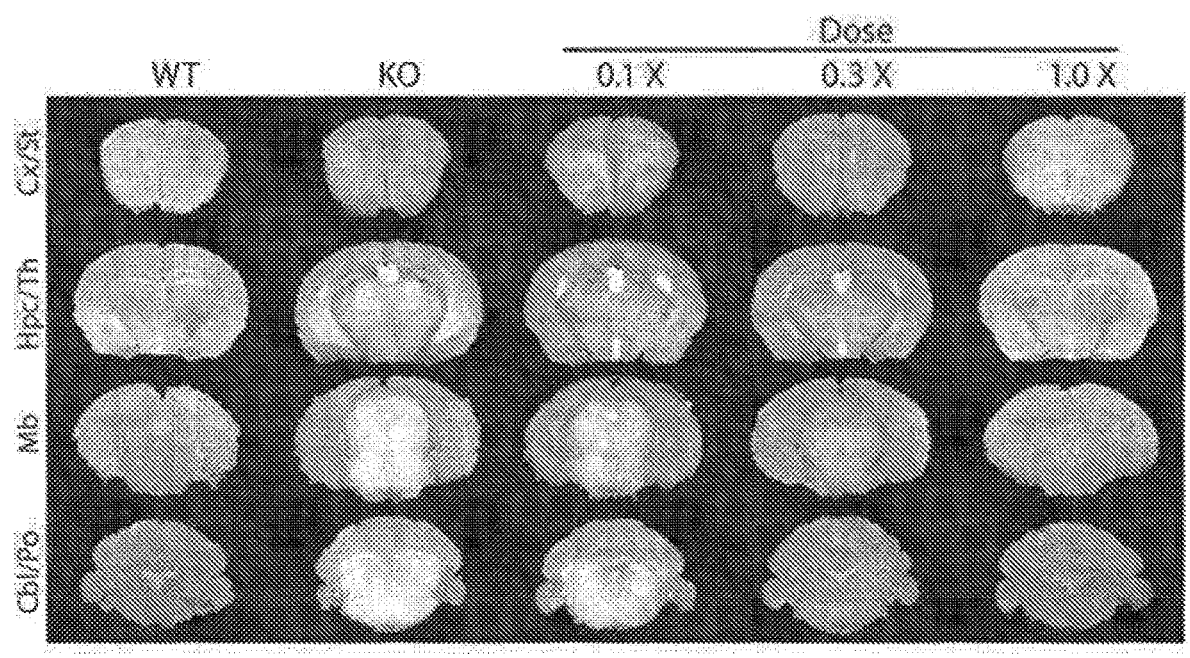
FIGS. 38A-38D show dose reduction of $3^{rd}$ generation therapy achieves efficacious disease rescue in CD KO mice. CD KO mice were treated at p1 via facial vein with either $4\times10^{10}$, $1.33\times10^{11}$, or $4\times10^{11}$ GC of $3^{rd}$ generation gene replacement therapy.
Figure 38B:
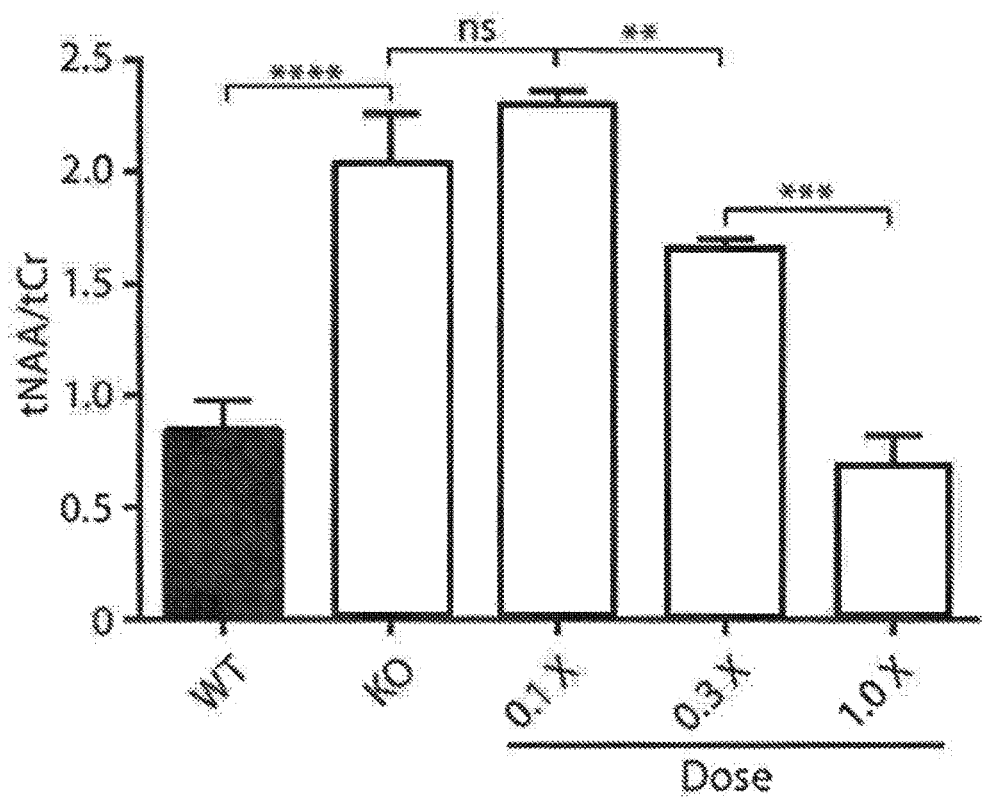
Figure 38C:
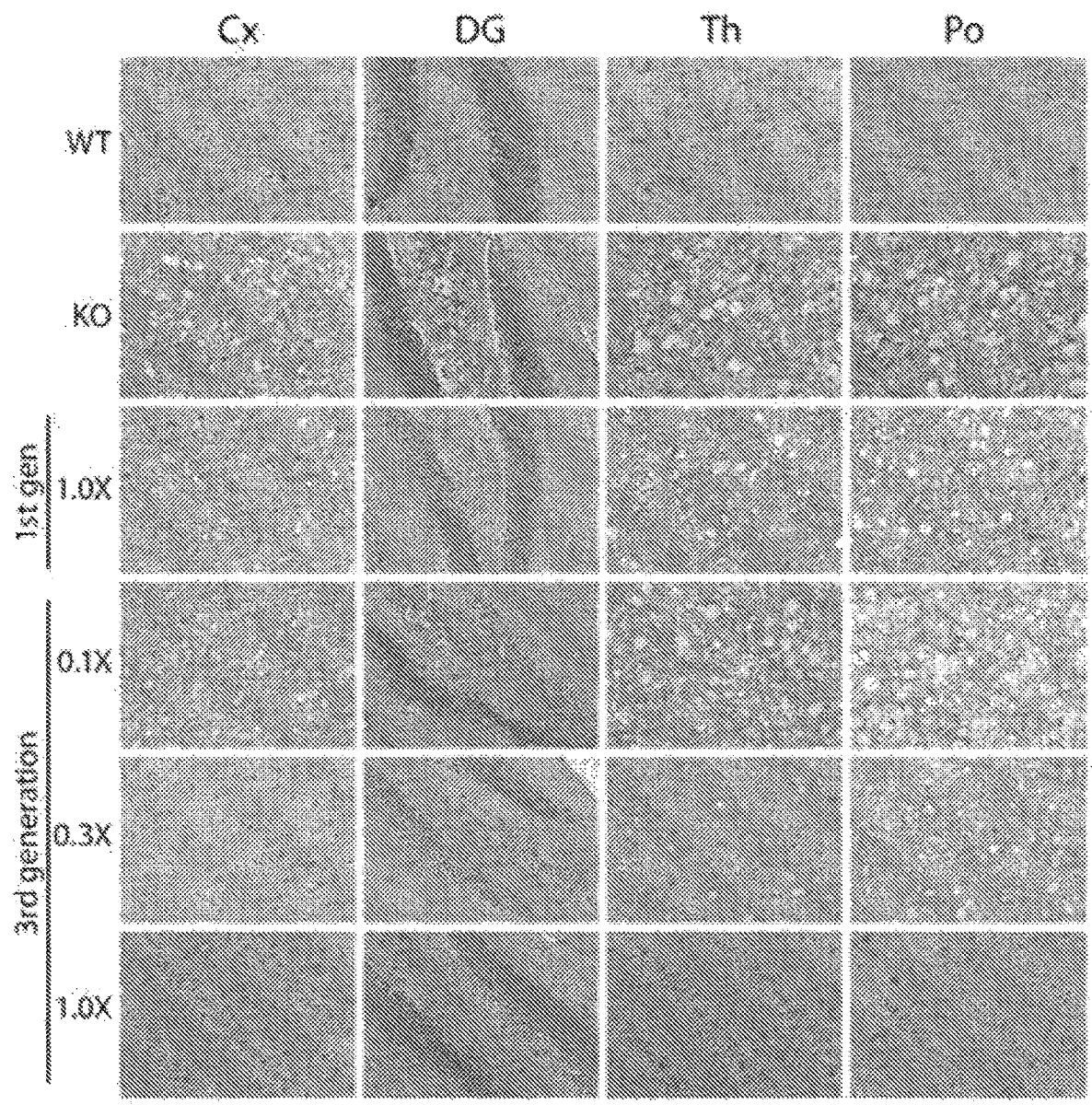
Figure 38D:
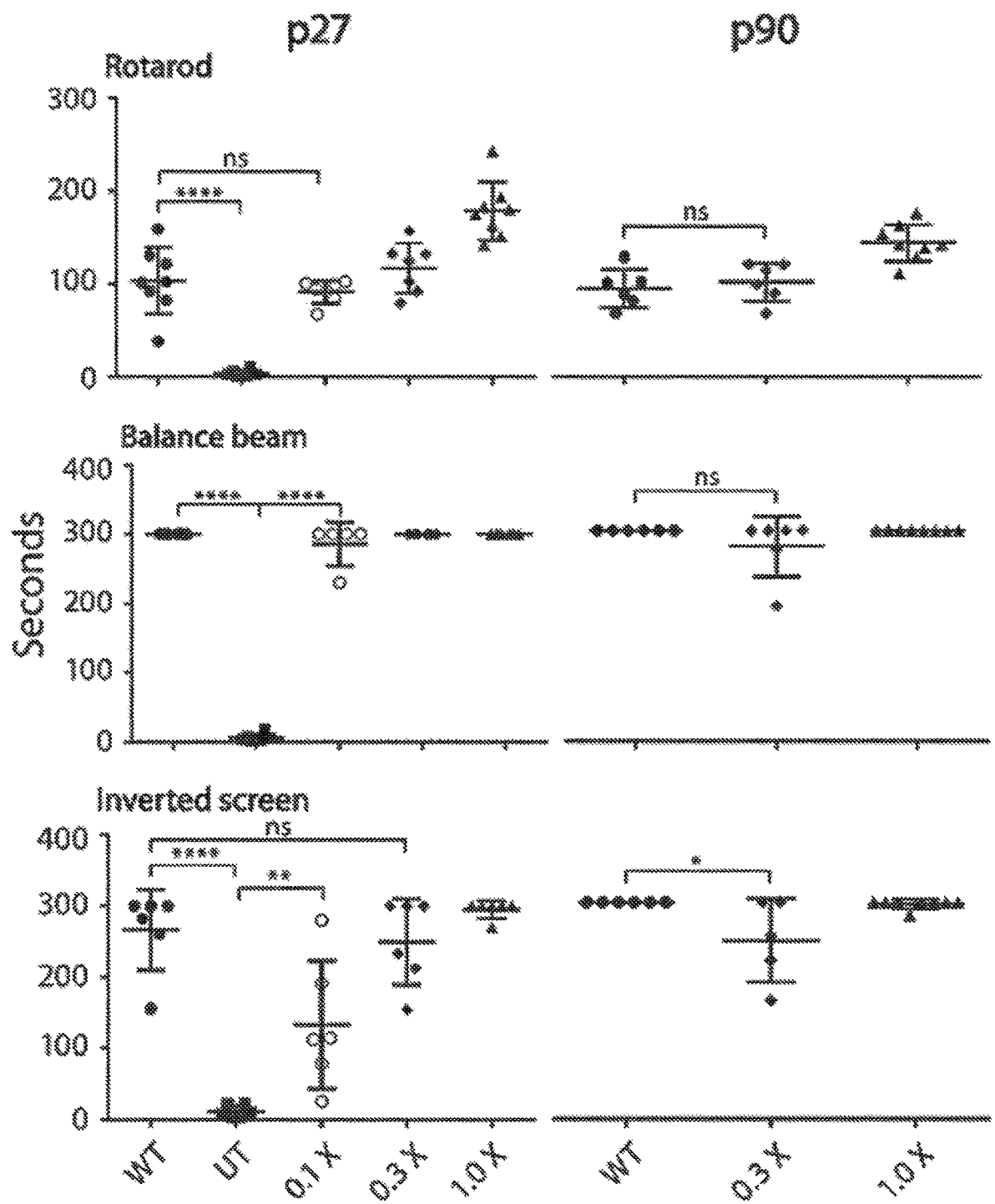
Figure 39:
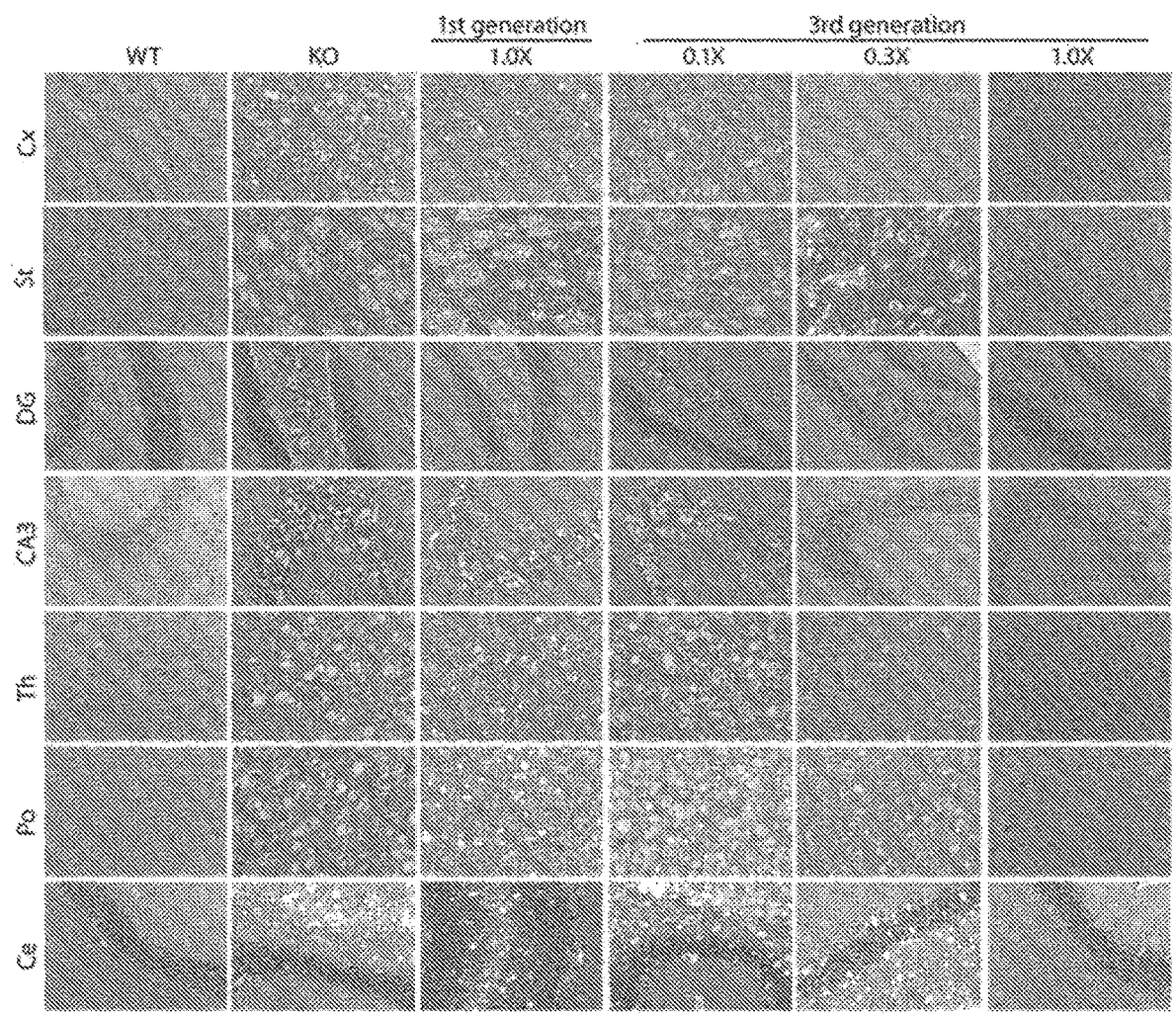
FIG. 39 shows dose-dependent neuropathology. CD KO pups were treated intravenously at p1 with either $4\times10^{11}$, $1.33\times10^{11}$, or $4\times10^{10}$ GC of $3^{rd}$ generation gene therapy. Mice were sacrificed at p25 and subjected to H&E staining and microscopy. Shown are 10× magnification of 7 different brain regions. Wild-type (WT) and untreated (KO) mice were used as controls. See FIG. 29 for legend.

Optimized Gene Therapy Achieves Efficacious Rescue of the Canavan Phenotype at Lower Doses One important aspect in translating gene therapy into the clinic is the vector dose, which is relevant to manufacturing burden, costs, and safety. Based on the performance of mice treated with a full-dose of hASPA construct, e.g., $4 \times 10^{11}$ genome copies (GCs)/animal, $3^{rd}$ generation gene therapy, 3-fold ($1.33 \times 10^{11}$ GC) and 10-fold ($4 \times 10^{10}$ GC) lower doses were then tested to compare their therapeutic outcomes. Within the first 4 weeks of life, 3- and 10-fold lower $3^{rd}$ generation treated mice showed significantly better weight gain than full-dose and 3-fold lower 1st generation treated mice (FIG. 27 and FIG. 37). This was further shown over the course of the entire study period for the 3-fold lower dose $3^{rd}$ generation group, which paralleled the weights of WT animals. In contrast, 3-fold lower dose $1^{st}$ generation treated mice declined starting at 16 weeks of age (FIG. 37). Again, the study mice were subjected to MRI and MRS for in vivo CNS assessment, but at an earlier time point (p25). T2 sequences showed hyperintensities particularly in thalamus, midbrain, cerebellum, and brain stem of untreated mice (FIG. 38A). This signal was reduced in a dose-dependent manner with the 3-fold lower dosing group showing the least hyperintense signal. As a control, WT and full-dose treated CD mice showed normalized T2 signals and were indistinguishable from each other (FIG. 38A). The MRI findings from the dose down-escalation study were also reflected in the NAA quantification by MRS (FIG. 38B). This was further supported by neuropathology analysis, showing a dose-dependent distribution of vacuoles with a similar pattern in $1^{st}$ generation full-dose treated mice and 10-fold lower $3^{rd}$ generation treated mice (FIG. 38C and FIG. 39). Finally, mice were tested on accelerating rotarod, balance beam, and inverted screen. At p27, 10-fold lower $3^{rd}$ generation treated mice performed as well as WT mice on rotarod and balance beam, but not as well on inverted screen test (FIG. 38D). Over time, this low-dose treatment group showed deterioration of motor function by p90. In contrast, at p27, 3-fold lower dose could restore the motor functions of CD KO mice to the levels of WT mice, as measured by all three aforementioned tests. By p90, these mice were still performing as well as WT mice on accelerating rotarod and balance beam, but not on inverted screen (FIG. 38D). These data indicate that the $3^{rd}$ generation gene therapy is significantly more potent, even at lower doses, than our $1^{st}$ generation gene therapy.

Figure 40:
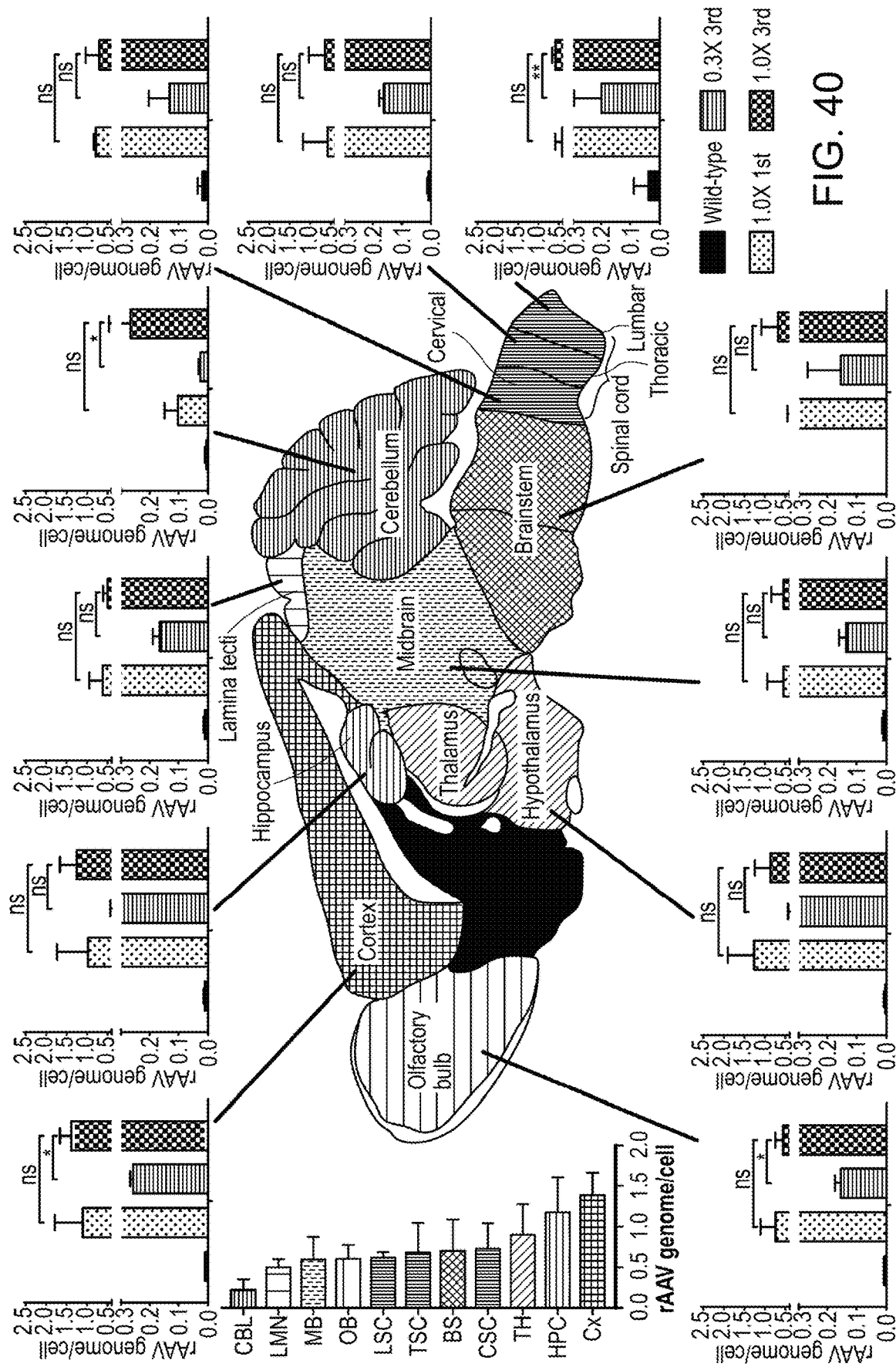
FIG. 40 shows rAAV vector genome copy numbers vary among brain regions of treated CD KO mice. 11 different regions of the CNS were analyzed for rAAV9 vector genome copy number per cell. Displayed is a schematic drawing of a sagittal section of mouse brain with 11 brain regions, including spinal cord, labeled and highlighted. Vector genome copy number is shown per diploid cell (rAAV genome/cell) for WT control, and 1-year-old CD KO mice treated with full dose $1^{st}$ generation, and full and 3-fold lower dose $3^{rd}$ generation gene therapy. On the left side, a ranking of the rAAV genome/cell of the $3^{rd}$ generation treated are shown. CBL=cerebellum, LMN=lamina tecti, MB=midbrain, OB=olfactory bulb, LSC=lumbar spinal cord, TSC=thoracic spinal cord, BS=brain stem, CSC=cervical spinal cord, TH=thalamus and hypothalamus, HPC=hippocampus, Cx=cortex. Error bars indicate mean±SD; n=3-4; * $p<0.05$;  $p<0.01$; * $p<0.001$; **** $p<0.0001$; ns=non-significant.

CNS Region Specific rAAV Genome Distribution Profile Coincides with Regional Neuropathology Since it was observed that expression cassette optimization correlates with higher hASPA protein expression (FIG. 26B), 11 CNS regions were analyzed to obtain further insight into CNS region specific pathology and rAAV transduction. No significant differences in vector GC number per diploid cell between full-dose $1^{st}$ and $3^{rd}$ generation treatment groups were detected, indicating that increased hASPA protein expression from the optimized expression cassette, but not improved vector genome delivery, was responsible for the significant therapeutic improvement of the $3^{rd}$ generation treated mice (FIG. 26B and FIG. 40). When regional distribution of vector genome was ranked, cortex showed the highest and cerebellum the lowest rAAV GC number per cell (FIG. 40). In relation to neuropathology, this indicates that certain brain regions have different therapeutic thresholds to achieve complete mitigation (FIG. 33A-33D and FIG. 34). Particularly the cerebellum showed minimal response comparing full-dose $1^{st}$ generation to 10- and 3-fold lower dose $3^{rd}$ generation gene therapy (FIG. 39). However, upon full-dose $3^{rd}$ generation treatment, complete rescue was achieved with rAAV GC numbers lower than in any other CNS region (FIG. 39 and FIG. 40).

Figure 41:
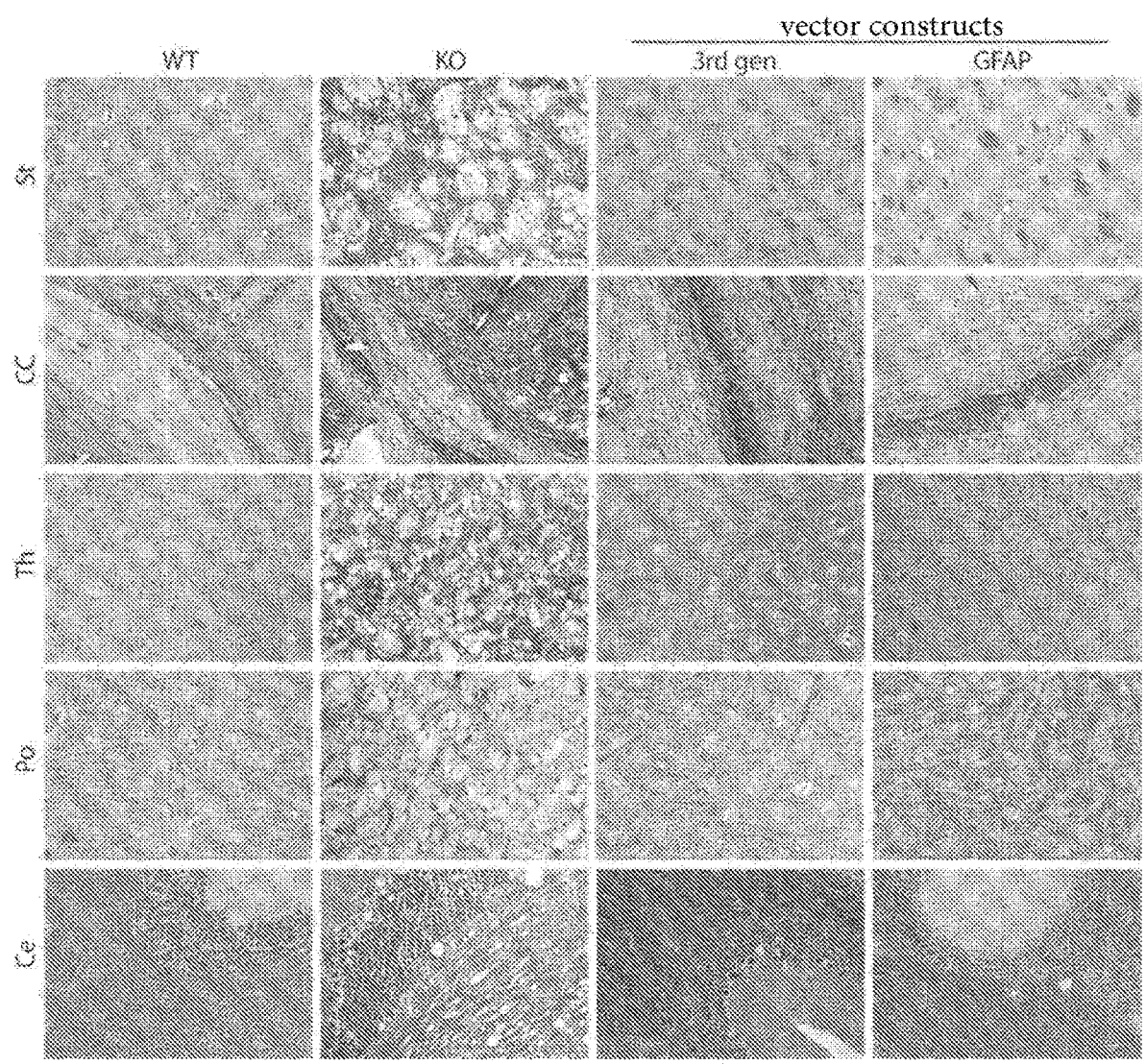
FIG. 41 shows luxol fast blue staining and astrocytic ASPA expression. CD KO mice were treated at p1 via facial vein with either $4\times10^{11}$ GC of $3^{rd}$ generation gene therapy or GFAP-hASPA-Opt in rAAV9. Shown are 5 brain regions of p25 mice vs. wild-type (WT) and untreated (KO) control mice. Shown are 10× magnifications. See FIG. 29 for legend.
Figure 42A:
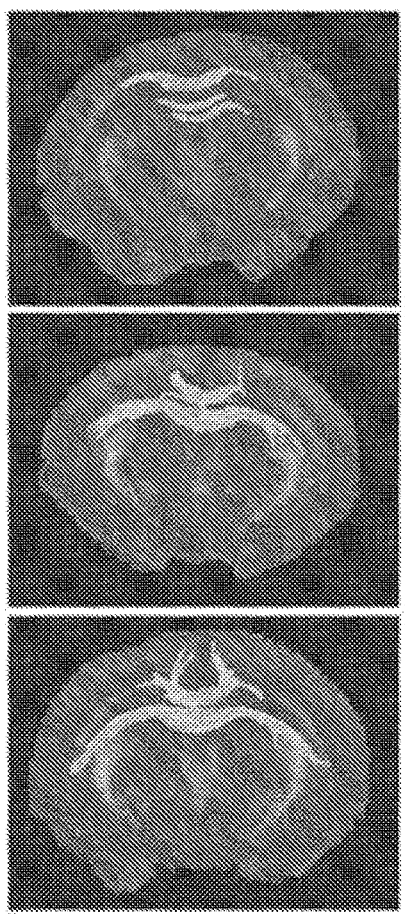
FIGS. 42A-42F show high-field imaging non-invasively evaluates therapy outcomes. Male mice were treated at p1 and imaged at p25, comparing untreated (UT) CD KO mice, wild-type (WT) mice, and treated (Tx) CD KO mice (n=8-10 each).
Figure 42C:
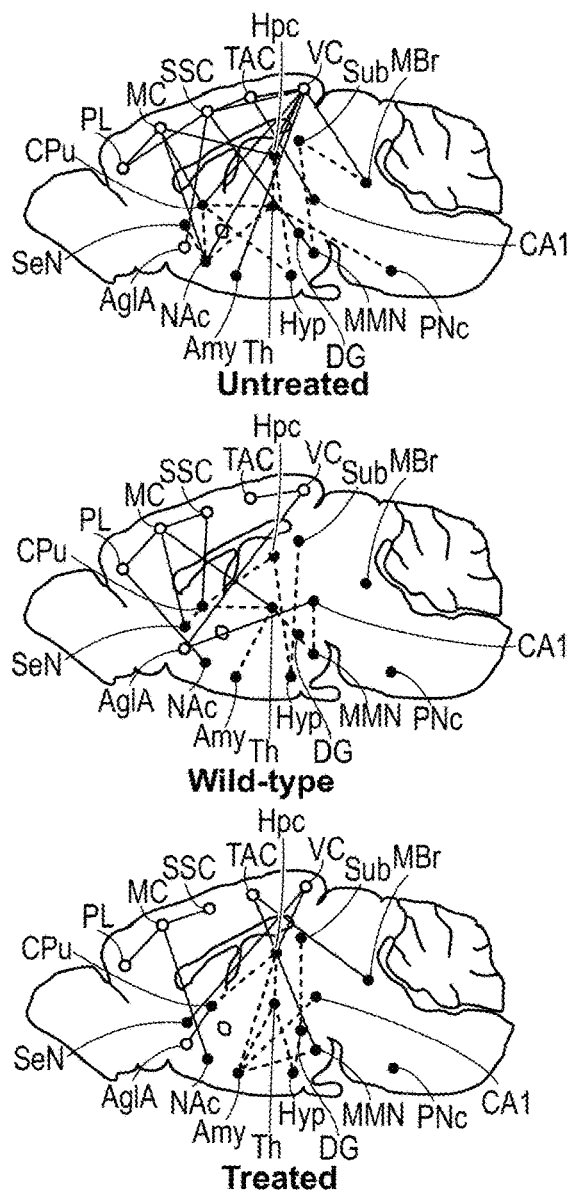
Figure 42B:
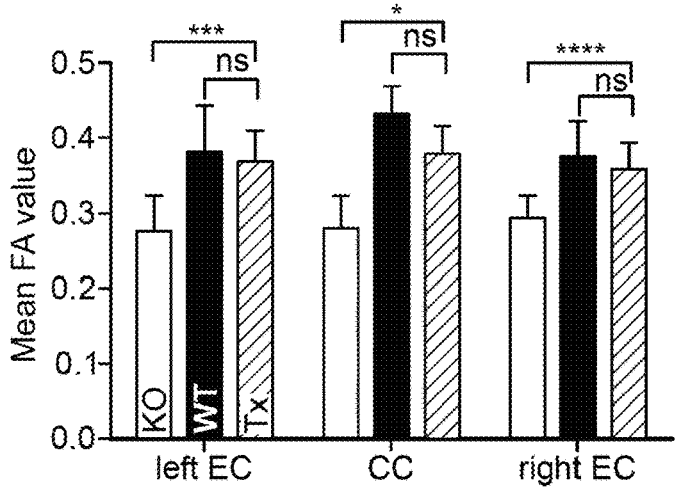

High Field Neuroimaging Enables Noninvasive Monitoring and Prediction of Therapeutic Outcomes One aspect of CD is the loss of myelin structures in the CNS. The myelin stain luxol fast blue showed widespread vacuoles and reduced myelin in untreated CD KO mice (FIG. 41). In contrast, myelin structures in WT and full-dose $3^{rd}$ generation treated mice were indistinguishable (FIG. 41). To evaluate if these findings can be monitored in the living mouse, high-field DTI was applied to assess myelin fiber tracts in the corpus callosum (CC) and the external capsule (EC). Tractography to obtain an overall assessment of fiber tract morphology showed substantially altered and shortened interhemispheric tracts of the CC in untreated mice, whereas WT and $3^{rd}$ generation treated mice were indistinguishable (FIG. 42A). For quantitative assessment, fractional anisotropy (FA) values of the CC and right and left EC were compared between groups. While there was no significant difference between WT and treated mice, untreated mice differed significantly, supporting the tractography data and indicating the value of DTI for non-invasive CNS gene therapy assessment (FIG. 42B).

Figure 42D:
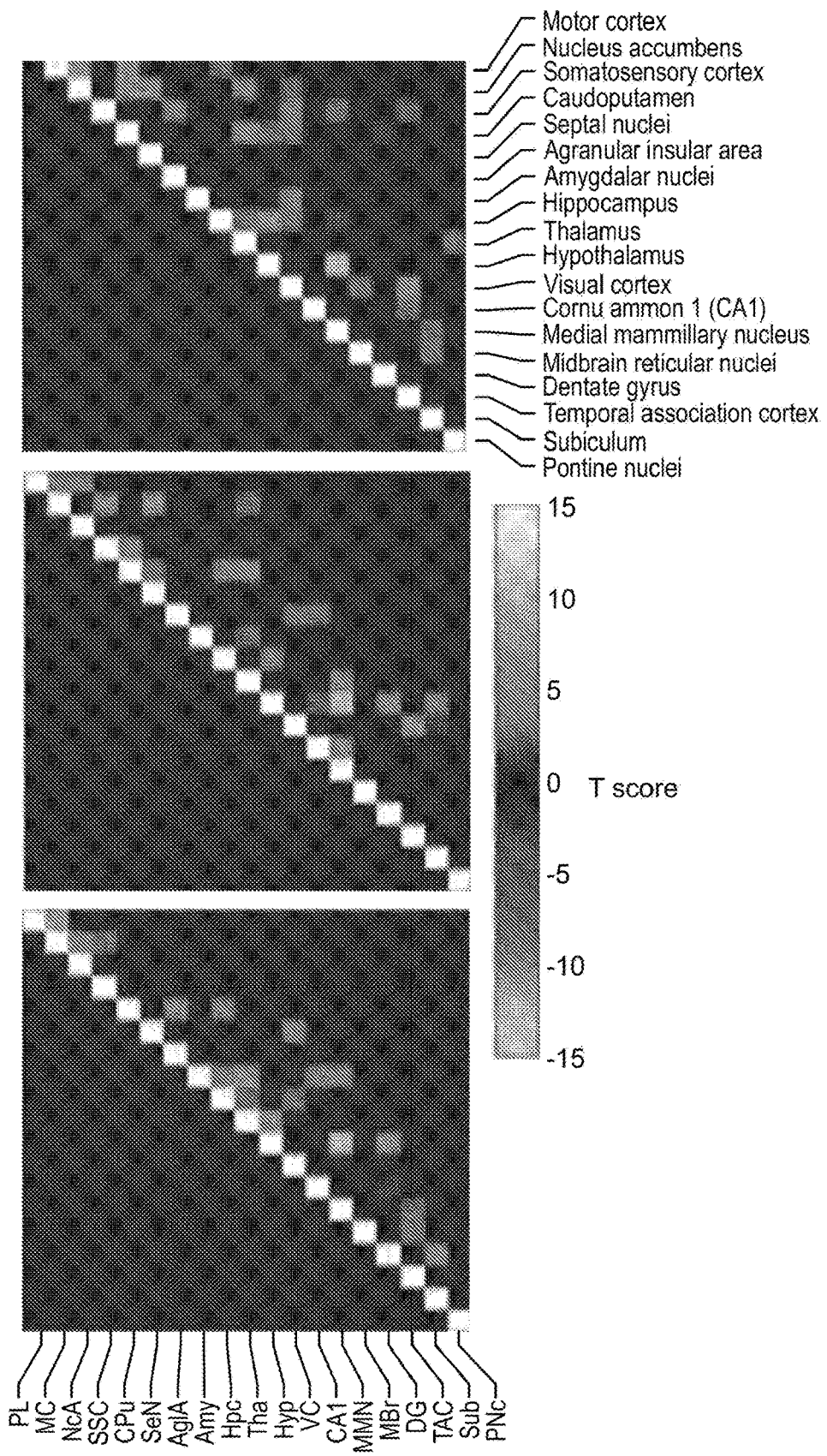
Figure 42E:
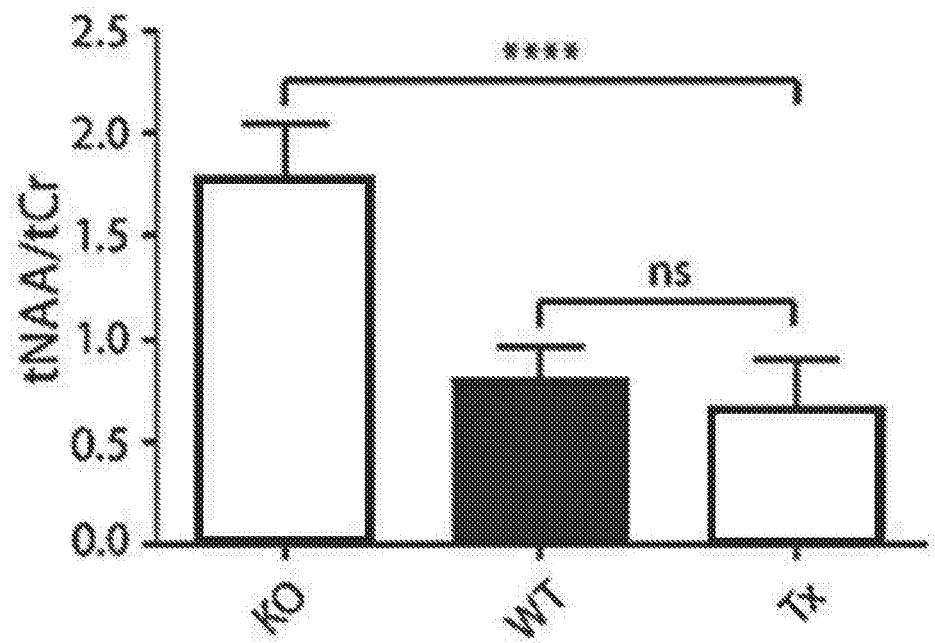
Figure 42F:
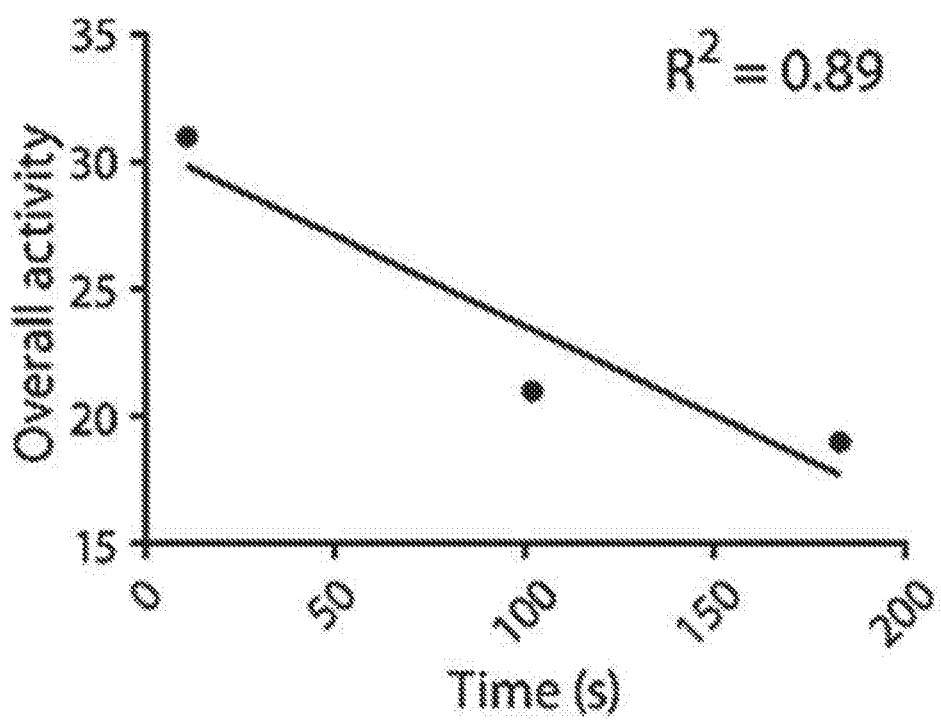
Figure 43:
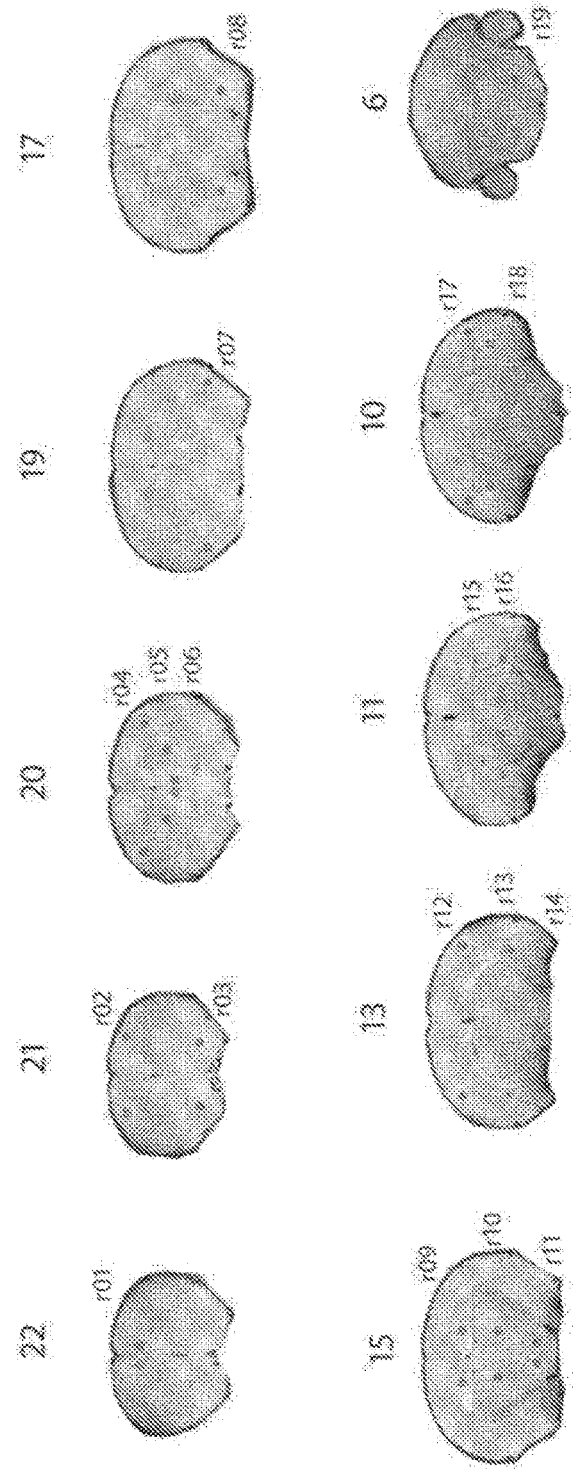
FIG. 43 shows resting state functional magnet resonance imaging (rs-fMRI) regions of interest. 19 regions of interest (ROI) were selected to represent regions of motor and cognitive function. N=9-10 mice per group were imaged while anesthetized to acquire rs-fMRI.

Resting state-functional MRI (rs-fMRI) was performed on groups of WT, untreated, and treated male mice to determine whether ubiquitous ASPA expression changes functional connectivity. A total of 19 different brain regions were analyzed (FIG. 43). Based on T score analysis, the most active brain regions were observed in untreated mice, with decreasing activity in WT and treated mice, indicating that the ASPA-deficient brain might have to engage more brain regions at baseline (FIGS. 42C-42D). Thus in some embodiments, ubiquitous ASPA expression in the brain facilitates the communication between brain regions and thus engages fewer brain regions at baseline (FIGS. 42C-42D). Correlation analysis between the average number of active brain regions and accelerated rotarod results revealed a negative correlation between overall functional connectivity and accelerated rotarod motor function, indicating that rs-fMRI supports the correlation between treatment and motor performance ($R^2$=0.89; FIGS. 42D-42F).

Example 6: NAA Levels Correlate with T2 Signal Intensities

Figure 44:
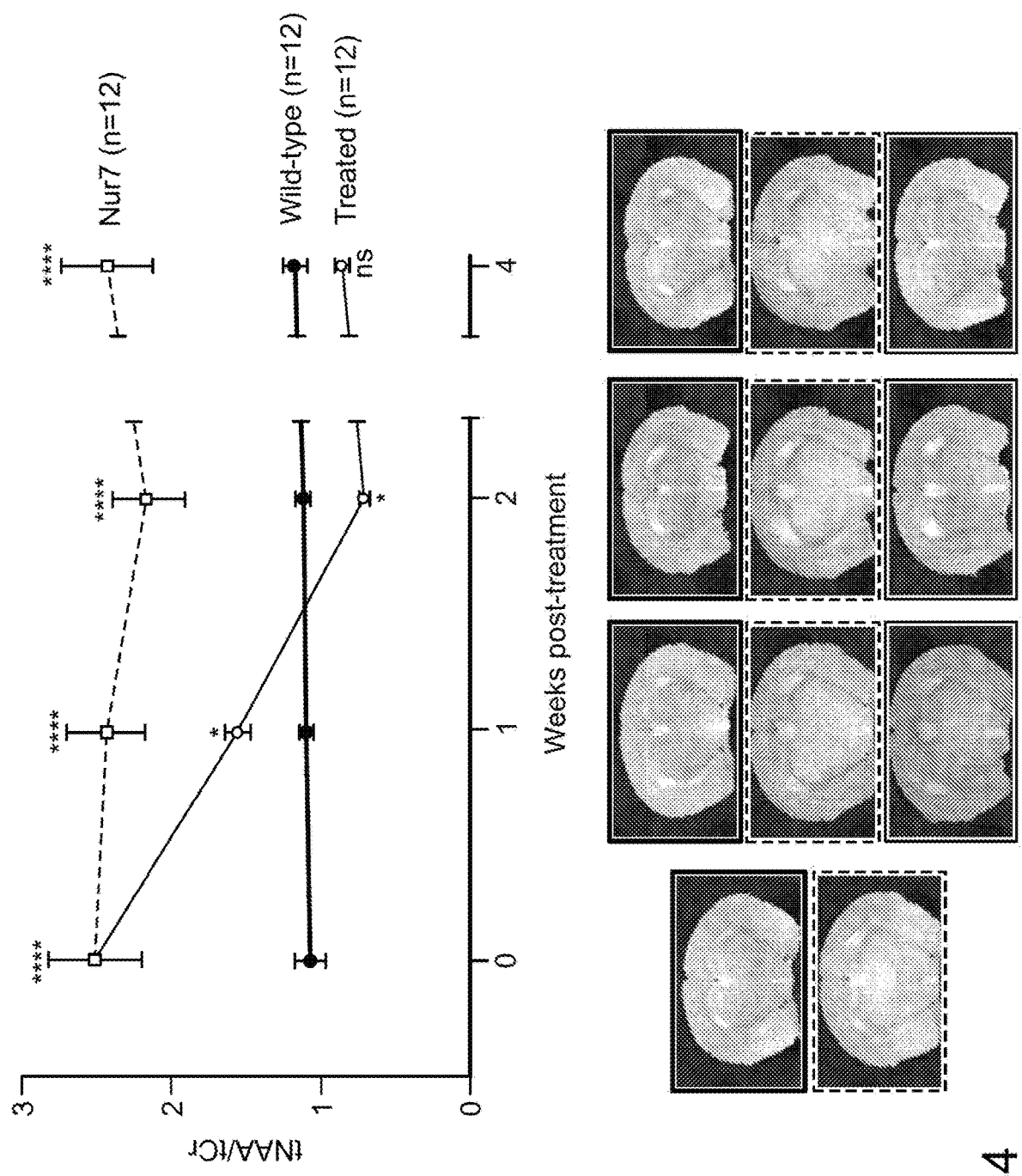
FIG. 44 shows NAA levels correlate with T2 Signal Intensities.

Mice were treated IV at Juvenile Age and monitored for four weeks by MRI/MRS. Brain NAA levels and corresponding T2 MRI sequences indicate that hyperintense signal decrease when NAA levels decrease in mice treated at 6 weeks of age (FIG. 44). This indicates that neuroradiologic correlates of pathology can be reversed when treated after the onset of pathology.

Example 7: Restoration of Myelin after hASPA Gene Therapy Treatment

Figure 45:
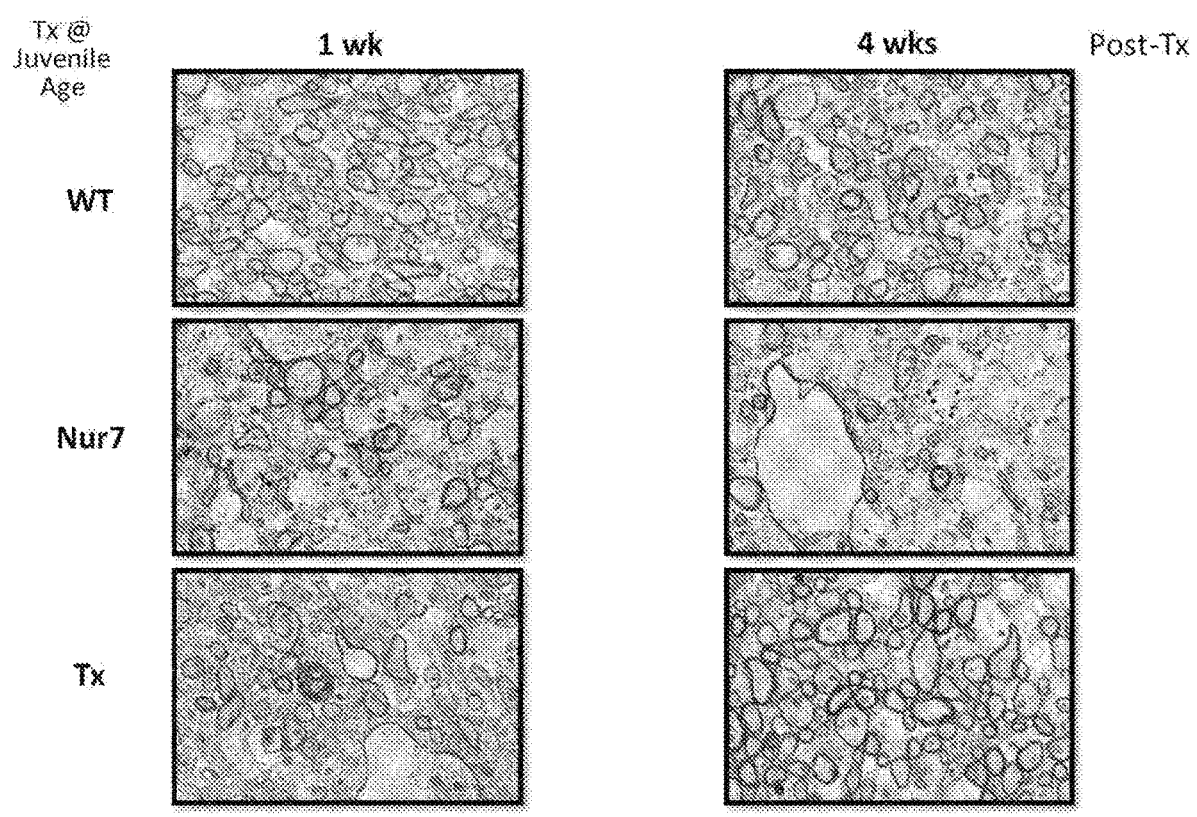
FIG. 45 shows restoration of myelin 4-weeks post-treatment with hASPA construct.

Six-week old ASPA deficient mice (juvenile) show a disrupted axon and myelin structure (FIG. 45, left). Four weeks after treatment, treated mice show a axon pattern and myelination indistinguishable to wild-type mice, indicating reversal of neuropathology (FIG. 45, right).

Figure 54:
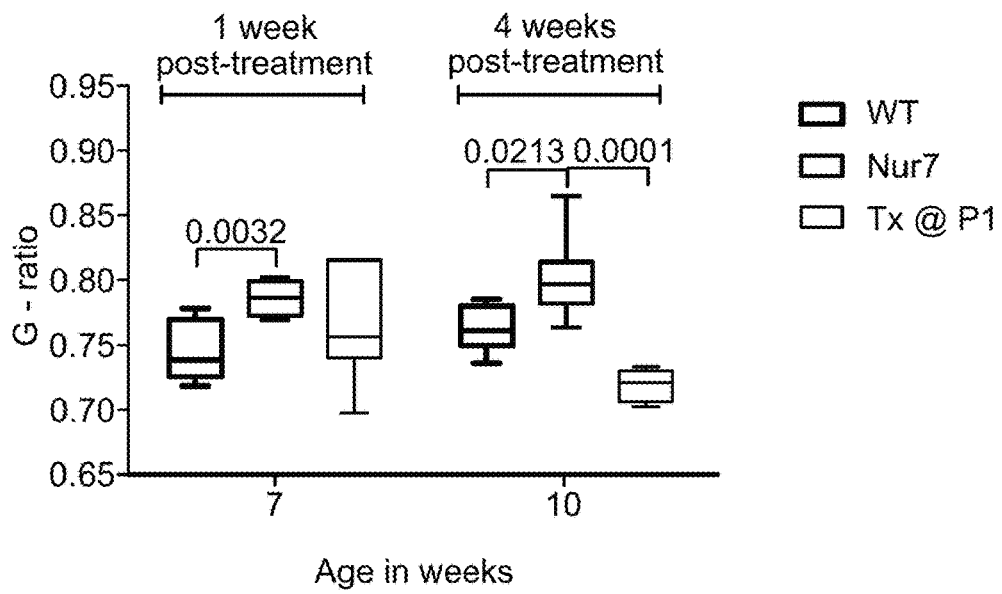
FIG. 54 shows data indicating that Nur7 mice treated with the $3^{rd}$ generation ASPA gene therapy construct have a significantly lower g-ratio than untreated Nur7 mice, indicating an increase in myelin thickness due to re-myelination.

Mice were treated at 6 weeks of age and sacrificed at 7 or 10 weeks of age for electron microscopy analysis of the anterior commissure. G-ratio is describes the ratio of inner over outer axon diameter and is indicative of myelin and axon thickness. The lower the value, the more myelin is present. Data indicates that at 7 weeks of age untreated mice (Nur7) have a significantly higher g-ratio than wild-type mice; this is also found for mice one week after treatment (FIG. 54). After 4 weeks of treatment (10 weeks of age), treated mice show a significantly lower g-ratio than untreated mice suggesting an increase in myelin thickness, most likely due to re-myelination (FIG. 54).

Example 8: Expanded Therapeutic Window Data

Figure 47:
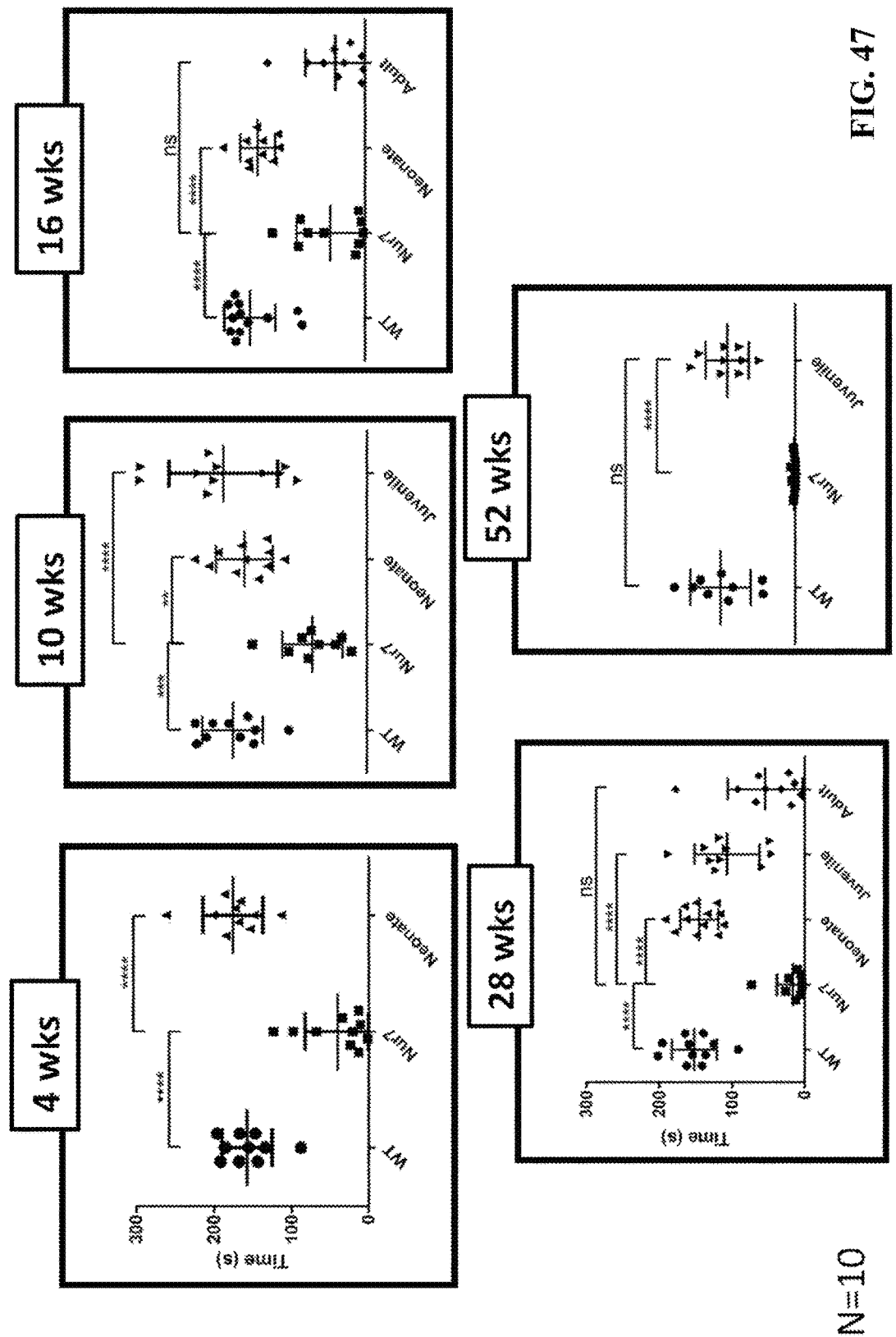
FIG. 47 shows rotarod assay data for female mice. Data indicates an expanded therapeutic window for ASPA gene therapy. Mice were assayed at 4 weeks, 10 weeks, 16 weeks, 28 weeks and 52 weeks.

FIGS. 46 and 47 show data relating to the expanded therapeutic window for treatment of a mouse model of CD in males (FIG. 46) and females (FIG. 47). Improved performance on the rotarod was observed in treated Nur7 mice compared to untreated Nur7 mice at 52 wks of age, indicating that ASPA gene therapy is capable of reversing CD pathology.

FIG. 48 shows that working/spatial memory is restored after treatment with the $3^{rd}$ generation hASPA gene therapy construct in Nur7 mice.

Example 9: Gait Analysis Data

CatWalk testing was conducted with the CatWalk XT system from Noldus, in a darkened room. Mice were placed within the CatWalk system, and allowed to freely walk towards the other end of the CatWalk tunnel. The attached computer records the paw prints and their associated time of contact with the illuminated floor, which are then used for the various calculations that generates the data presented. The mice are required to run for at least 5 complete runs within the CatWalk, and in between each run, the mice are able to turn around for the next run.

Figure 49:
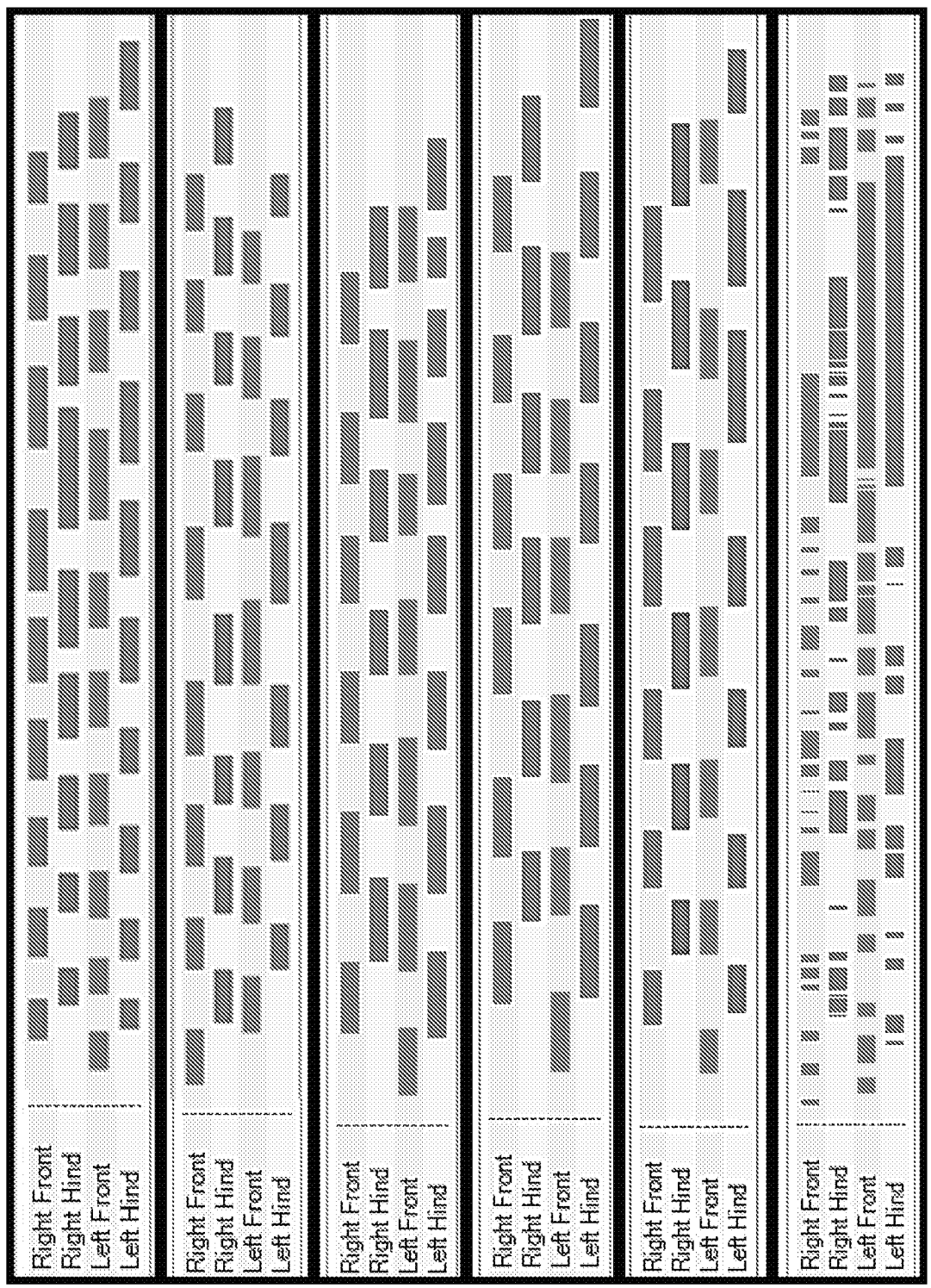
FIG. 49 shows gait analysis data indicating a therapeutic benefit for mice treated with $3^{rd}$ generation ASPA gene therapy at 6 months and earlier.

Gait analysis data indicates a therapeutic benefit for mice treated with ASPA gene therapy at 6 months and earlier (FIG. 49). Furthermore, gait analysis reveals that mice treated at mature adult age (p168) still benefit from gene therapy treatment (FIG. 50).

Example 10: Additional Metabolomics Data

This example describes real-time analysis of increased metabolic activity and oxygen consumption of ASPA deficient cells (HEK). Data were generated on a Seahorse XF24 system (Agilent) using about 50,000 cell/well. Each samples was run as triplicate or quadruplet. For metabolic analysis the XF Mito Fuel Flex Test (Agilent) or XF Cell Mito Stress Test (Agilent) were performed.

Figure 51:
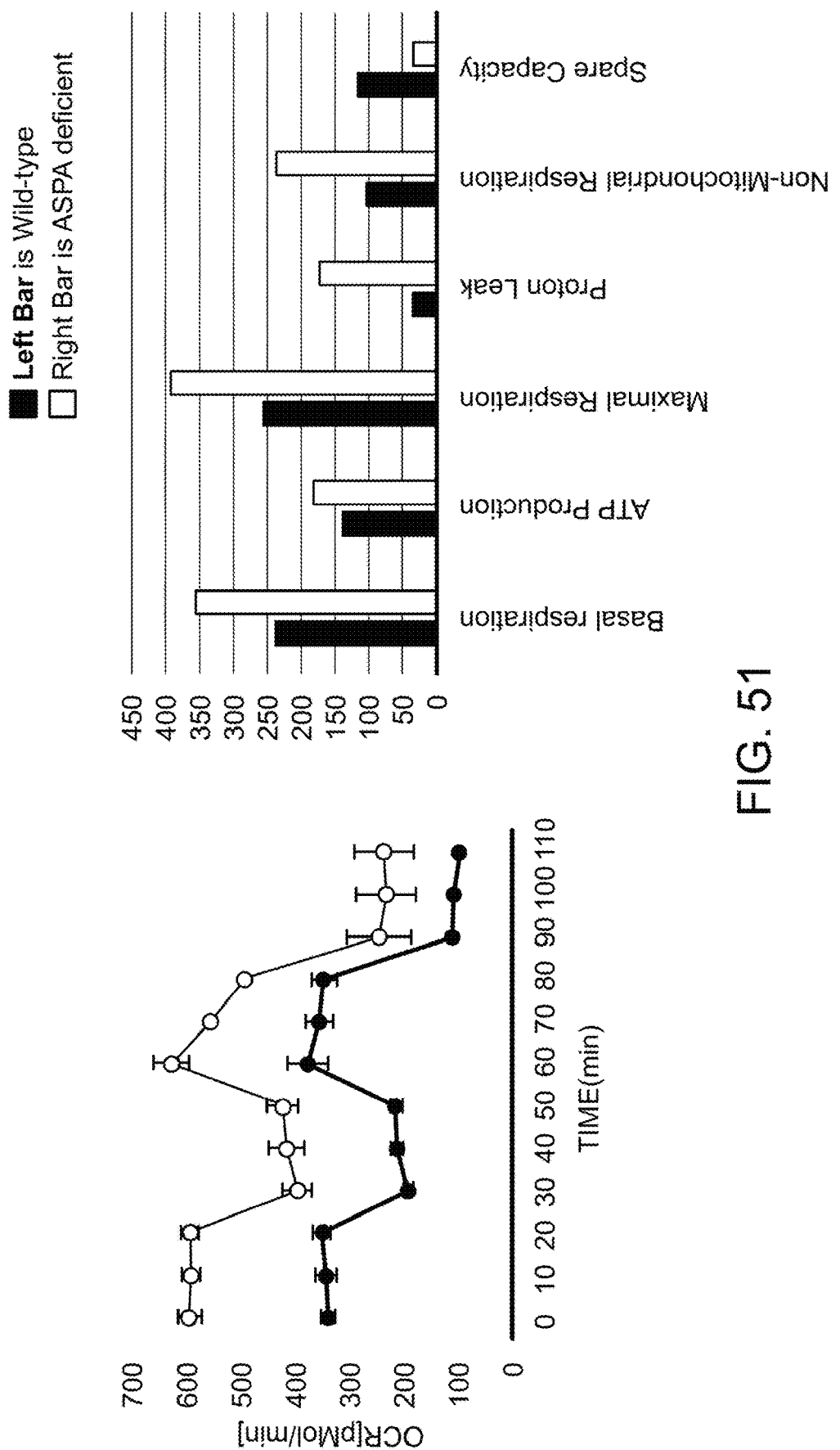
FIG. 51 shows Mito Stress Test data comparing ASPA deficient HEK cells to wild-type HEK cells (e.g., non ASPA deficient cells).
Figure 52:
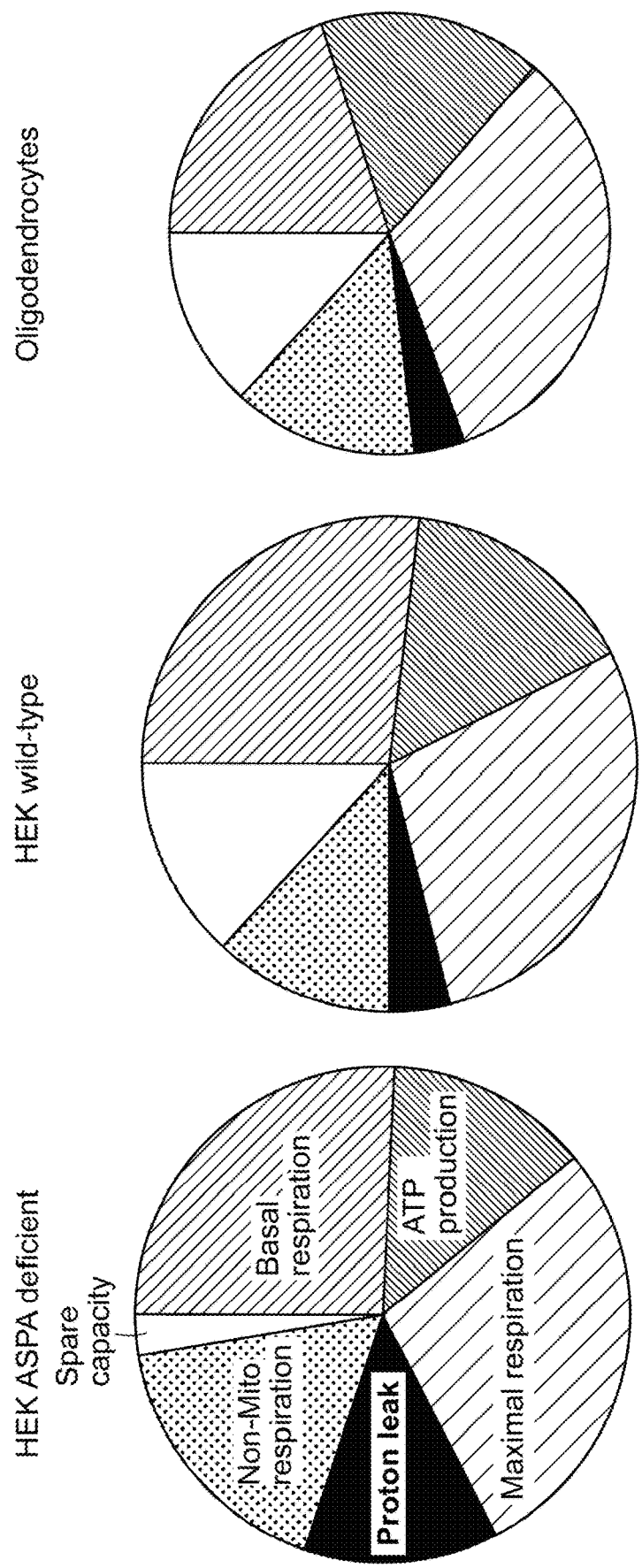
FIG. 52 shows mitochondrial profiling data for ASPA deficient HEK cells (HEK293 KO) compared to wild-type HEK cells (HEK293 WT).

The Mito Stress test was performed on WT on CRISPR-generated ASPA deficient HEK cells. Data indicates that the overall metabolic activity is increased in ASPA deficient cells (FIGS. 51 and 52). Increased basal respiration, which indicates increased oxygen consumption was observed (see Table 3).

TABLE 2

Metabolomics analysis results

| Significantly Altered Biochemicals | Total Biochemicals $p \leq 0.05$ | Biochemicals ($\uparrow\downarrow$) | Total Biochemicals $0.05 < p < 0.10$ | Biochemicals ($\uparrow\downarrow$) |
|---|---|---|---|---|
| KO / WT | 273 | 68\|205 | 32 | 7\|25 |
| rAAV Tx / rAAV Ctrl | 286 | 190\|96 | 29 | 14\|15 |
| rAAV Ctrl / WT | 293 | 81\|212 | 30 | 12\|18 |
| rAAV Tx / WT | 88 | 20\|68 | 41 | 9\|32 |
| rAAV Ctrl / KO | 44 | 26\|18 | 32 | 16\|16 |
| rAAV Tx / KO | 257 | 184\|73 | 41 | 21\|20 |

In addition, it was observed that ASPA deficient cells produce more ATP. For example, FIG. 52 shows data of the Mito stress test comparing ASPA deficient and wild-type HEK cells and human oligodendrocytes. The data indicates that oligodendrocyte wild-type cells have a similar percentage energy production profile as HEK wild-type cells. For example, HEK ASPA deficient cells have an reduced percentage of "spare capacity" or an increased percentage of "proton leak". In contrast, HEK wild-type and oligodendrocytes show a much more similar pattern. Interestingly, ASPA deficient cells have increased non-mitochondrial respiration, indicating that metabolic processed outside the mitochondria are increased as well. All data point shown are statistically significant with at least n=3 biological replicates.

A Mito flex test was also performed. FIG. 53 shows data indicating that ASPA deficient cells use more Fatty acids and Glutamine for energy production. FIG. 53 also shows data relating to the dependency, flexibility and capacity of wild-type or ASPA deficient cells to use glucose (GLC), glutamine (GLN) or fatty acids (FA) for energy production. Data indicates that ASPA deficient cells rely less on glucose for energy production than non-ASPA deficient cells. In contrast, ASPA deficient cells depend more on fatty acid oxidation to generate energy. Interestingly, the flexibility to use either glucose or FA is higher in ASPA deficient cells. However, the capacity to use glucose is reduced in ASPA deficient cells overall. Finally, ASPA deficient cells rely on glutamine for energy generation.

Figure 55:
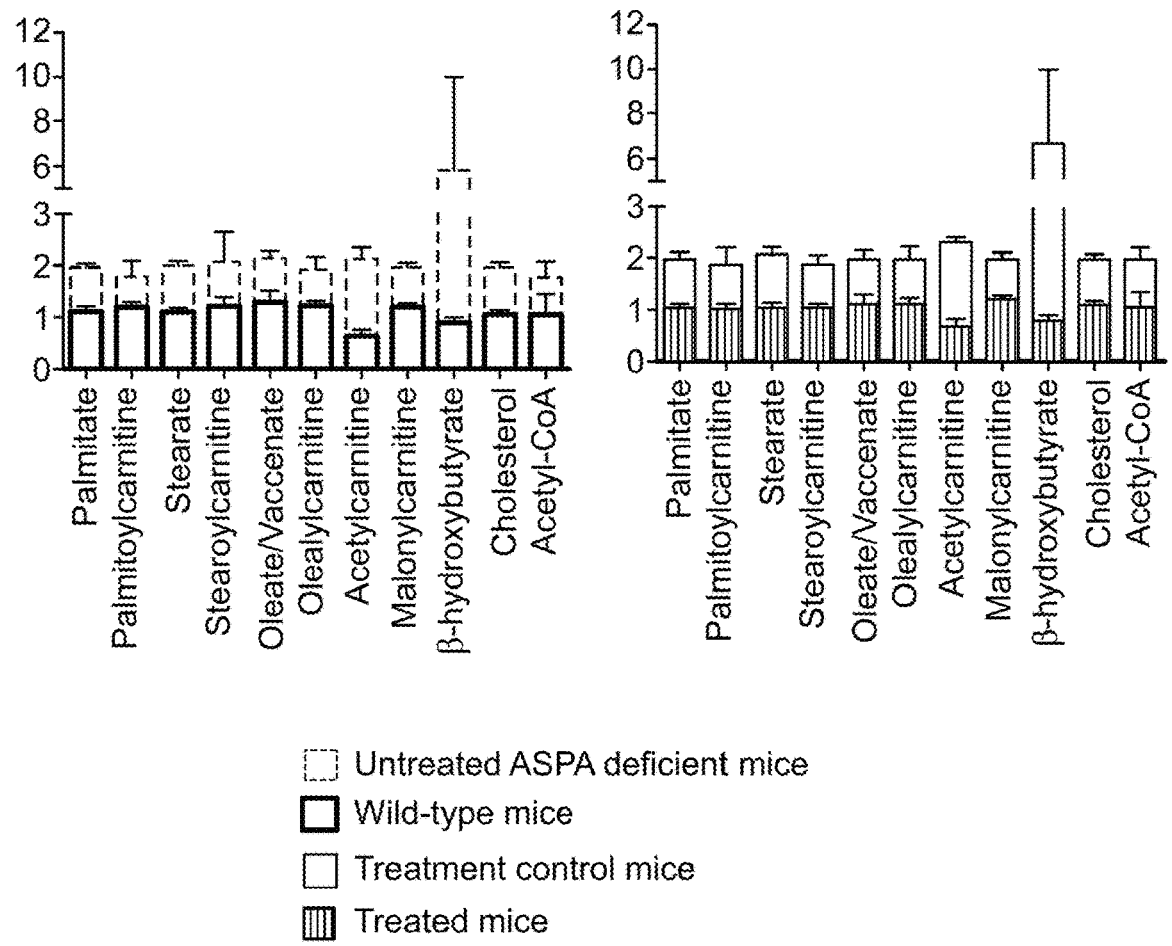
FIG. 55 shows data relating to measurement of beta-oxidation in untreated ASPA deficient mice, wild-type mice, treated control mice, and $3^{rd}$ generation ASPA gene therapy construct treated mice.
Figure 56:
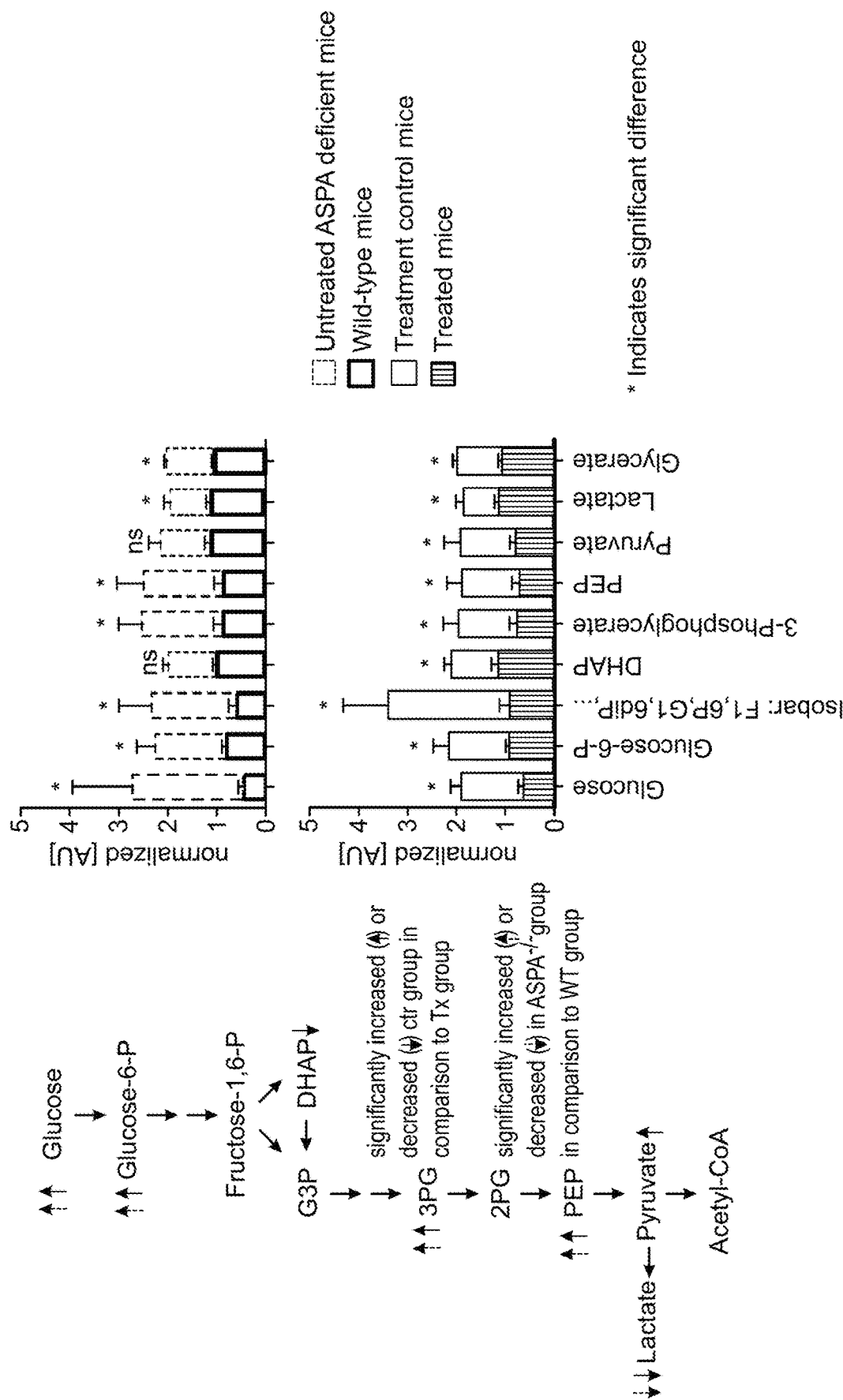
FIG. 56 shows decreased glycolysis in ASPA deficient brain and restoration upon ASPA reconstitution.
Figure 57:
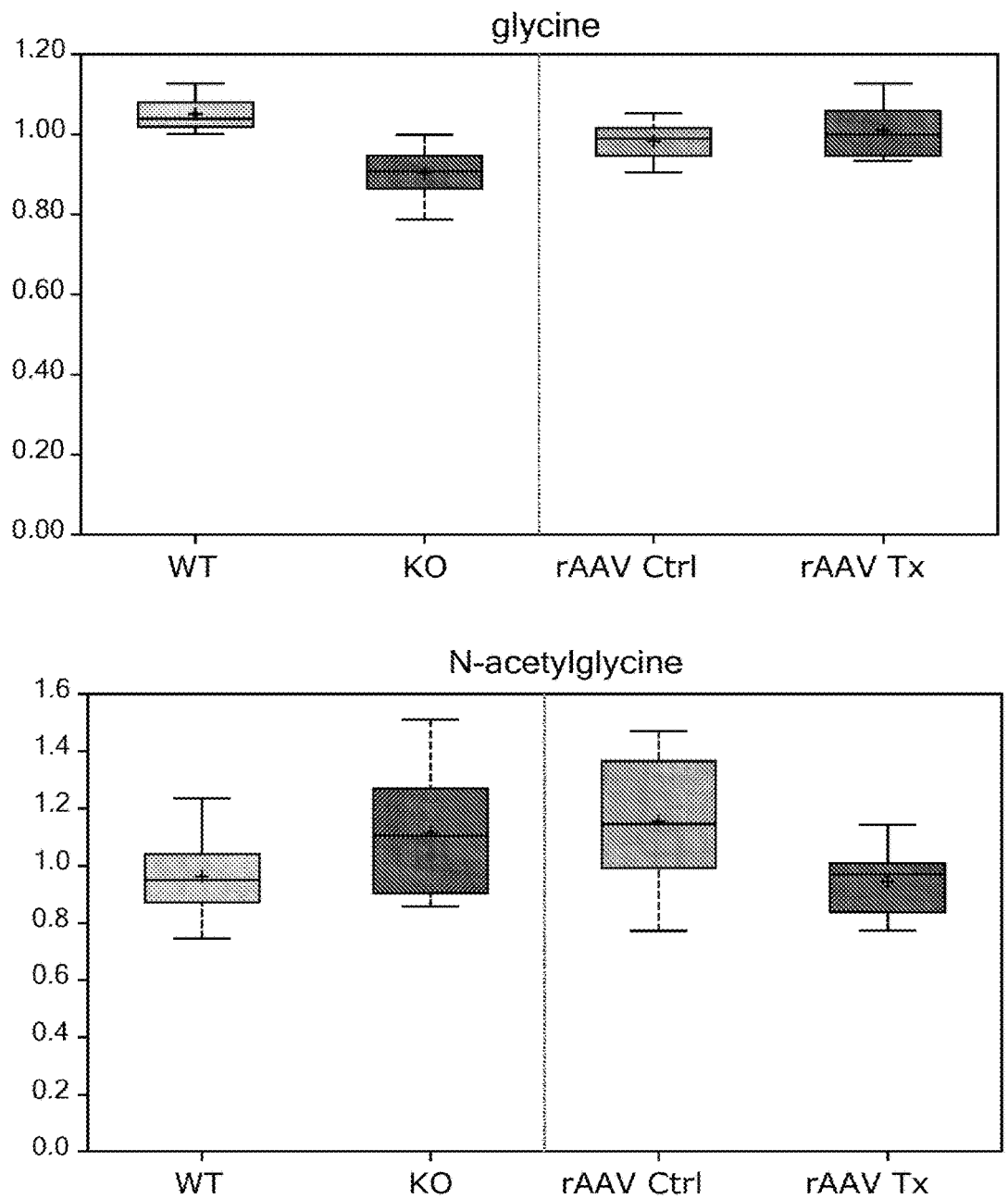
FIG. 57 shows additional data representative data for whole brain metabolome analysis in wild-type (WT) and ASPA knockout (KO) mice.
Figure 57:
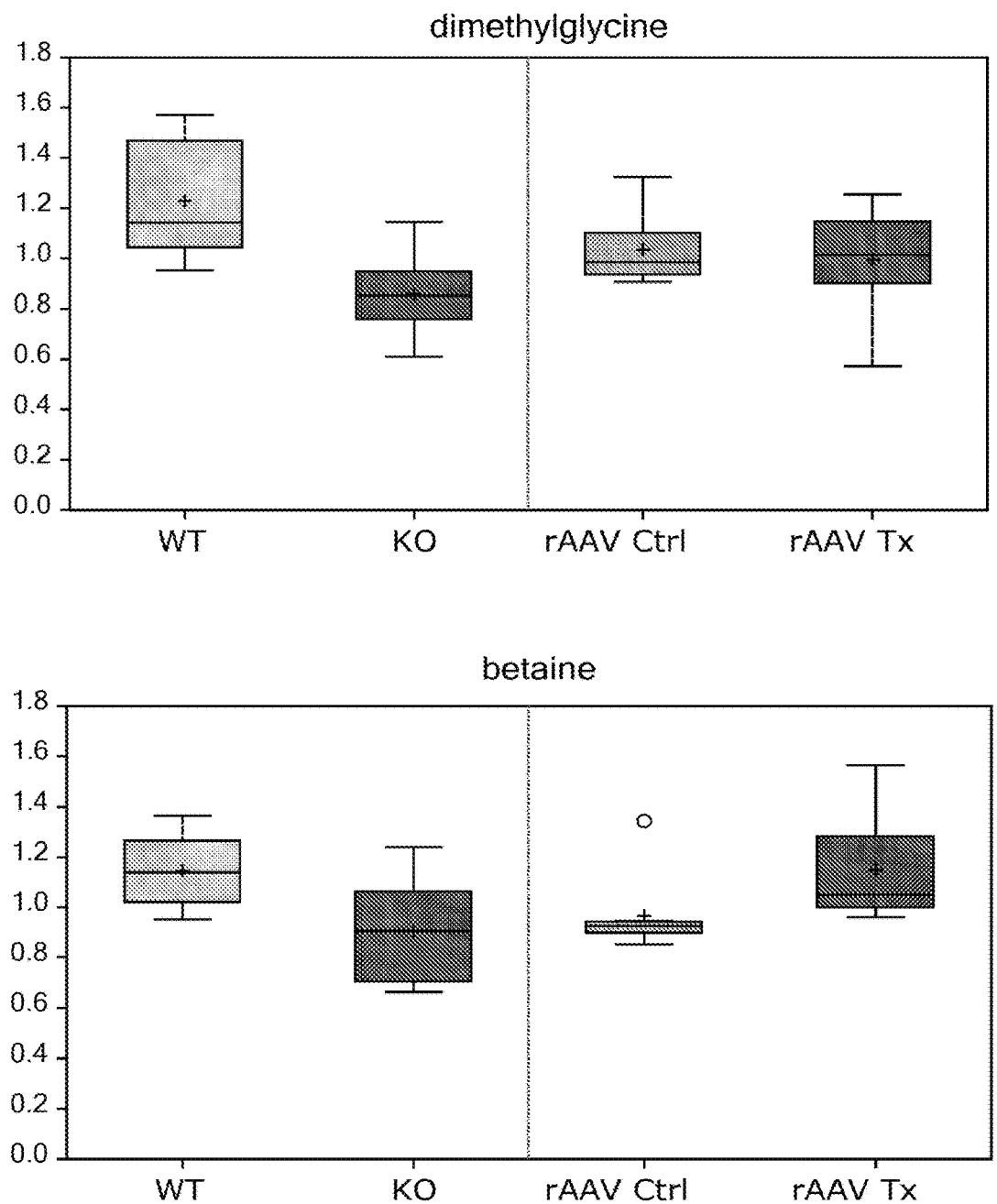
Figure 57:
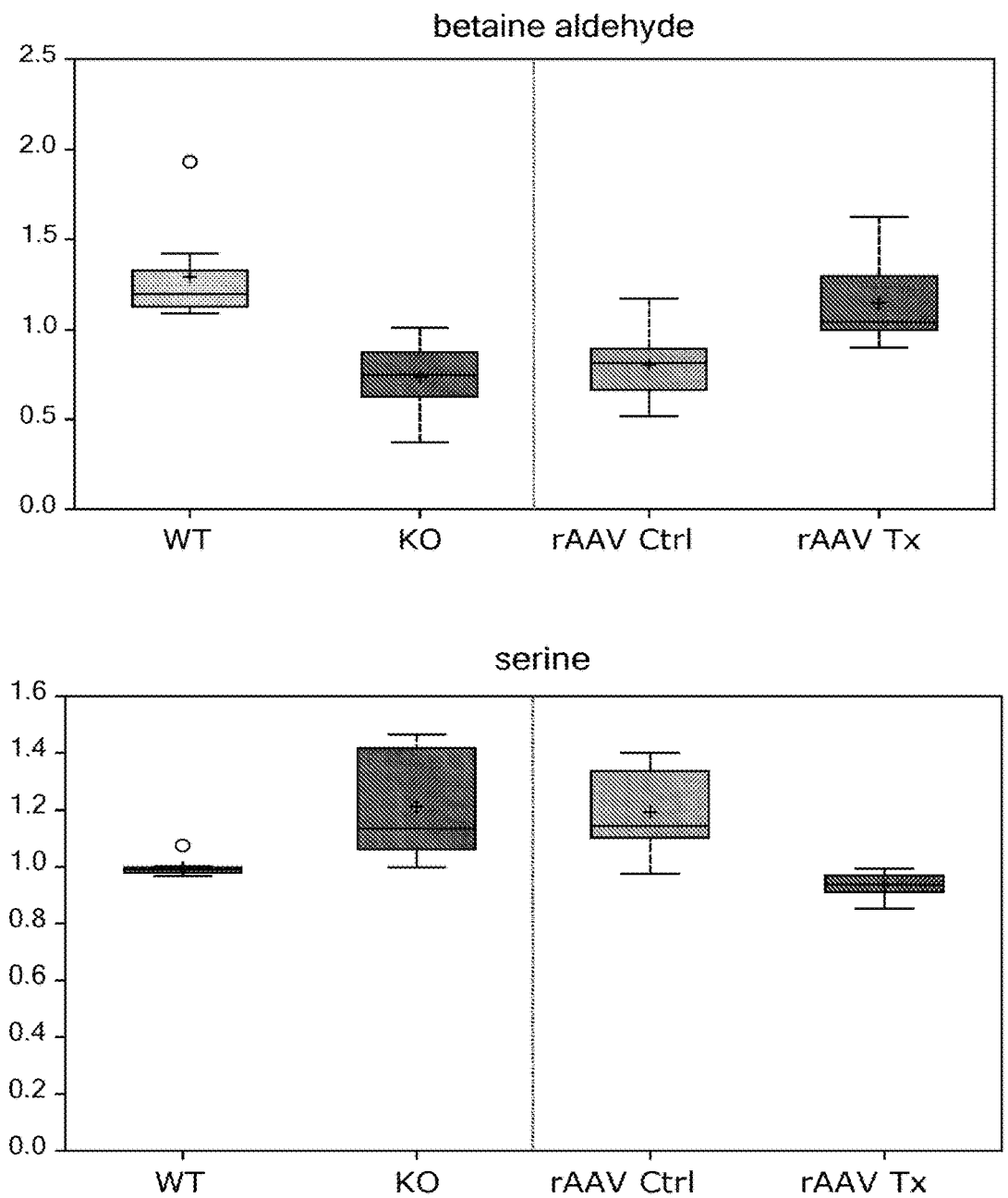
Figure 57:
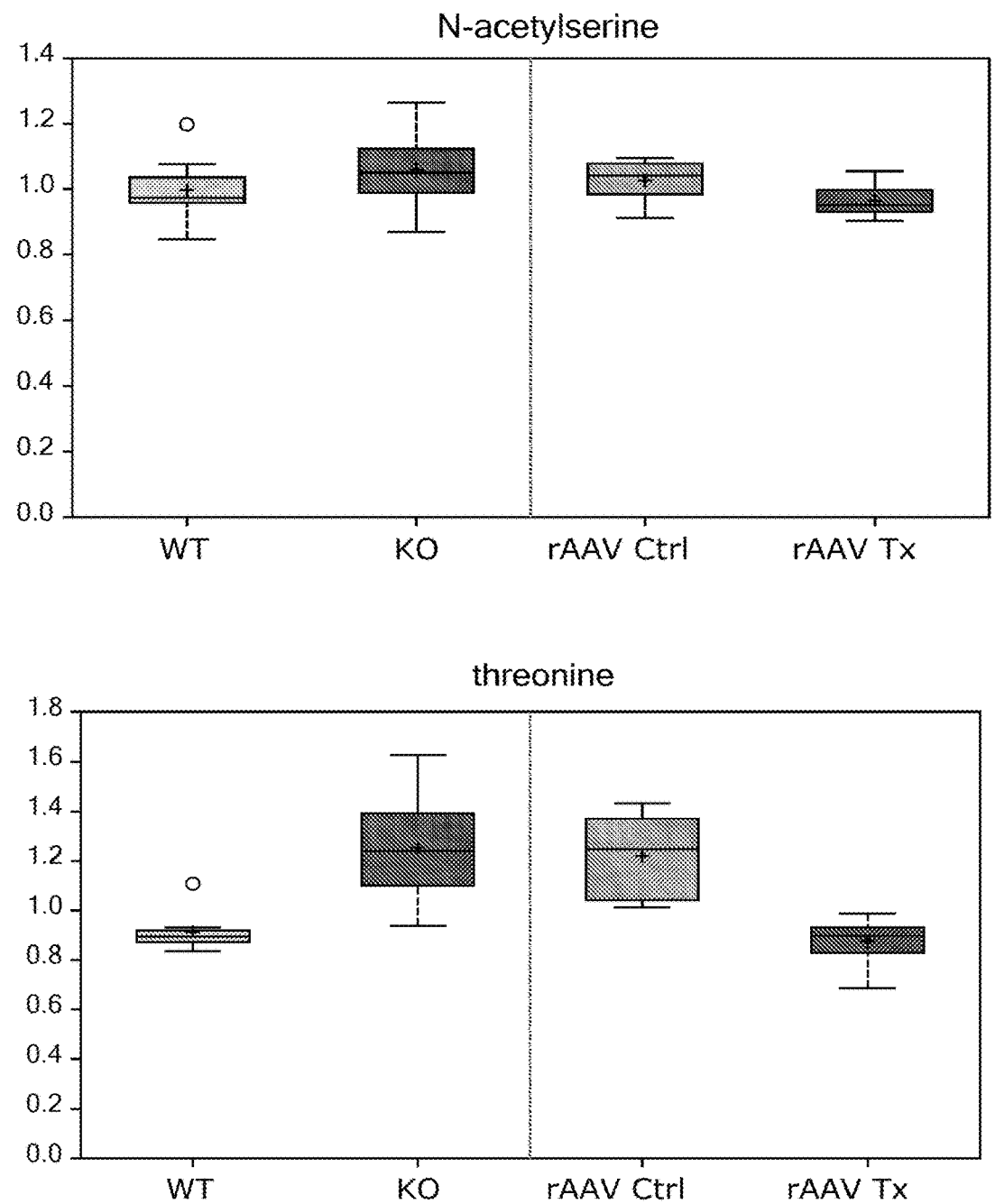
Figure 57:
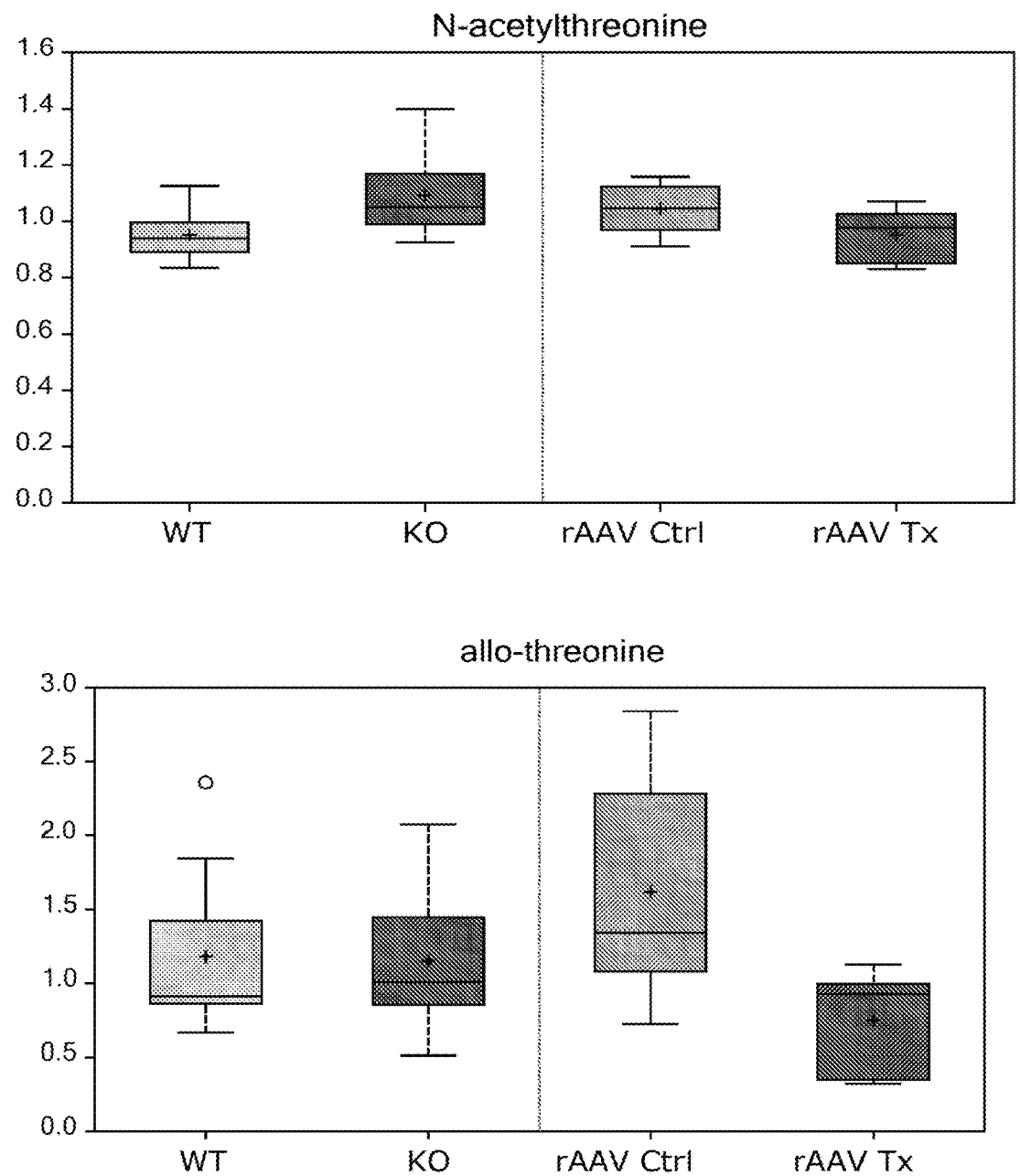
Figure 57:
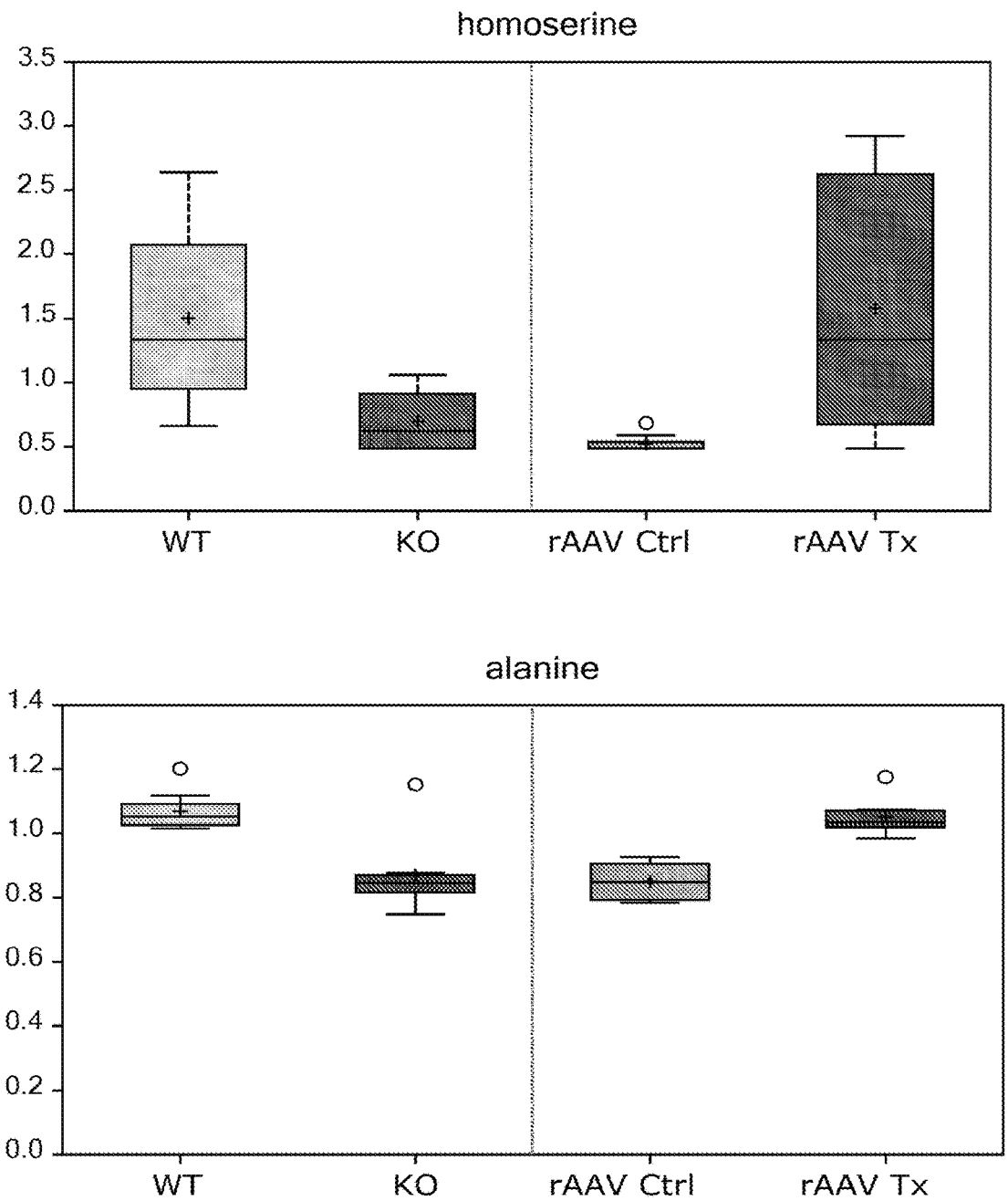
Figure 57:
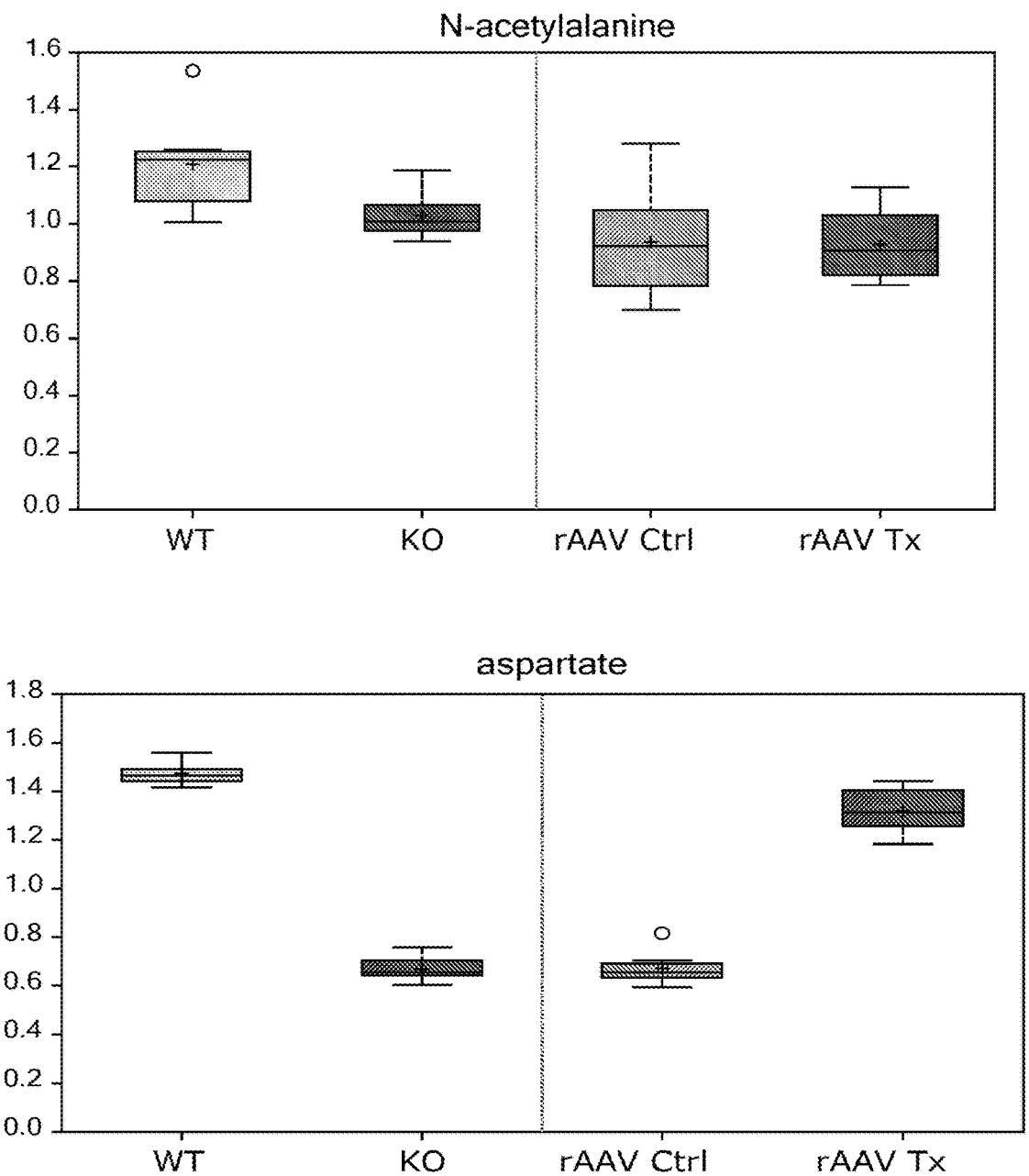
Figure 57:
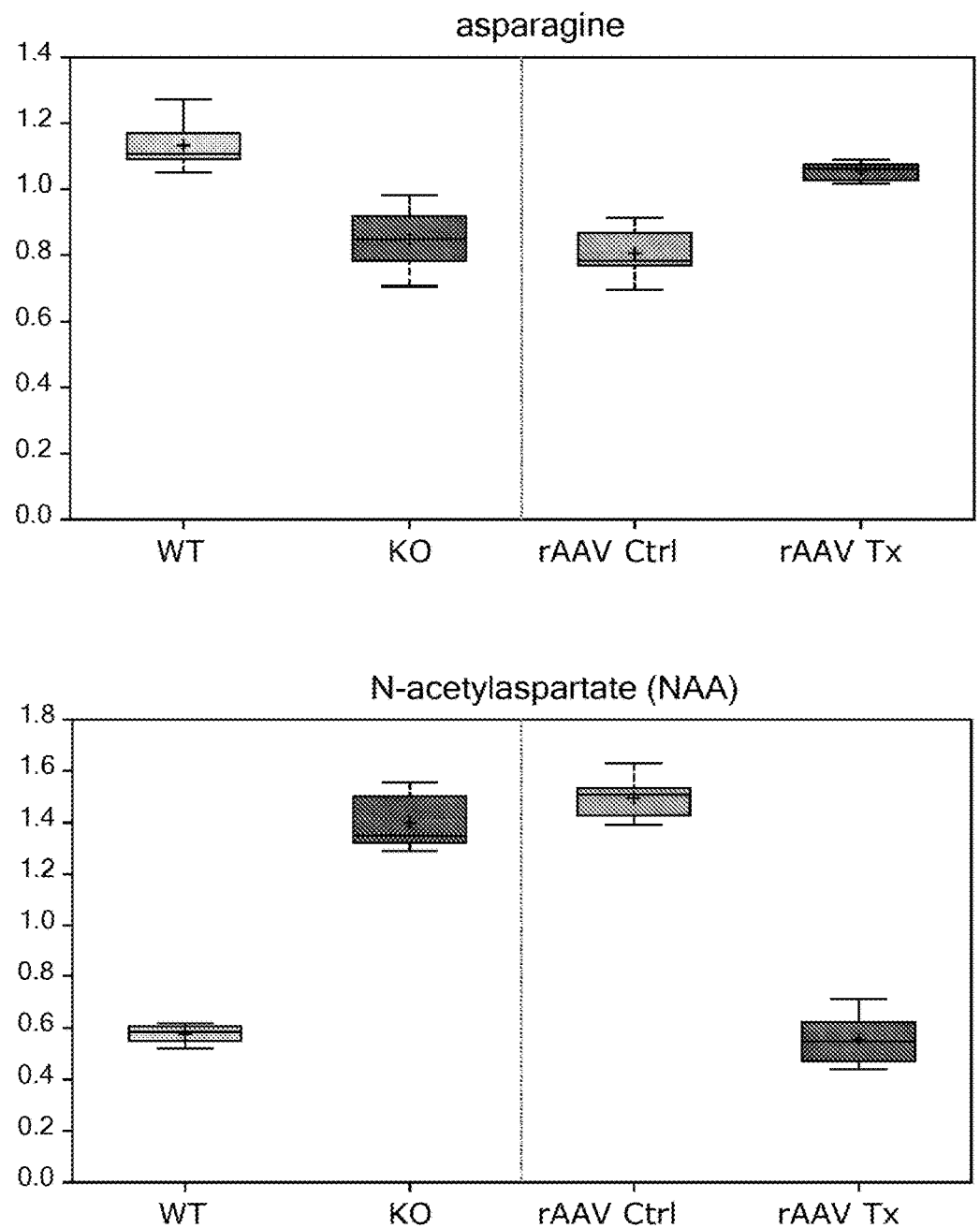
Figure 57:
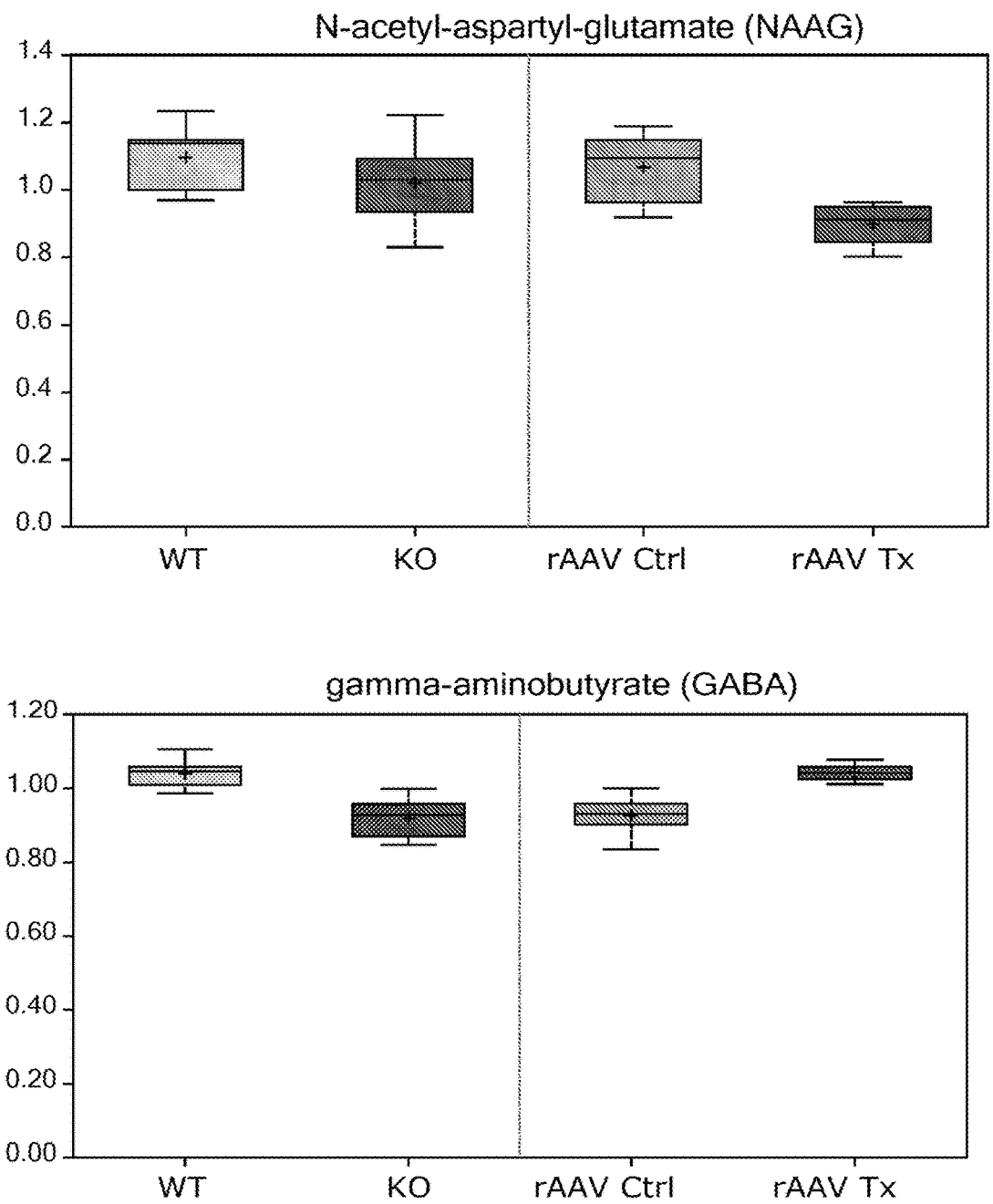
Figure 57:
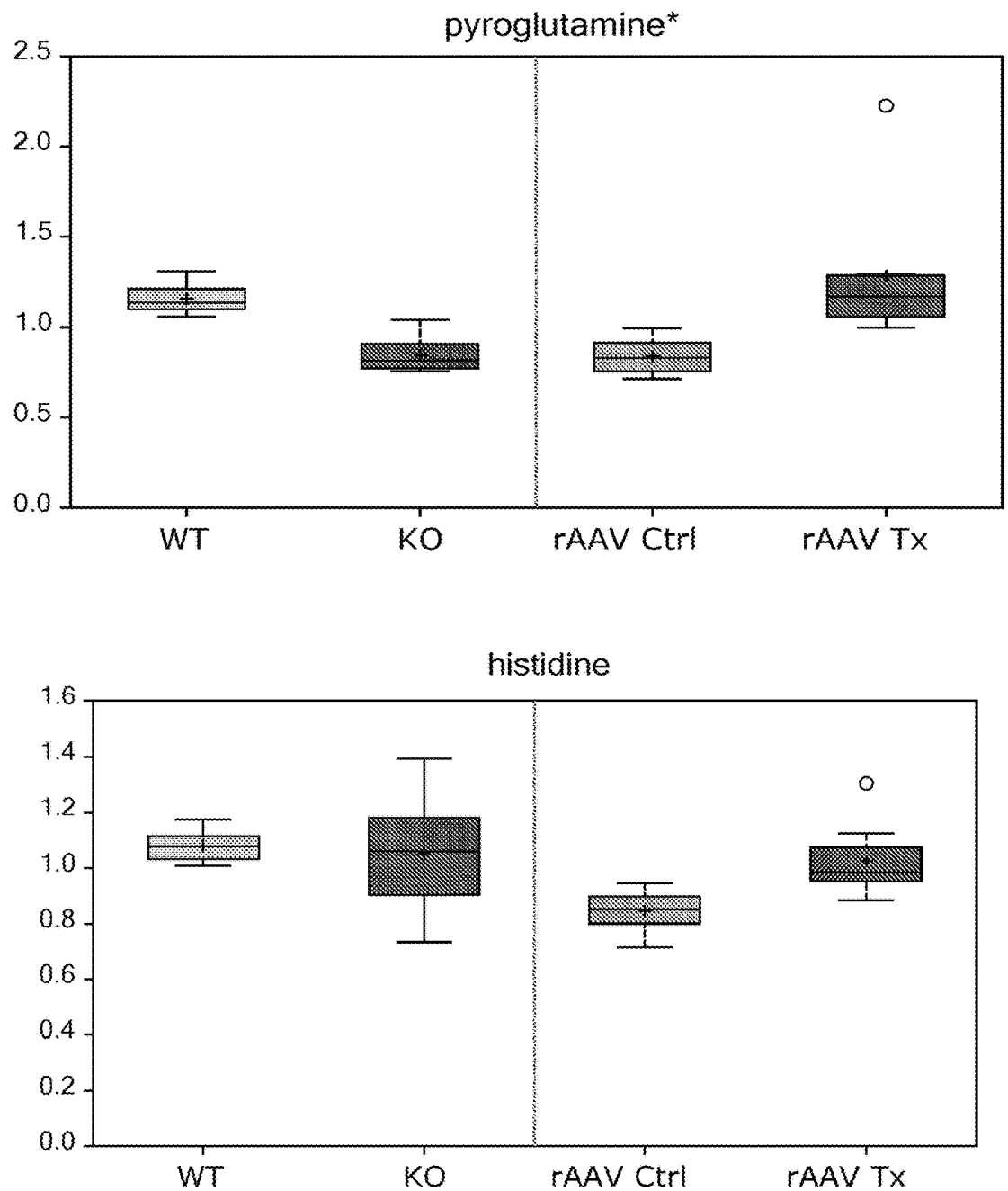
Figure 57:
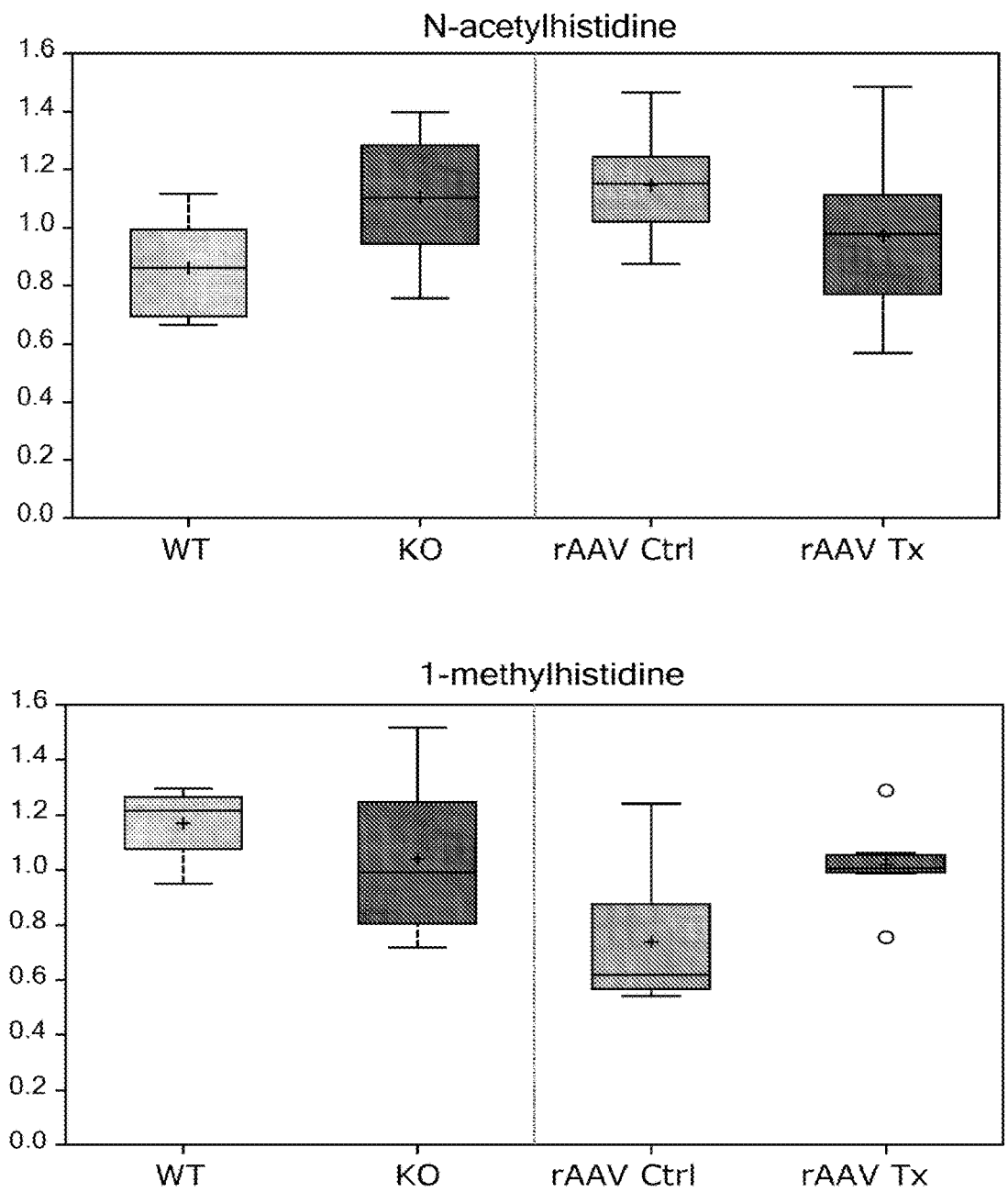
Figure 57:
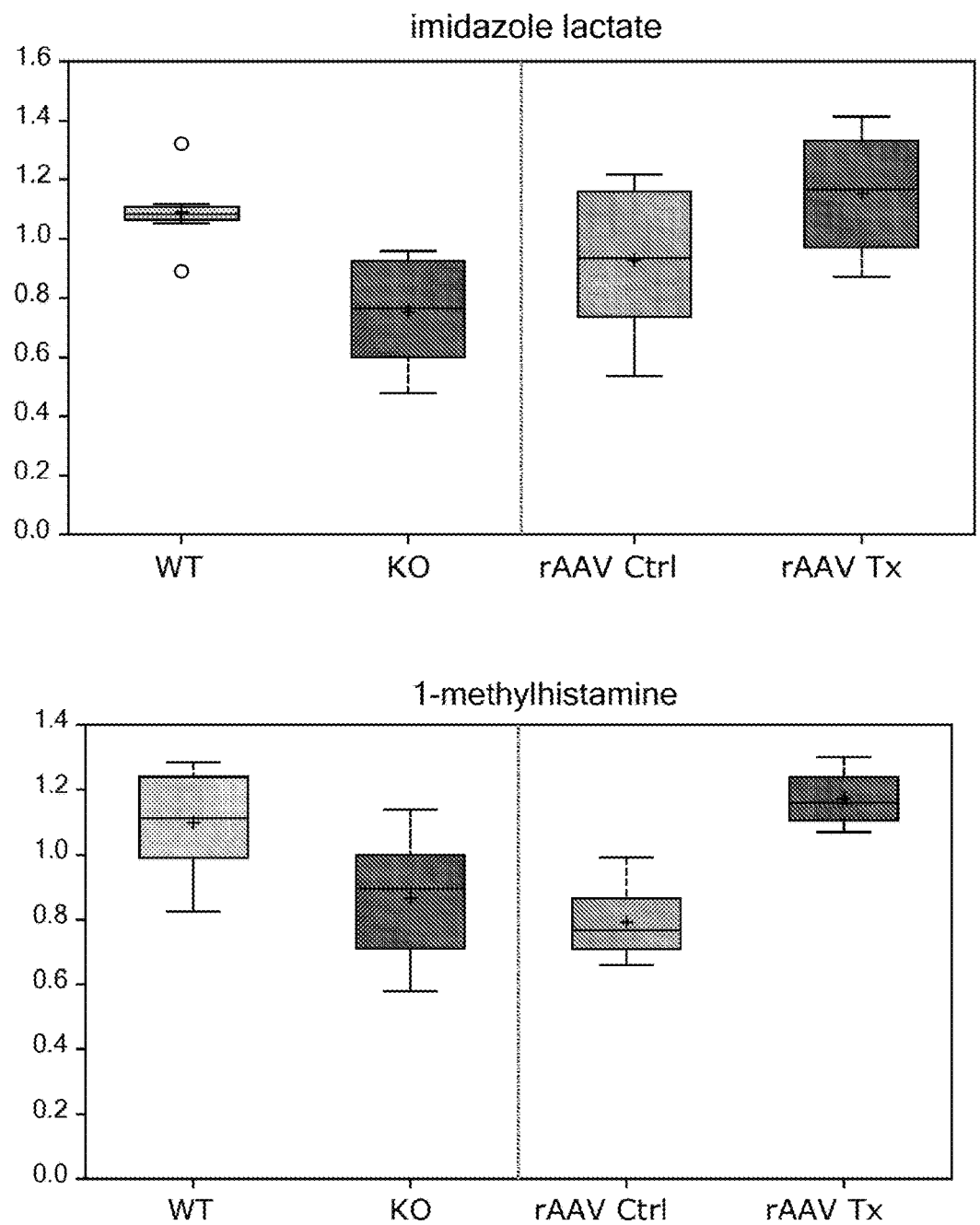
Figure 57:
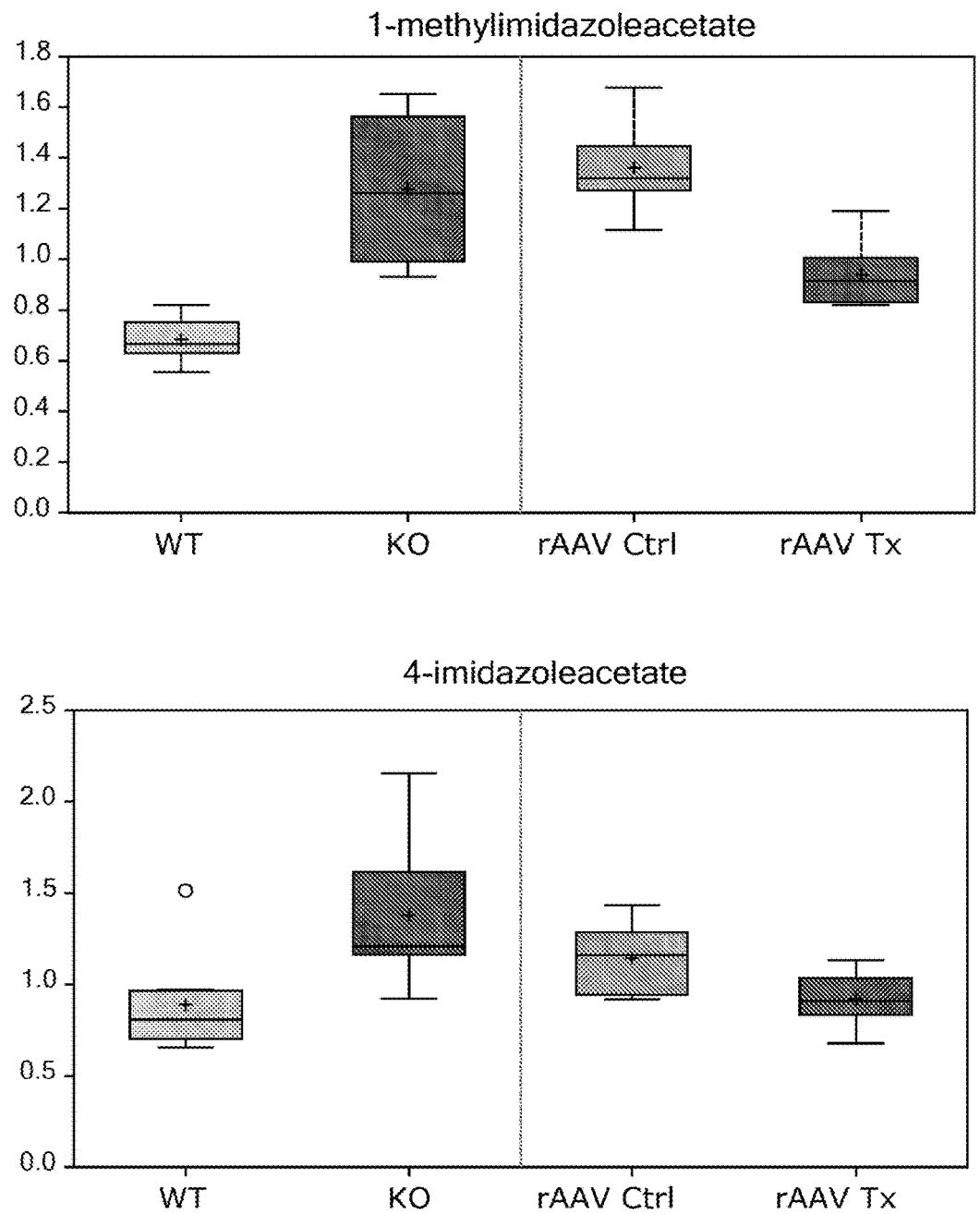
Figure 57:
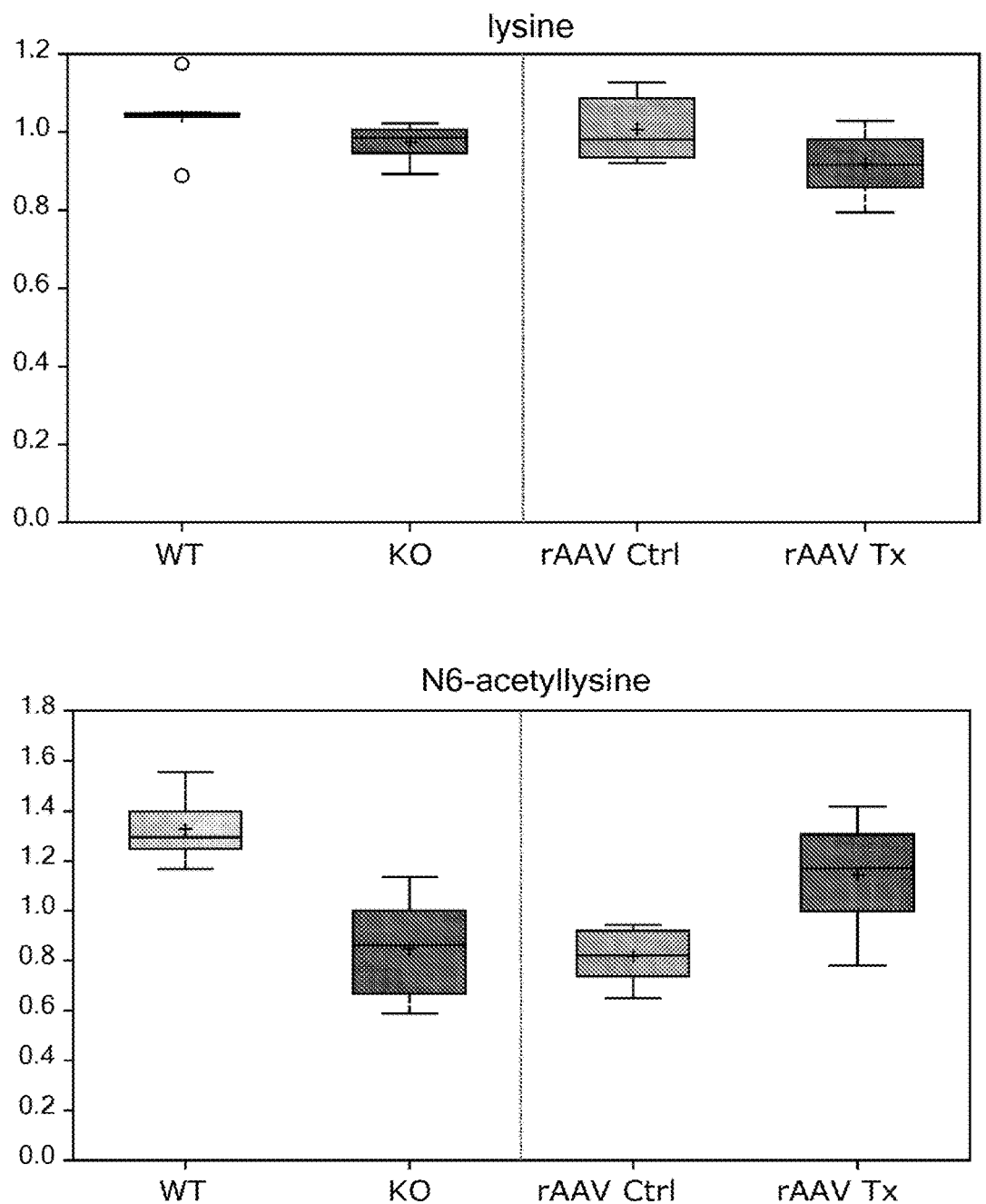
Figure 57:
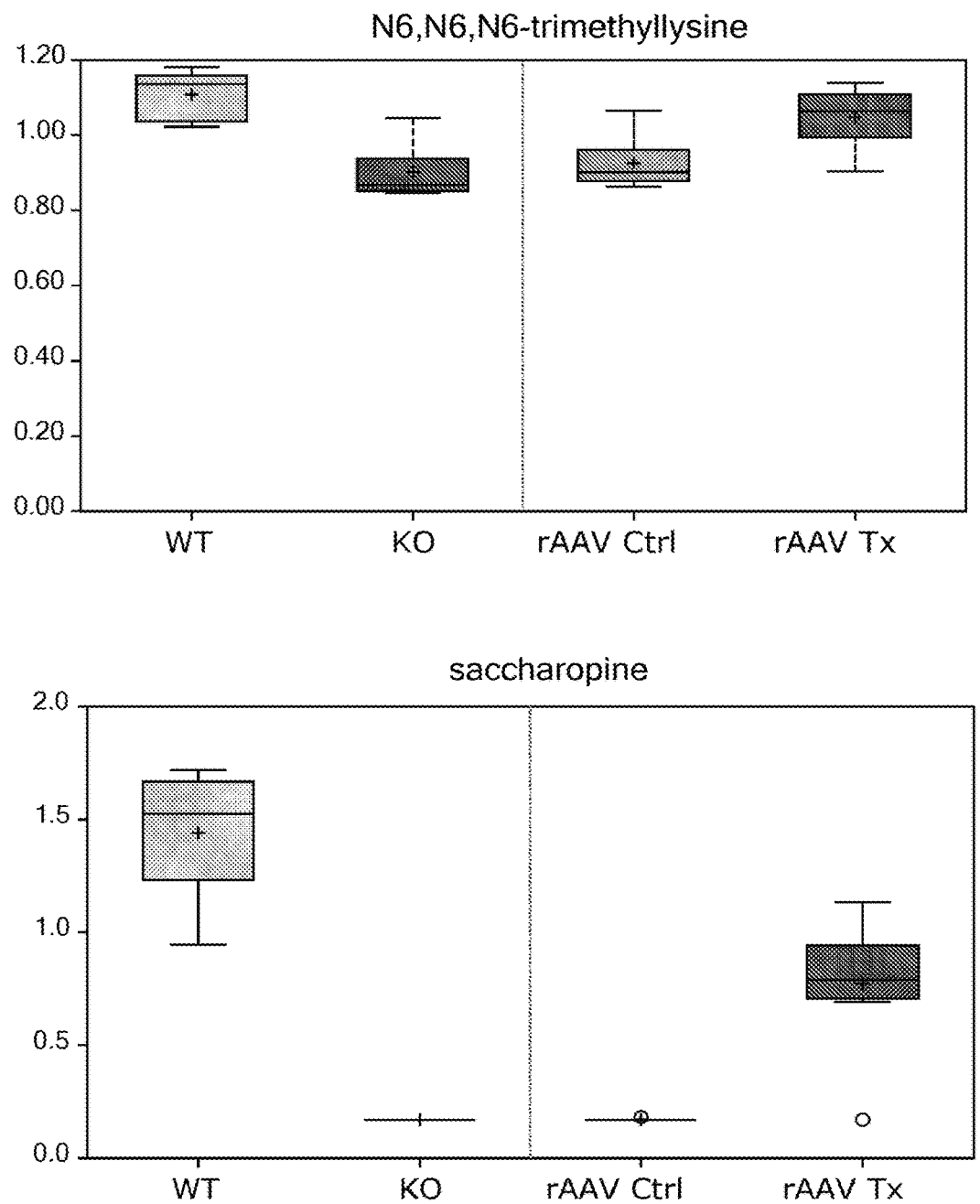
Figure 57:
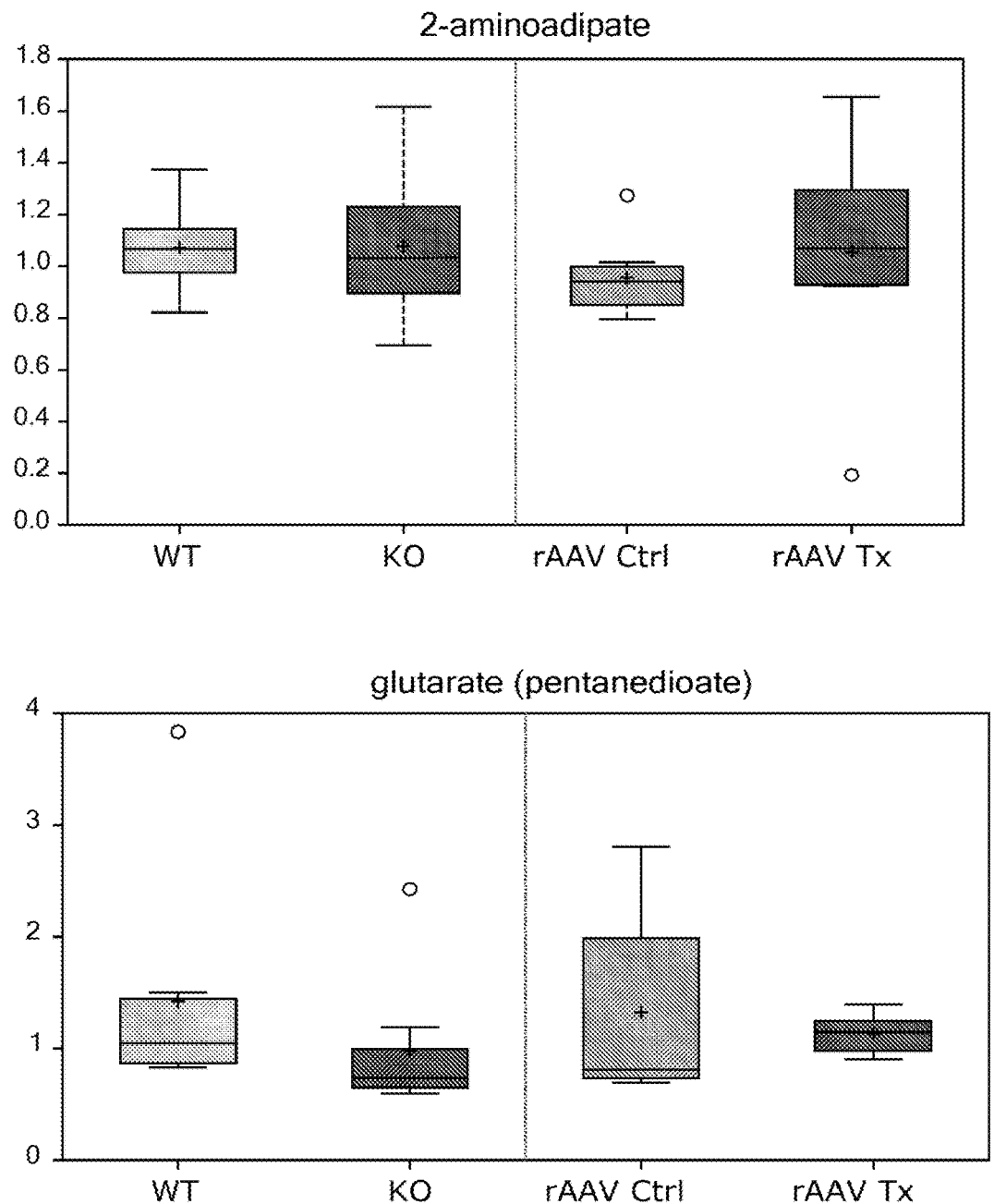
Figure 57:
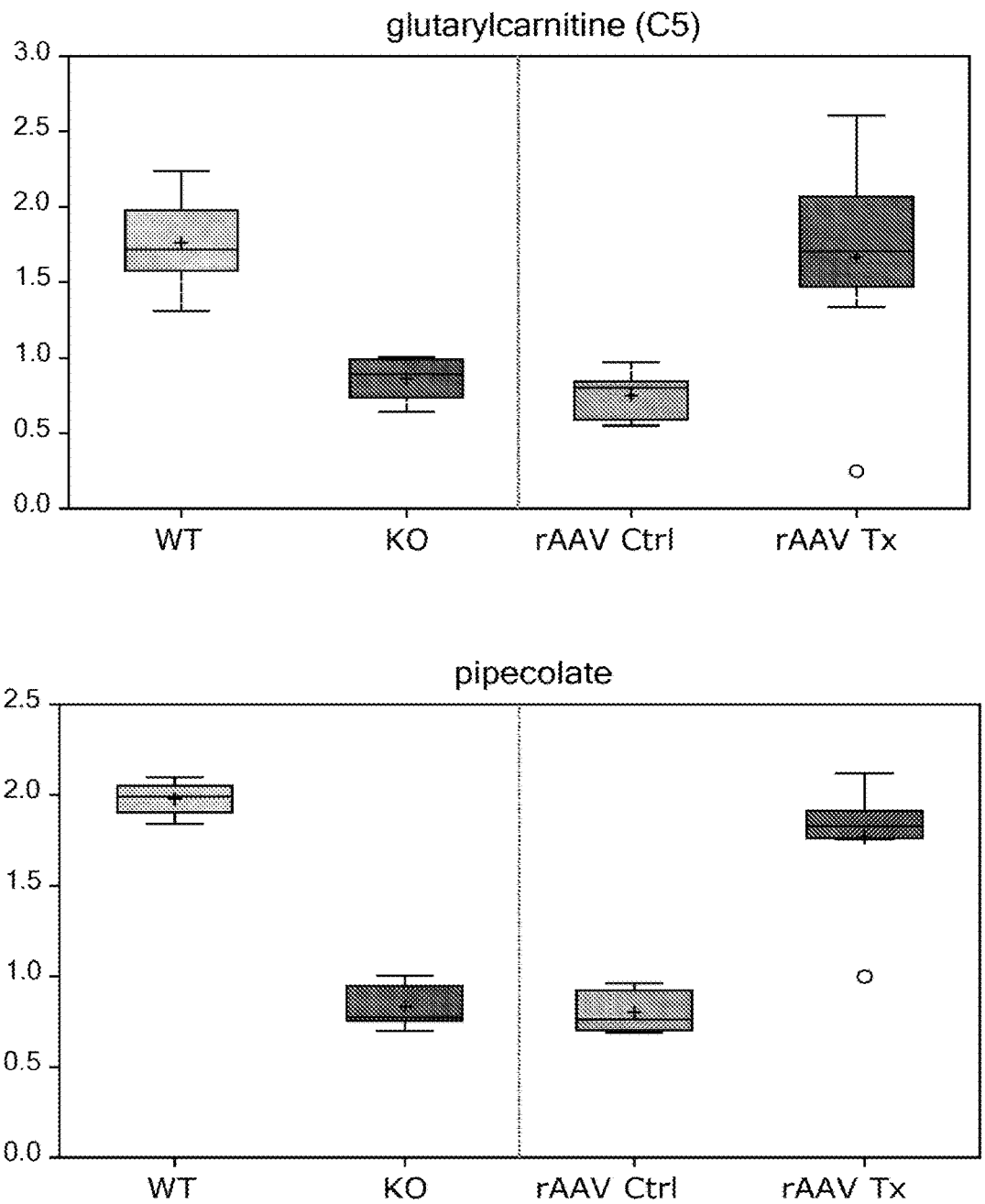
Figure 57:
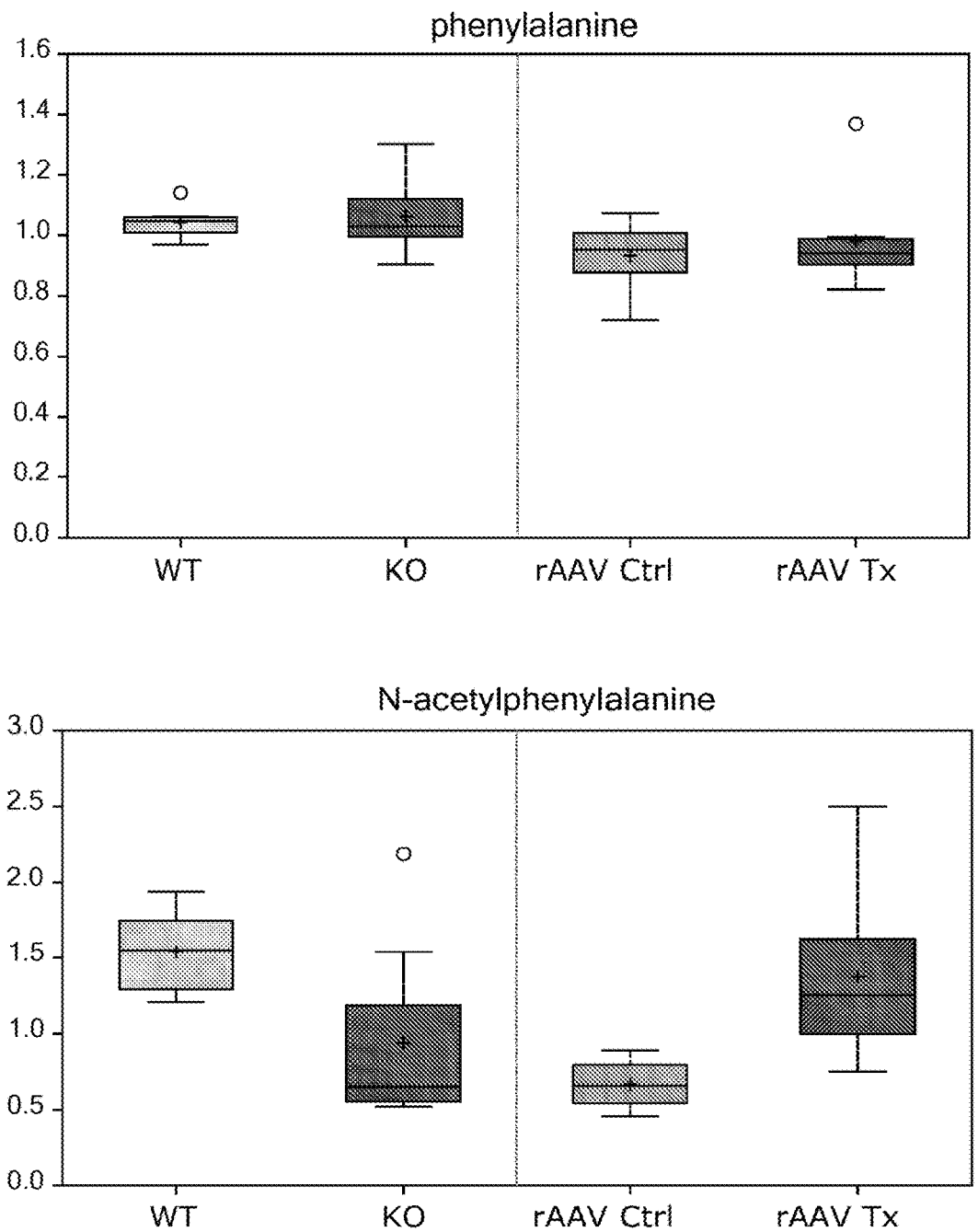
Figure 57:
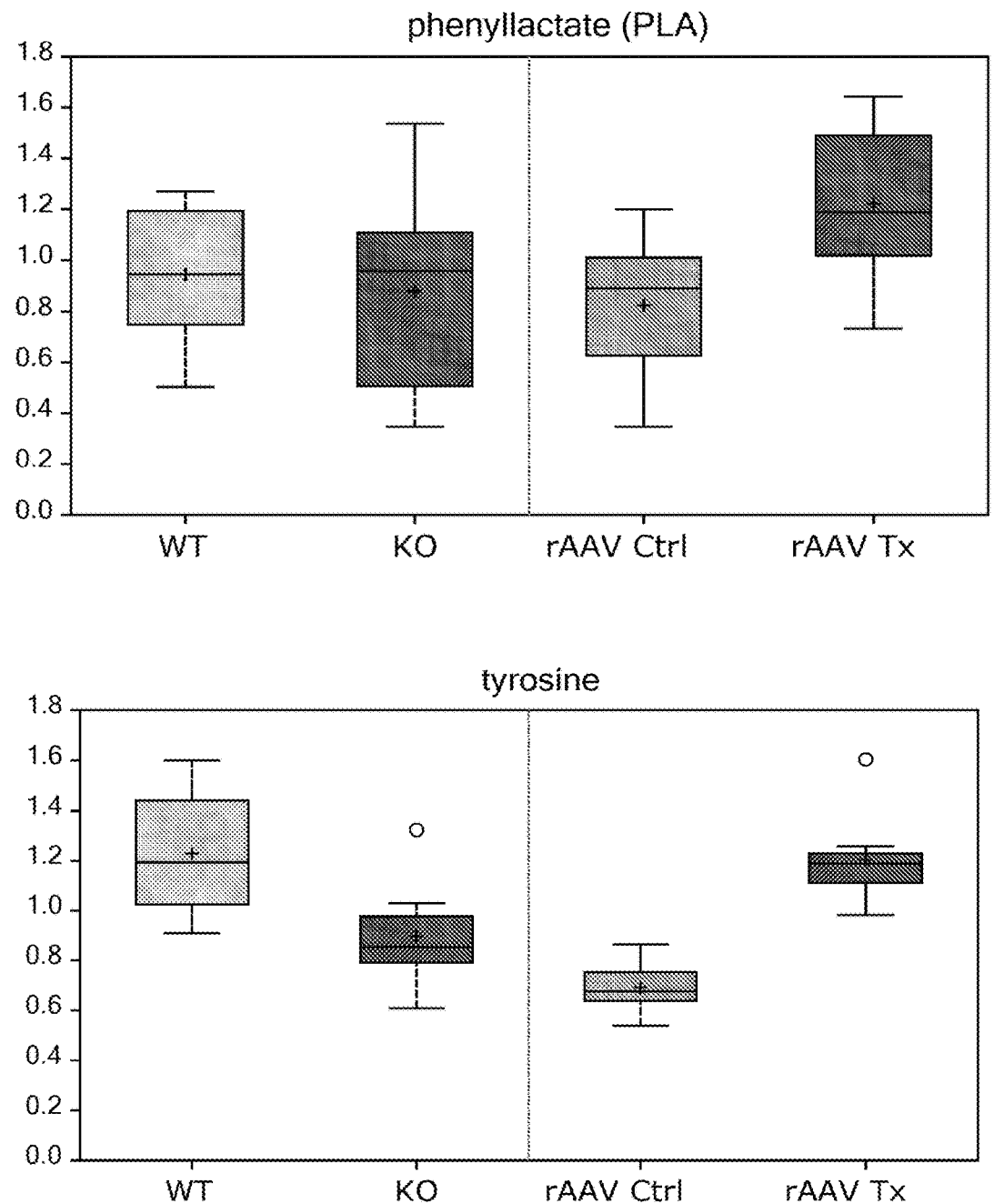
Figure 57:
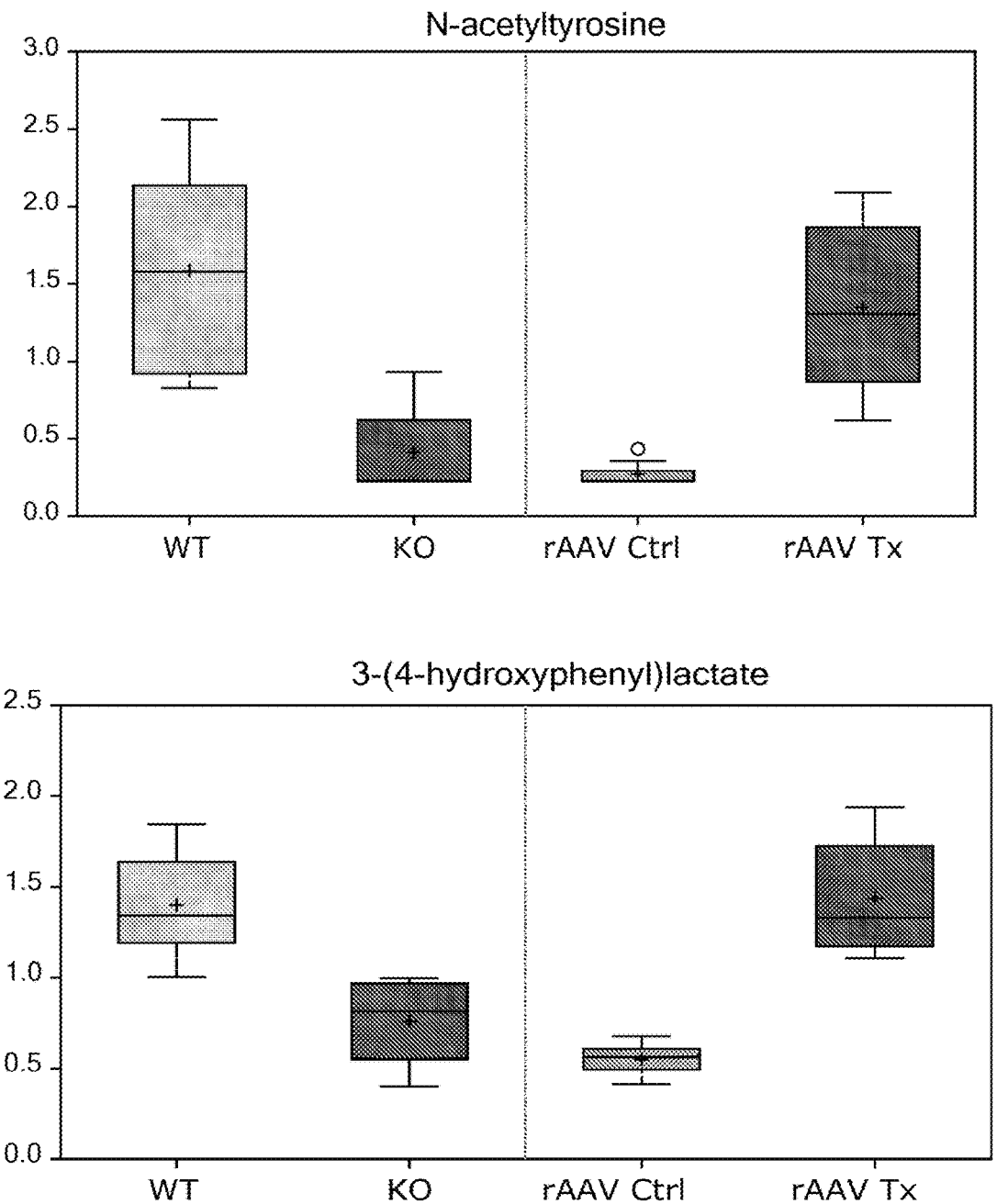
Figure 57:
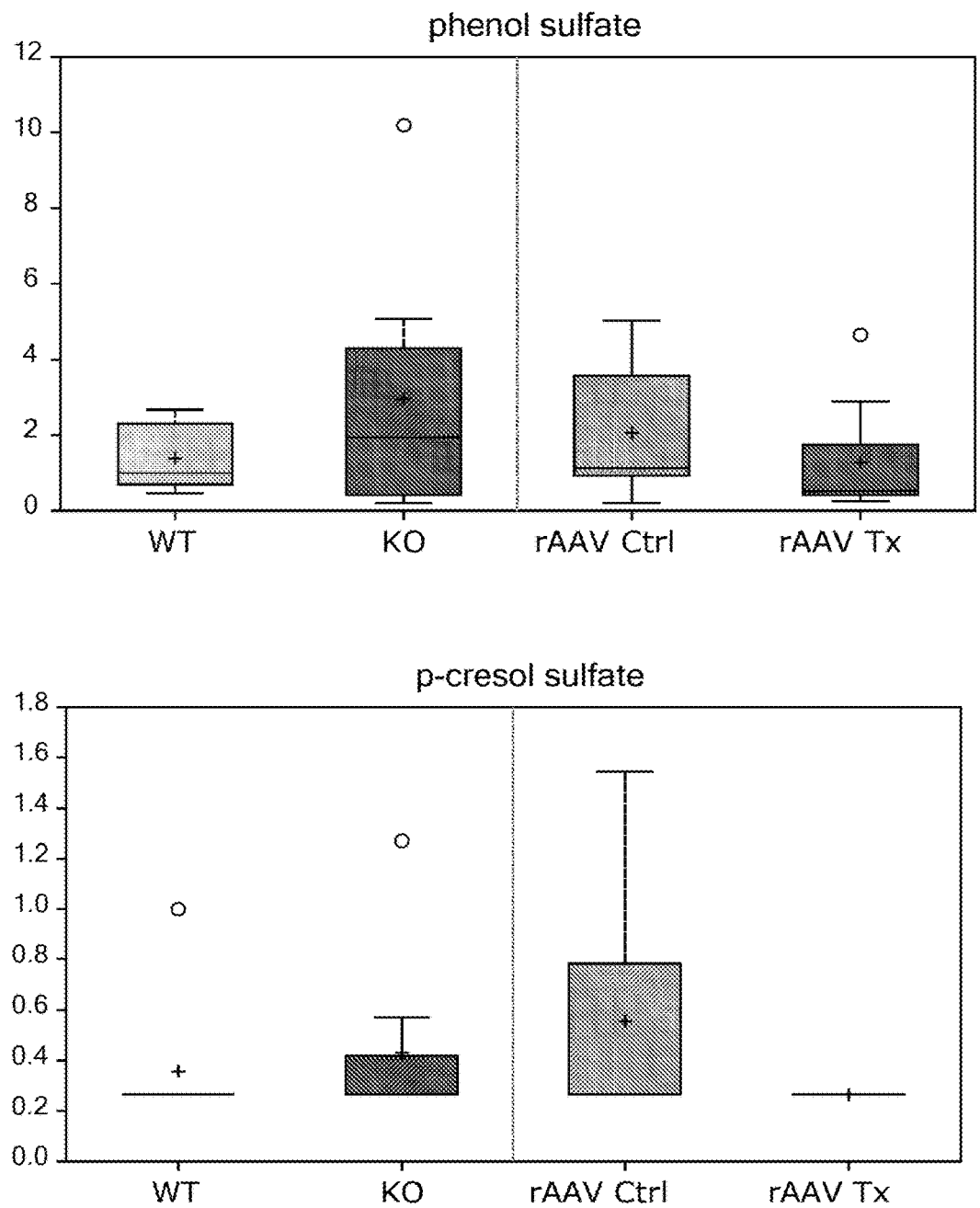
Figure 57:
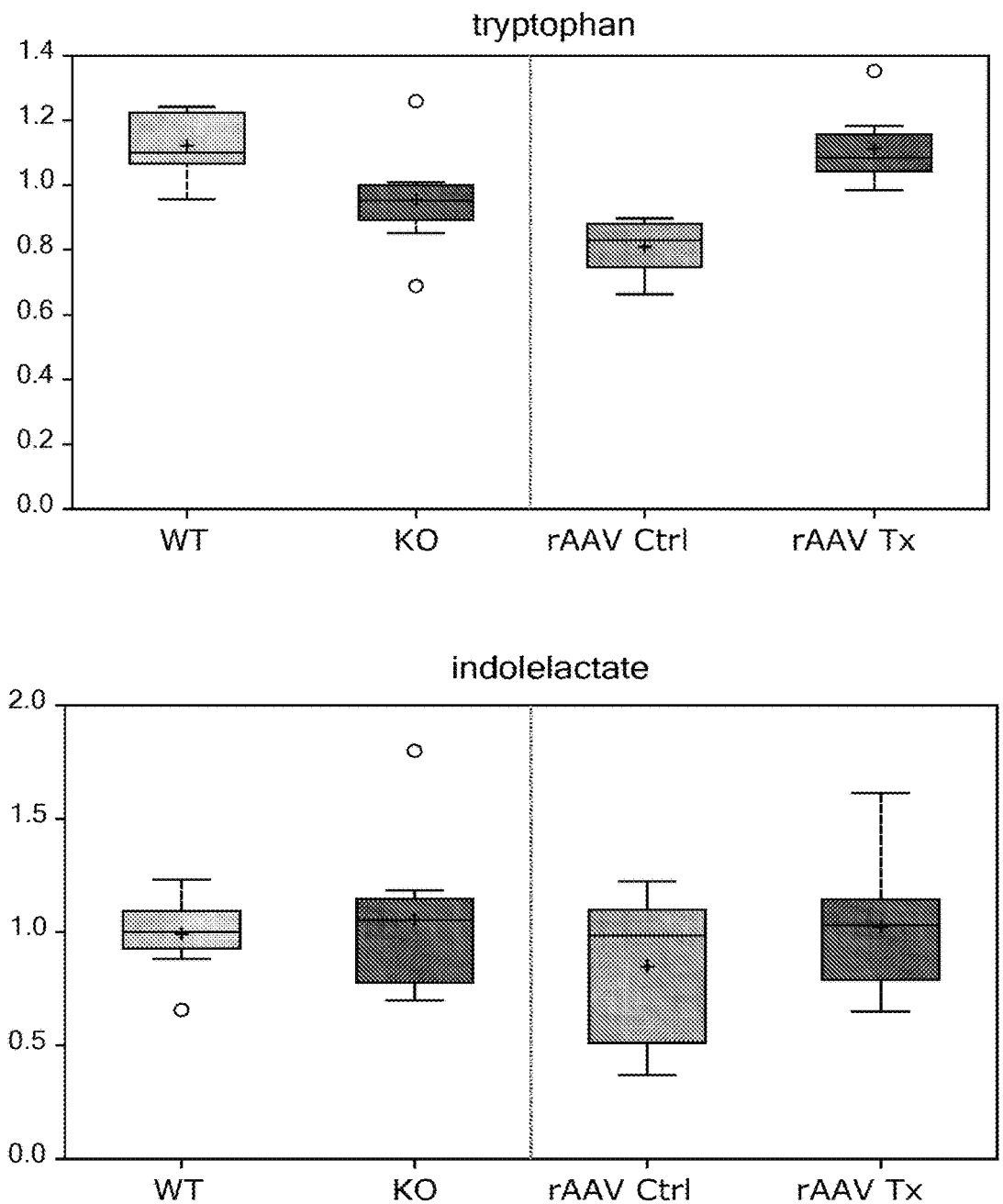
Figure 57:
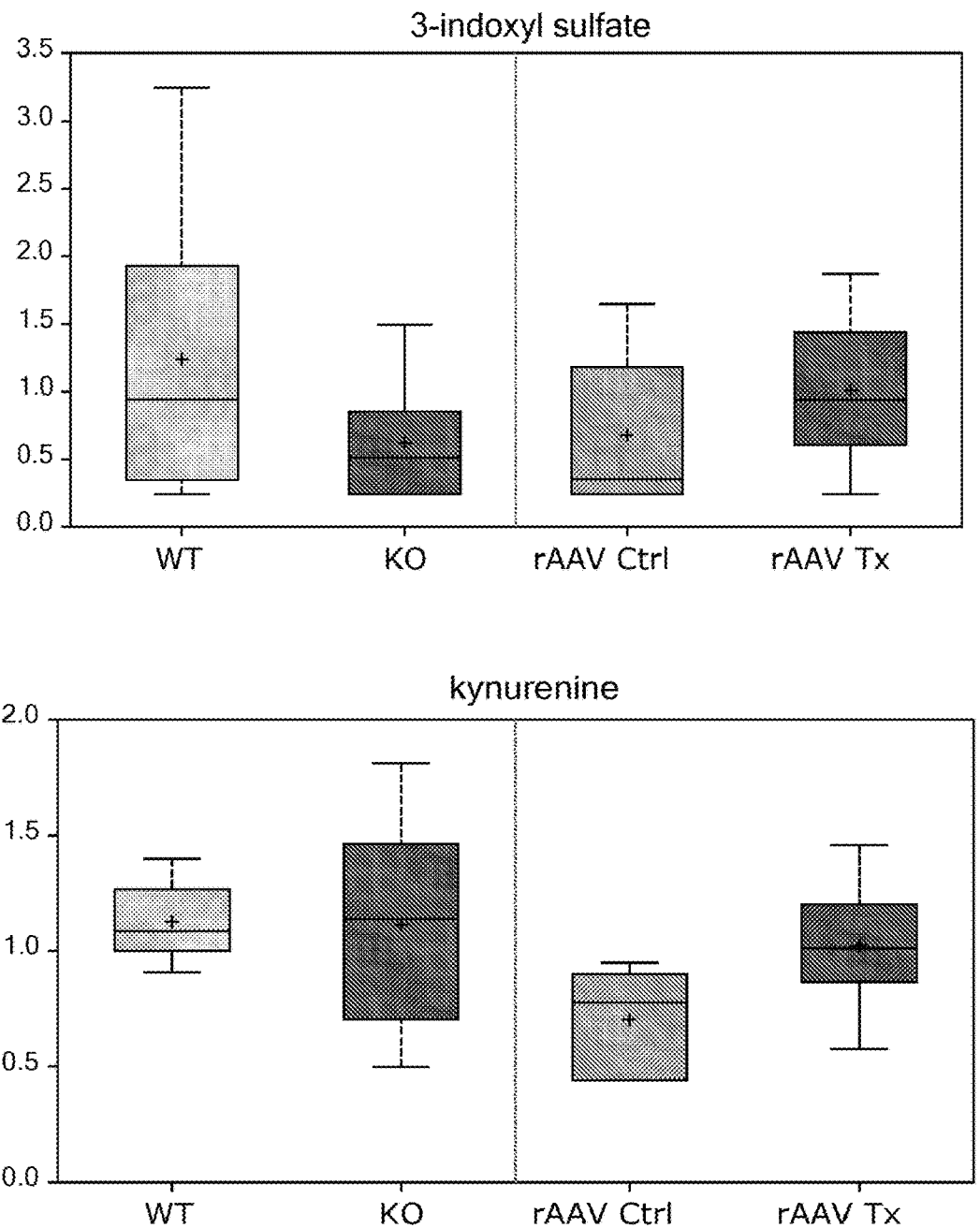
Figure 57:
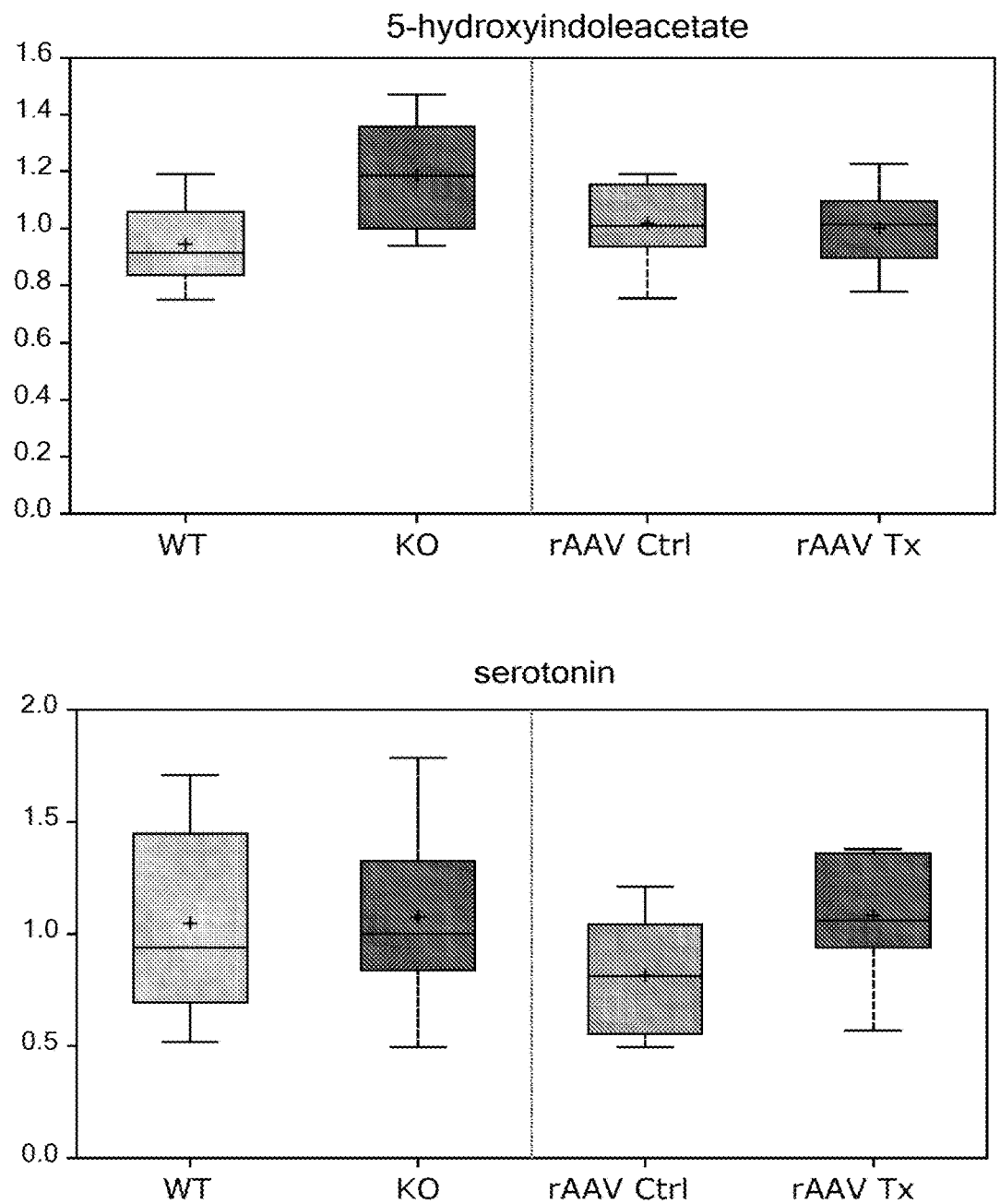
Figure 57:
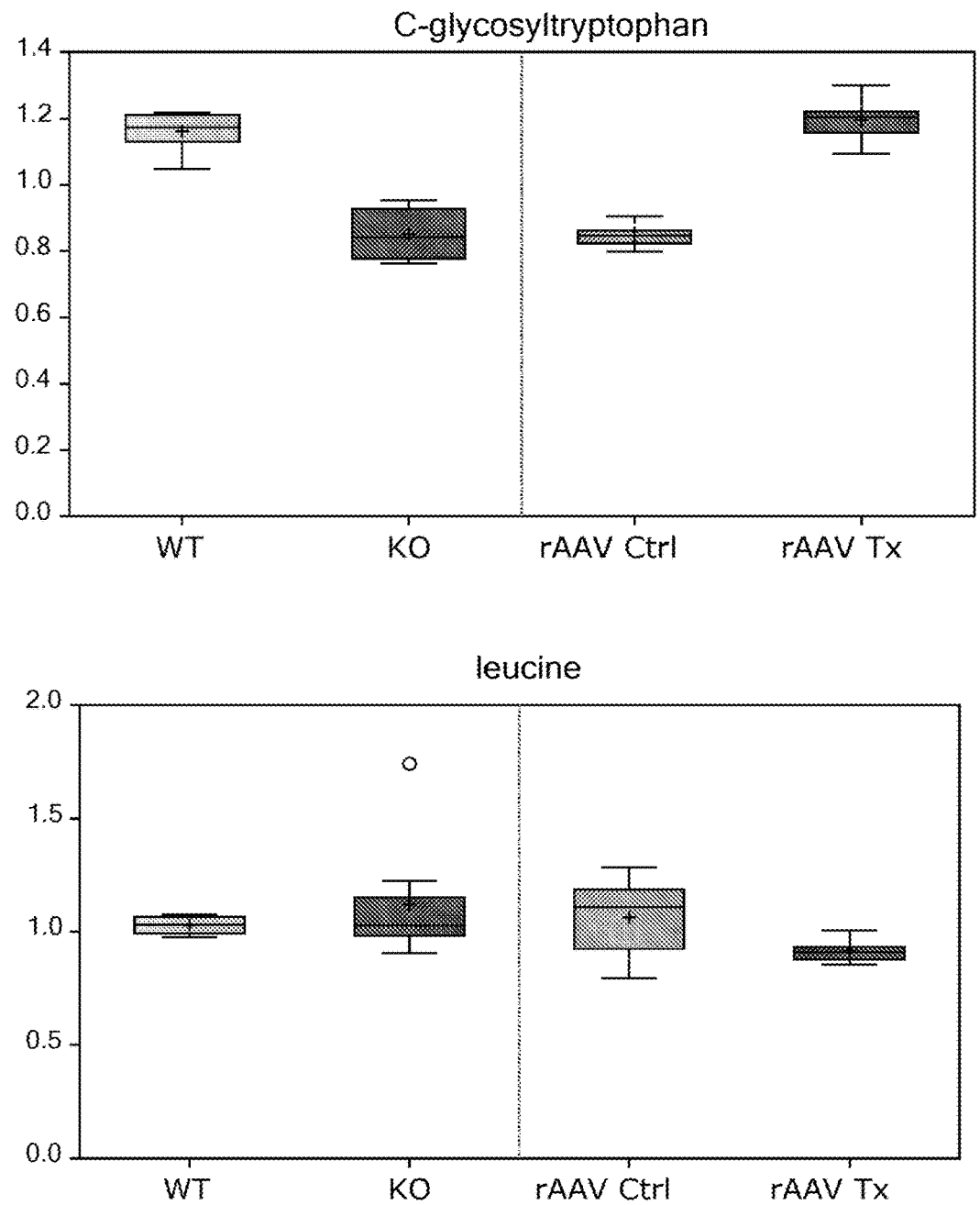
Figure 57:
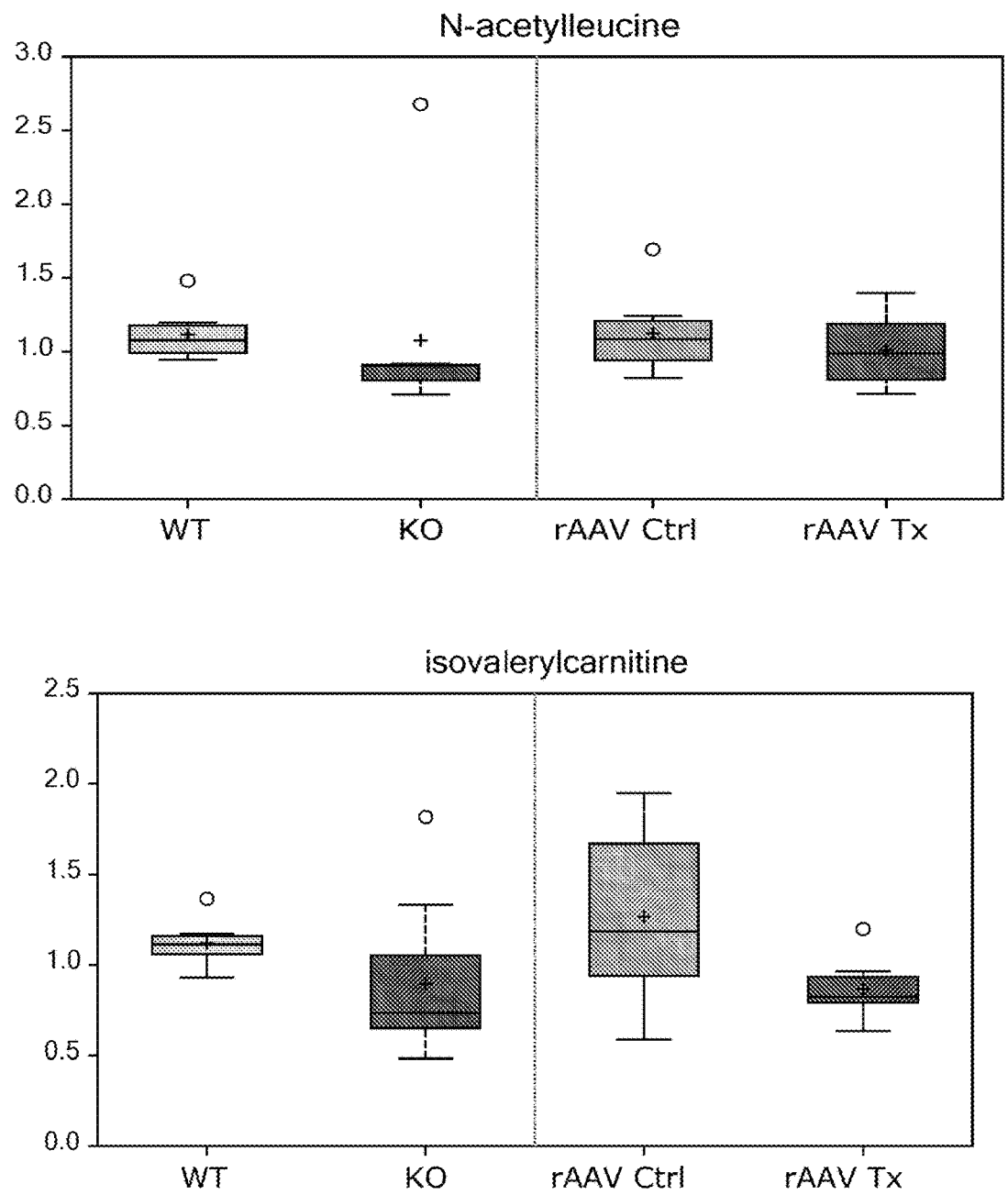
Figure 57:
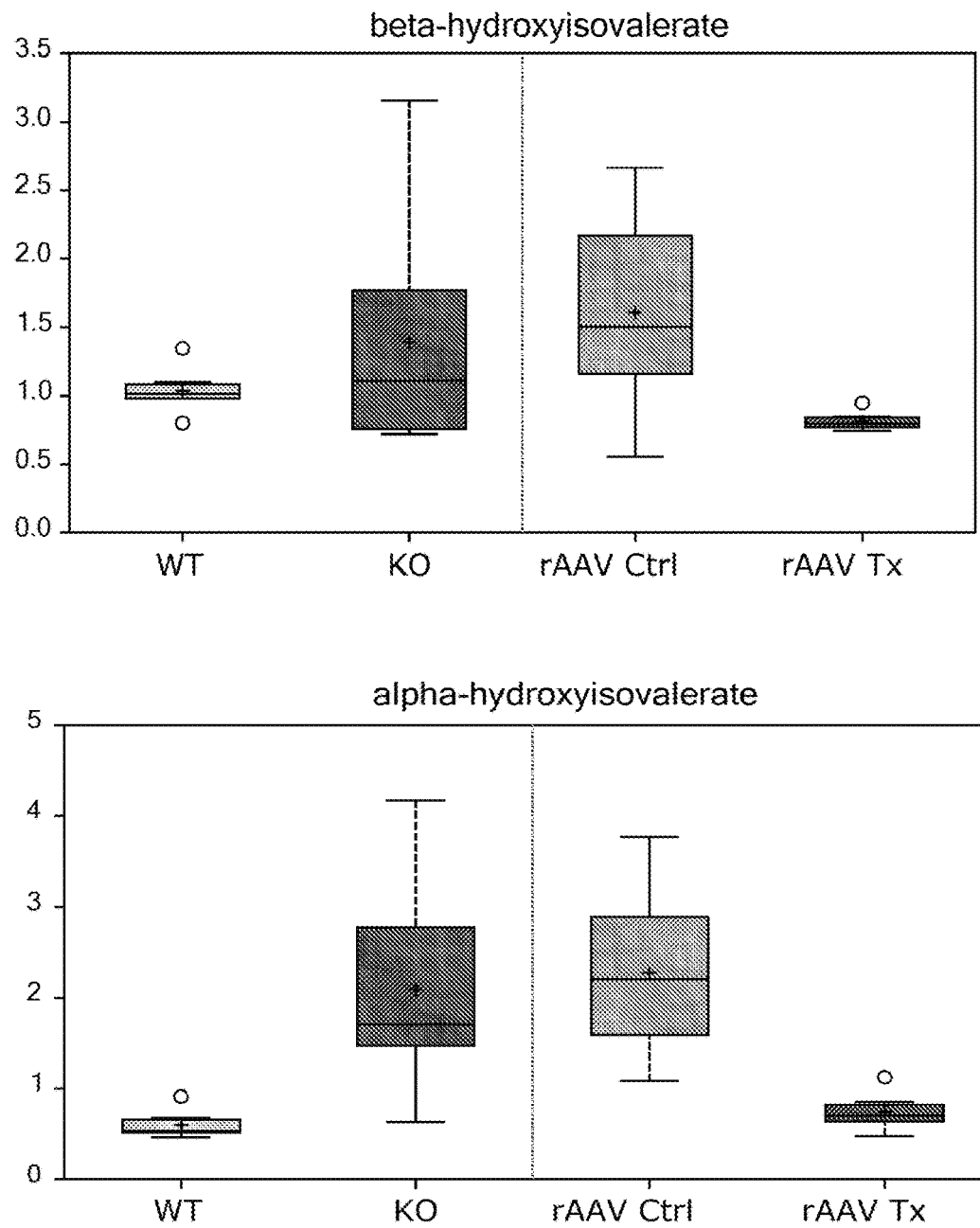
Figure 57:
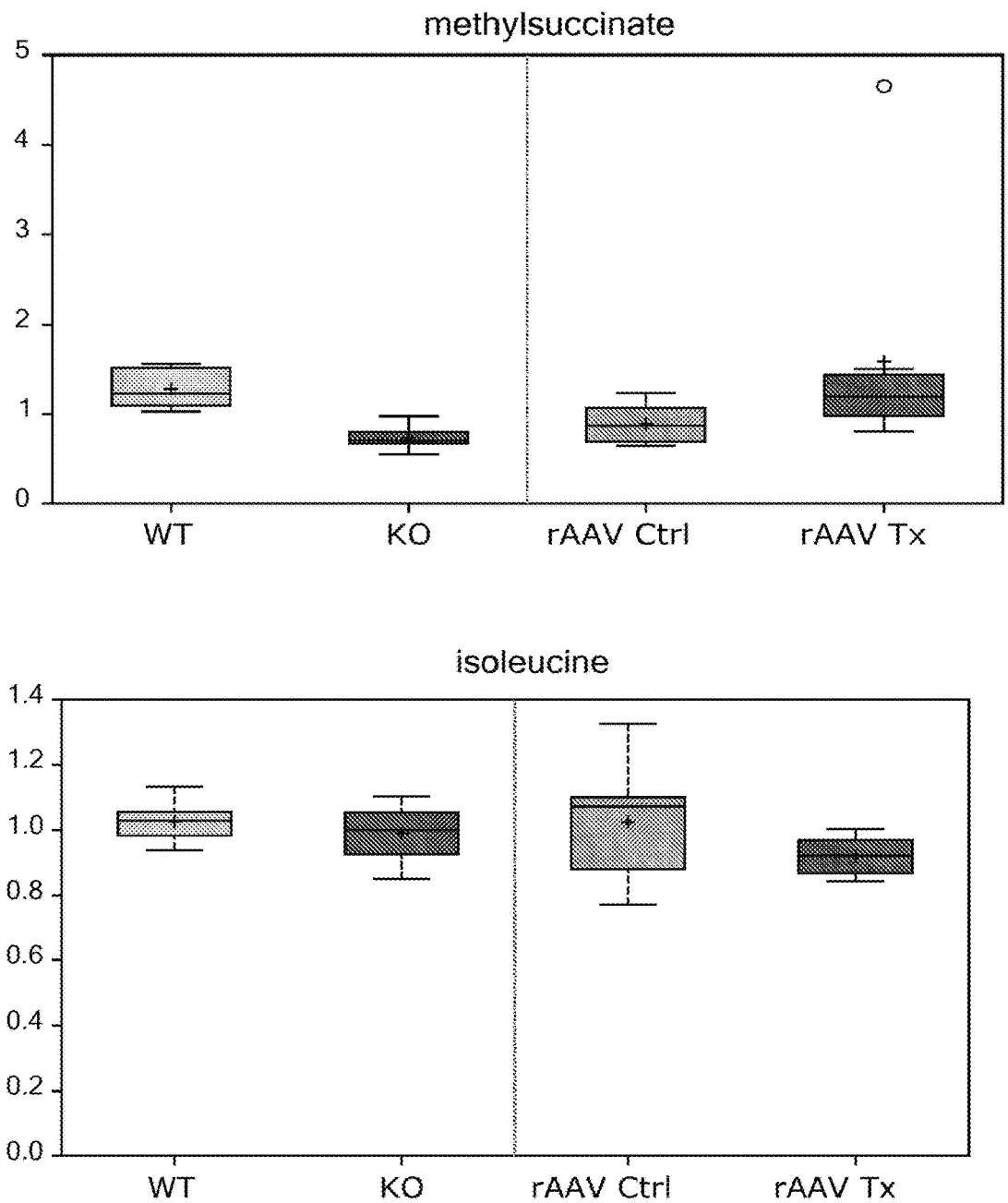
Figure 57:
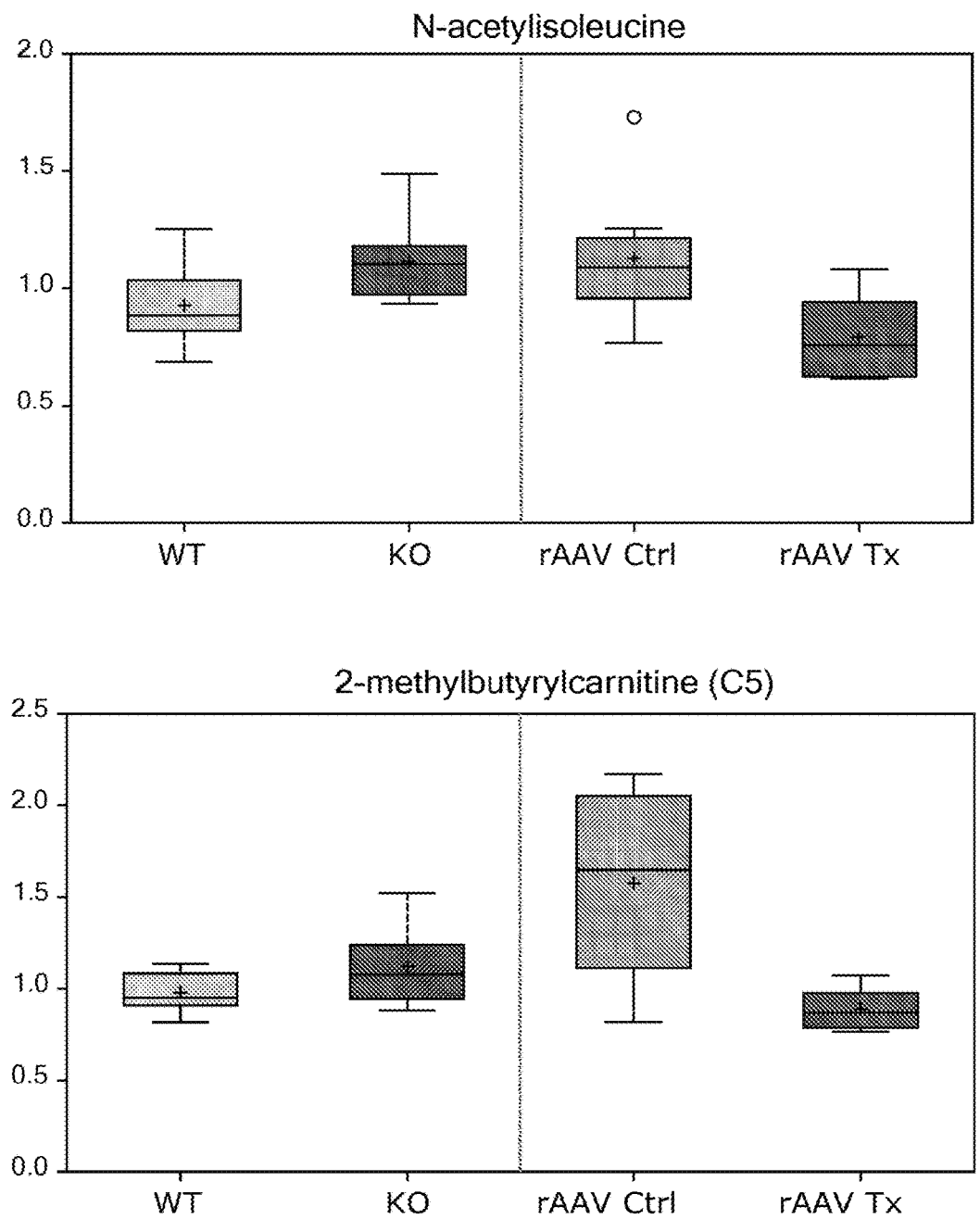
Figure 57:
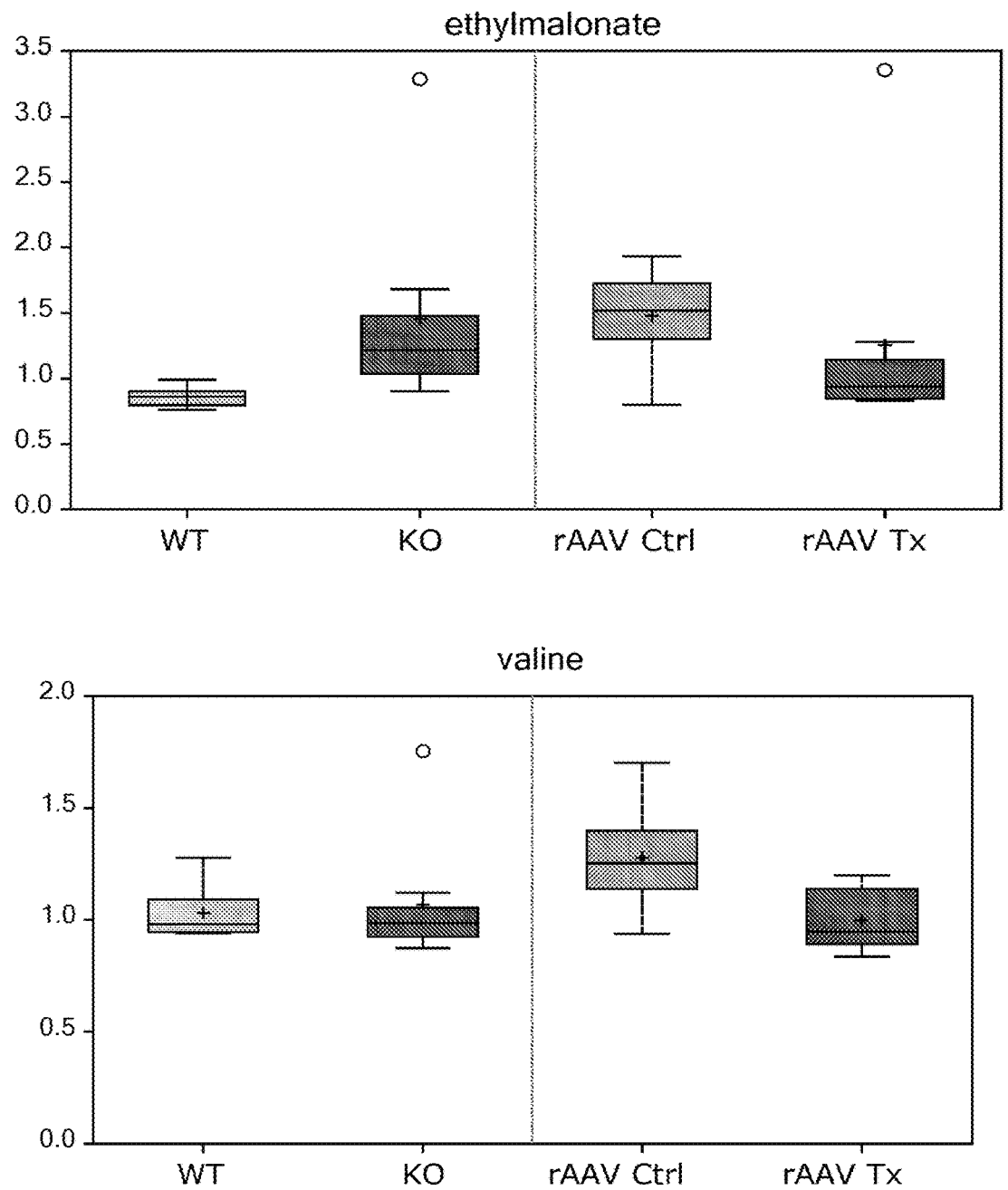
Figure 57:
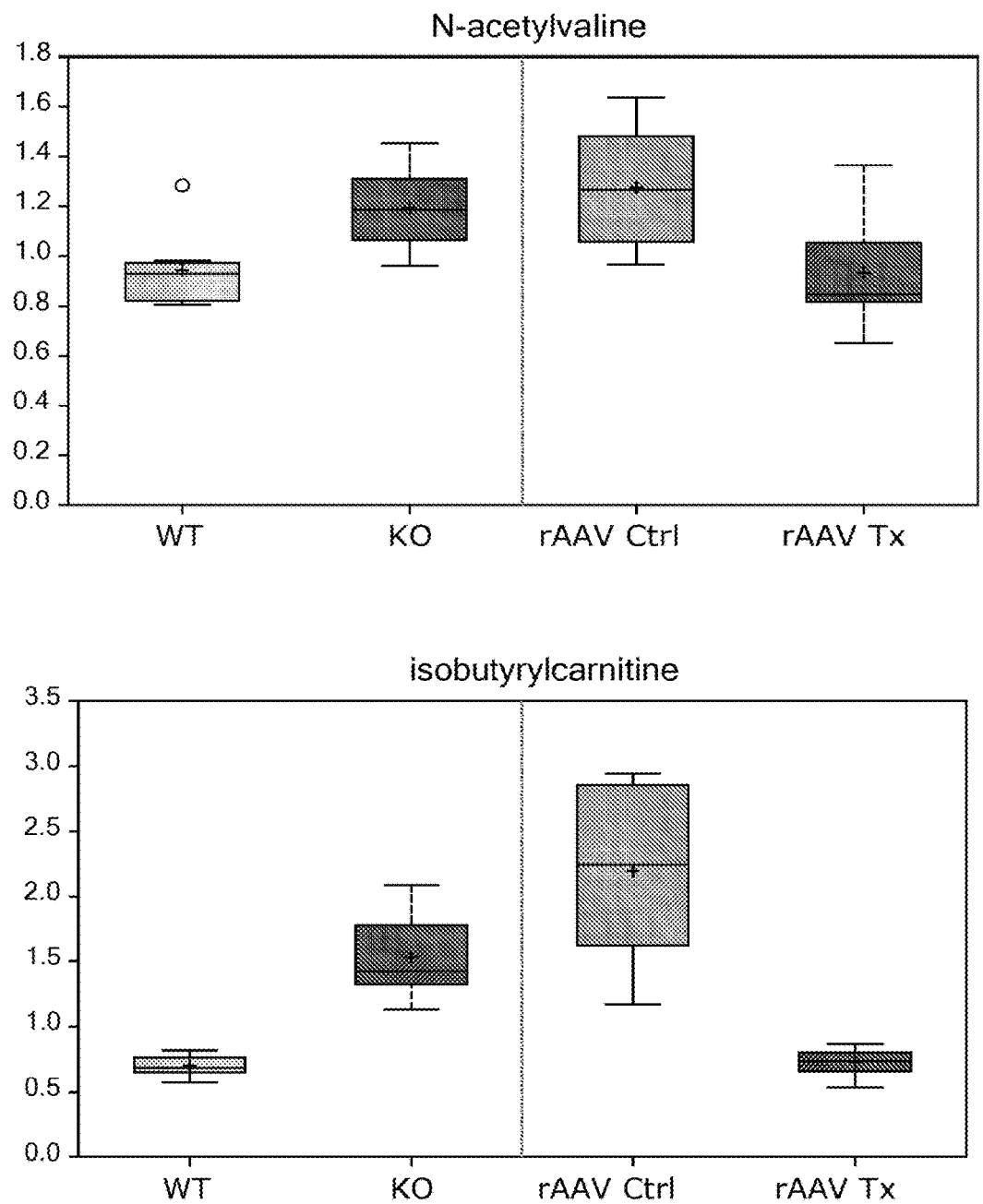
Figure 57:
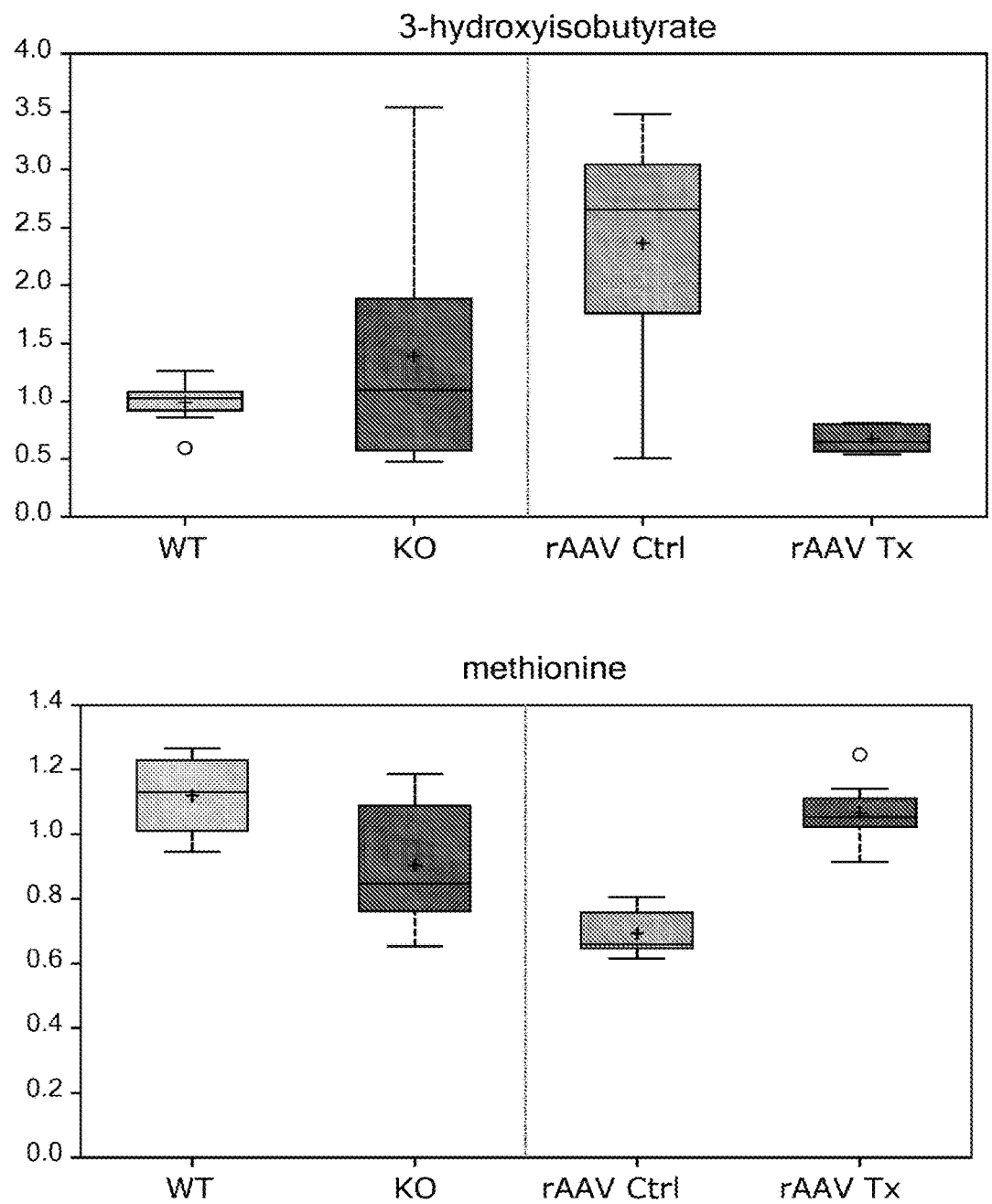
Figure 57:
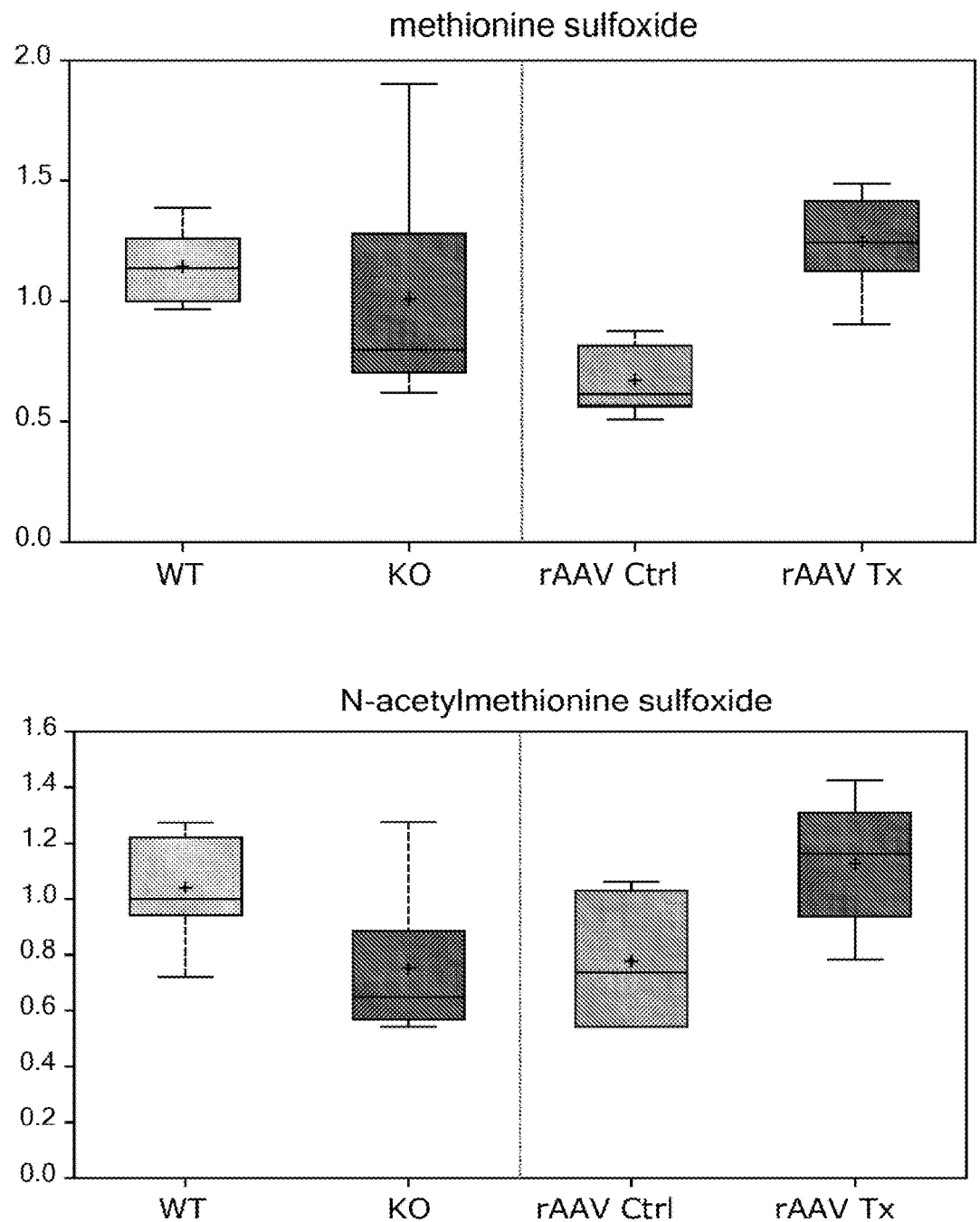
Figure 57:
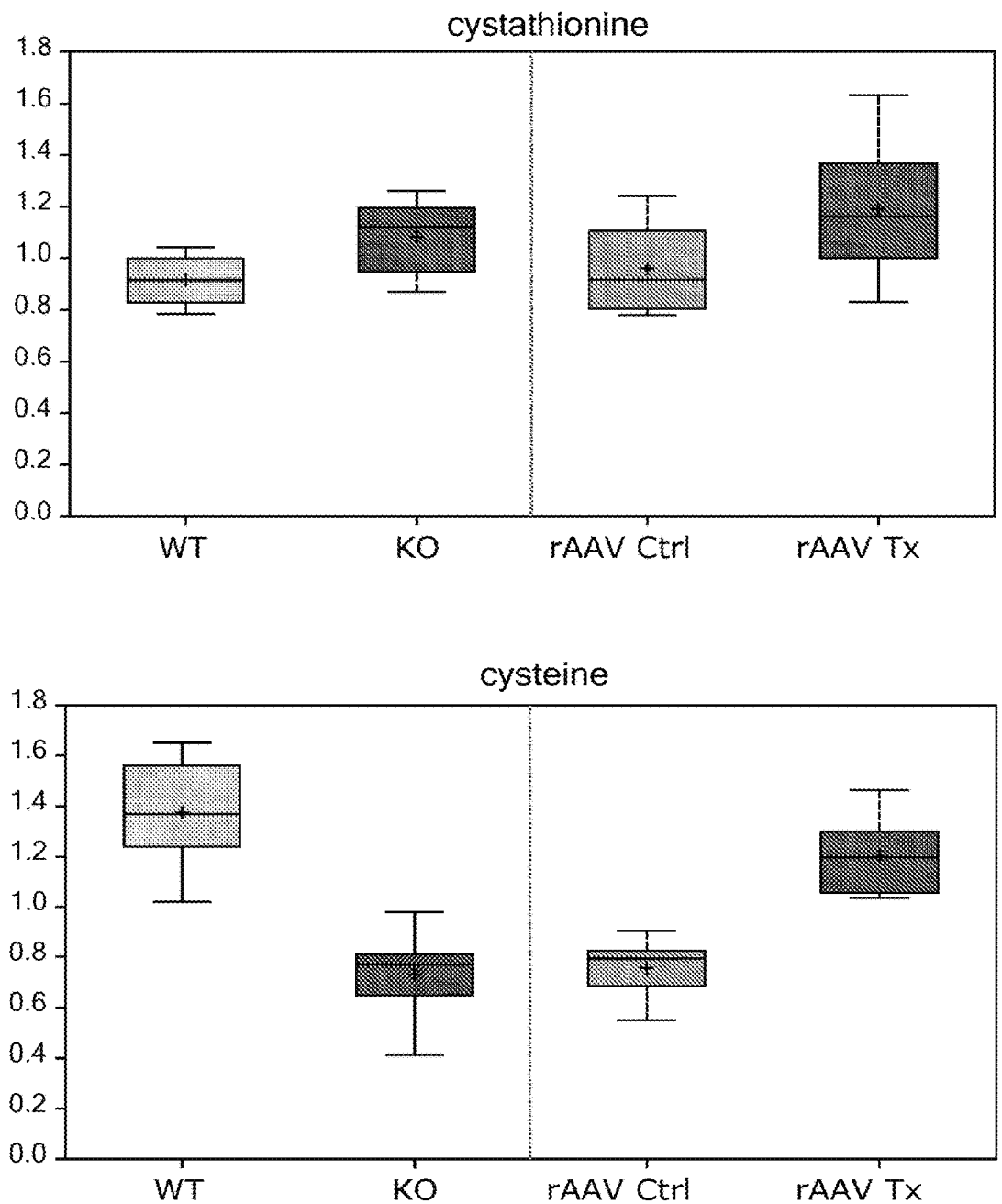
Figure 57:
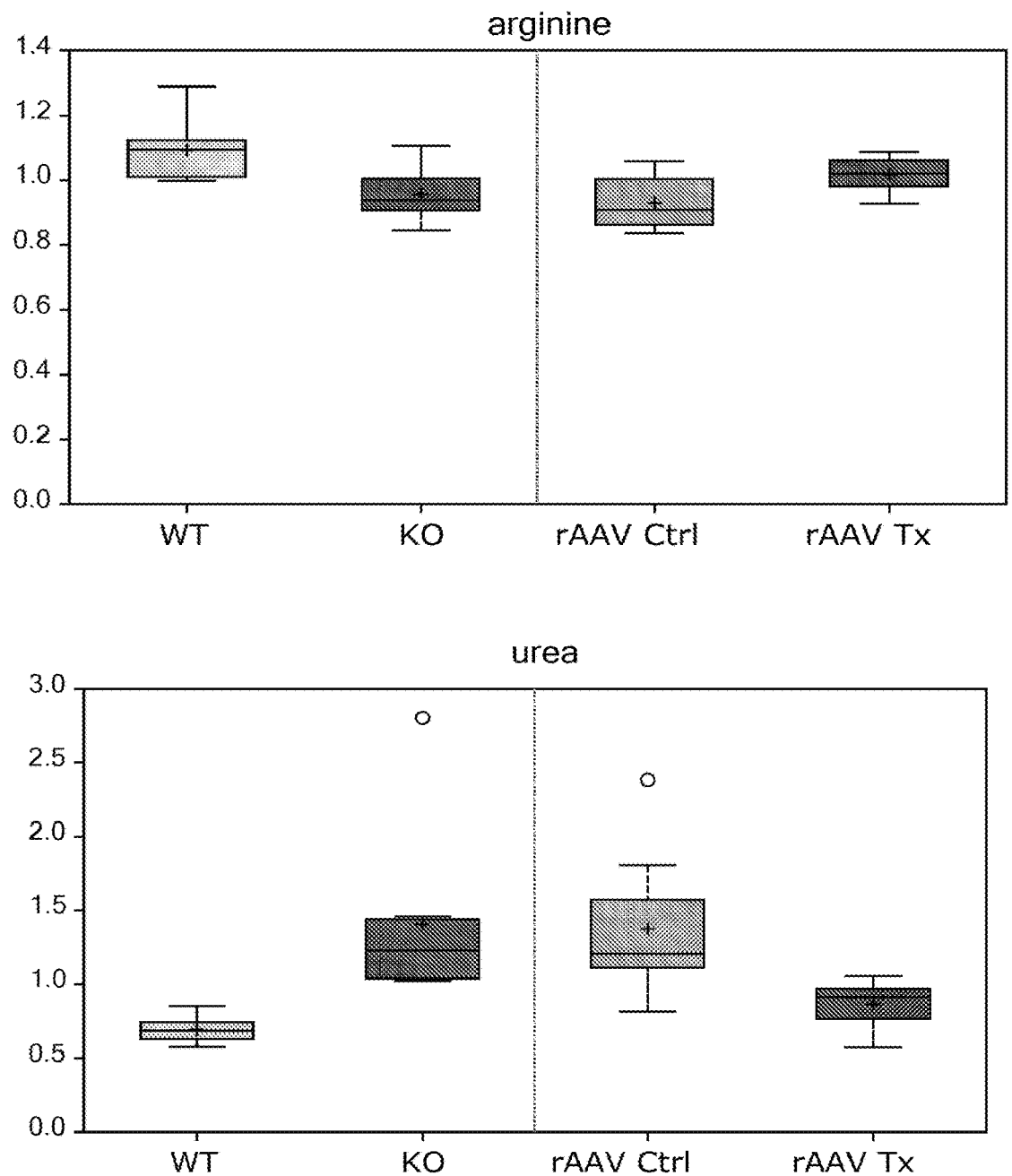
Figure 57:
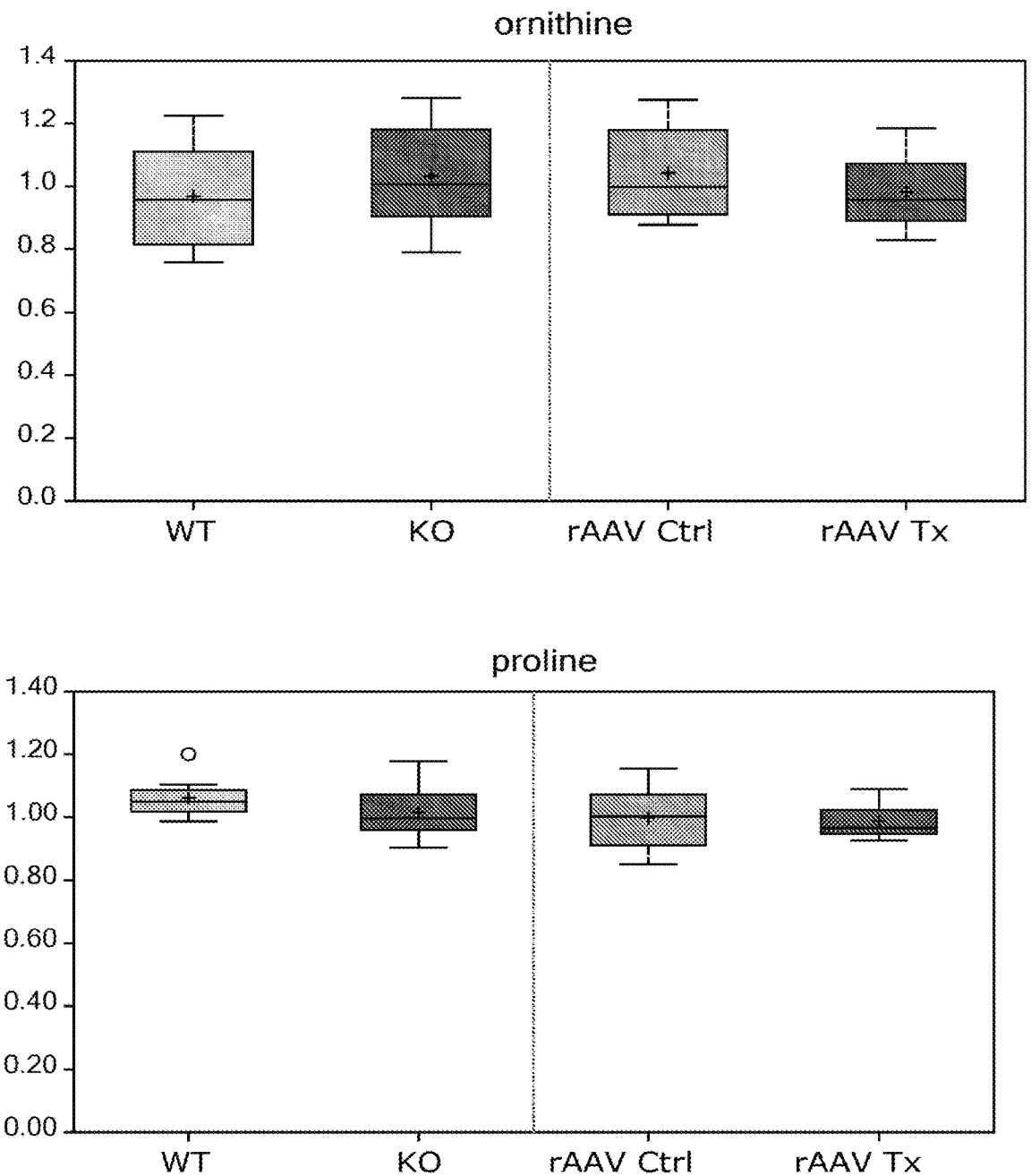
Figure 57:
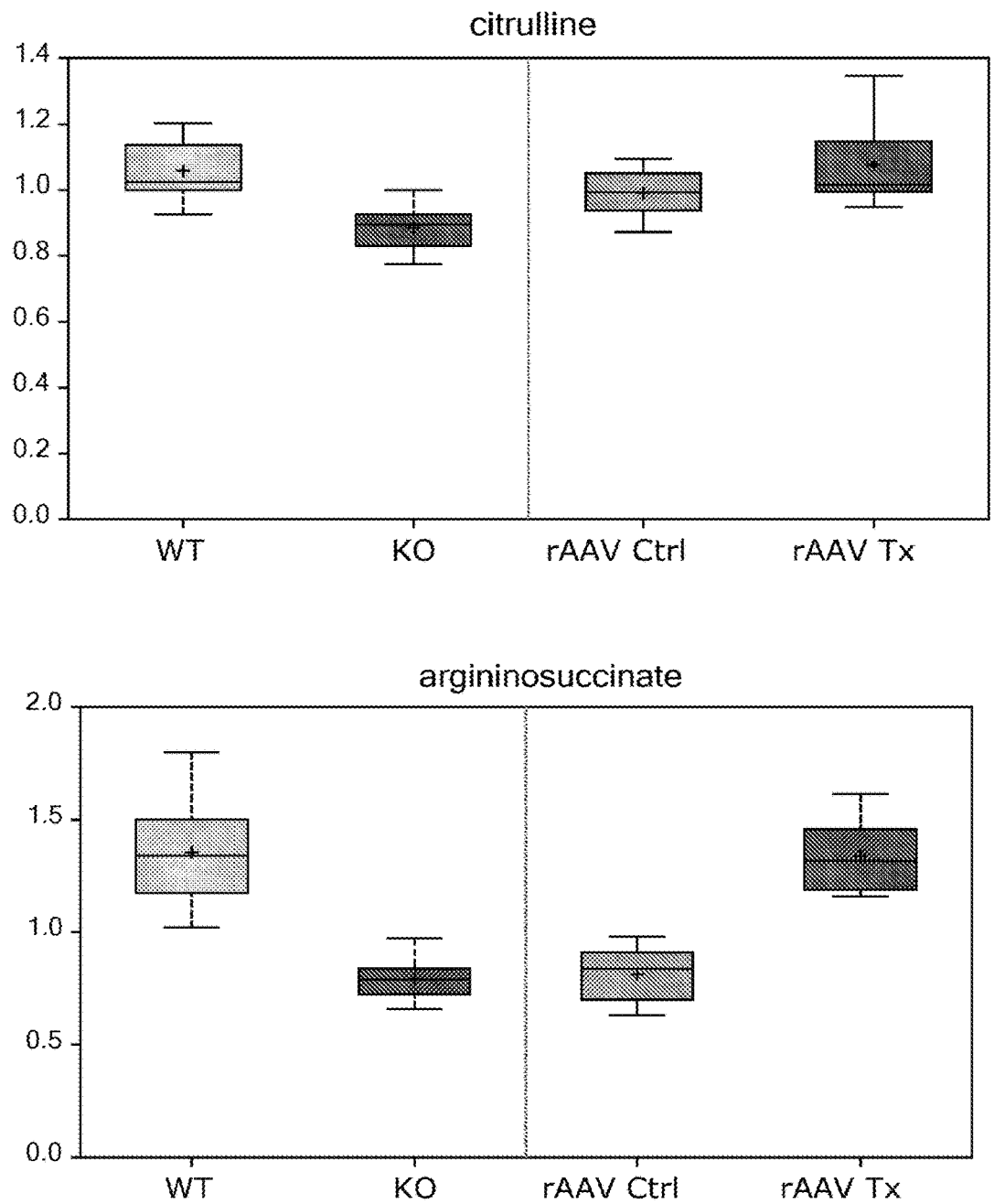
Figure 57:
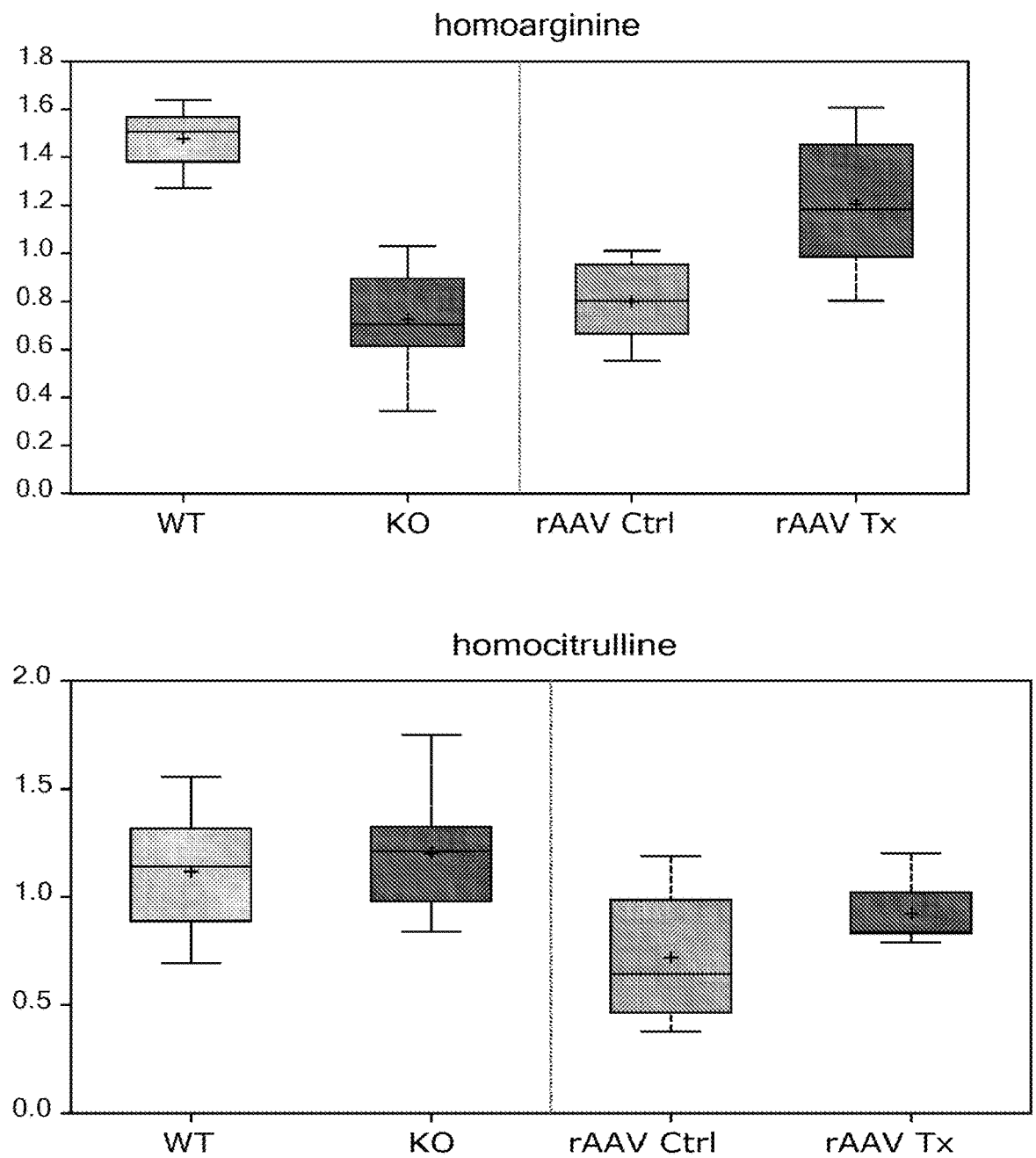
Figure 57:
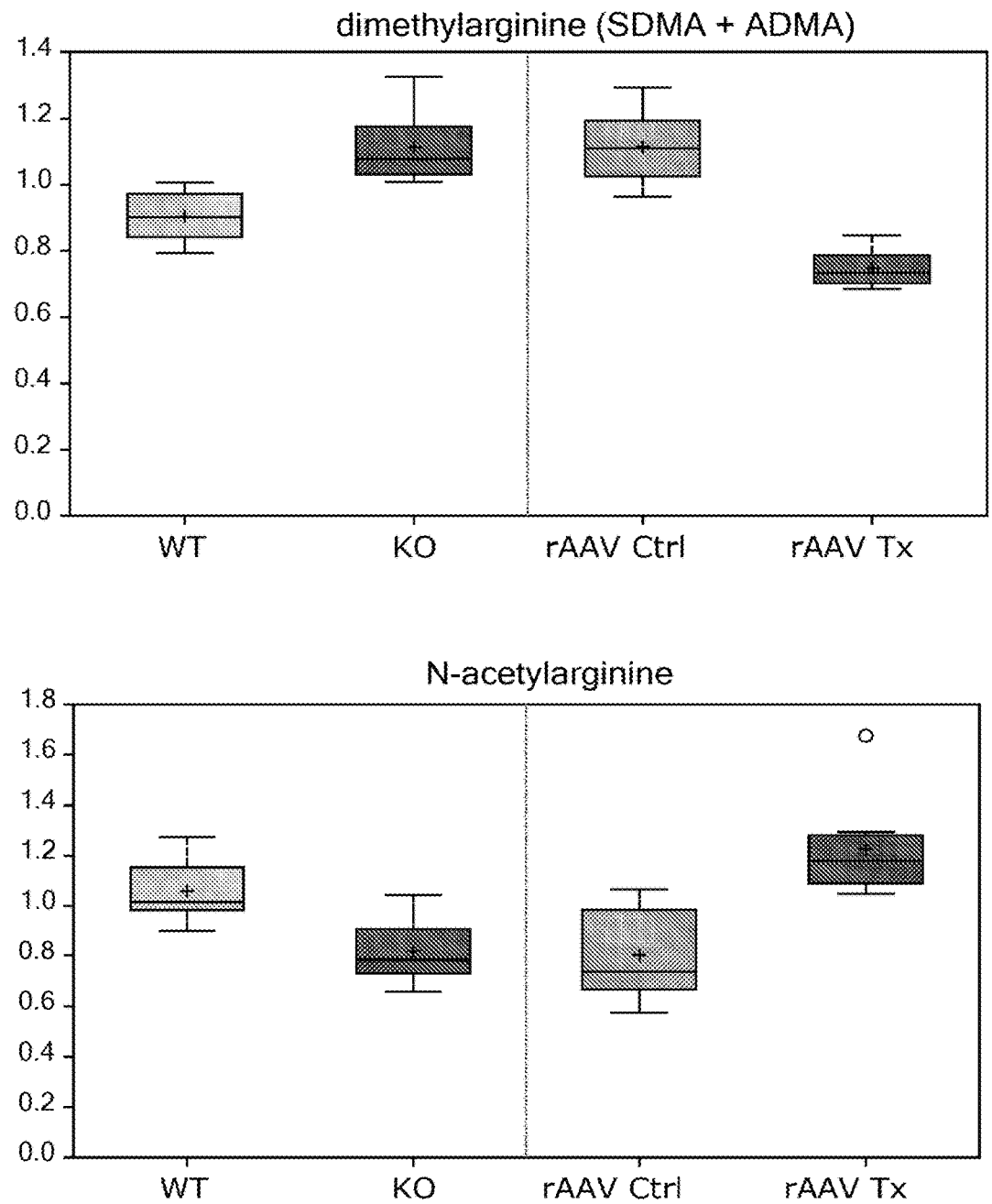
Figure 57:
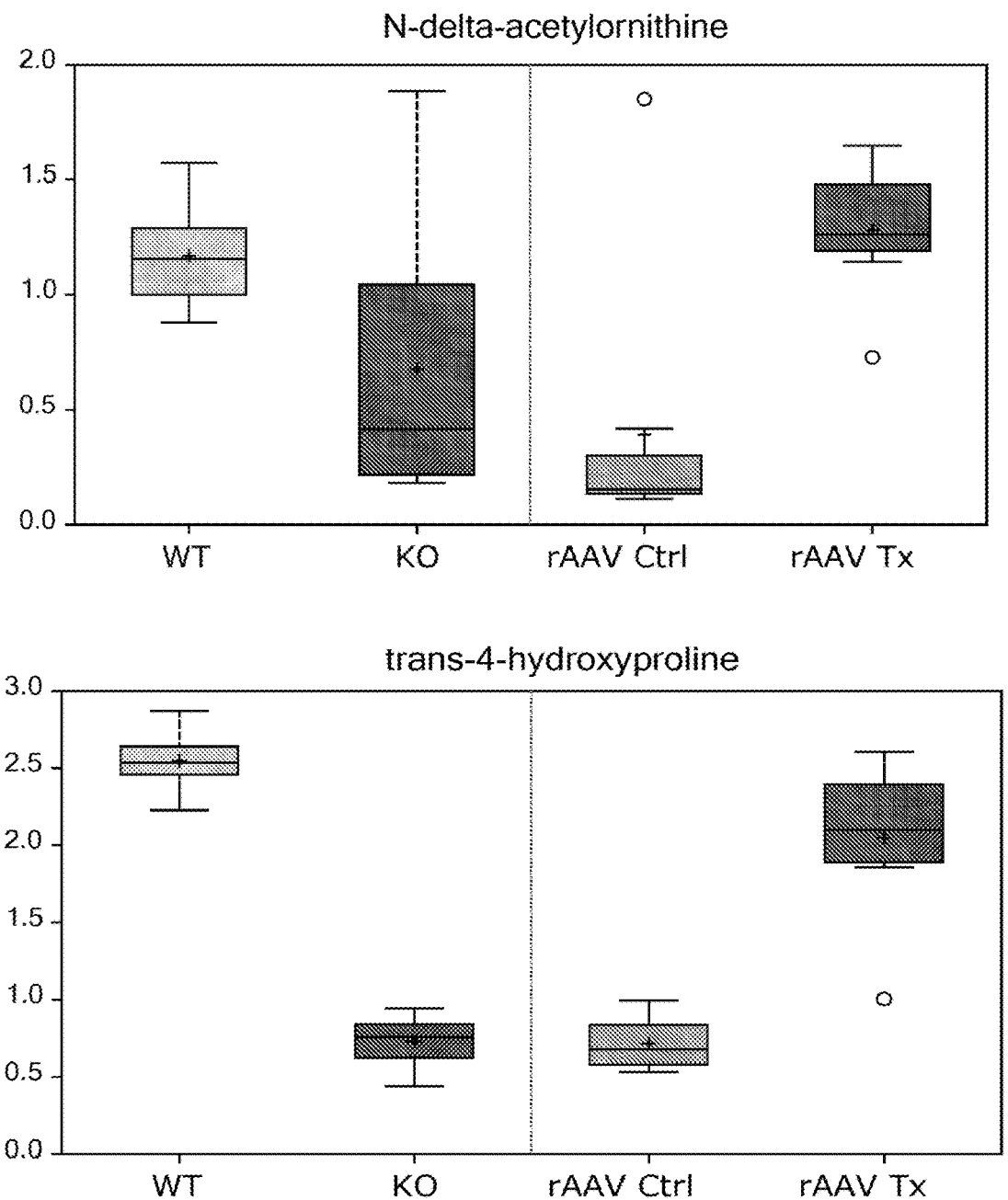
Figure 57:
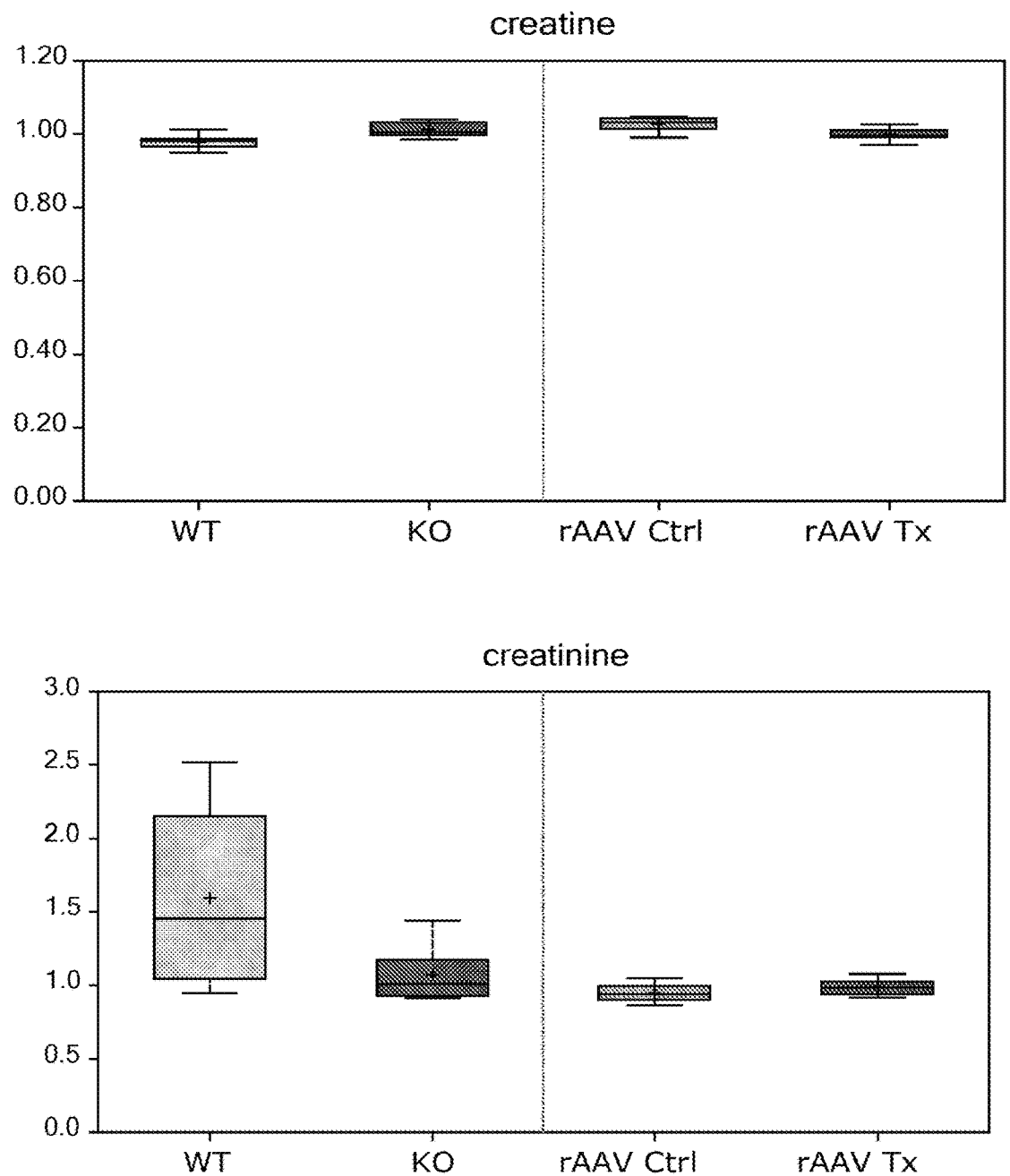
Figure 57:
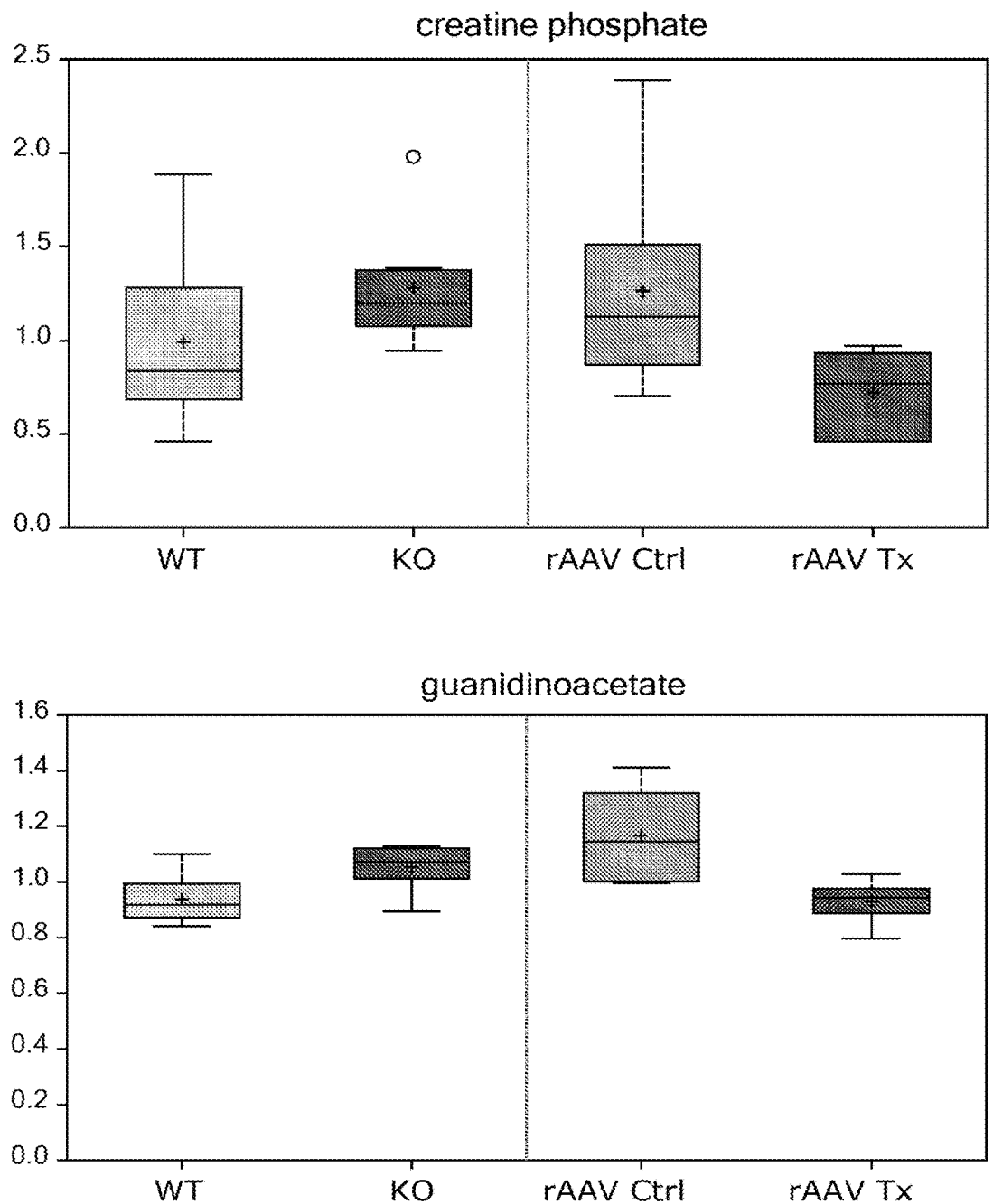
Figure 57:
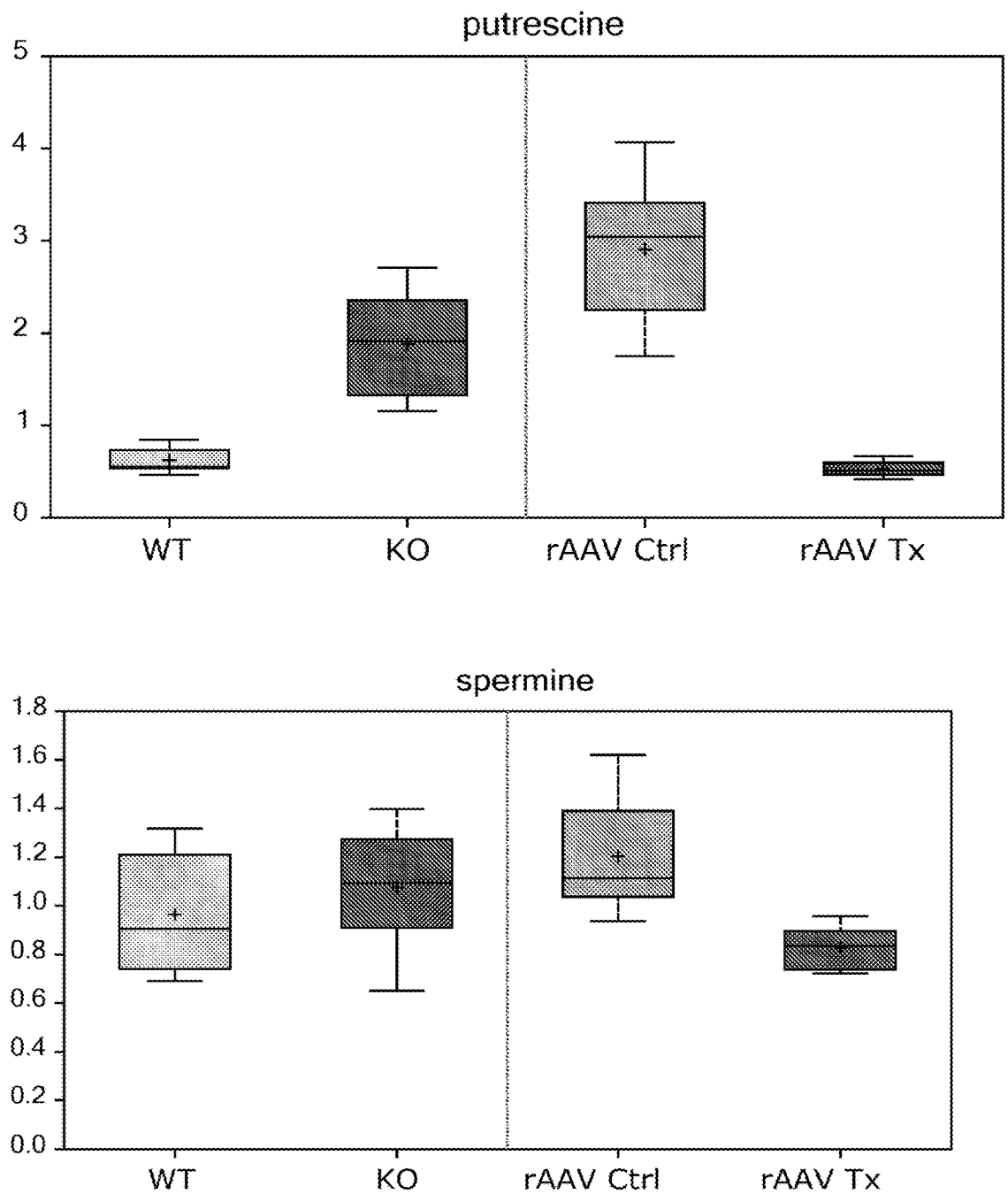
Figure 57:
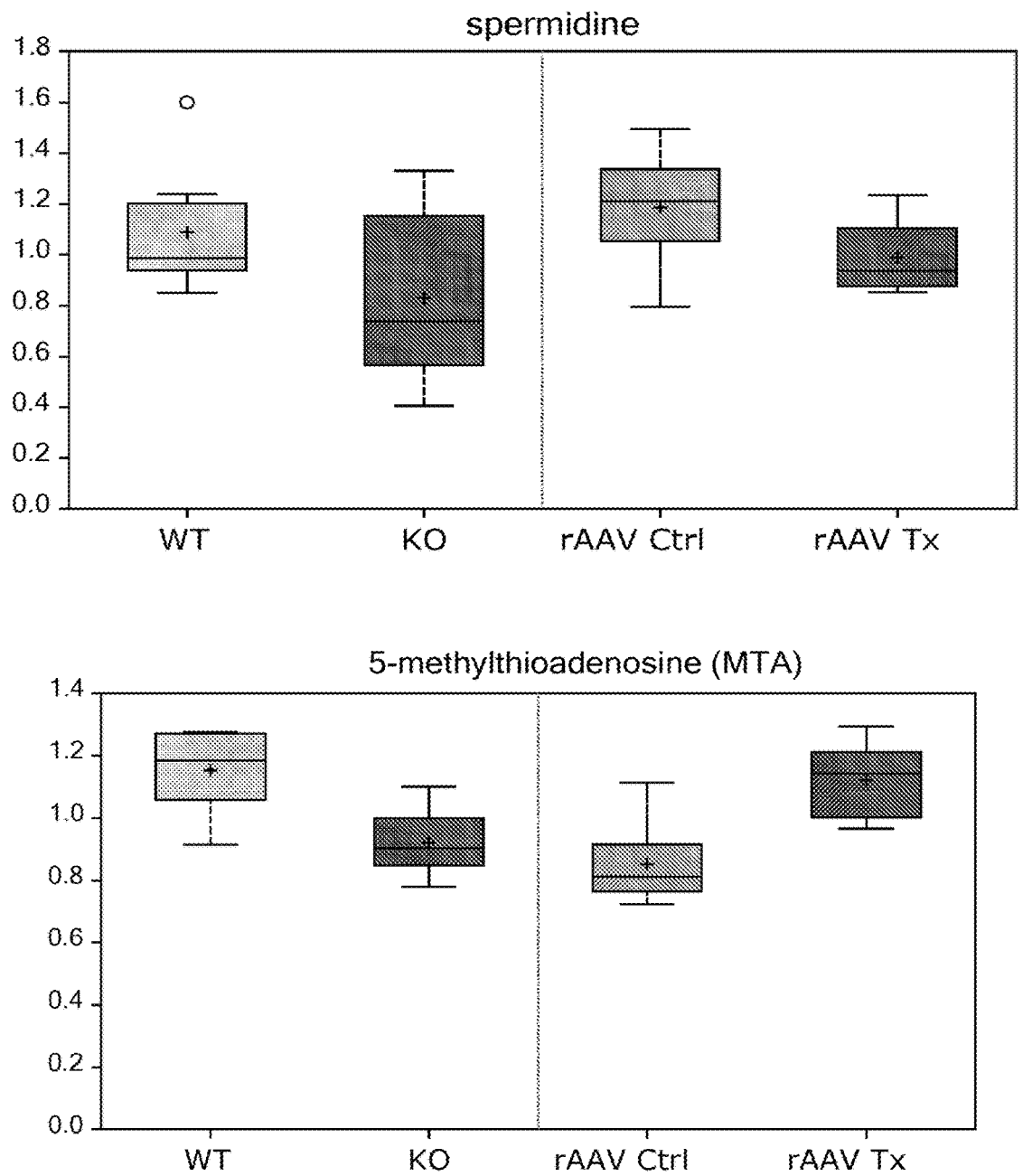
Figure 57:
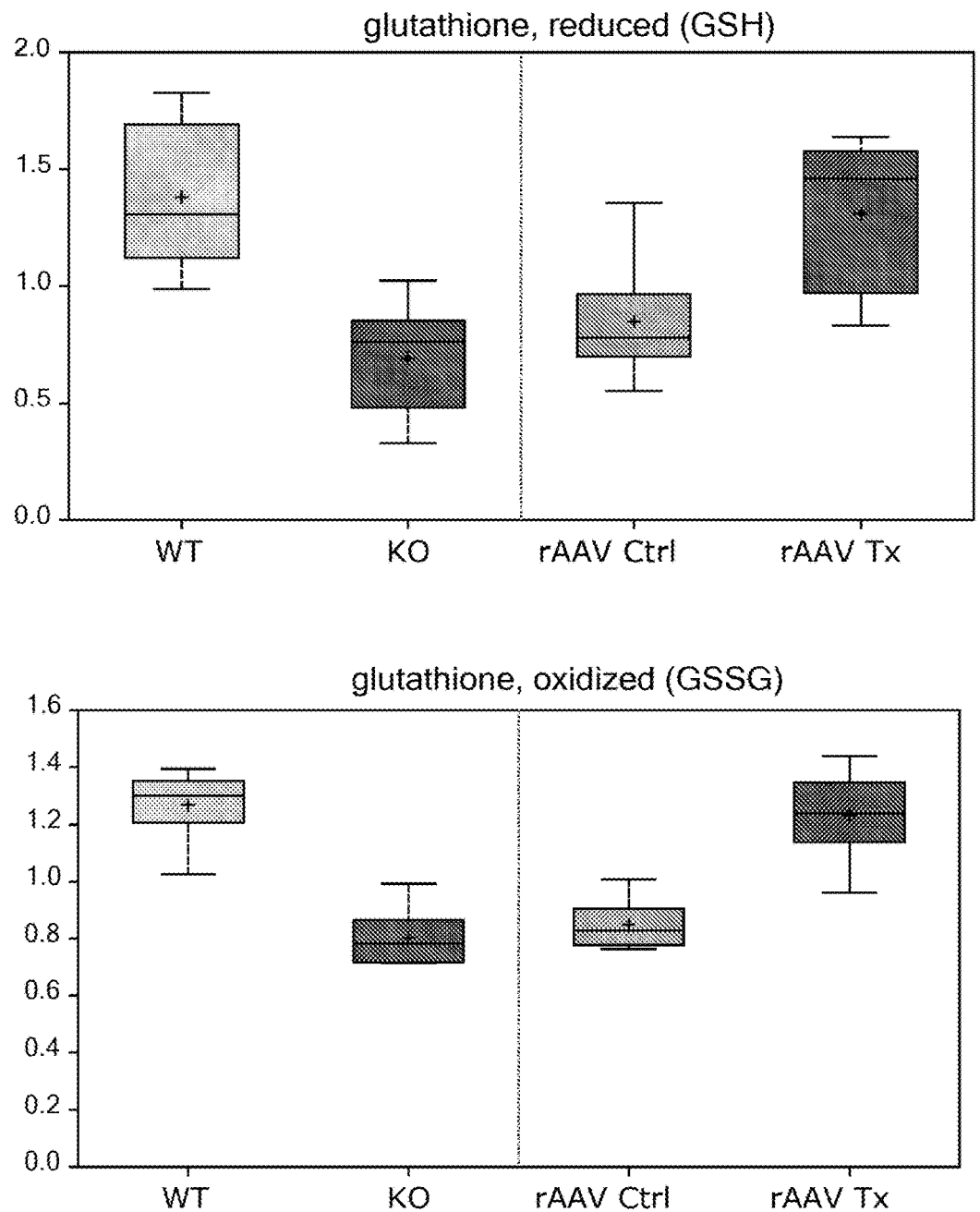
Figure 57:
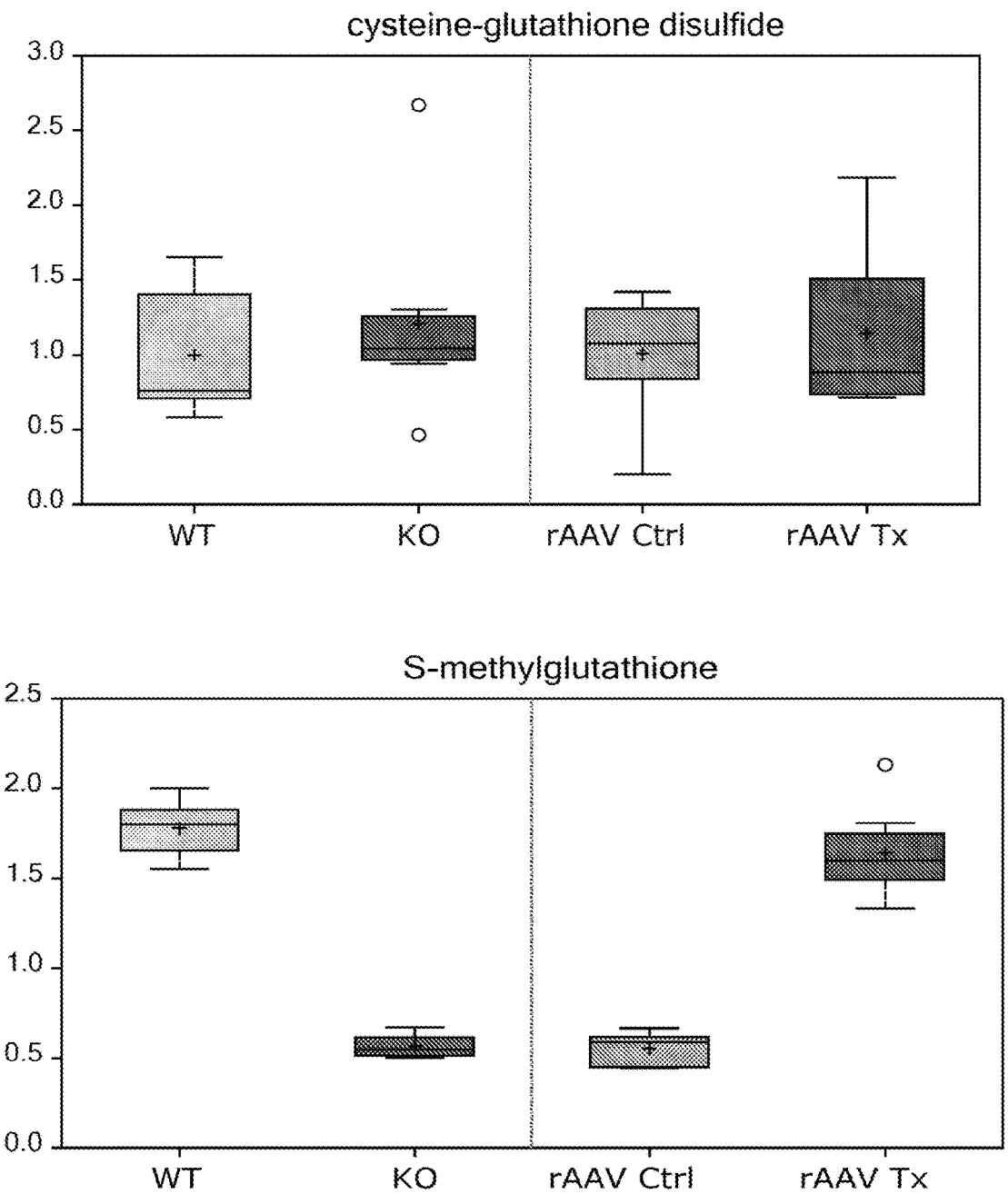
Figure 57:
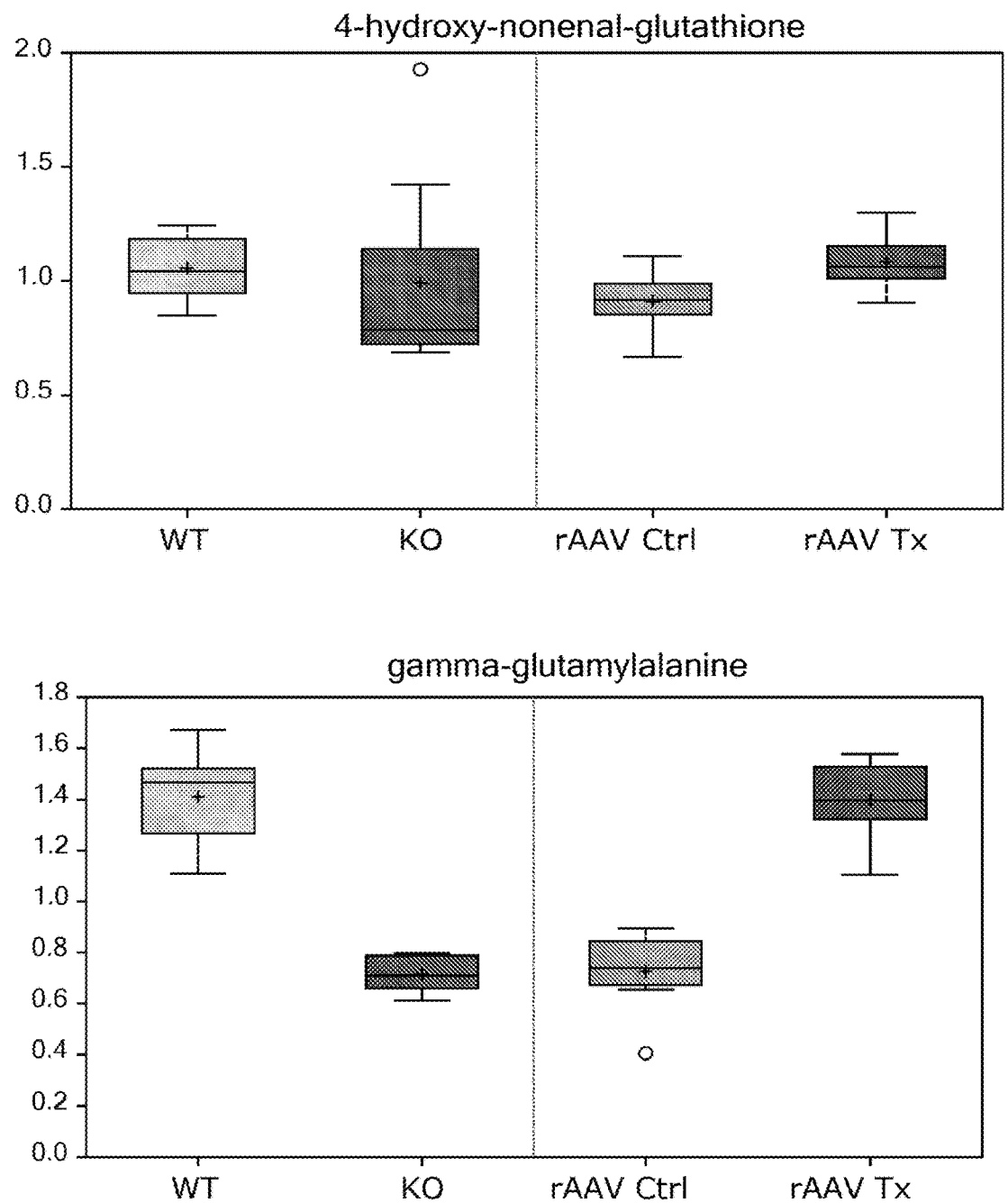
Figure 57:
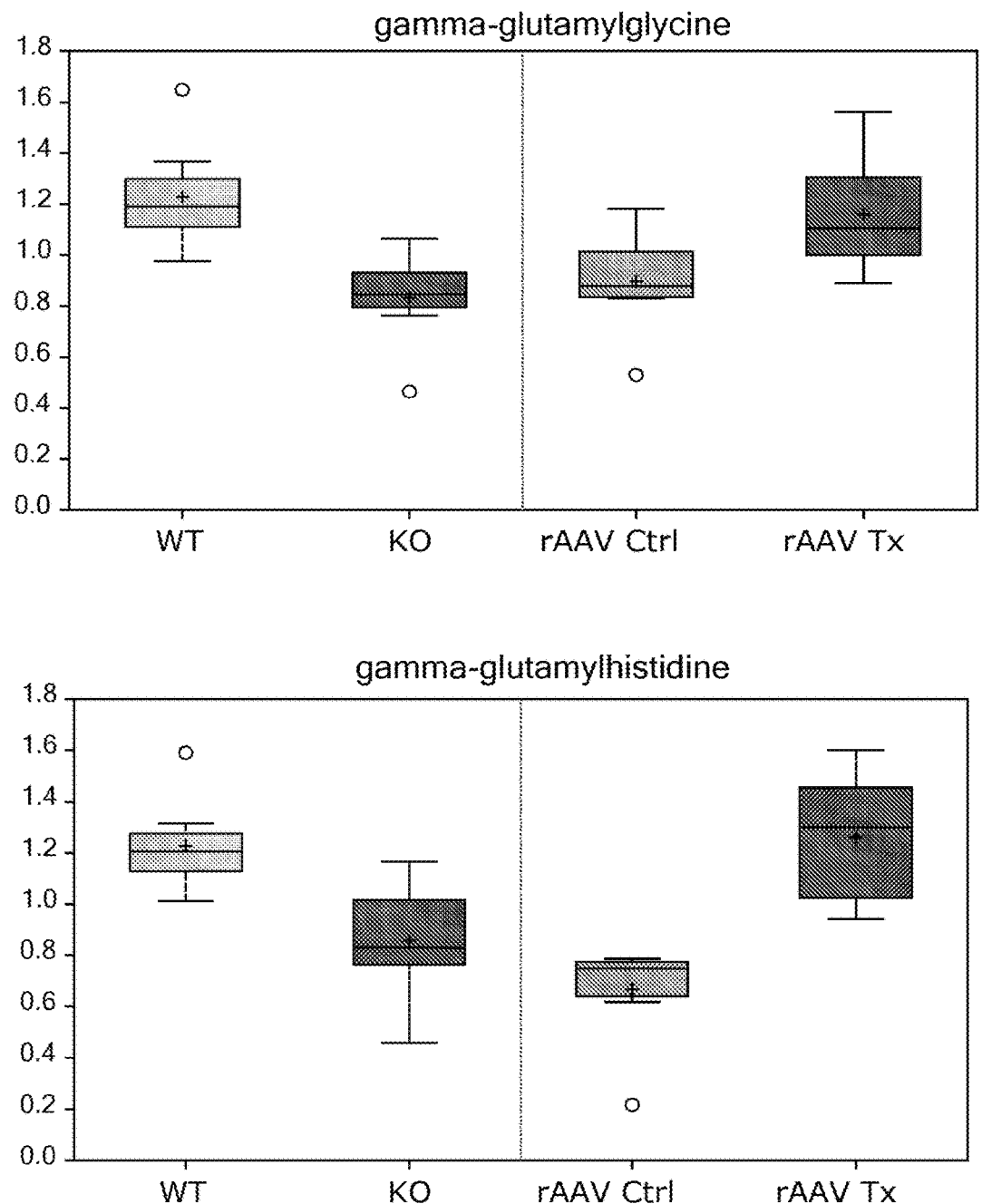
Figure 57:
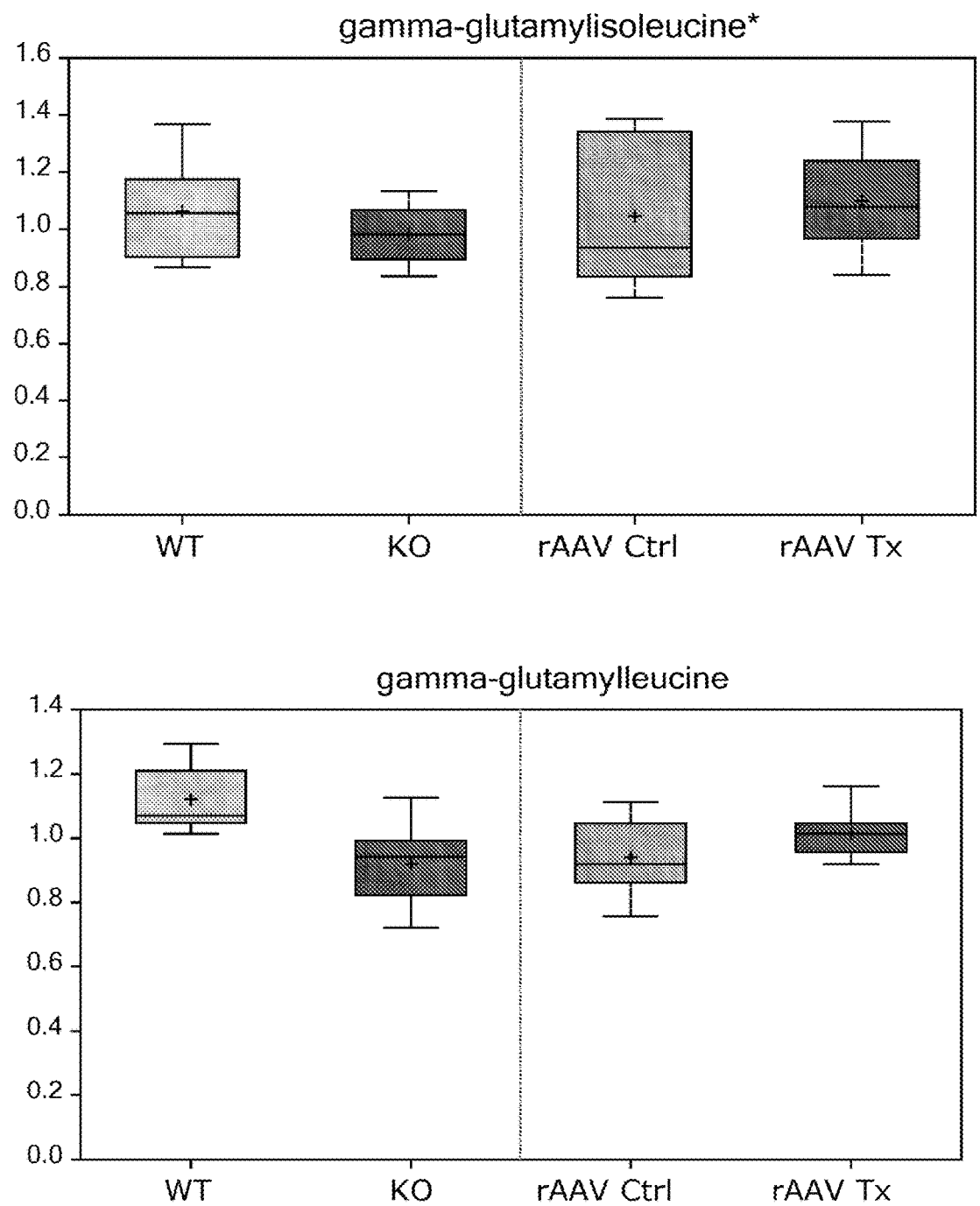
Figure 57:
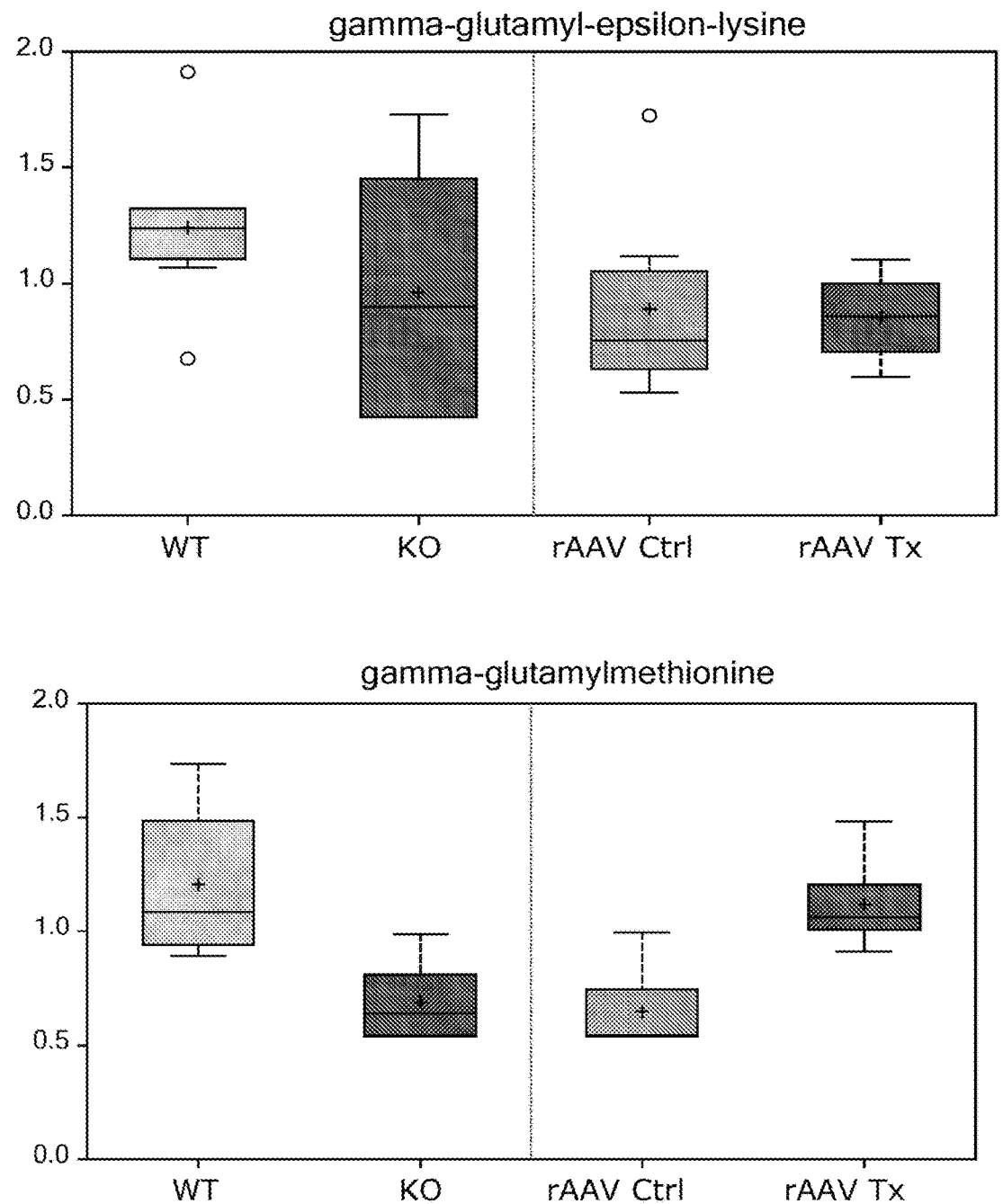
Figure 57:
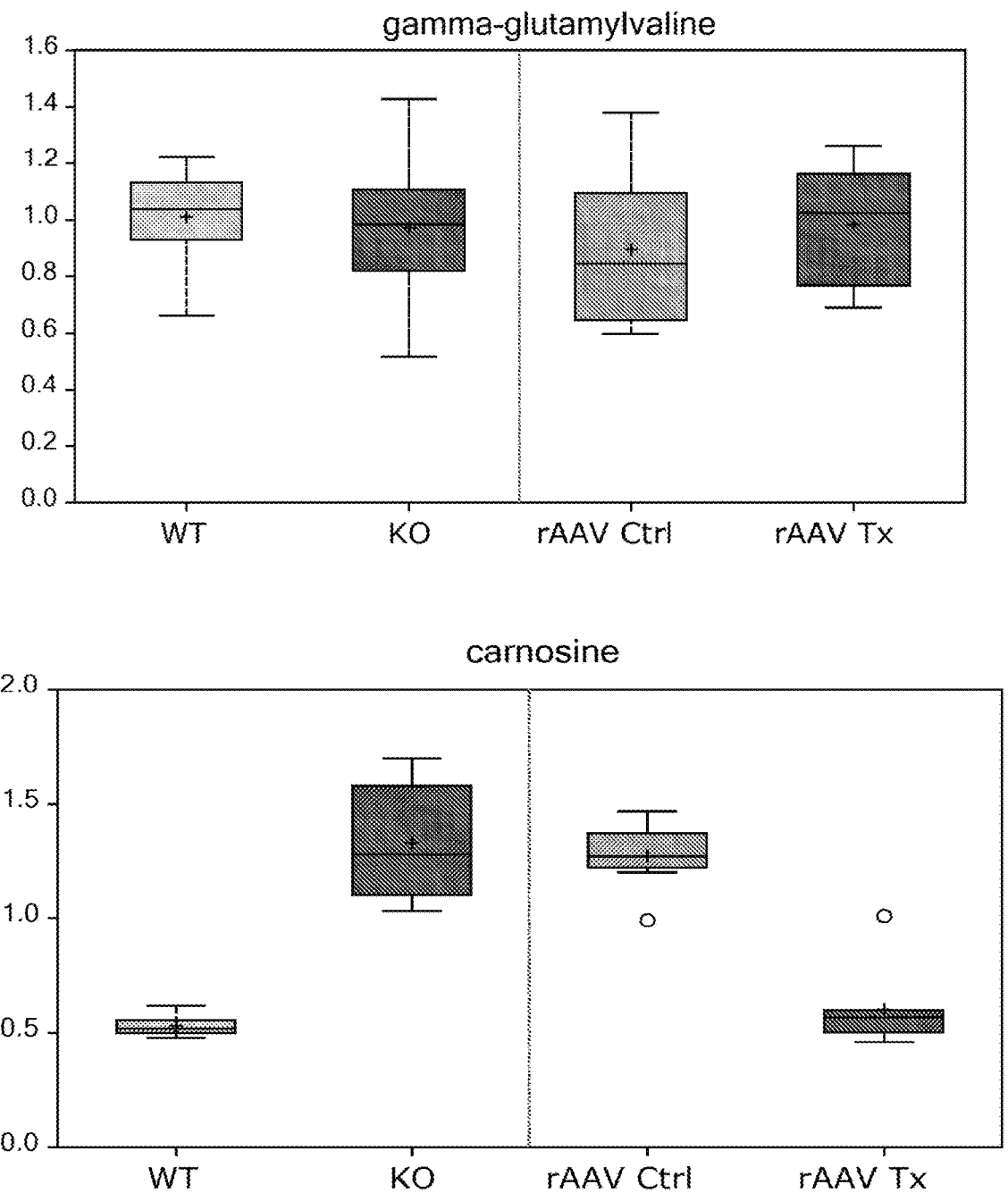
Figure 57:
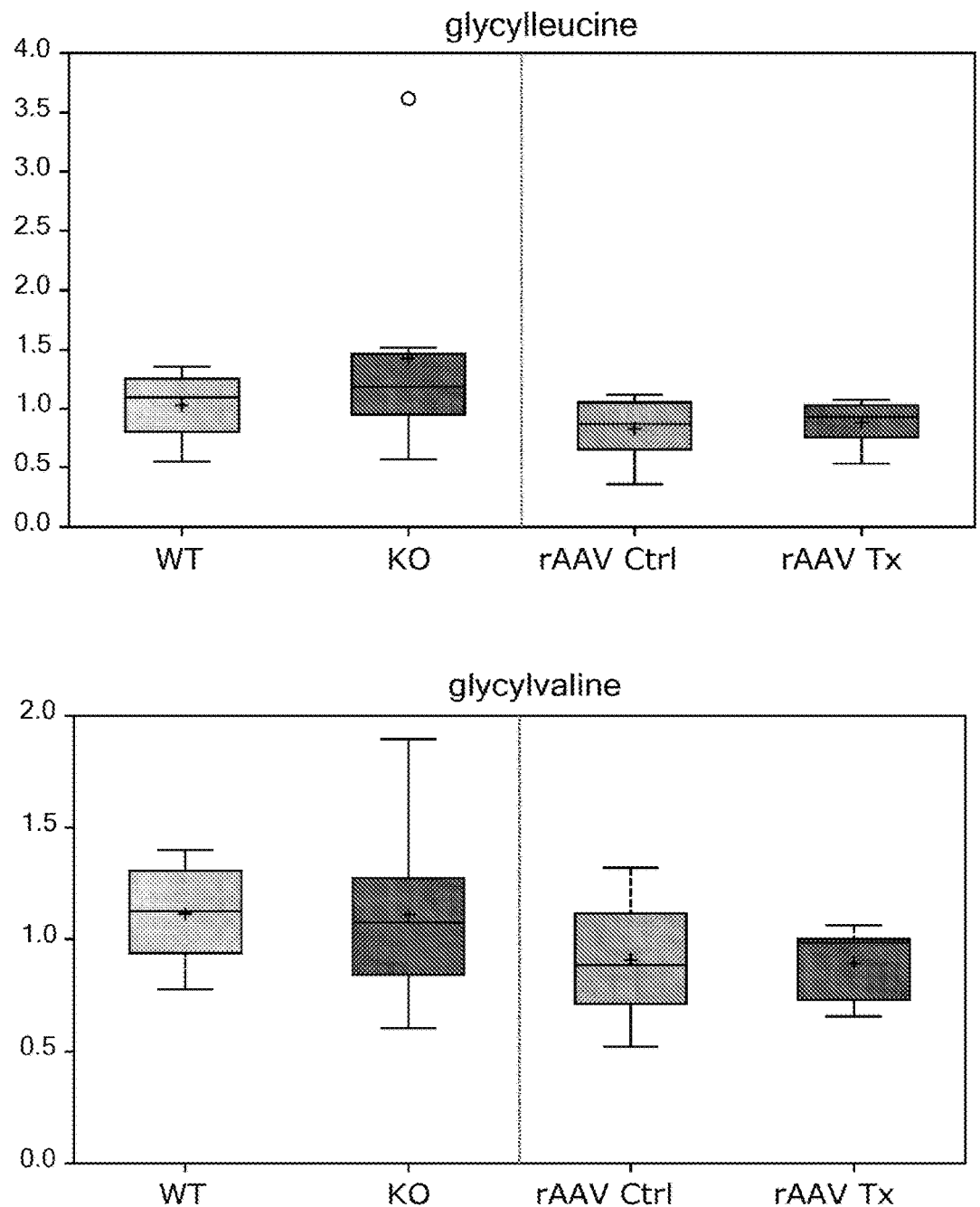
Figure 57:
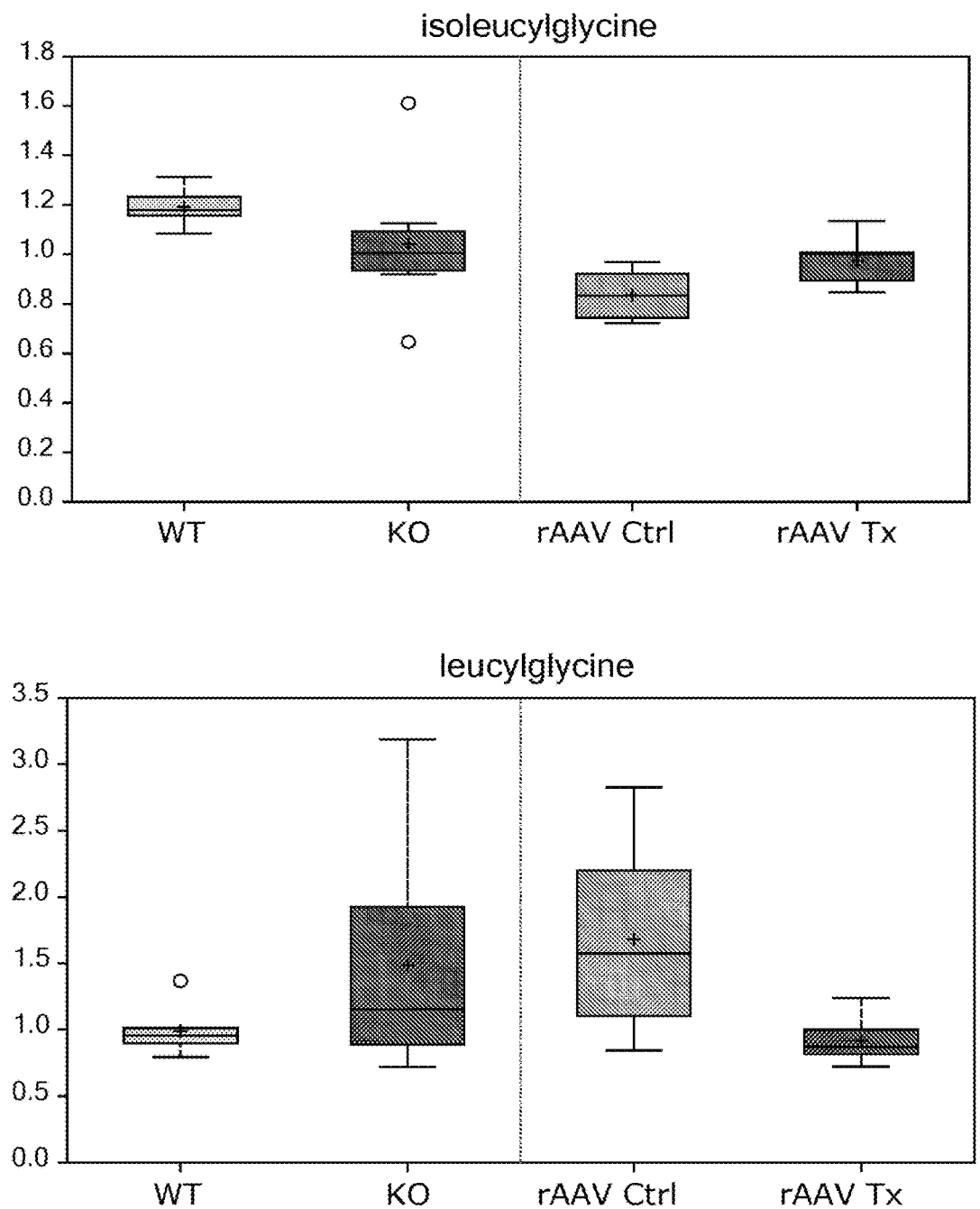
Figure 57:
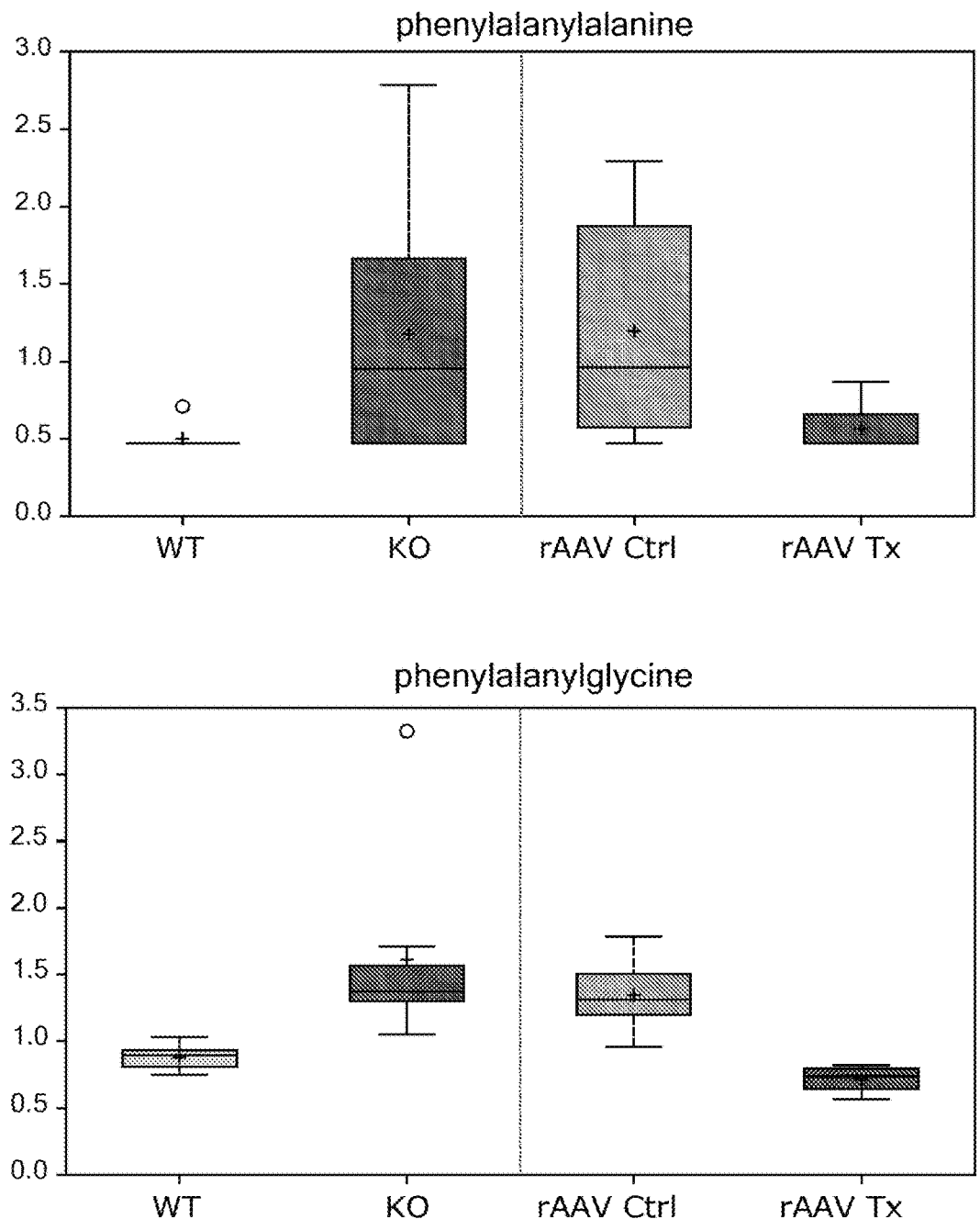
Figure 57:
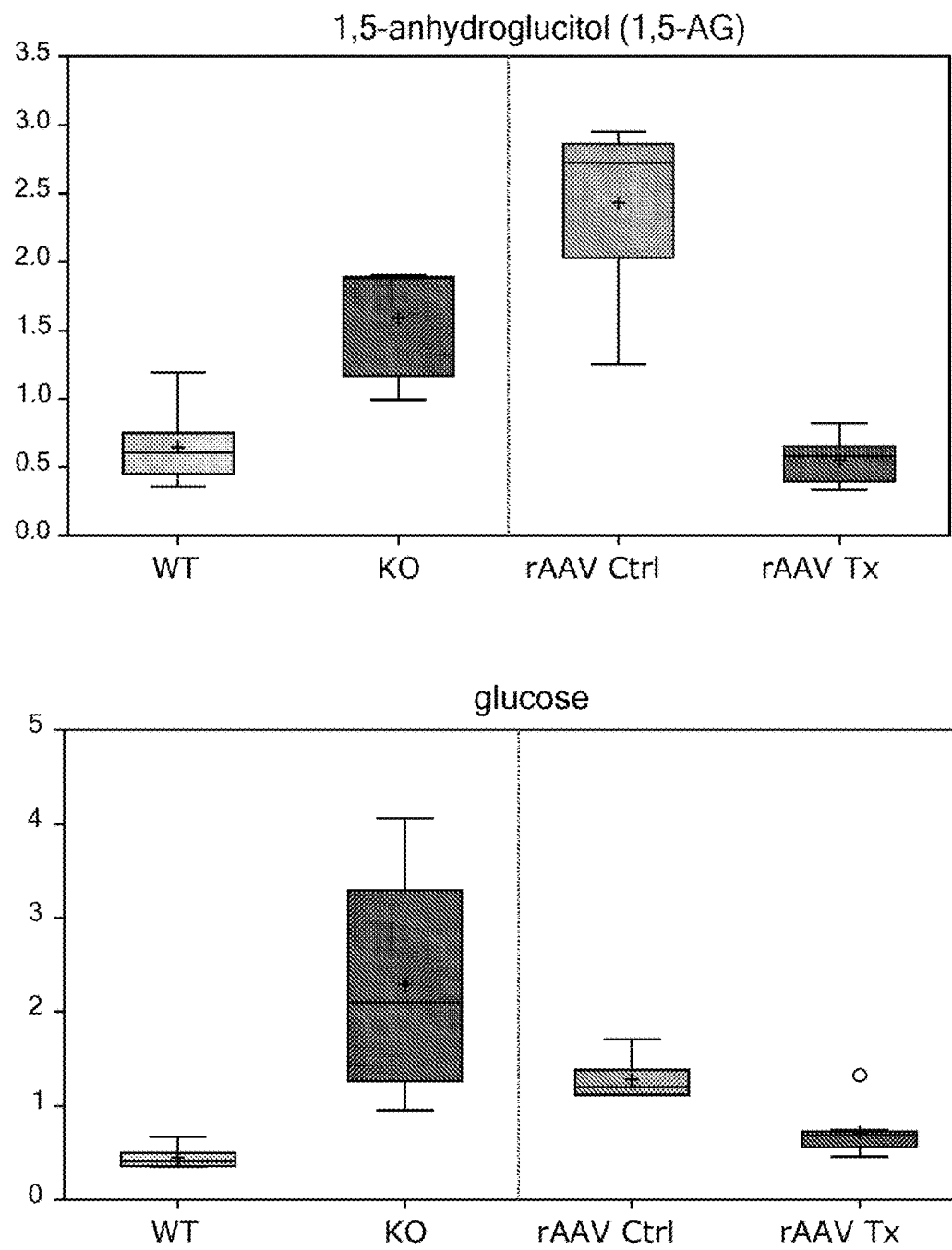
Figure 57:
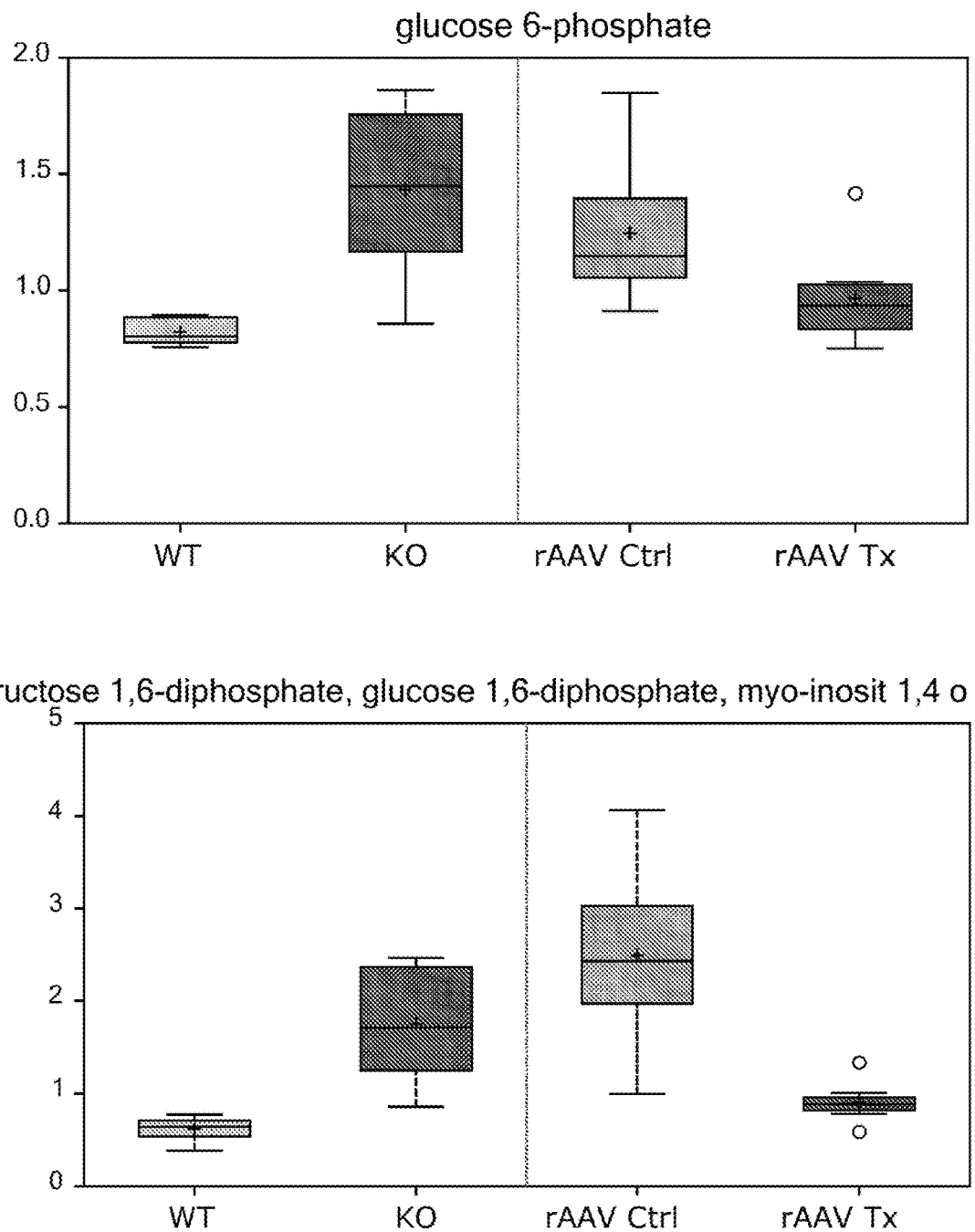
Figure 57:
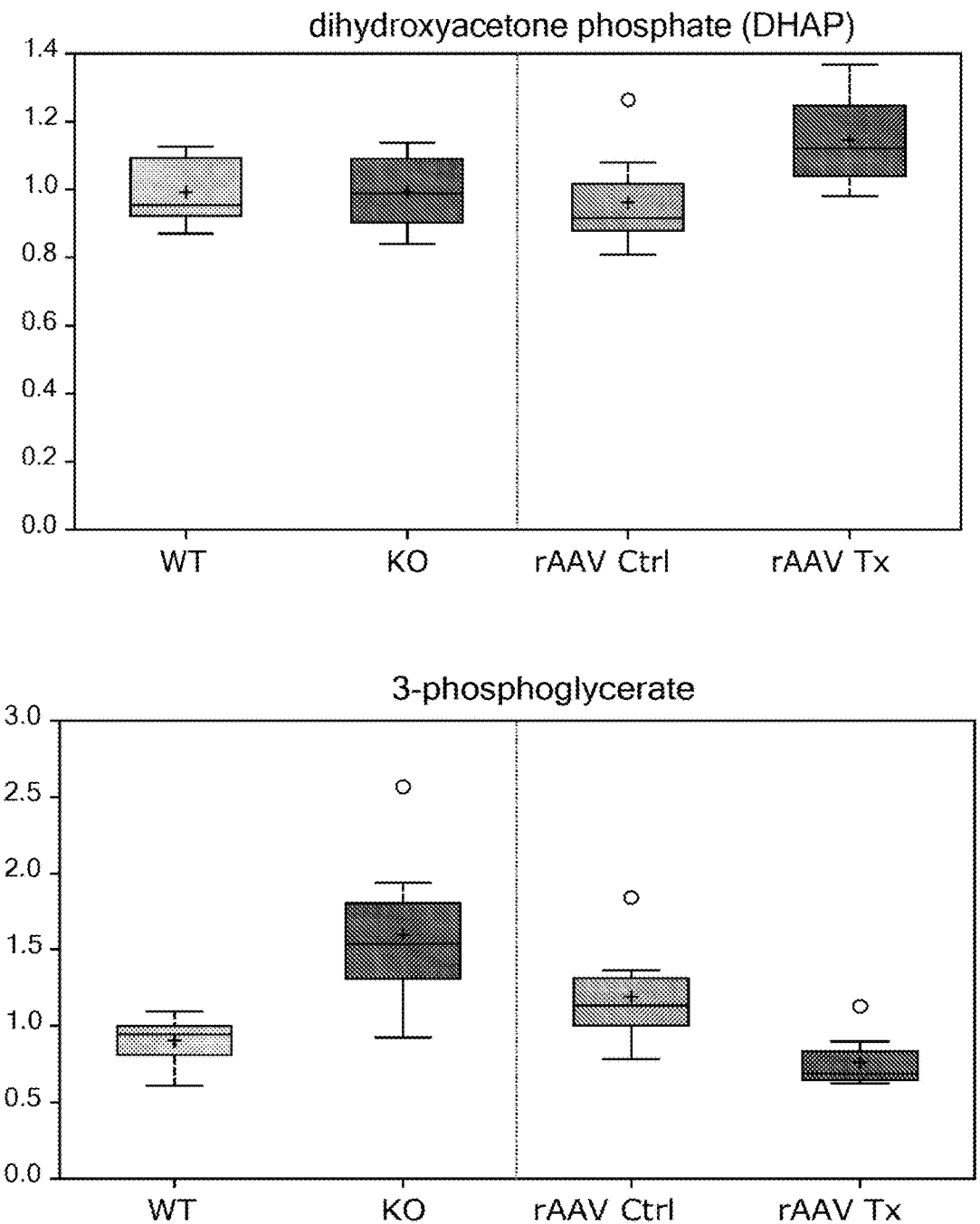
Figure 57:
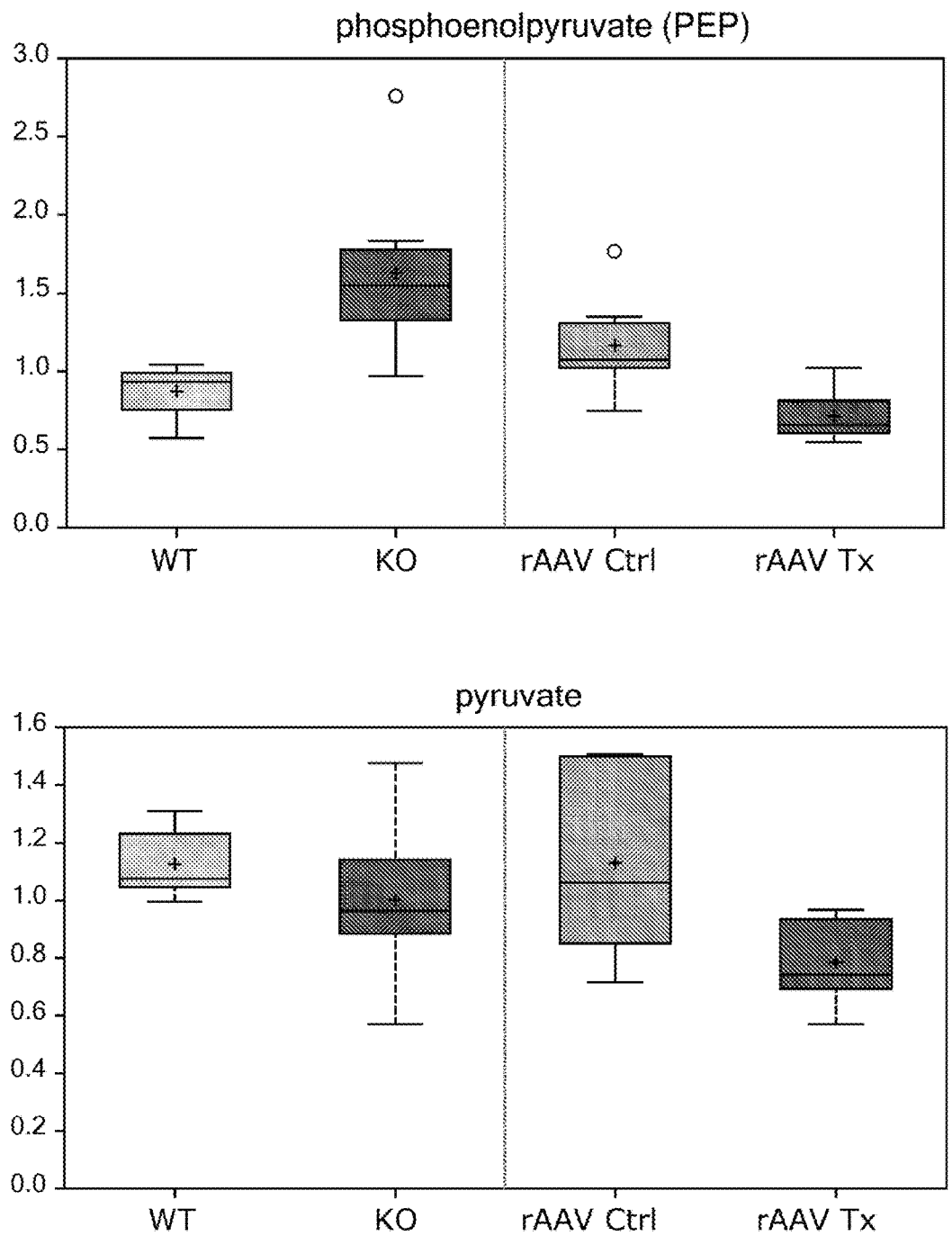
Figure 57:
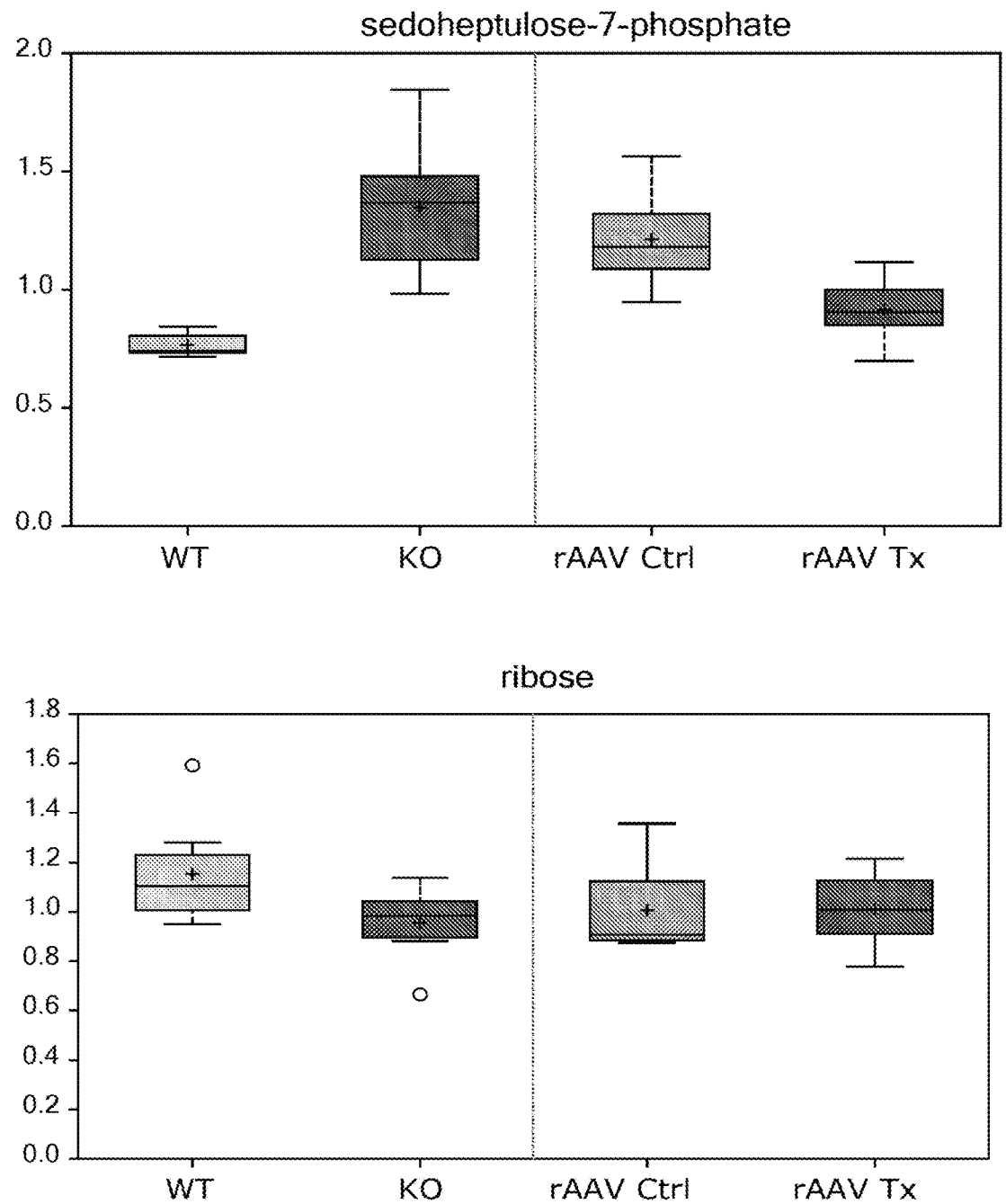
Figure 57:
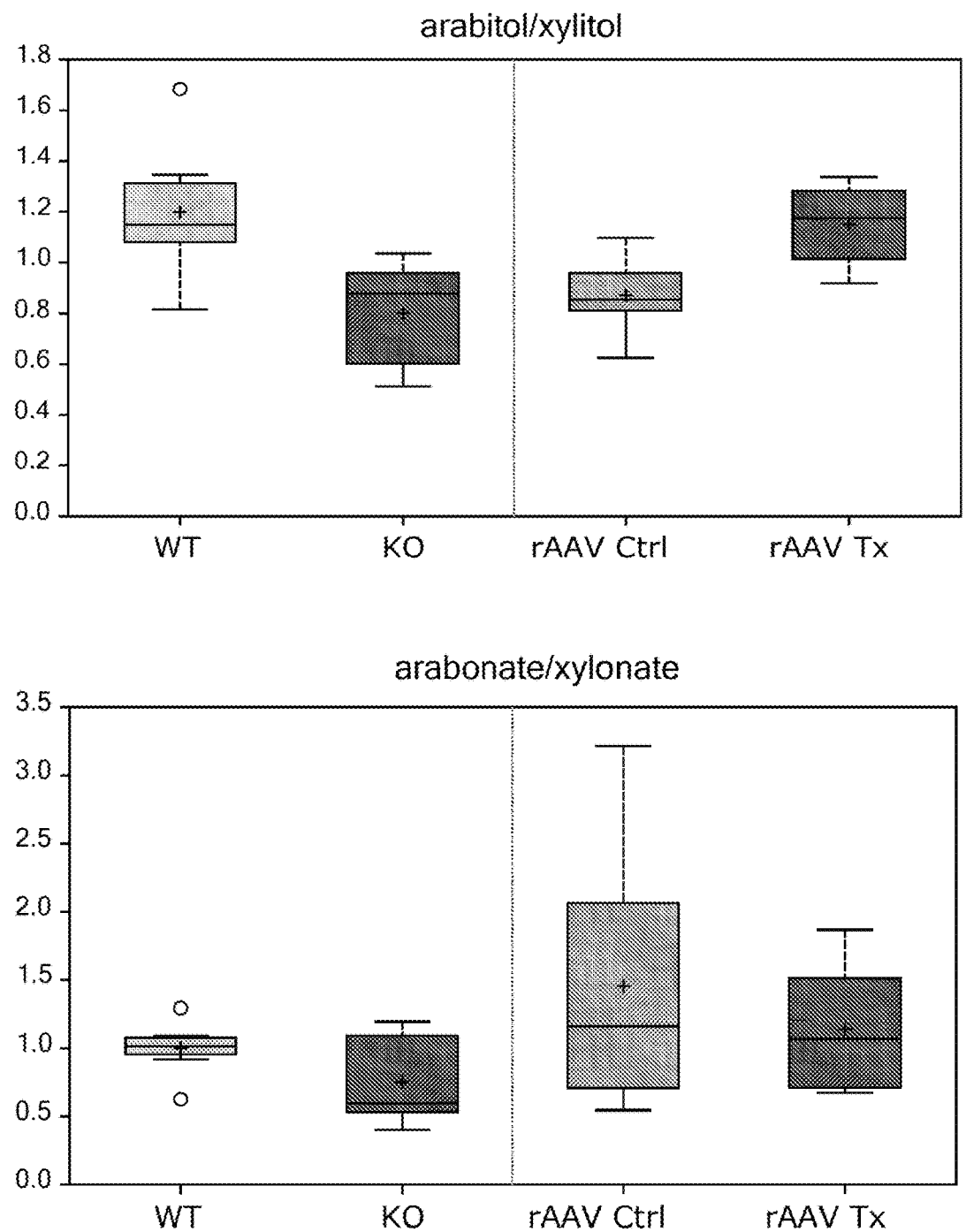
Figure 57:
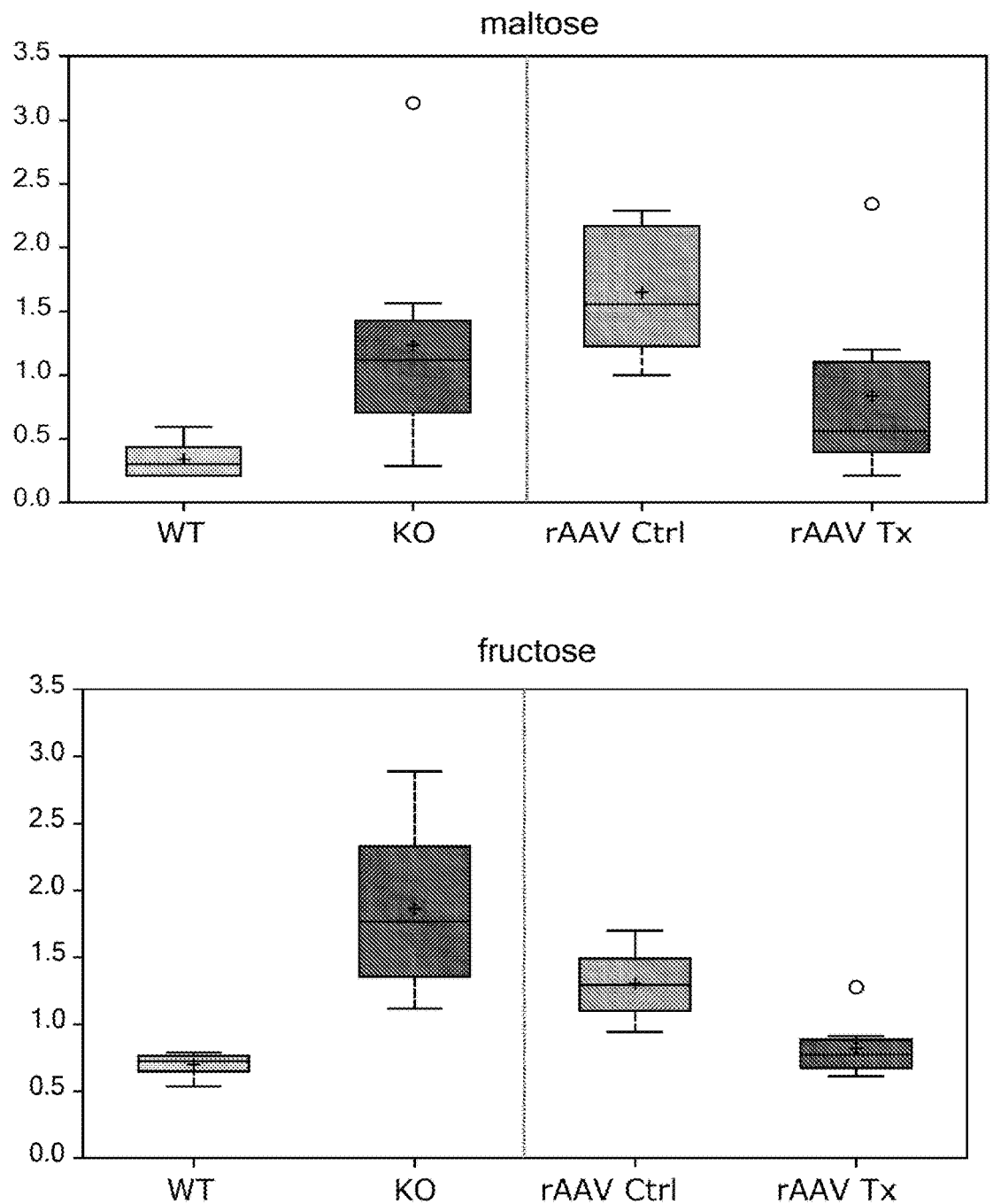
Figure 57:
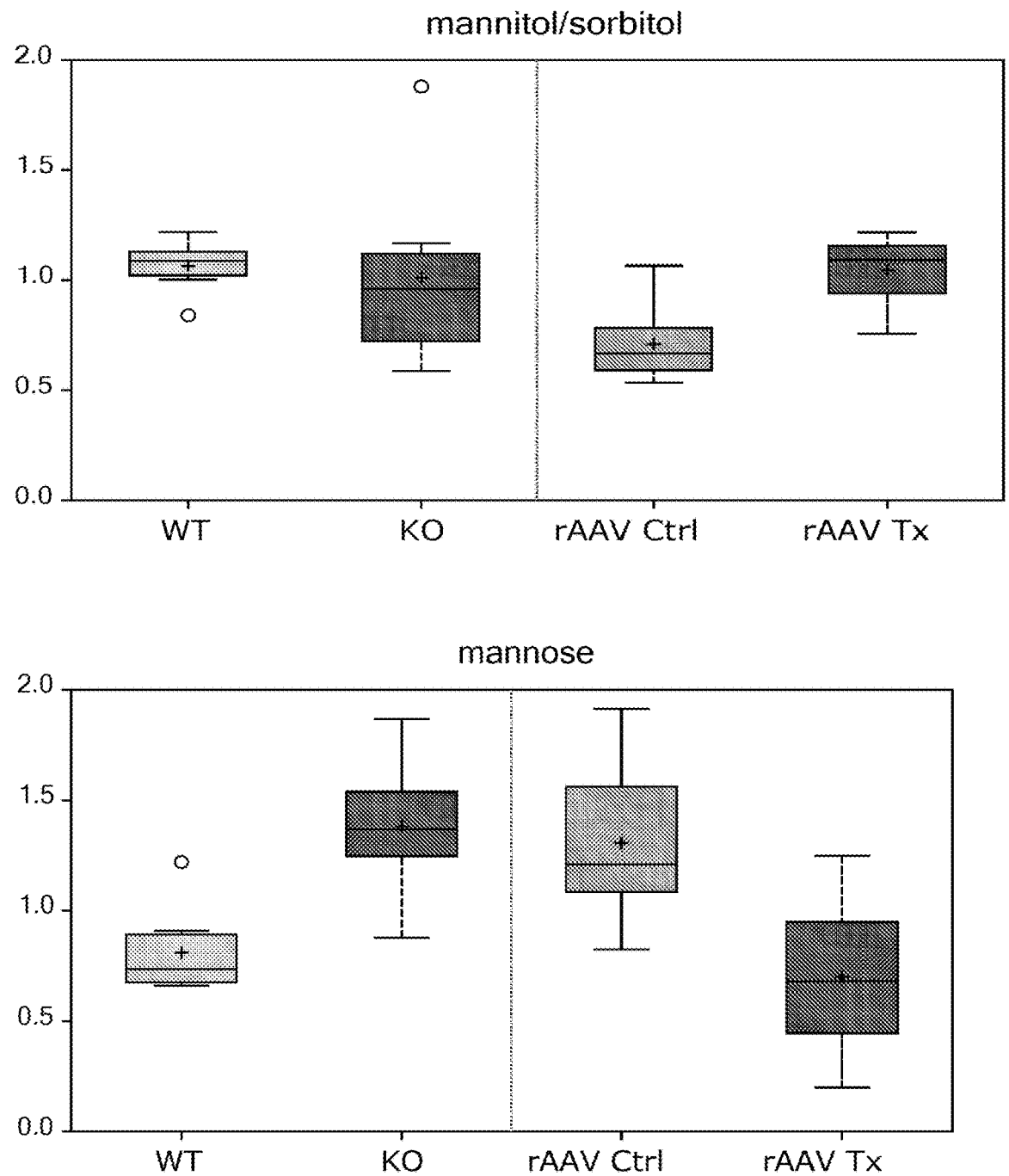
Figure 57:
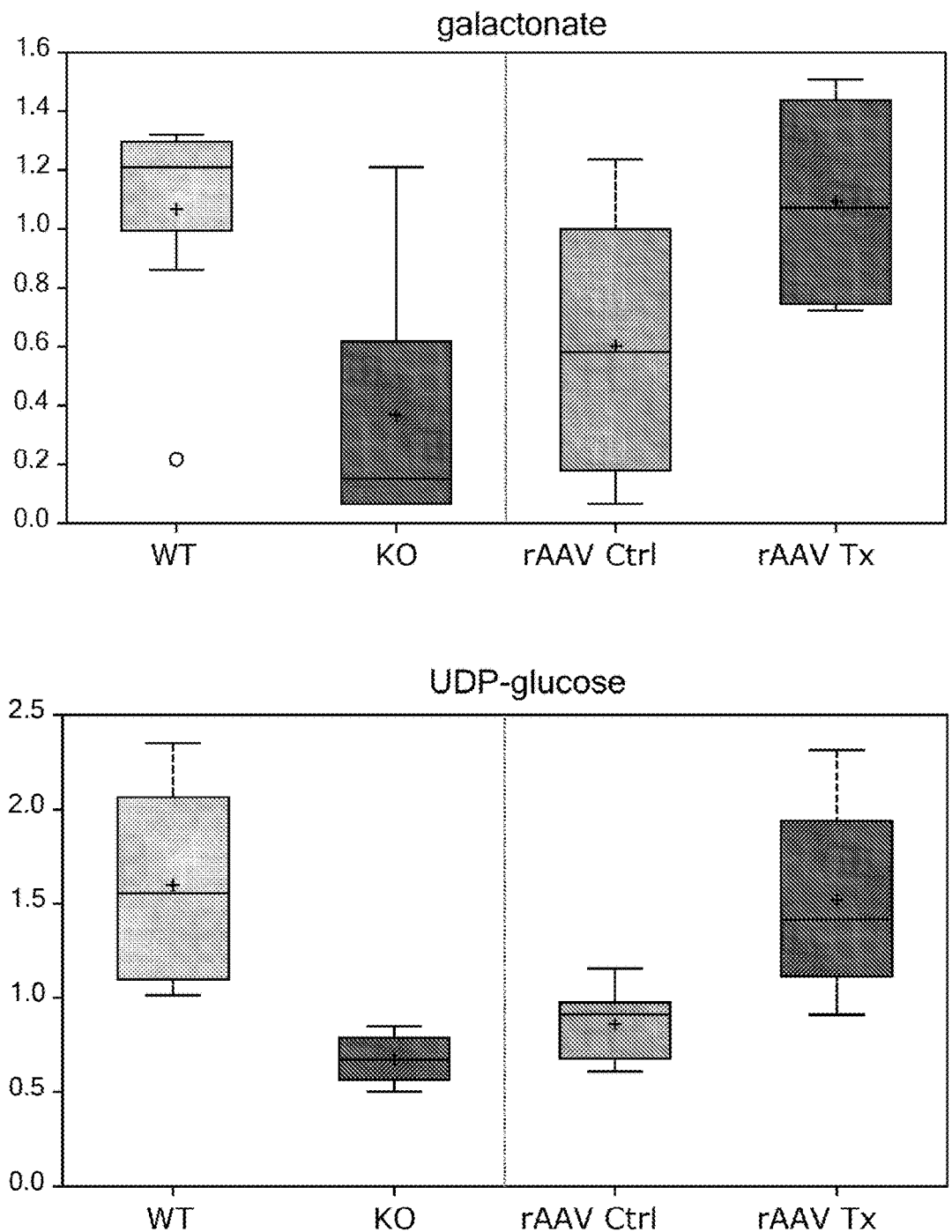
Figure 57:
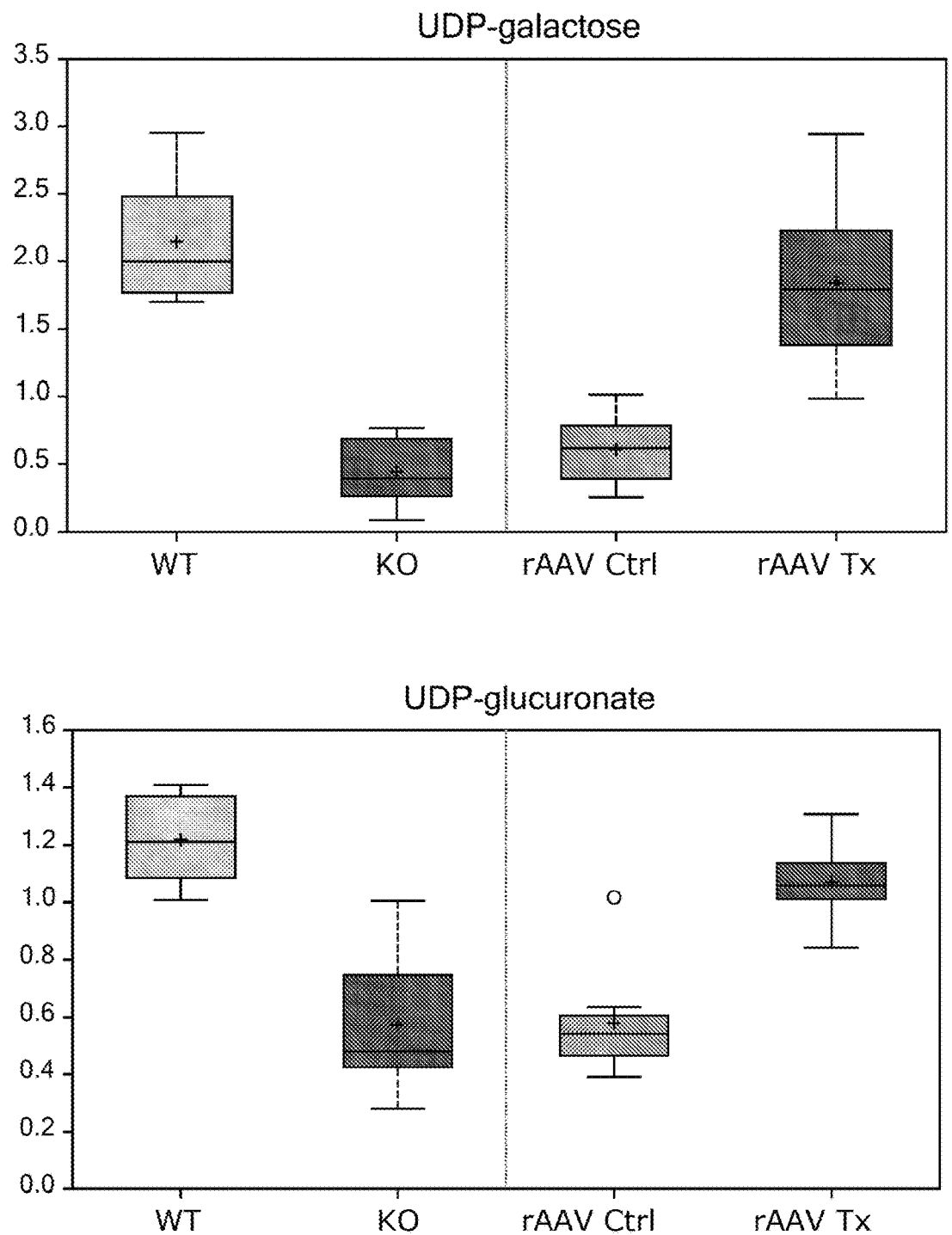
Figure 57:
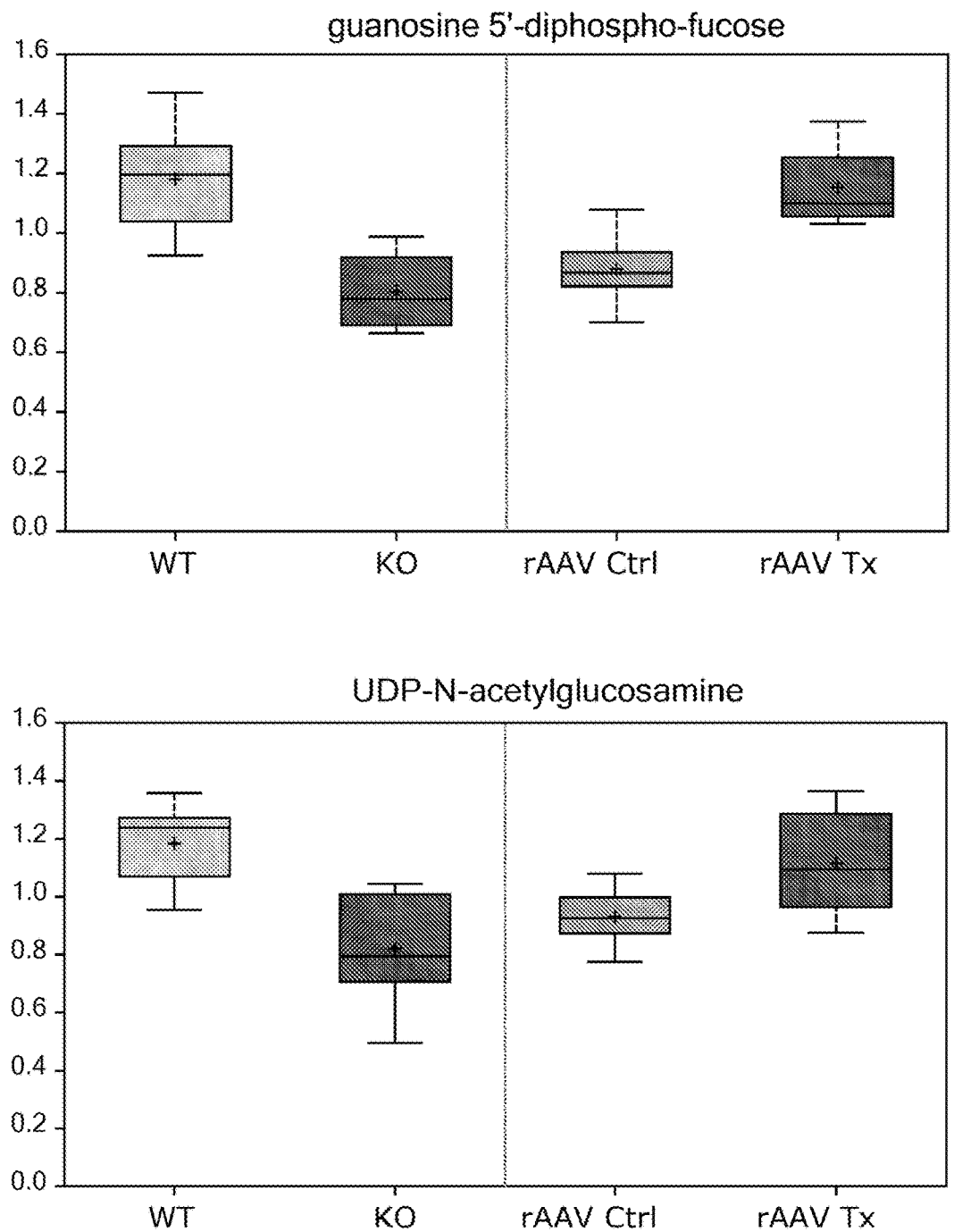
Figure 57:
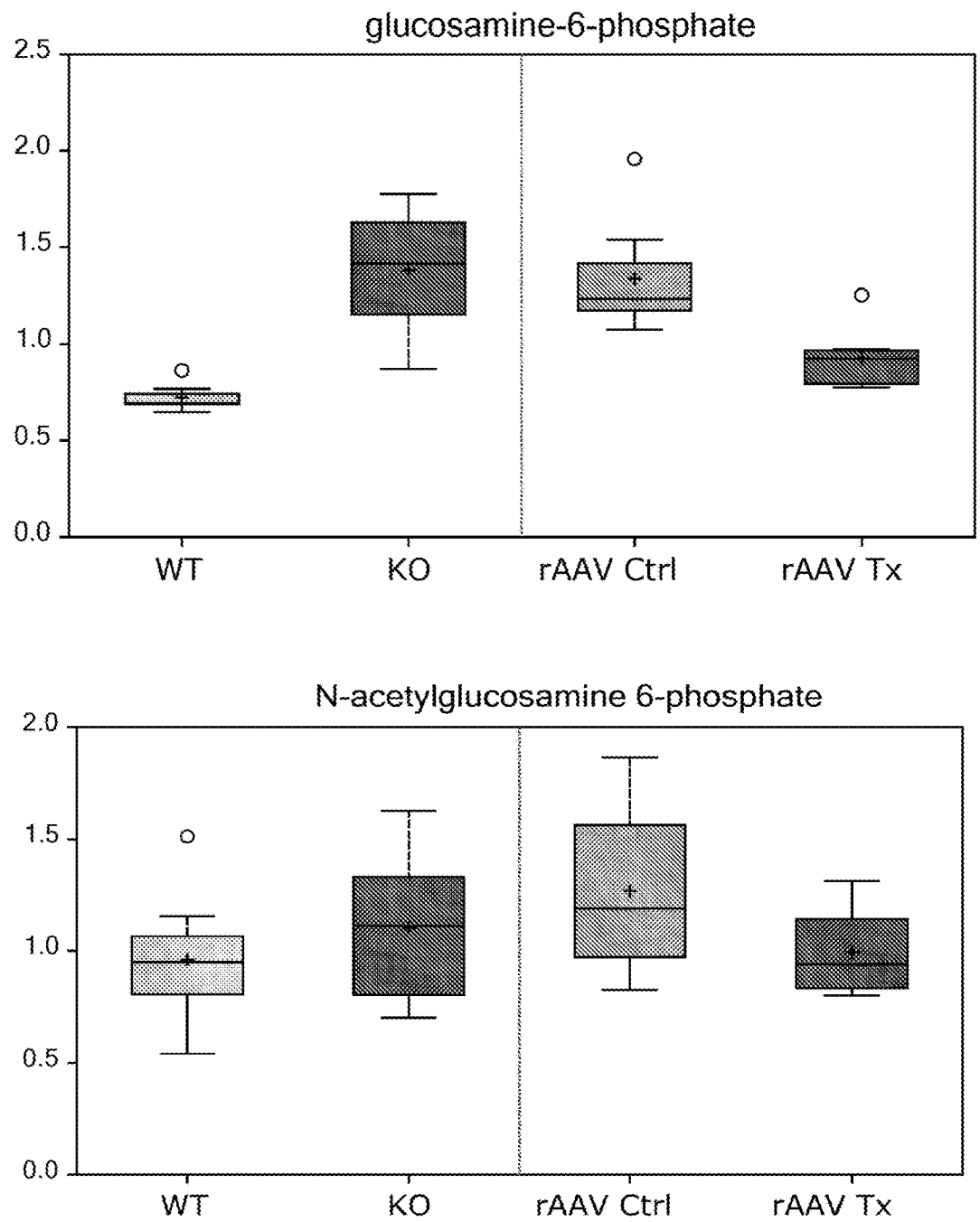
Figure 57:
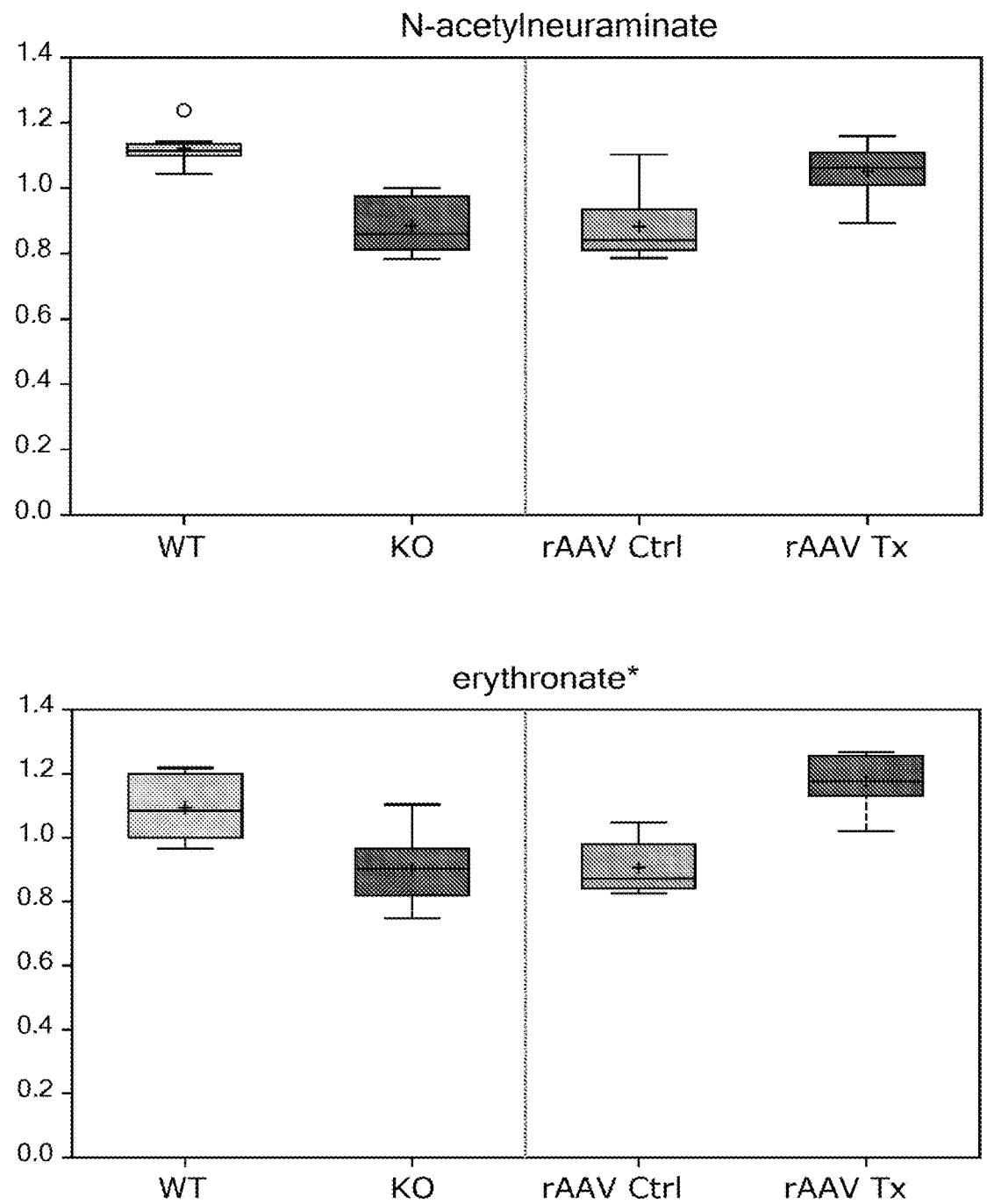
Figure 57:
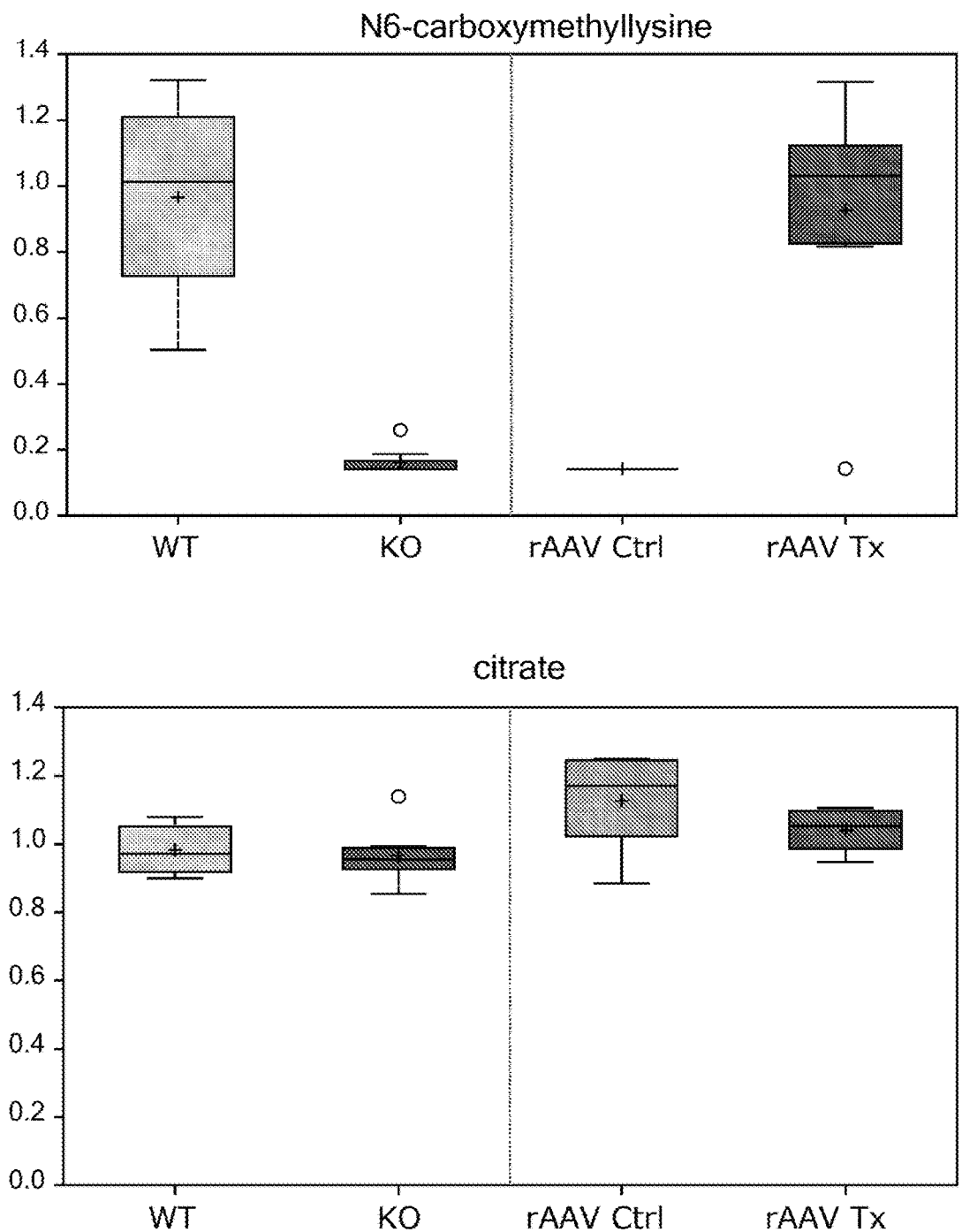
Figure 57:
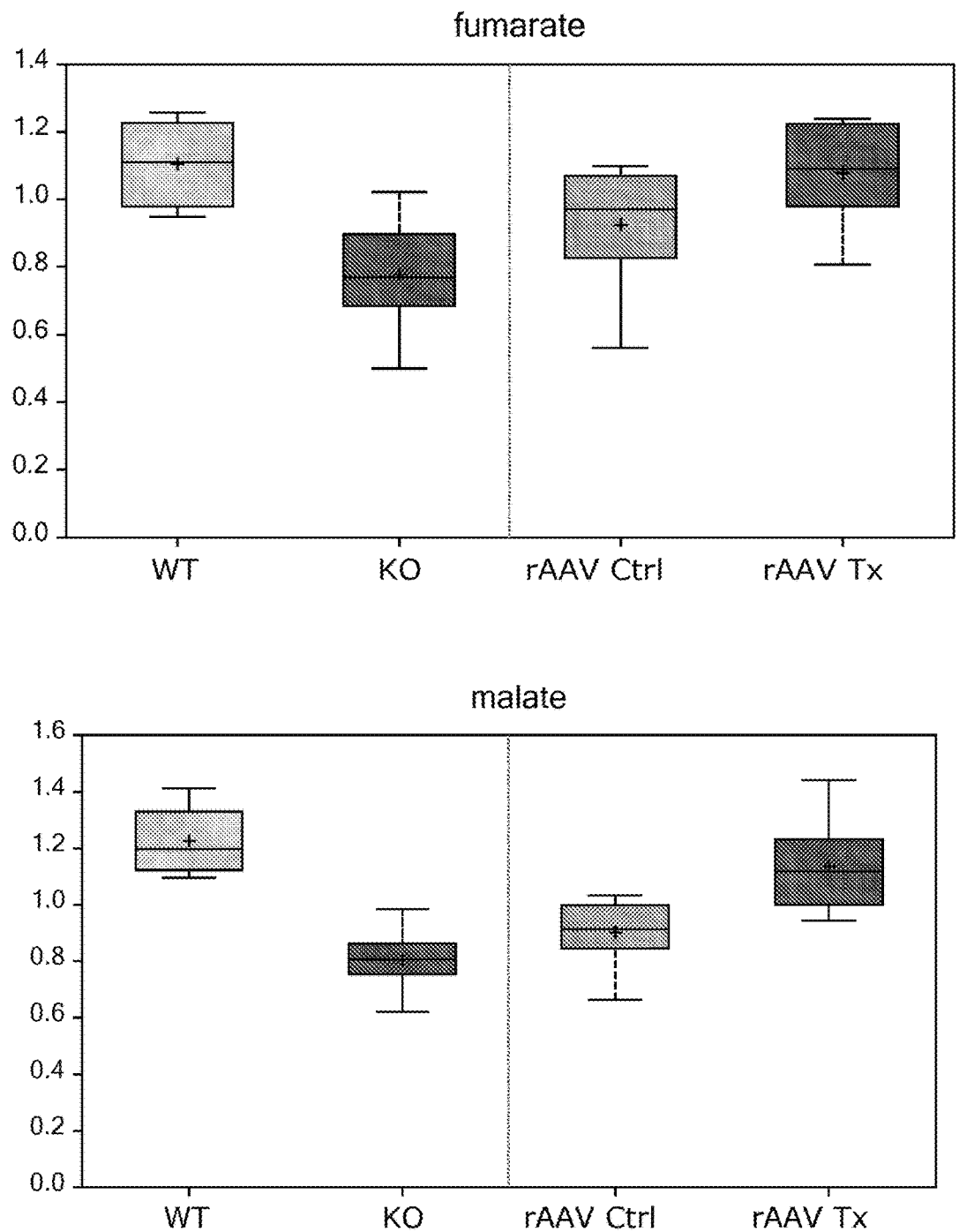
Figure 57:
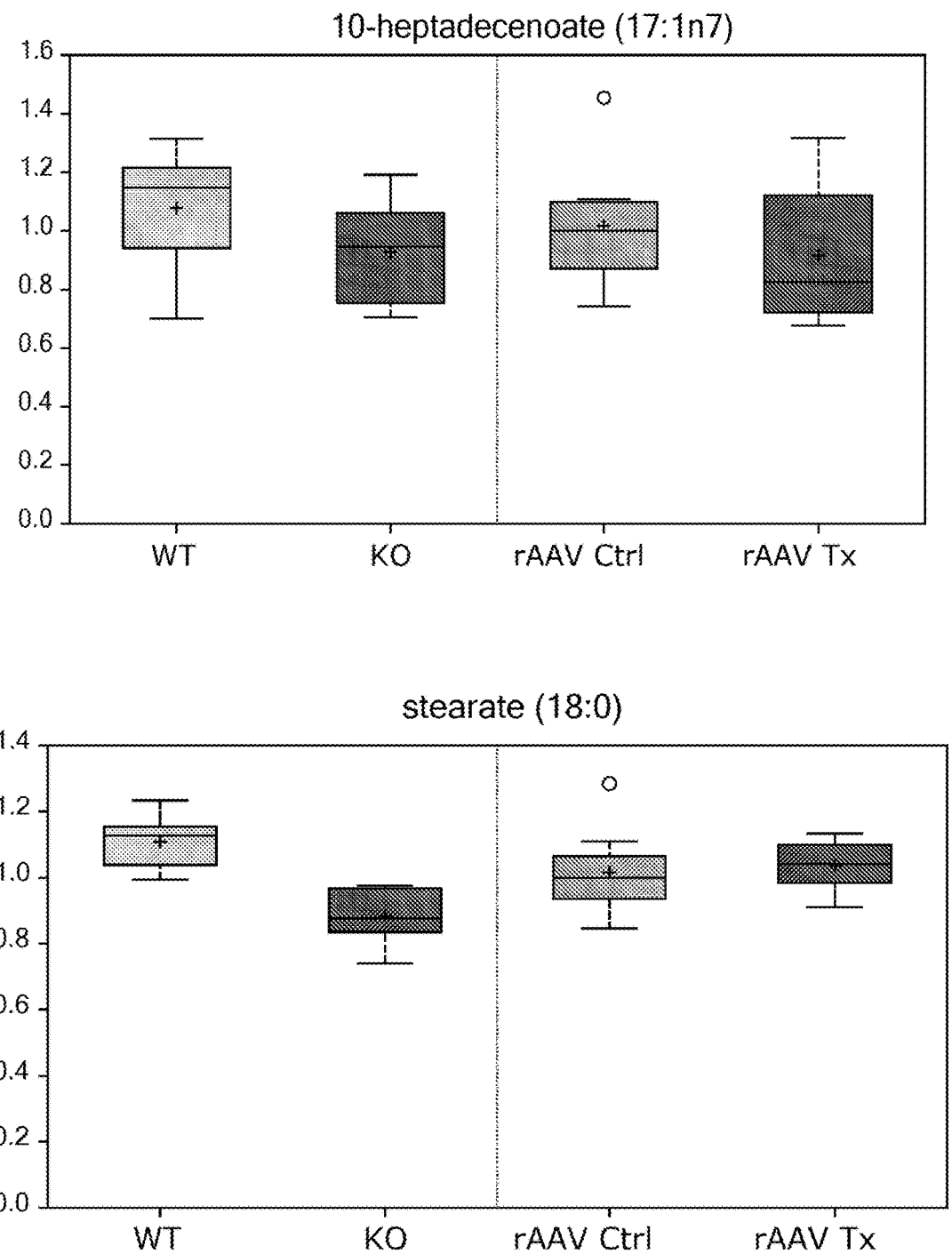
Figure 57:
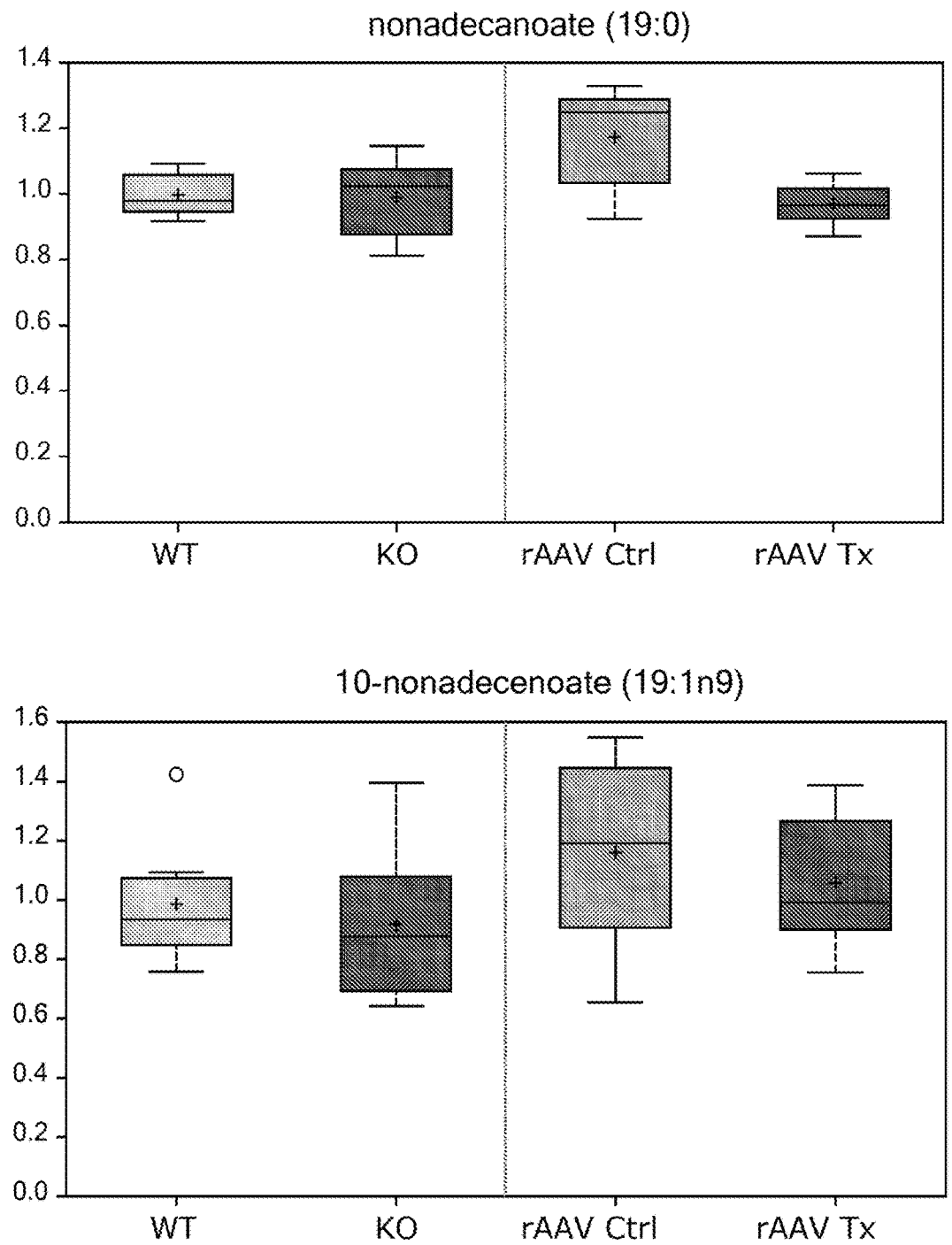
Figure 57:
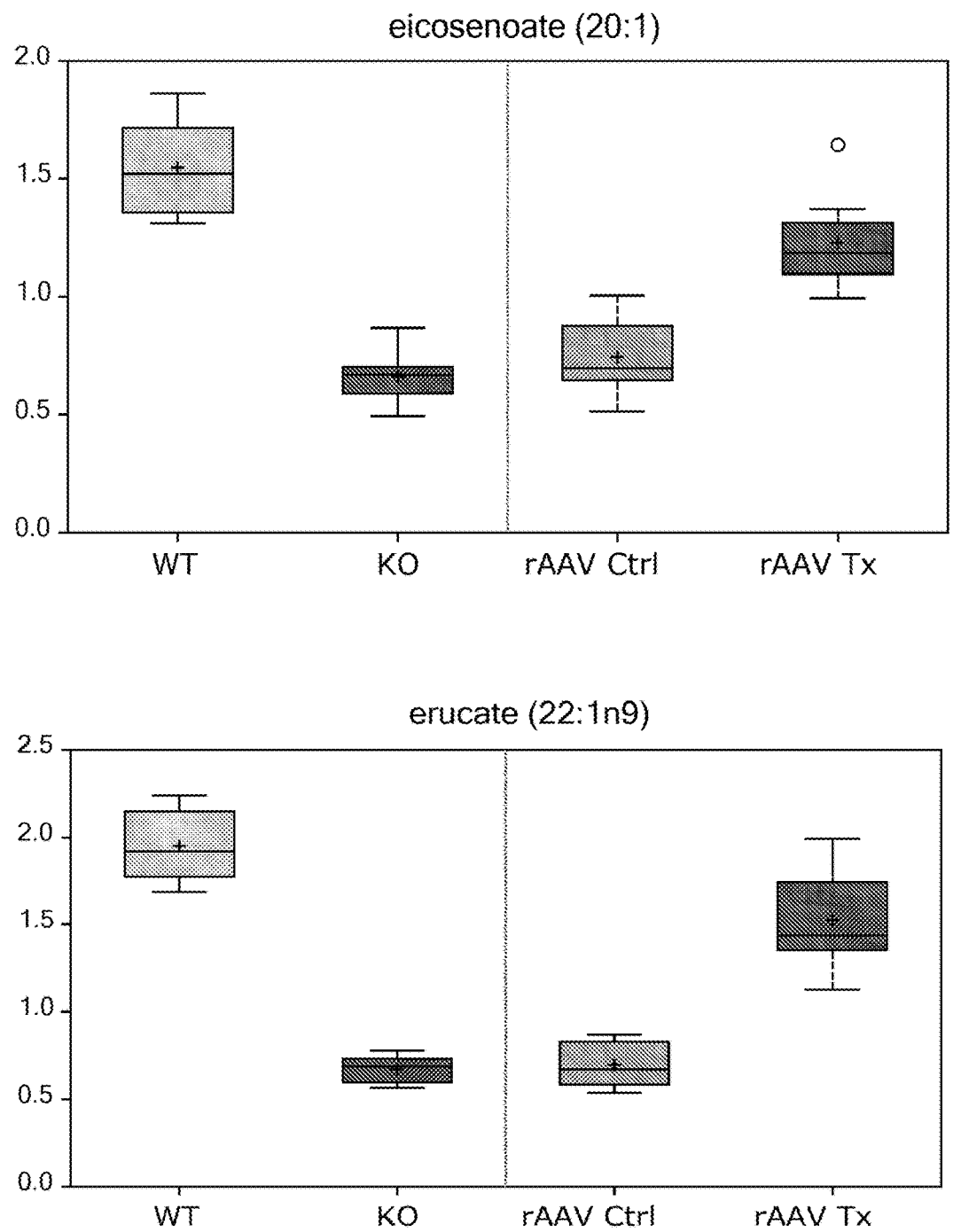
Figure 57:
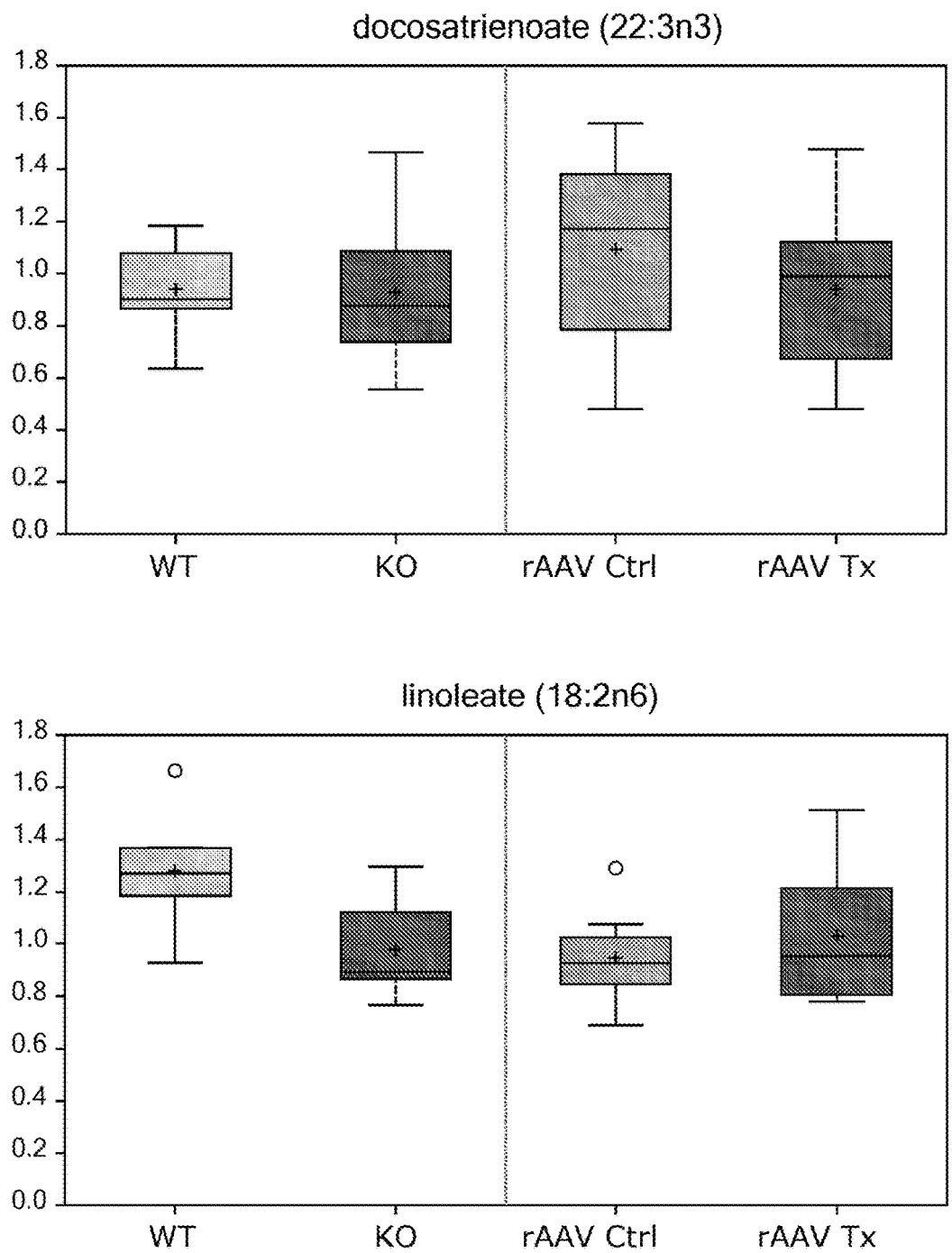
Figure 57:
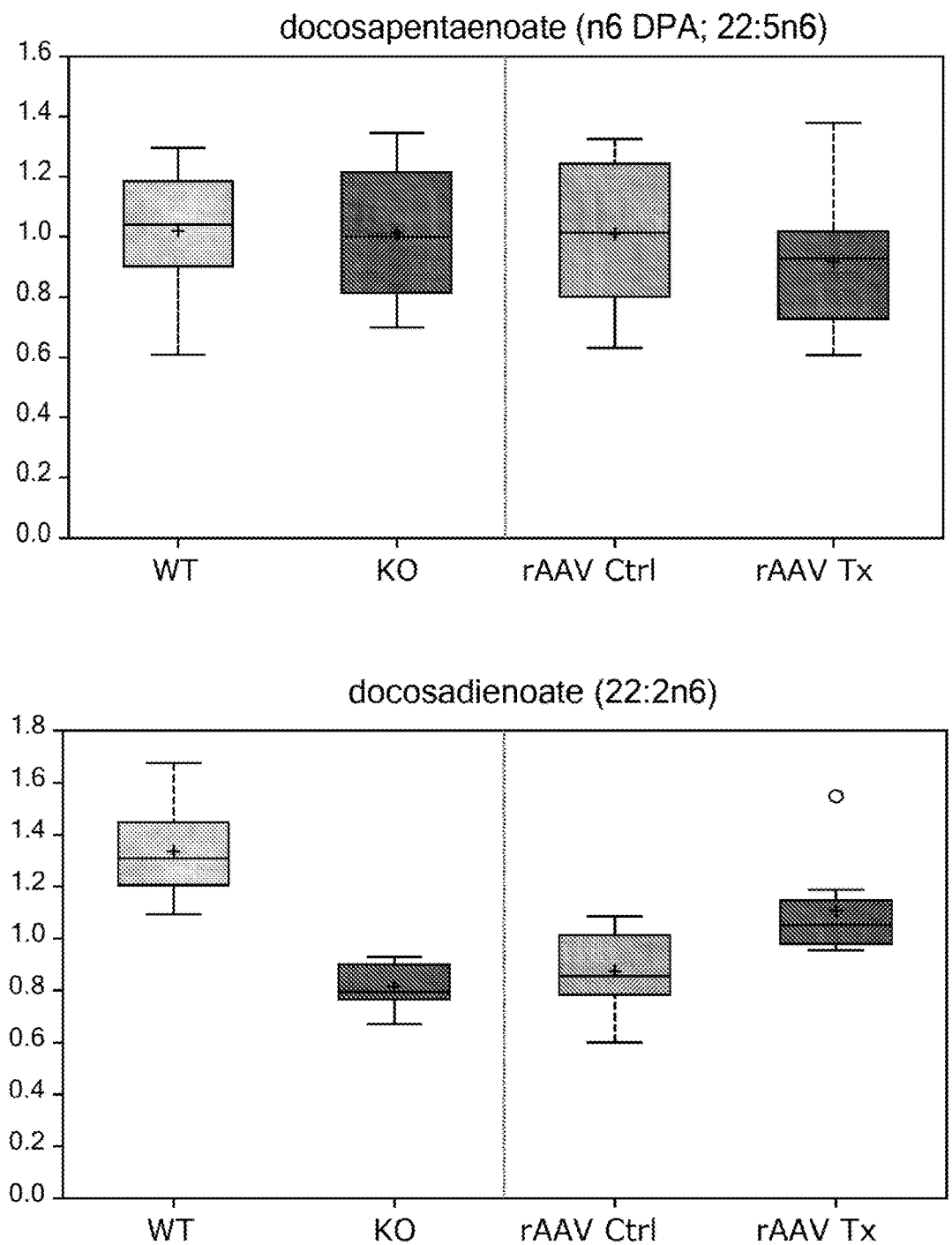
Figure 57:
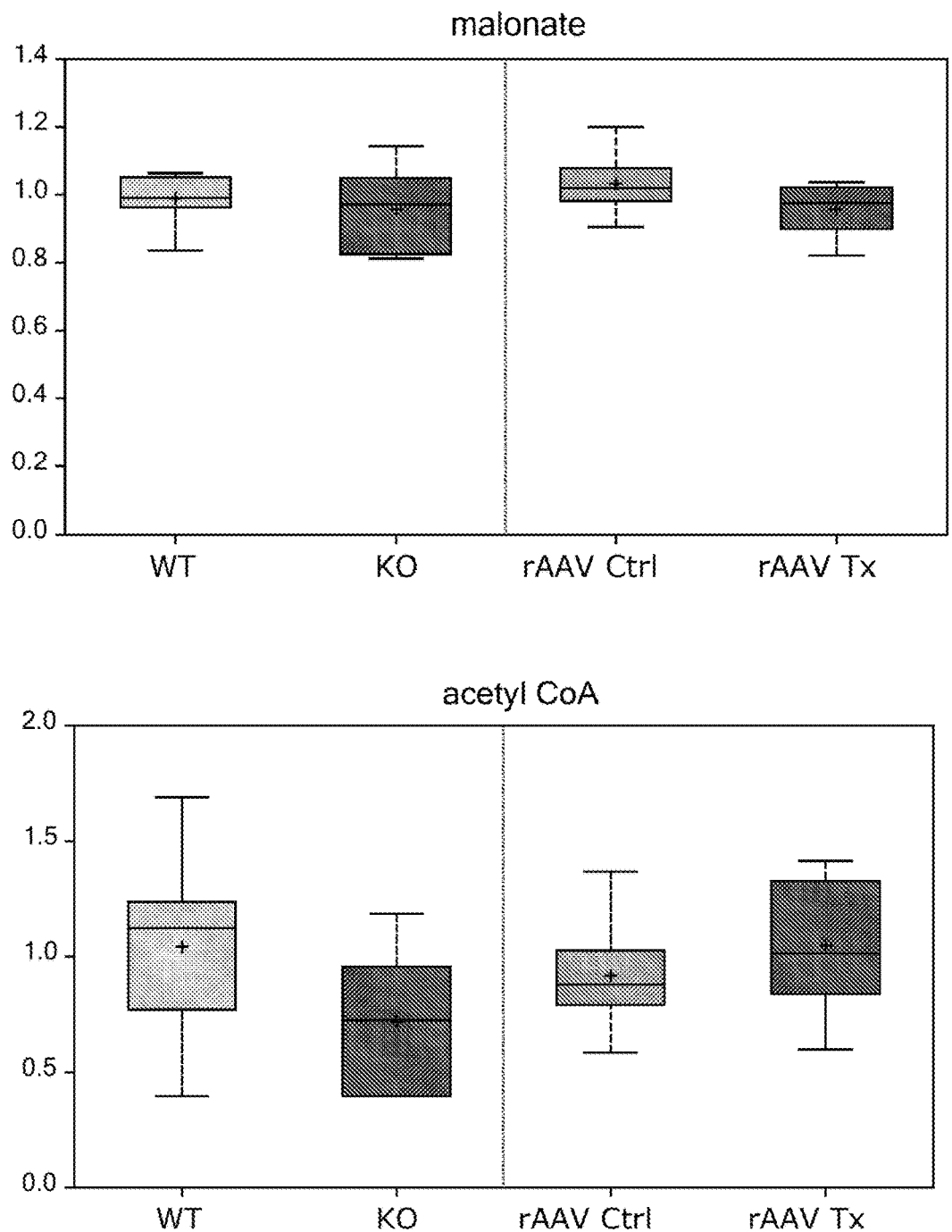
Figure 57:
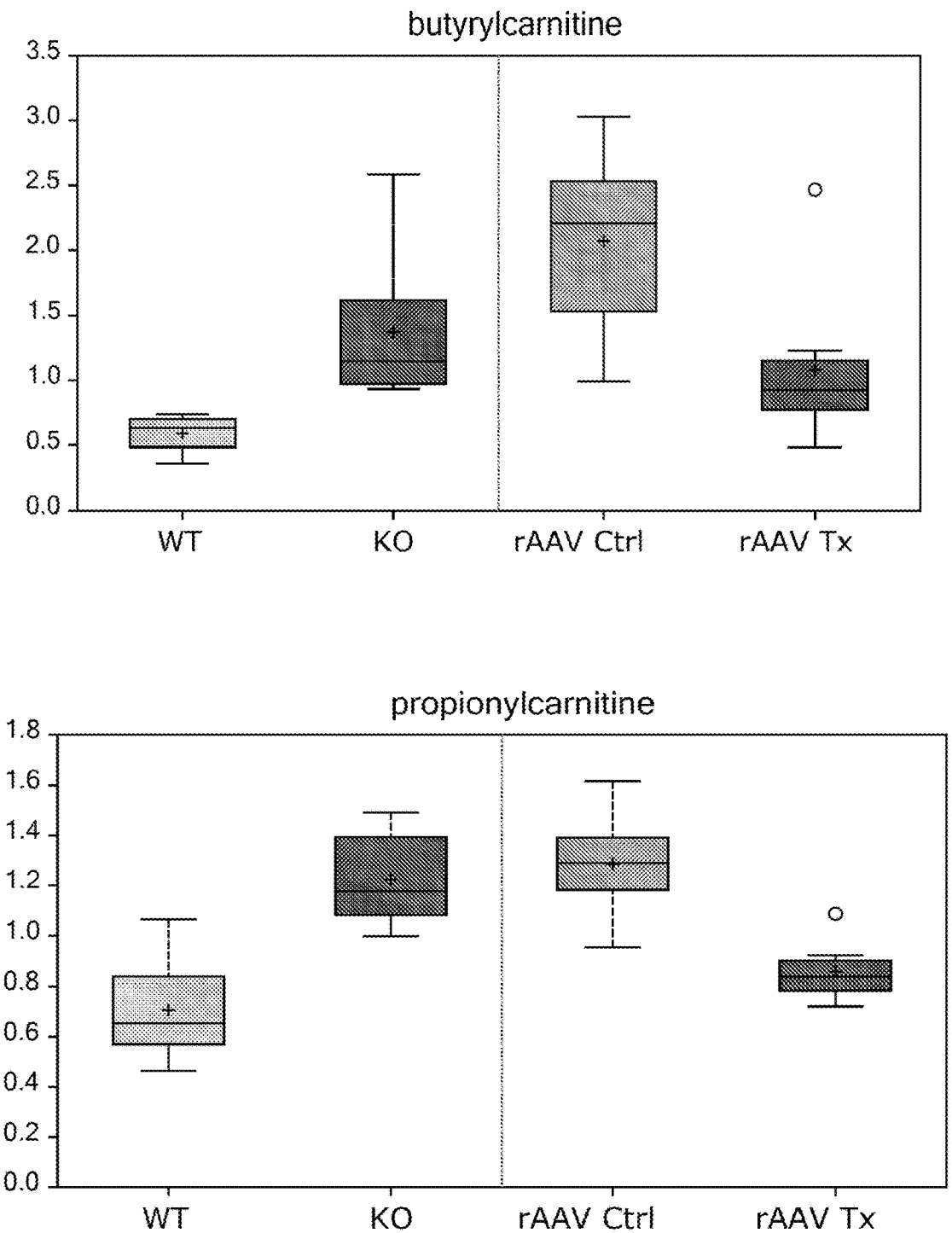
Figure 57:
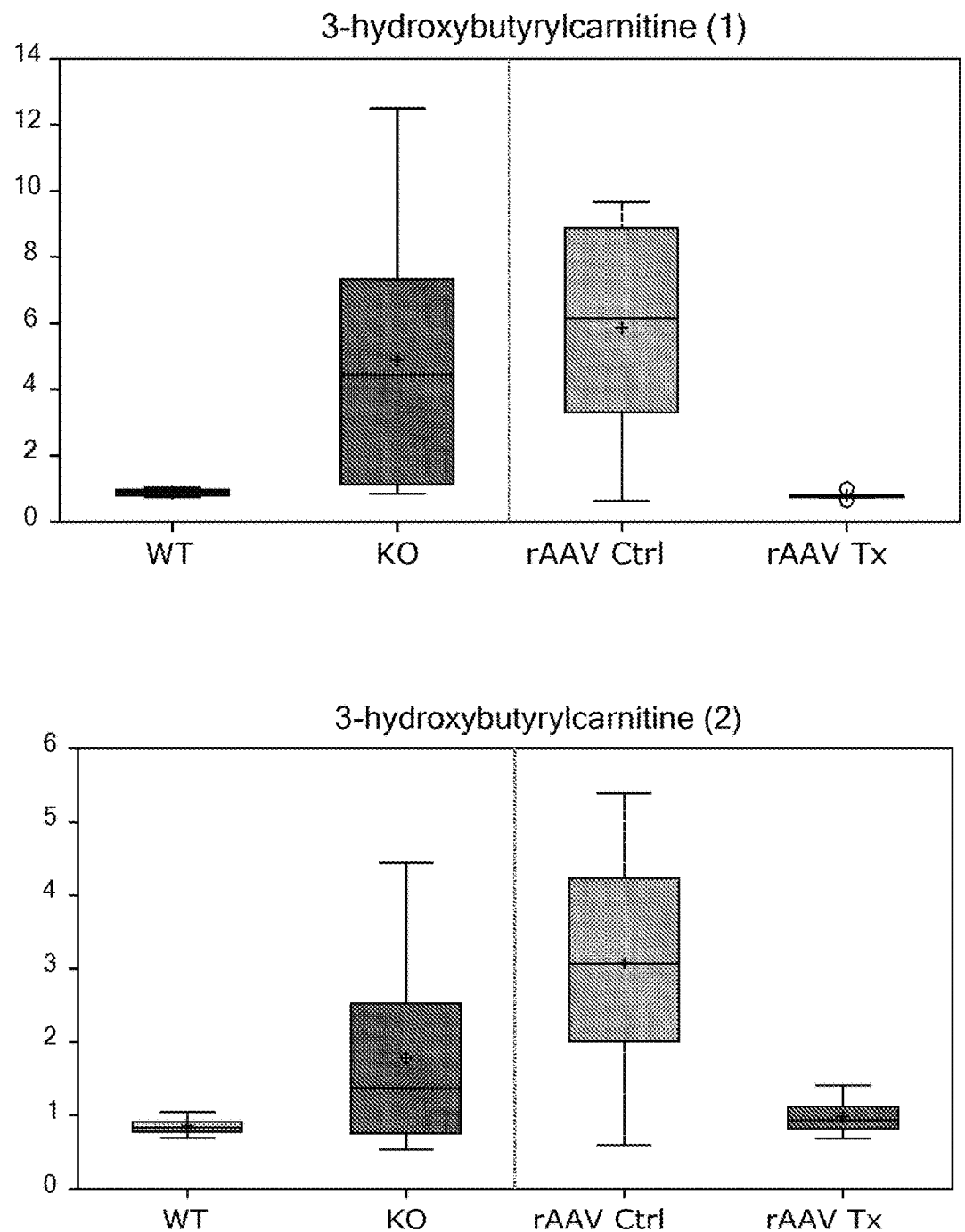
Figure 57:
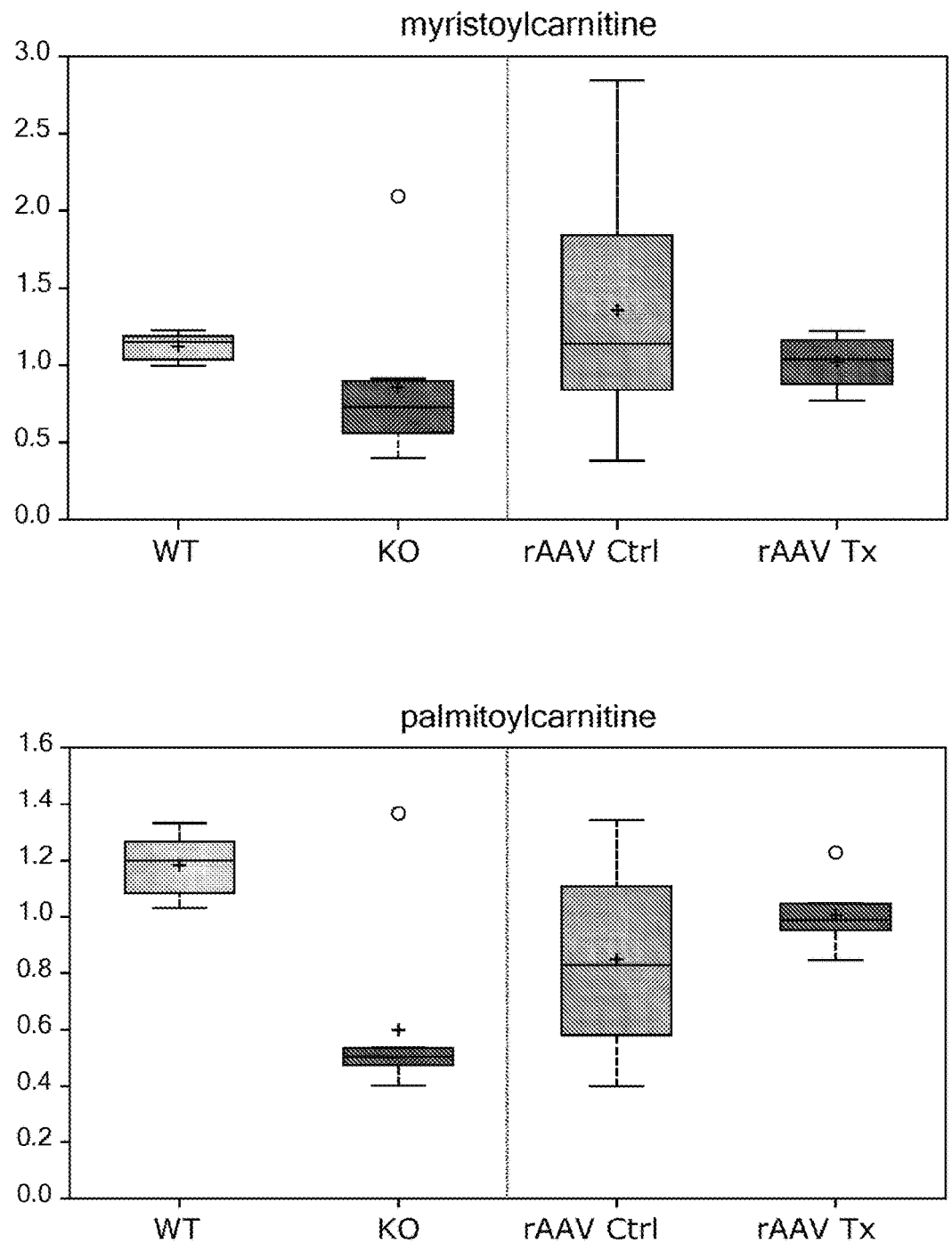
Figure 57:
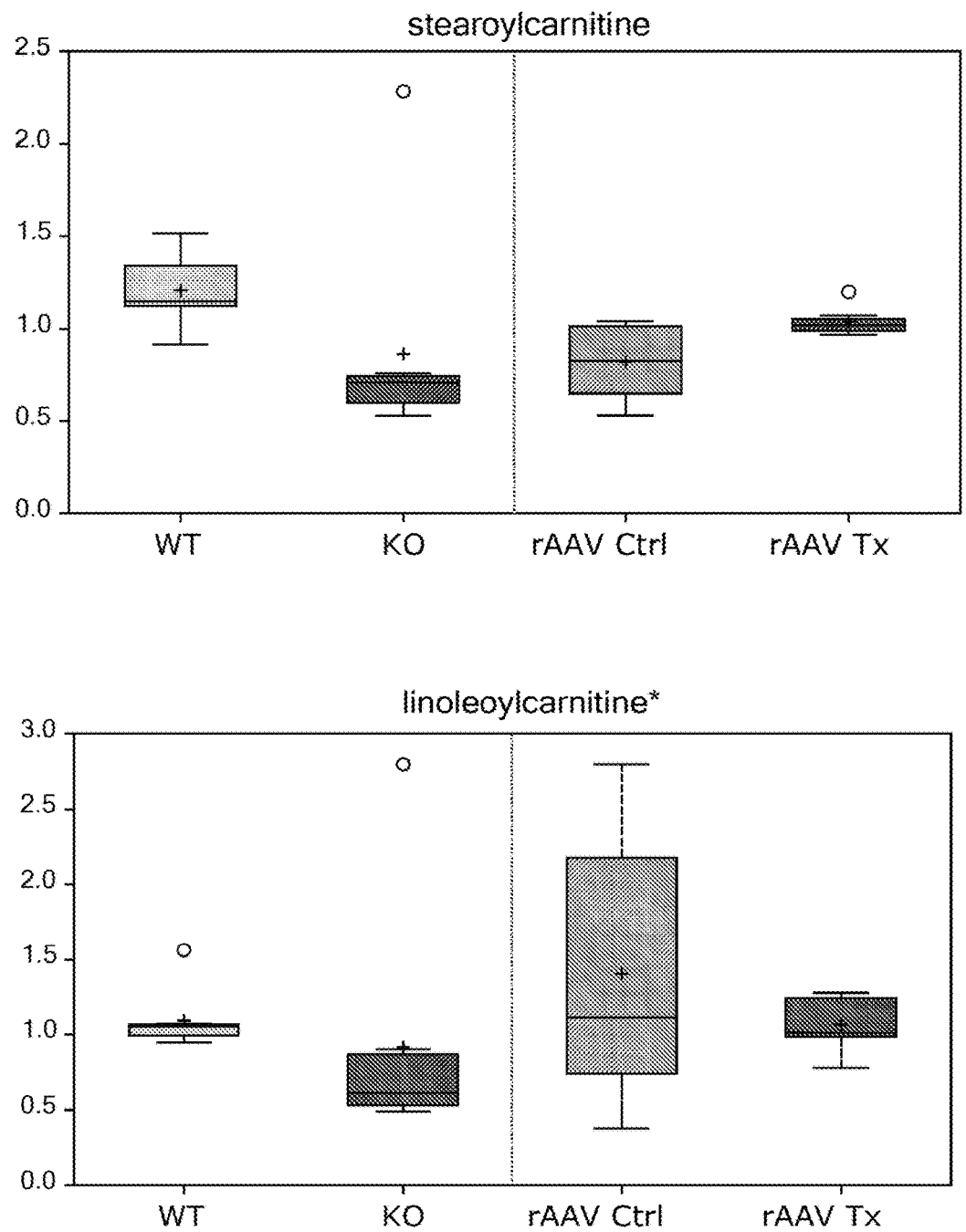
Figure 57:
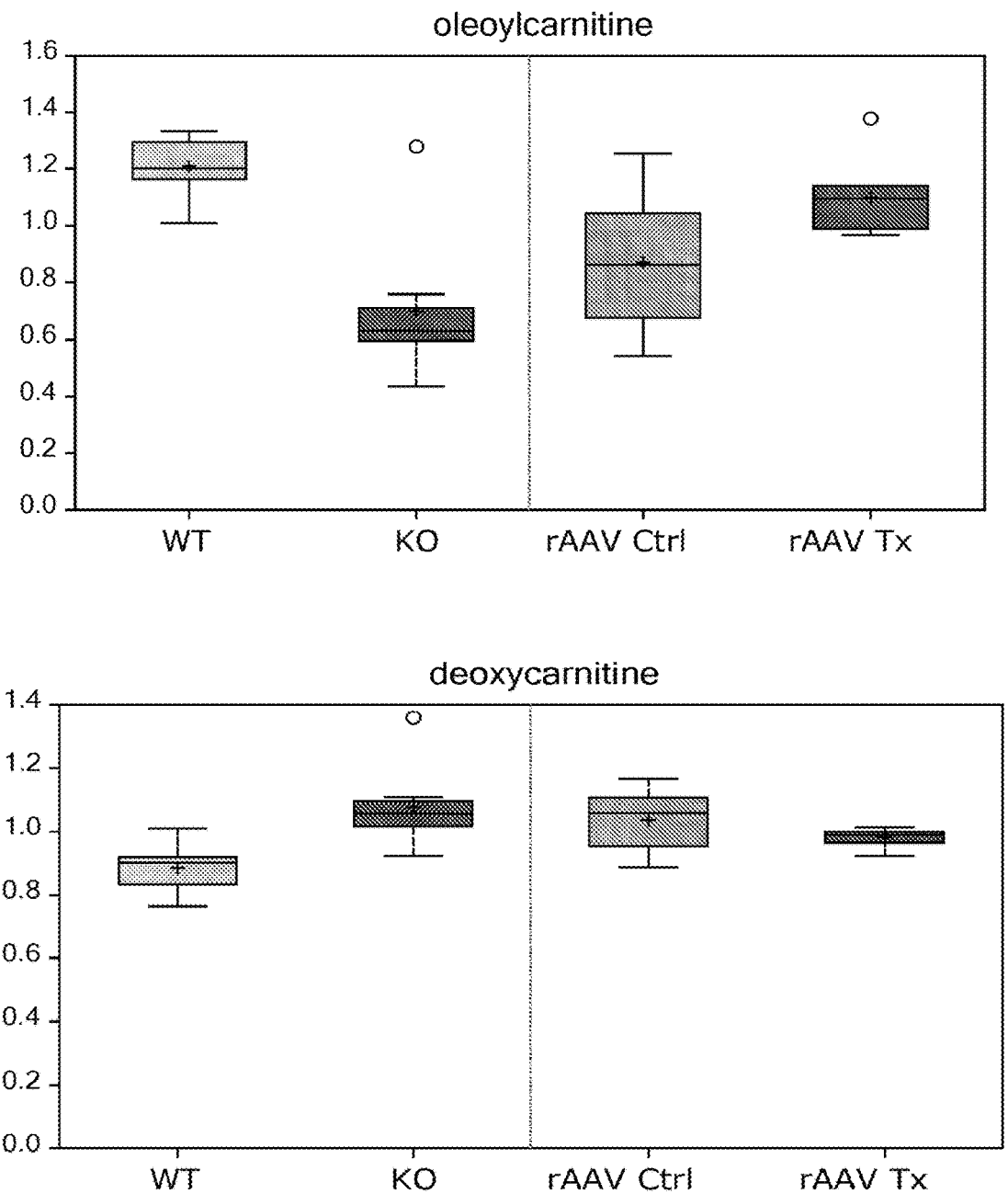
Figure 57:
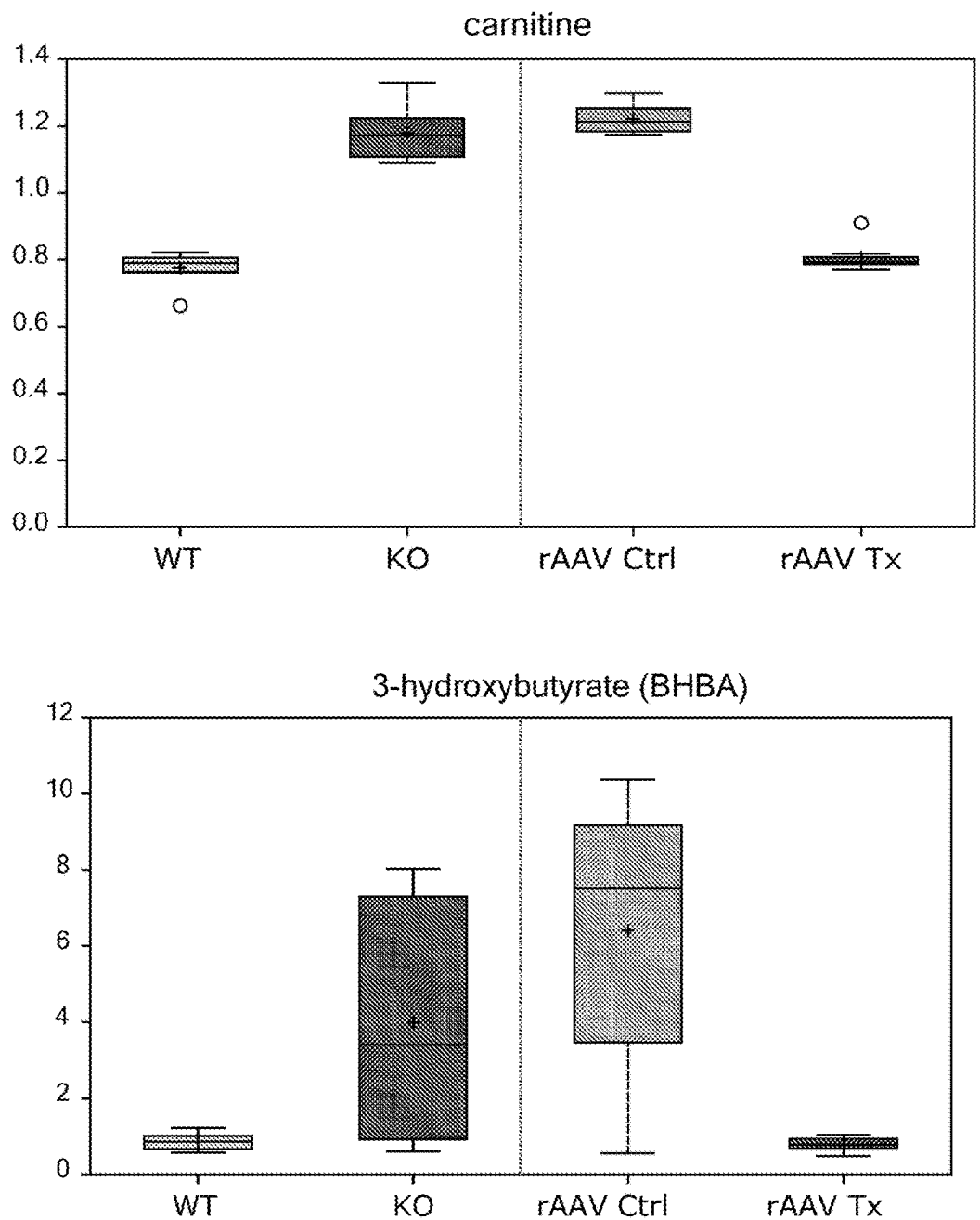
Figure 57:
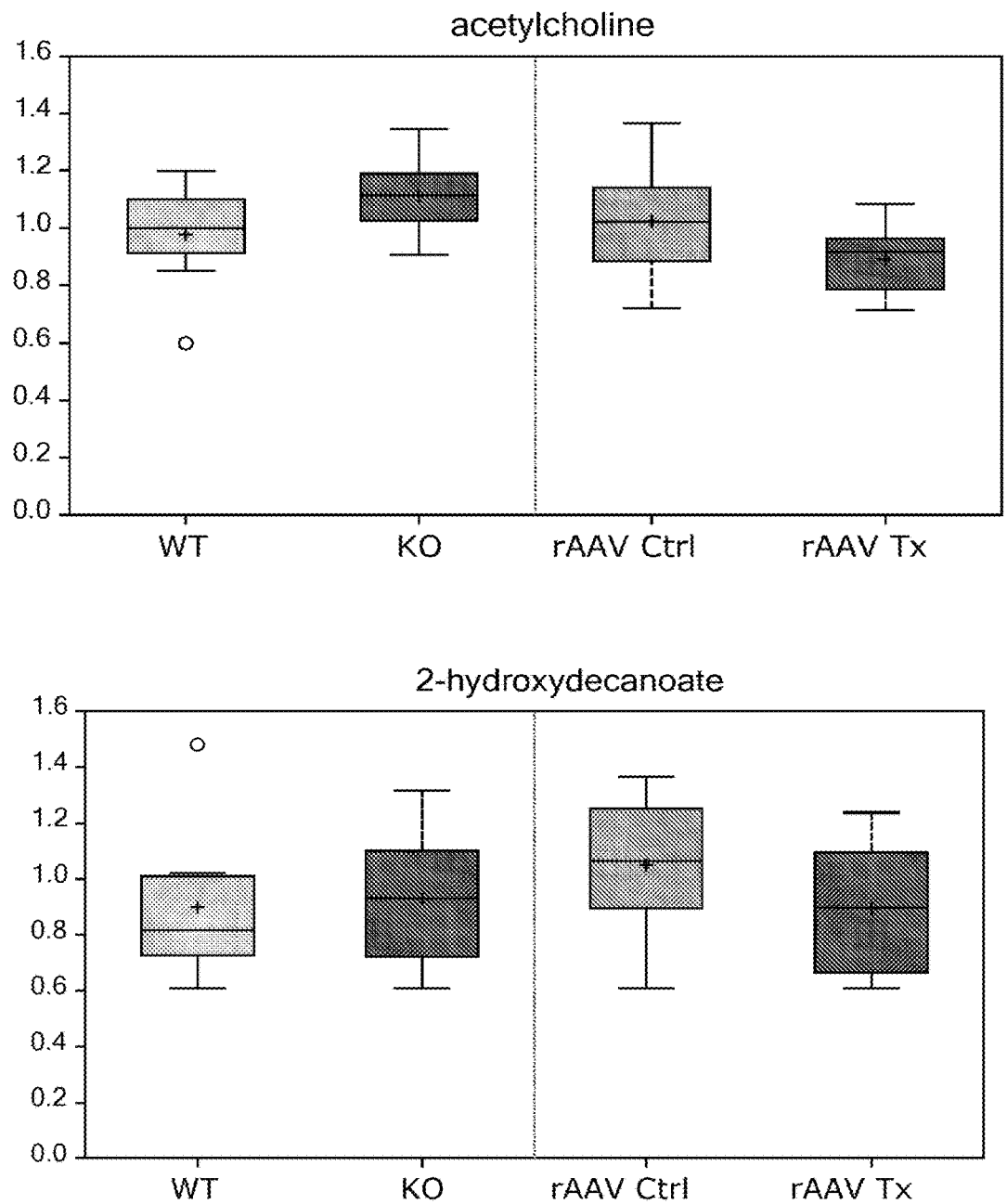
Figure 57:
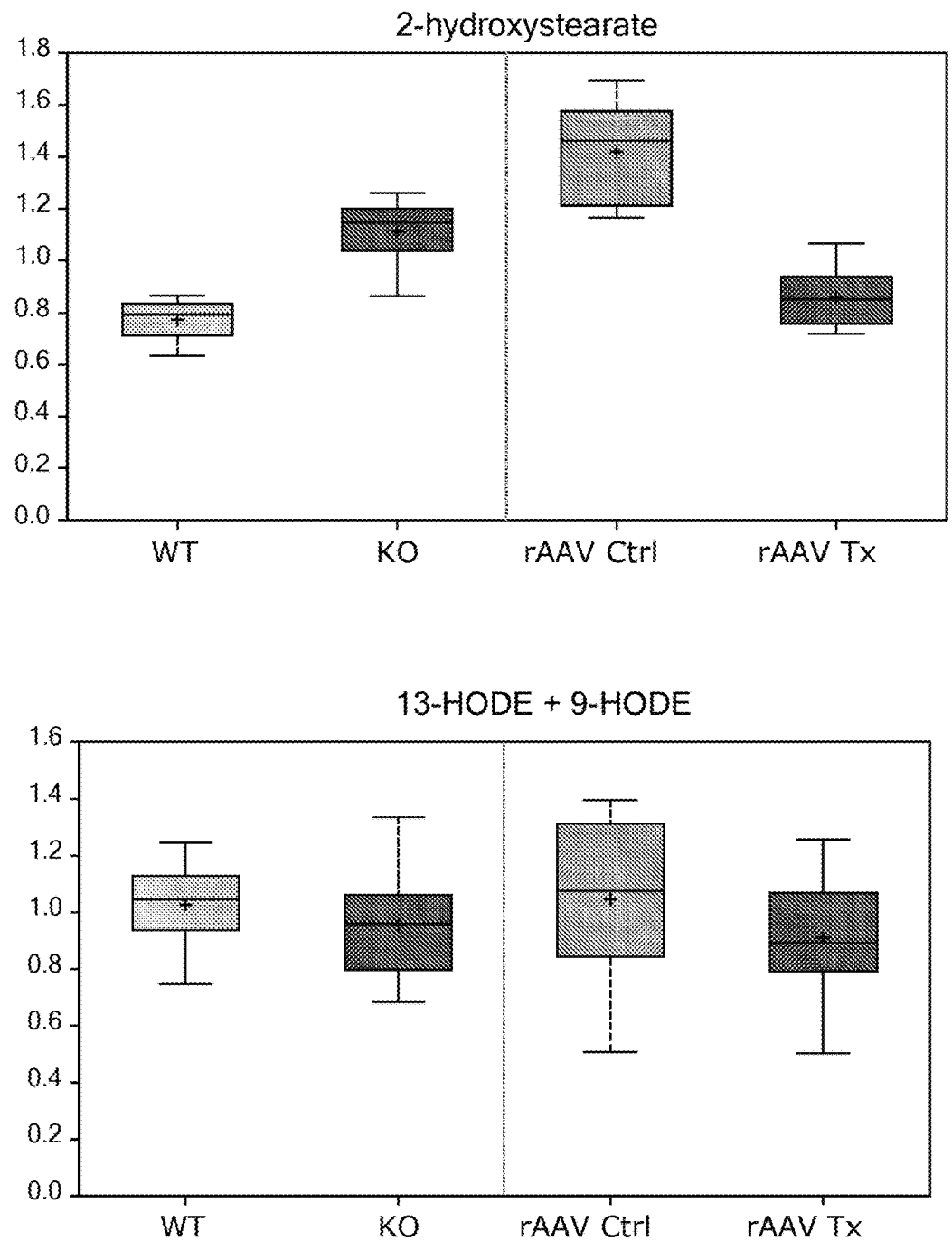
Figure 57:
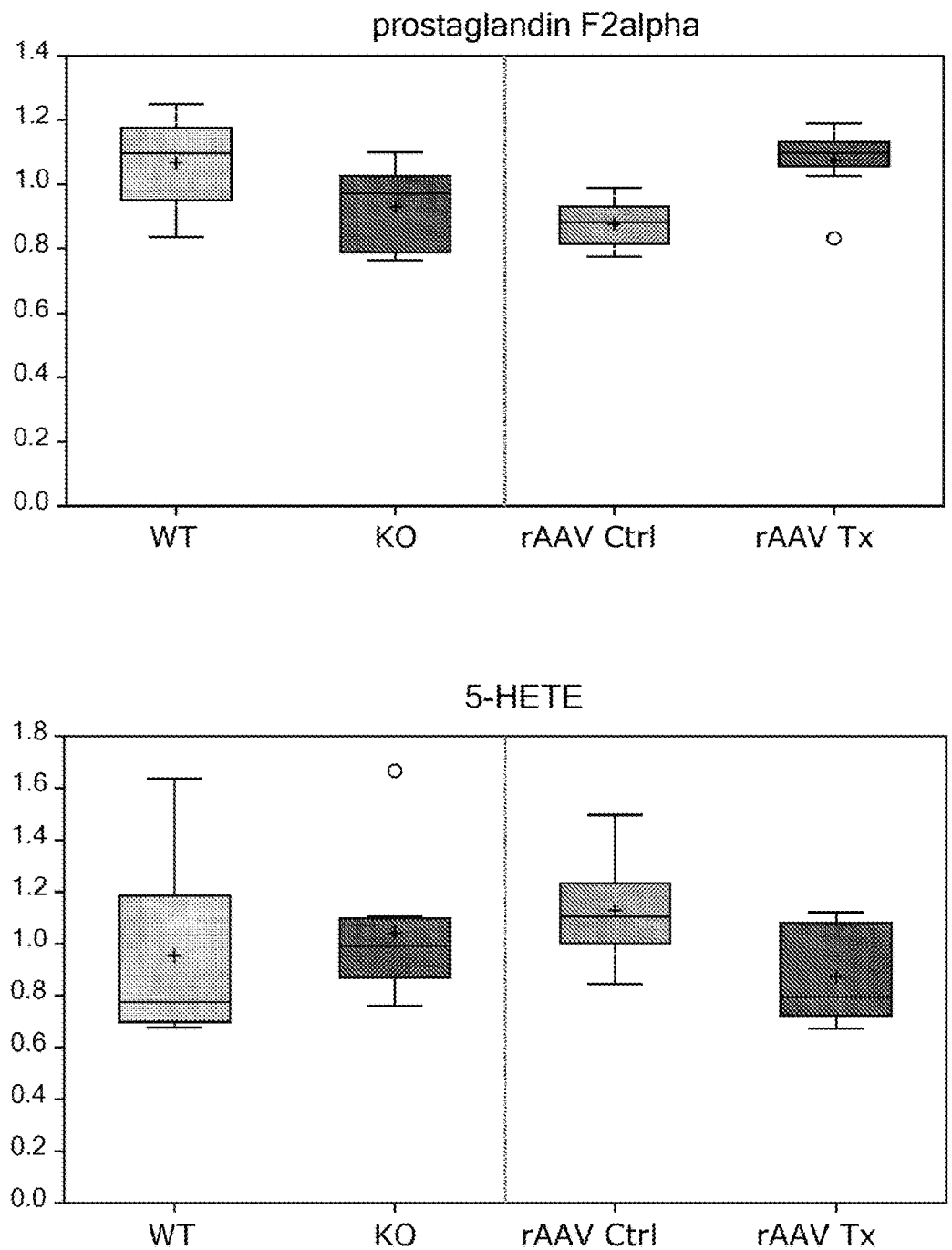
Figure 57:
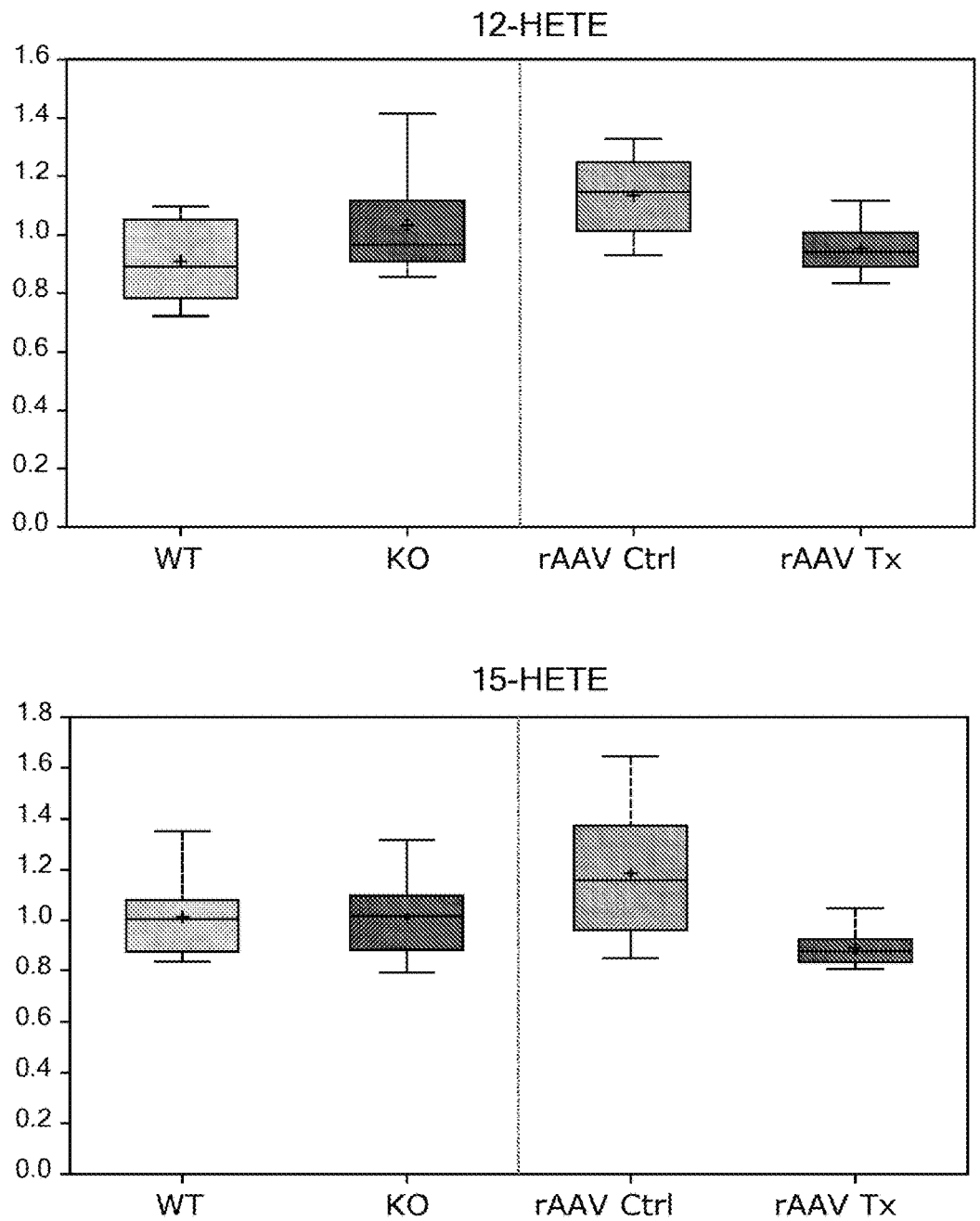
Figure 57:
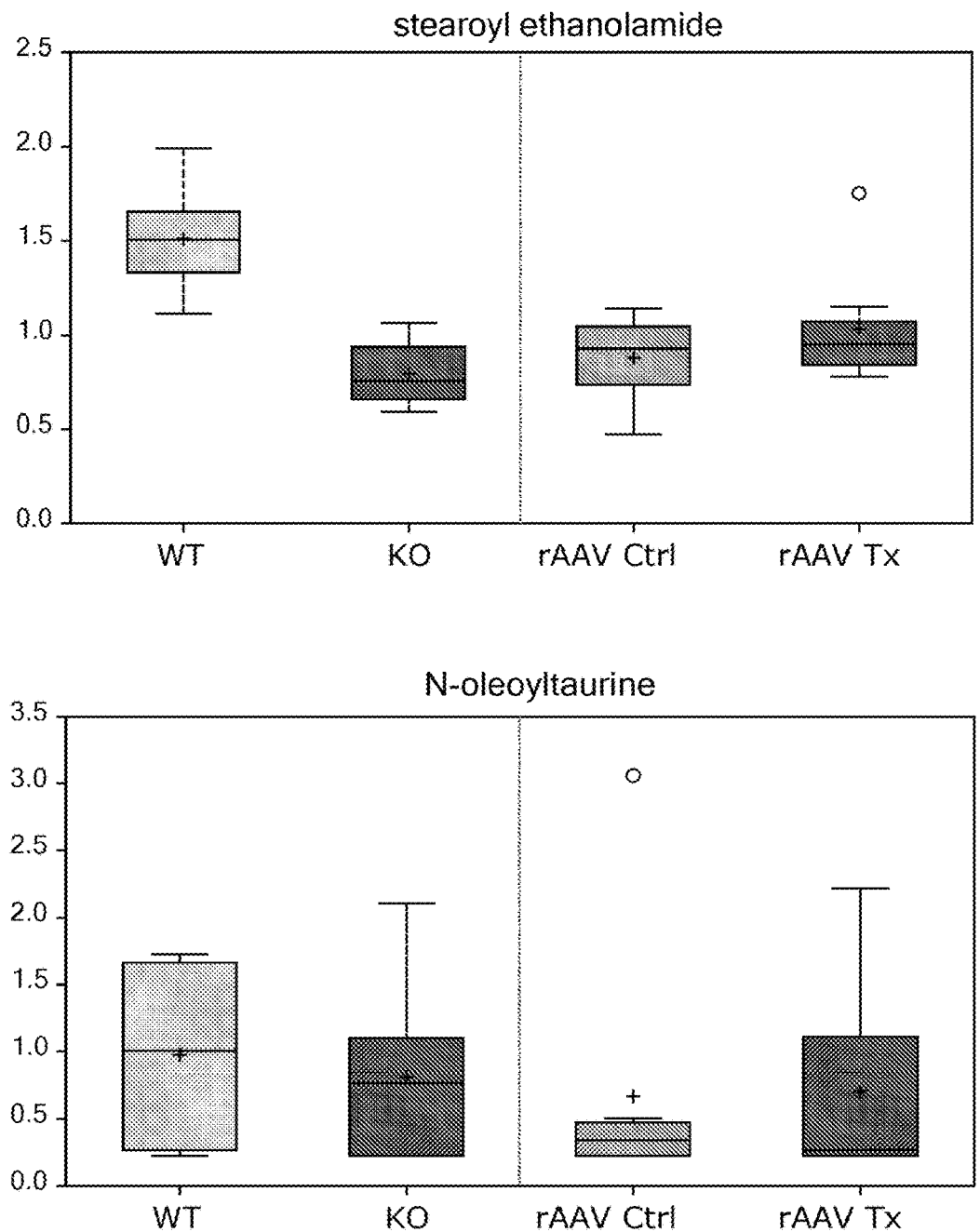
Figure 57:
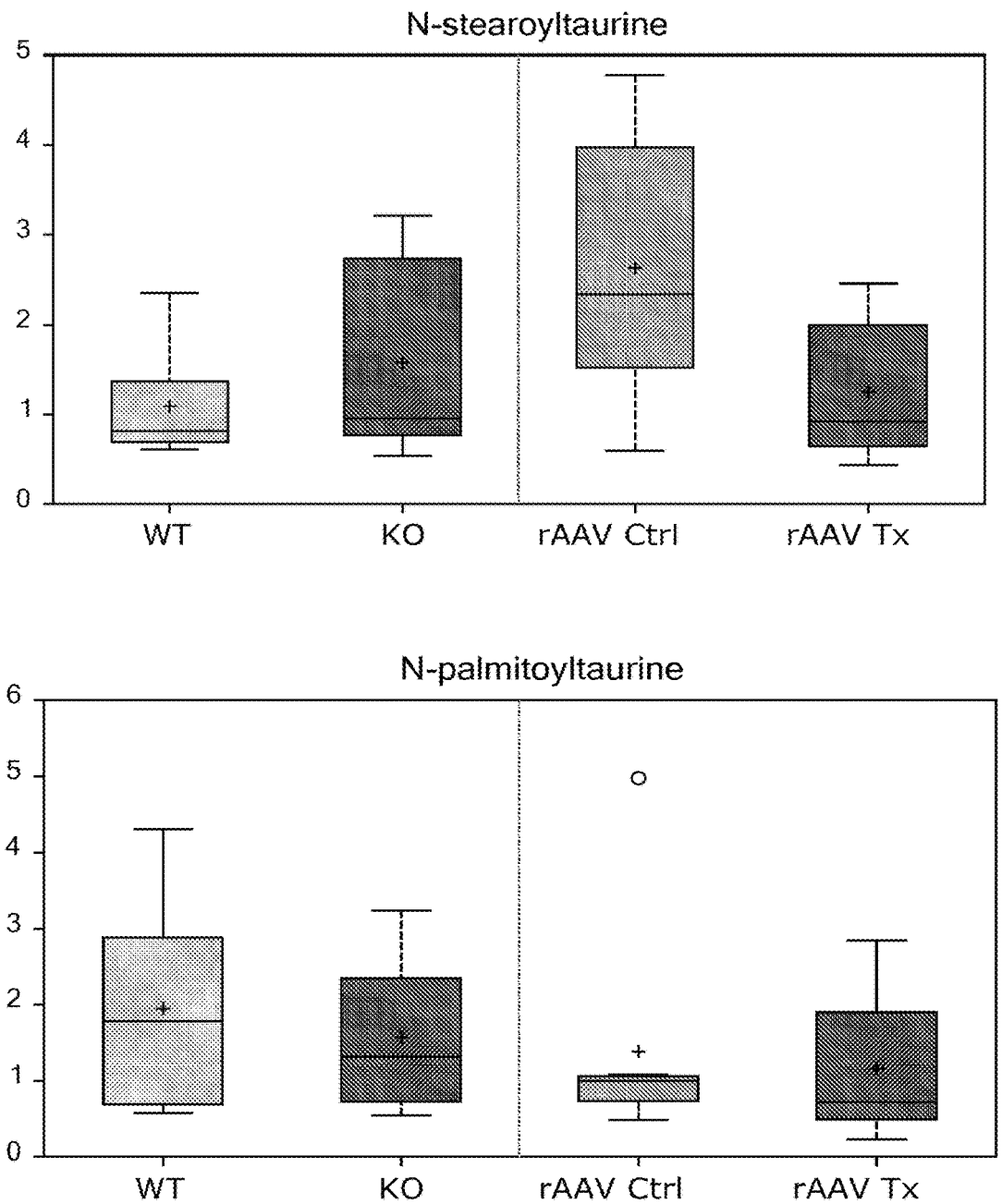
Figure 57:
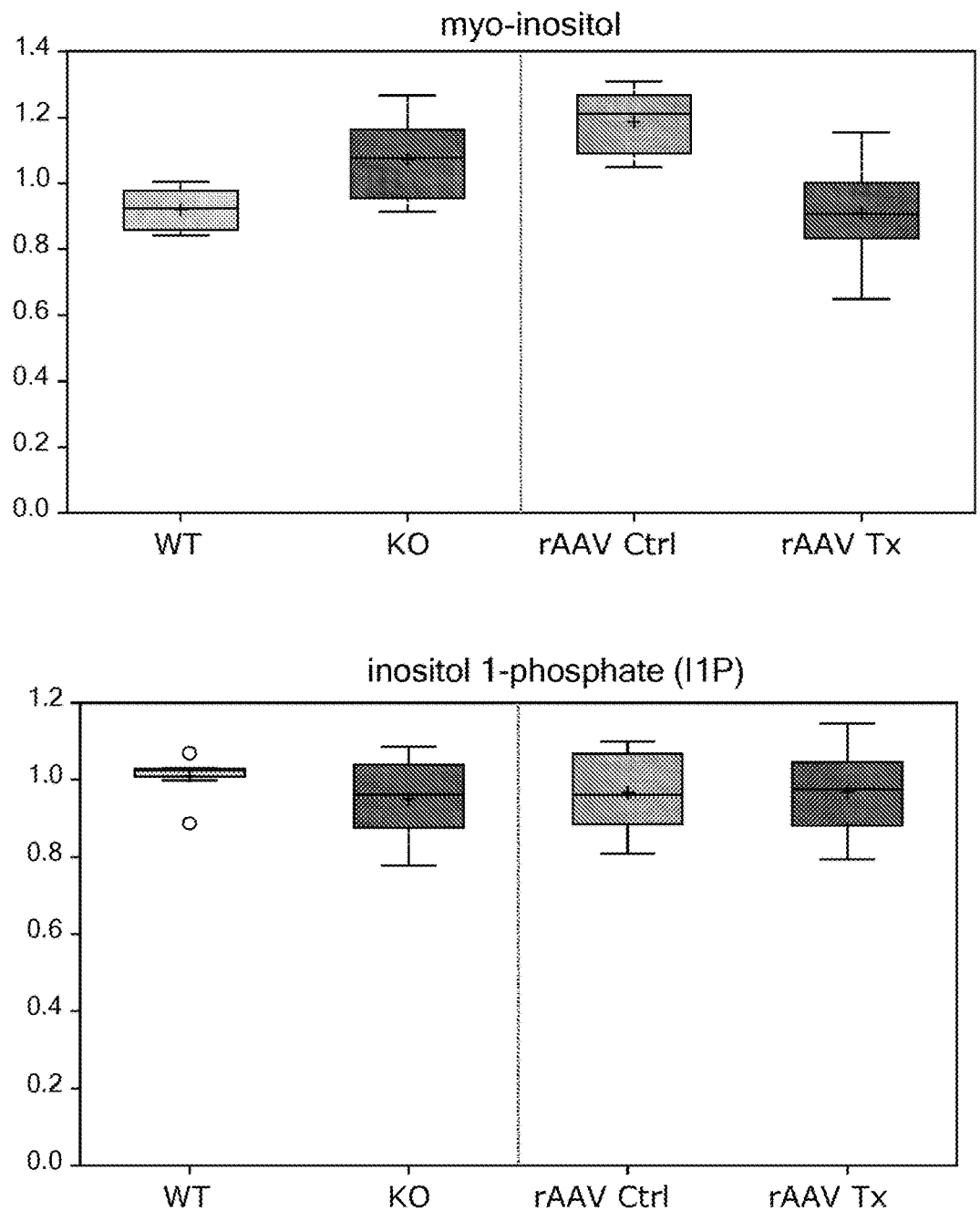
Figure 57:
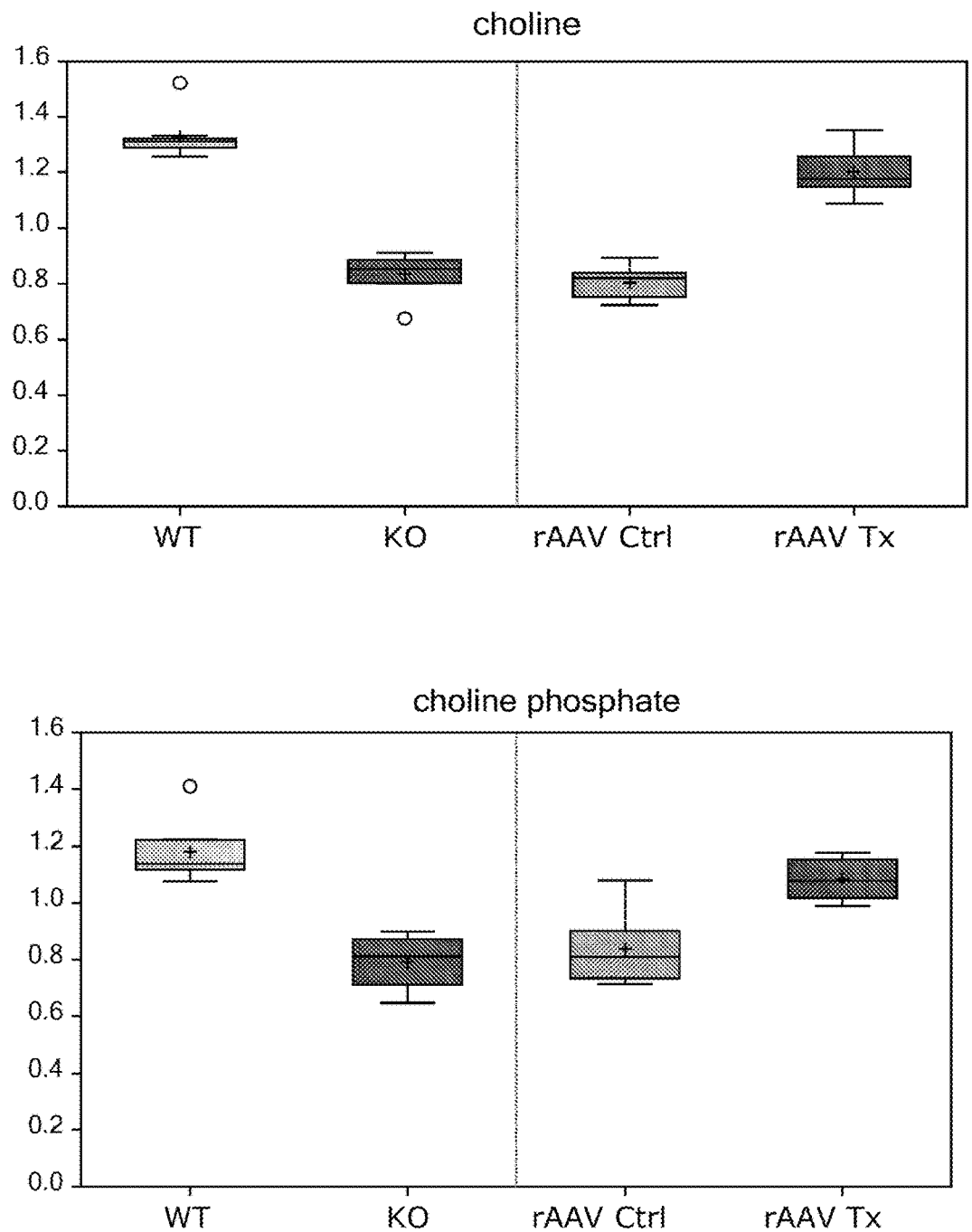
Figure 57:
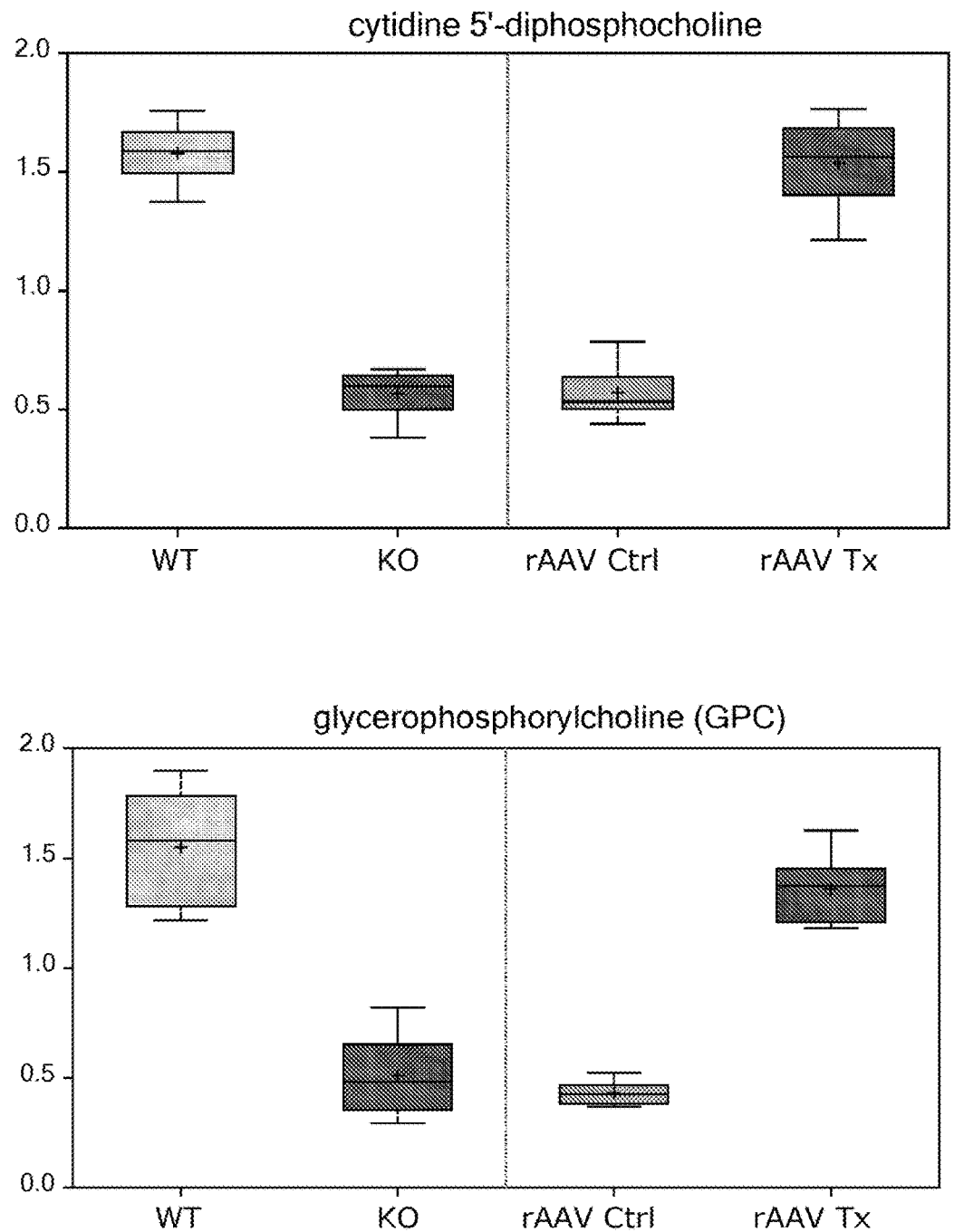
Figure 57:
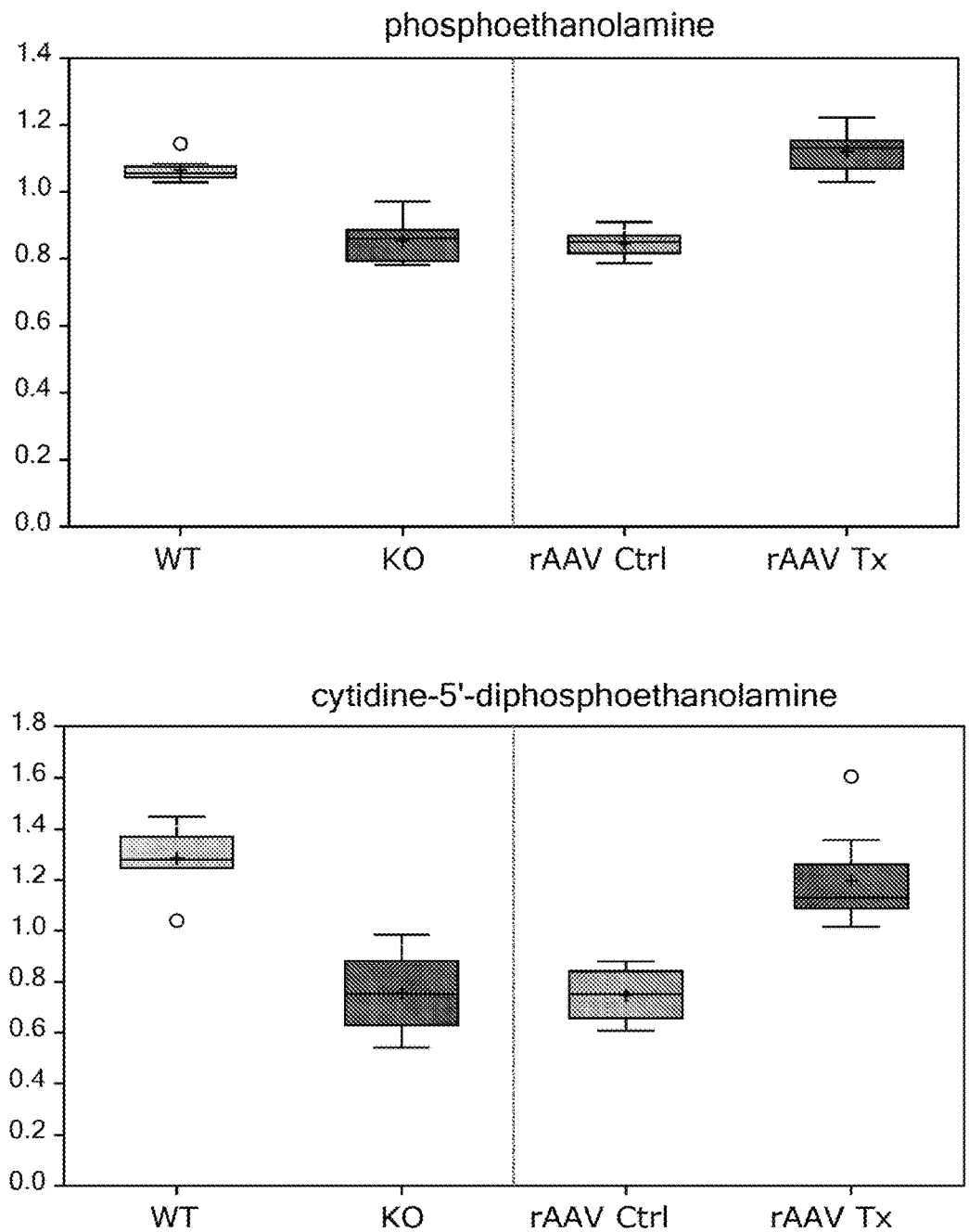
Figure 57:
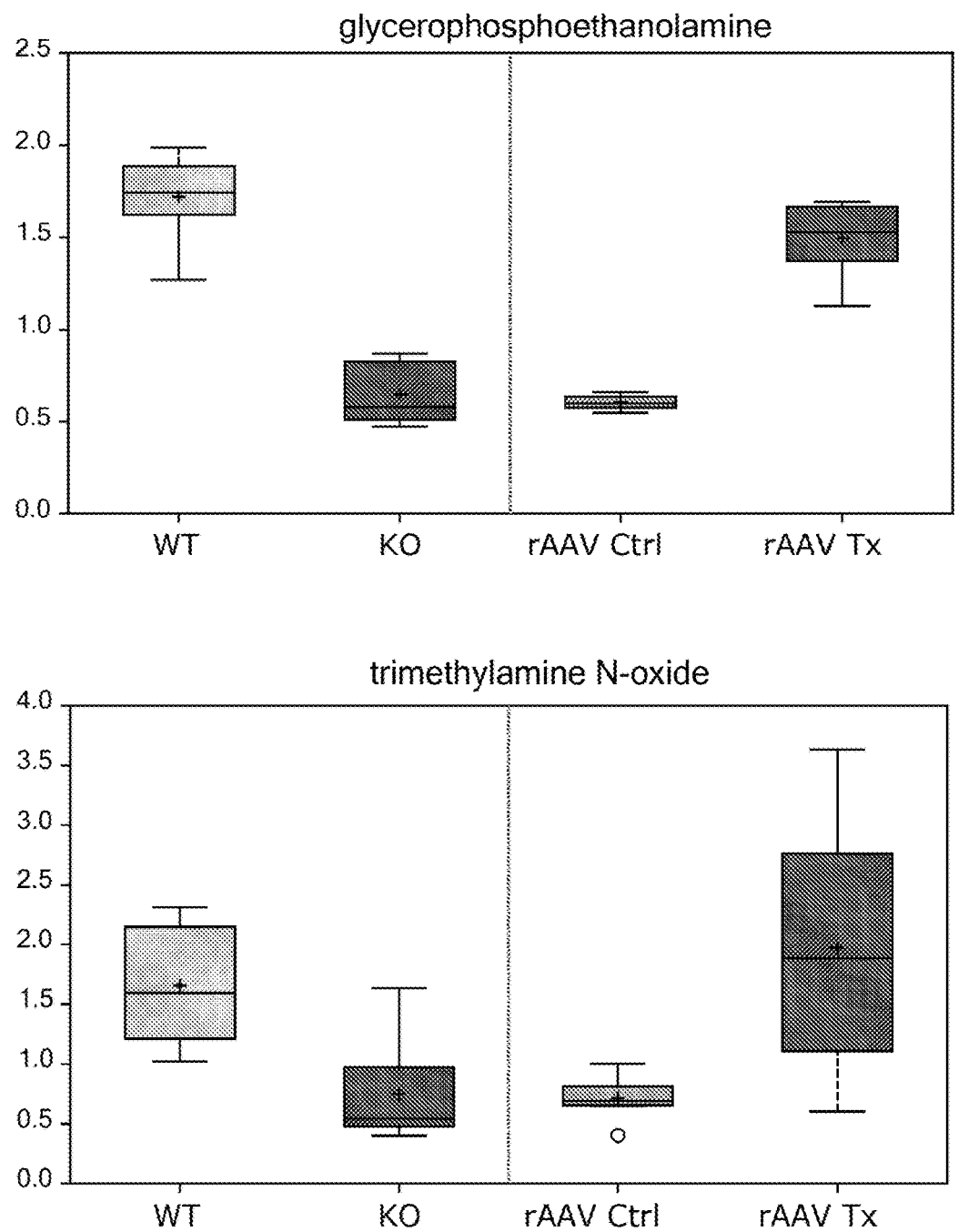
Figure 57:
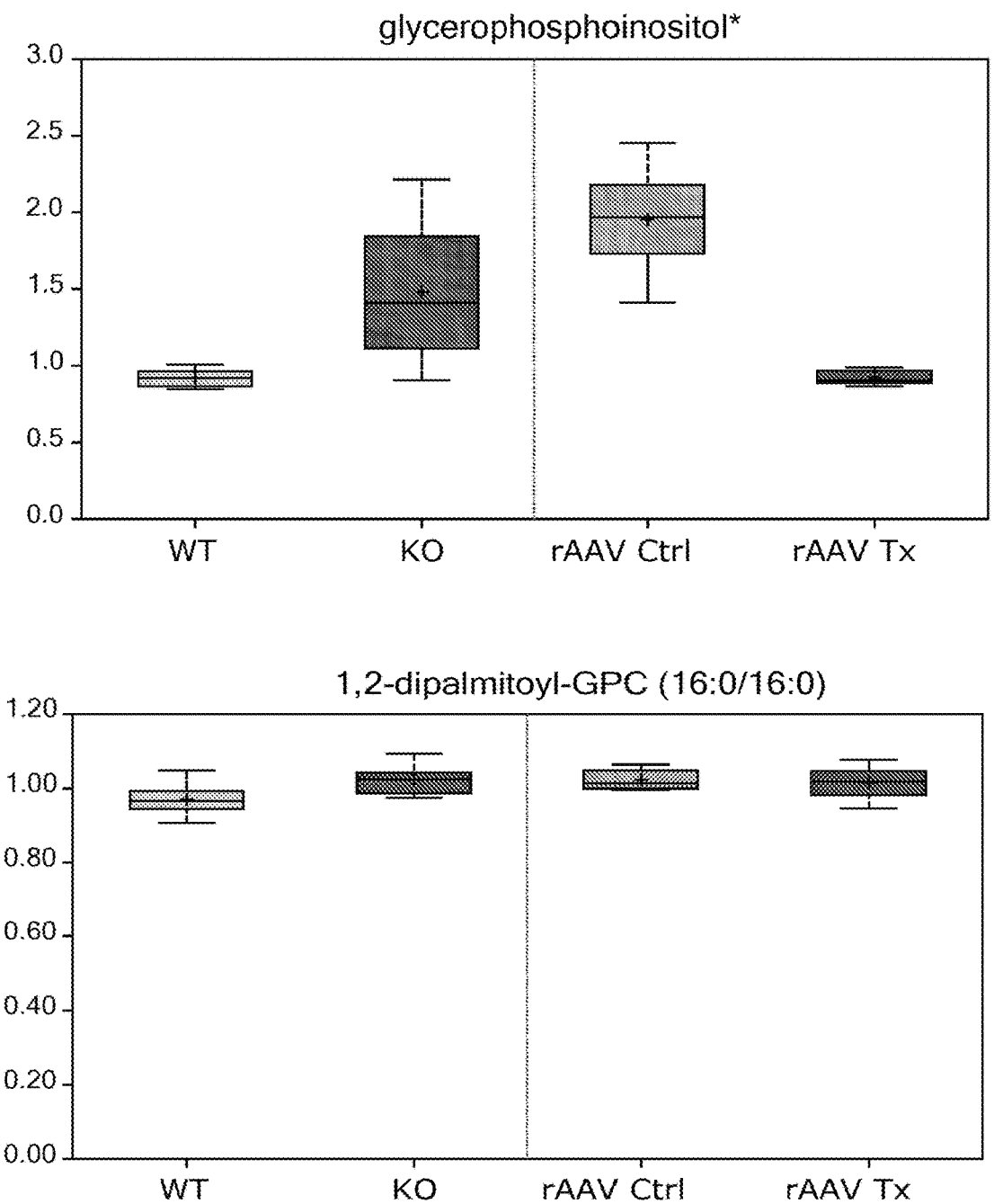
Figure 57:
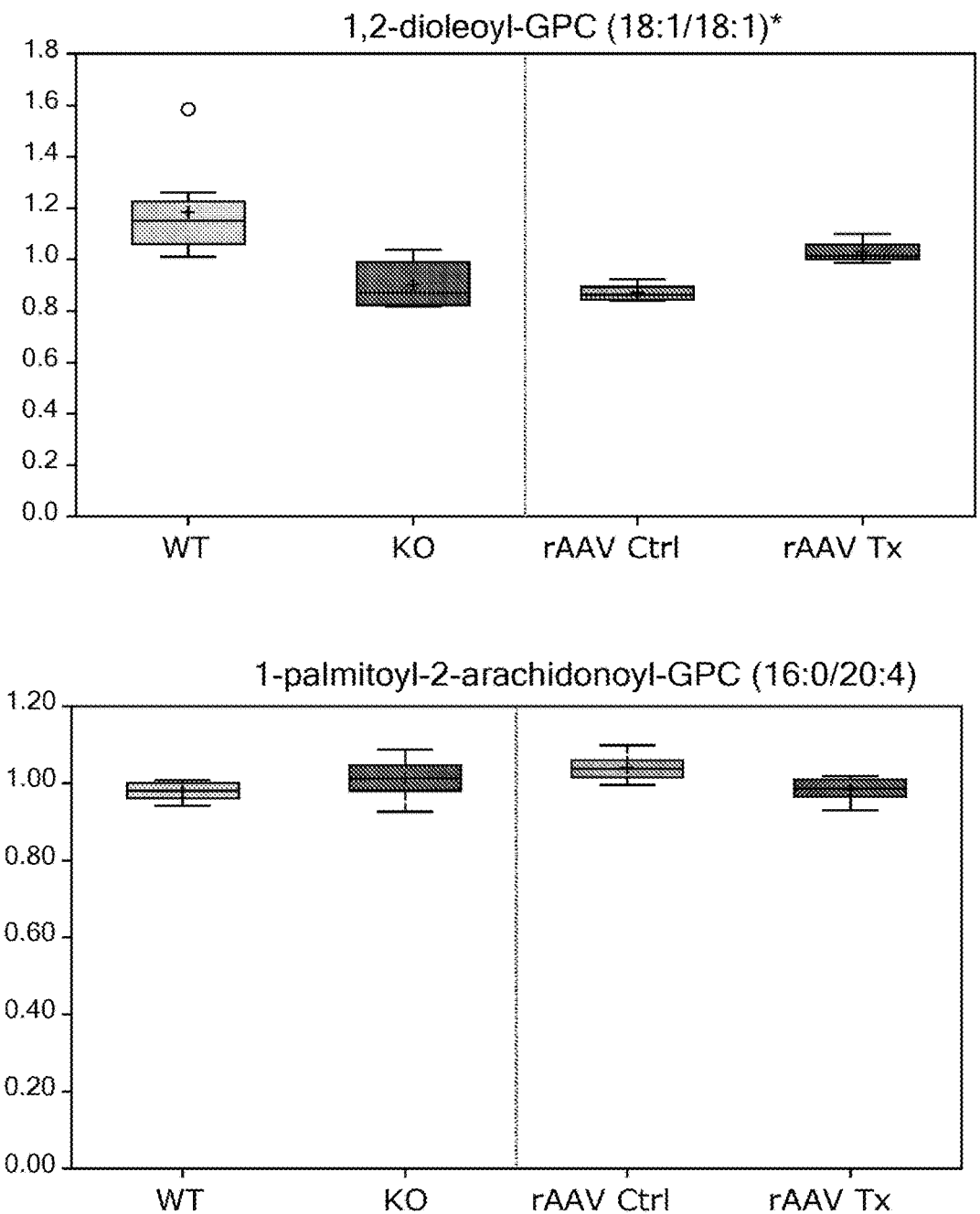
Figure 57:
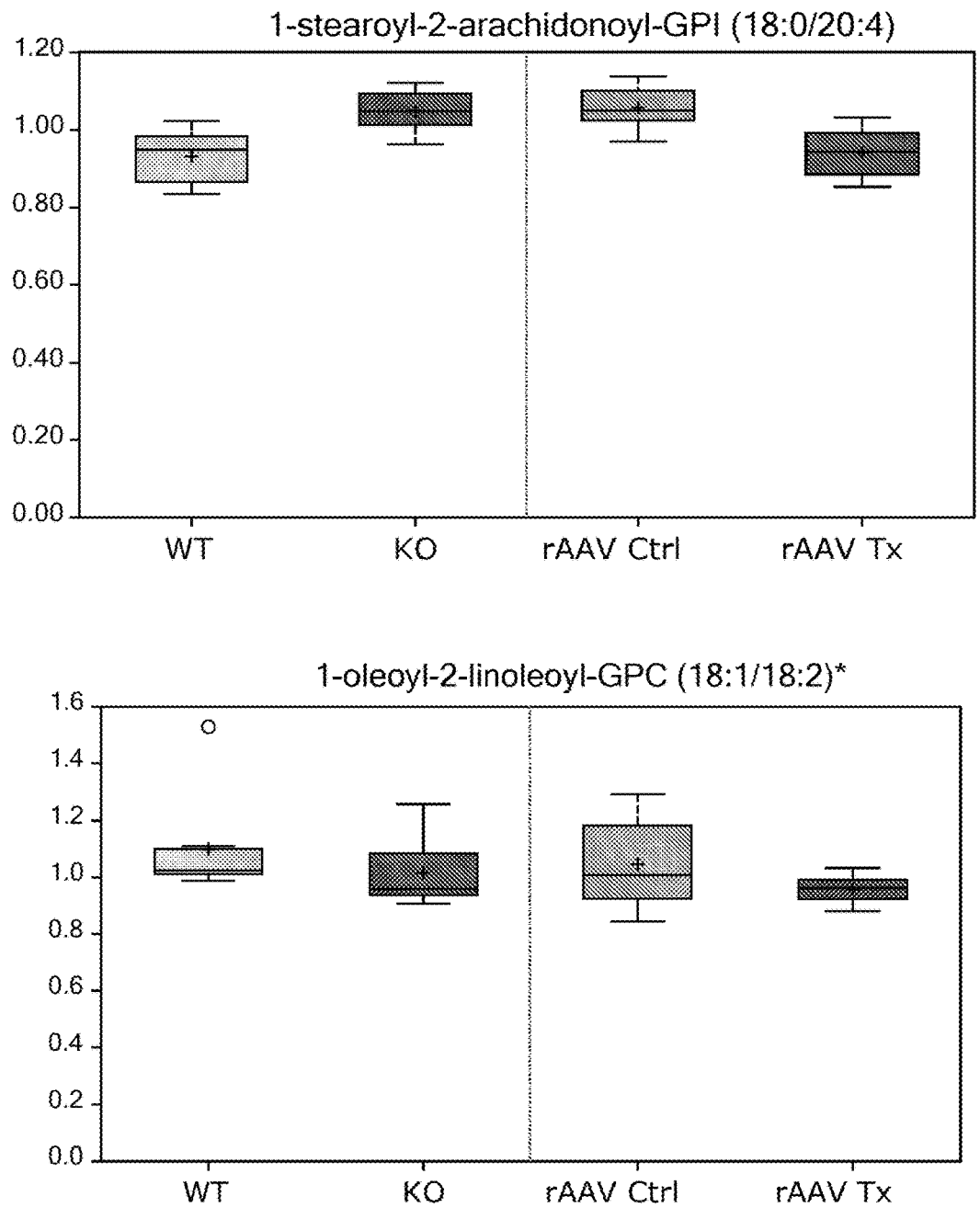
Figure 57:
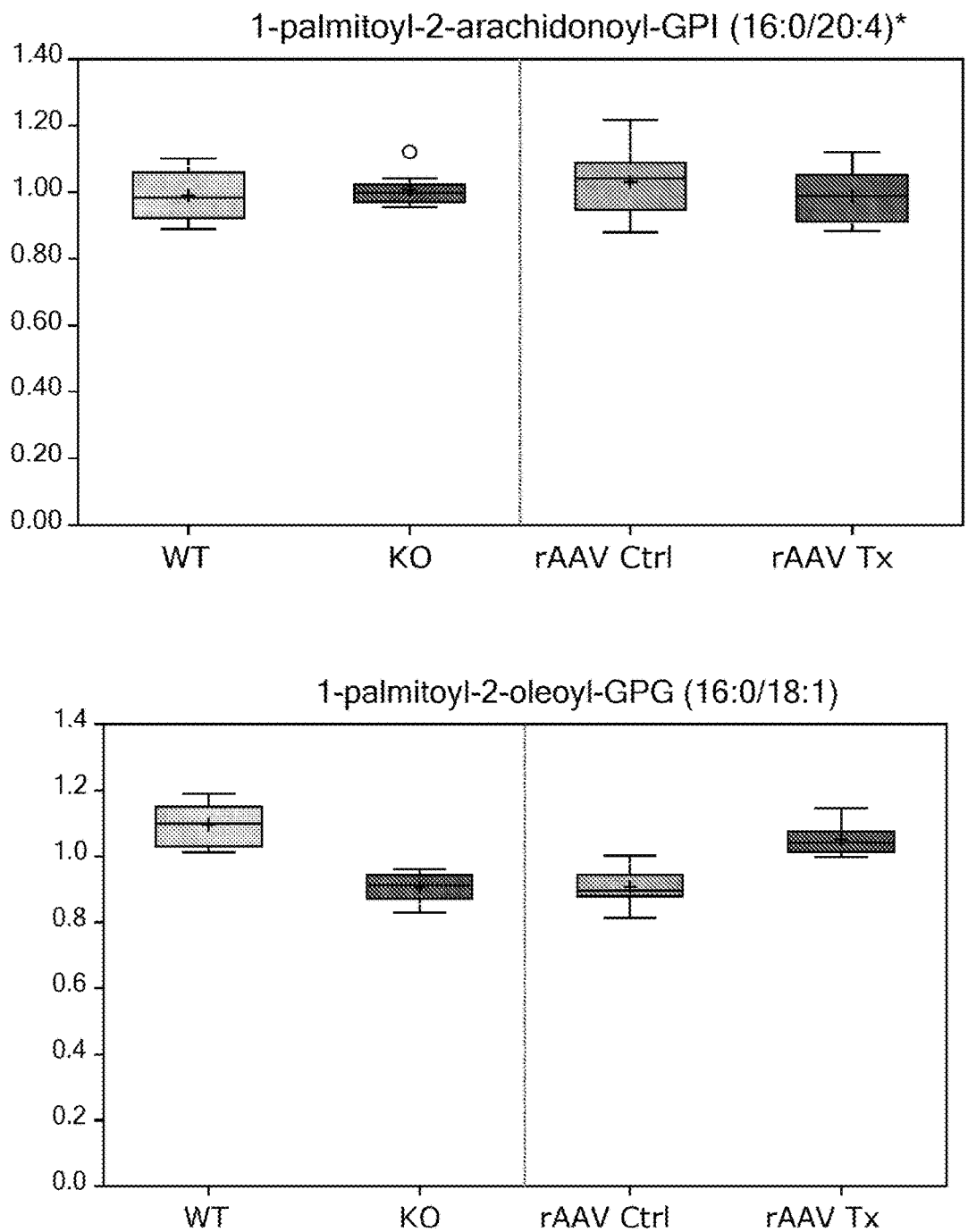
Figure 57:
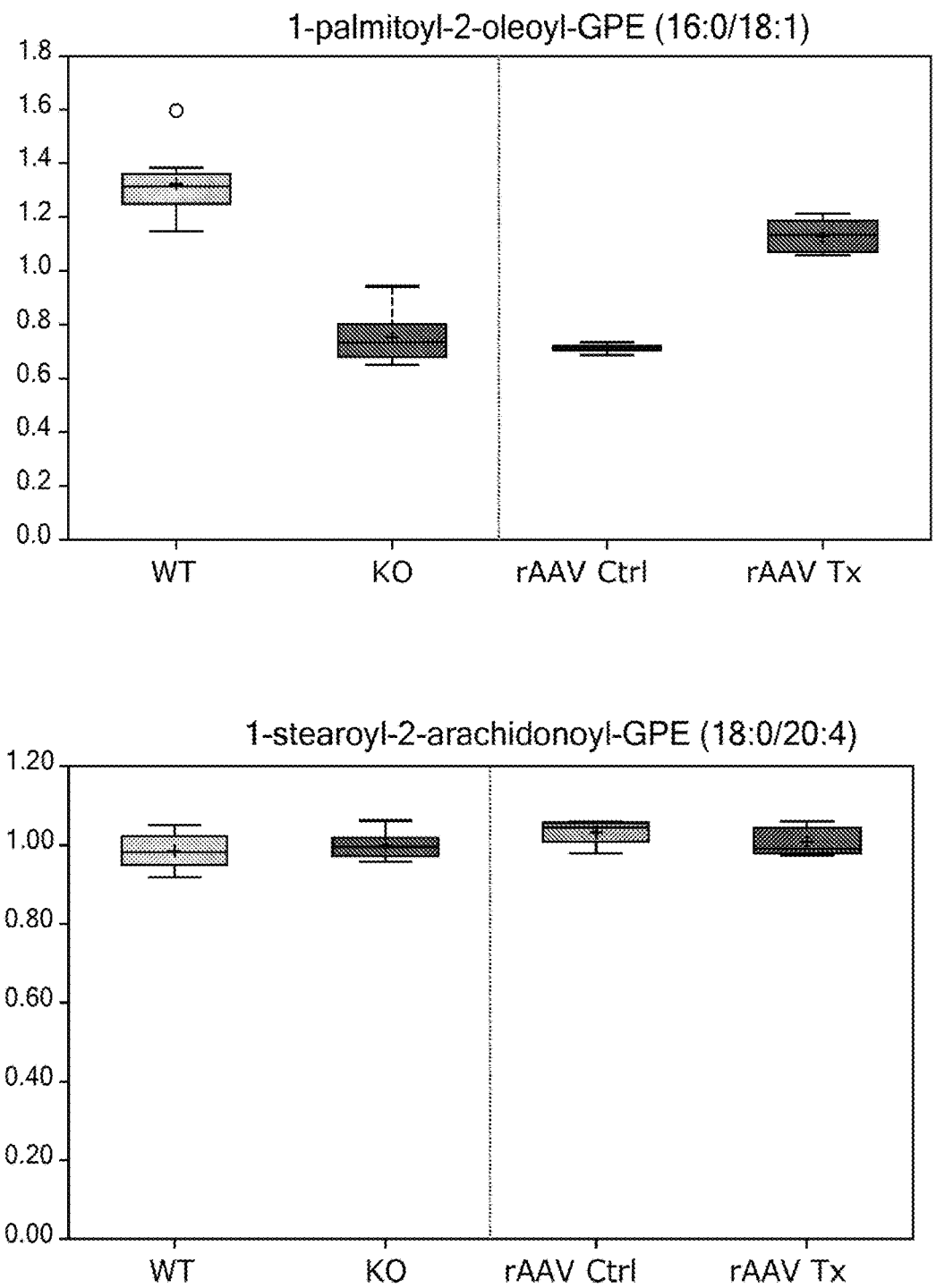
Figure 57:
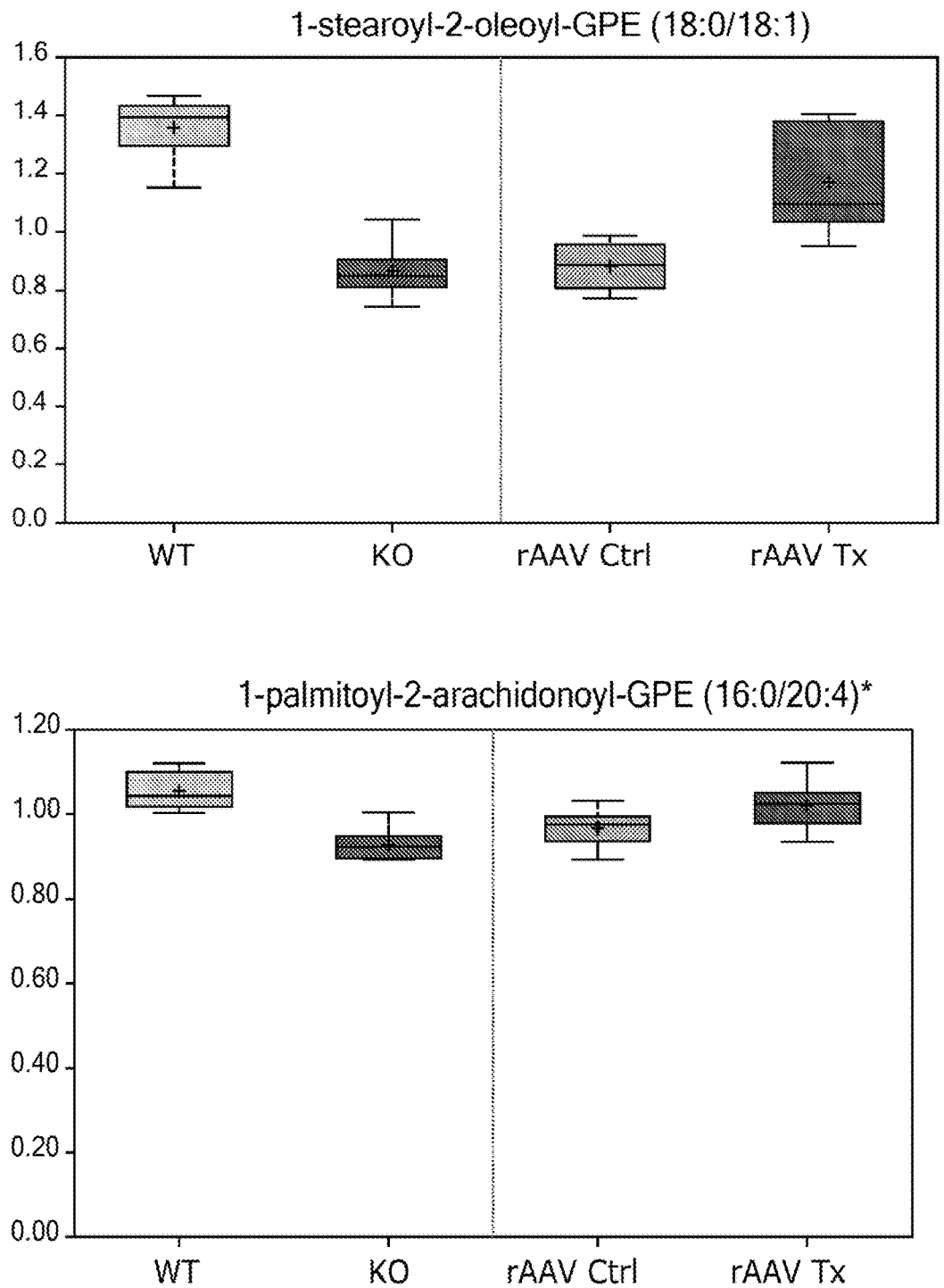
Figure 57:
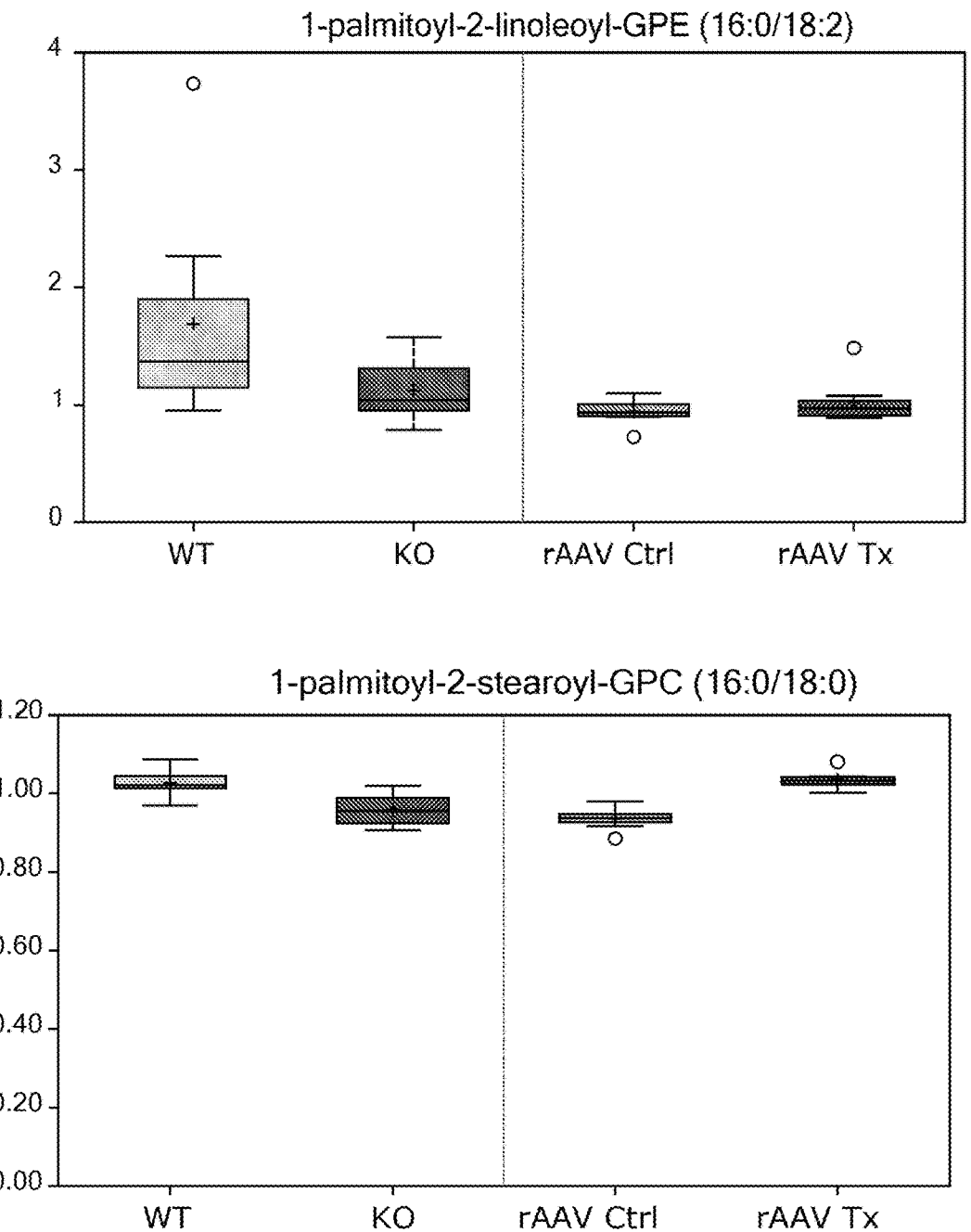
Figure 57:
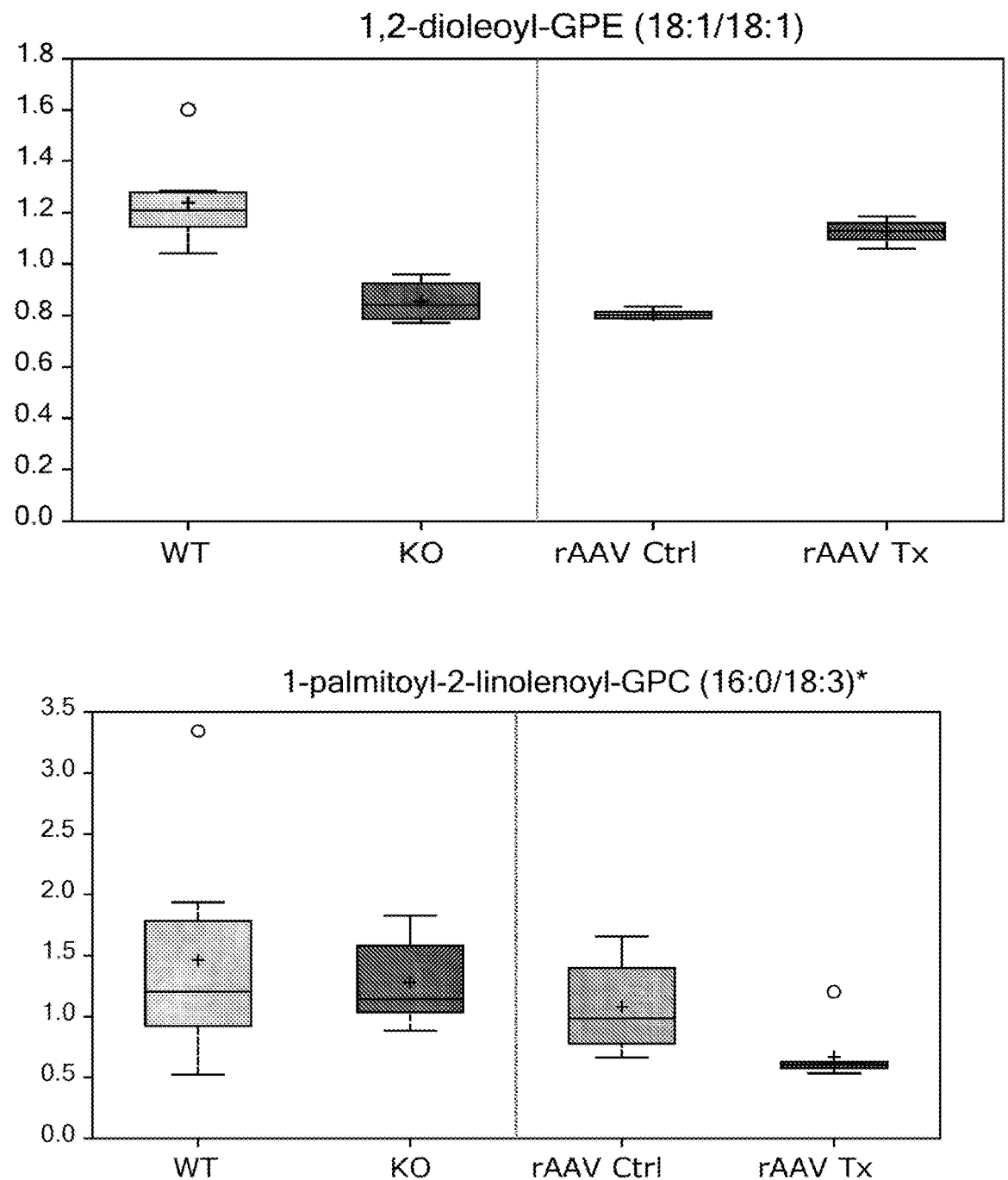
Figure 57:
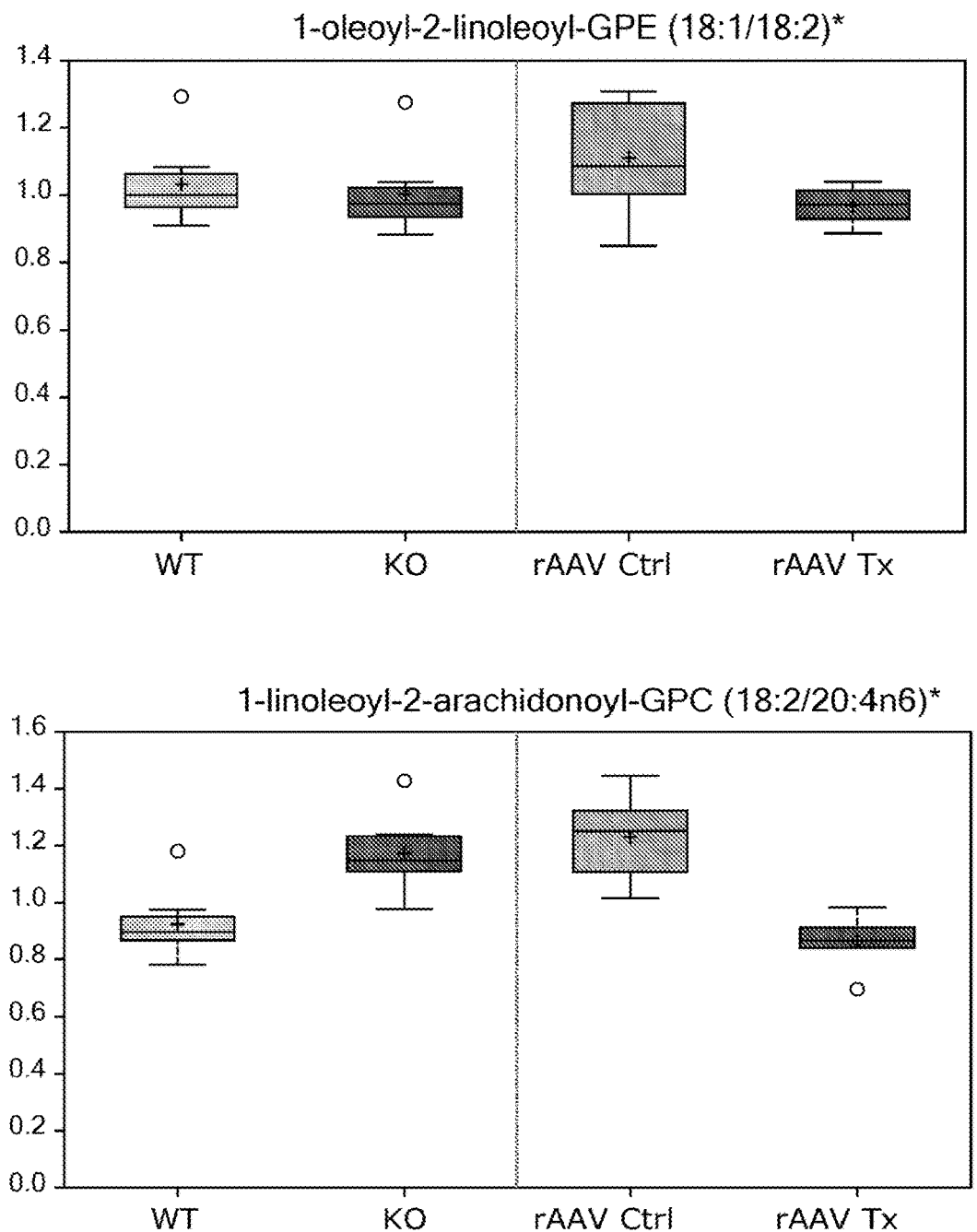
Figure 57:
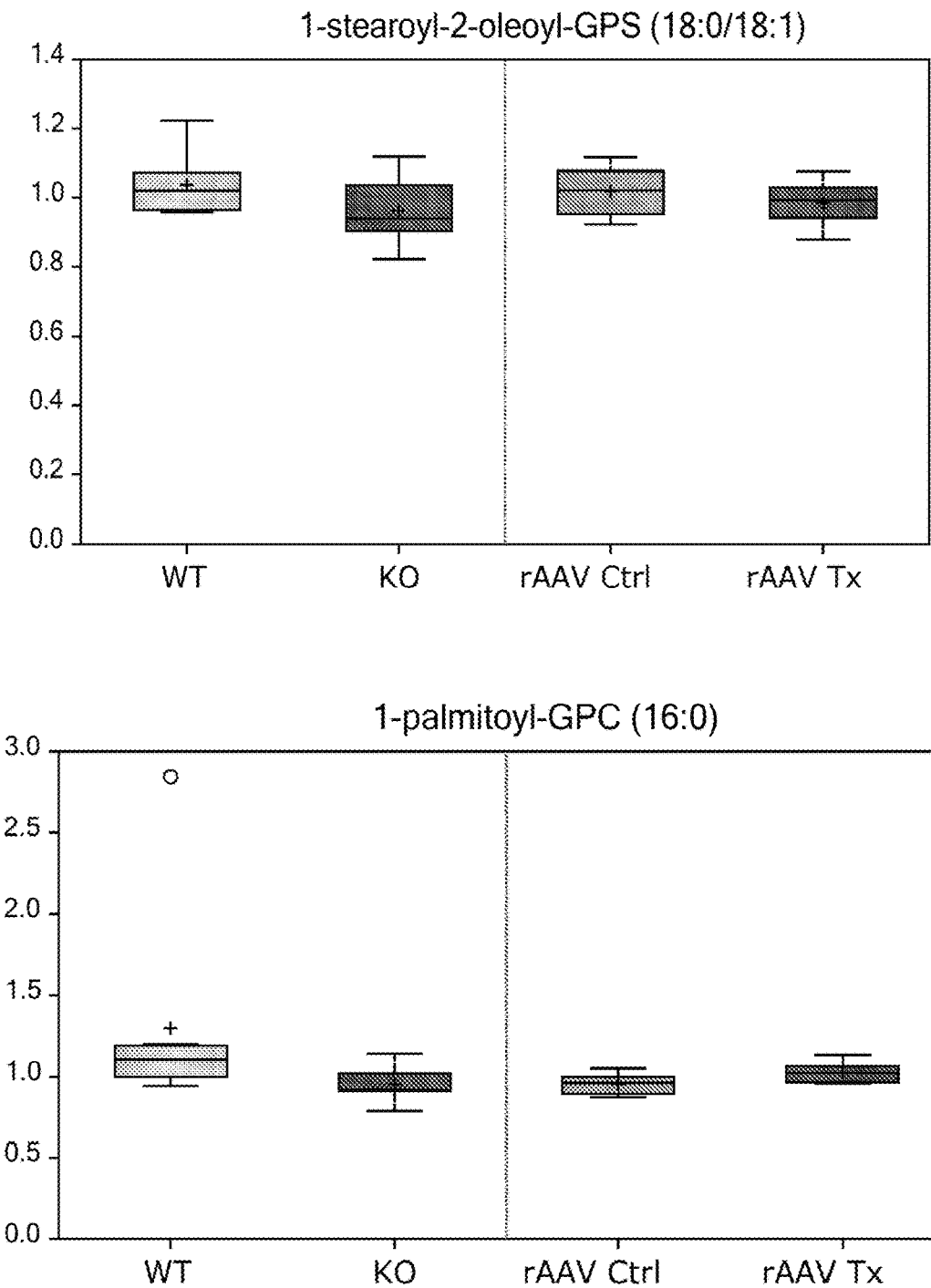
Figure 57:
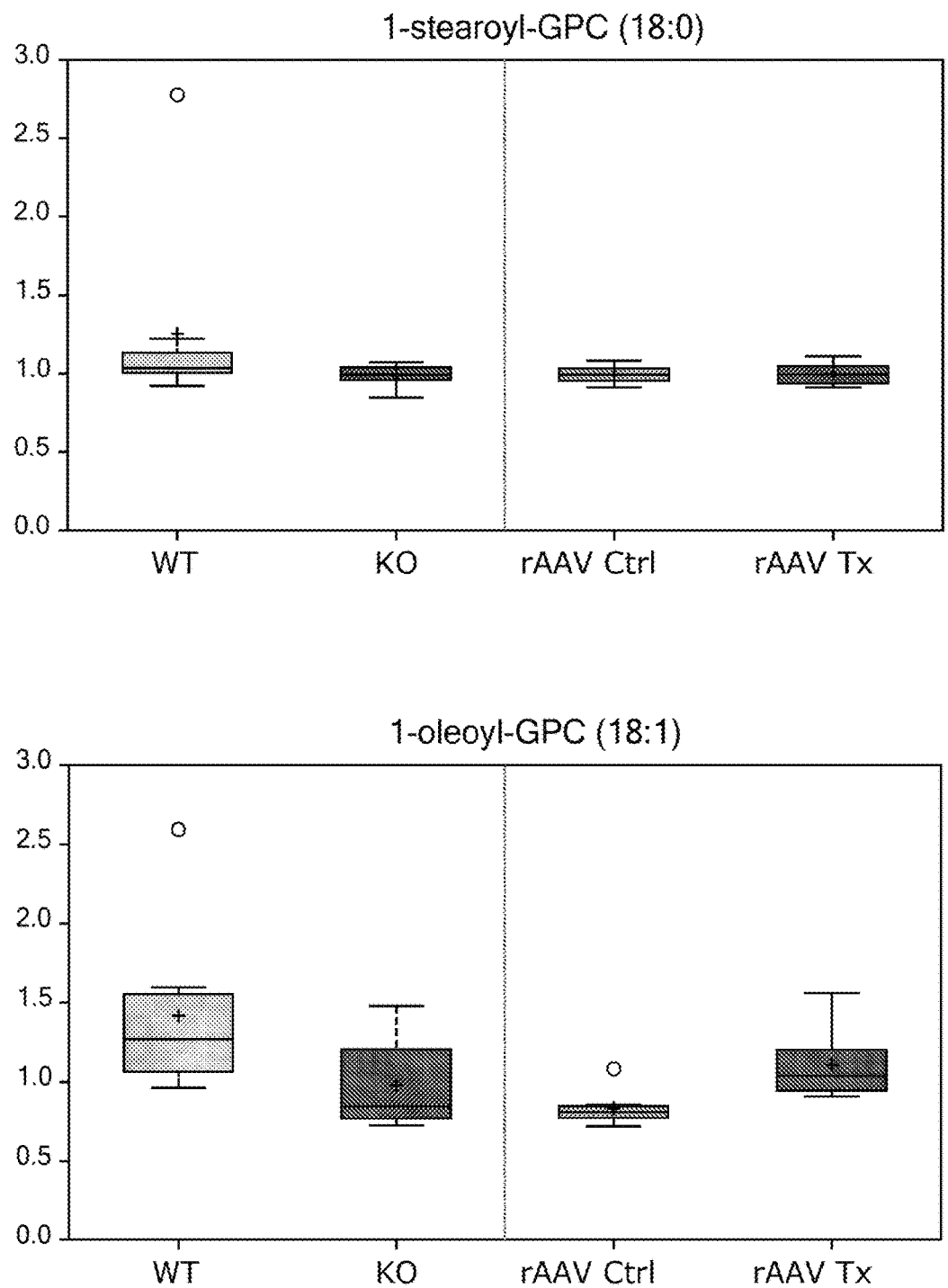
Figure 57:
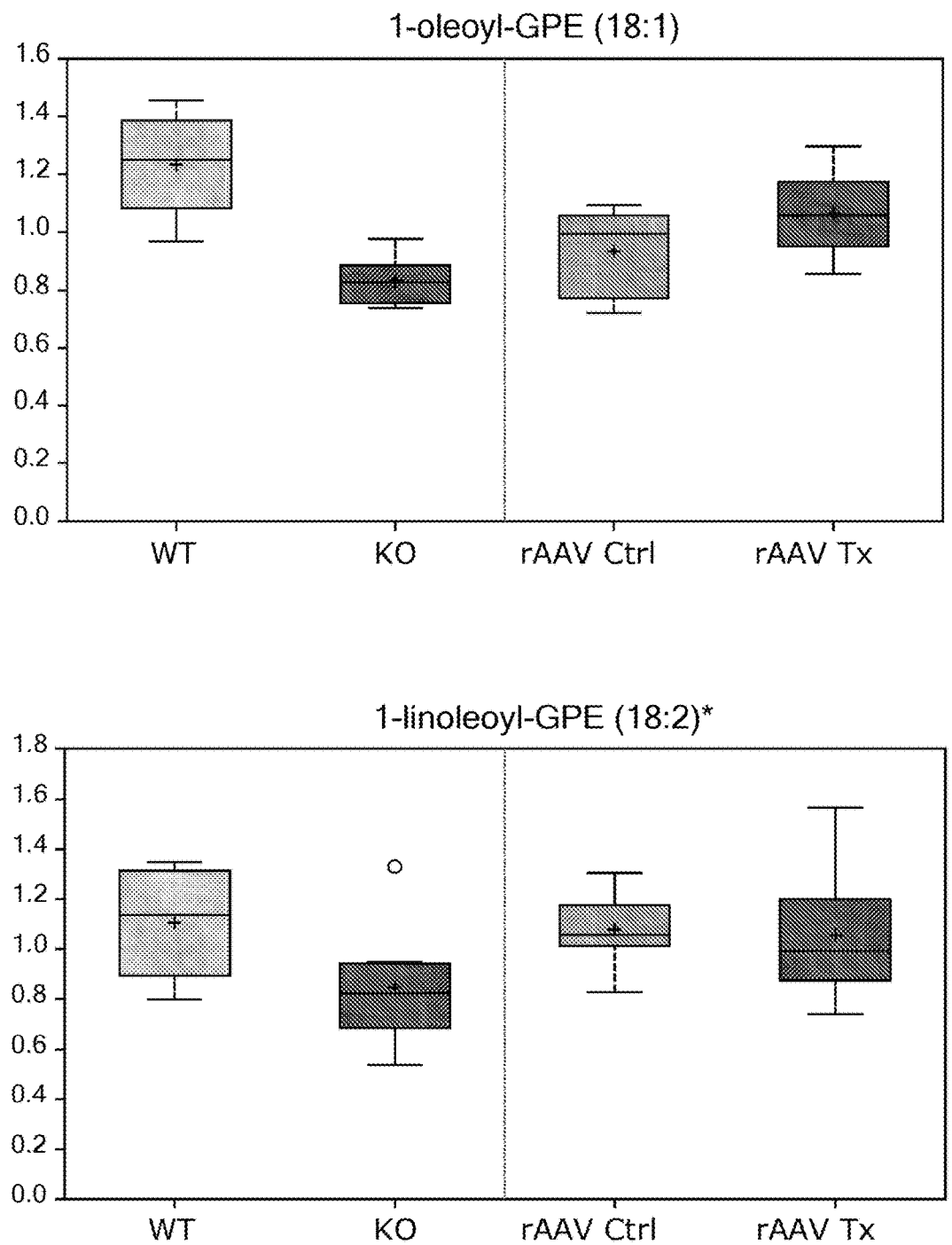
Figure 57:
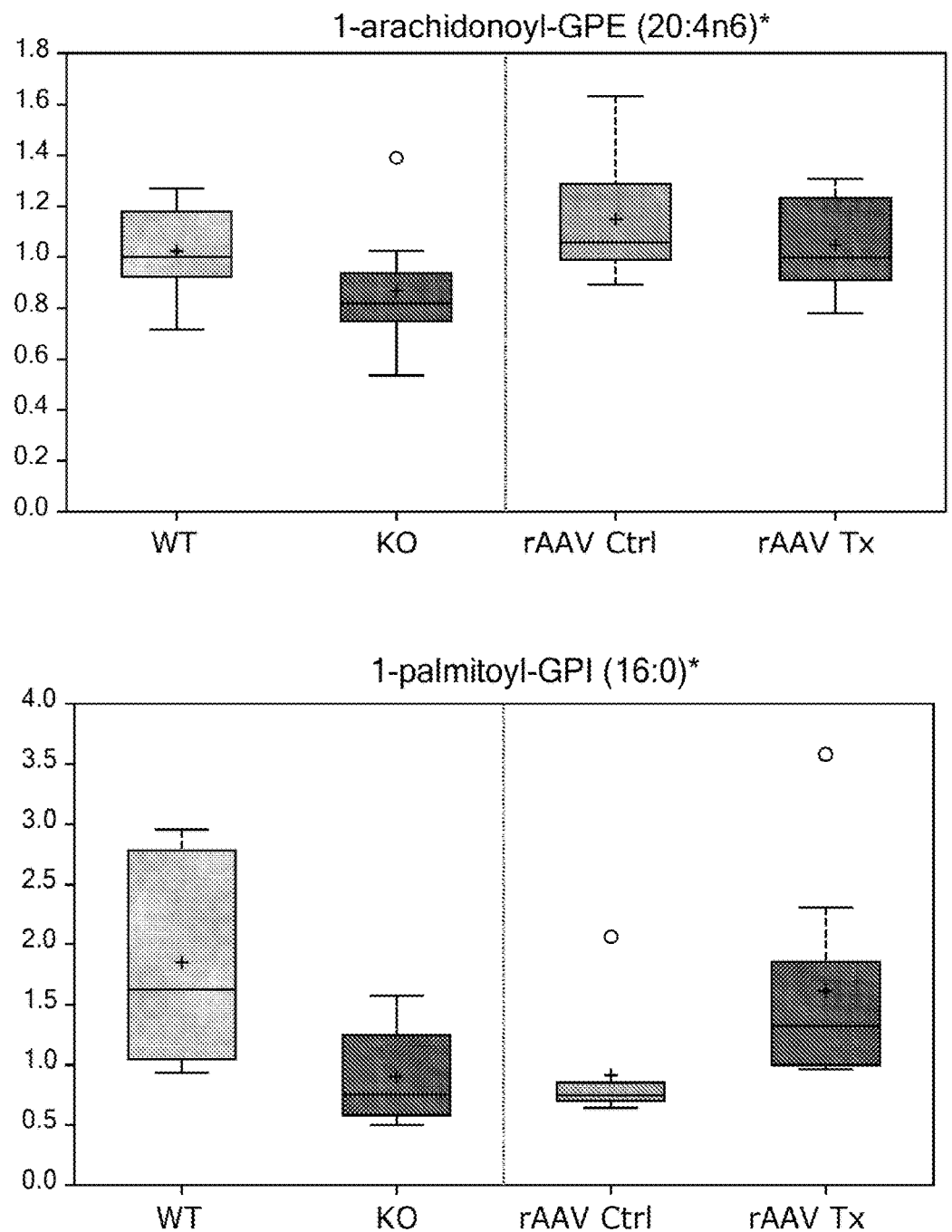
Figure 57:
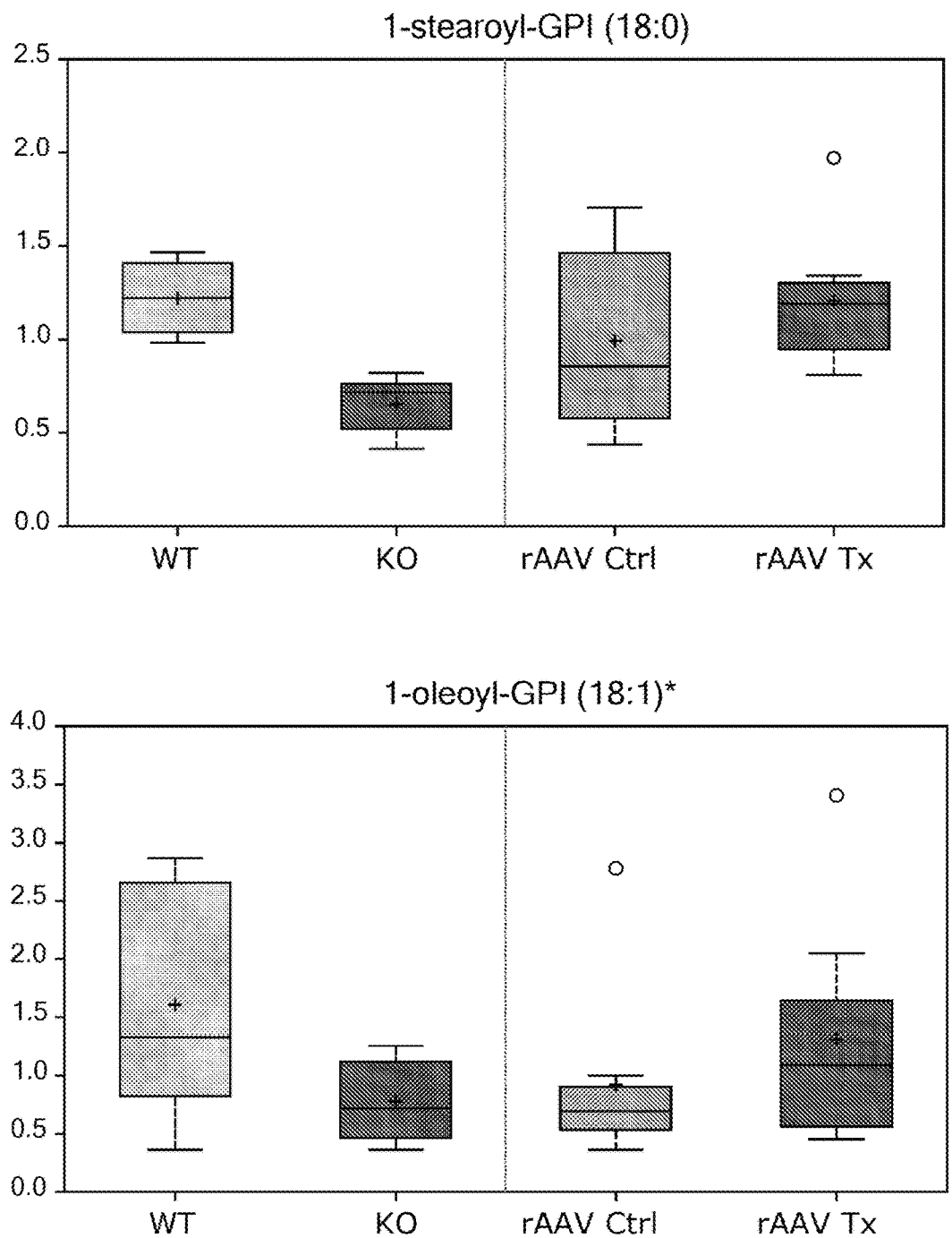
Figure 57:
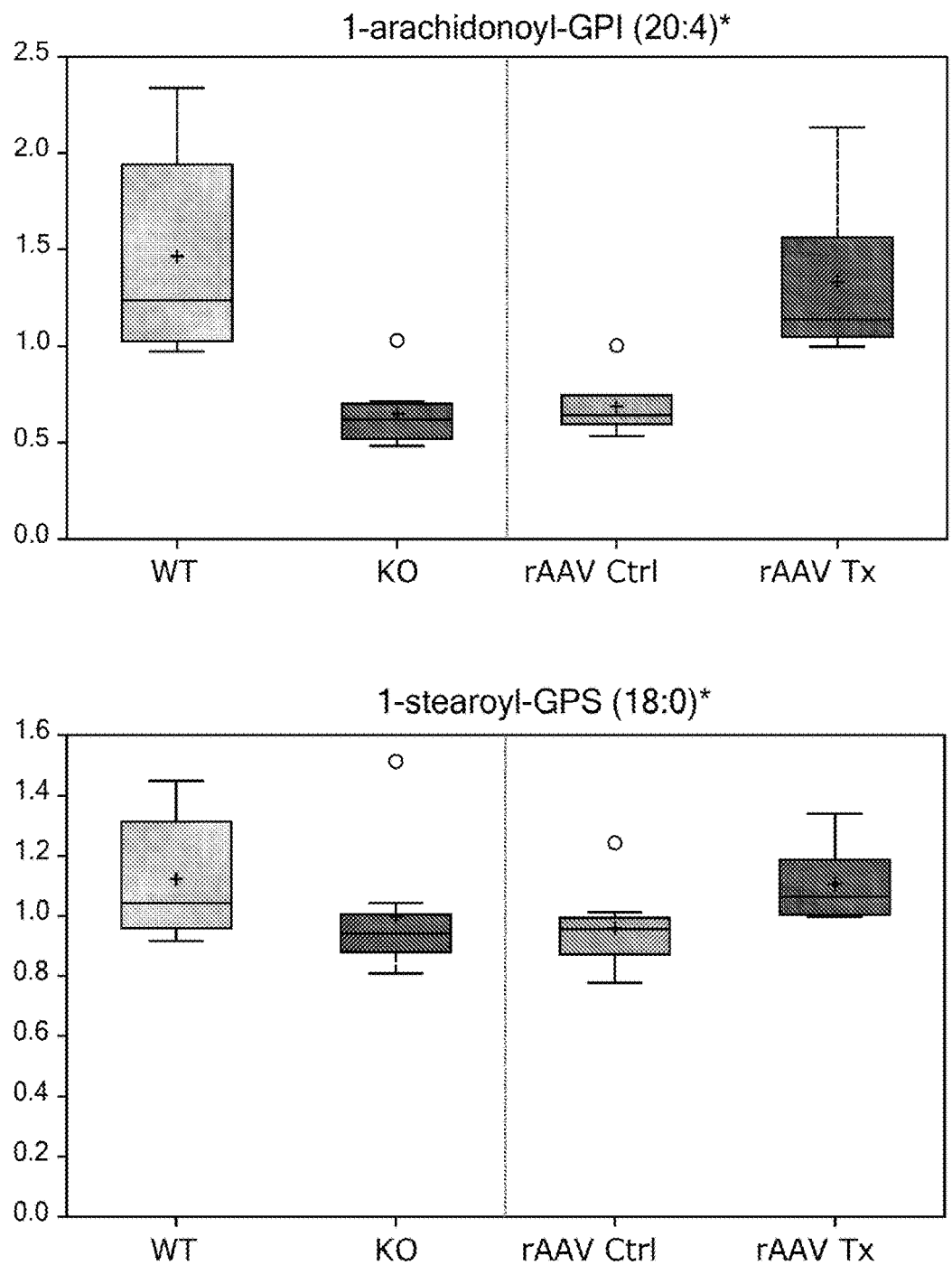
Figure 57:
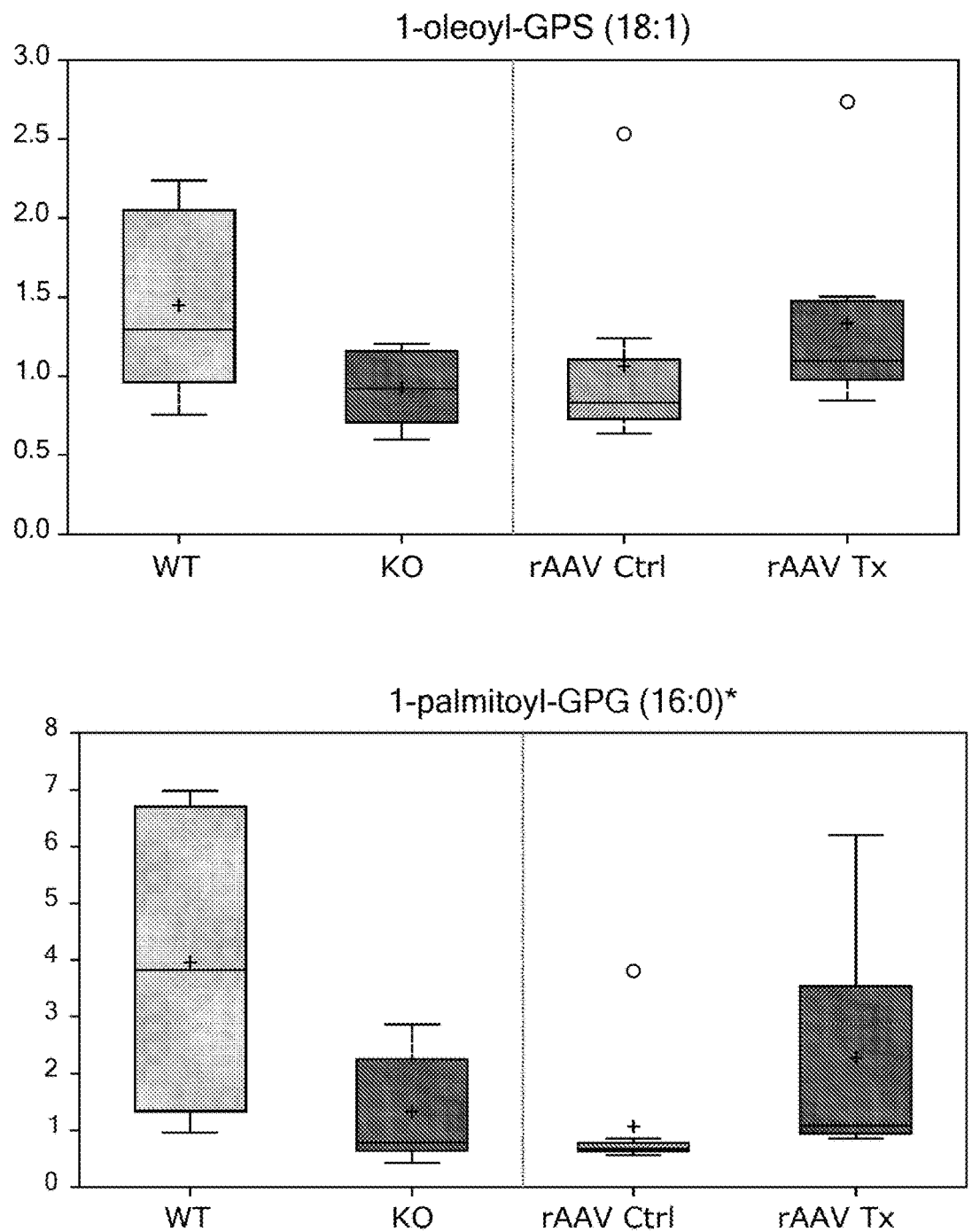
Figure 57:
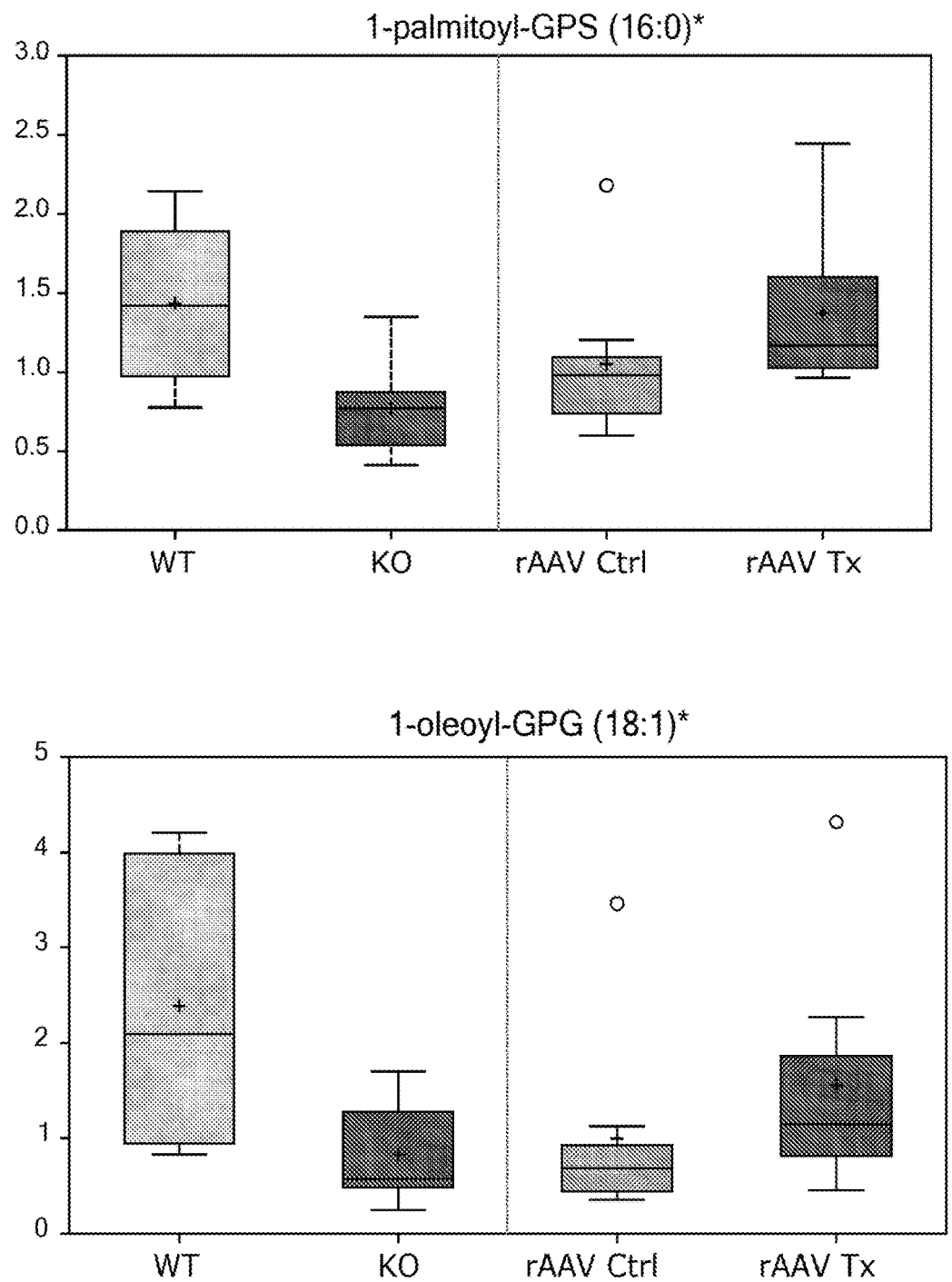
Figure 57:
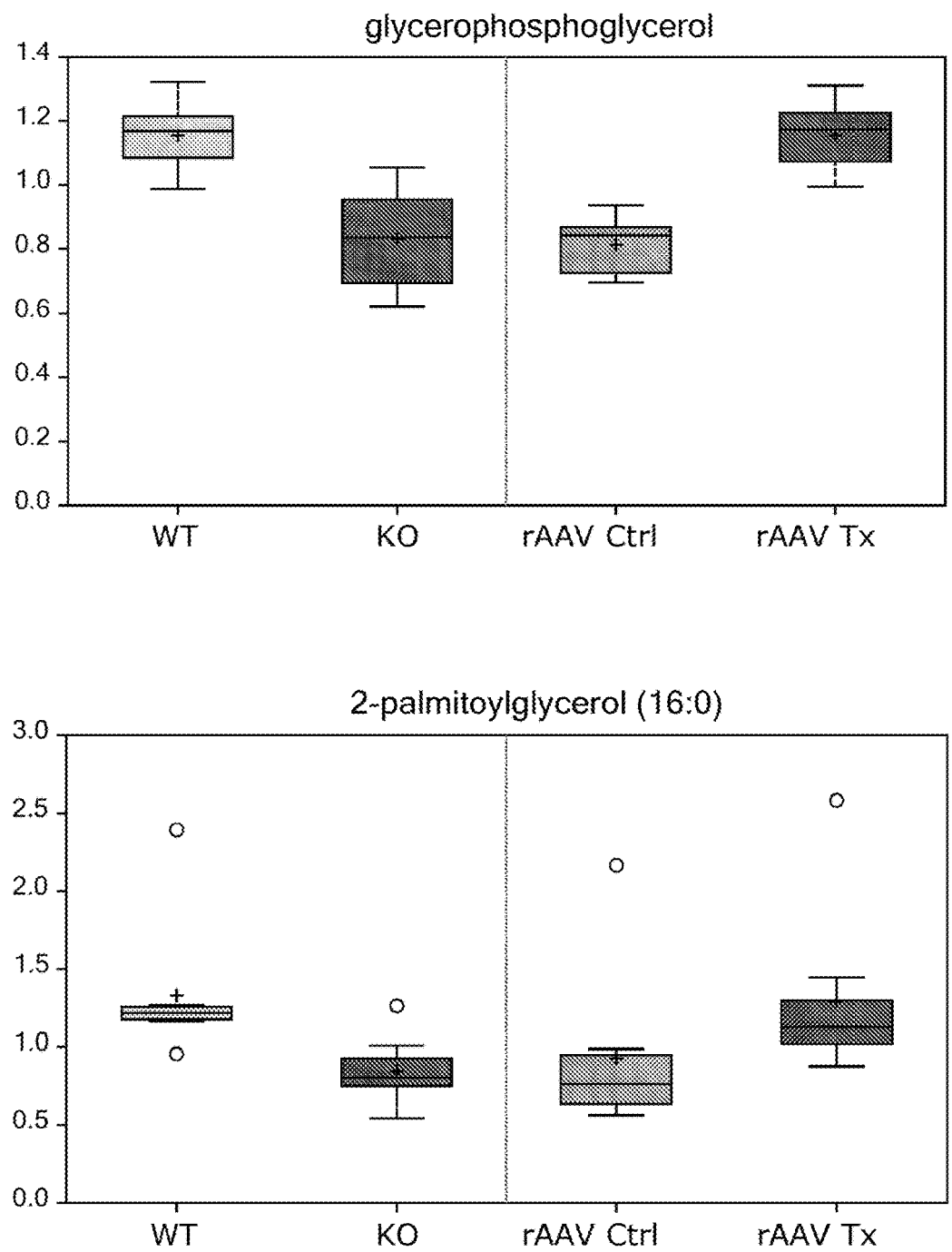
Figure 57:
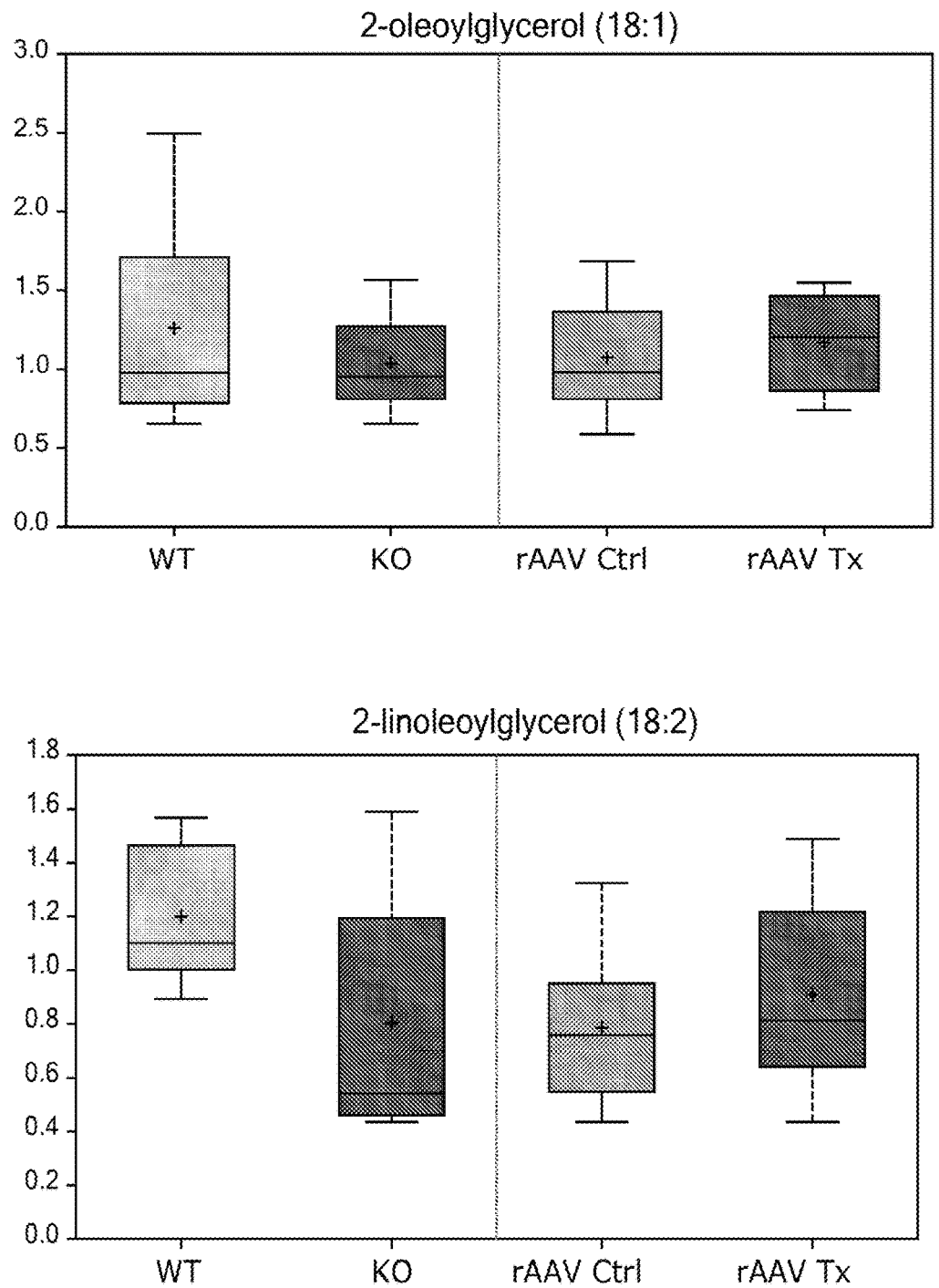
Figure 57:
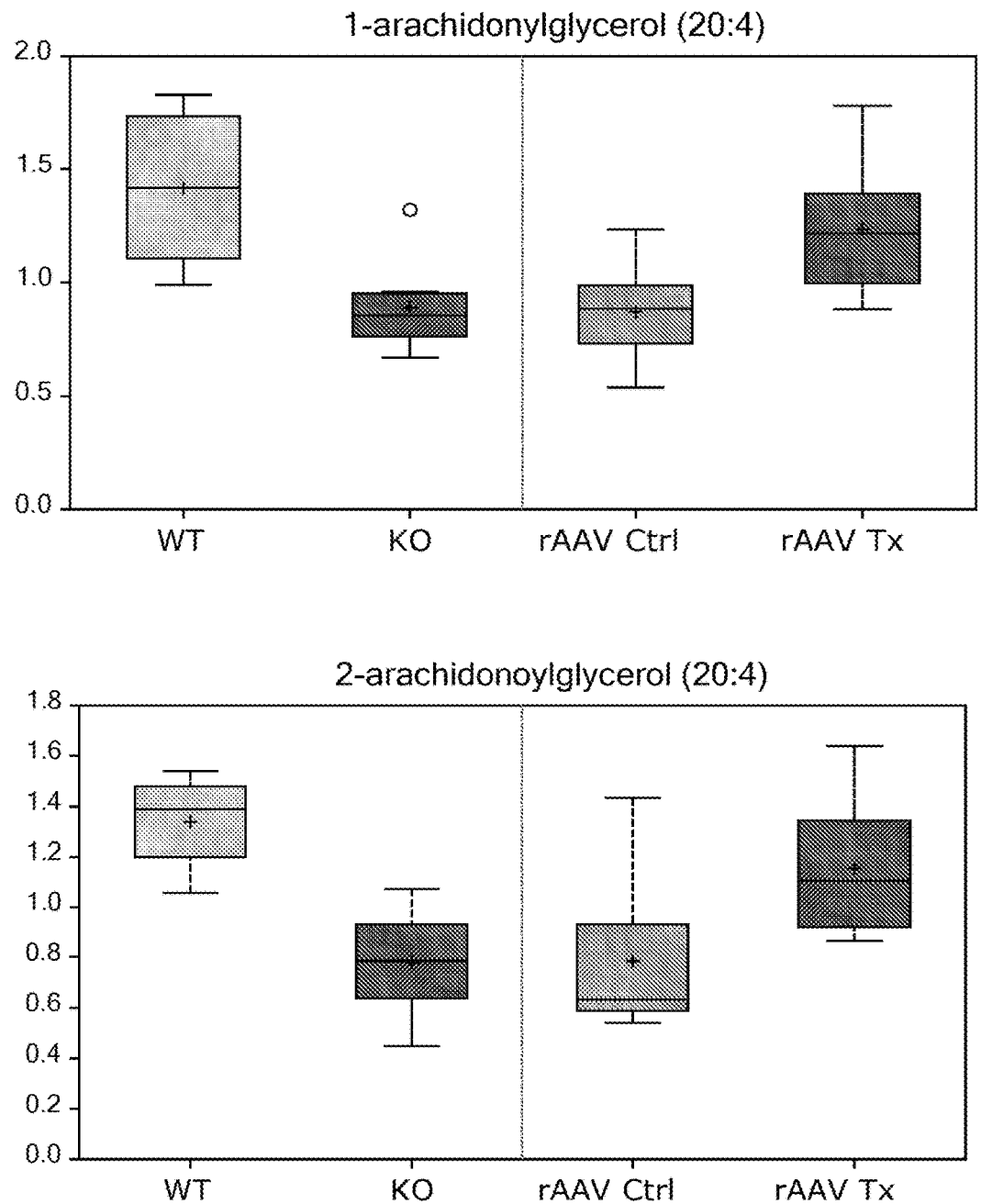
Figure 57:
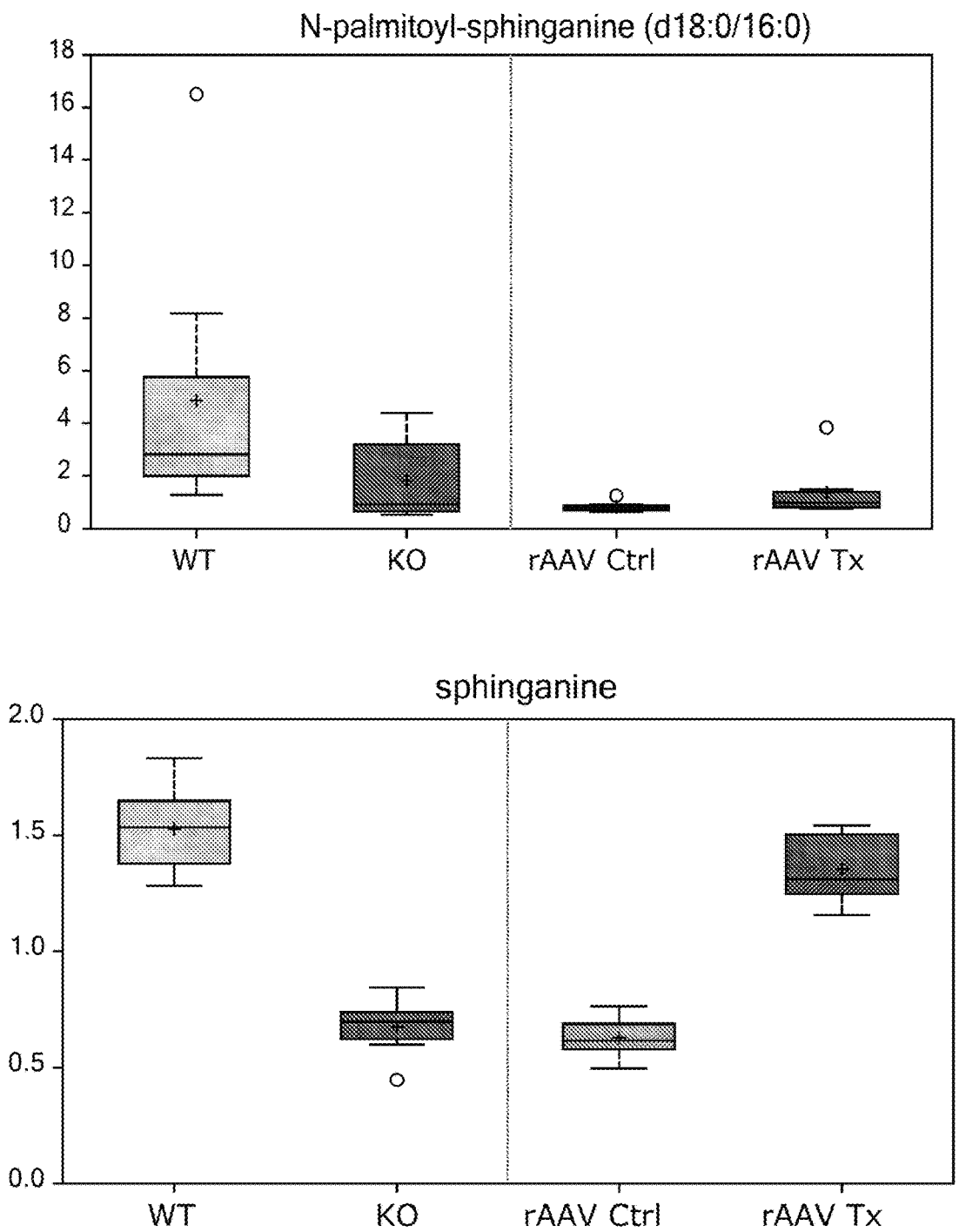
Figure 57:
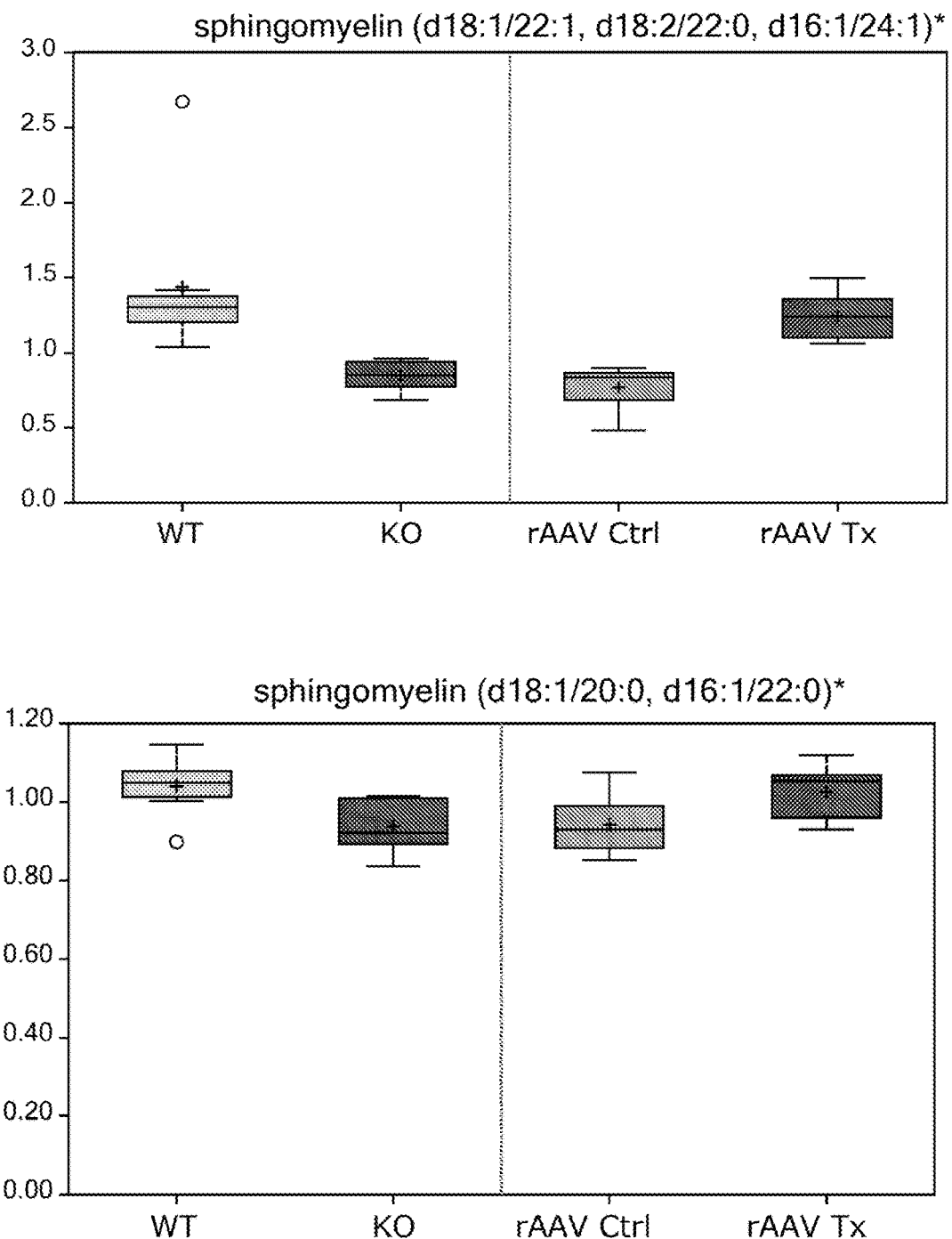
Figure 57:
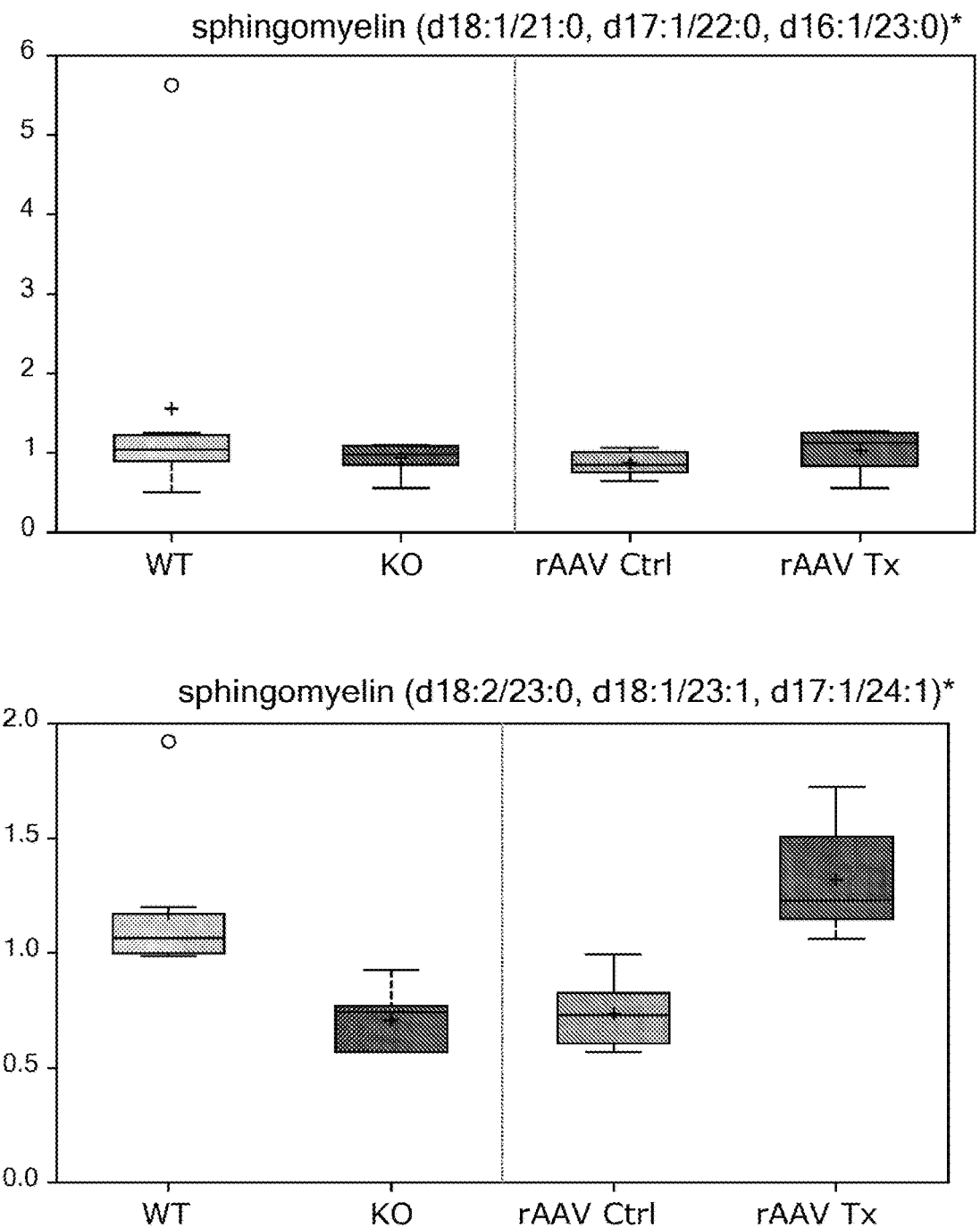
Figure 57:
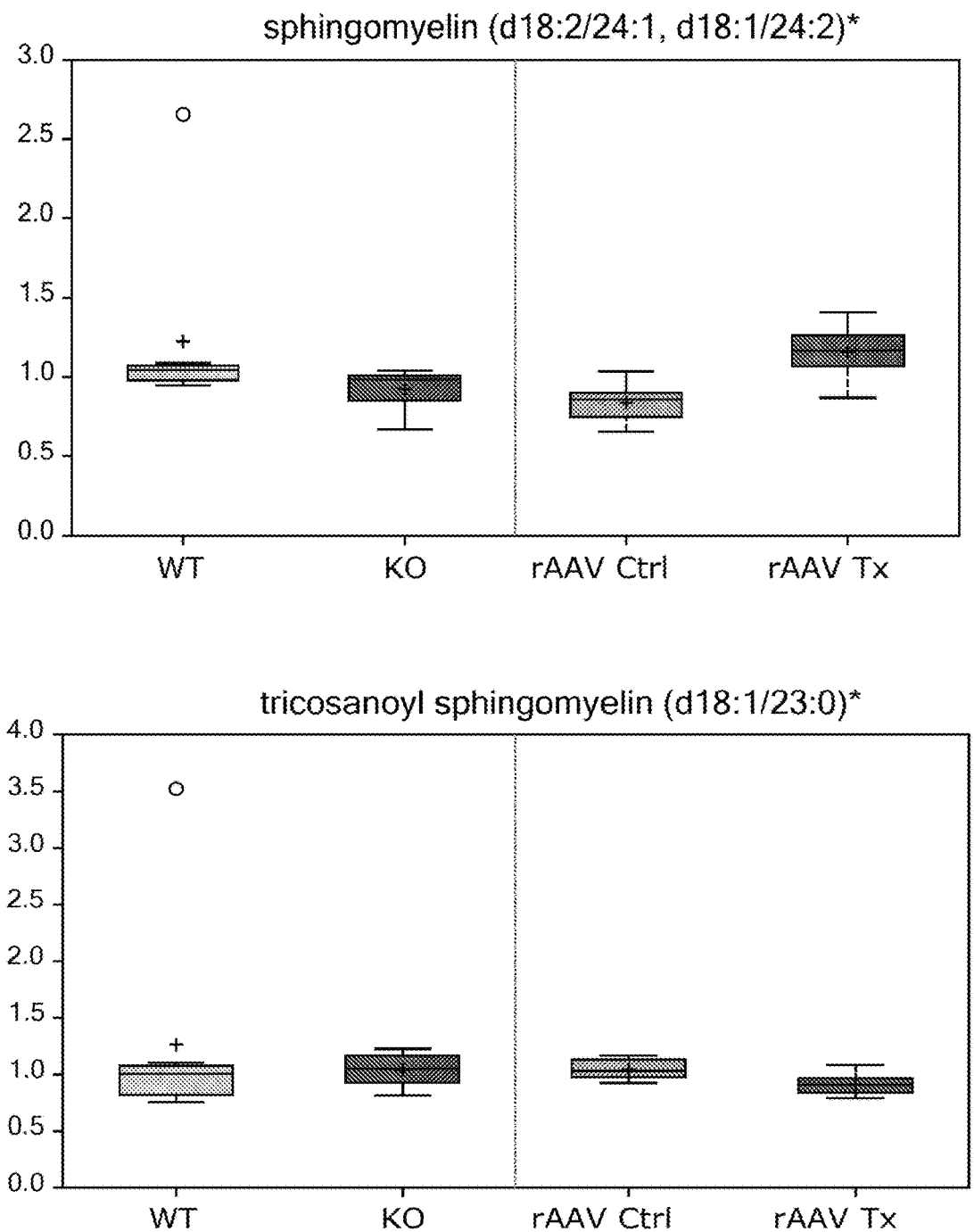
Figure 57:
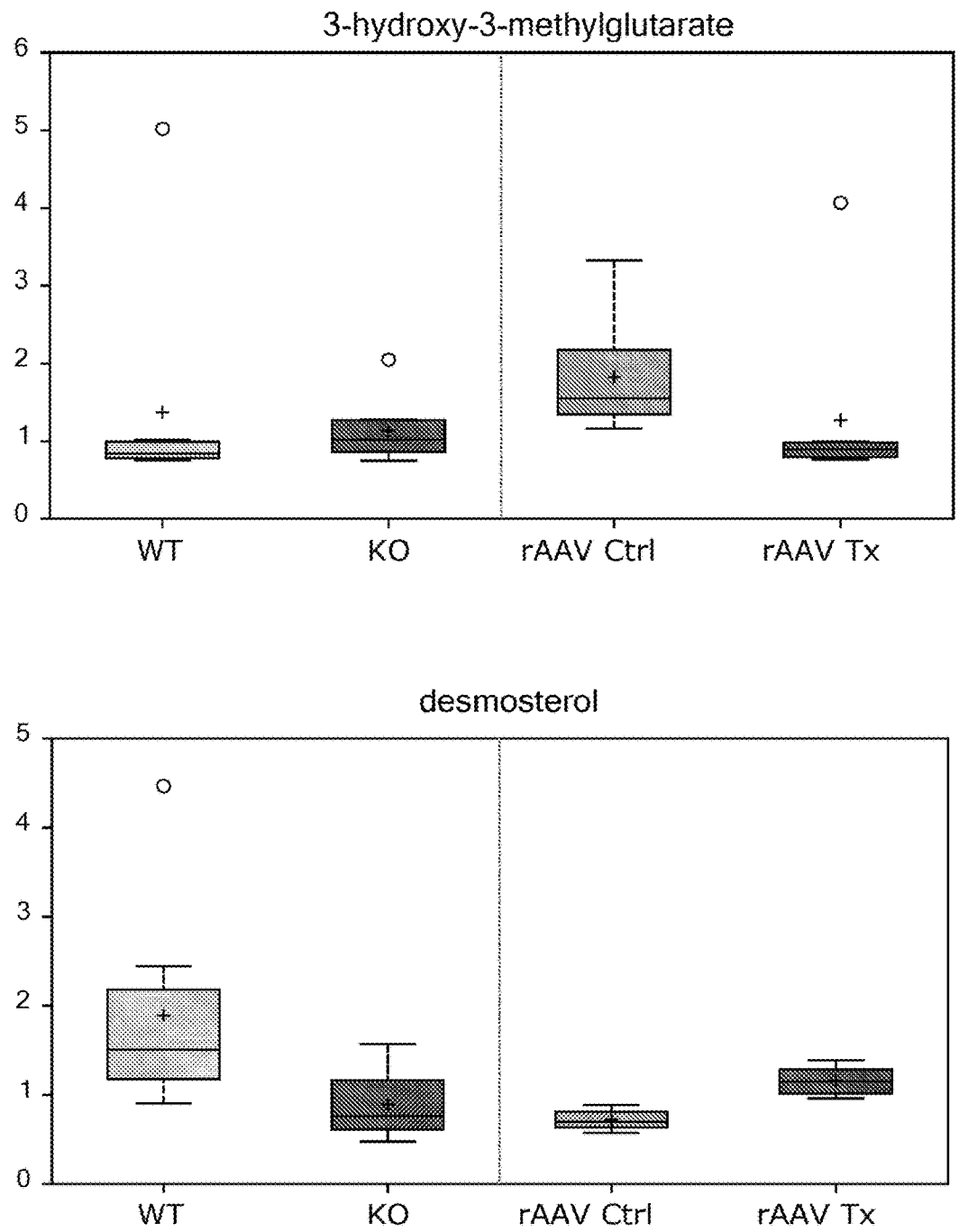
Figure 57:
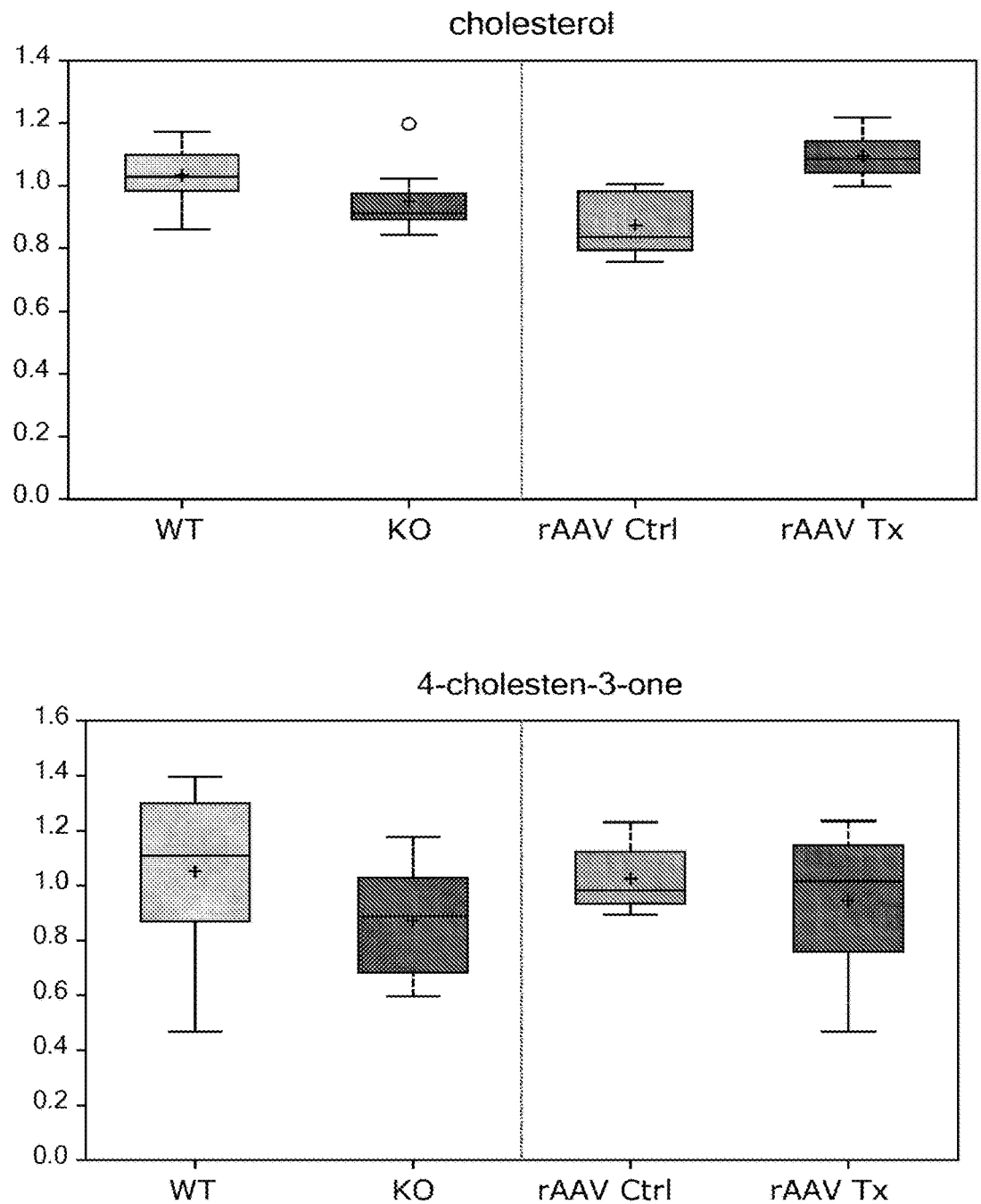
Figure 57:
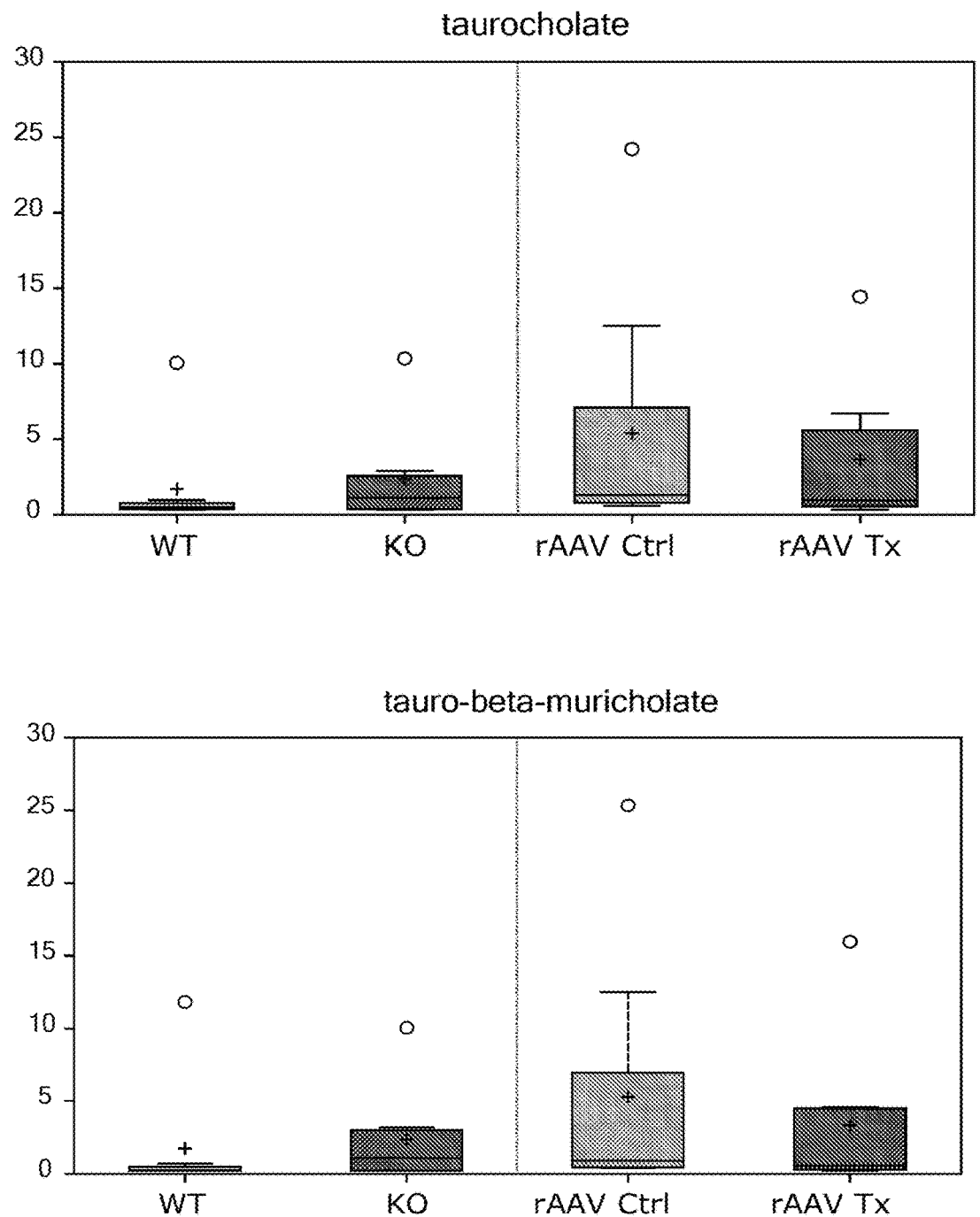
Figure 57:
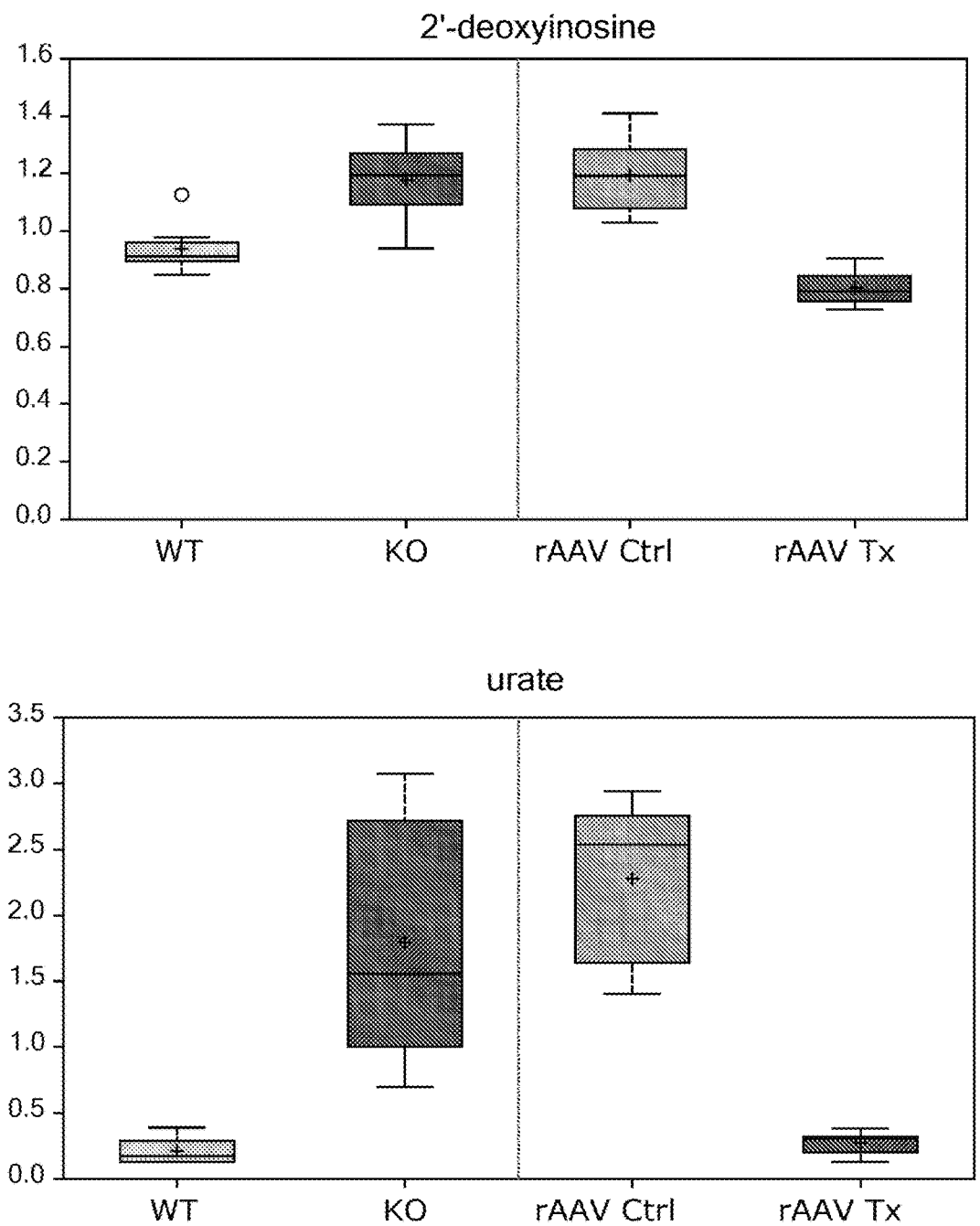
Figure 57:
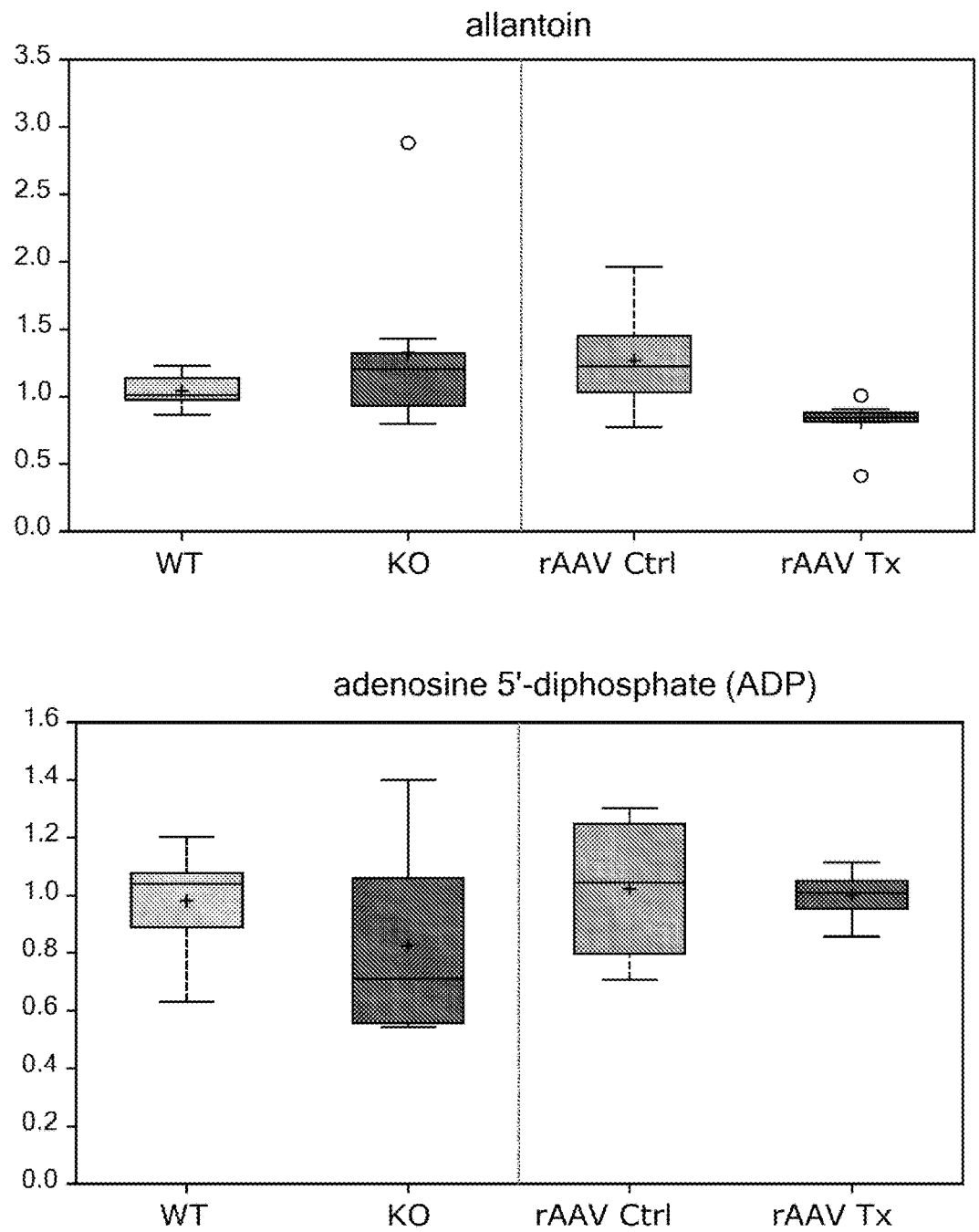
Figure 57:
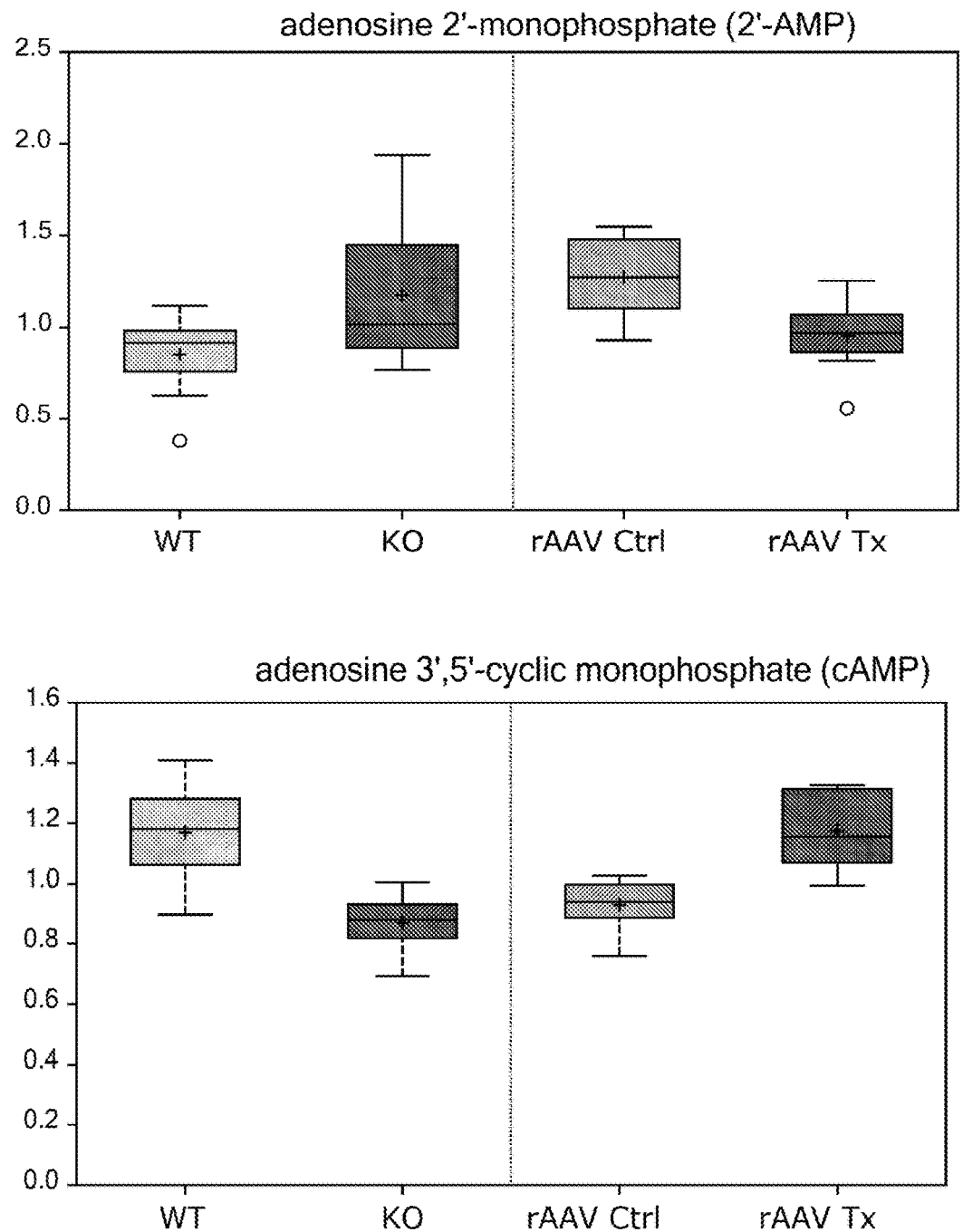
Figure 57:
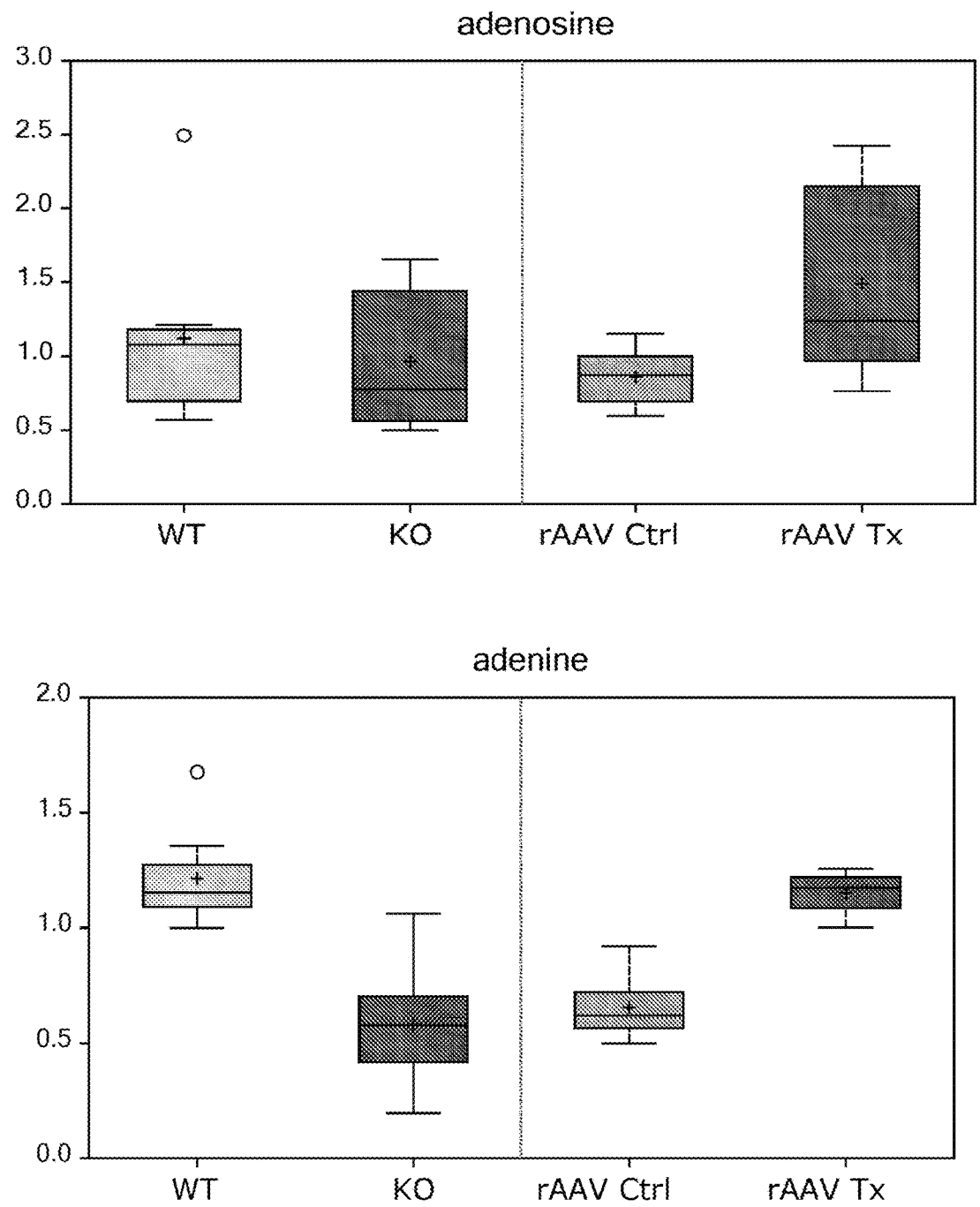
Figure 57:
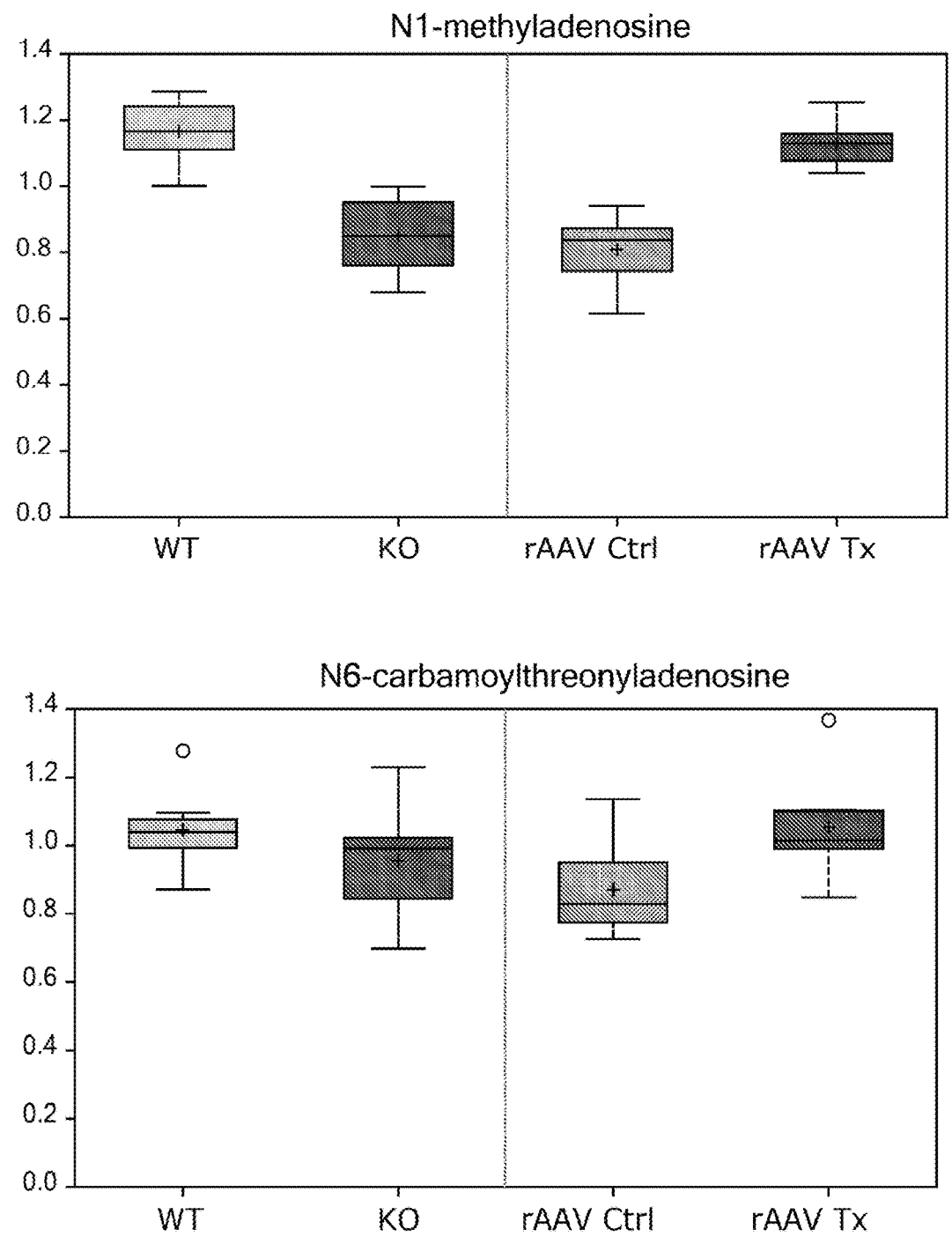
Figure 57:
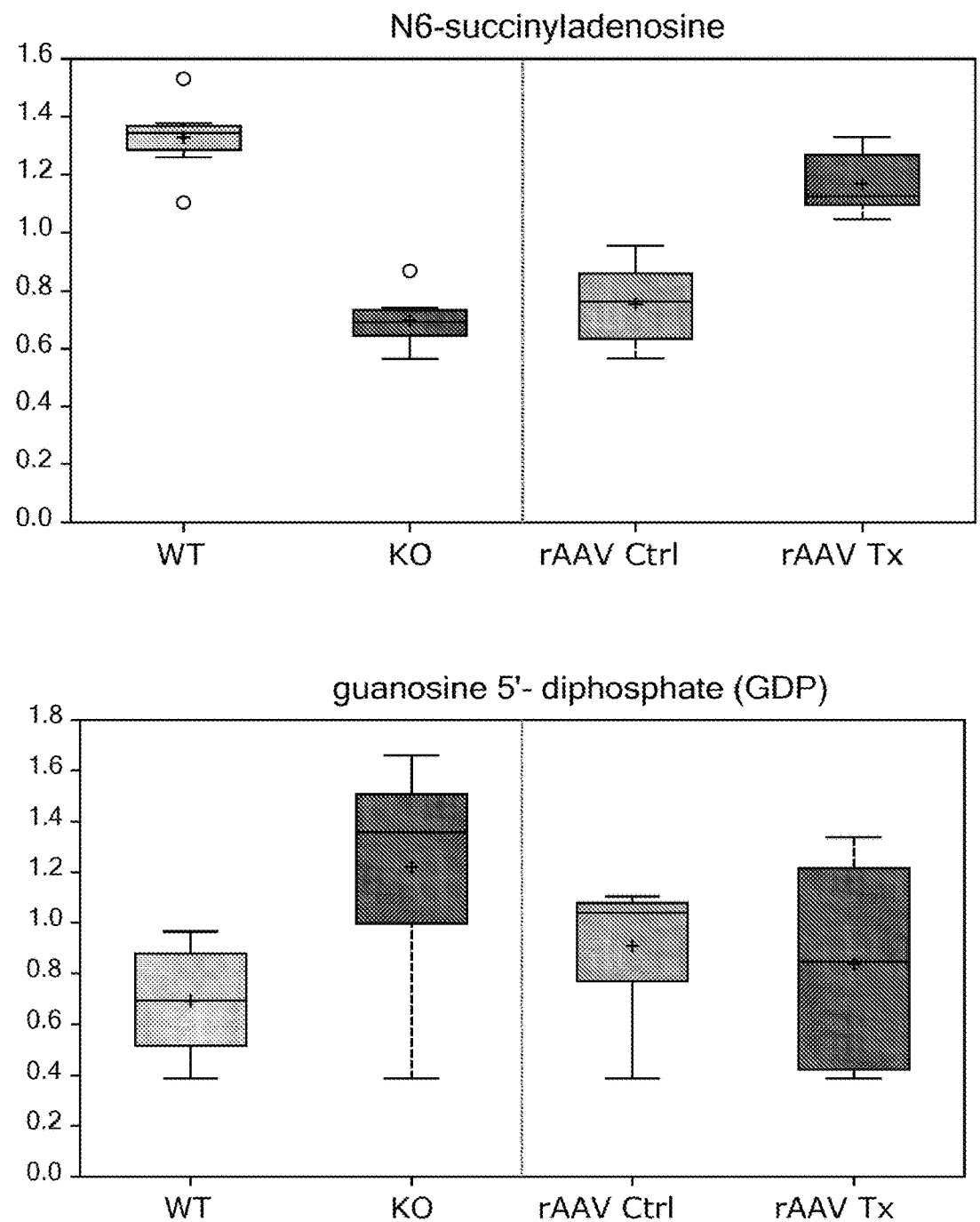
Figure 57:
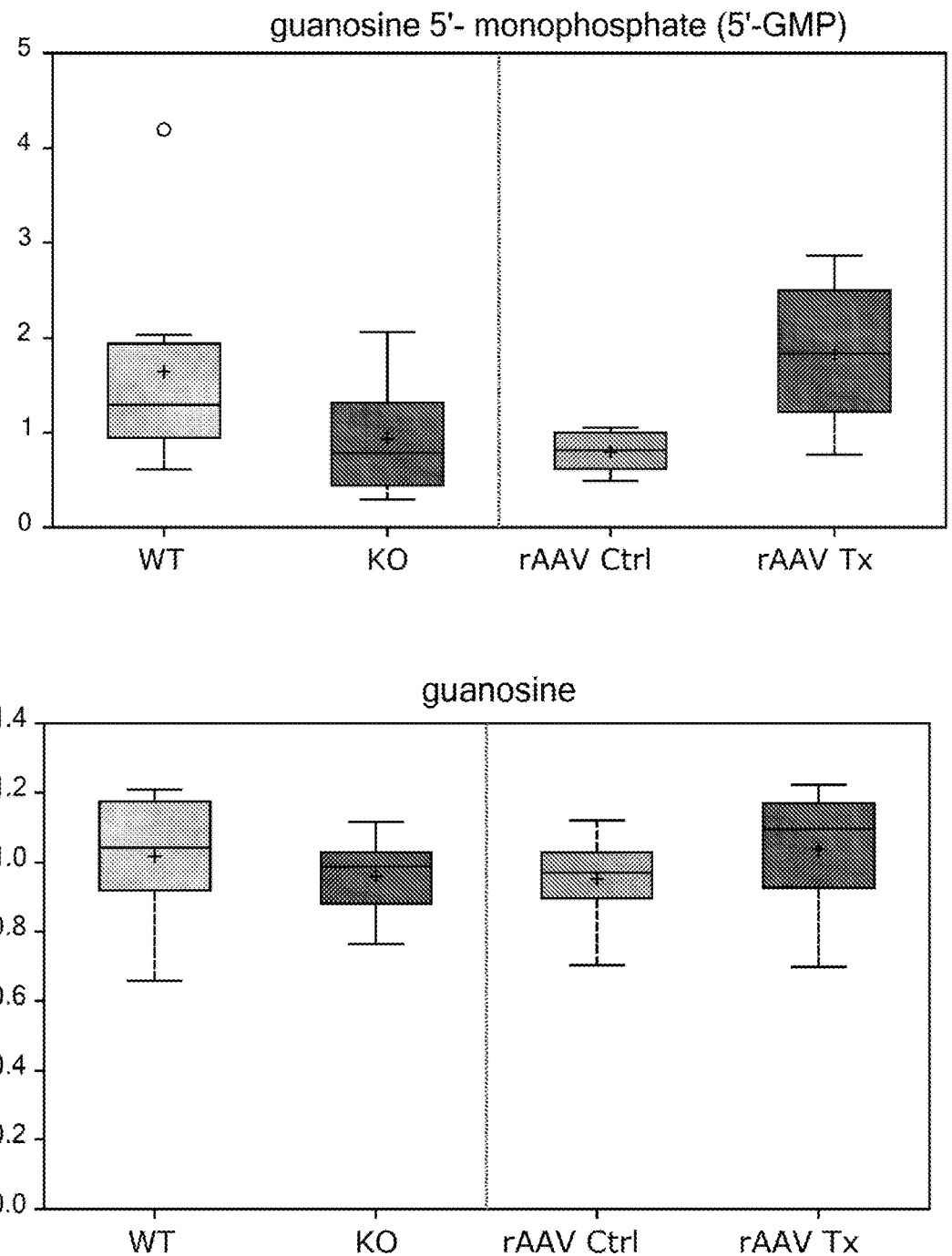
Figure 57:
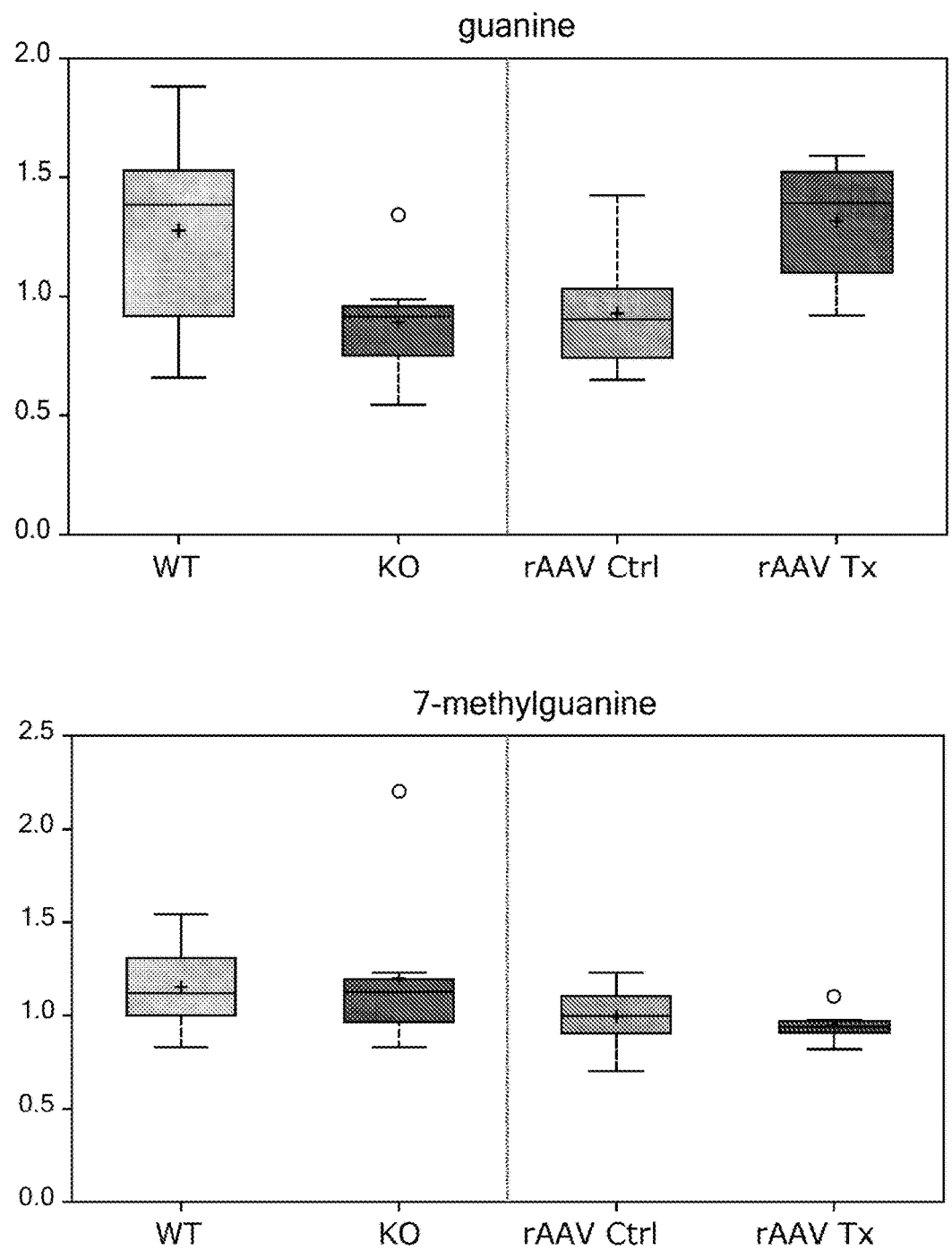
Figure 57:
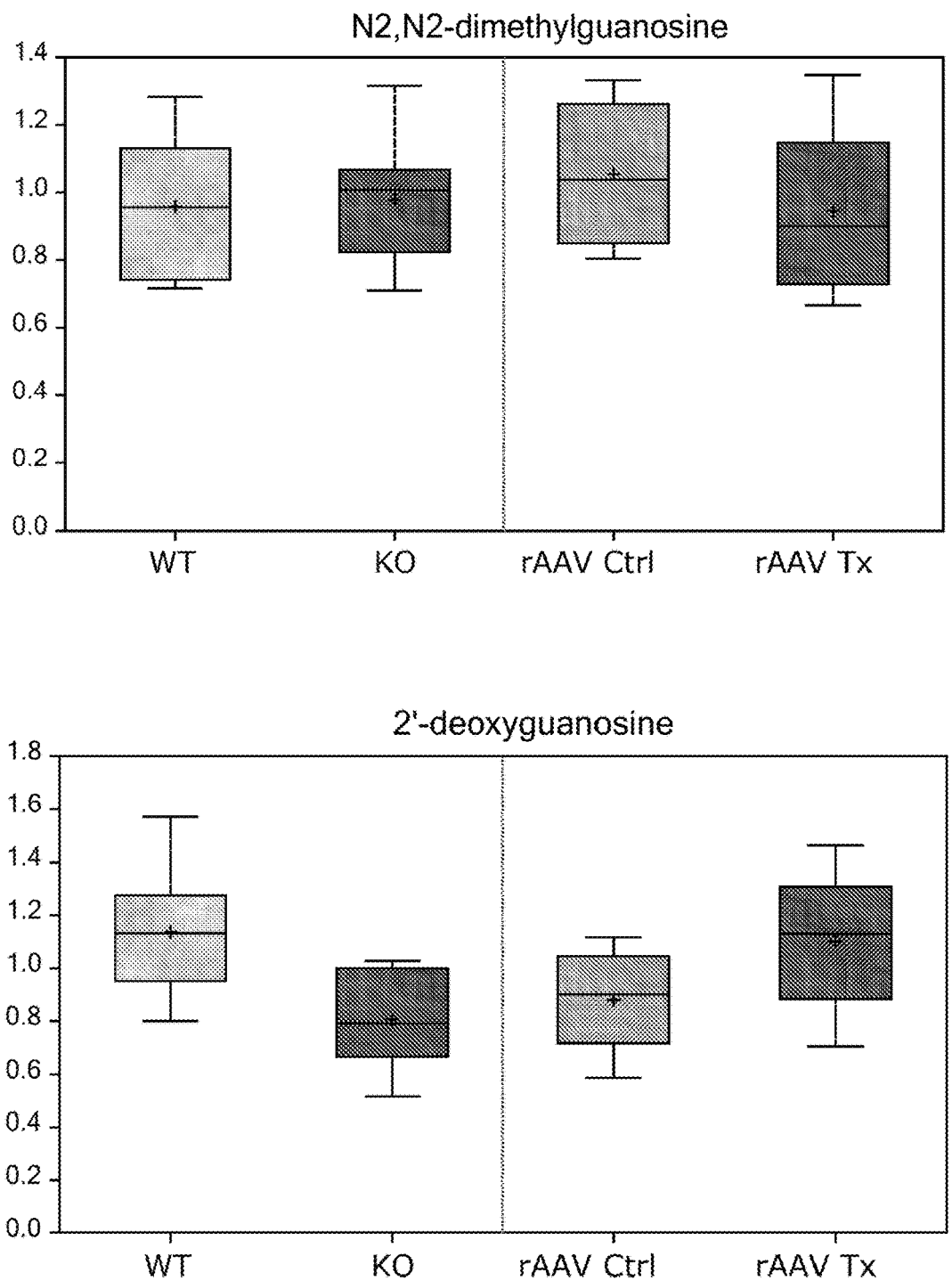
Figure 57:
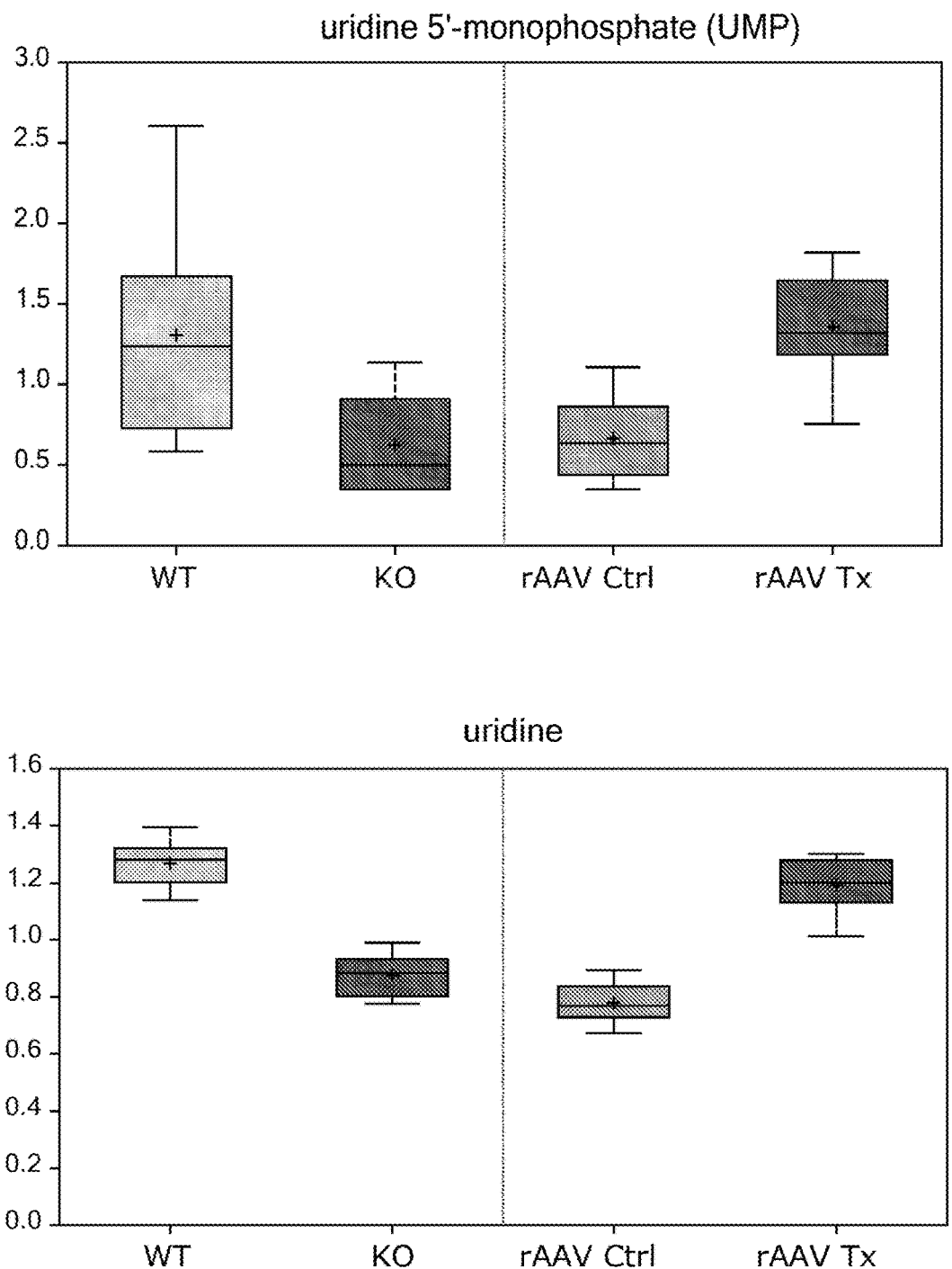
Figure 57:
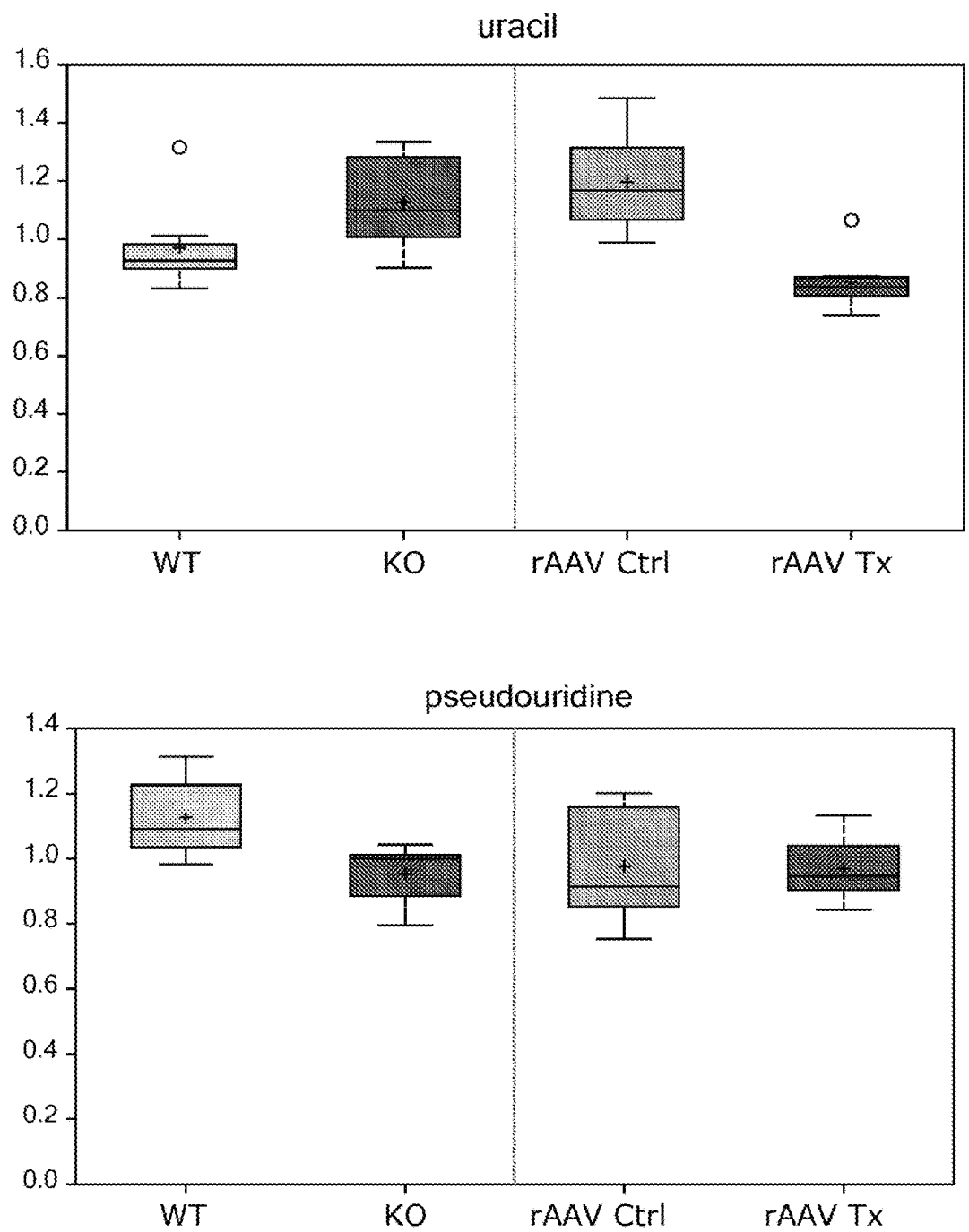
Figure 57:
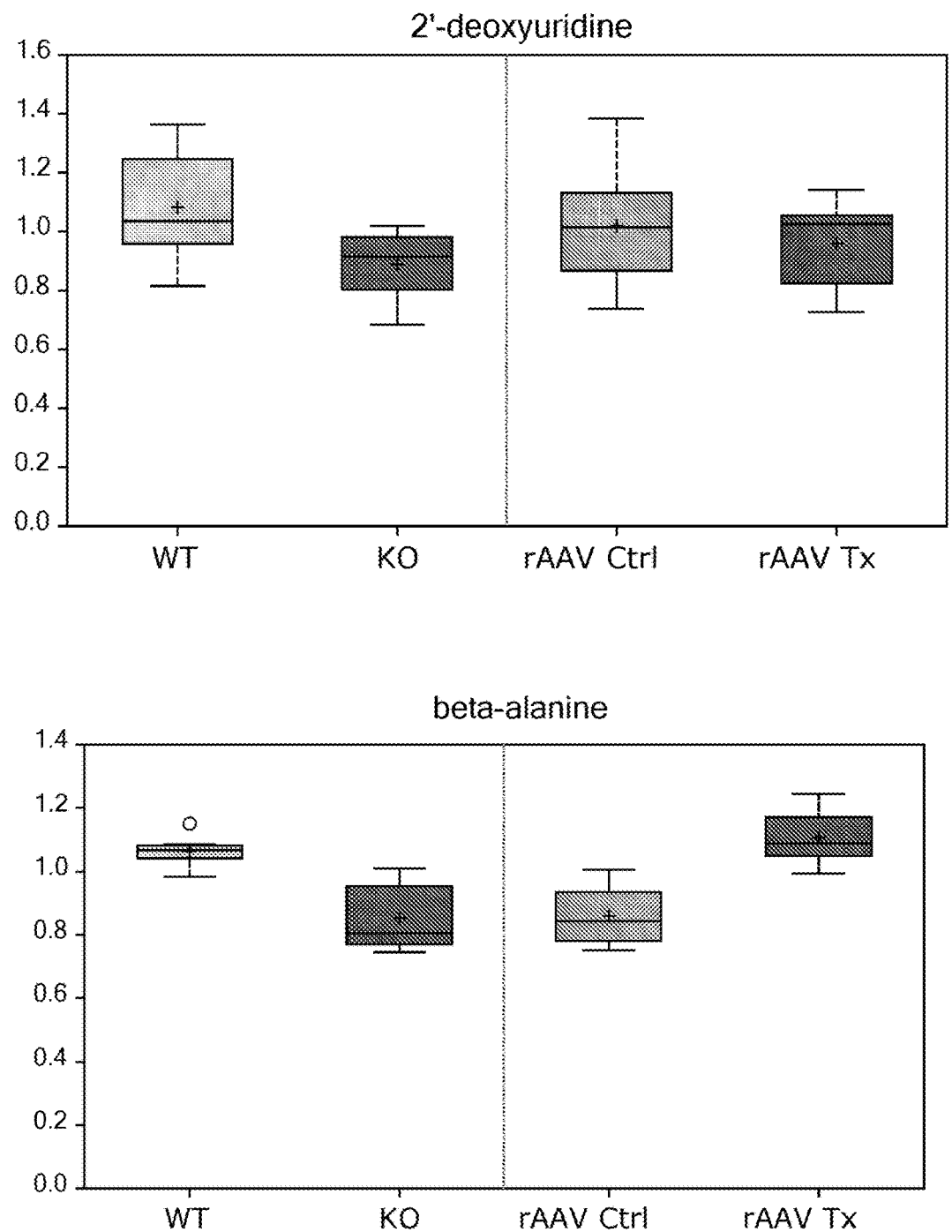
Figure 57:
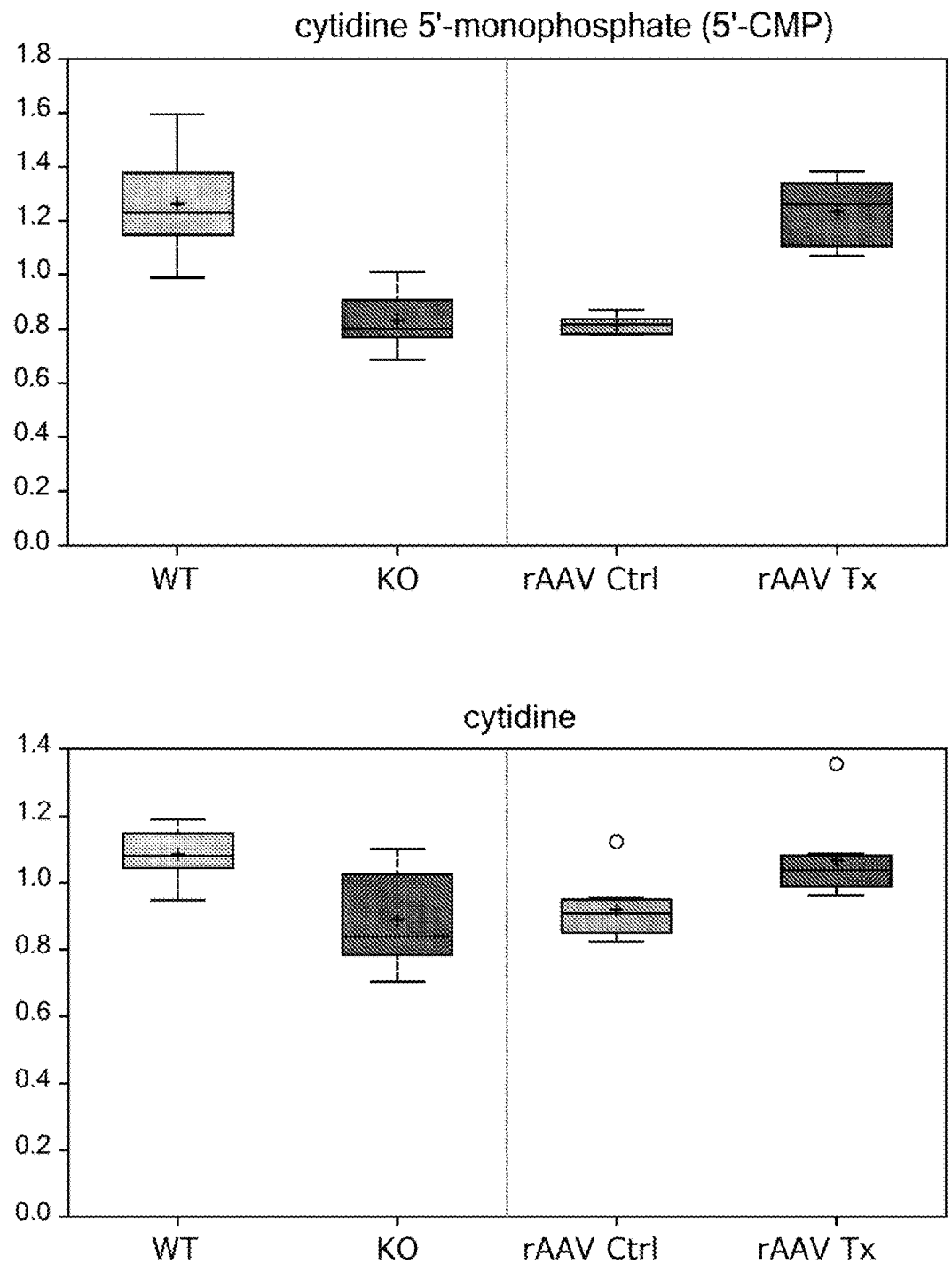
Figure 57:
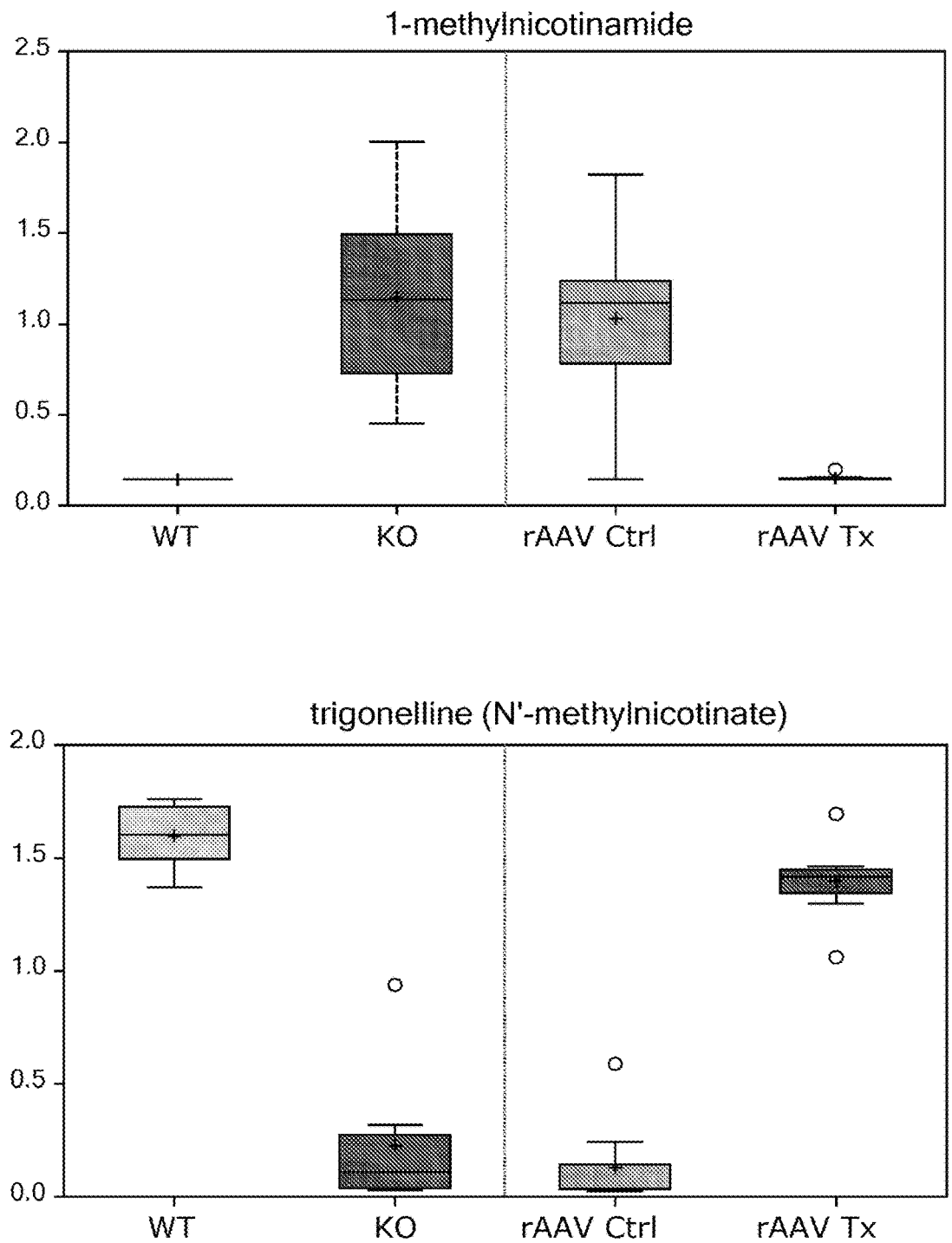
Figure 57:
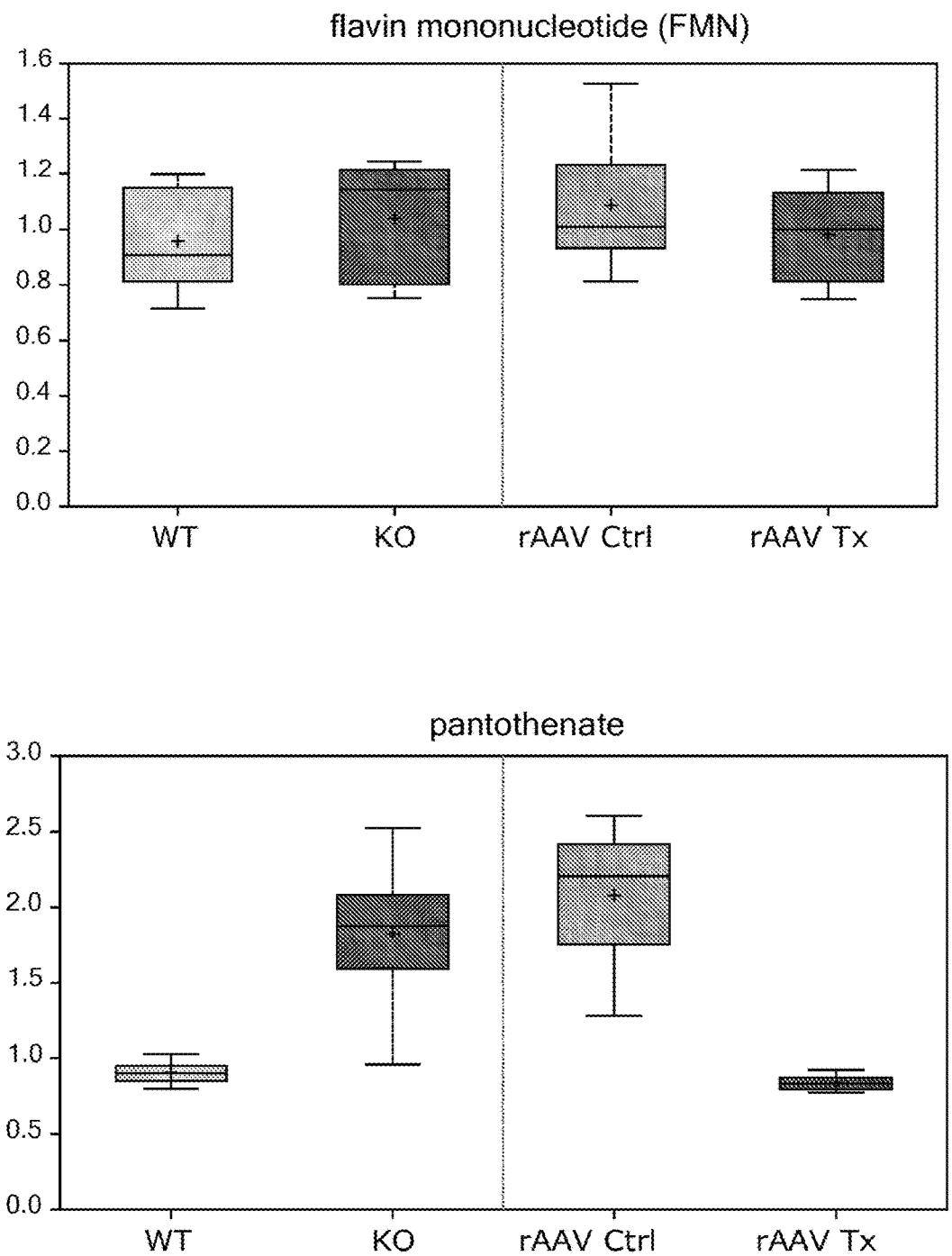
Figure 57:
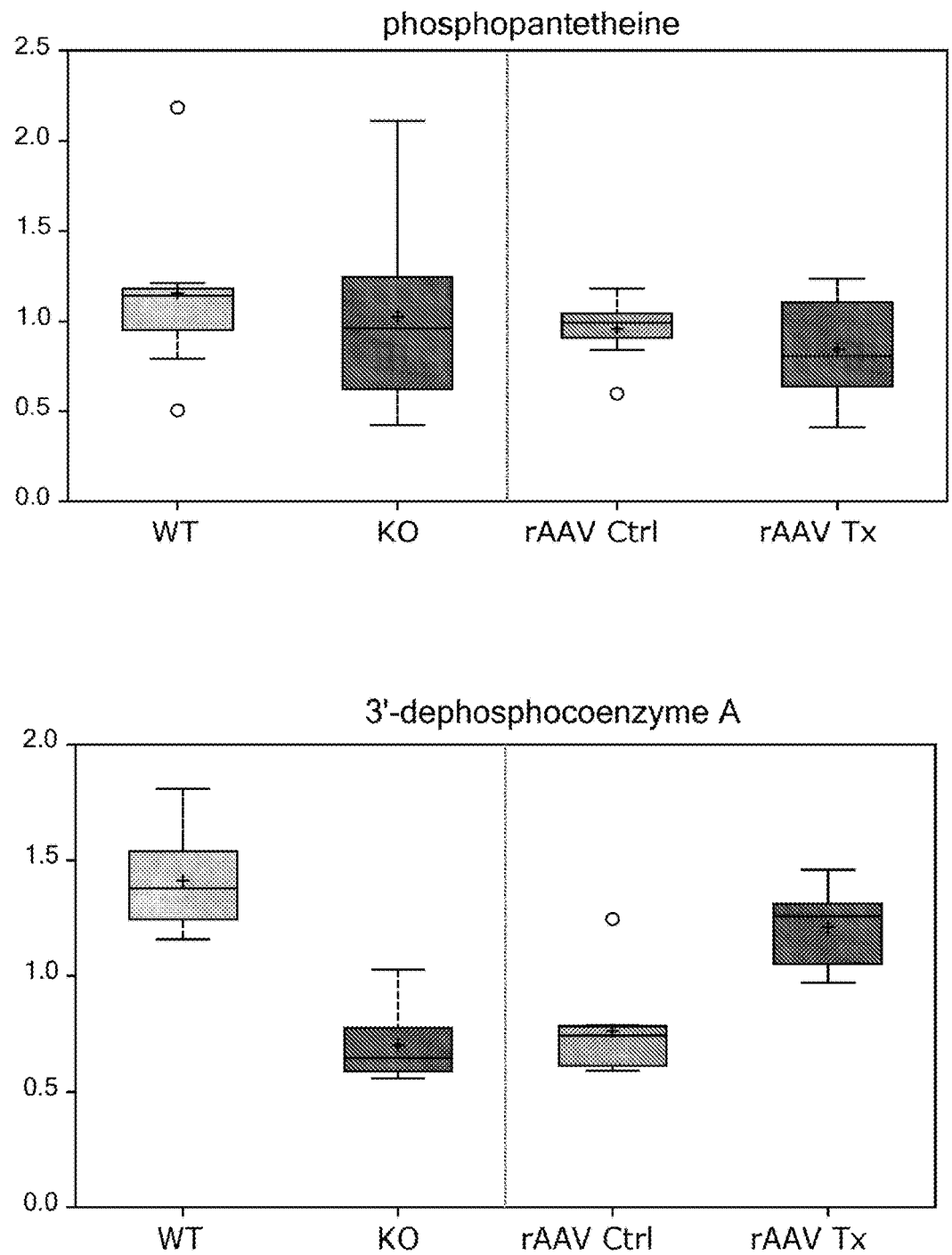
Figure 57:
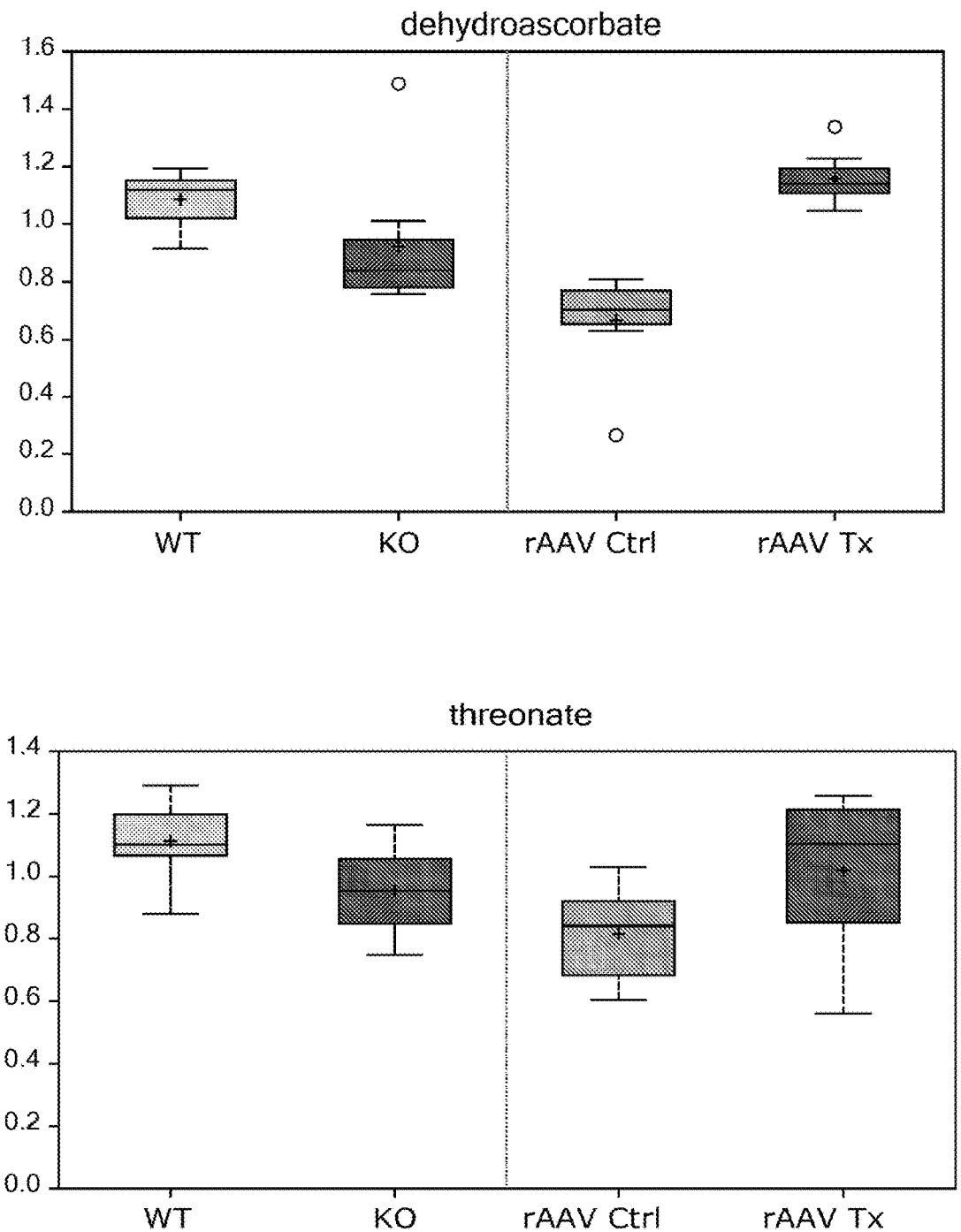
Figure 57:
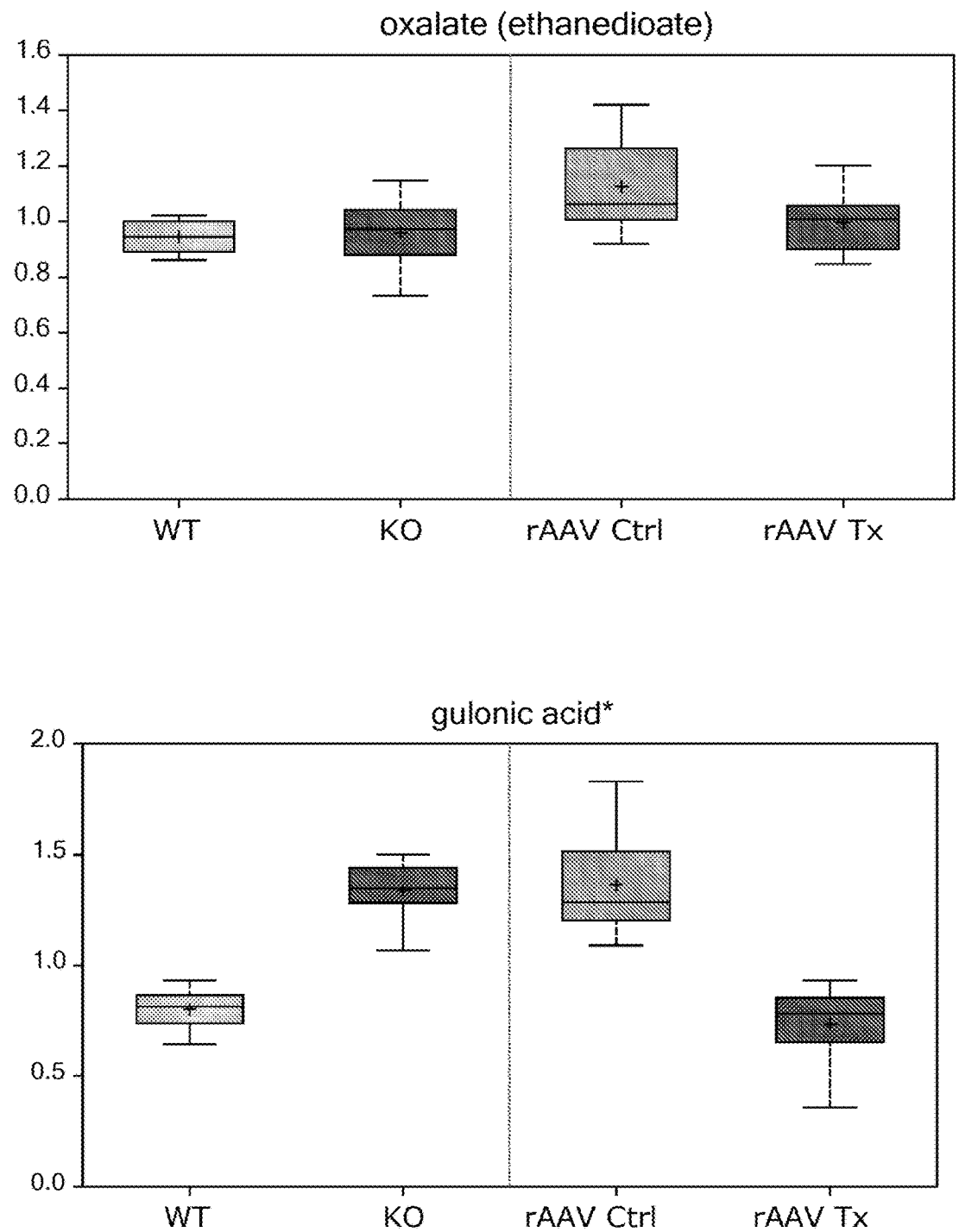
Figure 57:
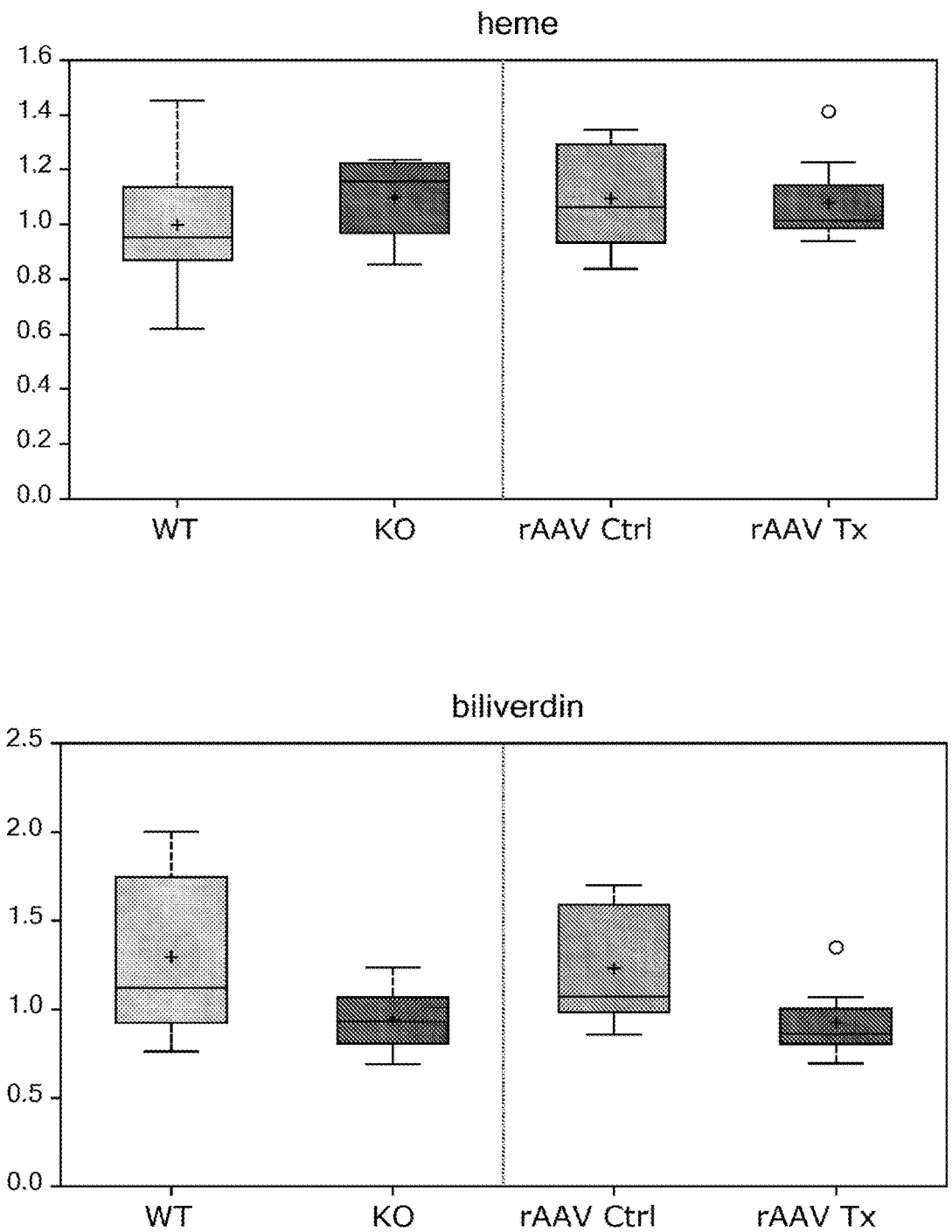
Figure 57:
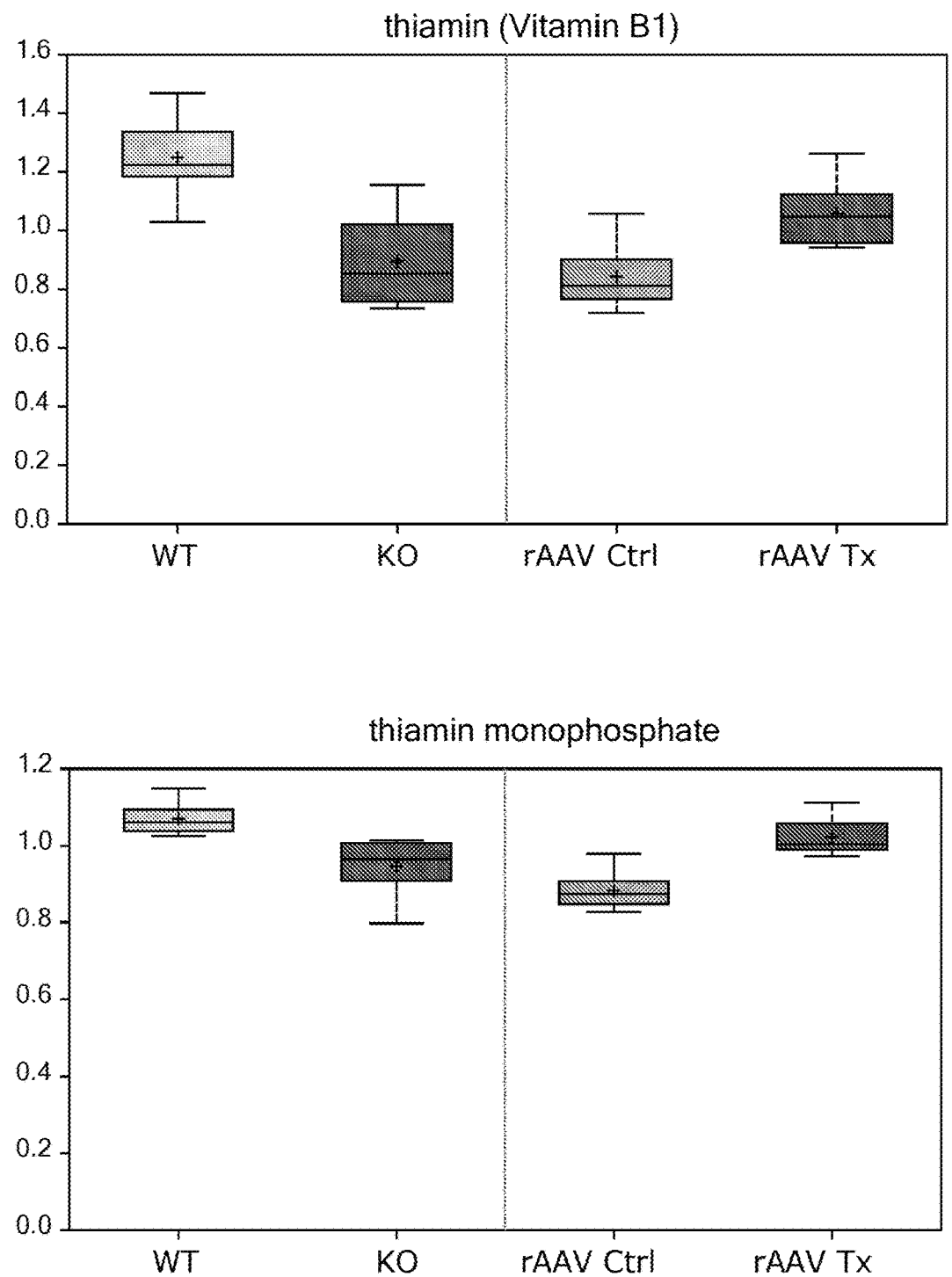
Figure 57:
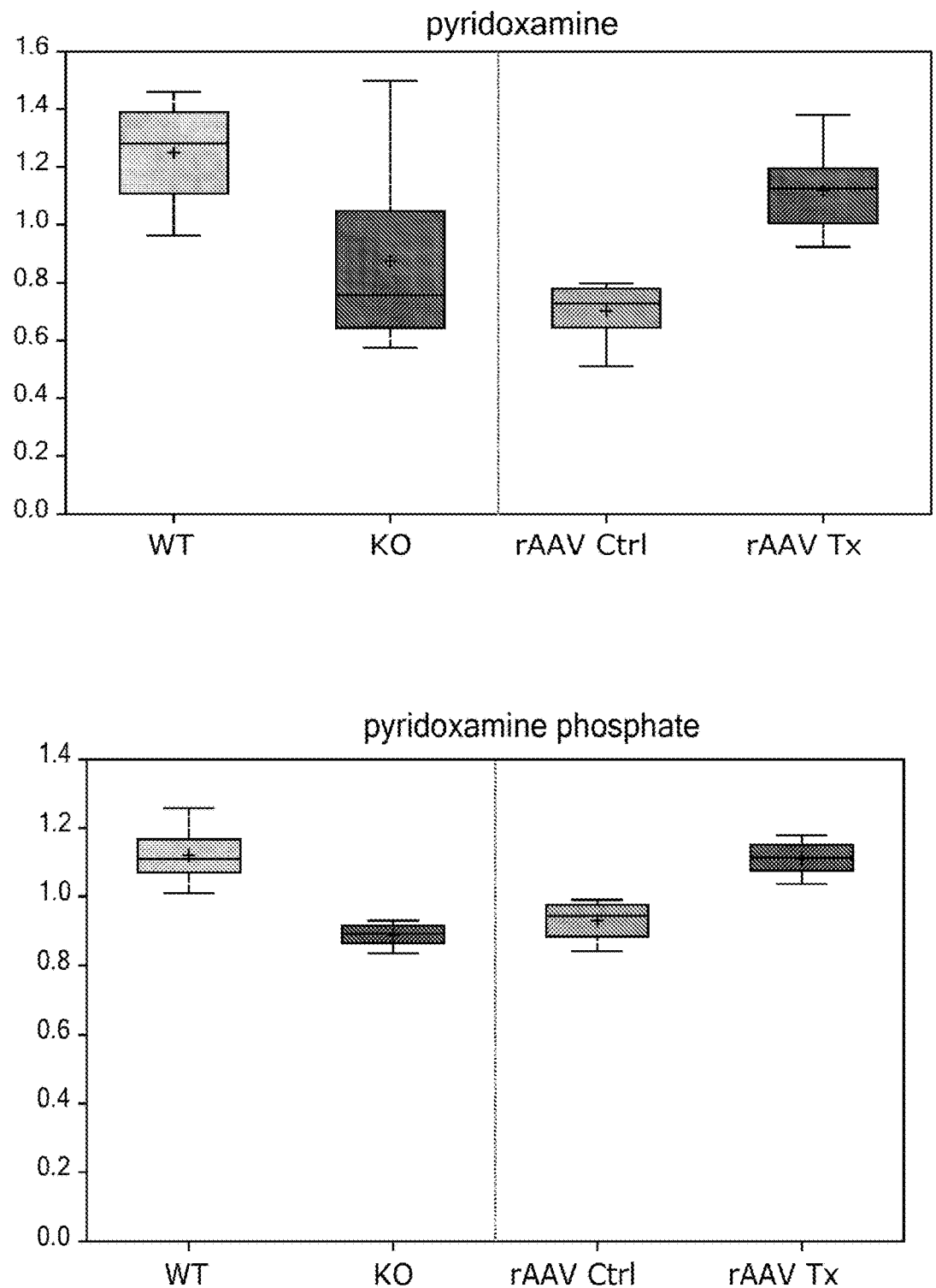
Figure 57:
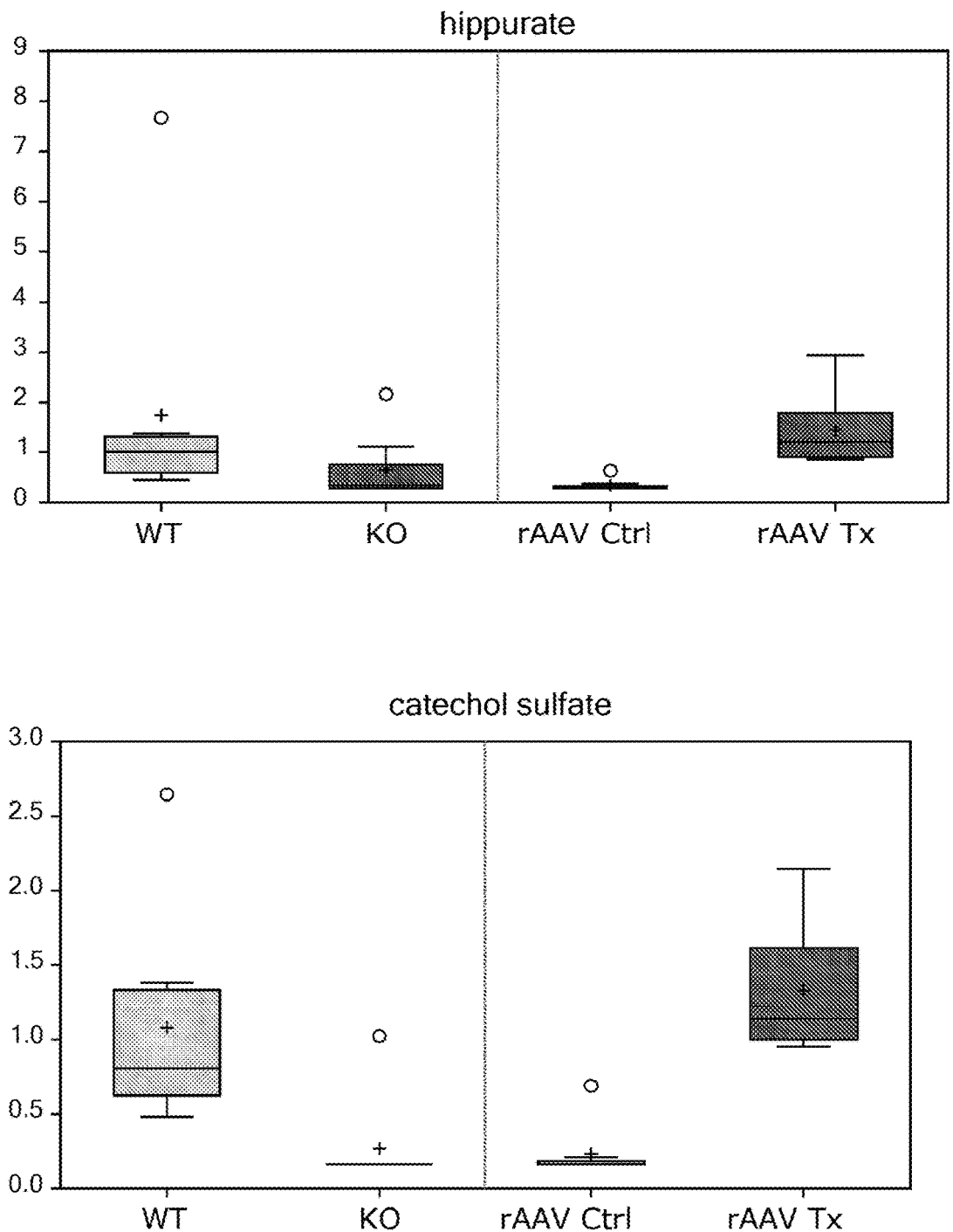
Figure 57:
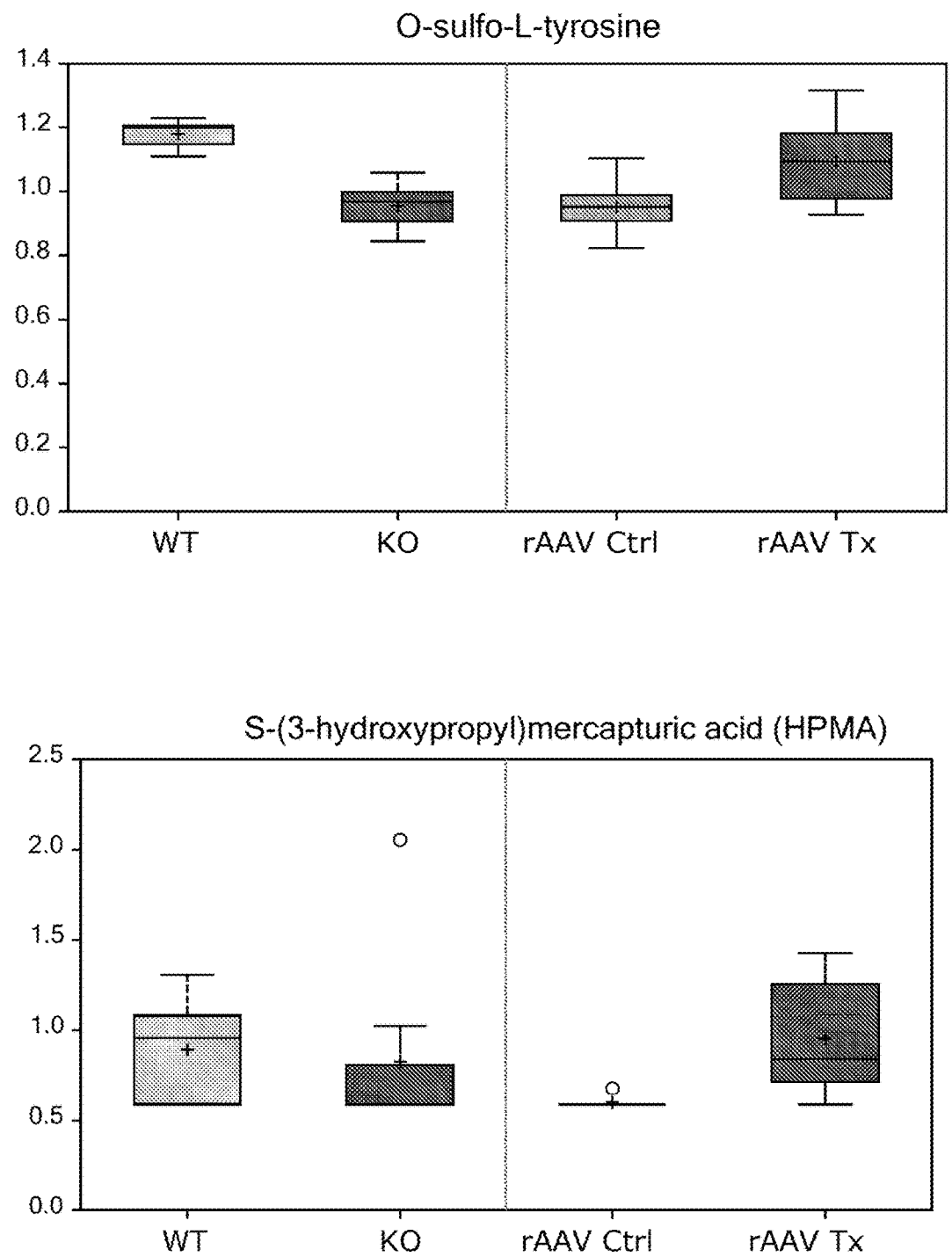
Figure 57:
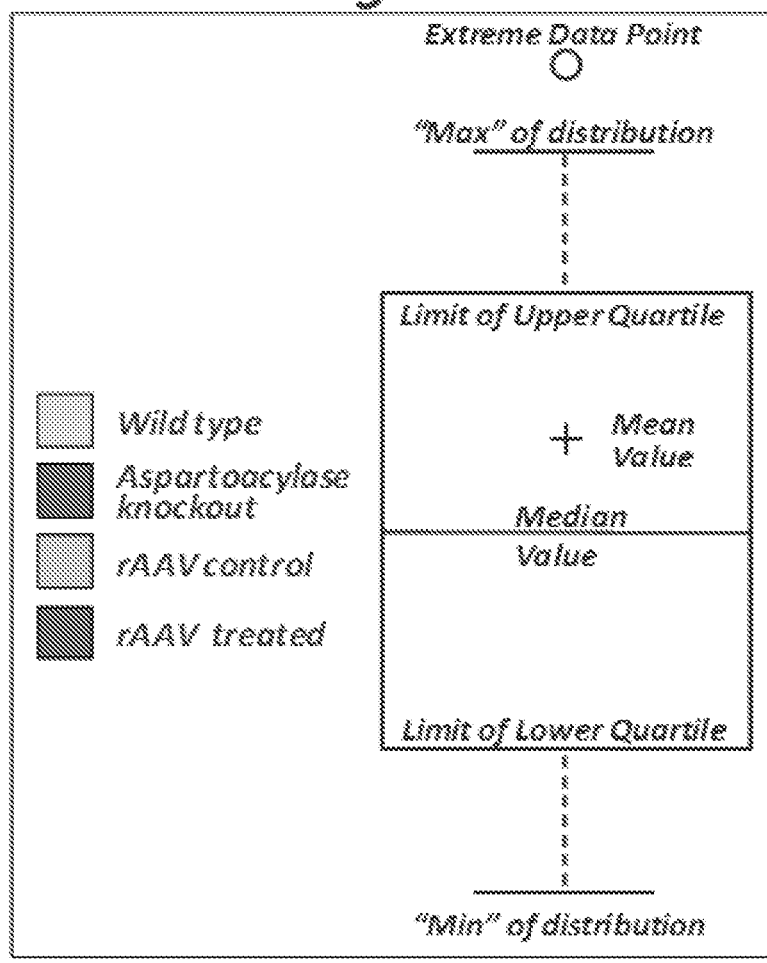

In general, these data are consistent with the metabolome data of mouse brain (described in Example 1 and in FIGS. 55 and 56), where ASPA deficient brains rely on FA oxidation to generate energy but do not utilize glucose to the extent of wild-type brains, and that glutamine is an important source of energy for the ASPA deficient brain (e.g., glutamine is reduced in the ASPA deficient brain).

SEQUENCES

>SEQ ID NO: 1-Codon-optimized human aspartoacylase (hASPA) cDNA (full Kozak sequence underlined)
<u>GCCACC</u>ATGACAAGCTGCCACATCGCCGAGGAGCACATCCAGAAAGTCGC
CATTTTTGGGGGAACTCACGGTAACGAACTCACAGGGGTCTTCCTGGTGA
AGCACTGGCTCGAGAACGGCGCAGAAATCCAGAGAACCGGACTGGAGGTG
AAACCCTTCATTACAAATCCTCGGGCCGTCAAGAAATGCACTCGCTACAT
CGACTGTGATCTGAACCGGATTTTTGATCTGGAAAATCTCGGCAAGAAAA
TGTCCGAGGACCTGCCATACGAAGTGAGGAGAGCTCAGGAGATCAACCAC
CTCTTCGGACCCAAGGACAGCGAAGATTCCTATGACATCATTTTTGATCT
GCATAACACCACATCAAATATGGGGTGCACCCTGATCCTCGAGGACAGCC
GCAACAATTTCCTGATCCAGATGTTTCACTATATTAAGACAAGTCTGGCA
CCACTCCCCTGTTACGTGTATCTGATTGAGCATCCCTCTCTCAAGTACGC
TACTACCCGAAGTATCGCAAATATCCTGTGGGGATTGAAGTCGGTCCTC
AGCCACAGGGAGTCCTGCGAGCCGATATCCTCGACCAGATGAGGAAGATG ATCAAACATGCTCTGGATTTCATTCACCACTTCAACGAGGGCAAGGAGTT
CCCCCCCTTGCGCCATCGAGGTGTACAAGATCATTGAAAAAGTCGATTATC
CTCGGGACGAGAACGGCGAAATTGCCGCTATCATTCACCCAAATCTGCAG
GACCAGGATTGGAAGCCCCTCCATCCTGGGGATCCAATGTTCCTGACACT
CGACGGTAAAACTATCCCACTGGGCGGAGACTGTACCGTGTACCCCGTGT
TTGTCAATGAGGCAGCCTACTATGAGAAGAAAGAAGCTTTCGCCAAAACA
ACAAAACTCACTCTCAATGCTAAATCTATTCGGTGCTGCCTCCACTGA >SEQ ID NO: 2-Codon-optimized human aspartoacylase (hASPA)
MTSCHIAEEHIQKVAIFGGTHGNELTGVFLVKHWLENGAEIQRTGLEVKP
FITNPRAVKKCTRYIDCDLNRIFDLENLGKKMSEDLPYEVRRAQEINHLF
GPKDSEDSYDIIFDLHNTTSNMGCTLILEDSRNNFLIQMFHYIKTSLAPL
PCYVYLIEHPSLKYATTRSIAKYPVGIEVGPQPQGVLRADILDQMRKMIK
HALDFIHHFNEGKEFPPCAIEVYKIIEKVDYPRDENGEIAAIIHPNLQDQ
DWKPLHPGDPMFLTLDGKTIPLGGDCTVYPVFVNEAAYYEKKEAFAKTTK
LTLNAKSIRCCLH >SEQ ID NO: 3-Codon-optimized human NAT8L cDNA (full Kozak sequence underlined)
<u>GCCACC</u>ATGCACTGCGGGCCACCTGATATGGTCTGTGAAACTAAGATTGT
CGCTGCCGAGGATCACGAGGCTCTGCCTGGAGCTAAAAAAGATGCTCTGC
TGGCCGCCGCCGGCGCCATGTGGCCCCCTCTGCCAGCAGCACCAGGACCA
GCAGCAGCACCACCCGCCCCTCCACCCGCCCCTGTGGCCCAGCCACACGG
CGGCGCCGGCGGCGCCGGCCCTCCAGGCGGCCGGGGCGTGTGCATCCGGG
AGTTCAGAGCAGCAGAGCAGGAGGCAGCAAGGAGAATCTTTTATGACGGC
ATCATGGAGCGGATCCCCAACACCGCCTTCAGGGGACTGAGGCAGCACCC
TAGAGCACAGCTGCTGTACGCACTGCTGGCCGCCCTGTGCTTTGCCGTGA
GCAGGTCCCTGCTGCTGACCTGTCTGGTGCCCGCCGCCCTGCTGGGACTG
AGGTACTATTACAGCCGGAAAGTGATCAGAGCCTATCTGGAGTGCGCCCT
GCACACAGACATGGCCGATATCGAGCAGTATTACATGAAGCCCCCTGGCT
CCTGTTTCTGGGTGGCCGTGCTGGACGGGAAACGTGGTGGGAATCGTGGCA
GCAAGGGCACACGAGGAGGACAATACCGTGGAGCTGCTGCGCATGTCTGT
GGATAGCAGGTTCCGCGGCAAGGGAATCGCAAAGGCCCTGGGAAGGAAGG
TGCTGGAGTTTGCCGTGGTGCACAATTACTCTGCCGTGGTGCTGGGCACC
ACAGCAGTGAAGGTGGCAGCCCACAAGCTGTATGAGTCCCTGGGCTTTAG
GCACATGGGCGCCTCTGATCACTACGTGCTGCCTGGCATGACACTGTCCC
TGGCCGAGAGACTGTTCTTCCAGGTCCGCTACCATAGATATAGACTGCAG
CTGAGGGAGGAGTGA >SEQ ID NO: 4-Codon-optimized human NAT8L
MHCGPPDMVCETKIVAAEDHEALPGAKKDALLAAAGAMWPPLPAAPGPAA
APPAPPPAPVAQPHGGAGGAGPPGGRGVCIREFRAAEQEAARRIFYDGIM
ERIPNTAFRGLRQHPRAQLLYALLAALCFAVSRSLLLTCLVPAALLGLRY
YYSRKVIRAYLECALHTDMADIEQYYMKPPGSCFWVAVLDGNVVGIVAAR
AHEEDNTVELLRMSVDSRFRGKGIAKALGRKVLEFAVVHNYSAVVLGTTA
VKVAAHKLYESLGFRHMGASDHYVLPGMTLSLAERLFFQVRYHRYRLQLR
EE

What is claimed is:

1. A method for treating leukodystrophy in a subject in need thereof, the method comprising administering to the subject a recombinant adeno-associated virus (rAAV) comprising: a capsid protein, and an isolated nucleic acid comprising a promoter operably linked to a transgene, wherein the transgene comprises the nucleic acid sequence of SEQ ID NO: 1 encoding aspartoacylase (ASPA).

2. The method of claim 1, wherein it has been determined that the leukodystrophy is associated with a metabolic imbalance comprising a shift from glycolysis to beta-oxidation in the subject, and wherein the method further comprises detecting the metabolic imbalance by evaluating levels of one or more glycolysis and/or beta-oxidation factors, optionally wherein the levels are evaluated using central nervous system (CNS) fluid obtained from the subject.

3. The method of claim 1, wherein it has been determined that the leukodystrophy is associated with a metabolic imbalance comprising a shift from glycolysis to beta-oxidation in the subject, and wherein the method further comprises:
(a) obtaining CNS fluid from the subject;
(b) detecting increased beta-oxidation in the CNS fluid; and
(c) based on the detection in (b), administering the rAAV to the subject.

4. The method of claim 1, wherein it has been determined that the leukodystrophy is associated with a metabolic imbalance comprising a shift from glycolysis to beta-oxidation in the subject, and wherein the determining comprises:
(a) measuring a metabolic profile of a biological sample obtained from the subject; and identifying a metabolic imbalance associated with the leukodystrophy based upon the metabolic profile.

5. The method of claim 4, wherein the leukodystrophy is associated with a condition selected from the group consisting of Canavan disease, adrenomyeloneuropathy, Alexander disease, cerebrotendineous xanthomatosis, Krabbe disease, metachromic leukodystrophy, adrenoleukodystrophy, Pelizaeur-Merzbacher disease, and Refum disease.

6. The method of claim 4, wherein measuring the metabolic profile comprises assaying the biological sample using liquid chromatography (LC), mass spectrometry (MS), liquid chromatography/mass spectrometry (LC/MS), or Ultrahigh Performance Liquid Chromatography-Tandem Mass Spectroscopy (UPLC-MS/MS).

7. The method of claim 4, wherein the biological sample comprises CNS tissue or cerebrospinal fluid (CSF).

8. The method of claim 7, wherein the CNS tissue is brain tissue.

9. The method of claim 4, wherein the metabolic profile comprises a level of a first biomarker selected from the group consisting of glucose, glucose-6-phosphate, 3-phosphoglycerate, pyruvate, lactate, and phosphoenolpyruvate; and optionally a level of a second biomarker selected from the group consisting of carnitine, malonylcarnitine, myristoylcarnitine, palmitoylcarnitine, malonylcarnitine, and beta-hydroxybutyrate.

10. The method of claim 4, further comprising:
(a) administering a small molecule metabolic modulator to the subject;
(b) prescribing to the subject a dietary intervention, wherein the dietary intervention promotes glycolysis and/or reduces beta-oxidation in the subject; or
(c) administering an immune-suppressing agent to the subject.

11. The method of claim 1, wherein the rAAV is administered via injection, optionally wherein the injection is selected from the group consisting of intravenous injection, intravascular injection, and intraventricular injection.

12. The method of claim 1, wherein the promoter is an astrocyte-specific promoter, optionally a glial fibrillary acidic protein (GFAP) promoter.

13. The method of claim 1, wherein the promoter is an enhanced chicken β-actin promoter.

14. The method of claim 1, wherein the ASPA comprises SEQ ID NO: 2.

15. The method of claim 1, wherein the capsid protein is an AAV9 capsid protein.

16. The method of claim 1, wherein it has been determined that the leukodystrophy is associated with a metabolic imbalance comprising a shift from glycolysis to beta-oxidation in the subject.

17. A method for treating Canavan disease in a subject in need thereof, comprising administering to the subject a recombinant adeno-associated virus (rAAV) comprising:
(a) a capsid protein; and
(b) a nucleic acid comprising a promoter operably linked to a transgene, wherein the transgene encodes aspartoacylase (ASPA), and
wherein the transgene comprises a codon-optimized human ASPA cDNA, comprising the nucleic acid sequence of SEQ ID NO: 1.

18. The method of claim 17, wherein the promoter is an enhanced chicken β-actin promoter.

19. The method of claim 17, wherein the ASPA comprises SEQ ID NO: 2.

20. The method of claim 17, wherein the capsid protein has the serotype AAV9.

21. A method for treating Canavan disease in a subject in need thereof, comprising administering to the subject a recombinant adeno-associated virus (rAAV) comprising:
(a) an AAV9 capsid protein; and
(b) a nucleic acid comprising a promoter operably linked to a transgene, wherein the transgene comprises SEQ ID NO: 1 and encodes aspartoacylase (ASPA),
and wherein the promoter is an enhanced chicken β-actin promoter.

* * * * *

SEQUENCE LISTING

<160> NUMBER OF SEQ ID NOS: 4

<210> SEQ ID NO 1
<211> LENGTH: 948
<212> TYPE: DNA
<213> ORGANISM: Artificial Sequence
<220> FEATURE:
<223> OTHER INFORMATION: Synthetic Polynucleotide

<400> SEQUENCE: 1
gccaccatga caagctgcca catcgccgag gagcacatcc agaaagtcgc cattttggg      60 ggaactcacg gtaacgaact cacaggggtc ttcctggtga agcactggct cgagaacggc    120
gcagaaatcc agagaaccgg actggaggtg aaacccttca ttacaaatcc tcgggccgtc    180
aagaaatgca ctcgctacat cgactgtgat ctgaaccgga ttttgatct ggaaaatctc     240 ggcaagaaaa tgtccgagga cctgccatac gaagtgagga gagctcagga gatcaaccac    300

```
ctcttcggac ccaaggacag cgaagattcc tatgacatca ttttgatct gcataacacc    360 acatcaaata tggggtgcac cctgatcctc gaggacagcc gcaacaattt cctgatccag    420
atgtttcact atattaagac aagtctggca ccactcccct gttacgtgta tctgattgag    480
catccctctc tcaagtacgc tactacccga agtatcgcaa aatatcctgt ggggattgaa    540
gtcggtcctc agccacaggg agtcctgcga gccgatatcc tcgaccagat gaggaagatg    600
atcaaacatg ctctggattt cattcaccac ttcaacgagg gcaaggagtt ccccccttgc    660
gccatcgagg tgtacaagat cattgaaaaa gtcgattatc ctcgggacga aacggcgaa     720 attgccgcta tcattcaccc aaatctgcag gaccaggatt ggaagcccct ccatcctggg    780
gatccaatgt tcctgacact cgacggtaaa actatcccac tgggcggaga ctgtaccgtg    840
taccccgtgt tgtcaatga ggcagcctac tatgagaaga aagaagcttt cgccaaaaca     900
acaaaactca ctctcaatgc taaatctatt cggtgctgcc tccactga                 948
```

<210> SEQ ID NO 2  
<211> LENGTH: 313  
<212> TYPE: PRT  
<213> ORGANISM: Artificial Sequence  
<220> FEATURE:  
<223> OTHER INFORMATION: Synthetic Polypeptide

<400> SEQUENCE: 2

```
Met Thr Ser Cys His Ile Ala Glu Glu His Ile Gln Lys Val Ala Ile
1               5                   10                  15

Phe Gly Gly Thr His Gly Asn Glu Leu Thr Gly Val Phe Leu Val Lys
                20                  25                  30

His Trp Leu Glu Asn Gly Ala Glu Ile Gln Arg Thr Gly Leu Glu Val
            35                  40                  45

Lys Pro Phe Ile Thr Asn Pro Arg Ala Val Lys Lys Cys Thr Arg Tyr
        50                  55                  60

Ile Asp Cys Asp Leu Asn Arg Ile Phe Asp Leu Glu Asn Leu Gly Lys
65                  70                  75                  80

Lys Met Ser Glu Asp Leu Pro Tyr Glu Val Arg Arg Ala Gln Glu Ile
                85                  90                  95

Asn His Leu Phe Gly Pro Lys Asp Ser Glu Asp Ser Tyr Asp Ile Ile
            100                 105                 110

Phe Asp Leu His Asn Thr Thr Ser Asn Met Gly Cys Thr Leu Ile Leu
        115                 120                 125

Glu Asp Ser Arg Asn Asn Phe Leu Ile Gln Met Phe His Tyr Ile Lys
130                 135                 140

Thr Ser Leu Ala Pro Leu Pro Cys Tyr Val Tyr Leu Ile Glu His Pro
145                 150                 155                 160

Ser Leu Lys Tyr Ala Thr Thr Arg Ser Ile Ala Lys Tyr Pro Val Gly
                165                 170                 175

Ile Glu Val Gly Pro Gln Pro Gln Gly Val Leu Arg Ala Asp Ile Leu
            180                 185                 190

Asp Gln Met Arg Lys Met Ile Lys His Ala Leu Asp Phe Ile His His
        195                 200                 205

Phe Asn Glu Gly Lys Glu Phe Pro Pro Cys Ala Ile Glu Val Tyr Lys
    210                 215                 220

Ile Ile Glu Lys Val Asp Tyr Pro Arg Asp Glu Asn Gly Glu Ile Ala
225                 230                 235                 240

Ala Ile Ile His Pro Asn Leu Gln Asp Gln Asp Trp Lys Pro Leu His
                245                 250                 255
```

```
Pro Gly Asp Pro Met Phe Leu Thr Leu Asp Gly Lys Thr Ile Pro Leu
            260                 265                 270

Gly Gly Asp Cys Thr Val Tyr Pro Val Phe Val Asn Glu Ala Ala Tyr
        275                 280                 285

Tyr Glu Lys Lys Glu Ala Phe Ala Lys Thr Thr Lys Leu Thr Leu Asn
    290                 295                 300

Ala Lys Ser Ile Arg Cys Cys Leu His
305                 310

<210> SEQ ID NO 3
<211> LENGTH: 915
<212> TYPE: DNA
<213> ORGANISM: Artificial Sequence
<220> FEATURE:
<223> OTHER INFORMATION: Synthetic Polynucleotide

<400> SEQUENCE: 3
gccaccatgc actgcgggcc acctgatatg gtctgtgaaa ctaagattgt cgctgccgag      60
gatcacgagg ctctgcctgg agctaaaaaa gatgctctgc tggccgccgc cggcgccatg     120
tggcccctc tgccagcagc accaggacca gcagcagcac cacccgcccc tccacccgcc      180
cctgtggccc agccacacgg cggcgccggc ggcgccggcc ctccaggcgg ccggggcgtg     240
tgcatccggg agttcagagc agcagagcag gaggcagcaa ggagaatctt ttatgacggc     300
atcatggagc ggatccccaa caccgccttc agggggactga ggcagcaccc tagagcacag    360
ctgctgtacg cactgctggc cgccctgtgc tttgccgtga caggtccct gctgctgacc       420
tgtctggtgc ccgccgccct gctgggactg aggtactatt acagccggaa agtgatcaga     480
gcctatctgg agtgcgccct gcacacagac atggccgata tcgagcagta ttacatgaag     540
ccccctggct cctgtttctg ggtggccgtg ctggacggaa acgtggtggg aatcgtggca     600
gcaagggcac acgaggagga caataccgtg gagctgctgc gcatgtctgt ggatagcagg     660
ttccgcggca agggaatcgc aaaggccctg ggaaggaagg tgctggagtt tgccgtggtg    720
cacaattact ctgccgtggt gctgggcacc acagcagtga aggtggcagc ccacaagctg    780
tatgagtccc tgggctttag gcacatgggc gcctctgatc actacgtgct gcctggcatg    840
acactgtccc tggccgagag actgttcttc caggtccgct accatagata tagactgcag    900
ctgagggagg agtga                                                     915

<210> SEQ ID NO 4
<211> LENGTH: 302
<212> TYPE: PRT
<213> ORGANISM: Artificial Sequence
<220> FEATURE:
<223> OTHER INFORMATION: Synthetic Polypeptide

<400> SEQUENCE: 4

Met His Cys Gly Pro Pro Asp Met Val Cys Glu Thr Lys Ile Val Ala
1               5                   10                  15

Ala Glu Asp His Glu Ala Leu Pro Gly Ala Lys Lys Asp Ala Leu Leu
            20                  25                  30

Ala Ala Ala Gly Ala Met Trp Pro Pro Leu Pro Ala Pro Gly Pro
        35                  40                  45

Ala Ala Ala Pro Pro Ala Pro Pro Ala Pro Val Ala Gln Pro His
    50                  55                  60

Gly Gly Ala Gly Gly Ala Gly Pro Pro Gly Gly Arg Gly Val Cys Ile
65                  70                  75                  80
```

-continued

```
Arg Glu Phe Arg Ala Ala Glu Gln Glu Ala Ala Arg Arg Ile Phe Tyr
                85              90              95
Asp Gly Ile Met Glu Arg Ile Pro Asn Thr Ala Phe Arg Gly Leu Arg
            100             105             110
Gln His Pro Arg Ala Gln Leu Leu Tyr Ala Leu Leu Ala Ala Leu Cys
        115             120             125
Phe Ala Val Ser Arg Ser Leu Leu Leu Thr Cys Leu Val Pro Ala Ala
    130             135             140
Leu Leu Gly Leu Arg Tyr Tyr Tyr Ser Arg Lys Val Ile Arg Ala Tyr
145             150             155             160
Leu Glu Cys Ala Leu His Thr Asp Met Ala Asp Ile Glu Gln Tyr Tyr
                165             170             175
Met Lys Pro Pro Gly Ser Cys Phe Trp Val Ala Val Leu Asp Gly Asn
            180             185             190
Val Val Gly Ile Val Ala Ala Arg Ala His Glu Glu Asp Asn Thr Val
        195             200             205
Glu Leu Leu Arg Met Ser Val Asp Ser Arg Phe Arg Gly Lys Gly Ile
    210             215             220
Ala Lys Ala Leu Gly Arg Lys Val Leu Glu Phe Ala Val Val His Asn
225             230             235             240
Tyr Ser Ala Val Val Leu Gly Thr Thr Ala Val Lys Val Ala Ala His
                245             250             255
Lys Leu Tyr Glu Ser Leu Gly Phe Arg His Met Gly Ala Ser Asp His
            260             265             270
Tyr Val Leu Pro Gly Met Thr Leu Ser Leu Ala Glu Arg Leu Phe Phe
        275             280             285
Gln Val Arg Tyr His Arg Tyr Arg Leu Gln Leu Arg Glu Glu
    290             295             300
```